United States Patent
Moore et al.

(10) Patent No.: US 12,241,063 B2
(45) Date of Patent: Mar. 4, 2025

(54) MODIFIED MESSENGER RNA COMPRISING FUNCTIONAL RNA ELEMENTS

(71) Applicant: ModernaTX, Inc., Cambridge, MA (US)

(72) Inventors: Melissa J. Moore, Cambridge, MA (US); Caroline Köhrer, Cambridge, MA (US); Ruchi Jain, Cambridge, MA (US); Vladimir Presnyak, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 17/933,500

(22) Filed: Sep. 20, 2022

(65) Prior Publication Data
US 2023/0257738 A1 Aug. 17, 2023

Related U.S. Application Data

(63) Continuation of application No. 16/614,245, filed as application No. PCT/US2018/033519 on May 18, 2018, now Pat. No. 11,485,972.

(60) Provisional application No. 62/667,824, filed on May 7, 2018, provisional application No. 62/519,800, filed on Jun. 14, 2017, provisional application No. 62/508,318, filed on May 18, 2017.

(51) Int. Cl.
| | |
|---|---|
| *C07H 21/02* | (2006.01) |
| *A61K 47/69* | (2017.01) |
| *C12N 15/11* | (2006.01) |
| *C12N 15/85* | (2006.01) |
| *C12N 15/88* | (2006.01) |

(52) U.S. Cl.
CPC .......... *C12N 15/11* (2013.01); *A61K 47/6929* (2017.08); *C12N 15/85* (2013.01); *C12N 15/88* (2013.01); *C12N 2310/321* (2013.01); *C12N 2310/322* (2013.01); *C12N 2310/335* (2013.01)

(58) Field of Classification Search
CPC ............................ C12N 15/11; A61K 31/7105
See application file for complete search history.

(56) References Cited

U.S. PATENT DOCUMENTS

| | | |
|---|---|---|
| 7,842,467 B1 | 11/2010 | Heidbrink et al. |
| 11,485,972 B2 | 11/2022 | Moore et al. |
| 2012/0283317 A1 | 11/2012 | Teitell et al. |
| 2016/0237134 A1 | 8/2016 | Hoge et al. |
| 2020/0208145 A1 | 7/2020 | Moore et al. |
| 2021/0163928 A1 | 6/2021 | Reid et al. |
| 2022/0251577 A1 | 8/2022 | Bicknell et al. |
| 2022/0387628 A1 | 12/2022 | Jain et al. |

FOREIGN PATENT DOCUMENTS

| | | | |
|---|---|---|---|
| WO | WO-2007044894 A2 * | 4/2007 | .......... C12N 9/1205 |
| WO | WO-2014111858 A1 | 7/2014 | |
| WO | WO-2017049275 A2 | 3/2017 | |
| WO | WO-2018081459 A1 | 5/2018 | |
| WO | WO-2018213789 A1 | 11/2018 | |
| WO | WO-2019104160 A2 | 5/2019 | |
| WO | WO-2019200171 A1 | 10/2019 | |
| WO | WO-2020263883 A1 | 12/2020 | |
| WO | WO-2020263985 A1 | 12/2020 | |

OTHER PUBLICATIONS

Barendt et al., "Broad-Specificity mRNA-rRNA Complementarity in Efficient Protein Translation," PLoS Genetics, 2012, 8(3): e1002598, 13 pages.
Bicknell and Ricci, "When mRNA translation meets decay," Biochemical Society Transactions (2017) 45, 339-351.
Boehm et al., "Interrogating The Degradation Pathways Of Unstable mRNAs With XRN1-resistant Sequences," Nature Communications, Dec. 5, 2016, 7:13691, 15 pages.
Braun and Young, "Coupling mRNA Synthesis and Decay," Molecular and Cellular Biology, Nov. 2014, vol. 34, No. 22, pp. 4078-4087.
Chin et al., "Optimized Mitochondrial Targeting of Proteins Encoded by Modified mRNAs Rescues Cells Harboring Mutations in mtATP6," Cell Reports, Mar. 13, 2018, 22, 2818-2826.
Chung et al., "The 3' Untranslated Region of Manganese Superoxide Dismutase RNA Contains a Translational Enhancer Element," Biochemistry 1998, 37, 16298-16306.
Database EMBL, "Sequence 163 from Patent WO2017201346," EBI Accession No. LP886038, Apr. 29, 2018, 1 page.
Ei-Brolosy et al., "Genetic compensation triggered by mutant mRNA degradation," Nature, Apr. 2019, vol. 568, pp. 193-197.
Firth and Brierley, "Non-canonical translation in RNA viruses," Journal of General Virology (2012), 93, 1385-1409.
Gold et al., "Visualization of cytosolic ribosomes on the surface of mitochondria by electron cryo-tomography," EMBO Reports, 2017, vol. 18, No. 10, 1786-1800.
International Preliminary Report on Patentability for International Application No. PCT/US2020/039228 mailed Jan. 6, 2022, 7 pages.
International Search Report and Written Opinion for Application No. PCT/US2020/039365, mailed Oct. 8, 2020, 11 pages.
International Search Report and Written Opinion for International Application No. PCT/US2020/039228, dated Sep. 22, 2020, 10 pages.
Kalef-Ezra et al., "Import of a major mitochondrial enzyme depends on synergy between two distinct helices of its presequence," Biochemical Journal (2016) 473: 2813-2829.
Knirsch and Clerch, "A Region in the 39 UTR of MnSOD RNA Enhances Translation of a Heterologous RNA," Biochemical and Biophysical Research Communications (2000) 272, 164-168.

(Continued)

*Primary Examiner* — Amy Rose Hudson
(74) *Attorney, Agent, or Firm* — Clark & Elbing LLP

(57) ABSTRACT

The present disclosure provides messenger RNAs (mRNAs) having chemical and/or structural modifications, including RNA elements and/or modified nucleotides, which provide a desired translational regulatory activity to the mRNA.

19 Claims, 12 Drawing Sheets

Specification includes a Sequence Listing.

(56) References Cited

OTHER PUBLICATIONS

Lesnik et al., "Localized translation near the mitochondrial outer membrane: An update," RNA Biology, Aug. 2015, 12:8, 801-809.
Margeot et al., "In Saccharomyces cerevisiae, ATP2 mRNA sorting to the vicinity of mitochondria is essential for respiratory function," The EMBO Journal, 2002, vol. 21, No. 24, pp. 6893-6904.
Medina et al., "Cytoplasmic 5'-3' Exonuclease Xrn1pis Also A Genome-wide Transcription Factor In Yeast," Frontiers In Genetics, Feb. 2014, vol. 5, Article 1, 10 pages.
Stacey et al., "Leaky Scanning Is the Predominant Mechanism for Translation of Human Papillomavirus Type 16 E7 Oncoprotein from E6/E7 Bicistronic mRNA," Journal of Virology, Aug. 2000, vol. 74, No. 16, pp. 7284-7297.
Sylvestre et al., "The Role of the 3' Untranslated Region in mRNA Sorting to the Vicinity of Mitochondria Is Conserved from Yeast to Human Cells," Molecular Biology of the Cell, Sep. 2003, vol. 14, pp. 3848-3856.
Wang et al., "PNPASE Regulates RNA Import into Mitochondria," Cell, 2010, 142(3): 456-467 (20 pages).
Williams et al., "Targeting and plasticity of mitochondrial proteins revealed by proximity-specific ribosome profiling," Science, 2014, 346(6210): 748-751 (10 pages).
Warren et al., "Highly Efficient Reprogramming to Pluripotency and Directed Differentiation of Human Cells with Synthetic Modified mRNA," Cell Stem Cell, Nov. 5, 2010, 7, 618-630.
Warren et al., Supplemental Information, Highly Efficient Reprogramming to Pluripotency and Directed Differentiation of Human Cells with Synthetic Modified mRNA, Cell Stem Cell, Nov. 5, 2010, 7, 13 pages.
Andries et al., "N(1)-methylpseudouridine-incorporated mRNA outperforms pseudouridine-incorporated mRNA by providing enhanced protein expression and reduced immunogenicity in mammalian cell lines and mice," Journal of Controlled Release, 217, 2015, 337-344.
Araujo et al., "Before It Gets Started: Regulating Translation at the 5' UTR," Comparative and Functional Genomics, 2012, vol. 2012, Article ID 475731, 8 pages.
Bab, I. et al., "Biosynthesis of Osteogenic Growth Peptide via Alternative Translational Initiation at AUG85 of Histone H4 mRNA," The Journal of Biological Chemistry, vol. 274(20)(Issue of May):14474-14481 (1999).
Babendure, J.R. et al., "Control of mammalian translation by mRNA structure near caps," RNA, vol. 12(5):851-861 (2006).
Hann, S. et al., "The alternatively initiated c-Myc proteins differentially regulate transcription through a noncanonical DNA-binding site," Genes & Development, vol. 8:2441-2452 (1994).
Hinnebusch et al. "Translational control by5'-untranslated regions of eukaryotic mRNAs," Science, 2016, 352, 6292, 1413-1416.
International Preliminary Report on Patentability for International Application No. PCT/US2020/039365 mailed Dec. 28, 2021, 7 pages.
International Preliminary Report on Patentability, PCT/US2018/033519, dated Nov. 19, 2019, 8 pages.
International Preliminary Report on Patentability, PCT/US2019/027089, dated Oct. 13, 2020, 12 pages.
International Search Report and Written Opinion, PCT/US2018/033519, dated Sep. 11, 2018, 13 pages.
International Search Report and Written Opinion, PCT/US2019/027089, dated Oct. 2, 2019, 20 pages.
Katayama S et al, "Antisense Transcription in the Mammalian Transcriptome" Science, American Association for the Advancement of Science. vol. 309.(5740), Sep. 2005, pp. 1564-1566.
Kozak, M., "Downstream secondary structure facilitates recognition of initiator codons by eukaryotic ribosomes," Proc. Nail. Acad. Sci., vol. 87:8301-8305 (1990).
Kozak, M. et al., "At least six nucleotides preceding the AUG initiator codon enhance translation in mammalian cells," Journal of Molecular Biology, vol. 196(4):947-950 (1987).
Kozak, M., "Influences of mRNA secondary structure on initiation by eukaryotic ribosomes," Proc. Nat. Acad. Sci., vol. 83: 2850-2854 (1986).
Kozak, M., "Recognition of AUG and alternative initiator codons is augmented by G in position +4 but is not generally affected by the nucleotides in positions +5 and +6," The EMBO Journal, vol. 16(9):2482-2492 (1997).
Kulendra, K. et al., "Elucidating the Role of Alternative RNA Export Promoting Signal Sequence Coding Regions in Potentiating Translation," A thesis submitted in conformity with the requirements for the degree of Doctor of Philosophy Graduate Department of Biochemistry University of Toronto, 197 pages (2016).
Pardi et al., "Expression kinetics of nucleoside-modified mRNA delivered in lipid nanoparticles to mice by various routes," Journal of Controlled Release, 217, 2015, 345-351.
Robbins-Pianka, A. et al., "The mRNA landscape at yeast translation initiation sites," Bioinformatics, vol. 26(21):2651-2655 (2010).
Sakai et al., "Human galactocerebrosidase gene: promoter analysis of the 5'-flanking, region and structural organization," Biochimica et Biophysica Acta 1395 (1998) 62-67.
Somers, J. et al., "A perspective on mammalian upstream open reading frame function," International Journal of Biochemistry and Cell Biology, vol. 45(8):1690-1700 (2013).
Toribio, R. et al., "New insights into the topology of the scanning ribosome during translation initiation: Lessons from viruses," RNA Biology, vol. 13(12) 1223-1227 (2016).
Tyurin A. et al., "Efficient expression of a heterologous gene in plants depends on the nucleotide composition of mRNA's 5'-region," Russian Journal of Plant Physiology, vol. 63(4):511-522(2016).
Yabe-Wada, T. et al., "TLR signals posttranscriptionally regulate the cytokine trafficking mediator sortilin," Scientific Report, vol. 6(1): 14 pages (2016).

\* cited by examiner

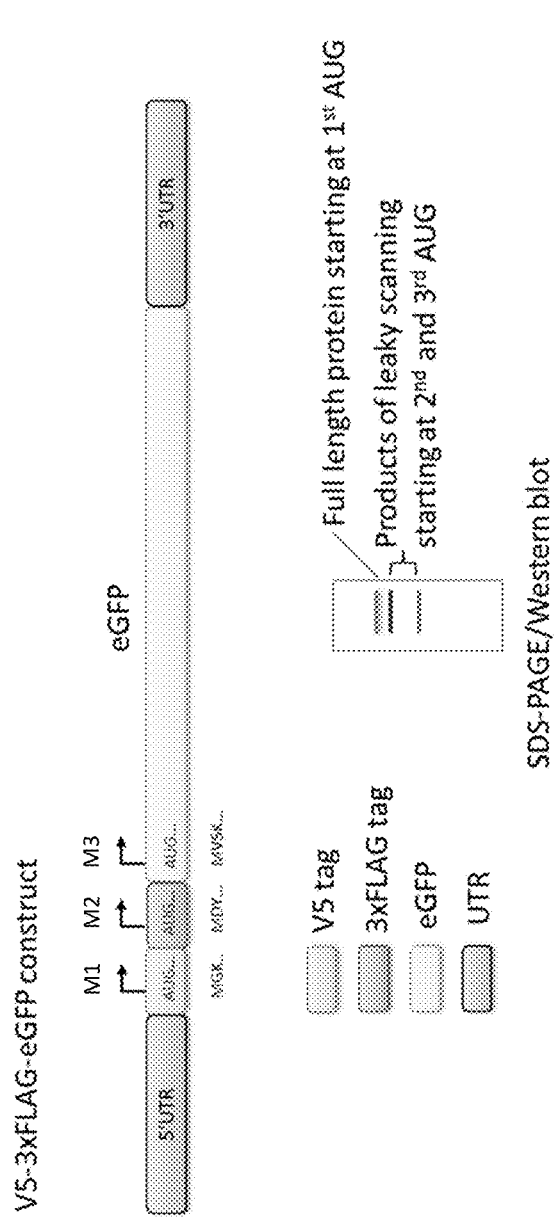

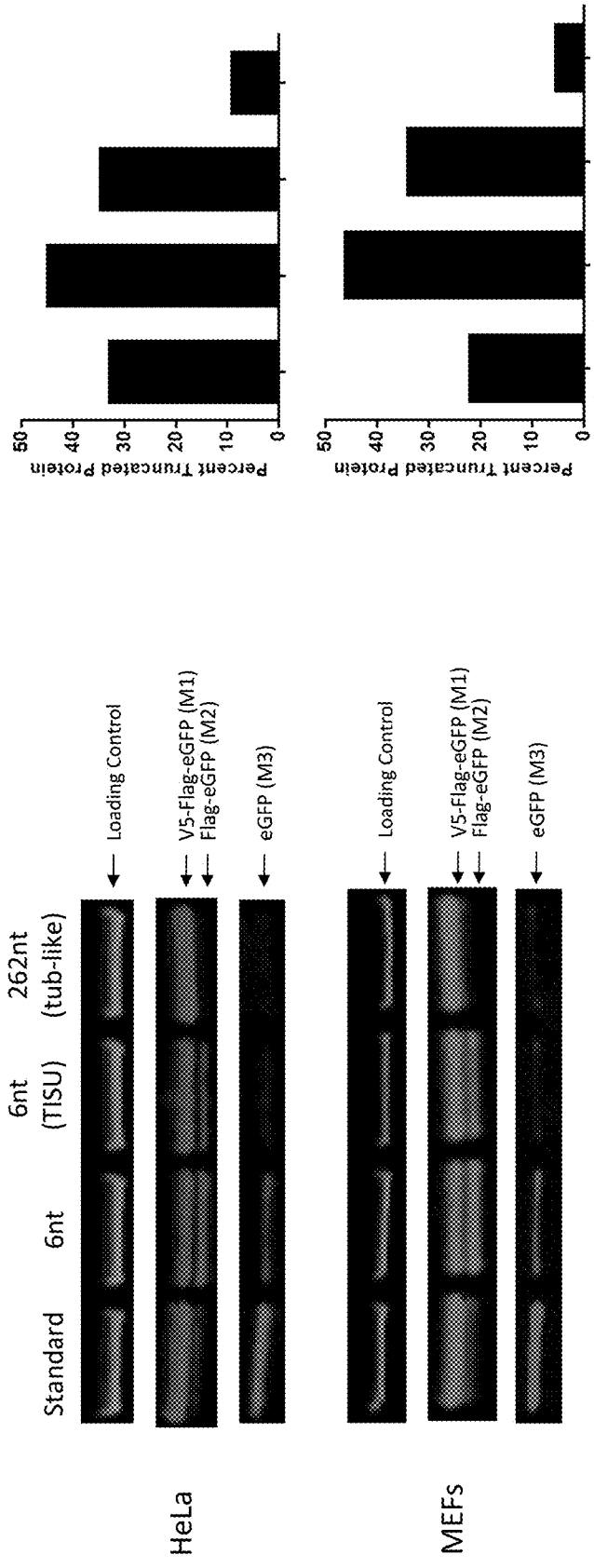
Figure 2A
Figure 2B
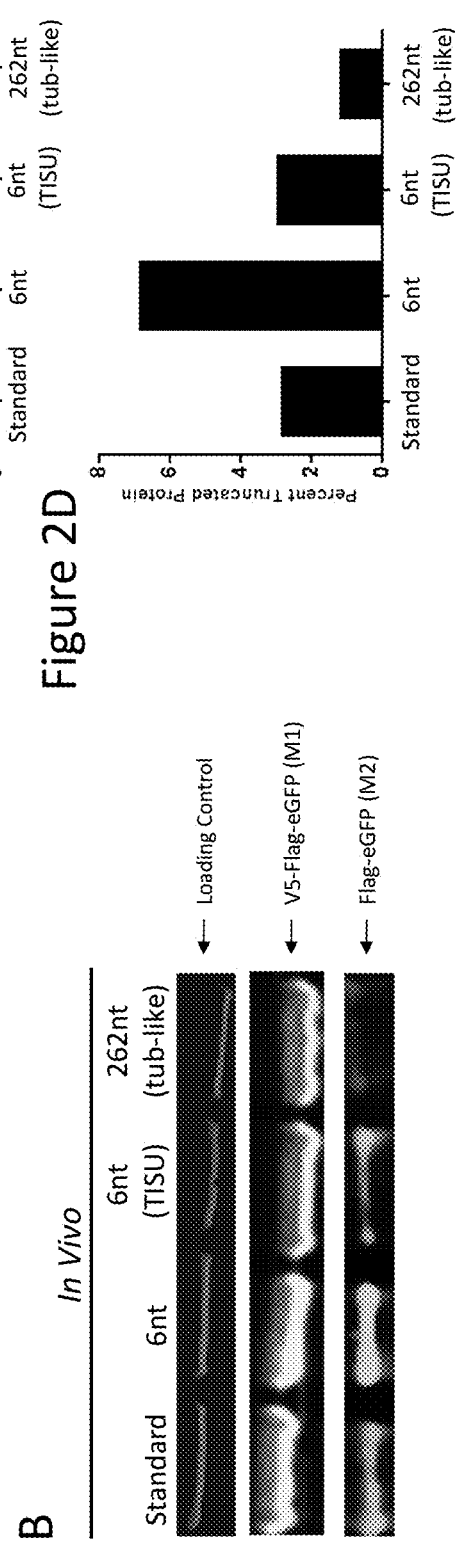
Figure 2C
Figure 2D

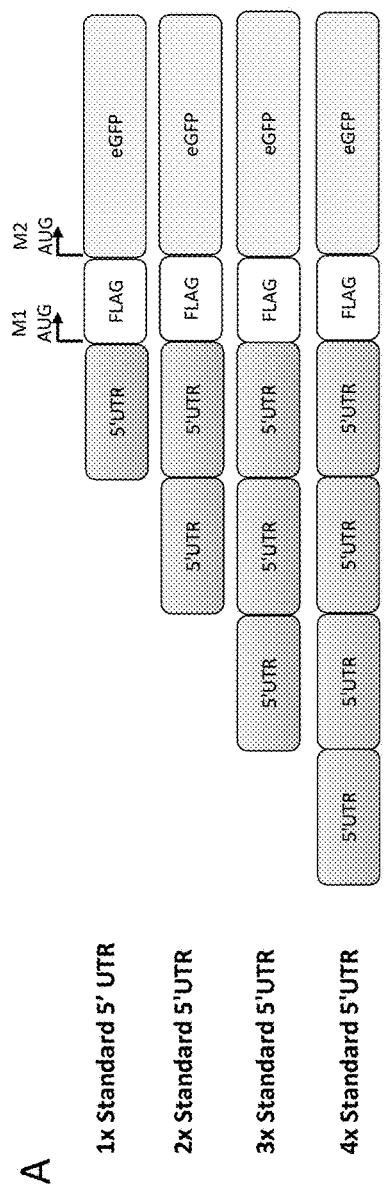
Figure 3A
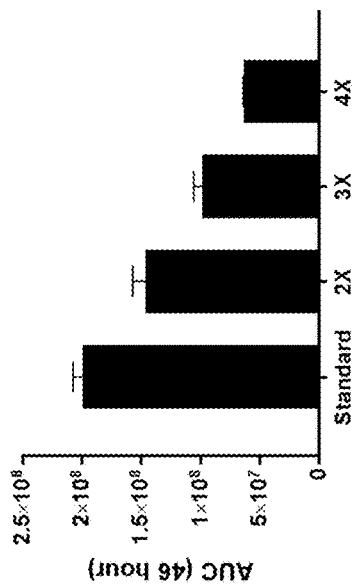
Figure 3D
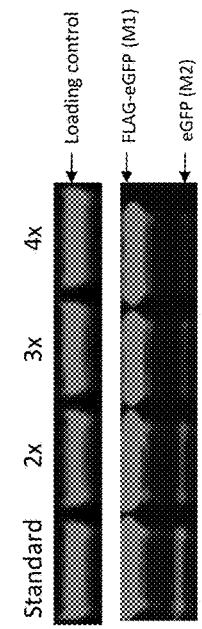
Figure 3C
Figure 3B

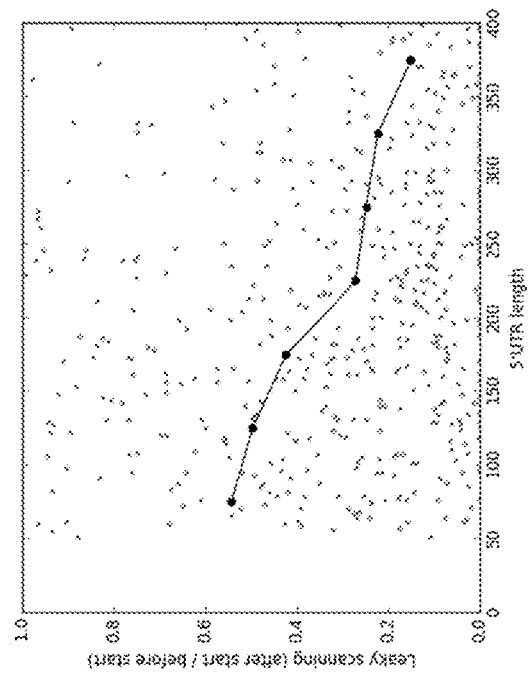
Figure 4A  HeLa
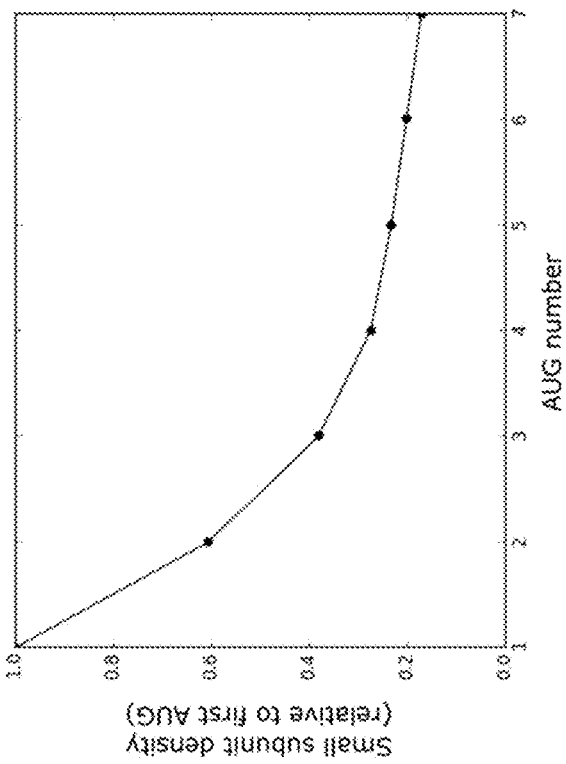
Figure 4B  Hepatocytes

Figure 8A

| # | 5'UTR | 5'UTR Sequence | % Cytosine of GC-Rich RNA Element |
|---|---|---|---|
| 1 | Standard | GGGAAATAAGAGAGAAAAGAAGAGTAAGAAGAAATATAAGAGCCACC | 0% |
| 2 | V1-UTR | GGGAAATAAGAGAGAAAAGAAGAGTAAGAAGAAATATAAGACCCCGGCGCCGCCACC | 70% |
| 3 | GC Scramble #1-UTR | GGGAAATAAGAGAGAAAAGAAGAGTAAGAAGAAATATAAGAGGGGCCCGGCGCCACC | 40% |
| 4 | GC Scramble #2-UTR | GGGAAATAAGAGAGAAAAGAAGAGTAAGAAGAAATATAAGAGCCCGCCCGCGCCACC | 70% |
| 5 | GC Scramble #3-UTR | GGGAAATAAGAGAGAAAAGAAGAGTAAGAAGAAATATAAGAGCGCCCCGCGGCCACC | 60% |
| 6 | GC1-UTR | GGGAAATAAGAGAGAAAAGAAGAGTAAGAAGAAATATAAGAGCGCCCCGGCGCCCGGCCACC | 60% |

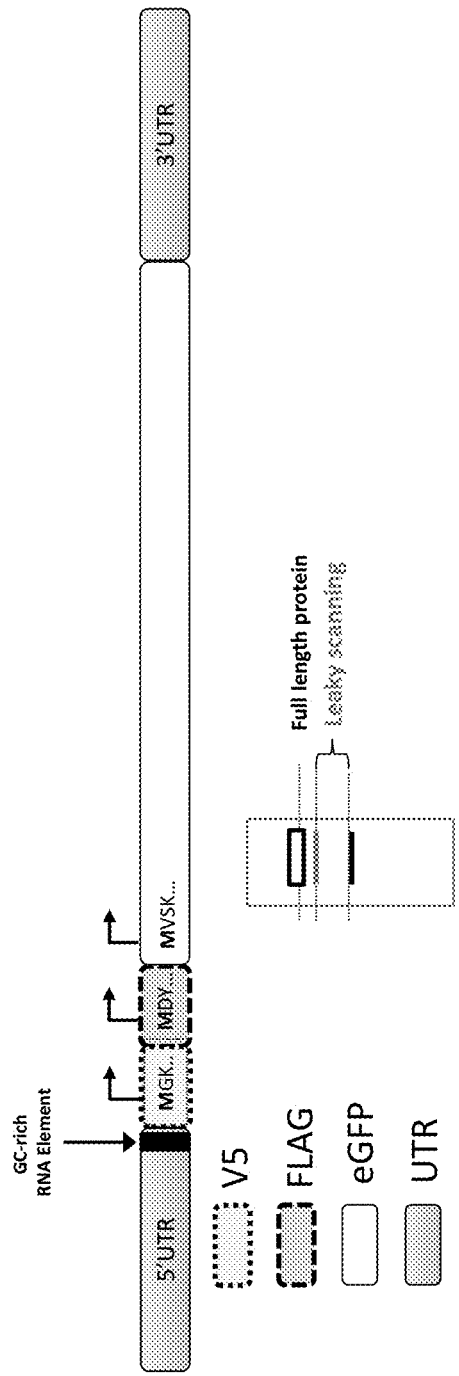

Figure 8B

SEQUENCE LISTING

```
Sequence total quantity: 535
SEQ ID NO: 1              moltype =   length =
SEQUENCE: 1
000

SEQ ID NO: 2              moltype = RNA   length = 10
FEATURE                   Location/Qualifiers
misc_feature              1..10
                          note = V1
source                    1..10
                          mol_type = other RNA
                          organism = synthetic construct
SEQUENCE: 2
ccccggcgcc                                                                    10
```

-continued

```
SEQ ID NO: 3              moltype =    length =
SEQUENCE: 3
000

SEQ ID NO: 4              moltype = RNA   length = 20
FEATURE                   Location/Qualifiers
misc_feature              1..20
                          note = CG1
source                    1..20
                          mol_type = other RNA
                          organism = synthetic construct
SEQUENCE: 4
gcgccccgcg gcgccccgcg                                                  20

SEQ ID NO: 5              moltype = RNA   length = 20
FEATURE                   Location/Qualifiers
misc_feature              1..20
                          note = CG2
source                    1..20
                          mol_type = other RNA
                          organism = synthetic construct
SEQUENCE: 5
cccgcccgcc ccgcccgcc                                                   20

SEQ ID NO: 6              moltype = RNA   length = 10
FEATURE                   Location/Qualifiers
misc_feature              1..10
                          note = GC Scramble #1
source                    1..10
                          mol_type = other RNA
                          organism = synthetic construct
SEQUENCE: 6
ggggcgcccg                                                             10

SEQ ID NO: 7              moltype = RNA   length = 10
FEATURE                   Location/Qualifiers
misc_feature              1..10
                          note = GC Scramble #2
source                    1..10
                          mol_type = other RNA
                          organism = synthetic construct
SEQUENCE: 7
gcccgcccgc                                                             10

SEQ ID NO: 8              moltype = RNA   length = 10
FEATURE                   Location/Qualifiers
misc_feature              1..10
                          note = GC Scramble #3
source                    1..10
                          mol_type = other RNA
                          organism = synthetic construct
SEQUENCE: 8
gcgccccgcg                                                             10

SEQ ID NO: 9              moltype =    length =
SEQUENCE: 9
000

SEQ ID NO: 10             moltype =    length =
SEQUENCE: 10
000

SEQ ID NO: 11             moltype =    length =
SEQUENCE: 11
000

SEQ ID NO: 12             moltype =    length =
SEQUENCE: 12
000

SEQ ID NO: 13             moltype = RNA   length = 12
FEATURE                   Location/Qualifiers
misc_feature              1..12
                          note = (CCG)4
source                    1..12
                          mol_type = other RNA
                          organism = synthetic construct
SEQUENCE: 13
```

```
ccgccgccgc cg                                                              12

SEQ ID NO: 14           moltype = RNA   length = 15
FEATURE                 Location/Qualifiers
misc_feature            1..15
                        note = (CCG)5
source                  1..15
                        mol_type = other RNA
                        organism = synthetic construct
SEQUENCE: 14
ccgccgccgc cgccg                                                           15

SEQ ID NO: 15           moltype = RNA   length = 18
FEATURE                 Location/Qualifiers
misc_feature            1..18
                        note = (CCG)6
source                  1..18
                        mol_type = other RNA
                        organism = synthetic construct
SEQUENCE: 15
ccgccgccgc cgccgccg                                                        18

SEQ ID NO: 16           moltype = RNA   length = 21
FEATURE                 Location/Qualifiers
misc_feature            1..21
                        note = (CCG)7
source                  1..21
                        mol_type = other RNA
                        organism = synthetic construct
SEQUENCE: 16
ccgccgccgc cgccgccgcc g                                                    21

SEQ ID NO: 17           moltype = RNA   length = 24
FEATURE                 Location/Qualifiers
misc_feature            1..24
                        note = (CCG)8
source                  1..24
                        mol_type = other RNA
                        organism = synthetic construct
SEQUENCE: 17
ccgccgccgc cgccgccgcc gccg                                                 24

SEQ ID NO: 18           moltype = RNA   length = 27
FEATURE                 Location/Qualifiers
misc_feature            1..27
                        note = (CCG)9
source                  1..27
                        mol_type = other RNA
                        organism = synthetic construct
SEQUENCE: 18
ccgccgccgc cgccgccgcc gccgccg                                              27

SEQ ID NO: 19           moltype = RNA   length = 30
FEATURE                 Location/Qualifiers
misc_feature            1..30
                        note = (CCG)10
source                  1..30
                        mol_type = other RNA
                        organism = synthetic construct
SEQUENCE: 19
ccgccgccgc cgccgccgcc gccgccgccg                                           30

SEQ ID NO: 20           moltype =    length =
SEQUENCE: 20
000

SEQ ID NO: 21           moltype = RNA   length = 12
FEATURE                 Location/Qualifiers
misc_feature            1..12
                        note = (GCC)4
source                  1..12
                        mol_type = other RNA
                        organism = synthetic construct
SEQUENCE: 21
gccgccgccg cc                                                              12

SEQ ID NO: 22           moltype = RNA   length = 15
FEATURE                 Location/Qualifiers
misc_feature            1..15
```

```
                        note = (GCC)5
source                  1..15
                        mol_type = other RNA
                        organism = synthetic construct
SEQUENCE: 22
gccgccgccg ccgcc                                                          15

SEQ ID NO: 23           moltype = RNA   length = 18
FEATURE                 Location/Qualifiers
misc_feature            1..18
                        note = (GCC)6
source                  1..18
                        mol_type = other RNA
                        organism = synthetic construct
SEQUENCE: 23
gccgccgccg ccgccgcc                                                       18

SEQ ID NO: 24           moltype = RNA   length = 21
FEATURE                 Location/Qualifiers
misc_feature            1..21
                        note = (GCC)7
source                  1..21
                        mol_type = other RNA
                        organism = synthetic construct
SEQUENCE: 24
gccgccgccg ccgccgccgc c                                                   21

SEQ ID NO: 25           moltype = RNA   length = 24
FEATURE                 Location/Qualifiers
misc_feature            1..24
                        note = (GCC)8
source                  1..24
                        mol_type = other RNA
                        organism = synthetic construct
SEQUENCE: 25
gccgccgccg ccgccgccgc cgcc                                                24

SEQ ID NO: 26           moltype = RNA   length = 27
FEATURE                 Location/Qualifiers
misc_feature            1..27
                        note = (GCC)9
source                  1..27
                        mol_type = other RNA
                        organism = synthetic construct
SEQUENCE: 26
gccgccgccg ccgccgccgc cgccgcc                                             27

SEQ ID NO: 27           moltype = RNA   length = 30
FEATURE                 Location/Qualifiers
misc_feature            1..30
                        note = (GCC)10
source                  1..30
                        mol_type = other RNA
                        organism = synthetic construct
SEQUENCE: 27
gccgccgccg ccgccgccgc cgccgccgcc                                          30

SEQ ID NO: 28           moltype = RNA   length = 16
FEATURE                 Location/Qualifiers
misc_feature            1..16
                        note = SL1
source                  1..16
                        mol_type = other RNA
                        organism = synthetic construct
SEQUENCE: 28
ccgcggcgcc ccgcgg                                                         16

SEQ ID NO: 29           moltype = RNA   length = 17
FEATURE                 Location/Qualifiers
misc_feature            1..17
                        note = SL2
source                  1..17
                        mol_type = other RNA
                        organism = synthetic construct
SEQUENCE: 29
gcgcgcatat agcgcgc                                                        17

SEQ ID NO: 30           moltype = RNA   length = 26
FEATURE                 Location/Qualifiers
```

```
misc_feature           1..26
                       note = SL3
source                 1..26
                       mol_type = other RNA
                       organism = synthetic construct
SEQUENCE: 30
catggtggcg gcccgccgcc accatg                                         26

SEQ ID NO: 31          moltype = RNA  length = 23
FEATURE                Location/Qualifiers
misc_feature           1..23
                       note = SL4
source                 1..23
                       mol_type = other RNA
                       organism = synthetic construct
SEQUENCE: 31
catggtggcc cgccgccacc atg                                            23

SEQ ID NO: 32          moltype = RNA  length = 22
FEATURE                Location/Qualifiers
misc_feature           1..22
                       note = SL5
source                 1..22
                       mol_type = other RNA
                       organism = synthetic construct
SEQUENCE: 32
catggtgccc gccgccacca tg                                             22

SEQ ID NO: 33          moltype = RNA  length = 47
FEATURE                Location/Qualifiers
misc_feature           1..47
                       note = Standard UTR
source                 1..47
                       mol_type = other RNA
                       organism = synthetic construct
SEQUENCE: 33
gggaaataag agagaaaaga agagtaagaa gaaatataag agccacc                  47

SEQ ID NO: 34          moltype = RNA  length = 57
FEATURE                Location/Qualifiers
misc_feature           1..57
                       note = V1-UTR
source                 1..57
                       mol_type = other RNA
                       organism = synthetic construct
SEQUENCE: 34
gggaaataag agagaaaaga agagtaagaa gaaatataag accccggcgc cgccacc       57

SEQ ID NO: 35          moltype = RNA  length = 57
FEATURE                Location/Qualifiers
misc_feature           1..57
                       note = V1-1-UTR
source                 1..57
                       mol_type = other RNA
                       organism = synthetic construct
SEQUENCE: 35
gggaaataag agagaaaaga agagtaagaa gaaatataag ccccggcgcc agccacc       57

SEQ ID NO: 36          moltype = RNA  length = 57
FEATURE                Location/Qualifiers
misc_feature           1..57
                       note = V1-2-UTR
source                 1..57
                       mol_type = other RNA
                       organism = synthetic construct
SEQUENCE: 36
gggaaataag agagaaaaga agagtaagaa gaaatataac cccggcgccg agccacc       57

SEQ ID NO: 37          moltype = RNA  length = 57
FEATURE                Location/Qualifiers
misc_feature           1..57
                       note = V1-3-UTR
source                 1..57
                       mol_type = other RNA
                       organism = synthetic construct
SEQUENCE: 37
gggaaataag agagaaaaga agagtaagaa gaaatatacc ccggcgccag agccacc       57

SEQ ID NO: 38          moltype = RNA  length = 57
```

```
FEATURE                 Location/Qualifiers
misc_feature            1..57
                        note = V1-4-UTR
source                  1..57
                        mol_type = other RNA
                        organism = synthetic construct
SEQUENCE: 38
gggaaataag agagaaaaga agagtaagaa gaaatatccc cggcgccaag agccacc         57

SEQ ID NO: 39           moltype = RNA  length = 57
FEATURE                 Location/Qualifiers
misc_feature            1..57
                        note = V1-5-UTR
source                  1..57
                        mol_type = other RNA
                        organism = synthetic construct
SEQUENCE: 39
gggaaataag agagaaaaga agagtaagaa gaaataccccc ggcgcctaag agccacc        57

SEQ ID NO: 40           moltype = RNA  length = 57
FEATURE                 Location/Qualifiers
misc_feature            1..57
                        note = V1-6-UTR
source                  1..57
                        mol_type = other RNA
                        organism = synthetic construct
SEQUENCE: 40
gggaaataag agagaaaaga agagtaagaa gaaatccccg gcgccataag agccacc         57

SEQ ID NO: 41           moltype = RNA  length = 57
FEATURE                 Location/Qualifiers
misc_feature            1..57
                        note = V1-7-UTR
source                  1..57
                        mol_type = other RNA
                        organism = synthetic construct
SEQUENCE: 41
gggaaataag agagaaaaga agagtaagaa gaaaccccgg cgcctataag agccacc         57

SEQ ID NO: 42           moltype = RNA  length = 57
FEATURE                 Location/Qualifiers
misc_feature            1..57
                        note = V1-8-UTR
source                  1..57
                        mol_type = other RNA
                        organism = synthetic construct
SEQUENCE: 42
gggaaataag agagaaaaga agagtaagaa gaaccccggc gccatataag agccacc         57

SEQ ID NO: 43           moltype = RNA  length = 57
FEATURE                 Location/Qualifiers
misc_feature            1..57
                        note = V1-9-UTR
source                  1..57
                        mol_type = other RNA
                        organism = synthetic construct
SEQUENCE: 43
gggaaataag agagaaaaga agagtaagaa gaccccggcg ccaatataag agccacc         57

SEQ ID NO: 44           moltype = RNA  length = 57
FEATURE                 Location/Qualifiers
misc_feature            1..57
                        note = V1-10-UTR
source                  1..57
                        mol_type = other RNA
                        organism = synthetic construct
SEQUENCE: 44
gggaaataag agagaaaaga agagtaagaa gccccggcgc caaatataag agccacc         57

SEQ ID NO: 45           moltype = RNA  length = 57
FEATURE                 Location/Qualifiers
misc_feature            1..57
                        note = V1-11-UTR
source                  1..57
                        mol_type = other RNA
                        organism = synthetic construct
SEQUENCE: 45
gggaaataag agagaaaaga agagtaagaa ccccggcgcc gaaatataag agccacc         57
```

```
SEQ ID NO: 46          moltype = RNA   length = 57
FEATURE                Location/Qualifiers
misc_feature           1..57
                       note = V1-12-UTR
source                 1..57
                       mol_type = other RNA
                       organism = synthetic construct
SEQUENCE: 46
gggaaataag agagaaaaga agagtaagac cccggcgcca gaaatataag agccacc         57

SEQ ID NO: 47          moltype = RNA   length = 57
FEATURE                Location/Qualifiers
misc_feature           1..57
                       note = V1-13-UTR
source                 1..57
                       mol_type = other RNA
                       organism = synthetic construct
SEQUENCE: 47
gggaaataag agagaaaaga agagtaagcc ccggcgccaa gaaatataag agccacc         57

SEQ ID NO: 48          moltype = RNA   length = 57
FEATURE                Location/Qualifiers
misc_feature           1..57
                       note = V1-14-UTR
source                 1..57
                       mol_type = other RNA
                       organism = synthetic construct
SEQUENCE: 48
gggaaataag agagaaaaga agagtaaccc cggcgccgaa gaaatataag agccacc         57

SEQ ID NO: 49          moltype = RNA   length = 57
FEATURE                Location/Qualifiers
misc_feature           1..57
                       note = V1-15-UTR
source                 1..57
                       mol_type = other RNA
                       organism = synthetic construct
SEQUENCE: 49
gggaaataag agagaaaaga agagtacccc ggcgccagaa gaaatataag agccacc         57

SEQ ID NO: 50          moltype = RNA   length = 57
FEATURE                Location/Qualifiers
misc_feature           1..57
                       note = V1-16-UTR
source                 1..57
                       mol_type = other RNA
                       organism = synthetic construct
SEQUENCE: 50
gggaaataag agagaaaaga agagtccccg gcgccaagaa gaaatataag agccacc         57

SEQ ID NO: 51          moltype = RNA   length = 57
FEATURE                Location/Qualifiers
misc_feature           1..57
                       note = V1-17-UTR
source                 1..57
                       mol_type = other RNA
                       organism = synthetic construct
SEQUENCE: 51
gggaaataag agagaaaaga agagccccgg cgcctaagaa gaaatataag agccacc         57

SEQ ID NO: 52          moltype = RNA   length = 57
FEATURE                Location/Qualifiers
misc_feature           1..57
                       note = V3-UTR
source                 1..57
                       mol_type = other RNA
                       organism = synthetic construct
SEQUENCE: 52
gggaaataag agagaaaaga agaccccggc gccgtaagaa gaaatataag agccacc         57

SEQ ID NO: 53          moltype = RNA   length = 57
FEATURE                Location/Qualifiers
misc_feature           1..57
                       note = V4-UTR
source                 1..57
                       mol_type = other RNA
                       organism = synthetic construct
SEQUENCE: 53
gggccccggc gccaaataag agagaaaaga agagtaagaa gaaatataag agccacc         57
```

```
SEQ ID NO: 54          moltype = RNA   length = 54
FEATURE                Location/Qualifiers
misc_feature           1..54
                       note = V2-UTR
source                 1..54
                       mol_type = other RNA
                       organism = synthetic construct
SEQUENCE: 54
gggaaataag agagaaaaga agagtaagaa gaaatataag accccggcgc cacc        54

SEQ ID NO: 55          moltype = RNA   length = 54
FEATURE                Location/Qualifiers
misc_feature           1..54
                       note = V2-1-UTR
source                 1..54
                       mol_type = other RNA
                       organism = synthetic construct
SEQUENCE: 55
gggaaataag agagaaaaga agagtaagaa gaaatataag ccccggcagc cacc        54

SEQ ID NO: 56          moltype = RNA   length = 54
FEATURE                Location/Qualifiers
misc_feature           1..54
                       note = V2-2-UTR
source                 1..54
                       mol_type = other RNA
                       organism = synthetic construct
SEQUENCE: 56
gggaaataag agagaaaaga agagtaagaa gaaatataac cccggcgagc cacc        54

SEQ ID NO: 57          moltype = RNA   length = 54
FEATURE                Location/Qualifiers
misc_feature           1..54
                       note = V2-3-UTR
source                 1..54
                       mol_type = other RNA
                       organism = synthetic construct
SEQUENCE: 57
gggaaataag agagaaaaga agagtaagaa gaaatatacc ccggcagagc cacc        54

SEQ ID NO: 58          moltype = RNA   length = 54
FEATURE                Location/Qualifiers
misc_feature           1..54
                       note = V2-4-UTR
source                 1..54
                       mol_type = other RNA
                       organism = synthetic construct
SEQUENCE: 58
gggaaataag agagaaaaga agagtaagaa gaaatatccc cggcaagagc cacc        54

SEQ ID NO: 59          moltype = RNA   length = 54
FEATURE                Location/Qualifiers
misc_feature           1..54
                       note = V2-5-UTR
source                 1..54
                       mol_type = other RNA
                       organism = synthetic construct
SEQUENCE: 59
gggaaataag agagaaaaga agagtaagaa gaaataccccc ggctaagagc cacc       54

SEQ ID NO: 60          moltype = RNA   length = 54
FEATURE                Location/Qualifiers
misc_feature           1..54
                       note = V2-6-UTR
source                 1..54
                       mol_type = other RNA
                       organism = synthetic construct
SEQUENCE: 60
gggaaataag agagaaaaga agagtaagaa gaaatccccg gcataagagc cacc        54

SEQ ID NO: 61          moltype = RNA   length = 54
FEATURE                Location/Qualifiers
misc_feature           1..54
                       note = V2-7-UTR
source                 1..54
                       mol_type = other RNA
                       organism = synthetic construct
SEQUENCE: 61
```

```
gggaaataag agagaaaaga agagtaagaa gaaaccccgg ctataagagc cacc            54

SEQ ID NO: 62           moltype = RNA   length = 54
FEATURE                 Location/Qualifiers
misc_feature            1..54
                        note = V2-8-UTR
source                  1..54
                        mol_type = other RNA
                        organism = synthetic construct
SEQUENCE: 62
gggaaataag agagaaaaga agagtaagaa gaaccccggc atataagagc cacc            54

SEQ ID NO: 63           moltype = RNA   length = 54
FEATURE                 Location/Qualifiers
misc_feature            1..54
                        note = V2-9-UTR
source                  1..54
                        mol_type = other RNA
                        organism = synthetic construct
SEQUENCE: 63
gggaaataag agagaaaaga agagtaagaa gaccccggca atataagagc cacc            54

SEQ ID NO: 64           moltype = RNA   length = 54
FEATURE                 Location/Qualifiers
misc_feature            1..54
                        note = V2-10-UTR
source                  1..54
                        mol_type = other RNA
                        organism = synthetic construct
SEQUENCE: 64
gggaaataag agagaaaaga agagtaagaa gccccggcaa atataagagc cacc            54

SEQ ID NO: 65           moltype = RNA   length = 54
FEATURE                 Location/Qualifiers
misc_feature            1..54
                        note = V2-11-UTR
source                  1..54
                        mol_type = other RNA
                        organism = synthetic construct
SEQUENCE: 65
gggaaataag agagaaaaga agagtaagaa ccccggcgaa atataagagc cacc            54

SEQ ID NO: 66           moltype = RNA   length = 54
FEATURE                 Location/Qualifiers
misc_feature            1..54
                        note = V2-12-UTR
source                  1..54
                        mol_type = other RNA
                        organism = synthetic construct
SEQUENCE: 66
gggaaataag agagaaaaga agagtaagac cccggcagaa atataagagc cacc            54

SEQ ID NO: 67           moltype = RNA   length = 54
FEATURE                 Location/Qualifiers
misc_feature            1..54
                        note = V2-13-UTR
source                  1..54
                        mol_type = other RNA
                        organism = synthetic construct
SEQUENCE: 67
gggaaataag agagaaaaga agagtaagcc ccggcaagaa atataagagc cacc            54

SEQ ID NO: 68           moltype = RNA   length = 54
FEATURE                 Location/Qualifiers
misc_feature            1..54
                        note = V2-14-UTR
source                  1..54
                        mol_type = other RNA
                        organism = synthetic construct
SEQUENCE: 68
gggaaataag agagaaaaga agagtaaccc cggcgaagaa atataagagc cacc            54

SEQ ID NO: 69           moltype = RNA   length = 54
FEATURE                 Location/Qualifiers
misc_feature            1..54
                        note = V2-15-UTR
source                  1..54
                        mol_type = other RNA
                        organism = synthetic construct
```

```
SEQUENCE: 69
gggaaataag agagaaaaga agagtaccc ggcagaagaa atataagagc cacc         54

SEQ ID NO: 70            moltype = RNA   length = 54
FEATURE                  Location/Qualifiers
misc_feature             1..54
                         note = V2-16-UTR
source                   1..54
                         mol_type = other RNA
                         organism = synthetic construct
SEQUENCE: 70
gggaaataag agagaaaaga agagtccccg gcaagaagaa atataagagc cacc         54

SEQ ID NO: 71            moltype = RNA   length = 54
FEATURE                  Location/Qualifiers
misc_feature             1..54
                         note = V2-17-UTR
source                   1..54
                         mol_type = other RNA
                         organism = synthetic construct
SEQUENCE: 71
gggaaataag agagaaaaga agagcccgg ctaagaagaa atataagagc cacc          54

SEQ ID NO: 72            moltype = RNA   length = 54
FEATURE                  Location/Qualifiers
misc_feature             1..54
                         note = V2-18-UTR
source                   1..54
                         mol_type = other RNA
                         organism = synthetic construct
SEQUENCE: 72
gggaaataag agagaaaaga agaccccggc gtaagaagaa atataagagc cacc         54

SEQ ID NO: 73            moltype = RNA   length = 67
FEATURE                  Location/Qualifiers
misc_feature             1..67
                         note = CG1-UTR
source                   1..67
                         mol_type = other RNA
                         organism = synthetic construct
SEQUENCE: 73
gggaaataag agagaaaaga agagtaagaa gaaatataag agcgccccgc ggcgccccgc   60
ggccacc                                                            67

SEQ ID NO: 74            moltype = RNA   length = 67
FEATURE                  Location/Qualifiers
misc_feature             1..67
                         note = CG1-1-UTR
source                   1..67
                         mol_type = other RNA
                         organism = synthetic construct
SEQUENCE: 74
gggaaataag agagaaaaga agagtaagaa gaaatataag gcgccccgcg gcgccccgcg   60
agccacc                                                            67

SEQ ID NO: 75            moltype = RNA   length = 67
FEATURE                  Location/Qualifiers
misc_feature             1..67
                         note = CG1-2-UTR
source                   1..67
                         mol_type = other RNA
                         organism = synthetic construct
SEQUENCE: 75
gggaaataag agagaaaaga agagtaagaa gaaatataag cgccccgcgg cgccccgcgg   60
agccacc                                                            67

SEQ ID NO: 76            moltype = RNA   length = 67
FEATURE                  Location/Qualifiers
misc_feature             1..67
                         note = CG1-3-UTR
source                   1..67
                         mol_type = other RNA
                         organism = synthetic construct
SEQUENCE: 76
gggaaataag agagaaaaga agagtaagaa gaaatatagc gccccgcggc gccccgcgag   60
agccacc                                                            67

SEQ ID NO: 77            moltype = RNA   length = 67
FEATURE                  Location/Qualifiers
```

```
misc_feature            1..67
                        note = CG1-4-UTR
source                  1..67
                        mol_type = other RNA
                        organism = synthetic construct
SEQUENCE: 77
gggaaataag agagaaaaga agagtaagaa gaaatatgcg ccccgcggcg ccccgcgaag    60
agccacc                                                              67

SEQ ID NO: 78           moltype = RNA   length = 67
FEATURE                 Location/Qualifiers
misc_feature            1..67
                        note = CG1-5-UTR
source                  1..67
                        mol_type = other RNA
                        organism = synthetic construct
SEQUENCE: 78
gggaaataag agagaaaaga agagtaagaa gaaatagcgc cccgcggcgc ccgcgtaag     60
agccacc                                                              67

SEQ ID NO: 79           moltype = RNA   length = 67
FEATURE                 Location/Qualifiers
misc_feature            1..67
                        note = CG1-6-UTR
source                  1..67
                        mol_type = other RNA
                        organism = synthetic construct
SEQUENCE: 79
gggaaataag agagaaaaga agagtaagaa gaaatgcgcc ccgcggcgcc ccgcgataag    60
agccacc                                                              67

SEQ ID NO: 80           moltype = RNA   length = 67
FEATURE                 Location/Qualifiers
misc_feature            1..67
                        note = CG1-7-UTR
source                  1..67
                        mol_type = other RNA
                        organism = synthetic construct
SEQUENCE: 80
gggaaataag agagaaaaga agagtaagaa gaaagcgccc cgcggcgccc cgcgtataag    60
agccacc                                                              67

SEQ ID NO: 81           moltype = RNA   length = 67
FEATURE                 Location/Qualifiers
misc_feature            1..67
                        note = CG1-8-UTR
source                  1..67
                        mol_type = other RNA
                        organism = synthetic construct
SEQUENCE: 81
gggaaataag agagaaaaga agagtaagaa gaagcgcccc gcggcgcccc gcgatataag    60
agccacc                                                              67

SEQ ID NO: 82           moltype = RNA   length = 67
FEATURE                 Location/Qualifiers
misc_feature            1..67
                        note = CG1-9-UTR
source                  1..67
                        mol_type = other RNA
                        organism = synthetic construct
SEQUENCE: 82
gggaaataag agagaaaaga agagtaagaa gagcgccccg cggcgccccg cgaatataag    60
agccacc                                                              67

SEQ ID NO: 83           moltype = RNA   length = 67
FEATURE                 Location/Qualifiers
misc_feature            1..67
                        note = CG1-10-UTR
source                  1..67
                        mol_type = other RNA
                        organism = synthetic construct
SEQUENCE: 83
gggaaataag agagaaaaga agagtaagaa ggcgccccgc ggcgccccgc gaaatataag    60
agccacc                                                              67

SEQ ID NO: 84           moltype = RNA   length = 67
FEATURE                 Location/Qualifiers
misc_feature            1..67
                        note = CG1-11-UTR
```

```
source                  1..67
                        mol_type = other RNA
                        organism = synthetic construct
SEQUENCE: 84
gggaaataag agagaaaaga agagtaagaa gcgccccgcg gcgccccgcg gaaatataag   60
agccacc                                                             67

SEQ ID NO: 85           moltype = RNA   length = 67
FEATURE                 Location/Qualifiers
misc_feature            1..67
                        note = CG1-12-UTR
source                  1..67
                        mol_type = other RNA
                        organism = synthetic construct
SEQUENCE: 85
gggaaataag agagaaaaga agagtaagag cgccccgcgg cgccccgcga gaaatataag   60
agccacc                                                             67

SEQ ID NO: 86           moltype = RNA   length = 67
FEATURE                 Location/Qualifiers
misc_feature            1..67
                        note = CG1-13-UTR
source                  1..67
                        mol_type = other RNA
                        organism = synthetic construct
SEQUENCE: 86
gggaaataag agagaaaaga agagtaaggc gccccgcggc gccccgcgaa gaaatataag   60
agccacc                                                             67

SEQ ID NO: 87           moltype = RNA   length = 67
FEATURE                 Location/Qualifiers
misc_feature            1..67
                        note = CG1-14-UTR
source                  1..67
                        mol_type = other RNA
                        organism = synthetic construct
SEQUENCE: 87
gggaaataag agagaaaaga agagtaagcg ccccgcggcg ccccgcggaa gaaatataag   60
agccacc                                                             67

SEQ ID NO: 88           moltype = RNA   length = 67
FEATURE                 Location/Qualifiers
misc_feature            1..67
                        note = CG1-15-UTR
source                  1..67
                        mol_type = other RNA
                        organism = synthetic construct
SEQUENCE: 88
gggaaataag agagaaaaga agagtagcgc cccgcggcgc cccgcgagaa gaaatataag   60
agccacc                                                             67

SEQ ID NO: 89           moltype = RNA   length = 67
FEATURE                 Location/Qualifiers
misc_feature            1..67
                        note = CG1-16-UTR
source                  1..67
                        mol_type = other RNA
                        organism = synthetic construct
SEQUENCE: 89
gggaaataag agagaaaaga agagtgcgcc ccgcggcgcc ccgcgaagaa gaaatataag   60
agccacc                                                             67

SEQ ID NO: 90           moltype = RNA   length = 67
FEATURE                 Location/Qualifiers
misc_feature            1..67
                        note = CG1-17-UTR
source                  1..67
                        mol_type = other RNA
                        organism = synthetic construct
SEQUENCE: 90
gggaaataag agagaaaaga agaggcgccc cgcggcgccc cgcgtaagaa gaaatataag   60
agccacc                                                             67

SEQ ID NO: 91           moltype = RNA   length = 67
FEATURE                 Location/Qualifiers
misc_feature            1..67
                        note = CG1-18-UTR
source                  1..67
                        mol_type = other RNA
```

```
                          organism = synthetic construct
SEQUENCE: 91
gggaaataag agagaaaaga agagcgcccc gcggcgcccc gcggtaagaa gaaatataag    60
agccacc                                                              67

SEQ ID NO: 92             moltype = RNA   length = 67
FEATURE                   Location/Qualifiers
misc_feature              1..67
                          note = CG2-UTR
source                    1..67
                          mol_type = other RNA
                          organism = synthetic construct
SEQUENCE: 92
gggaaataag agagaaaaga agagtaagaa gaaatataag acccgcccgc cccgccccgc    60
cgccacc                                                              67

SEQ ID NO: 93             moltype = RNA   length = 67
FEATURE                   Location/Qualifiers
misc_feature              1..67
                          note = CG2-1-UTR
source                    1..67
                          mol_type = other RNA
                          organism = synthetic construct
SEQUENCE: 93
gggaaataag agagaaaaga agagtaagaa gaaatataag cccgcccgcc ccgccccgcc    60
agccacc                                                              67

SEQ ID NO: 94             moltype = RNA   length = 67
FEATURE                   Location/Qualifiers
misc_feature              1..67
                          note = CG2-2-UTR
source                    1..67
                          mol_type = other RNA
                          organism = synthetic construct
SEQUENCE: 94
gggaaataag agagaaaaga agagtaagaa gaaatataac ccgcccgccc cgccccgccg    60
agccacc                                                              67

SEQ ID NO: 95             moltype = RNA   length = 67
FEATURE                   Location/Qualifiers
misc_feature              1..67
                          note = CG2-3-UTR
source                    1..67
                          mol_type = other RNA
                          organism = synthetic construct
SEQUENCE: 95
gggaaataag agagaaaaga agagtaagaa gaaatatacc cgcccgcccc gccccgccag    60
agccacc                                                              67

SEQ ID NO: 96             moltype = RNA   length = 67
FEATURE                   Location/Qualifiers
misc_feature              1..67
                          note = CG2-4-UTR
source                    1..67
                          mol_type = other RNA
                          organism = synthetic construct
SEQUENCE: 96
gggaaataag agagaaaaga agagtaagaa gaaatatccc gcccgccccg ccccgccaag    60
agccacc                                                              67

SEQ ID NO: 97             moltype = RNA   length = 67
FEATURE                   Location/Qualifiers
misc_feature              1..67
                          note = CG2-5-UTR
source                    1..67
                          mol_type = other RNA
                          organism = synthetic construct
SEQUENCE: 97
gggaaataag agagaaaaga agagtaagaa gaaatacccg cccgccccgc cccgcctaag    60
agccacc                                                              67

SEQ ID NO: 98             moltype = RNA   length = 67
FEATURE                   Location/Qualifiers
misc_feature              1..67
                          note = CG2-6-UTR
source                    1..67
                          mol_type = other RNA
                          organism = synthetic construct
SEQUENCE: 98
```

```
gggaaataag agagaaaaga agagtaagaa gaaatcccgc ccgccccgcc ccgccataag   60
agccacc                                                            67

SEQ ID NO: 99              moltype = RNA  length = 67
FEATURE                    Location/Qualifiers
misc_feature               1..67
                           note = CG2-7-UTR
source                     1..67
                           mol_type = other RNA
                           organism = synthetic construct
SEQUENCE: 99
gggaaataag agagaaaaga agagtaagaa gaaacccgcc cgccccgccc cgcctataag   60
agccacc                                                            67

SEQ ID NO: 100             moltype = RNA  length = 67
FEATURE                    Location/Qualifiers
misc_feature               1..67
                           note = CG2-8-UTR
source                     1..67
                           mol_type = other RNA
                           organism = synthetic construct
SEQUENCE: 100
gggaaataag agagaaaaga agagtaagaa gaacccgccc gccccgcccc gccatataag   60
agccacc                                                            67

SEQ ID NO: 101             moltype = RNA  length = 67
FEATURE                    Location/Qualifiers
misc_feature               1..67
                           note = CG2-9-UTR
source                     1..67
                           mol_type = other RNA
                           organism = synthetic construct
SEQUENCE: 101
gggaaataag agagaaaaga agagtaagaa gacccgcccg ccccgccccg ccaatataag   60
agccacc                                                            67

SEQ ID NO: 102             moltype = RNA  length = 67
FEATURE                    Location/Qualifiers
misc_feature               1..67
                           note = CG2-10-UTR
source                     1..67
                           mol_type = other RNA
                           organism = synthetic construct
SEQUENCE: 102
gggaaataag agagaaaaga agagtaagaa gcccgcccgc ccgccccgc caaatataag    60
agccacc                                                            67

SEQ ID NO: 103             moltype = RNA  length = 67
FEATURE                    Location/Qualifiers
misc_feature               1..67
                           note = CG2-11-UTR
source                     1..67
                           mol_type = other RNA
                           organism = synthetic construct
SEQUENCE: 103
gggaaataag agagaaaaga agagtaagaa cccgcccgcc ccgccccgcc gaaatataag   60
agccacc                                                            67

SEQ ID NO: 104             moltype = RNA  length = 67
FEATURE                    Location/Qualifiers
misc_feature               1..67
                           note = CG2-12-UTR
source                     1..67
                           mol_type = other RNA
                           organism = synthetic construct
SEQUENCE: 104
gggaaataag agagaaaaga agagtaagac ccgcccgccc cgccccgcca gaaatataag   60
agccacc                                                            67

SEQ ID NO: 105             moltype = RNA  length = 67
FEATURE                    Location/Qualifiers
misc_feature               1..67
                           note = CG2-13-UTR
source                     1..67
                           mol_type = other RNA
                           organism = synthetic construct
SEQUENCE: 105
gggaaataag agagaaaaga agagtaagcc cgcccgcccc gccccgccaa gaaatataag   60
agccacc                                                            67
```

```
SEQ ID NO: 106          moltype = RNA   length = 67
FEATURE                 Location/Qualifiers
misc_feature            1..67
                        note = CG2-14-UTR
source                  1..67
                        mol_type = other RNA
                        organism = synthetic construct
SEQUENCE: 106
gggaaataag agagaaaaga agagtaaccc gcccgccccg ccccgccgaa gaaatataag    60
agccacc                                                             67

SEQ ID NO: 107          moltype = RNA   length = 67
FEATURE                 Location/Qualifiers
misc_feature            1..67
                        note = CG2-15-UTR
source                  1..67
                        mol_type = other RNA
                        organism = synthetic construct
SEQUENCE: 107
gggaaataag agagaaaaga agagtacccg cccgccccgc cccgccagaa gaaatataag    60
agccacc                                                             67

SEQ ID NO: 108          moltype = RNA   length = 67
FEATURE                 Location/Qualifiers
misc_feature            1..67
                        note = CG2-16-UTR
source                  1..67
                        mol_type = other RNA
                        organism = synthetic construct
SEQUENCE: 108
gggaaataag agagaaaaga agagtcccgc ccgccccgcc ccgccaagaa gaaatataag    60
agccacc                                                             67

SEQ ID NO: 109          moltype = RNA   length = 67
FEATURE                 Location/Qualifiers
misc_feature            1..67
                        note = CG2-17-UTR
source                  1..67
                        mol_type = other RNA
                        organism = synthetic construct
SEQUENCE: 109
gggaaataag agagaaaaga agagcccgcc cgccccgccc cgcctaagaa gaaatataag    60
agccacc                                                             67

SEQ ID NO: 110          moltype = RNA   length = 67
FEATURE                 Location/Qualifiers
misc_feature            1..67
                        note = CG2-18-UTR
source                  1..67
                        mol_type = other RNA
                        organism = synthetic construct
SEQUENCE: 110
gggaaataag agagaaaaga agacccgccc gccccgcccc gccgtaagaa gaaatataag    60
agccacc                                                             67

SEQ ID NO: 111          moltype = RNA   length = 53
FEATURE                 Location/Qualifiers
misc_feature            1..53
                        note = EK1-UTR
source                  1..53
                        mol_type = other RNA
                        organism = synthetic construct
SEQUENCE: 111
gggaaataag agagaaaaga agagtaagaa gaaatataag acccgccgcc acc           53

SEQ ID NO: 112          moltype = RNA   length = 53
FEATURE                 Location/Qualifiers
misc_feature            1..53
                        note = EK1-1-UTR
source                  1..53
                        mol_type = other RNA
                        organism = synthetic construct
SEQUENCE: 112
gggaaataag agagaaaaga agagtaagaa gaaatataag cccgccagcc acc           53

SEQ ID NO: 113          moltype = RNA   length = 53
FEATURE                 Location/Qualifiers
misc_feature            1..53
```

```
                        note = EK1-2-UTR
source                  1..53
                        mol_type = other RNA
                        organism = synthetic construct
SEQUENCE: 113
gggaaataag agagaaaaga agagtaagaa gaaatataac ccgccgagcc acc      53

SEQ ID NO: 114          moltype = RNA   length = 53
FEATURE                 Location/Qualifiers
misc_feature            1..53
                        note = EK1-3-UTR
source                  1..53
                        mol_type = other RNA
                        organism = synthetic construct
SEQUENCE: 114
gggaaataag agagaaaaga agagtaagaa gaaatatacc cgccagagcc acc      53

SEQ ID NO: 115          moltype = RNA   length = 53
FEATURE                 Location/Qualifiers
misc_feature            1..53
                        note = EK1-4-UTR
source                  1..53
                        mol_type = other RNA
                        organism = synthetic construct
SEQUENCE: 115
gggaaataag agagaaaaga agagtaagaa gaaatatccc gccaagagcc acc      53

SEQ ID NO: 116          moltype = RNA   length = 53
FEATURE                 Location/Qualifiers
misc_feature            1..53
                        note = EK1-5-UTR
source                  1..53
                        mol_type = other RNA
                        organism = synthetic construct
SEQUENCE: 116
gggaaataag agagaaaaga agagtaagaa gaaatacccg cctaagagcc acc      53

SEQ ID NO: 117          moltype = RNA   length = 53
FEATURE                 Location/Qualifiers
misc_feature            1..53
                        note = EK1-6-UTR
source                  1..53
                        mol_type = other RNA
                        organism = synthetic construct
SEQUENCE: 117
gggaaataag agagaaaaga agagtaagaa gaaatcccgc cataagagcc acc      53

SEQ ID NO: 118          moltype = RNA   length = 53
FEATURE                 Location/Qualifiers
misc_feature            1..53
                        note = EK1-7-UTR
source                  1..53
                        mol_type = other RNA
                        organism = synthetic construct
SEQUENCE: 118
gggaaataag agagaaaaga agagtaagaa gaaacccgcc tataagagcc acc      53

SEQ ID NO: 119          moltype = RNA   length = 53
FEATURE                 Location/Qualifiers
misc_feature            1..53
                        note = EK1-8-UTR
source                  1..53
                        mol_type = other RNA
                        organism = synthetic construct
SEQUENCE: 119
gggaaataag agagaaaaga agagtaagaa gaacccgcca tataagagcc acc      53

SEQ ID NO: 120          moltype = RNA   length = 53
FEATURE                 Location/Qualifiers
misc_feature            1..53
                        note = EK1-9-UTR
source                  1..53
                        mol_type = other RNA
                        organism = synthetic construct
SEQUENCE: 120
gggaaataag agagaaaaga agagtaagaa gacccgccaa tataagagcc acc      53

SEQ ID NO: 121          moltype = RNA   length = 53
FEATURE                 Location/Qualifiers
```

```
misc_feature             1..53
                         note = EK1-10-UTR
source                   1..53
                         mol_type = other RNA
                         organism = synthetic construct
SEQUENCE: 121
gggaaataag agagaaaaga agagtaagaa gcccgccaaa tataagagcc acc          53

SEQ ID NO: 122           moltype = RNA   length = 53
FEATURE                  Location/Qualifiers
misc_feature             1..53
                         note = EK1-11-UTR
source                   1..53
                         mol_type = other RNA
                         organism = synthetic construct
SEQUENCE: 122
gggaaataag agagaaaaga agagtaagaa cccgccgaaa tataagagcc acc          53

SEQ ID NO: 123           moltype = RNA   length = 53
FEATURE                  Location/Qualifiers
misc_feature             1..53
                         note = EK1-12-UTR
source                   1..53
                         mol_type = other RNA
                         organism = synthetic construct
SEQUENCE: 123
gggaaataag agagaaaaga agagtaagac ccgccagaaa tataagagcc acc          53

SEQ ID NO: 124           moltype = RNA   length = 53
FEATURE                  Location/Qualifiers
misc_feature             1..53
                         note = EK1-13-UTR
source                   1..53
                         mol_type = other RNA
                         organism = synthetic construct
SEQUENCE: 124
gggaaataag agagaaaaga agagtaagcc cgccaagaaa tataagagcc acc          53

SEQ ID NO: 125           moltype = RNA   length = 53
FEATURE                  Location/Qualifiers
misc_feature             1..53
                         note = EK1-14-UTR
source                   1..53
                         mol_type = other RNA
                         organism = synthetic construct
SEQUENCE: 125
gggaaataag agagaaaaga agagtaaccc gccgaagaaa tataagagcc acc          53

SEQ ID NO: 126           moltype = RNA   length = 53
FEATURE                  Location/Qualifiers
misc_feature             1..53
                         note = EK1-15-UTR
source                   1..53
                         mol_type = other RNA
                         organism = synthetic construct
SEQUENCE: 126
gggaaataag agagaaaaga agagtacccg ccagaagaaa tataagagcc acc          53

SEQ ID NO: 127           moltype = RNA   length = 53
FEATURE                  Location/Qualifiers
misc_feature             1..53
                         note = EK1-16-UTR
source                   1..53
                         mol_type = other RNA
                         organism = synthetic construct
SEQUENCE: 127
gggaaataag agagaaaaga agagtcccgc caagaagaaa tataagagcc acc          53

SEQ ID NO: 128           moltype = RNA   length = 53
FEATURE                  Location/Qualifiers
misc_feature             1..53
                         note = EK1-17-UTR
source                   1..53
                         mol_type = other RNA
                         organism = synthetic construct
SEQUENCE: 128
gggaaataag agagaaaaga agagcccgcc taagaagaaa tataagagcc acc          53

SEQ ID NO: 129           moltype = RNA   length = 53
```

```
FEATURE                 Location/Qualifiers
misc_feature            1..53
                        note = EK1-18-UTR
source                  1..53
                        mol_type = other RNA
                        organism = synthetic construct
SEQUENCE: 129
gggaaataag agagaaaaga agacccgccg taagaagaaa tataagagcc acc      53

SEQ ID NO: 130          moltype = RNA   length = 53
FEATURE                 Location/Qualifiers
misc_feature            1..53
                        note = EK2-UTR
source                  1..53
                        mol_type = other RNA
                        organism = synthetic construct
SEQUENCE: 130
gggaaataag agagaaaaga agagtaagaa gaaatataag agccgccgcc acc      53

SEQ ID NO: 131          moltype = RNA   length = 53
FEATURE                 Location/Qualifiers
misc_feature            1..53
                        note = EK2-1-UTR
source                  1..53
                        mol_type = other RNA
                        organism = synthetic construct
SEQUENCE: 131
gggaaataag agagaaaaga agagtaagaa gaaatataag gccgccagcc acc      53

SEQ ID NO: 132          moltype = RNA   length = 53
FEATURE                 Location/Qualifiers
misc_feature            1..53
                        note = EK2-2-UTR
source                  1..53
                        mol_type = other RNA
                        organism = synthetic construct
SEQUENCE: 132
gggaaataag agagaaaaga agagtaagaa gaaatataag ccgccgagcc acc      53

SEQ ID NO: 133          moltype = RNA   length = 53
FEATURE                 Location/Qualifiers
misc_feature            1..53
                        note = EK2-3-UTR
source                  1..53
                        mol_type = other RNA
                        organism = synthetic construct
SEQUENCE: 133
gggaaataag agagaaaaga agagtaagaa gaaatatagc cgccagagcc acc      53

SEQ ID NO: 134          moltype = RNA   length = 53
FEATURE                 Location/Qualifiers
misc_feature            1..53
                        note = EK2-4-UTR
source                  1..53
                        mol_type = other RNA
                        organism = synthetic construct
SEQUENCE: 134
gggaaataag agagaaaaga agagtaagaa gaaatatgcc gccaagagcc acc      53

SEQ ID NO: 135          moltype = RNA   length = 53
FEATURE                 Location/Qualifiers
misc_feature            1..53
                        note = EK2-5-UTR
source                  1..53
                        mol_type = other RNA
                        organism = synthetic construct
SEQUENCE: 135
gggaaataag agagaaaaga agagtaagaa gaaatagccg cctaagagcc acc      53

SEQ ID NO: 136          moltype = RNA   length = 53
FEATURE                 Location/Qualifiers
misc_feature            1..53
                        note = EK2-6-UTR
source                  1..53
                        mol_type = other RNA
                        organism = synthetic construct
SEQUENCE: 136
gggaaataag agagaaaaga agagtaagaa gaaatgccgc cataagagcc acc      53
```

```
SEQ ID NO: 137          moltype = RNA   length = 53
FEATURE                 Location/Qualifiers
misc_feature            1..53
                        note = EK2-7-UTR
source                  1..53
                        mol_type = other RNA
                        organism = synthetic construct
SEQUENCE: 137
gggaaataag agagaaaaga agagtaagaa gaaagccgcc tataagagcc acc       53

SEQ ID NO: 138          moltype = RNA   length = 53
FEATURE                 Location/Qualifiers
misc_feature            1..53
                        note = EK2-8-UTR
source                  1..53
                        mol_type = other RNA
                        organism = synthetic construct
SEQUENCE: 138
gggaaataag agagaaaaga agagtaagaa gaagccgcca tataagagcc acc       53

SEQ ID NO: 139          moltype = RNA   length = 53
FEATURE                 Location/Qualifiers
misc_feature            1..53
                        note = EK2-9-UTR
source                  1..53
                        mol_type = other RNA
                        organism = synthetic construct
SEQUENCE: 139
gggaaataag agagaaaaga agagtaagaa gagccgccaa tataagagcc acc       53

SEQ ID NO: 140          moltype = RNA   length = 53
FEATURE                 Location/Qualifiers
misc_feature            1..53
                        note = EK2-10-UTR
source                  1..53
                        mol_type = other RNA
                        organism = synthetic construct
SEQUENCE: 140
gggaaataag agagaaaaga agagtaagaa ggccgccaaa tataagagcc acc       53

SEQ ID NO: 141          moltype = RNA   length = 53
FEATURE                 Location/Qualifiers
misc_feature            1..53
                        note = EK2-11-UTR
source                  1..53
                        mol_type = other RNA
                        organism = synthetic construct
SEQUENCE: 141
gggaaataag agagaaaaga agagtaagaa gccgccgaaa tataagagcc acc       53

SEQ ID NO: 142          moltype = RNA   length = 53
FEATURE                 Location/Qualifiers
misc_feature            1..53
                        note = EK2-12-UTR
source                  1..53
                        mol_type = other RNA
                        organism = synthetic construct
SEQUENCE: 142
gggaaataag agagaaaaga agagtaagag ccgccagaaa tataagagcc acc       53

SEQ ID NO: 143          moltype = RNA   length = 53
FEATURE                 Location/Qualifiers
misc_feature            1..53
                        note = EK2-13-UTR
source                  1..53
                        mol_type = other RNA
                        organism = synthetic construct
SEQUENCE: 143
gggaaataag agagaaaaga agagtaaggc cgccaagaaa tataagagcc acc       53

SEQ ID NO: 144          moltype = RNA   length = 53
FEATURE                 Location/Qualifiers
misc_feature            1..53
                        note = EK2-14-UTR
source                  1..53
                        mol_type = other RNA
                        organism = synthetic construct
SEQUENCE: 144
gggaaataag agagaaaaga agagtaagcc gccaagaaa tataagagcc acc        53
```

```
SEQ ID NO: 145          moltype = RNA   length = 53
FEATURE                 Location/Qualifiers
misc_feature            1..53
                        note = EK2-15-UTR
source                  1..53
                        mol_type = other RNA
                        organism = synthetic construct
SEQUENCE: 145
gggaaataag agagaaaaga agagtagccg ccagaagaaa tataagagcc acc          53

SEQ ID NO: 146          moltype = RNA   length = 53
FEATURE                 Location/Qualifiers
misc_feature            1..53
                        note = EK2-16-UTR
source                  1..53
                        mol_type = other RNA
                        organism = synthetic construct
SEQUENCE: 146
gggaaataag agagaaaaga agagtgccgc caagaagaaa tataagagcc acc          53

SEQ ID NO: 147          moltype = RNA   length = 53
FEATURE                 Location/Qualifiers
misc_feature            1..53
                        note = EK2-17-UTR
source                  1..53
                        mol_type = other RNA
                        organism = synthetic construct
SEQUENCE: 147
gggaaataag agagaaaaga agaggccgcc taagaagaaa tataagagcc acc          53

SEQ ID NO: 148          moltype = RNA   length = 53
FEATURE                 Location/Qualifiers
misc_feature            1..53
                        note = EK2-18-UTR
source                  1..53
                        mol_type = other RNA
                        organism = synthetic construct
SEQUENCE: 148
gggaaataag agagaaaaga agagccgccg taagaagaaa tataagagcc acc          53

SEQ ID NO: 149          moltype = RNA   length = 53
FEATURE                 Location/Qualifiers
misc_feature            1..53
                        note = EK3-UTR
source                  1..53
                        mol_type = other RNA
                        organism = synthetic construct
SEQUENCE: 149
gggaaataag agagaaaaga agagtaagaa gaaatataag accgccggcc acc          53

SEQ ID NO: 150          moltype = RNA   length = 53
FEATURE                 Location/Qualifiers
misc_feature            1..53
                        note = EK3-1-UTR
source                  1..53
                        mol_type = other RNA
                        organism = synthetic construct
SEQUENCE: 150
gggaaataag agagaaaaga agagtaagaa gaaatataag ccgccgagcc acc          53

SEQ ID NO: 151          moltype = RNA   length = 53
FEATURE                 Location/Qualifiers
misc_feature            1..53
                        note = EK3-2-UTR
source                  1..53
                        mol_type = other RNA
                        organism = synthetic construct
SEQUENCE: 151
gggaaataag agagaaaaga agagtaagaa gaaatataac cgccggagcc acc          53

SEQ ID NO: 152          moltype = RNA   length = 53
FEATURE                 Location/Qualifiers
misc_feature            1..53
                        note = EK3-3-UTR
source                  1..53
                        mol_type = other RNA
                        organism = synthetic construct
SEQUENCE: 152
```

```
gggaaataag agagaaaaga agagtaagaa gaaatatacc gccgagagcc acc        53

SEQ ID NO: 153         moltype = RNA   length = 53
FEATURE                Location/Qualifiers
misc_feature           1..53
                       note = EK3-4-UTR
source                 1..53
                       mol_type = other RNA
                       organism = synthetic construct
SEQUENCE: 153
gggaaataag agagaaaaga agagtaagaa gaaatatccg ccgaagagcc acc        53

SEQ ID NO: 154         moltype = RNA   length = 53
FEATURE                Location/Qualifiers
misc_feature           1..53
                       note = EK3-5-UTR
source                 1..53
                       mol_type = other RNA
                       organism = synthetic construct
SEQUENCE: 154
gggaaataag agagaaaaga agagtaagaa gaaataccgc cgtaagagcc acc        53

SEQ ID NO: 155         moltype = RNA   length = 53
FEATURE                Location/Qualifiers
misc_feature           1..53
                       note = EK3-6-UTR
source                 1..53
                       mol_type = other RNA
                       organism = synthetic construct
SEQUENCE: 155
gggaaataag agagaaaaga agagtaagaa gaaatccgcc gataagagcc acc        53

SEQ ID NO: 156         moltype = RNA   length = 53
FEATURE                Location/Qualifiers
misc_feature           1..53
                       note = EK3-7-UTR
source                 1..53
                       mol_type = other RNA
                       organism = synthetic construct
SEQUENCE: 156
gggaaataag agagaaaaga agagtaagaa gaaaccgccg ataagagcc acc         53

SEQ ID NO: 157         moltype = RNA   length = 53
FEATURE                Location/Qualifiers
misc_feature           1..53
                       note = EK3-8-UTR
source                 1..53
                       mol_type = other RNA
                       organism = synthetic construct
SEQUENCE: 157
gggaaataag agagaaaaga agagtaagaa gaaccgccga taagagcc acc          53

SEQ ID NO: 158         moltype = RNA   length = 53
FEATURE                Location/Qualifiers
misc_feature           1..53
                       note = EK3-9-UTR
source                 1..53
                       mol_type = other RNA
                       organism = synthetic construct
SEQUENCE: 158
gggaaataag agagaaaaga agagtaagaa gaccgccgaa tataagagcc acc        53

SEQ ID NO: 159         moltype = RNA   length = 53
FEATURE                Location/Qualifiers
misc_feature           1..53
                       note = EK3-10-UTR
source                 1..53
                       mol_type = other RNA
                       organism = synthetic construct
SEQUENCE: 159
gggaaataag agagaaaaga agagtaagaa gccgccgaaa tataagagcc acc        53

SEQ ID NO: 160         moltype = RNA   length = 53
FEATURE                Location/Qualifiers
misc_feature           1..53
                       note = EK3-11-UTR
source                 1..53
                       mol_type = other RNA
                       organism = synthetic construct
```

```
-continued

SEQUENCE: 160
gggaaataag agagaaaaga agagtaagaa ccgccggaaa tataagagcc acc          53

SEQ ID NO: 161          moltype = RNA   length = 53
FEATURE                 Location/Qualifiers
misc_feature            1..53
                        note = EK3-12-UTR
source                  1..53
                        mol_type = other RNA
                        organism = synthetic construct
SEQUENCE: 161
gggaaataag agagaaaaga agagtaagac cgccgagaaa tataagagcc acc          53

SEQ ID NO: 162          moltype = RNA   length = 53
FEATURE                 Location/Qualifiers
misc_feature            1..53
                        note = EK3-13-UTR
source                  1..53
                        mol_type = other RNA
                        organism = synthetic construct
SEQUENCE: 162
gggaaataag agagaaaaga agagtaagcc gccgaagaaa tataagagcc acc          53

SEQ ID NO: 163          moltype = RNA   length = 53
FEATURE                 Location/Qualifiers
misc_feature            1..53
                        note = EK3-14-UTR
source                  1..53
                        mol_type = other RNA
                        organism = synthetic construct
SEQUENCE: 163
gggaaataag agagaaaaga agagtaaccg ccggagaaa tataagagcc acc           53

SEQ ID NO: 164          moltype = RNA   length = 53
FEATURE                 Location/Qualifiers
misc_feature            1..53
                        note = EK3-15-UTR
source                  1..53
                        mol_type = other RNA
                        organism = synthetic construct
SEQUENCE: 164
gggaaataag agagaaaaga agagtaccgc cgagaagaaa tataagagcc acc          53

SEQ ID NO: 165          moltype = RNA   length = 53
FEATURE                 Location/Qualifiers
misc_feature            1..53
                        note = EK3-16-UTR
source                  1..53
                        mol_type = other RNA
                        organism = synthetic construct
SEQUENCE: 165
gggaaataag agagaaaaga agagtccgcc gaagaagaaa tataagagcc acc          53

SEQ ID NO: 166          moltype = RNA   length = 53
FEATURE                 Location/Qualifiers
misc_feature            1..53
                        note = EK3-17-UTR
source                  1..53
                        mol_type = other RNA
                        organism = synthetic construct
SEQUENCE: 166
gggaaataag agagaaaaga agagccgccg taagaagaaa tataagagcc acc          53

SEQ ID NO: 167          moltype = RNA   length = 53
FEATURE                 Location/Qualifiers
misc_feature            1..53
                        note = EK3-18-UTR
source                  1..53
                        mol_type = other RNA
                        organism = synthetic construct
SEQUENCE: 167
gggaaataag agagaaaaga agaccgccgg taagaagaaa tataagagcc acc          53

SEQ ID NO: 168          moltype = RNA   length = 56
FEATURE                 Location/Qualifiers
misc_feature            1..56
                        note = (CCG)3-UTR
source                  1..56
                        mol_type = other RNA
```

```
                                 -continued
                       organism = synthetic construct
SEQUENCE: 168
gggaaataag agagaaaaga agagtaagaa gaaatataag accgccgccg gccacc        56

SEQ ID NO: 169         moltype = RNA   length = 56
FEATURE                Location/Qualifiers
misc_feature           1..56
                       note = (CCG)3-1-UTR
source                 1..56
                       mol_type = other RNA
                       organism = synthetic construct
SEQUENCE: 169
gggaaataag agagaaaaga agagtaagaa gaaatataag ccgccgccga gccacc        56

SEQ ID NO: 170         moltype = RNA   length = 56
FEATURE                Location/Qualifiers
misc_feature           1..56
                       note = (CCG)3-2-UTR
source                 1..56
                       mol_type = other RNA
                       organism = synthetic construct
SEQUENCE: 170
gggaaataag agagaaaaga agagtaagaa gaaatataac cgccgccgga gccacc        56

SEQ ID NO: 171         moltype = RNA   length = 56
FEATURE                Location/Qualifiers
misc_feature           1..56
                       note = (CCG)3-3-UTR
source                 1..56
                       mol_type = other RNA
                       organism = synthetic construct
SEQUENCE: 171
gggaaataag agagaaaaga agagtaagaa gaaatatacc gccgccgaga gccacc        56

SEQ ID NO: 172         moltype = RNA   length = 56
FEATURE                Location/Qualifiers
misc_feature           1..56
                       note = (CCG)3-4-UTR
source                 1..56
                       mol_type = other RNA
                       organism = synthetic construct
SEQUENCE: 172
gggaaataag agagaaaaga agagtaagaa gaaatatccg ccgccgaaga gccacc        56

SEQ ID NO: 173         moltype = RNA   length = 56
FEATURE                Location/Qualifiers
misc_feature           1..56
                       note = (CCG)3-5-UTR
source                 1..56
                       mol_type = other RNA
                       organism = synthetic construct
SEQUENCE: 173
gggaaataag agagaaaaga agagtaagaa gaaataccgc cgccgtaaga gccacc        56

SEQ ID NO: 174         moltype = RNA   length = 56
FEATURE                Location/Qualifiers
misc_feature           1..56
                       note = (CCG)3-6-UTR
source                 1..56
                       mol_type = other RNA
                       organism = synthetic construct
SEQUENCE: 174
gggaaataag agagaaaaga agagtaagaa gaaatccgcc gccgataaga gccacc        56

SEQ ID NO: 175         moltype = RNA   length = 56
FEATURE                Location/Qualifiers
misc_feature           1..56
                       note = (CCG)3-7-UTR
source                 1..56
                       mol_type = other RNA
                       organism = synthetic construct
SEQUENCE: 175
gggaaataag agagaaaaga agagtaagaa gaaaccgccg ccgtataaga gccacc        56

SEQ ID NO: 176         moltype = RNA   length = 56
FEATURE                Location/Qualifiers
misc_feature           1..56
                       note = (CCG)3-8-UTR
source                 1..56
```

```
                        mol_type = other RNA
                        organism = synthetic construct
SEQUENCE: 176
gggaaataag agagaaaaga agagtaagaa gaaccgccgc cgatataaga gccacc        56

SEQ ID NO: 177          moltype = RNA   length = 56
FEATURE                 Location/Qualifiers
misc_feature            1..56
                        note = (CCG)3-9-UTR
source                  1..56
                        mol_type = other RNA
                        organism = synthetic construct
SEQUENCE: 177
gggaaataag agagaaaaga agagtaagaa gaccgccgcc gaatataaga gccacc        56

SEQ ID NO: 178          moltype = RNA   length = 56
FEATURE                 Location/Qualifiers
misc_feature            1..56
                        note = (CCG)3-10-UTR
source                  1..56
                        mol_type = other RNA
                        organism = synthetic construct
SEQUENCE: 178
gggaaataag agagaaaaga agagtaagaa gccgccgccg aaatataaga gccacc        56

SEQ ID NO: 179          moltype = RNA   length = 56
FEATURE                 Location/Qualifiers
misc_feature            1..56
                        note = (CCG)3-11-UTR
source                  1..56
                        mol_type = other RNA
                        organism = synthetic construct
SEQUENCE: 179
gggaaataag agagaaaaga agagtaagaa ccgccgccgg aaatataaga gccacc        56

SEQ ID NO: 180          moltype = RNA   length = 56
FEATURE                 Location/Qualifiers
misc_feature            1..56
                        note = (CCG)3-12-UTR
source                  1..56
                        mol_type = other RNA
                        organism = synthetic construct
SEQUENCE: 180
gggaaataag agagaaaaga agagtaagac cgccgccgag aaatataaga gccacc        56

SEQ ID NO: 181          moltype = RNA   length = 56
FEATURE                 Location/Qualifiers
misc_feature            1..56
                        note = (CCG)3-13-UTR
source                  1..56
                        mol_type = other RNA
                        organism = synthetic construct
SEQUENCE: 181
gggaaataag agagaaaaga agagtaagcc gccgccgaag aaatataaga gccacc        56

SEQ ID NO: 182          moltype = RNA   length = 56
FEATURE                 Location/Qualifiers
misc_feature            1..56
                        note = (CCG)3-14-UTR
source                  1..56
                        mol_type = other RNA
                        organism = synthetic construct
SEQUENCE: 182
gggaaataag agagaaaaga agagtaaccg ccgccggaag aaatataaga gccacc        56

SEQ ID NO: 183          moltype = RNA   length = 56
FEATURE                 Location/Qualifiers
misc_feature            1..56
                        note = (CCG)3-15-UTR
source                  1..56
                        mol_type = other RNA
                        organism = synthetic construct
SEQUENCE: 183
gggaaataag agagaaaaga agagtaccgc cgccgagaag aaatataaga gccacc        56

SEQ ID NO: 184          moltype = RNA   length = 56
FEATURE                 Location/Qualifiers
misc_feature            1..56
                        note = (CCG)3-16-UTR
```

```
source                       1..56
                             mol_type = other RNA
                             organism = synthetic construct
SEQUENCE: 184
gggaaataag agagaaaaga agagtccgcc gccgaagaag aaatataaga gccacc         56

SEQ ID NO: 185               moltype = RNA   length = 56
FEATURE                      Location/Qualifiers
misc_feature                 1..56
                             note = (CCG)3-17-UTR
source                       1..56
                             mol_type = other RNA
                             organism = synthetic construct
SEQUENCE: 185
gggaaataag agagaaaaga agagccgccg ccgtaagaag aaatataaga gccacc         56

SEQ ID NO: 186               moltype = RNA   length = 56
FEATURE                      Location/Qualifiers
misc_feature                 1..56
                             note = (CCG)3-18-UTR
source                       1..56
                             mol_type = other RNA
                             organism = synthetic construct
SEQUENCE: 186
gggaaataag agagaaaaga agaccgccgc cggtaagaag aaatataaga gccacc         56

SEQ ID NO: 187               moltype = RNA   length = 59
FEATURE                      Location/Qualifiers
misc_feature                 1..59
                             note = (CCG)4-UTR
source                       1..59
                             mol_type = other RNA
                             organism = synthetic construct
SEQUENCE: 187
gggaaataag agagaaaaga agagtaagaa gaaatataag accgccgccg ccggccacc      59

SEQ ID NO: 188               moltype = RNA   length = 59
FEATURE                      Location/Qualifiers
misc_feature                 1..59
                             note = (CCG)4-1-UTR
source                       1..59
                             mol_type = other RNA
                             organism = synthetic construct
SEQUENCE: 188
gggaaataag agagaaaaga agagtaagaa gaaatataag ccgccgccgc cgagccacc      59

SEQ ID NO: 189               moltype = RNA   length = 59
FEATURE                      Location/Qualifiers
misc_feature                 1..59
                             note = (CCG)4-2-UTR
source                       1..59
                             mol_type = other RNA
                             organism = synthetic construct
SEQUENCE: 189
gggaaataag agagaaaaga agagtaagaa gaaatataac cgccgccgcc ggagccacc      59

SEQ ID NO: 190               moltype = RNA   length = 59
FEATURE                      Location/Qualifiers
misc_feature                 1..59
                             note = (CCG)4-3-UTR
source                       1..59
                             mol_type = other RNA
                             organism = synthetic construct
SEQUENCE: 190
gggaaataag agagaaaaga agagtaagaa gaaatatacc gccgccgccg agagccacc      59

SEQ ID NO: 191               moltype = RNA   length = 59
FEATURE                      Location/Qualifiers
misc_feature                 1..59
                             note = (CCG)4-4-UTR
source                       1..59
                             mol_type = other RNA
                             organism = synthetic construct
SEQUENCE: 191
gggaaataag agagaaaaga agagtaagaa gaaatatccg ccgccgccga agagccacc      59

SEQ ID NO: 192               moltype = RNA   length = 59
FEATURE                      Location/Qualifiers
misc_feature                 1..59
```

```
                        note = (CCG)4-5-UTR
source                  1..59
                        mol_type = other RNA
                        organism = synthetic construct
SEQUENCE: 192
gggaaataag agagaaaaga agagtaagaa gaaataccgc cgccgccgta agagccacc    59

SEQ ID NO: 193          moltype = RNA  length = 59
FEATURE                 Location/Qualifiers
misc_feature            1..59
                        note = (CCG)4-6-UTR
source                  1..59
                        mol_type = other RNA
                        organism = synthetic construct
SEQUENCE: 193
gggaaataag agagaaaaga agagtaagaa gaaatccgcc gccgccgata agagccacc    59

SEQ ID NO: 194          moltype = RNA  length = 59
FEATURE                 Location/Qualifiers
misc_feature            1..59
                        note = (CCG)4-7-UTR
source                  1..59
                        mol_type = other RNA
                        organism = synthetic construct
SEQUENCE: 194
gggaaataag agagaaaaga agagtaagaa gaaaccgccg ccgccgtata agagccacc    59

SEQ ID NO: 195          moltype = RNA  length = 59
FEATURE                 Location/Qualifiers
misc_feature            1..59
                        note = (CCG)4-8-UTR
source                  1..59
                        mol_type = other RNA
                        organism = synthetic construct
SEQUENCE: 195
gggaaataag agagaaaaga agagtaagaa gaaccgccgc cgccgatata agagccacc    59

SEQ ID NO: 196          moltype = RNA  length = 59
FEATURE                 Location/Qualifiers
misc_feature            1..59
                        note = (CCG)4-9-UTR
source                  1..59
                        mol_type = other RNA
                        organism = synthetic construct
SEQUENCE: 196
gggaaataag agagaaaaga agagtaagaa gaccgccgcc gccgaatata agagccacc    59

SEQ ID NO: 197          moltype = RNA  length = 59
FEATURE                 Location/Qualifiers
misc_feature            1..59
                        note = (CCG)4-10-UTR
source                  1..59
                        mol_type = other RNA
                        organism = synthetic construct
SEQUENCE: 197
gggaaataag agagaaaaga agagtaagaa gccgccgccg ccgaaatata agagccacc    59

SEQ ID NO: 198          moltype = RNA  length = 59
FEATURE                 Location/Qualifiers
misc_feature            1..59
                        note = (CCG)4-11-UTR
source                  1..59
                        mol_type = other RNA
                        organism = synthetic construct
SEQUENCE: 198
gggaaataag agagaaaaga agagtaagaa ccgccgccgc cggaaatata agagccacc    59

SEQ ID NO: 199          moltype = RNA  length = 59
FEATURE                 Location/Qualifiers
misc_feature            1..59
                        note = (CCG)4-12-UTR
source                  1..59
                        mol_type = other RNA
                        organism = synthetic construct
SEQUENCE: 199
gggaaataag agagaaaaga agagtaagac cgccgccgcc gagaaatata agagccacc    59

SEQ ID NO: 200          moltype = RNA  length = 59
FEATURE                 Location/Qualifiers
```

```
misc_feature            1..59
                        note = (CCG)4-13-UTR
source                  1..59
                        mol_type = other RNA
                        organism = synthetic construct
SEQUENCE: 200
gggaaataag agagaaaaga agagtaagcc gccgccgccg aagaaatata agagccacc    59

SEQ ID NO: 201          moltype = RNA  length = 59
FEATURE                 Location/Qualifiers
misc_feature            1..59
                        note = (CCG)4-14-UTR
source                  1..59
                        mol_type = other RNA
                        organism = synthetic construct
SEQUENCE: 201
gggaaataag agagaaaaga agagtaaccg ccgccgccgg aagaaatata agagccacc    59

SEQ ID NO: 202          moltype = RNA  length = 59
FEATURE                 Location/Qualifiers
misc_feature            1..59
                        note = (CCG)4-15-UTR
source                  1..59
                        mol_type = other RNA
                        organism = synthetic construct
SEQUENCE: 202
gggaaataag agagaaaaga agagtaccgc cgccgccgag aagaaatata agagccacc    59

SEQ ID NO: 203          moltype = RNA  length = 59
FEATURE                 Location/Qualifiers
misc_feature            1..59
                        note = (CCG)4-16-UTR
source                  1..59
                        mol_type = other RNA
                        organism = synthetic construct
SEQUENCE: 203
gggaaataag agagaaaaga agagtccgcc gccgccgaag aagaaatata agagccacc    59

SEQ ID NO: 204          moltype = RNA  length = 59
FEATURE                 Location/Qualifiers
misc_feature            1..59
                        note = (CCG)4-17-UTR
source                  1..59
                        mol_type = other RNA
                        organism = synthetic construct
SEQUENCE: 204
gggaaataag agagaaaaga agagccgccg ccgccgtaag aagaaatata agagccacc    59

SEQ ID NO: 205          moltype = RNA  length = 59
FEATURE                 Location/Qualifiers
misc_feature            1..59
                        note = (CCG)4-18-UTR
source                  1..59
                        mol_type = other RNA
                        organism = synthetic construct
SEQUENCE: 205
gggaaataag agagaaaaga agaccgccgc cgccggtaag aagaaatata agagccacc    59

SEQ ID NO: 206          moltype = RNA  length = 62
FEATURE                 Location/Qualifiers
misc_feature            1..62
                        note = (CCG)5-UTR
source                  1..62
                        mol_type = other RNA
                        organism = synthetic construct
SEQUENCE: 206
gggaaataag agagaaaaga agagtaagaa gaaatataag accgccgccg ccgccggcca    60
cc                                                                 62

SEQ ID NO: 207          moltype = RNA  length = 62
FEATURE                 Location/Qualifiers
misc_feature            1..62
                        note = (CCG)5-1-UTR
source                  1..62
                        mol_type = other RNA
                        organism = synthetic construct
SEQUENCE: 207
gggaaataag agagaaaaga agagtaagaa gaaatataag ccgccgccgc cgccgagcca    60
cc                                                                 62
```

```
SEQ ID NO: 208          moltype = RNA   length = 62
FEATURE                 Location/Qualifiers
misc_feature            1..62
                        note = (CCG)5-2-UTR
source                  1..62
                        mol_type = other RNA
                        organism = synthetic construct
SEQUENCE: 208
gggaaataag agagaaaaga agagtaagaa gaaatataac cgccgccgcc gccggagcca   60
cc                                                                 62

SEQ ID NO: 209          moltype = RNA   length = 62
FEATURE                 Location/Qualifiers
misc_feature            1..62
                        note = (CCG)5-3-UTR
source                  1..62
                        mol_type = other RNA
                        organism = synthetic construct
SEQUENCE: 209
gggaaataag agagaaaaga agagtaagaa gaaatatacc gccgccgccg ccgagagcca   60
cc                                                                 62

SEQ ID NO: 210          moltype = RNA   length = 62
FEATURE                 Location/Qualifiers
misc_feature            1..62
                        note = (CCG)5-4-UTR
source                  1..62
                        mol_type = other RNA
                        organism = synthetic construct
SEQUENCE: 210
gggaaataag agagaaaaga agagtaagaa gaaatatccg ccgccgccgc cgaagagcca   60
cc                                                                 62

SEQ ID NO: 211          moltype = RNA   length = 62
FEATURE                 Location/Qualifiers
misc_feature            1..62
                        note = (CCG)5-5-UTR
source                  1..62
                        mol_type = other RNA
                        organism = synthetic construct
SEQUENCE: 211
gggaaataag agagaaaaga agagtaagaa gaaataccgc cgccgccgcc gtaagagcca   60
cc                                                                 62

SEQ ID NO: 212          moltype = RNA   length = 62
FEATURE                 Location/Qualifiers
misc_feature            1..62
                        note = (CCG)5-6-UTR
source                  1..62
                        mol_type = other RNA
                        organism = synthetic construct
SEQUENCE: 212
gggaaataag agagaaaaga agagtaagaa gaaatccgcc gccgccgccg ataagagcca   60
cc                                                                 62

SEQ ID NO: 213          moltype = RNA   length = 62
FEATURE                 Location/Qualifiers
misc_feature            1..62
                        note = (CCG)5-7-UTR
source                  1..62
                        mol_type = other RNA
                        organism = synthetic construct
SEQUENCE: 213
gggaaataag agagaaaaga agagtaagaa gaaaccgccg ccgccgccgt ataagagcca   60
cc                                                                 62

SEQ ID NO: 214          moltype = RNA   length = 62
FEATURE                 Location/Qualifiers
misc_feature            1..62
                        note = (CCG)5-8-UTR
source                  1..62
                        mol_type = other RNA
                        organism = synthetic construct
SEQUENCE: 214
gggaaataag agagaaaaga agagtaagaa gaaccgccgc cgccgccgat ataagagcca   60
cc                                                                 62

SEQ ID NO: 215          moltype = RNA   length = 62
```

```
FEATURE              Location/Qualifiers
misc_feature         1..62
                     note = (CCG)5-9-UTR
source               1..62
                     mol_type = other RNA
                     organism = synthetic construct
SEQUENCE: 215
gggaaataag agagaaaaga agagtaagaa gaccgccgcc gccgccgaat ataagagcca    60
cc                                                                  62

SEQ ID NO: 216       moltype = RNA   length = 62
FEATURE              Location/Qualifiers
misc_feature         1..62
                     note = (CCG)5-10-UTR
source               1..62
                     mol_type = other RNA
                     organism = synthetic construct
SEQUENCE: 216
gggaaataag agagaaaaga agagtaagaa gccgccgccg ccgccgaaat ataagagcca    60
cc                                                                  62

SEQ ID NO: 217       moltype = RNA   length = 62
FEATURE              Location/Qualifiers
misc_feature         1..62
                     note = (CCG)5-11-UTR
source               1..62
                     mol_type = other RNA
                     organism = synthetic construct
SEQUENCE: 217
gggaaataag agagaaaaga agagtaagaa ccgccgccgc cgccggaaat ataagagcca    60
cc                                                                  62

SEQ ID NO: 218       moltype = RNA   length = 62
FEATURE              Location/Qualifiers
misc_feature         1..62
                     note = (CCG)5-12-UTR
source               1..62
                     mol_type = other RNA
                     organism = synthetic construct
SEQUENCE: 218
gggaaataag agagaaaaga agagtaagac cgccgccgcc gccgagaaat ataagagcca    60
cc                                                                  62

SEQ ID NO: 219       moltype = RNA   length = 62
FEATURE              Location/Qualifiers
misc_feature         1..62
                     note = (CCG)5-13-UTR
source               1..62
                     mol_type = other RNA
                     organism = synthetic construct
SEQUENCE: 219
gggaaataag agagaaaaga agagtaagcc gccgccgccg ccgaagaaat ataagagcca    60
cc                                                                  62

SEQ ID NO: 220       moltype = RNA   length = 62
FEATURE              Location/Qualifiers
misc_feature         1..62
                     note = (CCG)5-14-UTR
source               1..62
                     mol_type = other RNA
                     organism = synthetic construct
SEQUENCE: 220
gggaaataag agagaaaaga agagtaaccg ccgccgccgc cggaagaaat ataagagcca    60
cc                                                                  62

SEQ ID NO: 221       moltype = RNA   length = 62
FEATURE              Location/Qualifiers
misc_feature         1..62
                     note = (CCG)5-15-UTR
source               1..62
                     mol_type = other RNA
                     organism = synthetic construct
SEQUENCE: 221
gggaaataag agagaaaaga agagtaccgc cgccgccgcc gagaagaaat ataagagcca    60
cc                                                                  62

SEQ ID NO: 222       moltype = RNA   length = 62
FEATURE              Location/Qualifiers
misc_feature         1..62
```

```
                        note = (CCG)5-16-UTR
source                  1..62
                        mol_type = other RNA
                        organism = synthetic construct
SEQUENCE: 222
gggaaataag agagaaaaga agagtccgcc gccgccgccg aagaagaaat ataagagcca    60
cc                                                                  62

SEQ ID NO: 223          moltype = RNA  length = 62
FEATURE                 Location/Qualifiers
misc_feature            1..62
                        note = (CCG)5-17-UTR
source                  1..62
                        mol_type = other RNA
                        organism = synthetic construct
SEQUENCE: 223
gggaaataag agagaaaaga agagccgccg ccgccgccgt aagaagaaat ataagagcca    60
cc                                                                  62

SEQ ID NO: 224          moltype = RNA  length = 62
FEATURE                 Location/Qualifiers
misc_feature            1..62
                        note = (CCG)5-18-UTR
source                  1..62
                        mol_type = other RNA
                        organism = synthetic construct
SEQUENCE: 224
gggaaataag agagaaaaga agaccgccgc cgccgccggt aagaagaaat ataagagcca    60
cc                                                                  62

SEQ ID NO: 225          moltype = RNA  length = 65
FEATURE                 Location/Qualifiers
misc_feature            1..65
                        note = (CCG)6-UTR
source                  1..65
                        mol_type = other RNA
                        organism = synthetic construct
SEQUENCE: 225
gggaaataag agagaaaaga agagtaagaa gaaatataag accgccgccg ccgccgccgg    60
ccacc                                                               65

SEQ ID NO: 226          moltype = RNA  length = 65
FEATURE                 Location/Qualifiers
misc_feature            1..65
                        note = (CCG)6-1-UTR
source                  1..65
                        mol_type = other RNA
                        organism = synthetic construct
SEQUENCE: 226
gggaaataag agagaaaaga agagtaagaa gaaatataag ccgccgccgc cgccgccgag    60
ccacc                                                               65

SEQ ID NO: 227          moltype = RNA  length = 65
FEATURE                 Location/Qualifiers
misc_feature            1..65
                        note = (CCG)6-2-UTR
source                  1..65
                        mol_type = other RNA
                        organism = synthetic construct
SEQUENCE: 227
gggaaataag agagaaaaga agagtaagaa gaaatataac cgccgccgcc gccgccggag    60
ccacc                                                               65

SEQ ID NO: 228          moltype = RNA  length = 65
FEATURE                 Location/Qualifiers
misc_feature            1..65
                        note = (CCG)6-3-UTR
source                  1..65
                        mol_type = other RNA
                        organism = synthetic construct
SEQUENCE: 228
gggaaataag agagaaaaga agagtaagaa gaaatatacc gccgccgccg ccgccgagag    60
ccacc                                                               65

SEQ ID NO: 229          moltype = RNA  length = 65
FEATURE                 Location/Qualifiers
misc_feature            1..65
                        note = (CCG)6-4-UTR
source                  1..65
```

```
                    mol_type = other RNA
                    organism = synthetic construct
SEQUENCE: 229
gggaaataag agagaaaaga agagtaagaa gaaatatccg ccgccgccgc cgccgaagag    60
ccacc                                                                65

SEQ ID NO: 230          moltype = RNA   length = 65
FEATURE                 Location/Qualifiers
misc_feature            1..65
                        note = (CCG)6-5-UTR
source                  1..65
                        mol_type = other RNA
                        organism = synthetic construct
SEQUENCE: 230
gggaaataag agagaaaaga agagtaagaa gaaataccgc cgccgccgcc gccgtaagag    60
ccacc                                                                65

SEQ ID NO: 231          moltype = RNA   length = 65
FEATURE                 Location/Qualifiers
misc_feature            1..65
                        note = (CCG)6-6-UTR
source                  1..65
                        mol_type = other RNA
                        organism = synthetic construct
SEQUENCE: 231
gggaaataag agagaaaaga agagtaagaa gaaatccgcc gccgccgccg ccgataagag    60
ccacc                                                                65

SEQ ID NO: 232          moltype = RNA   length = 65
FEATURE                 Location/Qualifiers
misc_feature            1..65
                        note = (CCG)6-7-UTR
source                  1..65
                        mol_type = other RNA
                        organism = synthetic construct
SEQUENCE: 232
gggaaataag agagaaaaga agagtaagaa gaaaccgccg ccgccgccgc cgtataagag    60
ccacc                                                                65

SEQ ID NO: 233          moltype = RNA   length = 65
FEATURE                 Location/Qualifiers
misc_feature            1..65
                        note = (CCG)6-8-UTR
source                  1..65
                        mol_type = other RNA
                        organism = synthetic construct
SEQUENCE: 233
gggaaataag agagaaaaga agagtaagaa gaaccgccgc cgccgccgcc gatataagag    60
ccacc                                                                65

SEQ ID NO: 234          moltype = RNA   length = 65
FEATURE                 Location/Qualifiers
misc_feature            1..65
                        note = (CCG)6-9-UTR
source                  1..65
                        mol_type = other RNA
                        organism = synthetic construct
SEQUENCE: 234
gggaaataag agagaaaaga agagtaagaa gaccgccgcc gccgccgccg aatataagag    60
ccacc                                                                65

SEQ ID NO: 235          moltype = RNA   length = 65
FEATURE                 Location/Qualifiers
misc_feature            1..65
                        note = (CCG)6-10-UTR
source                  1..65
                        mol_type = other RNA
                        organism = synthetic construct
SEQUENCE: 235
gggaaataag agagaaaaga agagtaagaa gccgccgccg ccgccgccga aatataagag    60
ccacc                                                                65

SEQ ID NO: 236          moltype = RNA   length = 65
FEATURE                 Location/Qualifiers
misc_feature            1..65
                        note = (CCG)6-11-UTR
source                  1..65
                        mol_type = other RNA
                        organism = synthetic construct
```

```
SEQUENCE: 236
gggaaataag agagaaaaga agagtaagaa ccgccgccgc cgccgccgga aatataagag    60
ccacc                                                                65

SEQ ID NO: 237          moltype = RNA   length = 65
FEATURE                 Location/Qualifiers
misc_feature            1..65
                        note = (CCG)6-12-UTR
source                  1..65
                        mol_type = other RNA
                        organism = synthetic construct
SEQUENCE: 237
gggaaataag agagaaaaga agagtaagac cgccgccgcc gccgccgaga aatataagag    60
ccacc                                                                65

SEQ ID NO: 238          moltype = RNA   length = 65
FEATURE                 Location/Qualifiers
misc_feature            1..65
                        note = (CCG)6-13-UTR
source                  1..65
                        mol_type = other RNA
                        organism = synthetic construct
SEQUENCE: 238
gggaaataag agagaaaaga agagtaagcc gccgccgccg ccgccgaaga aatataagag    60
ccacc                                                                65

SEQ ID NO: 239          moltype = RNA   length = 65
FEATURE                 Location/Qualifiers
misc_feature            1..65
                        note = (CCG)6-14-UTR
source                  1..65
                        mol_type = other RNA
                        organism = synthetic construct
SEQUENCE: 239
gggaaataag agagaaaaga agagtaaccg ccgccgccgc cgccggaaga aatataagag    60
ccacc                                                                65

SEQ ID NO: 240          moltype = RNA   length = 65
FEATURE                 Location/Qualifiers
misc_feature            1..65
                        note = (CCG)6-15-UTR
source                  1..65
                        mol_type = other RNA
                        organism = synthetic construct
SEQUENCE: 240
gggaaataag agagaaaaga agagtaccgc cgccgccgcc gccgagaaga aatataagag    60
ccacc                                                                65

SEQ ID NO: 241          moltype = RNA   length = 65
FEATURE                 Location/Qualifiers
misc_feature            1..65
                        note = (CCG)6-16-UTR
source                  1..65
                        mol_type = other RNA
                        organism = synthetic construct
SEQUENCE: 241
gggaaataag agagaaaaga agagtccgcc gccgccgccg ccgaagaaga aatataagag    60
ccacc                                                                65

SEQ ID NO: 242          moltype = RNA   length = 65
FEATURE                 Location/Qualifiers
misc_feature            1..65
                        note = (CCG)6-17-UTR
source                  1..65
                        mol_type = other RNA
                        organism = synthetic construct
SEQUENCE: 242
gggaaataag agagaaaaga agagccgccg ccgccgccgc cgtaagaaga aatataagag    60
ccacc                                                                65

SEQ ID NO: 243          moltype = RNA   length = 65
FEATURE                 Location/Qualifiers
misc_feature            1..65
                        note = (CCG)6-18-UTR
source                  1..65
                        mol_type = other RNA
                        organism = synthetic construct
SEQUENCE: 243
gggaaataag agagaaaaga agaccgccgc cgccgccgcc ggtaagaaga aatataagag    60
```

```
ccacc                                                                       65

SEQ ID NO: 244           moltype = RNA   length = 68
FEATURE                  Location/Qualifiers
misc_feature             1..68
                         note = (CCG)7-UTR
source                   1..68
                         mol_type = other RNA
                         organism = synthetic construct
SEQUENCE: 244
gggaaataag agagaaaaga agagtaagaa gaaatataag accgccgccg ccgccgccgc           60
cggccacc                                                                   68

SEQ ID NO: 245           moltype = RNA   length = 68
FEATURE                  Location/Qualifiers
misc_feature             1..68
                         note = (CCG)7-1-UTR
source                   1..68
                         mol_type = other RNA
                         organism = synthetic construct
SEQUENCE: 245
gggaaataag agagaaaaga agagtaagaa gaaatataag ccgccgccgc cgccgccgcc           60
gagccacc                                                                   68

SEQ ID NO: 246           moltype = RNA   length = 68
FEATURE                  Location/Qualifiers
misc_feature             1..68
                         note = (CCG)7-2-UTR
source                   1..68
                         mol_type = other RNA
                         organism = synthetic construct
SEQUENCE: 246
gggaaataag agagaaaaga agagtaagaa gaaatataac cgccgccgcc gccgccgccg           60
gagccacc                                                                   68

SEQ ID NO: 247           moltype = RNA   length = 68
FEATURE                  Location/Qualifiers
misc_feature             1..68
                         note = (CCG)7-3-UTR
source                   1..68
                         mol_type = other RNA
                         organism = synthetic construct
SEQUENCE: 247
gggaaataag agagaaaaga agagtaagaa gaaatatacc gccgccgccg ccgccgccga           60
gagccacc                                                                   68

SEQ ID NO: 248           moltype = RNA   length = 68
FEATURE                  Location/Qualifiers
misc_feature             1..68
                         note = (CCG)7-4-UTR
source                   1..68
                         mol_type = other RNA
                         organism = synthetic construct
SEQUENCE: 248
gggaaataag agagaaaaga agagtaagaa gaaatatccg ccgccgccgc cgccgccgaa           60
gagccacc                                                                   68

SEQ ID NO: 249           moltype = RNA   length = 68
FEATURE                  Location/Qualifiers
misc_feature             1..68
                         note = (CCG)7-5-UTR
source                   1..68
                         mol_type = other RNA
                         organism = synthetic construct
SEQUENCE: 249
gggaaataag agagaaaaga agagtaagaa gaaataccgc cgccgccgcc gccgcgtaa            60
gagccacc                                                                   68

SEQ ID NO: 250           moltype = RNA   length = 68
FEATURE                  Location/Qualifiers
misc_feature             1..68
                         note = (CCG)7-6-UTR
source                   1..68
                         mol_type = other RNA
                         organism = synthetic construct
SEQUENCE: 250
gggaaataag agagaaaaga agagtaagaa gaaatccgcc gccgccgccg ccgccgataa           60
gagccacc                                                                   68
```

-continued

```
SEQ ID NO: 251              moltype = RNA   length = 68
FEATURE                     Location/Qualifiers
misc_feature                1..68
                            note = (CCG)7-7-UTR
source                      1..68
                            mol_type = other RNA
                            organism = synthetic construct
SEQUENCE: 251
gggaaataag agagaaaaga agagtaagaa gaaaccgccg ccgccgccgc cgccgtataa   60
gagccacc                                                           68

SEQ ID NO: 252              moltype = RNA   length = 68
FEATURE                     Location/Qualifiers
misc_feature                1..68
                            note = (CCG)7-8-UTR
source                      1..68
                            mol_type = other RNA
                            organism = synthetic construct
SEQUENCE: 252
gggaaataag agagaaaaga agagtaagaa gaaccgccgc cgccgccgcc gccgatataa   60
gagccacc                                                           68

SEQ ID NO: 253              moltype = RNA   length = 68
FEATURE                     Location/Qualifiers
misc_feature                1..68
                            note = (CCG)7-9-UTR
source                      1..68
                            mol_type = other RNA
                            organism = synthetic construct
SEQUENCE: 253
gggaaataag agagaaaaga agagtaagaa gaccgccgcc gccgccgccg ccgaatataa   60
gagccacc                                                           68

SEQ ID NO: 254              moltype = RNA   length = 68
FEATURE                     Location/Qualifiers
misc_feature                1..68
                            note = (CCG)7-10-UTR
source                      1..68
                            mol_type = other RNA
                            organism = synthetic construct
SEQUENCE: 254
gggaaataag agagaaaaga agagtaagaa gccgccgccg ccgccgccgc cgaaatataa   60
gagccacc                                                           68

SEQ ID NO: 255              moltype = RNA   length = 68
FEATURE                     Location/Qualifiers
misc_feature                1..68
                            note = (CCG)7-11-UTR
source                      1..68
                            mol_type = other RNA
                            organism = synthetic construct
SEQUENCE: 255
gggaaataag agagaaaaga agagtaagaa ccgccgccgc cgccgccgcc ggaaatataa   60
gagccacc                                                           68

SEQ ID NO: 256              moltype = RNA   length = 68
FEATURE                     Location/Qualifiers
misc_feature                1..68
                            note = (CCG)7-12-UTR
source                      1..68
                            mol_type = other RNA
                            organism = synthetic construct
SEQUENCE: 256
gggaaataag agagaaaaga agagtaagac cgccgccgcc gccgccgccg agaaatataa   60
gagccacc                                                           68

SEQ ID NO: 257              moltype = RNA   length = 68
FEATURE                     Location/Qualifiers
misc_feature                1..68
                            note = (CCG)7-13-UTR
source                      1..68
                            mol_type = other RNA
                            organism = synthetic construct
SEQUENCE: 257
gggaaataag agagaaaaga agagtaagcc gccgccgccg ccgccgccga agaaatataa   60
gagccacc                                                           68

SEQ ID NO: 258              moltype = RNA   length = 68
FEATURE                     Location/Qualifiers
```

```
misc_feature               1..68
                           note = (CCG)7-14-UTR
source                     1..68
                           mol_type = other RNA
                           organism = synthetic construct
SEQUENCE: 258
gggaaataag agagaaaaga agagtaaccg ccgccgccgc cgccgccgga agaaatataa     60
gagccacc                                                             68

SEQ ID NO: 259             moltype = RNA   length = 68
FEATURE                    Location/Qualifiers
misc_feature               1..68
                           note = (CCG)7-15-UTR
source                     1..68
                           mol_type = other RNA
                           organism = synthetic construct
SEQUENCE: 259
gggaaataag agagaaaaga agagtaccgc cgccgccgcc gccgcgaga agaaatataa      60
gagccacc                                                             68

SEQ ID NO: 260             moltype = RNA   length = 68
FEATURE                    Location/Qualifiers
misc_feature               1..68
                           note = (CCG)7-16-UTR
source                     1..68
                           mol_type = other RNA
                           organism = synthetic construct
SEQUENCE: 260
gggaaataag agagaaaaga agagtccgcc gccgccgccg ccgccgaaga agaaatataa    60
gagccacc                                                             68

SEQ ID NO: 261             moltype = RNA   length = 68
FEATURE                    Location/Qualifiers
misc_feature               1..68
                           note = (CCG)7-17-UTR
source                     1..68
                           mol_type = other RNA
                           organism = synthetic construct
SEQUENCE: 261
gggaaataag agagaaaaga agagccgccg ccgccgccgc cgccgtaaga agaaatataa    60
gagccacc                                                             68

SEQ ID NO: 262             moltype = RNA   length = 68
FEATURE                    Location/Qualifiers
misc_feature               1..68
                           note = (CCG)7-18-UTR
source                     1..68
                           mol_type = other RNA
                           organism = synthetic construct
SEQUENCE: 262
gggaaataag agagaaaaga agaccgccgc cgccgccgcc gccggtaaga agaaatataa    60
gagccacc                                                             68

SEQ ID NO: 263             moltype = RNA   length = 71
FEATURE                    Location/Qualifiers
misc_feature               1..71
                           note = (CCG)8-UTR
source                     1..71
                           mol_type = other RNA
                           organism = synthetic construct
SEQUENCE: 263
gggaaataag agagaaaaga agagtaagaa gaaatataag accgccgccg ccgccgccgc    60
cgccggccac c                                                         71

SEQ ID NO: 264             moltype = RNA   length = 71
FEATURE                    Location/Qualifiers
misc_feature               1..71
                           note = (CCG)8-1-UTR
source                     1..71
                           mol_type = other RNA
                           organism = synthetic construct
SEQUENCE: 264
gggaaataag agagaaaaga agagtaagaa gaaatataag ccgccgccgc cgccgccgcc    60
gccgagccac c                                                         71

SEQ ID NO: 265             moltype = RNA   length = 71
FEATURE                    Location/Qualifiers
misc_feature               1..71
                           note = (CCG)8-2-UTR
```

```
source                    1..71
                          mol_type = other RNA
                          organism = synthetic construct
SEQUENCE: 265
gggaaataag agagaaaaga agagtaagaa gaaatataac cgccgccgcc gccgccgccg    60
ccggagccac c                                                        71

SEQ ID NO: 266            moltype = RNA  length = 71
FEATURE                   Location/Qualifiers
misc_feature              1..71
                          note = (CCG)8-3-UTR
source                    1..71
                          mol_type = other RNA
                          organism = synthetic construct
SEQUENCE: 266
gggaaataag agagaaaaga agagtaagaa gaaatatacc gccgccgccg ccgccgccgc    60
cgagagccac c                                                        71

SEQ ID NO: 267            moltype = RNA  length = 71
FEATURE                   Location/Qualifiers
misc_feature              1..71
                          note = (CCG)8-4-UTR
source                    1..71
                          mol_type = other RNA
                          organism = synthetic construct
SEQUENCE: 267
gggaaataag agagaaaaga agagtaagaa gaaatatccg ccgccgccgc cgccgccgcc    60
gaagagccac c                                                        71

SEQ ID NO: 268            moltype = RNA  length = 71
FEATURE                   Location/Qualifiers
misc_feature              1..71
                          note = (CCG)8-5-UTR
source                    1..71
                          mol_type = other RNA
                          organism = synthetic construct
SEQUENCE: 268
gggaaataag agagaaaaga agagtaagaa gaaataccgc cgccgccgcc ggcgccgccg    60
taagagccac c                                                        71

SEQ ID NO: 269            moltype = RNA  length = 71
FEATURE                   Location/Qualifiers
misc_feature              1..71
                          note = (CCG)8-6-UTR
source                    1..71
                          mol_type = other RNA
                          organism = synthetic construct
SEQUENCE: 269
gggaaataag agagaaaaga agagtaagaa gaaatccgcc gccgccgccg ccgccgcga     60
taagagccac c                                                        71

SEQ ID NO: 270            moltype = RNA  length = 71
FEATURE                   Location/Qualifiers
misc_feature              1..71
                          note = (CCG)8-7-UTR
source                    1..71
                          mol_type = other RNA
                          organism = synthetic construct
SEQUENCE: 270
gggaaataag agagaaaaga agagtaagaa gaaaccgccg ccgccgccgc cgccgccgta    60
taagagccac c                                                        71

SEQ ID NO: 271            moltype = RNA  length = 71
FEATURE                   Location/Qualifiers
misc_feature              1..71
                          note = (CCG)8-8-UTR
source                    1..71
                          mol_type = other RNA
                          organism = synthetic construct
SEQUENCE: 271
gggaaataag agagaaaaga agagtaagaa gaaccgccgc cgccgccgcc gccgccgata    60
taagagccac c                                                        71

SEQ ID NO: 272            moltype = RNA  length = 71
FEATURE                   Location/Qualifiers
misc_feature              1..71
                          note = (CCG)8-9-UTR
source                    1..71
                          mol_type = other RNA
```

```
                                organism = synthetic construct
SEQUENCE: 272
gggaaataag agagaaaaga agagtaagaa gaccgccgcc gccgccgcg ccgccgaata    60
taagagccac c                                                       71

SEQ ID NO: 273          moltype = RNA   length = 71
FEATURE                 Location/Qualifiers
misc_feature            1..71
                        note = (CCG)8-10-UTR
source                  1..71
                        mol_type = other RNA
                        organism = synthetic construct
SEQUENCE: 273
gggaaataag agagaaaaga agagtaagaa gccgccgccg ccgccgccgc cgccgaaata    60
taagagccac c                                                       71

SEQ ID NO: 274          moltype = RNA   length = 71
FEATURE                 Location/Qualifiers
misc_feature            1..71
                        note = (CCG)8-11-UTR
source                  1..71
                        mol_type = other RNA
                        organism = synthetic construct
SEQUENCE: 274
gggaaataag agagaaaaga agagtaagaa ccgccgccgc cgccgccgcc gccggaaata    60
taagagccac c                                                       71

SEQ ID NO: 275          moltype = RNA   length = 71
FEATURE                 Location/Qualifiers
misc_feature            1..71
                        note = (CCG)8-12-UTR
source                  1..71
                        mol_type = other RNA
                        organism = synthetic construct
SEQUENCE: 275
gggaaataag agagaaaaga agagtaagac cgccgccgcc gccgccgccg ccgagaaata    60
taagagccac c                                                       71

SEQ ID NO: 276          moltype = RNA   length = 71
FEATURE                 Location/Qualifiers
misc_feature            1..71
                        note = (CCG)8-13-UTR
source                  1..71
                        mol_type = other RNA
                        organism = synthetic construct
SEQUENCE: 276
gggaaataag agagaaaaga agagtaagcc gccgccgccg ccgccgccgc cgaagaaata    60
taagagccac c                                                       71

SEQ ID NO: 277          moltype = RNA   length = 71
FEATURE                 Location/Qualifiers
misc_feature            1..71
                        note = (CCG)8-14-UTR
source                  1..71
                        mol_type = other RNA
                        organism = synthetic construct
SEQUENCE: 277
gggaaataag agagaaaaga agagtaaccg ccgccgccgc cgccgccgcc ggaagaaata    60
taagagccac c                                                       71

SEQ ID NO: 278          moltype = RNA   length = 71
FEATURE                 Location/Qualifiers
misc_feature            1..71
                        note = (CCG)8-15-UTR
source                  1..71
                        mol_type = other RNA
                        organism = synthetic construct
SEQUENCE: 278
gggaaataag agagaaaaga agagtaccgc cgccgccgcc gccgccgccg agaagaaata    60
taagagccac c                                                       71

SEQ ID NO: 279          moltype = RNA   length = 71
FEATURE                 Location/Qualifiers
misc_feature            1..71
                        note = (CCG)8-16-UTR
source                  1..71
                        mol_type = other RNA
                        organism = synthetic construct
SEQUENCE: 279
```

```
gggaaataag agagaaaaga agagtccgcc gccgccgccg ccgccgccga agaagaaata      60
taagagccac c                                                           71

SEQ ID NO: 280          moltype = RNA   length = 71
FEATURE                 Location/Qualifiers
misc_feature            1..71
                        note = (CCG)8-17-UTR
source                  1..71
                        mol_type = other RNA
                        organism = synthetic construct
SEQUENCE: 280
gggaaataag agagaaaaga agagccgccg ccgccgccgc cgccgccgta agaagaaata      60
taagagccac c                                                           71

SEQ ID NO: 281          moltype = RNA   length = 71
FEATURE                 Location/Qualifiers
misc_feature            1..71
                        note = (CCG)8-18-UTR
source                  1..71
                        mol_type = other RNA
                        organism = synthetic construct
SEQUENCE: 281
gggaaataag agagaaaaga agaccgccgc cgccgccgcc gccgccggta agaagaaata      60
taagagccac c                                                           71

SEQ ID NO: 282          moltype = RNA   length = 74
FEATURE                 Location/Qualifiers
misc_feature            1..74
                        note = (CCG)9-UTR
source                  1..74
                        mol_type = other RNA
                        organism = synthetic construct
SEQUENCE: 282
gggaaataag agagaaaaga agagtaagaa gaaatataag accgccgccg ccgccgccgc      60
cgccgccggc cacc                                                        74

SEQ ID NO: 283          moltype = RNA   length = 74
FEATURE                 Location/Qualifiers
misc_feature            1..74
                        note = (CCG)9-1-UTR
source                  1..74
                        mol_type = other RNA
                        organism = synthetic construct
SEQUENCE: 283
gggaaataag agagaaaaga agagtaagaa gaaatataag ccgccgccgc cgccgccgcc      60
gccgccgagc cacc                                                        74

SEQ ID NO: 284          moltype = RNA   length = 74
FEATURE                 Location/Qualifiers
misc_feature            1..74
                        note = (CCG)9-2-UTR
source                  1..74
                        mol_type = other RNA
                        organism = synthetic construct
SEQUENCE: 284
gggaaataag agagaaaaga agagtaagaa gaaatataac cgccgccgcc gccgccgccg      60
ccgccggagc cacc                                                        74

SEQ ID NO: 285          moltype = RNA   length = 74
FEATURE                 Location/Qualifiers
misc_feature            1..74
                        note = (CCG)9-3-UTR
source                  1..74
                        mol_type = other RNA
                        organism = synthetic construct
SEQUENCE: 285
gggaaataag agagaaaaga agagtaagaa gaaatatacc gccgccgccg ccgccgccgc      60
cgccgagagc cacc                                                        74

SEQ ID NO: 286          moltype = RNA   length = 74
FEATURE                 Location/Qualifiers
misc_feature            1..74
                        note = (CCG)9-4-UTR
source                  1..74
                        mol_type = other RNA
                        organism = synthetic construct
SEQUENCE: 286
gggaaataag agagaaaaga agagtaagaa gaaatatccg ccgccgccgc cgccgccgcc      60
gccgaagagc cacc                                                        74
```

```
SEQ ID NO: 287            moltype = RNA   length = 74
FEATURE                   Location/Qualifiers
misc_feature              1..74
                          note = (CCG)9-5-UTR
source                    1..74
                          mol_type = other RNA
                          organism = synthetic construct
SEQUENCE: 287
gggaaataag agagaaaaga agagtaagaa gaaataccgc cgccgccgcc gccgccgccg    60
ccgtaagagc cacc                                                     74

SEQ ID NO: 288            moltype = RNA   length = 74
FEATURE                   Location/Qualifiers
misc_feature              1..74
                          note = (CCG)9-6-UTR
source                    1..74
                          mol_type = other RNA
                          organism = synthetic construct
SEQUENCE: 288
gggaaataag agagaaaaga agagtaagaa gaaatccgcc gccgccgccg ccgccgccgc    60
cgataagagc cacc                                                     74

SEQ ID NO: 289            moltype = RNA   length = 74
FEATURE                   Location/Qualifiers
misc_feature              1..74
                          note = (CCG)9-7-UTR
source                    1..74
                          mol_type = other RNA
                          organism = synthetic construct
SEQUENCE: 289
gggaaataag agagaaaaga agagtaagaa gaaaccgccg ccgccgccgc cgccgccgcc    60
gtataagagc cacc                                                     74

SEQ ID NO: 290            moltype = RNA   length = 74
FEATURE                   Location/Qualifiers
misc_feature              1..74
                          note = (CCG)9-8-UTR
source                    1..74
                          mol_type = other RNA
                          organism = synthetic construct
SEQUENCE: 290
gggaaataag agagaaaaga agagtaagaa gaaccgccgc cgccgccgcc gccgccgccg    60
atataagagc cacc                                                     74

SEQ ID NO: 291            moltype = RNA   length = 74
FEATURE                   Location/Qualifiers
misc_feature              1..74
                          note = (CCG)9-9-UTR
source                    1..74
                          mol_type = other RNA
                          organism = synthetic construct
SEQUENCE: 291
gggaaataag agagaaaaga agagtaagaa gaccgccgcc gccgccgccg ccgccgccga    60
atataagagc cacc                                                     74

SEQ ID NO: 292            moltype = RNA   length = 74
FEATURE                   Location/Qualifiers
misc_feature              1..74
                          note = (CCG)9-10-UTR
source                    1..74
                          mol_type = other RNA
                          organism = synthetic construct
SEQUENCE: 292
gggaaataag agagaaaaga agagtaagaa gccgccgccg ccgccgccgc cgccgccgaa    60
atataagagc cacc                                                     74

SEQ ID NO: 293            moltype = RNA   length = 74
FEATURE                   Location/Qualifiers
misc_feature              1..74
                          note = (CCG)9-11-UTR
source                    1..74
                          mol_type = other RNA
                          organism = synthetic construct
SEQUENCE: 293
gggaaataag agagaaaaga agagtaagaa ccgccgccgc cgccgccgcc gccgcggaa     60
atataagagc cacc                                                     74

SEQ ID NO: 294            moltype = RNA   length = 74
```

```
FEATURE                 Location/Qualifiers
misc_feature            1..74
                        note = (CCG)9-12-UTR
source                  1..74
                        mol_type = other RNA
                        organism = synthetic construct
SEQUENCE: 294
gggaaataag agagaaaaga agagtaagac cgccgccgcc gccgccgccg ccgccgagaa    60
atataagagc cacc                                                     74

SEQ ID NO: 295          moltype = RNA   length = 74
FEATURE                 Location/Qualifiers
misc_feature            1..74
                        note = (CCG)9-13-UTR
source                  1..74
                        mol_type = other RNA
                        organism = synthetic construct
SEQUENCE: 295
gggaaataag agagaaaaga agagtaagcc gccgccgccg ccgccgccgc cgccgaagaa    60
atataagagc cacc                                                     74

SEQ ID NO: 296          moltype = RNA   length = 74
FEATURE                 Location/Qualifiers
misc_feature            1..74
                        note = (CCG)9-14-UTR
source                  1..74
                        mol_type = other RNA
                        organism = synthetic construct
SEQUENCE: 296
gggaaataag agagaaaaga agagtaaccg ccgccgccgc cgccgccgcc gccggaagaa    60
atataagagc cacc                                                     74

SEQ ID NO: 297          moltype = RNA   length = 74
FEATURE                 Location/Qualifiers
misc_feature            1..74
                        note = (CCG)9-15-UTR
source                  1..74
                        mol_type = other RNA
                        organism = synthetic construct
SEQUENCE: 297
gggaaataag agagaaaaga agagtaccgc cgccgccgcc gccgccgccg ccgagaagaa    60
atataagagc cacc                                                     74

SEQ ID NO: 298          moltype = RNA   length = 74
FEATURE                 Location/Qualifiers
misc_feature            1..74
                        note = (CCG)9-16-UTR
source                  1..74
                        mol_type = other RNA
                        organism = synthetic construct
SEQUENCE: 298
gggaaataag agagaaaaga agagtccgcc gccgccgccg ccgccgccgc cgaagaagaa    60
atataagagc cacc                                                     74

SEQ ID NO: 299          moltype = RNA   length = 74
FEATURE                 Location/Qualifiers
misc_feature            1..74
                        note = (CCG)9-17-UTR
source                  1..74
                        mol_type = other RNA
                        organism = synthetic construct
SEQUENCE: 299
gggaaataag agagaaaaga agagccgccg ccgccgccgc cgccgccgcc gtaagaagaa    60
atataagagc cacc                                                     74

SEQ ID NO: 300          moltype = RNA   length = 74
FEATURE                 Location/Qualifiers
misc_feature            1..74
                        note = (CCG)9-18-UTR
source                  1..74
                        mol_type = other RNA
                        organism = synthetic construct
SEQUENCE: 300
gggaaataag agagaaaaga agaccgccgc cgccgccgcc gccgccgccg gtaagaagaa    60
atataagagc cacc                                                     74

SEQ ID NO: 301          moltype = RNA   length = 77
FEATURE                 Location/Qualifiers
misc_feature            1..77
```

```
                        note = (CCG)10-UTR
source                  1..77
                        mol_type = other RNA
                        organism = synthetic construct
SEQUENCE: 301
gggaaataag agagaaaaga agagtaagaa gaaatataag accgccgccg ccgccgccgc    60
cgccgccgcc ggccacc                                                  77

SEQ ID NO: 302          moltype = RNA   length = 77
FEATURE                 Location/Qualifiers
misc_feature            1..77
                        note = (CCG)10-1-UTR
source                  1..77
                        mol_type = other RNA
                        organism = synthetic construct
SEQUENCE: 302
gggaaataag agagaaaaga agagtaagaa gaaatataag ccgccgccgc cgccgccgcc    60
gccgccgccg agccacc                                                  77

SEQ ID NO: 303          moltype = RNA   length = 77
FEATURE                 Location/Qualifiers
misc_feature            1..77
                        note = (CCG)10-2-UTR
source                  1..77
                        mol_type = other RNA
                        organism = synthetic construct
SEQUENCE: 303
gggaaataag agagaaaaga agagtaagaa gaaatataac cgccgccgcc gccgccgccg    60
ccgccgccgg agccacc                                                  77

SEQ ID NO: 304          moltype = RNA   length = 77
FEATURE                 Location/Qualifiers
misc_feature            1..77
                        note = (CCG)10-3-UTR
source                  1..77
                        mol_type = other RNA
                        organism = synthetic construct
SEQUENCE: 304
gggaaataag agagaaaaga agagtaagaa gaaatatacc gccgccgccg ccgccgccgc    60
cgccgccgag agccacc                                                  77

SEQ ID NO: 305          moltype = RNA   length = 77
FEATURE                 Location/Qualifiers
misc_feature            1..77
                        note = (CCG)10-4-UTR
source                  1..77
                        mol_type = other RNA
                        organism = synthetic construct
SEQUENCE: 305
gggaaataag agagaaaaga agagtaagaa gaaatatccg ccgccgccgc cgccgccgcc    60
gccgccgaag agccacc                                                  77

SEQ ID NO: 306          moltype = RNA   length = 77
FEATURE                 Location/Qualifiers
misc_feature            1..77
                        note = (CCG)10-5-UTR
source                  1..77
                        mol_type = other RNA
                        organism = synthetic construct
SEQUENCE: 306
gggaaataag agagaaaaga agagtaagaa gaaataccgc cgccgccgcc gccgccgccg    60
ccgccgtaag agccacc                                                  77

SEQ ID NO: 307          moltype = RNA   length = 77
FEATURE                 Location/Qualifiers
misc_feature            1..77
                        note = (CCG)10-6-UTR
source                  1..77
                        mol_type = other RNA
                        organism = synthetic construct
SEQUENCE: 307
gggaaataag agagaaaaga agagtaagaa gaaatccgcc gccgccgccg ccgccgccgc    60
cgccgataag agccacc                                                  77

SEQ ID NO: 308          moltype = RNA   length = 77
FEATURE                 Location/Qualifiers
misc_feature            1..77
                        note = (CCG)10-7-UTR
source                  1..77
```

```
                         mol_type = other RNA
                         organism = synthetic construct
SEQUENCE: 308
gggaaataag agagaaaaga agagtaagaa gaaaccgccg ccgccgccgc cgccgccgcc    60
gccgtataag agccacc                                                  77

SEQ ID NO: 309           moltype = RNA   length = 77
FEATURE                  Location/Qualifiers
misc_feature             1..77
                         note = (CCG)10-8-UTR
source                   1..77
                         mol_type = other RNA
                         organism = synthetic construct
SEQUENCE: 309
gggaaataag agagaaaaga agagtaagaa gaaccgccgc cgccgccgcc gccgccgccg    60
ccgatataag agccacc                                                  77

SEQ ID NO: 310           moltype = RNA   length = 77
FEATURE                  Location/Qualifiers
misc_feature             1..77
                         note = (CCG)10-9-UTR
source                   1..77
                         mol_type = other RNA
                         organism = synthetic construct
SEQUENCE: 310
gggaaataag agagaaaaga agagtaagaa gaccgccgcc gccgccgccg ccgccgccgc    60
cgaatataag agccacc                                                  77

SEQ ID NO: 311           moltype = RNA   length = 77
FEATURE                  Location/Qualifiers
misc_feature             1..77
                         note = (CCG)10-10-UTR
source                   1..77
                         mol_type = other RNA
                         organism = synthetic construct
SEQUENCE: 311
gggaaataag agagaaaaga agagtaagaa gccgccgccg ccgccgccgc cgccgccgcc    60
gaaatataag agccacc                                                  77

SEQ ID NO: 312           moltype = RNA   length = 77
FEATURE                  Location/Qualifiers
misc_feature             1..77
                         note = (CCG)10-11-UTR
source                   1..77
                         mol_type = other RNA
                         organism = synthetic construct
SEQUENCE: 312
gggaaataag agagaaaaga agagtaagaa ccgccgccgc cgccgccgcc gccgccgccg    60
gaaatataag agccacc                                                  77

SEQ ID NO: 313           moltype = RNA   length = 77
FEATURE                  Location/Qualifiers
misc_feature             1..77
                         note = (CCG)10-12-UTR
source                   1..77
                         mol_type = other RNA
                         organism = synthetic construct
SEQUENCE: 313
gggaaataag agagaaaaga agagtaagac cgccgccgcc gccgccgccg ccgccgccga    60
gaaatataag agccacc                                                  77

SEQ ID NO: 314           moltype = RNA   length = 77
FEATURE                  Location/Qualifiers
misc_feature             1..77
                         note = (CCG)10-13-UTR
source                   1..77
                         mol_type = other RNA
                         organism = synthetic construct
SEQUENCE: 314
gggaaataag agagaaaaga agagtaagcc gccgccgccg ccgccgccgc cgccgccgaa    60
gaaatataag agccacc                                                  77

SEQ ID NO: 315           moltype = RNA   length = 77
FEATURE                  Location/Qualifiers
misc_feature             1..77
                         note = (CCG)10-14-UTR
source                   1..77
                         mol_type = other RNA
                         organism = synthetic construct
```

```
                              -continued

SEQUENCE: 315
gggaaataag agagaaaaga agagtaaccg ccgccgccgc cgccgccgcc gccgccggaa    60
gaaatataag agccacc                                                  77

SEQ ID NO: 316          moltype = RNA   length = 77
FEATURE                 Location/Qualifiers
misc_feature            1..77
                        note = (CCG)10-15-UTR
source                  1..77
                        mol_type = other RNA
                        organism = synthetic construct
SEQUENCE: 316
gggaaataag agagaaaaga agagtaccgc cgccgccgcc gccgccgccg ccgccgagaa    60
gaaatataag agccacc                                                  77

SEQ ID NO: 317          moltype = RNA   length = 77
FEATURE                 Location/Qualifiers
misc_feature            1..77
                        note = (CCG)10-16-UTR
source                  1..77
                        mol_type = other RNA
                        organism = synthetic construct
SEQUENCE: 317
gggaaataag agagaaaaga agagtccgcc gccgccgccg ccgccgccgc cgccgaagaa    60
gaaatataag agccacc                                                  77

SEQ ID NO: 318          moltype = RNA   length = 77
FEATURE                 Location/Qualifiers
misc_feature            1..77
                        note = (CCG)10-17-UTR
source                  1..77
                        mol_type = other RNA
                        organism = synthetic construct
SEQUENCE: 318
gggaaataag agagaaaaga agagccgccg ccgccgccgc cgccgccgcc gccgtaagaa    60
gaaatataag agccacc                                                  77

SEQ ID NO: 319          moltype = RNA   length = 77
FEATURE                 Location/Qualifiers
misc_feature            1..77
                        note = (CCG)10-18-UTR
source                  1..77
                        mol_type = other RNA
                        organism = synthetic construct
SEQUENCE: 319
gggaaataag agagaaaaga agaccgccgc cgccgccgcc gccgccgccg ccggtaagaa    60
gaaatataag agccacc                                                  77

SEQ ID NO: 320          moltype = RNA   length = 56
FEATURE                 Location/Qualifiers
misc_feature            1..56
                        note = (GCC)3-UTR
source                  1..56
                        mol_type = other RNA
                        organism = synthetic construct
SEQUENCE: 320
gggaaataag agagaaaaga agagtaagaa gaaatataag agccgccgcc gccacc        56

SEQ ID NO: 321          moltype = RNA   length = 56
FEATURE                 Location/Qualifiers
misc_feature            1..56
                        note = (GCC)3-1-UTR
source                  1..56
                        mol_type = other RNA
                        organism = synthetic construct
SEQUENCE: 321
gggaaataag agagaaaaga agagtaagaa gaaatataag gccgccgcca gccacc        56

SEQ ID NO: 322          moltype = RNA   length = 56
FEATURE                 Location/Qualifiers
misc_feature            1..56
                        note = (GCC)3-2-UTR
source                  1..56
                        mol_type = other RNA
                        organism = synthetic construct
SEQUENCE: 322
gggaaataag agagaaaaga agagtaagaa gaaatataag ccgccgccga gccacc        56

SEQ ID NO: 323          moltype = RNA   length = 56
```

```
FEATURE                 Location/Qualifiers
misc_feature            1..56
                        note = (GCC)3-3-UTR
source                  1..56
                        mol_type = other RNA
                        organism = synthetic construct
SEQUENCE: 323
gggaaataag agagaaaaga agagtaagaa gaaatatagc cgccgccaga gccacc        56

SEQ ID NO: 324          moltype = RNA   length = 56
FEATURE                 Location/Qualifiers
misc_feature            1..56
                        note = (GCC)3-4-UTR
source                  1..56
                        mol_type = other RNA
                        organism = synthetic construct
SEQUENCE: 324
gggaaataag agagaaaaga agagtaagaa gaaatatgcc gccgccaaga gccacc        56

SEQ ID NO: 325          moltype = RNA   length = 56
FEATURE                 Location/Qualifiers
misc_feature            1..56
                        note = (GCC)3-5-UTR
source                  1..56
                        mol_type = other RNA
                        organism = synthetic construct
SEQUENCE: 325
gggaaataag agagaaaaga agagtaagaa gaaatagccg ccgcctaaga gccacc        56

SEQ ID NO: 326          moltype = RNA   length = 56
FEATURE                 Location/Qualifiers
misc_feature            1..56
                        note = (GCC)3-6-UTR
source                  1..56
                        mol_type = other RNA
                        organism = synthetic construct
SEQUENCE: 326
gggaaataag agagaaaaga agagtaagaa gaaatgccgc cgccataaga gccacc        56

SEQ ID NO: 327          moltype = RNA   length = 56
FEATURE                 Location/Qualifiers
misc_feature            1..56
                        note = (GCC)3-7-UTR
source                  1..56
                        mol_type = other RNA
                        organism = synthetic construct
SEQUENCE: 327
gggaaataag agagaaaaga agagtaagaa gaaagccgcc gcctataaga gccacc        56

SEQ ID NO: 328          moltype = RNA   length = 56
FEATURE                 Location/Qualifiers
misc_feature            1..56
                        note = (GCC)3-8-UTR
source                  1..56
                        mol_type = other RNA
                        organism = synthetic construct
SEQUENCE: 328
gggaaataag agagaaaaga agagtaagaa gaagccgccg ccatataaga gccacc        56

SEQ ID NO: 329          moltype = RNA   length = 56
FEATURE                 Location/Qualifiers
misc_feature            1..56
                        note = (GCC)3-9-UTR
source                  1..56
                        mol_type = other RNA
                        organism = synthetic construct
SEQUENCE: 329
gggaaataag agagaaaaga agagtaagaa gagccgccgc caatataaga gccacc        56

SEQ ID NO: 330          moltype = RNA   length = 56
FEATURE                 Location/Qualifiers
misc_feature            1..56
                        note = (GCC)3-10-UTR
source                  1..56
                        mol_type = other RNA
                        organism = synthetic construct
SEQUENCE: 330
gggaaataag agagaaaaga agagtaagaa ggccgccgcc aaatataaga gccacc        56
```

```
SEQ ID NO: 331           moltype = RNA  length = 56
FEATURE                  Location/Qualifiers
misc_feature             1..56
                         note = (GCC)3-11-UTR
source                   1..56
                         mol_type = other RNA
                         organism = synthetic construct
SEQUENCE: 331
gggaaataag agagaaaaga agagtaagaa gccgccgccg aaatataaga gccacc         56

SEQ ID NO: 332           moltype = RNA  length = 56
FEATURE                  Location/Qualifiers
misc_feature             1..56
                         note = (GCC)3-12-UTR
source                   1..56
                         mol_type = other RNA
                         organism = synthetic construct
SEQUENCE: 332
gggaaataag agagaaaaga agagtaagag ccgccgccag aaatataaga gccacc         56

SEQ ID NO: 333           moltype = RNA  length = 56
FEATURE                  Location/Qualifiers
misc_feature             1..56
                         note = (GCC)3-13-UTR
source                   1..56
                         mol_type = other RNA
                         organism = synthetic construct
SEQUENCE: 333
gggaaataag agagaaaaga agagtaaggc cgccgccaag aaatataaga gccacc         56

SEQ ID NO: 334           moltype = RNA  length = 56
FEATURE                  Location/Qualifiers
misc_feature             1..56
                         note = (GCC)3-14-UTR
source                   1..56
                         mol_type = other RNA
                         organism = synthetic construct
SEQUENCE: 334
gggaaataag agagaaaaga agagtaagcc gccgccgaag aaatataaga gccacc         56

SEQ ID NO: 335           moltype = RNA  length = 56
FEATURE                  Location/Qualifiers
misc_feature             1..56
                         note = (GCC)3-15-UTR
source                   1..56
                         mol_type = other RNA
                         organism = synthetic construct
SEQUENCE: 335
gggaaataag agagaaaaga agagtagccg ccgccagaag aaatataaga gccacc         56

SEQ ID NO: 336           moltype = RNA  length = 56
FEATURE                  Location/Qualifiers
misc_feature             1..56
                         note = (GCC)3-16-UTR
source                   1..56
                         mol_type = other RNA
                         organism = synthetic construct
SEQUENCE: 336
gggaaataag agagaaaaga agagtgccgc cgccaagaag aaatataaga gccacc         56

SEQ ID NO: 337           moltype = RNA  length = 56
FEATURE                  Location/Qualifiers
misc_feature             1..56
                         note = (GCC)3-17-UTR
source                   1..56
                         mol_type = other RNA
                         organism = synthetic construct
SEQUENCE: 337
gggaaataag agagaaaaga agaggccgcc gcctaagaag aaatataaga gccacc         56

SEQ ID NO: 338           moltype = RNA  length = 56
FEATURE                  Location/Qualifiers
misc_feature             1..56
                         note = (GCC)3-18-UTR
source                   1..56
                         mol_type = other RNA
                         organism = synthetic construct
SEQUENCE: 338
gggaaataag agagaaaaga agagccgccg ccgtaagaag aaatataaga gccacc         56
```

```
SEQ ID NO: 339          moltype = RNA   length = 59
FEATURE                 Location/Qualifiers
misc_feature            1..59
                        note = (GCC)4-UTR
source                  1..59
                        mol_type = other RNA
                        organism = synthetic construct
SEQUENCE: 339
gggaaataag agagaaaaga agagtaagaa gaaatataag agccgccgcc gccgccacc    59

SEQ ID NO: 340          moltype = RNA   length = 59
FEATURE                 Location/Qualifiers
misc_feature            1..59
                        note = (GCC)4-1-UTR
source                  1..59
                        mol_type = other RNA
                        organism = synthetic construct
SEQUENCE: 340
gggaaataag agagaaaaga agagtaagaa gaaatataag gccgccgccg ccagccacc    59

SEQ ID NO: 341          moltype = RNA   length = 59
FEATURE                 Location/Qualifiers
misc_feature            1..59
                        note = (GCC)4-2-UTR
source                  1..59
                        mol_type = other RNA
                        organism = synthetic construct
SEQUENCE: 341
gggaaataag agagaaaaga agagtaagaa gaaatataag ccgccgccgc cgagccacc    59

SEQ ID NO: 342          moltype = RNA   length = 59
FEATURE                 Location/Qualifiers
misc_feature            1..59
                        note = (GCC)4-3-UTR
source                  1..59
                        mol_type = other RNA
                        organism = synthetic construct
SEQUENCE: 342
gggaaataag agagaaaaga agagtaagaa gaaatatagc cgccgccgcc agagccacc    59

SEQ ID NO: 343          moltype = RNA   length = 59
FEATURE                 Location/Qualifiers
misc_feature            1..59
                        note = (GCC)4-4-UTR
source                  1..59
                        mol_type = other RNA
                        organism = synthetic construct
SEQUENCE: 343
gggaaataag agagaaaaga agagtaagaa gaaatatgcc gccgccgcca agagccacc    59

SEQ ID NO: 344          moltype = RNA   length = 59
FEATURE                 Location/Qualifiers
misc_feature            1..59
                        note = (GCC)4-5-UTR
source                  1..59
                        mol_type = other RNA
                        organism = synthetic construct
SEQUENCE: 344
gggaaataag agagaaaaga agagtaagaa gaaatagccg ccgccgccta agagccacc    59

SEQ ID NO: 345          moltype = RNA   length = 59
FEATURE                 Location/Qualifiers
misc_feature            1..59
                        note = (GCC)4-6-UTR
source                  1..59
                        mol_type = other RNA
                        organism = synthetic construct
SEQUENCE: 345
gggaaataag agagaaaaga agagtaagaa gaaatgccgc cgccgccata agagccacc    59

SEQ ID NO: 346          moltype = RNA   length = 59
FEATURE                 Location/Qualifiers
misc_feature            1..59
                        note = (GCC)4-7-UTR
source                  1..59
                        mol_type = other RNA
                        organism = synthetic construct
SEQUENCE: 346
```

```
gggaaataag agagaaaaga agagtaagaa gaaagccgcc gccgcctata agagccacc      59

SEQ ID NO: 347          moltype = RNA   length = 59
FEATURE                 Location/Qualifiers
misc_feature            1..59
                        note = (GCC)4-8-UTR
source                  1..59
                        mol_type = other RNA
                        organism = synthetic construct
SEQUENCE: 347
gggaaataag agagaaaaga agagtaagaa gaagccgccg ccgccatata agagccacc      59

SEQ ID NO: 348          moltype = RNA   length = 59
FEATURE                 Location/Qualifiers
misc_feature            1..59
                        note = (GCC)4-9-UTR
source                  1..59
                        mol_type = other RNA
                        organism = synthetic construct
SEQUENCE: 348
gggaaataag agagaaaaga agagtaagaa gagccgccgc cgccaatata agagccacc      59

SEQ ID NO: 349          moltype = RNA   length = 59
FEATURE                 Location/Qualifiers
misc_feature            1..59
                        note = (GCC)4-10-UTR
source                  1..59
                        mol_type = other RNA
                        organism = synthetic construct
SEQUENCE: 349
gggaaataag agagaaaaga agagtaagaa ggccgccgcc gccaaatata agagccacc      59

SEQ ID NO: 350          moltype = RNA   length = 59
FEATURE                 Location/Qualifiers
misc_feature            1..59
                        note = (GCC)4-11-UTR
source                  1..59
                        mol_type = other RNA
                        organism = synthetic construct
SEQUENCE: 350
gggaaataag agagaaaaga agagtaagaa gccgccgccg ccgaaatata agagccacc      59

SEQ ID NO: 351          moltype = RNA   length = 59
FEATURE                 Location/Qualifiers
misc_feature            1..59
                        note = (GCC)4-12-UTR
source                  1..59
                        mol_type = other RNA
                        organism = synthetic construct
SEQUENCE: 351
gggaaataag agagaaaaga agagtaagag ccgccgccgc cagaaatata agagccacc      59

SEQ ID NO: 352          moltype = RNA   length = 59
FEATURE                 Location/Qualifiers
misc_feature            1..59
                        note = (GCC)4-13-UTR
source                  1..59
                        mol_type = other RNA
                        organism = synthetic construct
SEQUENCE: 352
gggaaataag agagaaaaga agagtaaggc cgccgccgcc aagaaatata agagccacc      59

SEQ ID NO: 353          moltype = RNA   length = 59
FEATURE                 Location/Qualifiers
misc_feature            1..59
                        note = (GCC)4-14-UTR
source                  1..59
                        mol_type = other RNA
                        organism = synthetic construct
SEQUENCE: 353
gggaaataag agagaaaaga agagtaagcc gccgccgccg aagaaatata agagccacc      59

SEQ ID NO: 354          moltype = RNA   length = 59
FEATURE                 Location/Qualifiers
misc_feature            1..59
                        note = (GCC)4-15-UTR
source                  1..59
                        mol_type = other RNA
                        organism = synthetic construct
```

```
SEQUENCE: 354
gggaaataag agagaaaaga agagtagccg ccgccgccag aagaaatata agagccacc    59

SEQ ID NO: 355          moltype = RNA    length = 59
FEATURE                 Location/Qualifiers
misc_feature            1..59
                        note = (GCC)4-16-UTR
source                  1..59
                        mol_type = other RNA
                        organism = synthetic construct
SEQUENCE: 355
gggaaataag agagaaaaga agagtgccgc cgccgccaag aagaaatata agagccacc    59

SEQ ID NO: 356          moltype = RNA    length = 59
FEATURE                 Location/Qualifiers
misc_feature            1..59
                        note = (GCC)4-17-UTR
source                  1..59
                        mol_type = other RNA
                        organism = synthetic construct
SEQUENCE: 356
gggaaataag agagaaaaga agaggccgcc gccgcctaag aagaaatata agagccacc    59

SEQ ID NO: 357          moltype = RNA    length = 59
FEATURE                 Location/Qualifiers
misc_feature            1..59
                        note = (GCC)4-18-UTR
source                  1..59
                        mol_type = other RNA
                        organism = synthetic construct
SEQUENCE: 357
gggaaataag agagaaaaga agagccgccg ccgccgtaag aagaaatata agagccacc    59

SEQ ID NO: 358          moltype = RNA    length = 62
FEATURE                 Location/Qualifiers
misc_feature            1..62
                        note = (GCC)5-UTR
source                  1..62
                        mol_type = other RNA
                        organism = synthetic construct
SEQUENCE: 358
gggaaataag agagaaaaga agagtaagaa gaaatataag agccgccgcc gccgccgcca    60
cc                                                                  62

SEQ ID NO: 359          moltype = RNA    length = 62
FEATURE                 Location/Qualifiers
misc_feature            1..62
                        note = (GCC)5-1-UTR
source                  1..62
                        mol_type = other RNA
                        organism = synthetic construct
SEQUENCE: 359
gggaaataag agagaaaaga agagtaagaa gaaatataag gccgccgccg ccgccagcca    60
cc                                                                  62

SEQ ID NO: 360          moltype = RNA    length = 62
FEATURE                 Location/Qualifiers
misc_feature            1..62
                        note = (GCC)5-2-UTR
source                  1..62
                        mol_type = other RNA
                        organism = synthetic construct
SEQUENCE: 360
gggaaataag agagaaaaga agagtaagaa gaaatataag ccgccgccgc cgccgagcca    60
cc                                                                  62

SEQ ID NO: 361          moltype = RNA    length = 62
FEATURE                 Location/Qualifiers
misc_feature            1..62
                        note = (GCC)5-3-UTR
source                  1..62
                        mol_type = other RNA
                        organism = synthetic construct
SEQUENCE: 361
gggaaataag agagaaaaga agagtaagaa gaaatatagc cgccgccgcc gccagagcca    60
cc                                                                  62

SEQ ID NO: 362          moltype = RNA    length = 62
FEATURE                 Location/Qualifiers
```

```
misc_feature           1..62
                       note = (GCC)5-4-UTR
source                 1..62
                       mol_type = other RNA
                       organism = synthetic construct
SEQUENCE: 362
gggaaataag agagaaaaga agagtaagaa gaaatatgcc gccgccgccg ccaagagcca   60
cc                                                                 62

SEQ ID NO: 363         moltype = RNA  length = 62
FEATURE                Location/Qualifiers
misc_feature           1..62
                       note = (GCC)5-5-UTR
source                 1..62
                       mol_type = other RNA
                       organism = synthetic construct
SEQUENCE: 363
gggaaataag agagaaaaga agagtaagaa gaaatagccg ccgccgccgc ctaagagcca   60
cc                                                                 62

SEQ ID NO: 364         moltype = RNA  length = 62
FEATURE                Location/Qualifiers
misc_feature           1..62
                       note = (GCC)5-6-UTR
source                 1..62
                       mol_type = other RNA
                       organism = synthetic construct
SEQUENCE: 364
gggaaataag agagaaaaga agagtaagaa gaaatgccgc cgccgccgcc ataagagcca   60
cc                                                                 62

SEQ ID NO: 365         moltype = RNA  length = 62
FEATURE                Location/Qualifiers
misc_feature           1..62
                       note = (GCC)5-7-UTR
source                 1..62
                       mol_type = other RNA
                       organism = synthetic construct
SEQUENCE: 365
gggaaataag agagaaaaga agagtaagaa gaaagccgcc gccgccgcct ataagagcca   60
cc                                                                 62

SEQ ID NO: 366         moltype = RNA  length = 62
FEATURE                Location/Qualifiers
misc_feature           1..62
                       note = (GCC)5-8-UTR
source                 1..62
                       mol_type = other RNA
                       organism = synthetic construct
SEQUENCE: 366
gggaaataag agagaaaaga agagtaagaa gaagccgccg ccgccgccat ataagagcca   60
cc                                                                 62

SEQ ID NO: 367         moltype = RNA  length = 62
FEATURE                Location/Qualifiers
misc_feature           1..62
                       note = (GCC)5-9-UTR
source                 1..62
                       mol_type = other RNA
                       organism = synthetic construct
SEQUENCE: 367
gggaaataag agagaaaaga agagtaagaa gagccgccgc cgccgccaat ataagagcca   60
cc                                                                 62

SEQ ID NO: 368         moltype = RNA  length = 62
FEATURE                Location/Qualifiers
misc_feature           1..62
                       note = (GCC)5-10-UTR
source                 1..62
                       mol_type = other RNA
                       organism = synthetic construct
SEQUENCE: 368
gggaaataag agagaaaaga agagtaagaa ggccgccgcc gccgccaaat ataagagcca   60
cc                                                                 62

SEQ ID NO: 369         moltype = RNA  length = 62
FEATURE                Location/Qualifiers
misc_feature           1..62
                       note = (GCC)5-11-UTR
```

```
                    source          1..62
                                    mol_type = other RNA
                                    organism = synthetic construct
SEQUENCE: 369
gggaaataag agagaaaaga agagtaagaa gccgccgccg ccgccgaaat ataagagcca     60
cc                                                                   62

SEQ ID NO: 370          moltype = RNA   length = 62
FEATURE                 Location/Qualifiers
misc_feature            1..62
                        note = (GCC)5-12-UTR
source                  1..62
                        mol_type = other RNA
                        organism = synthetic construct
SEQUENCE: 370
gggaaataag agagaaaaga agagtaagag ccgccgccgc cgccagaaat ataagagcca     60
cc                                                                   62

SEQ ID NO: 371          moltype = RNA   length = 62
FEATURE                 Location/Qualifiers
misc_feature            1..62
                        note = (GCC)5-13-UTR
source                  1..62
                        mol_type = other RNA
                        organism = synthetic construct
SEQUENCE: 371
gggaaataag agagaaaaga agagtaaggc cgccgccgcc gccaagaaat ataagagcca     60
cc                                                                   62

SEQ ID NO: 372          moltype = RNA   length = 62
FEATURE                 Location/Qualifiers
misc_feature            1..62
                        note = (GCC)5-14-UTR
source                  1..62
                        mol_type = other RNA
                        organism = synthetic construct
SEQUENCE: 372
gggaaataag agagaaaaga agagtaagcc gccgccgccg ccgaagaaat ataagagcca     60
cc                                                                   62

SEQ ID NO: 373          moltype = RNA   length = 62
FEATURE                 Location/Qualifiers
misc_feature            1..62
                        note = (GCC)5-15-UTR
source                  1..62
                        mol_type = other RNA
                        organism = synthetic construct
SEQUENCE: 373
gggaaataag agagaaaaga agagtagccg ccgccgccgc cagaagaaat ataagagcca     60
cc                                                                   62

SEQ ID NO: 374          moltype = RNA   length = 62
FEATURE                 Location/Qualifiers
misc_feature            1..62
                        note = (GCC)5-16-UTR
source                  1..62
                        mol_type = other RNA
                        organism = synthetic construct
SEQUENCE: 374
gggaaataag agagaaaaga agagtgccgc cgccgccgcc aagaagaaat ataagagcca     60
cc                                                                   62

SEQ ID NO: 375          moltype = RNA   length = 62
FEATURE                 Location/Qualifiers
misc_feature            1..62
                        note = (GCC)5-17-UTR
source                  1..62
                        mol_type = other RNA
                        organism = synthetic construct
SEQUENCE: 375
gggaaataag agagaaaaga agaggccgcc gccgccgcct aagaagaaat ataagagcca     60
cc                                                                   62

SEQ ID NO: 376          moltype = RNA   length = 62
FEATURE                 Location/Qualifiers
misc_feature            1..62
                        note = (GCC)5-18-UTR
source                  1..62
                        mol_type = other RNA
```

```
                        organism = synthetic construct
SEQUENCE: 376
gggaaataag agagaaaaga agagccgccg ccgccgccgt aagaagaaat ataagagcca    60
cc                                                                  62

SEQ ID NO: 377          moltype = RNA   length = 65
FEATURE                 Location/Qualifiers
misc_feature            1..65
                        note = (GCC)6-UTR
source                  1..65
                        mol_type = other RNA
                        organism = synthetic construct
SEQUENCE: 377
gggaaataag agagaaaaga agagtaagaa gaaatataag agccgccgcc gccgccgccg    60
ccacc                                                               65

SEQ ID NO: 378          moltype = RNA   length = 65
FEATURE                 Location/Qualifiers
misc_feature            1..65
                        note = (GCC)6-1-UTR
source                  1..65
                        mol_type = other RNA
                        organism = synthetic construct
SEQUENCE: 378
gggaaataag agagaaaaga agagtaagaa gaaatataag gccgccgccg ccgccgccag    60
ccacc                                                               65

SEQ ID NO: 379          moltype = RNA   length = 65
FEATURE                 Location/Qualifiers
misc_feature            1..65
                        note = (GCC)6-2-UTR
source                  1..65
                        mol_type = other RNA
                        organism = synthetic construct
SEQUENCE: 379
gggaaataag agagaaaaga agagtaagaa gaaatataag ccgccgccgc cgccgccgag    60
ccacc                                                               65

SEQ ID NO: 380          moltype = RNA   length = 65
FEATURE                 Location/Qualifiers
misc_feature            1..65
                        note = (GCC)6-3-UTR
source                  1..65
                        mol_type = other RNA
                        organism = synthetic construct
SEQUENCE: 380
gggaaataag agagaaaaga agagtaagaa gaaatatagc cgccgccgcc gccgccagag    60
ccacc                                                               65

SEQ ID NO: 381          moltype = RNA   length = 65
FEATURE                 Location/Qualifiers
misc_feature            1..65
                        note = (GCC)6-4-UTR
source                  1..65
                        mol_type = other RNA
                        organism = synthetic construct
SEQUENCE: 381
gggaaataag agagaaaaga agagtaagaa gaaatatgcc gccgccgccg ccgccaagag    60
ccacc                                                               65

SEQ ID NO: 382          moltype = RNA   length = 65
FEATURE                 Location/Qualifiers
misc_feature            1..65
                        note = (GCC)6-5-UTR
source                  1..65
                        mol_type = other RNA
                        organism = synthetic construct
SEQUENCE: 382
gggaaataag agagaaaaga agagtaagaa gaaatagccg ccgccgccgc cgcctaagag    60
ccacc                                                               65

SEQ ID NO: 383          moltype = RNA   length = 65
FEATURE                 Location/Qualifiers
misc_feature            1..65
                        note = (GCC)6-6-UTR
source                  1..65
                        mol_type = other RNA
                        organism = synthetic construct
SEQUENCE: 383
```

```
gggaaataag agagaaaaga agagtaagaa gaaatgccgc cgccgccgcc gccataagag    60
ccacc                                                               65

SEQ ID NO: 384          moltype = RNA   length = 65
FEATURE                 Location/Qualifiers
misc_feature            1..65
                        note = (GCC)6-7-UTR
source                  1..65
                        mol_type = other RNA
                        organism = synthetic construct
SEQUENCE: 384
gggaaataag agagaaaaga agagtaagaa gaaagccgcc gccgccgccg cctataagag    60
ccacc                                                               65

SEQ ID NO: 385          moltype = RNA   length = 65
FEATURE                 Location/Qualifiers
misc_feature            1..65
                        note = (GCC)6-8-UTR
source                  1..65
                        mol_type = other RNA
                        organism = synthetic construct
SEQUENCE: 385
gggaaataag agagaaaaga agagtaagaa gaagccgccg ccgccgccgc catataagag    60
ccacc                                                               65

SEQ ID NO: 386          moltype = RNA   length = 65
FEATURE                 Location/Qualifiers
misc_feature            1..65
                        note = (GCC)6-9-UTR
source                  1..65
                        mol_type = other RNA
                        organism = synthetic construct
SEQUENCE: 386
gggaaataag agagaaaaga agagtaagaa gagccgccgc cgccgccgcc aatataagag    60
ccacc                                                               65

SEQ ID NO: 387          moltype = RNA   length = 65
FEATURE                 Location/Qualifiers
misc_feature            1..65
                        note = (GCC)6-10-UTR
source                  1..65
                        mol_type = other RNA
                        organism = synthetic construct
SEQUENCE: 387
gggaaataag agagaaaaga agagtaagaa ggccgccgcc gccgccgcca aatataagag    60
ccacc                                                               65

SEQ ID NO: 388          moltype = RNA   length = 65
FEATURE                 Location/Qualifiers
misc_feature            1..65
                        note = (GCC)6-11-UTR
source                  1..65
                        mol_type = other RNA
                        organism = synthetic construct
SEQUENCE: 388
gggaaataag agagaaaaga agagtaagaa gccgccgccg ccgccgccga aatataagag    60
ccacc                                                               65

SEQ ID NO: 389          moltype = RNA   length = 65
FEATURE                 Location/Qualifiers
misc_feature            1..65
                        note = (GCC)6-12-UTR
source                  1..65
                        mol_type = other RNA
                        organism = synthetic construct
SEQUENCE: 389
gggaaataag agagaaaaga agagtaagag ccgccgccgc cgccgccaga aatataagag    60
ccacc                                                               65

SEQ ID NO: 390          moltype = RNA   length = 65
FEATURE                 Location/Qualifiers
misc_feature            1..65
                        note = (GCC)6-13-UTR
source                  1..65
                        mol_type = other RNA
                        organism = synthetic construct
SEQUENCE: 390
gggaaataag agagaaaaga agagtaaggc cgccgccgcc gccgccaaga aatataagag    60
ccacc                                                               65
```

```
SEQ ID NO: 391         moltype = RNA   length = 65
FEATURE                Location/Qualifiers
misc_feature           1..65
                       note = (GCC)6-14-UTR
source                 1..65
                       mol_type = other RNA
                       organism = synthetic construct
SEQUENCE: 391
gggaaataag agagaaaaga agagtaagcc gccgccgccg ccgccgaaga aatataagag    60
ccacc                                                               65

SEQ ID NO: 392         moltype = RNA   length = 65
FEATURE                Location/Qualifiers
misc_feature           1..65
                       note = (GCC)6-15-UTR
source                 1..65
                       mol_type = other RNA
                       organism = synthetic construct
SEQUENCE: 392
gggaaataag agagaaaaga agagtagccg ccgccgccgc cgccagaaga aatataagag    60
ccacc                                                               65

SEQ ID NO: 393         moltype = RNA   length = 65
FEATURE                Location/Qualifiers
misc_feature           1..65
                       note = (GCC)6-16-UTR
source                 1..65
                       mol_type = other RNA
                       organism = synthetic construct
SEQUENCE: 393
gggaaataag agagaaaaga agagtgccgc cgccgccgcc gccaagaaga aatataagag    60
ccacc                                                               65

SEQ ID NO: 394         moltype = RNA   length = 65
FEATURE                Location/Qualifiers
misc_feature           1..65
                       note = (GCC)6-17-UTR
source                 1..65
                       mol_type = other RNA
                       organism = synthetic construct
SEQUENCE: 394
gggaaataag agagaaaaga agaggccgcc gccgccgccg cctaagaaga aatataagag    60
ccacc                                                               65

SEQ ID NO: 395         moltype = RNA   length = 65
FEATURE                Location/Qualifiers
misc_feature           1..65
                       note = (GCC)6-18-UTR
source                 1..65
                       mol_type = other RNA
                       organism = synthetic construct
SEQUENCE: 395
gggaaataag agagaaaaga agagccgccg ccgccgccgc cgtaagaaga aatataagag    60
ccacc                                                               65

SEQ ID NO: 396         moltype = RNA   length = 68
FEATURE                Location/Qualifiers
misc_feature           1..68
                       note = (GCC)7-UTR
source                 1..68
                       mol_type = other RNA
                       organism = synthetic construct
SEQUENCE: 396
gggaaataag agagaaaaga agagtaagaa gaaatataag agccgccgcc gccgccgccg    60
ccgccacc                                                            68

SEQ ID NO: 397         moltype = RNA   length = 68
FEATURE                Location/Qualifiers
misc_feature           1..68
                       note = (GCC)7-1-UTR
source                 1..68
                       mol_type = other RNA
                       organism = synthetic construct
SEQUENCE: 397
gggaaataag agagaaaaga agagtaagaa gaaatataag gccgccgccg ccgccgccgc    60
cagccacc                                                            68

SEQ ID NO: 398         moltype = RNA   length = 68
```

```
FEATURE            Location/Qualifiers
misc_feature       1..68
                   note = (GCC)7-2-UTR
source             1..68
                   mol_type = other RNA
                   organism = synthetic construct
SEQUENCE: 398
gggaaataag agagaaaaga agagtaagaa gaaatataag ccgccgccgc cgccgccgcc    60
gagccacc                                                            68

SEQ ID NO: 399     moltype = RNA   length = 68
FEATURE            Location/Qualifiers
misc_feature       1..68
                   note = (GCC)7-3-UTR
source             1..68
                   mol_type = other RNA
                   organism = synthetic construct
SEQUENCE: 399
gggaaataag agagaaaaga agagtaagaa gaaatatagc cgccgccgcc gccgccgcca    60
gagccacc                                                            68

SEQ ID NO: 400     moltype = RNA   length = 68
FEATURE            Location/Qualifiers
misc_feature       1..68
                   note = (GCC)7-4-UTR
source             1..68
                   mol_type = other RNA
                   organism = synthetic construct
SEQUENCE: 400
gggaaataag agagaaaaga agagtaagaa gaaatatgcc gccgccgccg ccgccgccaa    60
gagccacc                                                            68

SEQ ID NO: 401     moltype = RNA   length = 68
FEATURE            Location/Qualifiers
misc_feature       1..68
                   note = (GCC)7-5-UTR
source             1..68
                   mol_type = other RNA
                   organism = synthetic construct
SEQUENCE: 401
gggaaataag agagaaaaga agagtaagaa gaaatagccg ccgccgccgc cgccgcctaa    60
gagccacc                                                            68

SEQ ID NO: 402     moltype = RNA   length = 68
FEATURE            Location/Qualifiers
misc_feature       1..68
                   note = (GCC)7-6-UTR
source             1..68
                   mol_type = other RNA
                   organism = synthetic construct
SEQUENCE: 402
gggaaataag agagaaaaga agagtaagaa gaaatgccgc cgccgccgcc gccgccataa    60
gagccacc                                                            68

SEQ ID NO: 403     moltype = RNA   length = 68
FEATURE            Location/Qualifiers
misc_feature       1..68
                   note = (GCC)7-7-UTR
source             1..68
                   mol_type = other RNA
                   organism = synthetic construct
SEQUENCE: 403
gggaaataag agagaaaaga agagtaagaa gaaagccgcc gccgccgccg ccgcctataa    60
gagccacc                                                            68

SEQ ID NO: 404     moltype = RNA   length = 68
FEATURE            Location/Qualifiers
misc_feature       1..68
                   note = (GCC)7-8-UTR
source             1..68
                   mol_type = other RNA
                   organism = synthetic construct
SEQUENCE: 404
gggaaataag agagaaaaga agagtaagaa gaagccgccg ccgccgccgc cgccatataa    60
gagccacc                                                            68

SEQ ID NO: 405     moltype = RNA   length = 68
FEATURE            Location/Qualifiers
misc_feature       1..68
```

```
                        note = (GCC)7-9-UTR
source                  1..68
                        mol_type = other RNA
                        organism = synthetic construct
SEQUENCE: 405
gggaaataag agagaaaaga agagtaagaa gagccgccgc cgccgccgcc gccaatataa    60
gagccacc                                                            68

SEQ ID NO: 406          moltype = RNA   length = 68
FEATURE                 Location/Qualifiers
misc_feature            1..68
                        note = (GCC)7-10-UTR
source                  1..68
                        mol_type = other RNA
                        organism = synthetic construct
SEQUENCE: 406
gggaaataag agagaaaaga agagtaagaa ggccgccgcc gccgccgccg ccaaatataa    60
gagccacc                                                            68

SEQ ID NO: 407          moltype = RNA   length = 68
FEATURE                 Location/Qualifiers
misc_feature            1..68
                        note = (GCC)7-11-UTR
source                  1..68
                        mol_type = other RNA
                        organism = synthetic construct
SEQUENCE: 407
gggaaataag agagaaaaga agagtaagaa gccgccgccg ccgccgccgc cgaaatataa    60
gagccacc                                                            68

SEQ ID NO: 408          moltype = RNA   length = 68
FEATURE                 Location/Qualifiers
misc_feature            1..68
                        note = (GCC)7-12-UTR
source                  1..68
                        mol_type = other RNA
                        organism = synthetic construct
SEQUENCE: 408
gggaaataag agagaaaaga agagtaagag ccgccgccgc cgccgccgcc agaaatataa    60
gagccacc                                                            68

SEQ ID NO: 409          moltype = RNA   length = 68
FEATURE                 Location/Qualifiers
misc_feature            1..68
                        note = (GCC)7-13-UTR
source                  1..68
                        mol_type = other RNA
                        organism = synthetic construct
SEQUENCE: 409
gggaaataag agagaaaaga agagtaaggc cgccgccgcc gccgccgcca agaaatataa    60
gagccacc                                                            68

SEQ ID NO: 410          moltype = RNA   length = 68
FEATURE                 Location/Qualifiers
misc_feature            1..68
                        note = (GCC)7-14-UTR
source                  1..68
                        mol_type = other RNA
                        organism = synthetic construct
SEQUENCE: 410
gggaaataag agagaaaaga agagtaagcc gccgccgccg ccgccgccga agaaatataa    60
gagccacc                                                            68

SEQ ID NO: 411          moltype = RNA   length = 68
FEATURE                 Location/Qualifiers
misc_feature            1..68
                        note = (GCC)7-15-UTR
source                  1..68
                        mol_type = other RNA
                        organism = synthetic construct
SEQUENCE: 411
gggaaataag agagaaaaga agagtagccg ccgccgccgc cgccgccaga agaaatataa    60
gagccacc                                                            68

SEQ ID NO: 412          moltype = RNA   length = 68
FEATURE                 Location/Qualifiers
misc_feature            1..68
                        note = (GCC)7-16-UTR
source                  1..68
```

```
                            mol_type = other RNA
                            organism = synthetic construct
SEQUENCE: 412
gggaaataag agagaaaaga agagtgccgc cgccgccgcc gccgccaaga agaaatataa    60
gagccacc                                                            68

SEQ ID NO: 413              moltype = RNA   length = 68
FEATURE                     Location/Qualifiers
misc_feature                1..68
                            note = (GCC)7-17-UTR
source                      1..68
                            mol_type = other RNA
                            organism = synthetic construct
SEQUENCE: 413
gggaaataag agagaaaaga agaggccgcc gccgccgccg ccgcctaaga agaaatataa    60
gagccacc                                                            68

SEQ ID NO: 414              moltype = RNA   length = 68
FEATURE                     Location/Qualifiers
misc_feature                1..68
                            note = (GCC)7-18-UTR
source                      1..68
                            mol_type = other RNA
                            organism = synthetic construct
SEQUENCE: 414
gggaaataag agagaaaaga agagccgccg ccgccgccgc cgccgtaaga agaaatataa    60
gagccacc                                                            68

SEQ ID NO: 415              moltype = RNA   length = 71
FEATURE                     Location/Qualifiers
misc_feature                1..71
                            note = (GCC)8-UTR
source                      1..71
                            mol_type = other RNA
                            organism = synthetic construct
SEQUENCE: 415
gggaaataag agagaaaaga agagtaagaa gaaatataag agccgccgcc gccgccgccg    60
ccgccgccac c                                                        71

SEQ ID NO: 416              moltype = RNA   length = 71
FEATURE                     Location/Qualifiers
misc_feature                1..71
                            note = (GCC)8-1-UTR
source                      1..71
                            mol_type = other RNA
                            organism = synthetic construct
SEQUENCE: 416
gggaaataag agagaaaaga agagtaagaa gaaatataag gccgccgccg ccgccgccgc    60
cgccagccac c                                                        71

SEQ ID NO: 417              moltype = RNA   length = 71
FEATURE                     Location/Qualifiers
misc_feature                1..71
                            note = (GCC)8-2-UTR
source                      1..71
                            mol_type = other RNA
                            organism = synthetic construct
SEQUENCE: 417
gggaaataag agagaaaaga agagtaagaa gaaatataag ccgccgccgc cgccgccgcc    60
gccgagccac c                                                        71

SEQ ID NO: 418              moltype = RNA   length = 71
FEATURE                     Location/Qualifiers
misc_feature                1..71
                            note = (GCC)8-3-UTR
source                      1..71
                            mol_type = other RNA
                            organism = synthetic construct
SEQUENCE: 418
gggaaataag agagaaaaga agagtaagaa gaaatatagc cgccgccgcc gccgccgccg    60
ccagagccac c                                                        71

SEQ ID NO: 419              moltype = RNA   length = 71
FEATURE                     Location/Qualifiers
misc_feature                1..71
                            note = (GCC)8-4-UTR
source                      1..71
                            mol_type = other RNA
                            organism = synthetic construct
```

```
SEQUENCE: 419
gggaaataag agagaaaaga agagtaagaa gaaatatgcc gccgccgccg ccgccgccgc    60
caagagccac c                                                        71

SEQ ID NO: 420          moltype = RNA   length = 71
FEATURE                 Location/Qualifiers
misc_feature            1..71
                        note = (GCC)8-5-UTR
source                  1..71
                        mol_type = other RNA
                        organism = synthetic construct
SEQUENCE: 420
gggaaataag agagaaaaga agagtaagaa gaaatagccg ccgccgccgc cgccgccgcc    60
taagagccac c                                                        71

SEQ ID NO: 421          moltype = RNA   length = 71
FEATURE                 Location/Qualifiers
misc_feature            1..71
                        note = (GCC)8-6-UTR
source                  1..71
                        mol_type = other RNA
                        organism = synthetic construct
SEQUENCE: 421
gggaaataag agagaaaaga agagtaagaa gaaatgccgc cgccgccgcc gccgccgcca    60
taagagccac c                                                        71

SEQ ID NO: 422          moltype = RNA   length = 71
FEATURE                 Location/Qualifiers
misc_feature            1..71
                        note = (GCC)8-7-UTR
source                  1..71
                        mol_type = other RNA
                        organism = synthetic construct
SEQUENCE: 422
gggaaataag agagaaaaga agagtaagaa gaaagccgcc gccgccgccg ccgccgccta    60
taagagccac c                                                        71

SEQ ID NO: 423          moltype = RNA   length = 71
FEATURE                 Location/Qualifiers
misc_feature            1..71
                        note = (GCC)8-8-UTR
source                  1..71
                        mol_type = other RNA
                        organism = synthetic construct
SEQUENCE: 423
gggaaataag agagaaaaga agagtaagaa gaagccgccg ccgccgccgc cgccgccata    60
taagagccac c                                                        71

SEQ ID NO: 424          moltype = RNA   length = 71
FEATURE                 Location/Qualifiers
misc_feature            1..71
                        note = (GCC)8-9-UTR
source                  1..71
                        mol_type = other RNA
                        organism = synthetic construct
SEQUENCE: 424
gggaaataag agagaaaaga agagtaagaa gagccgccgc cgccgccgcc gccgccaata    60
taagagccac c                                                        71

SEQ ID NO: 425          moltype = RNA   length = 71
FEATURE                 Location/Qualifiers
misc_feature            1..71
                        note = (GCC)8-10-UTR
source                  1..71
                        mol_type = other RNA
                        organism = synthetic construct
SEQUENCE: 425
gggaaataag agagaaaaga agagtaagaa ggccgccgcc gccgccgccg ccgccaaata    60
taagagccac c                                                        71

SEQ ID NO: 426          moltype = RNA   length = 71
FEATURE                 Location/Qualifiers
misc_feature            1..71
                        note = (GCC)8-11-UTR
source                  1..71
                        mol_type = other RNA
                        organism = synthetic construct
SEQUENCE: 426
gggaaataag agagaaaaga agagtaagaa gccgccgccg ccgccgccgc cgccgaaata    60
```

```
taagagccac c                                                            71

SEQ ID NO: 427          moltype = RNA   length = 71
FEATURE                 Location/Qualifiers
misc_feature            1..71
                        note = (GCC)8-12-UTR
source                  1..71
                        mol_type = other RNA
                        organism = synthetic construct
SEQUENCE: 427
gggaaataag agagaaaaga agagtaagag ccgccgccgc cgccgccgcc gccagaaata      60
taagagccac c                                                            71

SEQ ID NO: 428          moltype = RNA   length = 71
FEATURE                 Location/Qualifiers
misc_feature            1..71
                        note = (GCC)8-13-UTR
source                  1..71
                        mol_type = other RNA
                        organism = synthetic construct
SEQUENCE: 428
gggaaataag agagaaaaga agagtaaggc cgccgccgcc gccgccgccg ccaagaaata      60
taagagccac c                                                            71

SEQ ID NO: 429          moltype = RNA   length = 71
FEATURE                 Location/Qualifiers
misc_feature            1..71
                        note = (GCC)8-14-UTR
source                  1..71
                        mol_type = other RNA
                        organism = synthetic construct
SEQUENCE: 429
gggaaataag agagaaaaga agagtaagcc gccgccgccg ccgccgccgc cgaagaaata      60
taagagccac c                                                            71

SEQ ID NO: 430          moltype = RNA   length = 71
FEATURE                 Location/Qualifiers
misc_feature            1..71
                        note = (GCC)8-15-UTR
source                  1..71
                        mol_type = other RNA
                        organism = synthetic construct
SEQUENCE: 430
gggaaataag agagaaaaga agagtagccg ccgccgccgc cgccgccgcc agaagaaata      60
taagagccac c                                                            71

SEQ ID NO: 431          moltype = RNA   length = 71
FEATURE                 Location/Qualifiers
misc_feature            1..71
                        note = (GCC)8-16-UTR
source                  1..71
                        mol_type = other RNA
                        organism = synthetic construct
SEQUENCE: 431
gggaaataag agagaaaaga agagtgccgc cgccgccgcc gccgccgcca agaagaaata      60
taagagccac c                                                            71

SEQ ID NO: 432          moltype = RNA   length = 71
FEATURE                 Location/Qualifiers
misc_feature            1..71
                        note = (GCC)8-17-UTR
source                  1..71
                        mol_type = other RNA
                        organism = synthetic construct
SEQUENCE: 432
gggaaataag agagaaaaga agaggccgcc gccgccgccg ccgccgccta agaagaaata      60
taagagccac c                                                            71

SEQ ID NO: 433          moltype = RNA   length = 71
FEATURE                 Location/Qualifiers
misc_feature            1..71
                        note = (GCC)8-18-UTR
source                  1..71
                        mol_type = other RNA
                        organism = synthetic construct
SEQUENCE: 433
gggaaataag agagaaaaga agagccgccg ccgccgccgc cgccgccgta agaagaaata      60
taagagccac c                                                            71
```

```
SEQ ID NO: 434          moltype = RNA   length = 74
FEATURE                 Location/Qualifiers
misc_feature            1..74
                        note = (GCC)9-UTR
source                  1..74
                        mol_type = other RNA
                        organism = synthetic construct
SEQUENCE: 434
gggaaataag agagaaaaga agagtaagaa gaaatataag agccgccgcc gccgccgccg      60
ccgccgccgc cacc                                                       74

SEQ ID NO: 435          moltype = RNA   length = 74
FEATURE                 Location/Qualifiers
misc_feature            1..74
                        note = (GCC)9-1-UTR
source                  1..74
                        mol_type = other RNA
                        organism = synthetic construct
SEQUENCE: 435
gggaaataag agagaaaaga agagtaagaa gaaatataag gccgccgccg ccgccgccgc      60
cgccgccagc cacc                                                       74

SEQ ID NO: 436          moltype = RNA   length = 74
FEATURE                 Location/Qualifiers
misc_feature            1..74
                        note = (GCC)9-2-UTR
source                  1..74
                        mol_type = other RNA
                        organism = synthetic construct
SEQUENCE: 436
gggaaataag agagaaaaga agagtaagaa gaaatataag ccgccgccgc cgccgccgcc      60
gccgccgagc cacc                                                       74

SEQ ID NO: 437          moltype = RNA   length = 74
FEATURE                 Location/Qualifiers
misc_feature            1..74
                        note = (GCC)9-3-UTR
source                  1..74
                        mol_type = other RNA
                        organism = synthetic construct
SEQUENCE: 437
gggaaataag agagaaaaga agagtaagaa gaaatatagc cgccgccgcc gccgccgccg      60
ccgccagagc cacc                                                       74

SEQ ID NO: 438          moltype = RNA   length = 74
FEATURE                 Location/Qualifiers
misc_feature            1..74
                        note = (GCC)9-4-UTR
source                  1..74
                        mol_type = other RNA
                        organism = synthetic construct
SEQUENCE: 438
gggaaataag agagaaaaga agagtaagaa gaaatatgcc gccgccgccg ccgccgccgc      60
cgccaagagc cacc                                                       74

SEQ ID NO: 439          moltype = RNA   length = 74
FEATURE                 Location/Qualifiers
misc_feature            1..74
                        note = (GCC)9-5-UTR
source                  1..74
                        mol_type = other RNA
                        organism = synthetic construct
SEQUENCE: 439
gggaaataag agagaaaaga agagtaagaa gaaatagccg ccgccgccgc cgccgccgcc      60
gcctaagagc cacc                                                       74

SEQ ID NO: 440          moltype = RNA   length = 74
FEATURE                 Location/Qualifiers
misc_feature            1..74
                        note = (GCC)9-6-UTR
source                  1..74
                        mol_type = other RNA
                        organism = synthetic construct
SEQUENCE: 440
gggaaataag agagaaaaga agagtaagaa gaaatgccgc cgccgccgcc gccgccgccg      60
ccataagagc cacc                                                       74

SEQ ID NO: 441          moltype = RNA   length = 74
FEATURE                 Location/Qualifiers
```

```
misc_feature          1..74
                      note = (GCC)9-7-UTR
source                1..74
                      mol_type = other RNA
                      organism = synthetic construct
SEQUENCE: 441
gggaaataag agagaaaaga agagtaagaa gaaagccgcc gccgccgccg ccgccgccgc    60
ctataagagc cacc                                                     74

SEQ ID NO: 442        moltype = RNA   length = 74
FEATURE               Location/Qualifiers
misc_feature          1..74
                      note = (GCC)9-8-UTR
source                1..74
                      mol_type = other RNA
                      organism = synthetic construct
SEQUENCE: 442
gggaaataag agagaaaaga agagtaagaa gaagccgccg ccgccgccgc cgccgccgcc    60
atataagagc cacc                                                     74

SEQ ID NO: 443        moltype = RNA   length = 74
FEATURE               Location/Qualifiers
misc_feature          1..74
                      note = (GCC)9-9-UTR
source                1..74
                      mol_type = other RNA
                      organism = synthetic construct
SEQUENCE: 443
gggaaataag agagaaaaga agagtaagaa gagccgccgc cgccgccgcc gccgccgcca    60
atataagagc cacc                                                     74

SEQ ID NO: 444        moltype = RNA   length = 74
FEATURE               Location/Qualifiers
misc_feature          1..74
                      note = (GCC)9-10-UTR
source                1..74
                      mol_type = other RNA
                      organism = synthetic construct
SEQUENCE: 444
gggaaataag agagaaaaga agagtaagaa ggccgccgcc gccgccgccg ccgccgccaa    60
atataagagc cacc                                                     74

SEQ ID NO: 445        moltype = RNA   length = 74
FEATURE               Location/Qualifiers
misc_feature          1..74
                      note = (GCC)9-11-UTR
source                1..74
                      mol_type = other RNA
                      organism = synthetic construct
SEQUENCE: 445
gggaaataag agagaaaaga agagtaagaa gccgccgccg ccgccgccgc cgccgccgaa    60
atataagagc cacc                                                     74

SEQ ID NO: 446        moltype = RNA   length = 74
FEATURE               Location/Qualifiers
misc_feature          1..74
                      note = (GCC)9-12-UTR
source                1..74
                      mol_type = other RNA
                      organism = synthetic construct
SEQUENCE: 446
gggaaataag agagaaaaga agagtaagag ccgccgccgc cgccgccgcc gccgccagaa    60
atataagagc cacc                                                     74

SEQ ID NO: 447        moltype = RNA   length = 74
FEATURE               Location/Qualifiers
misc_feature          1..74
                      note = (GCC)9-13-UTR
source                1..74
                      mol_type = other RNA
                      organism = synthetic construct
SEQUENCE: 447
gggaaataag agagaaaaga agagtaaggc cgccgccgcc gccgccgccg ccgccaagaa    60
atataagagc cacc                                                     74

SEQ ID NO: 448        moltype = RNA   length = 74
FEATURE               Location/Qualifiers
misc_feature          1..74
                      note = (GCC)9-14-UTR
```

```
source                  1..74
                        mol_type = other RNA
                        organism = synthetic construct
SEQUENCE: 448
gggaaataag agagaaaaga agagtaagcc gccgccgccg ccgccgccgc cgccgaagaa    60
atataagagc cacc                                                     74

SEQ ID NO: 449          moltype = RNA   length = 74
FEATURE                 Location/Qualifiers
misc_feature            1..74
                        note = (GCC)9-15-UTR
source                  1..74
                        mol_type = other RNA
                        organism = synthetic construct
SEQUENCE: 449
gggaaataag agagaaaaga agagtagccg ccgccgccgc cgccgccgcc gccagaagaa    60
atataagagc cacc                                                     74

SEQ ID NO: 450          moltype = RNA   length = 74
FEATURE                 Location/Qualifiers
misc_feature            1..74
                        note = (GCC)9-16-UTR
source                  1..74
                        mol_type = other RNA
                        organism = synthetic construct
SEQUENCE: 450
gggaaataag agagaaaaga agagtgccgc cgccgccgcc gccgccgccg ccaagaagaa    60
atataagagc cacc                                                     74

SEQ ID NO: 451          moltype = RNA   length = 74
FEATURE                 Location/Qualifiers
misc_feature            1..74
                        note = (GCC)9-17-UTR
source                  1..74
                        mol_type = other RNA
                        organism = synthetic construct
SEQUENCE: 451
gggaaataag agagaaaaga agaggccgcc gccgccgccg ccgccgccgc ctaagaagaa    60
atataagagc cacc                                                     74

SEQ ID NO: 452          moltype = RNA   length = 74
FEATURE                 Location/Qualifiers
misc_feature            1..74
                        note = (GCC)9-18-UTR
source                  1..74
                        mol_type = other RNA
                        organism = synthetic construct
SEQUENCE: 452
gggaaataag agagaaaaga agagccgccg ccgccgccgc cgccgccgcc gtaagaagaa    60
atataagagc cacc                                                     74

SEQ ID NO: 453          moltype = RNA   length = 77
FEATURE                 Location/Qualifiers
misc_feature            1..77
                        note = (GCC)10-UTR
source                  1..77
                        mol_type = other RNA
                        organism = synthetic construct
SEQUENCE: 453
gggaaataag agagaaaaga agagtaagaa gaaatataag agccgccgcc gccgccgccg    60
ccgccgccgc cgccacc                                                  77

SEQ ID NO: 454          moltype = RNA   length = 77
FEATURE                 Location/Qualifiers
misc_feature            1..77
                        note = (GCC)10-1-UTR
source                  1..77
                        mol_type = other RNA
                        organism = synthetic construct
SEQUENCE: 454
gggaaataag agagaaaaga agagtaagaa gaaatataag gccgccgccg ccgccgccgc    60
cgccgccgcc agccacc                                                  77

SEQ ID NO: 455          moltype = RNA   length = 77
FEATURE                 Location/Qualifiers
misc_feature            1..77
                        note = (GCC)10-2-UTR
source                  1..77
                        mol_type = other RNA
```

```
                              organism = synthetic construct
SEQUENCE: 455
gggaaataag agagaaaaga agagtaagaa gaaatataag ccgccgccgc cgccgccgcc    60
gccgccgccg agccacc                                                  77

SEQ ID NO: 456         moltype = RNA   length = 77
FEATURE                Location/Qualifiers
misc_feature           1..77
                       note = (GCC)10-3-UTR
source                 1..77
                       mol_type = other RNA
                       organism = synthetic construct
SEQUENCE: 456
gggaaataag agagaaaaga agagtaagaa gaaatatagc cgccgccgcc gccgccgccg    60
ccgccgccag agccacc                                                  77

SEQ ID NO: 457         moltype = RNA   length = 77
FEATURE                Location/Qualifiers
misc_feature           1..77
                       note = (GCC)10-4-UTR
source                 1..77
                       mol_type = other RNA
                       organism = synthetic construct
SEQUENCE: 457
gggaaataag agagaaaaga agagtaagaa gaaatatgcc gccgccgccg ccgccgccgc    60
cgccgccaag agccacc                                                  77

SEQ ID NO: 458         moltype = RNA   length = 77
FEATURE                Location/Qualifiers
misc_feature           1..77
                       note = (GCC)10-5-UTR
source                 1..77
                       mol_type = other RNA
                       organism = synthetic construct
SEQUENCE: 458
gggaaataag agagaaaaga agagtaagaa gaaatagccg ccgccgccgc cgccgccgcc    60
gccgcctaag agccacc                                                  77

SEQ ID NO: 459         moltype = RNA   length = 77
FEATURE                Location/Qualifiers
misc_feature           1..77
                       note = (GCC)10-6-UTR
source                 1..77
                       mol_type = other RNA
                       organism = synthetic construct
SEQUENCE: 459
gggaaataag agagaaaaga agagtaagaa gaaatgccgc cgccgccgcc gccgccgccg    60
ccgccataag agccacc                                                  77

SEQ ID NO: 460         moltype = RNA   length = 77
FEATURE                Location/Qualifiers
misc_feature           1..77
                       note = (GCC)10-7-UTR
source                 1..77
                       mol_type = other RNA
                       organism = synthetic construct
SEQUENCE: 460
gggaaataag agagaaaaga agagtaagaa gaaagccgcc gccgccgccg ccgccgccgc    60
cgcctataag agccacc                                                  77

SEQ ID NO: 461         moltype = RNA   length = 77
FEATURE                Location/Qualifiers
misc_feature           1..77
                       note = (GCC)10-8-UTR
source                 1..77
                       mol_type = other RNA
                       organism = synthetic construct
SEQUENCE: 461
gggaaataag agagaaaaga agagtaagaa gaagccgccg ccgccgccgc cgccgccgcc    60
gccatataag agccacc                                                  77

SEQ ID NO: 462         moltype = RNA   length = 77
FEATURE                Location/Qualifiers
misc_feature           1..77
                       note = (GCC)10-9-UTR
source                 1..77
                       mol_type = other RNA
                       organism = synthetic construct
SEQUENCE: 462
```

```
gggaaataag agagaaaaga agagtaagaa gagccgccgc cgccgccgcc gccgccgccg    60
ccaatataag agccacc                                                  77

SEQ ID NO: 463          moltype = RNA   length = 77
FEATURE                 Location/Qualifiers
misc_feature            1..77
                        note = (GCC)10-10-UTR
source                  1..77
                        mol_type = other RNA
                        organism = synthetic construct
SEQUENCE: 463
gggaaataag agagaaaaga agagtaagaa ggccgccgcc gccgccgccg ccgccgccgc    60
caaatataag agccacc                                                  77

SEQ ID NO: 464          moltype = RNA   length = 77
FEATURE                 Location/Qualifiers
misc_feature            1..77
                        note = (GCC)10-11-UTR
source                  1..77
                        mol_type = other RNA
                        organism = synthetic construct
SEQUENCE: 464
gggaaataag agagaaaaga agagtaagaa gccgccgccg ccgccgccgc cgccgccgcc    60
gaaatataag agccacc                                                  77

SEQ ID NO: 465          moltype = RNA   length = 77
FEATURE                 Location/Qualifiers
misc_feature            1..77
                        note = (GCC)10-12-UTR
source                  1..77
                        mol_type = other RNA
                        organism = synthetic construct
SEQUENCE: 465
gggaaataag agagaaaaga agagtaagag ccgccgccgc cgccgccgcc gccgccgcca    60
gaaatataag agccacc                                                  77

SEQ ID NO: 466          moltype = RNA   length = 77
FEATURE                 Location/Qualifiers
misc_feature            1..77
                        note = (GCC)10-13-UTR
source                  1..77
                        mol_type = other RNA
                        organism = synthetic construct
SEQUENCE: 466
gggaaataag agagaaaaga agagtaaggc cgccgccgcc gccgccgccg ccgccgccaa    60
gaaatataag agccacc                                                  77

SEQ ID NO: 467          moltype = RNA   length = 77
FEATURE                 Location/Qualifiers
misc_feature            1..77
                        note = (GCC)10-14-UTR
source                  1..77
                        mol_type = other RNA
                        organism = synthetic construct
SEQUENCE: 467
gggaaataag agagaaaaga agagtaagcc gccgccgccg ccgccgccgc cgccgccgaa    60
gaaatataag agccacc                                                  77

SEQ ID NO: 468          moltype = RNA   length = 77
FEATURE                 Location/Qualifiers
misc_feature            1..77
                        note = (GCC)10-15-UTR
source                  1..77
                        mol_type = other RNA
                        organism = synthetic construct
SEQUENCE: 468
gggaaataag agagaaaaga agagtagccg ccgccgccgc cgccgccgcc gccgccagaa    60
gaaatataag agccacc                                                  77

SEQ ID NO: 469          moltype = RNA   length = 77
FEATURE                 Location/Qualifiers
misc_feature            1..77
                        note = (GCC)10-16-UTR
source                  1..77
                        mol_type = other RNA
                        organism = synthetic construct
SEQUENCE: 469
gggaaataag agagaaaaga agagtgccgc cgccgccgcc gccgccgccg ccgccaagaa    60
gaaatataag agccacc                                                  77
```

```
SEQ ID NO: 470           moltype = RNA  length = 77
FEATURE                  Location/Qualifiers
misc_feature             1..77
                         note = (GCC)10-17-UTR
source                   1..77
                         mol_type = other RNA
                         organism = synthetic construct
SEQUENCE: 470
gggaaataag agagaaaaga agaggccgcc gccgccgccg ccgccgccgc cgcctaagaa    60
gaaatataag agccacc                                                  77

SEQ ID NO: 471           moltype = RNA  length = 77
FEATURE                  Location/Qualifiers
misc_feature             1..77
                         note = (GCC)10-18-UTR
source                   1..77
                         mol_type = other RNA
                         organism = synthetic construct
SEQUENCE: 471
gggaaataag agagaaaaga agagccgccg ccgccgccgc cgccgccgcc gccgtaagaa    60
gaaatataag agccacc                                                  77

SEQ ID NO: 472           moltype = RNA  length = 15
FEATURE                  Location/Qualifiers
misc_feature             1..15
                         note = KT1-UTR
source                   1..15
                         mol_type = other RNA
                         organism = synthetic construct
SEQUENCE: 472
gggcccgccg ccaac                                                    15

SEQ ID NO: 473           moltype = RNA  length = 15
FEATURE                  Location/Qualifiers
misc_feature             1..15
                         note = KT2-UTR
source                   1..15
                         mol_type = other RNA
                         organism = synthetic construct
SEQUENCE: 473
gggcccgccg ccacc                                                    15

SEQ ID NO: 474           moltype = RNA  length = 15
FEATURE                  Location/Qualifiers
misc_feature             1..15
                         note = KT3-UTR
source                   1..15
                         mol_type = other RNA
                         organism = synthetic construct
SEQUENCE: 474
gggcccgccg ccgac                                                    15

SEQ ID NO: 475           moltype = RNA  length = 15
FEATURE                  Location/Qualifiers
misc_feature             1..15
                         note = KT4-UTR
source                   1..15
                         mol_type = other RNA
                         organism = synthetic construct
SEQUENCE: 475
gggcccgccg ccgcc                                                    15

SEQ ID NO: 476           moltype = RNA  length = 47
FEATURE                  Location/Qualifiers
misc_feature             1..47
                         note = 5UTR-001, Upstream UTR
source                   1..47
                         mol_type = other RNA
                         organism = synthetic construct
SEQUENCE: 476
gggaaataag agaaaaaga agagtaagaa gaaatataag agccacc                  47

SEQ ID NO: 477           moltype = RNA  length = 47
FEATURE                  Location/Qualifiers
misc_feature             1..47
                         note = 5UTR-002, Upstream UTR
source                   1..47
                         mol_type = other RNA
```

```
                           organism = synthetic construct
SEQUENCE: 477
gggagatcag agagaaaaga agagtaagaa gaaatataag agccacc                47

SEQ ID NO: 478             moltype = RNA   length = 145
FEATURE                    Location/Qualifiers
misc_feature               1..145
                           note = 5UTR-003, Upstream UTR
source                     1..145
                           mol_type = other RNA
                           organism = synthetic construct
SEQUENCE: 478
ggaataaaag tctcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gcaac                                       145

SEQ ID NO: 479             moltype = RNA   length = 42
FEATURE                    Location/Qualifiers
misc_feature               1..42
                           note = 5UTR-004, Upstream UTR
source                     1..42
                           mol_type = other RNA
                           organism = synthetic construct
SEQUENCE: 479
gggagacaag cttggcattc cggtactgtt ggtaaagcca cc                     42

SEQ ID NO: 480             moltype = RNA   length = 47
FEATURE                    Location/Qualifiers
misc_feature               1..47
                           note = 5UTR-005, Upstream UTR
source                     1..47
                           mol_type = other RNA
                           organism = synthetic construct
SEQUENCE: 480
gggagatcag agagaaaaga agagtaagaa gaaatataag agccacc                47

SEQ ID NO: 481             moltype = RNA   length = 145
FEATURE                    Location/Qualifiers
misc_feature               1..145
                           note = 5UTR-006, Upstream UTR
source                     1..145
                           mol_type = other RNA
                           organism = synthetic construct
SEQUENCE: 481
ggaataaaag tctcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gcaac                                       145

SEQ ID NO: 482             moltype = RNA   length = 42
FEATURE                    Location/Qualifiers
misc_feature               1..42
                           note = 5UTR-007, Upstream UTR
source                     1..42
                           mol_type = other RNA
                           organism = synthetic construct
SEQUENCE: 482
gggagacaag cttggcattc cggtactgtt ggtaaagcca cc                     42

SEQ ID NO: 483             moltype = RNA   length = 47
FEATURE                    Location/Qualifiers
misc_feature               1..47
                           note = 5UTR-008, Upstream UTR
source                     1..47
                           mol_type = other RNA
                           organism = synthetic construct
SEQUENCE: 483
gggaattaac agagaaaaga agagtaagaa gaaatataag agccacc                47

SEQ ID NO: 484             moltype = RNA   length = 47
FEATURE                    Location/Qualifiers
misc_feature               1..47
                           note = 5UTR-009, Upstream UTR
source                     1..47
                           mol_type = other RNA
                           organism = synthetic construct
SEQUENCE: 484
gggaaattag acagaaaaga agagtaagaa gaaatataag agccacc                47

SEQ ID NO: 485             moltype = RNA   length = 47
```

```
FEATURE                 Location/Qualifiers
misc_feature            1..47
                        note = 5UTR-010, Upstream UTR
source                  1..47
                        mol_type = other RNA
                        organism = synthetic construct
SEQUENCE: 485
gggaaataag agagtaaaga acagtaagaa gaaatataag agccacc             47

SEQ ID NO: 486          moltype = RNA   length = 47
FEATURE                 Location/Qualifiers
misc_feature            1..47
                        note = 5UTR-011, Upstream UTR
source                  1..47
                        mol_type = other RNA
                        organism = synthetic construct
SEQUENCE: 486
gggaaaaaag agagaaaaga agactaagaa gaaatataag agccacc             47

SEQ ID NO: 487          moltype = RNA   length = 47
FEATURE                 Location/Qualifiers
misc_feature            1..47
                        note = 5UTR-012, Upstream UTR
source                  1..47
                        mol_type = other RNA
                        organism = synthetic construct
SEQUENCE: 487
gggaaataag agagaaaaga agagtaagaa gatatataag agccacc             47

SEQ ID NO: 488          moltype = RNA   length = 47
FEATURE                 Location/Qualifiers
misc_feature            1..47
                        note = 5UTR-013, Upstream UTR
source                  1..47
                        mol_type = other RNA
                        organism = synthetic construct
SEQUENCE: 488
gggaaataag agacaaaaca agagtaagaa gaaatataag agccacc             47

SEQ ID NO: 489          moltype = RNA   length = 47
FEATURE                 Location/Qualifiers
misc_feature            1..47
                        note = 5UTR-014, Upstream UTR
source                  1..47
                        mol_type = other RNA
                        organism = synthetic construct
SEQUENCE: 489
gggaaattag agagtaaaga acagtaagta gaattaaaag agccacc             47

SEQ ID NO: 490          moltype = RNA   length = 47
FEATURE                 Location/Qualifiers
misc_feature            1..47
                        note = 5UTR-015, Upstream UTR
source                  1..47
                        mol_type = other RNA
                        organism = synthetic construct
SEQUENCE: 490
gggaaataag agagaataga agagtaagaa gaaatataag agccacc             47

SEQ ID NO: 491          moltype = RNA   length = 47
FEATURE                 Location/Qualifiers
misc_feature            1..47
                        note = 5UTR-016, Upstream UTR
source                  1..47
                        mol_type = other RNA
                        organism = synthetic construct
SEQUENCE: 491
gggaaataag agagaaaaga agagtaagaa gaaaattaag agccacc             47

SEQ ID NO: 492          moltype = RNA   length = 47
FEATURE                 Location/Qualifiers
misc_feature            1..47
                        note = 5UTR-017, Upstream UTR
source                  1..47
                        mol_type = other RNA
                        organism = synthetic construct
SEQUENCE: 492
gggaaataag agagaaaaga agagtaagaa gaaatttaag agccacc             47
```

```
SEQ ID NO: 493            moltype = RNA   length = 47
FEATURE                   Location/Qualifiers
misc_feature              1..47
                          note = 5UTR-018, Upstream UTR
source                    1..47
                          mol_type = other RNA
                          organism = synthetic construct
SEQUENCE: 493
gggaaataag agagaaaaga agagtaagaa gaaatataag agccacc                    47

SEQ ID NO: 494            moltype = RNA   length = 92
FEATURE                   Location/Qualifiers
misc_feature              1..92
                          note = 5UTR-019, Upstream UTR
source                    1..92
                          mol_type = other RNA
                          organism = synthetic construct
SEQUENCE: 494
tcaagctttt ggaccctcgt acagaagcta atacgactca ctatagggaa ataagagaga      60
aaagaagagt aagaagaaat ataagagcca cc                                    92

SEQ ID NO: 495            moltype = RNA   length = 140
FEATURE                   Location/Qualifiers
misc_feature              1..140
                          note = 5UTR-020, Upstream UTR
source                    1..140
                          mol_type = other RNA
                          organism = synthetic construct
SEQUENCE: 495
ggacagatcg cctggagacg ccatccacgc tgttttgacc tccatagaag acaccgggac      60
cgatccagcc tccgcggccg ggaacggtgc attggaacgc ggattccccg tgccaagagt     120
gactcaccgt ccttgacacg                                                 140

SEQ ID NO: 496            moltype = RNA   length = 42
FEATURE                   Location/Qualifiers
misc_feature              1..42
                          note = 5UTR-021, Upstream UTR
source                    1..42
                          mol_type = other RNA
                          organism = synthetic construct
SEQUENCE: 496
ggcgctgcct acggaggtgg cagccatctc cttctcggca tc                         42

SEQ ID NO: 497            moltype = RNA   length = 371
FEATURE                   Location/Qualifiers
misc_feature              1..371
                          note = 3UTR-001 - Creatine Kinase
source                    1..371
                          mol_type = other RNA
                          organism = synthetic construct
SEQUENCE: 497
gcgcctgccc acctgccacc gactgctgga acccagccag tgggagggcc tggcccacca      60
gagtcctgct ccctcactcc tcgccccgcc cctgtcccca gagtcccacc tggggggctct    120
ctccacccctt ctcagagttc cagttttcaac cagagttcca accatgggc tccatcctct   180
ggattctggc caatgaaata tctccctggc agggtcctct tctttccca gagctccacc     240
ccaaccagga gctctagtta atggagagct cccagcacac tcggagcttg tgctttgtct    300
ccacgcaaag cgataaataa aagcattggt ggcctttggt ctttgaataa agcctgagta    360
ggaagtctag a                                                         371

SEQ ID NO: 498            moltype = RNA   length = 568
FEATURE                   Location/Qualifiers
misc_feature              1..568
                          note = 3UTR-002 - Myoglobin
source                    1..568
                          mol_type = other RNA
                          organism = synthetic construct
SEQUENCE: 498
gccctgccg ctcccacccc cacccatctg ggccccgggt tcaagagaga gcggggtctg       60
atctcgtgta gccatataga gtttgcttct gagtgtctgc tttgtttagt agaggtgggc     120
aggaggagct gaggggctgg ggctggggt ttgaagttgg cttttcatgc ccagcgatgc     180
gcctccctgt gggatgtcat cacccctggga acgggagtg gccttggct cactgtgttc    240
tgcatggttt ggatctgaat taattgtcct ttcttctaaa tcccaaccga acttcttcca    300
acctccaaac tggctgtaac cccaaatcca agccattaac tacacctgac agtagcaatt   360
gtctgattaa tcactggccc cttgaagaca cagaatgtc cctttgcaat gaggaggaa     420
tctgggctgg gcgggccagc tggggaagca tttgactatc tggaacttgt gtgtgcctcc   480
tcaggtatgg cagtgactca cctggttttta ataaacaac ctgcaacatc tcatggtctt   540
tgaataaagc ctgagtagga agtctaga                                       568

SEQ ID NO: 499            moltype = RNA   length = 289
```

```
FEATURE                 Location/Qualifiers
misc_feature            1..289
                        note = 3UTR-003 - alpha-actin
source                  1..289
                        mol_type = other RNA
                        organism = synthetic construct
SEQUENCE: 499
acacactcca cctccagcac gcgacttctc aggacgacga atcttctcaa tgggggggcg    60
gctgagctcc agccaccccg cagtcacttt ctttgtaaca acttccgttg ctgccatcgt   120
aaactgacac agtgtttata acgtgtacat acattaactt attacctcat tttgttattt   180
ttcgaaacaa agccctgtgg aagaaaatgg aaaacttgaa gaagcattaa agtcattctg   240
ttaagctgcg taaatggtct ttgaataaag cctgagtagg aagtctaga                289

SEQ ID NO: 500          moltype = RNA   length = 379
FEATURE                 Location/Qualifiers
misc_feature            1..379
                        note = 3UTR-004 - Albumin
source                  1..379
                        mol_type = other RNA
                        organism = synthetic construct
SEQUENCE: 500
catcacattt aaaagcatct cagcctacca tgagaataag agaaagaaaa tgaagatcaa    60
aagcttattc atctgttttt cttttttcgtt ggtgtaaagc caacaccctg tctaaaaaac  120
ataaatttct ttaatcattt tgcctctttt ctctgtgctt caattaataa aaaatgaaa   180
gaatctaata gagtggtaca gcactgttat ttttcaaaga tgtgttgcta tcctgaaaat   240
tctgtaggtt ctgtggaagt tccagtgttc tctcttattc cacttcggta gaggatttct   300
agtttcttgt gggctaatta aataaatcat taatactctt ctaatggtct ttgaataaag   360
cctgagtagg aagtctaga                                                 379

SEQ ID NO: 501          moltype = RNA   length = 118
FEATURE                 Location/Qualifiers
misc_feature            1..118
                        note = 3UTR-005 - alpha-globin
source                  1..118
                        mol_type = other RNA
                        organism = synthetic construct
SEQUENCE: 501
gctgccttct gcggggcttg ccttctggcc atgcccttct tctctcccctt gcacctgtac   60
ctcttggtct ttgaataaag cctgagtagg aaggcggccg ctcgagcatg catctaga    118

SEQ ID NO: 502          moltype = RNA   length = 908
FEATURE                 Location/Qualifiers
misc_feature            1..908
                        note = 3UTR-006 - G-CSF
source                  1..908
                        mol_type = other RNA
                        organism = synthetic construct
SEQUENCE: 502
gccaagccct cccccatccca tgtatttatc tctatttaat atttatgtct atttaagcct   60
catatttaaa gacagggaag agcagaacgg agccccaggc ctctgtgtcc ttccctgcat   120
ttctgagttt cattctcctg cctgtagcag tgagaaaaag ctcctgtcct cccatcccct   180
ggactgggag gtagataggt aaataccaag tatttattac tatgactgct ccccagccct   240
ggctctgcaa tgggcactgg gatgagccgc tgtgagcccc tggtcctgag gtccccacc    300
tgggacccctt gagagtatca ggtctcccac gtgggagaca agaaatccct gtttaatatt   360
taaacagcag tgttcccccat ctgggtcctt gcaccctcc tctgccctc agccgactgc    420
acagcggccc ctgcatcccc ttggctgtga ggcccctgga caagcagagg tggccagagc   480
tgggaggcat ggccctgggg tcccacgaat ttgctgggga atctcgtttt tcttcttaag   540
acttttggga catggtttga ctcccgaaca tcaccgacgc gtctcctgtt tttctgggtg   600
gcctcgggac acctgcctg ccccacgag ggtcaggact gtgactcttt ttagggcag   660
gcaggtgcct ggacatttgc cttgctggac ggggactggg gatgtgggag ggagcagaca   720
ggaggaatca tgtcaggcct gtgtgtgaaa ggaagctcca ctgtcaccct ccacctcttc   780
acccccccact caccagtgtc ccctccactg tcacattgta actgaacttc aggataataa   840
agtgtttgcc tccatggtct ttgaataaag cctgagtagg aaggcggccg ctcgagcatg   900
catctaga                                                             908

SEQ ID NO: 503          moltype = RNA   length = 835
FEATURE                 Location/Qualifiers
misc_feature            1..835
                        note = 3UTR-007 - Col1a2; collagen, type I, alpha 2
source                  1..835
                        mol_type = other RNA
                        organism = synthetic construct
SEQUENCE: 503
actcaatcta aattaaaaaa gaaagaaatt tgaaaaaact ttctctttgc catttcttct    60
tcttcttttt taactgaaag ctgaatcctt ccatttcttc tgcacatcta cttgcttaaa   120
ttgtgggcaa aagagaaaaa gaaggattga tcagagcatt gtgcaataca gtttcattaa   180
ctccttcccc cgctccccca aaatttgaa tttttttttc aacactctta cacctgttat   240
ggaaaatgtc aaccttgta agaaaaccaa aataaaaatt gaaaaataaa aaccataaac   300
atttgcacca cttgtggctt ttgaatatct tccacagagg gaagttaaaa acccaaactt   360
```

-continued

```
ccaaaggttt aaactacctc aaaacacttt cccatgagtg tgatccacat tgttaggtgc   420
tgacctagac agagatgaac tgaggtcctc gttttgtttt gttcataata caaaggtgct   480
aattaatagt atttcagata cttgaagaat gttgatggtg ctagaagaat ttgagaagaa   540
atactcctgt attgagttgt atcgtgtggt gtattttta aaaatttga tttagcattc    600
atattttcca tcttattccc aattaaaagt atgcagatta ttttgcccaaa tcttcttcag  660
attcagcatt tgttctttgc cagtctcatt ttcatcttct tccatggttc cacagaagct   720
ttgtttcttg ggcaagcaga aaaattaaat tgtacctatt ttgtatatgt gagatgttta   780
aataaattgt gaaaaaaatg aaataaagca tgtttggttt tccaaaagaa catat        835
```

```
SEQ ID NO: 504           moltype = RNA   length = 297
FEATURE                  Location/Qualifiers
misc_feature             1..297
                         note = 3UTR-008 - Col6a2; collagen, type VI, alpha 2
source                   1..297
                         mol_type = other RNA
                         organism = synthetic construct
SEQUENCE: 504
cgccgccgcc cgggcccgc agtcgagggt cgtgagccca ccccgtccat ggtgctaagc    60
gggcccgggt cccacacggc cagcaccgct gctcactcgg acgacgccct gggcctgcac   120
ctctccagct cctcccacgg ggtccccgta gccccggccc ccgcccagcc ccaggtctcc   180
ccaggccctc cgcaggctgc ccggcctccc tcccctgca gccatcccaa ggctcctgac    240
ctacctggcc cctgagctct ggagcaagcc ctgacccaat aaaggctttg aacccat      297
```

```
SEQ ID NO: 505           moltype = RNA   length = 602
FEATURE                  Location/Qualifiers
misc_feature             1..602
                         note = 3UTR-009 - RPN1; ribophorin I
source                   1..602
                         mol_type = other RNA
                         organism = synthetic construct
SEQUENCE: 505
ggggctagag ccctctccgc acagcgtgga gacgggcaa ggaggggggt tattaggatt     60
ggtggttttg ttttgctttg tttaaagccg tgggaaaatg gcacaacttt acctctgtgg   120
gagatgcaac actgagagcc aaggggtggg agttgggata attttatat aaaagaagtt   180
tttccacttt gaattgctaa aagtggcatt tttcctatgt gcagtcactc ctctcatttc   240
taaaataggg acgtggccag gcacggtggc tcatgcctgt aatcccagca ctttgggagg   300
ccgaggcagg cggctcacga ggtcaggaga tcgagactat cctggctaac acggtaaaac   360
cctgtctcta ctaaaagtac aaaaaattag ctgggcgtgt ggtgggcac ctgtagtccc    420
agctactcgg gaggctgagg caggagaaag gcatgaatcc aagaggcgga gcttgcagtg   480
agctgagatc acgccattgc actccagcct gggcaacagt gttaagactc tgtctcaaat   540
ataaataaat aaaataataa ataaatatat aaataaaaat aaagcgagat gttgccctca   600
aa                                                                 602
```

```
SEQ ID NO: 506           moltype = RNA   length = 785
FEATURE                  Location/Qualifiers
misc_feature             1..785
                         note = 3UTR-010 - LRP1; low density
                         lipoproteinreceptor-related protein 1
source                   1..785
                         mol_type = other RNA
                         organism = synthetic construct
SEQUENCE: 506
ggccctgccc cgtcggactg ccccagaaa gcctcctgcc cctgccagt gaagtccttc      60
agtgagcccc tccccagcca gcccttccct ggccccgccg gatgtataaa tgtaaaaatg   120
aaggaattac attttatatg tgagcgagca agccggcaag cgagcacagt attatttctc   180
catcccctcc ctgcctgctc cttggcaccc ccatgctgcc ttcagggaga caggcaggga   240
gggcttgggg ctgcacctcc taccctccca ccagaacgca cccacctggg agagctggtg   300
gtgcagcctt cccctccctg tataagacac tttgccaagg ctctcccctc tcgcccatc    360
cctgcttgcc cgctcccaca gcttcctgag ggctaattac gggaagggaa agttctttgc   420
tgccctgtc tggaagacgt ggctctgggt gaggtaggcg ggaaaggatg gagtgtttta   480
gttcttgggg gaggccaccc caaacccag ccccaactcc aggggcacct atgagatggc    540
catgctcaac cccctccca gacaggccct cctgtctcc agggccccca ccgaggttcc     600
cagggctgga gacttcctct ggtaaacatt cctccagcct ccctcccct ggggacgcca    660
aggaggtggg ccacacccag gaagggaaag cgggcagccc cgtttggggg acgtgaacgt   720
tttaataatt tttgctgaat tccttacaa ctaaataaca cagatattgt tataaataaa    780
attgt                                                              785
```

```
SEQ ID NO: 507           moltype = RNA   length = 3001
FEATURE                  Location/Qualifiers
misc_feature             1..3001
                         note = 3UTR-011 - Nnt1; cardiotrophin-like cytokine factor 1
source                   1..3001
                         mol_type = other RNA
                         organism = synthetic construct
SEQUENCE: 507
atattaagga tcaagctgtt agctaataat gccacctctg cagttttggg aacaggcaaa    60
taaagtatca gtatacatgg tgatgtacat ctgtagcaaa gctcttggag aaaatgaaga   120
ctgaagaaag caaagcaaaa actgtataga gagatttttc aaaagcagta atccctcaat   180
tttaaaaaag gattgaaaat tctaaatgtc tttctgtgca tatttttgt gttaggaatc    240
```

```
aaaagtattt tataaaagga gaaagaacag cctcatttta gatgtagtcc tgttggattt    300
tttatgcctc ctcagtaacc agaaatgttt taaaaaacta agtgtttagg atttcaagac    360
aacattatac atggctctga aatatctgac acaatgtaaa cattgcaggc acctgcattt    420
tatgttttt  ttttcaacaa atgtgactaa tttgaaactt ttatgaactt ctgagctgtc    480
cccttgcaat tcaaccgcag tttgaattaa tcatatcaaa tcagttttaa ttttttaaat    540
tgtacttcag agtctatatt tcaagggcac attttctcac tactattta  atacattaaa    600
ggactaaata tcttttcaga gatgctggaa acaaatcatt tgctttatat gtttcattag    660
aataccaatg aaacatacaa cttgaaaatt agtaatagta tttttgaaga tcccatttct    720
aattggagat ctctttaatt tcgatcaact tataatgtgt agtactatat taagtgcact    780
tgagtggaat tcaacatttg actaataaaa tgagttcatc atgttggcaa gtgatgtggc    840
aattatctct ggtgacaaaa gagtaaaatc aaatatttct gcctgttaca aatatcaagg    900
aagacctgct actatgaaat agtgacatt  aatctgtctt cactgtttat aatacggatg    960
gatttttttt caaatcagtg tgtgttttga ggtcttatgt aattgatgac atttgagaga   1020
aatggtggct tttttagct  acctctttgt tcatttaagc accagtaaag atcatgtctt   1080
tttataaag  tgtagatttt ctttgtgact ttgctatcgt gcctaaagct ctaaatatag   1140
gtgaatgtgt gatgaatact cagattattt gtctctctat ataattagtt tggtactaag   1200
tttctcaaaa aattattaac acatgaaaga caatctctaa accagaaaaa gaagtagtac   1260
aaattttgtt actgtaatgc tcgcgtttag tgagtttaaa acacacagta tcttttggtt   1320
ttataatcag tttctatttt gctgtgcctg agattaagat ctgtgtatgt gtgtgtgtgt   1380
gtgtgtgcgt ttgtgtgtta aagcagaaaa gactttttta aaagtttttaa gtgataaatg   1440
caatttgtta attgatctta gatcactagt aaactcaggg ctgaattata ccatgtatat   1500
tctattagaa gaaagtaaac accatcttta ttcctgccct tttcttctc  tcaaagtagt   1560
tgtagttata tctagaaaga agcaattttg atttcttgaa aaggtagttc ctgcactcag   1620
tttaaactaa aaataatcat acttggattt tattttattt tgtcatagta aaaattttaa   1680
tttatatata ttttattta  gtattatctt attctttgct atttgccaat cctttgtcat   1740
caattgtgtt aaatgaattg aaaattcatg ccctgttcat tttattttac tttattggtt   1800
aggatattta aaggatttt  gtatatataa tttcttaaat taatattcca aaaggttagt   1860
ggacttagat tataaaattat ggcaaaaatc taaaaacaac aaaaatgatt tttatacatt   1920
ctatttcatt attcctcttt ttccaataag tcatacaatt ggtagatatg acttatttta   1980
tttttgtatt attcactata tctttatgat atttaagtat aaataattaa aaaaatttat   2040
tgtaccttat agtctgtcac caaaaaaaaa aaattatctg taggtagtga aatgctaatg   2100
ttgatttgtc tttaagggct tgttaactat cctttatttt ctcatttgtc ttaaattagg   2160
agtttgtgtt taaattactc atctaagcaa aaaatgtata taaatcccat tactgggtat   2220
atacccaaag gattataaat catgctgcta taaagcacaca tgcacacgta tgtttattgc   2280
agcactattc acaatagcaa agacttggaa ccaacccaaa tgtccatcaa tgatagactt   2340
gattaagaaa atgtgcacat ataccacatg gaatactatg cagccataaa aaaggatgag   2400
ttcatgtcct ttgtagggac atggataaag ctggaaacca tcattctgag caaactattg   2460
caaggacaga aaaccaaaca ctgcatgttc tcactcatag gtgggaattg aacaatgaga   2520
acacttggac acaaggtggg gaacaccaca caccagggcc tgtcatgggg tgggggagtg   2580
ggggagggat agcattagga gatataccta atgtaaatga tgagttaatg ggtgcagcac   2640
accaacatgg cacatgtata catatgtagc aaacctgcac gttgtgcaca tgtacccctag   2700
aacttaaagt ataattaaaa aaaaaagaa  acagaagct  atttataaag aagttatttg   2760
ctgaaataaa tgtgatcttt cccattaaaa aaataaagaa attttggggt aaaaaaacac   2820
aatatattgt attcttgaaa aattctaaga gagtggatgt gaagtgttct caccacaaaa   2880
gtgataacta attgaggtaa tgcacatatt aattagaaag attttgtcat tccacaatgt   2940
atatatactt aaaaatatgt tatacacaat aaatacatac attaaaaaat aagtaaatgt   3000
a                                                                   3001
```

```
SEQ ID NO: 508           moltype = RNA   length = 1037
FEATURE                  Location/Qualifiers
misc_feature             1..1037
                         note = 3UTR-012 - Col6a1; collagen, type VI, alpha 1
source                   1..1037
                         mol_type = other RNA
                         organism = synthetic construct
SEQUENCE: 508
cccaccctgc acgccggcac caaaccctgt cctcccaccc ctcccactc  atcactaaac     60
agagtaaaat gtgatgcgaa tttttcccgac caacctgatt cgctagattt tttttaagga   120
aaagcttgga aagccaggac acaacgctgc tgcctgcttt gtgcagggtc ctccggggct    180
cagccctgag ttggcatcac ctgcgcaggg ccctctgggg ctcagccctg agctagtgtc    240
acctgcacag ggccctctga ggctcagccc tgagctggcg tcacctgtgc agggccctct    300
ggggctcagc cctgagctgg cctcacctgg gttcccacc  ccgggctctc ctgccctgcc    360
ctcctgcccg ccctccctcc tgcctgcgca gctccttccc taggcacctc tgtgctgcat    420
cccaccagcc tgagcaagac gccctctcgg ggctgtgcc gcactagcct ccctctcctc    480
tgtccccata gctggttttt cccaccaatc ctcacctaac agttacttta caattaaact    540
caaagcaagc tcttctcctc agcttggggc agccattggc ctctgtctcg ttttgggaaa    600
ccaaggtcag gaggccgttg cagacataaa tctcggcgca tcggcccgt  ctcctgaggg    660
tcctgctggt gaccggcctg gaccttggcc ctacagccct ggaggccgct gctgaccagc    720
actgacccg  acctcagaga gtactcgcag gggcgctggc tgcactcaag accctgggaa    780
ttaacggtgc taaccccgtc tgctcctccc tcccgcagag actgggcct  ggactggaca    840
tgagagcccc ttggtgccac agagggctgt gtcttactag aaacaacgca aacctctcct    900
tcctcagaat agtgatgtgt tcgacgtttt atcaaaggcc ccctttctat gttcatgtta    960
gtttttgctcc ttctgtgttt ttttctgaac catatccatg ttgctgactt ttccaaataa   1020
aggttttcac tcctctc                                                  1037
```

```
SEQ ID NO: 509           moltype = RNA   length = 577
FEATURE                  Location/Qualifiers
misc_feature             1..577
                         note = 3UTR-013 - Calr; calreticulin
```

```
source                  1..577
                        mol_type = other RNA
                        organism = synthetic construct
SEQUENCE: 509
agaggcctgc ctccagggct ggactgaggc ctgagcgctc ctgccgcaga gctggccgcg    60
ccaaataatg tctctgtgag actcgagaac tttcattttt ttccaggctg gttcggattt   120
ggggtggatt ttggttttgt tcccctcctc cactctcccc caccccctcc ccgccctttt   180
tttttttttt tttaaactg gtattttatc tttgattctc cttcagccct caccctggt    240
tctcatcttt cttgatcaac atcttttctt gcctctgtcc ccttctctca tctcttagct   300
ccctccaac ctgggggca gtggtgtgga aagccacag gcctgagatt tcatctgctc     360
tccttcctgg agcccagagg agggcagcag aaggggtgg tgtctccaac ccccagcac    420
tgaggaagaa cggggctctt ctcatttcac ccctcccttt ctccctgcc cccaggactg    480
ggccacttct gggtggggca gtgggtccca gattggctca cactgagaat gtaagaacta   540
caaacaaaat ttctattaaa ttaaattttg tgtctcc                            577

SEQ ID NO: 510          moltype = RNA length = 2212
FEATURE                 Location/Qualifiers
misc_feature            1..2212
                        note = 3UTR-014 - Col1a1; collagen, type I, alpha 1
source                  1..2212
                        mol_type = other RNA
                        organism = synthetic construct
SEQUENCE: 510
ctccctccat cccaacctgg ctccctccca cccaaccaac tttcccccca acccggaaac    60
agacaagcaa cccaaactga acccctcaa aagccaaaaa atgggagaca atttcacatg   120
gactttggaa aatatttttt tcctttgcat tcatctctca aacttagttt ttatctttga   180
ccaaccgaac atgaccaaaa accaaaagtg cattcaacct taccaaaaaa aaaaaaaaaa   240
aaagaataaa taaataactt tttaaaaag aagcttggt ccacttgctt gaagacccat     300
gcggggtaa gtcccttct gccgttggg cttatgaaac cccaatgctg ccctttctgc     360
tccttctcc acaccccccct tggggcctcc cctccactcc ttcccaaatc tgtctcccca   420
gaagacacag gaaacaatgt attgtctgcc cagcaatcaa aggcaatgct caaacaccca   480
agtggccccc accctcagcc cgctcctgcc cgcccagcac cccaggccc tgggggacct    540
ggggttctca gactgccaaa gaagccttgc catctggcgc tcccatggct cttgcaacat   600
ctccccttcg tttttgaggg ggtcatgccg ggggagccac cagcccctca ctgggttcgg   660
aggagagtca ggaagggcca cgacaaagca gaaacatcgg catttgggga cgcgtgtcaa   720
tcccttgtgc cgcagggctg ggcgggagag actgttctgt tccttgtgta actgtgttgc   780
tgaaagacta cctcgttctt gtcttgatgt gtcaccgggg caactgcctg ggggcgggga   840
tgggggcagg gtggaagcgg ctcccatttt tataccaaag gtgctacatc tatgtgatgg   900
gtgggggtgg gagggaatca ctggtgctat agaaattgag atgccccccc aggccagcaa   960
atgttccttt ttgttcaaag tctatttta ttccttgata ttttttcttt tttttttttt  1020
tttttgtgga tggggacttg tgaattttc taaaggtgct atttaacatg gaggagagc   1080
gtgtgcggct ccagcccagc ccgctgctca ctttccaccc tctctccacc tgcctctggc  1140
ttctcaggcc tctgctctcc gacctctctc tctgaaacc tctcaccaca gctgcagccn  1200
atcctcccgg ctccctccta gtctgtcctg cgtcctctgt cccgggttt cagagacaac  1260
ttcccaaagc acaaagcagt ttttccccct aggggtggga ggaagcaaaa gactctgtac  1320
ctattttgta tgtgtataat aatttgagat gttttaatt attttgattg ctggaataaa  1380
gcatgtggaa atgacccaaa cataatccgc agtggcctc taatttcctt ctttggagtt  1440
gggggagggg tagacatggg gaaggggctt tggggtgatg gcttgcctt ccattcctgc   1500
cctttccctc ccactattc tcttctagat ccctccataa cccactccc ctttctctca   1560
cccttcttat accgcaaacc tttctacttc ctctttcatt ttcattctt gcaatttcct  1620
tgcaccttt ccaaatcctc ttctcccctg caataccata caggcaatcc acgtgcaaa   1680
cacacacaca cactcttcac atctggggtt gtccaaacct catacccact cccccttcaag 1740
cccatccact ctccaccccc tggatgccct gcacttggtg gcgtgggat gctcatggat   1800
actgggaggg tgagggagt ggaacccgtg aggaggacct gggggcctct ccttgaactg   1860
acatgaaggg tcatctggcc tctgctccct ctcacccac gctgacctcc tgccgaagga  1920
gcaacgcaac aggagagggg tctgctgagc ctggcgaggg tctggagggg accaggagga  1980
aggcgtgctc cctgctcgct gtcctggccc tgggggagtg agggagacag acacctggga  2040
gagctgtggg gaaggcactc gcaccgtgct cttgggaagg aaggagacct ggccctgctc  2100
accacggact gggtgcctcg acctcctgaa tcccagaac acaacccccc tgggctgggg   2160
tggtctgggg aaccatcgtg ccccgcctc cgcctactc ctttttaagc tt            2212

SEQ ID NO: 511          moltype = RNA length = 729
FEATURE                 Location/Qualifiers
misc_feature            1..729
                        note = 3UTR-015 - Plod1; procollagen-lysine,
                        2-oxoglutarate5-dioxygenase 1
source                  1..729
                        mol_type = other RNA
                        organism = synthetic construct
SEQUENCE: 511
ttggccaggc ctgaccctct tggaccttc ttctttgccg acaaccactg cccagcagcc    60
tctgggacct cggggtccca gggaacccag tccagcctcc tggctgttga cttcccattg   120
ctcttggagc accaatcaa agagattcaa agagattcct gcaggccaga ggcggaacac   180
accttatgg ctggggctct ccgtggttgtt ctggacccag ccccgtggaga caccattcac   240
ttttactgct ttgtagtgac tcgtgctctc caacctgtct tcctgaaaaa ccaaggcccc   300
cttccccac ctcttccatg gggtgagact tgagcagaac aggggcttcc ccaagttgcc   360
cagaaagact gtctgggtga gaagccatgg ccagagcttc tcccaggcac aggtgttgca   420
ccagggactt ctgcttcaag ttttgggta agacacctg gatcagactc caagggctgc   480
cctgagtctg ggacttctgc ctccatggct ggtcatgaga gcaaaccgta gtcccctgga   540
```

```
gacagcgact ccagagaacc tcttgggaga cagaagaggc atctgtgcac agctcgatct  600
tctacttgcc tgtggggagg ggagtgacag gtccacacac cacactgggt caccctgtcc  660
tggatgcctc tgaagagagg gacagaccgt cagaaactgg agagtttcta ttaaaggtca  720
tttaaaacca                                                         729

SEQ ID NO: 512           moltype = RNA   length = 847
FEATURE                  Location/Qualifiers
misc_feature             1..847
                         note = 3UTR-016 - Nucb1; nucleobindin 1
source                   1..847
                         mol_type = other RNA
                         organism = synthetic construct
SEQUENCE: 512
tcctccggga ccccagccct caggattcct gatgctccaa ggcgactgat gggcgctgga   60
tgaagtggca cagtcagctt ccctgggggc tggtgtcatg ttgggctcct ggggcggggg  120
cacggcctgg catttcacgc attgctgcca cccaggtcc acctgtctcc actttcacag   180
cctccaagtc tgtggctctt cccttctgtc tccgagggg cttgccttct ctcgtgtcca   240
gtgaggtgct cagtgatcgg cttaacttag agaagcccgc cccctcccct tctccgtctg  300
tcccaagagg gtctgctctg agcctgcgtt cctaggtggc tcggcctcag ctgcctgggt  360
tgtggccgcc ctagcatcct gtatgcccac agctactgga atccccgctg ctgctccggg  420
ccaagcttct ggttgattaa tgagggcatg gggtggtccc tcaagacctt cccctacctt  480
ttgtggaacc agtgatgcct caaagacagt gtccctccca gctgggtg ccaggggcag   540
gggatcctca gtatagccgg tgaaccctga taccaggagc ctgggcctcc ctgaacccct  600
ggcttccagc catctcatcg ccagcctcct cctggacctc ttggcccca gcccttccc    660
cacacagccc cagaagggtc ccagagctga ccccactcca ggacctaggc ccagccctc   720
agcctcatct ggagcccctg aagaccagtc ccacccacct ttctggcctc atctgacact  780
gctccgcatc ctgctgtgtg tcctgttcca tgttccggtt ccatccaaat acactttctg  840
gaacaaa                                                            847

SEQ ID NO: 513           moltype = RNA   length = 110
FEATURE                  Location/Qualifiers
misc_feature             1..110
                         note = 3UTR-017 - alpha-globin
source                   1..110
                         mol_type = other RNA
                         organism = synthetic construct
SEQUENCE: 513
gctggagcct cggtggccat gcttcttgcc ccttgggcct ccccccagcc cctcctcccc   60
ttcctgcacc cgtaccccg tggtctttga ataaagtctg agtgggcggc               110

SEQ ID NO: 514           moltype = RNA   length = 116
FEATURE                  Location/Qualifiers
misc_feature             1..116
                         note = 3UTR-018 - Downstream UTR
source                   1..116
                         mol_type = other RNA
                         organism = synthetic construct
SEQUENCE: 514
taataggctg gagcctcggt ggccatgctt cttgccccct tgggcctccc ccagccctc   60
ctccccttcc tgcacccgta ccccgtggt ctttgaataa agtctgagtg ggcggc       116

SEQ ID NO: 515           moltype = RNA   length = 118
FEATURE                  Location/Qualifiers
misc_feature             1..118
                         note = 3UTR-019- Downstream UTR
source                   1..118
                         mol_type = other RNA
                         organism = synthetic construct
SEQUENCE: 515
tgataatagg ctggagcctc ggtggccatg cttcttgccc cttgggcctc ccccagccc   60
ctcctcccct tcctgcaccc gtaccccctg tctttgaat aaagtctgag tgggcggc    118

SEQ ID NO: 516           moltype = RNA   length = 138
FEATURE                  Location/Qualifiers
misc_feature             1..138
                         note = 3UTR-018 + miR-122-5p binding site
source                   1..138
                         mol_type = other RNA
                         organism = synthetic construct
SEQUENCE: 516
taataggctg gagcctcggt ggccatgctt cttgccccct tgggcctccc ccagccctc   60
ctccccttcc tgcacccgta ccccccaaac accattgtca cactccagtg gtctttgaat  120
aaagtctgag tgggcggc                                                138

SEQ ID NO: 517           moltype = RNA   length = 138
FEATURE                  Location/Qualifiers
misc_feature             1..138
                         note = 3UTR-018 + miR-122-3p binding site
source                   1..138
```

```
                            mol_type = other RNA
                            organism = synthetic construct
SEQUENCE: 517
taataggctg gagcctcggt ggccatgctt cttgccccctt gggcctcccc ccagccctc      60
ctcccttcc tgcacccgta cccctattt agtgtgataa tggcgttgtg gtctttgaat        120
aaagtctgag tgggcggc                                                    138

SEQ ID NO: 518          moltype = RNA   length = 141
FEATURE                 Location/Qualifiers
misc_feature            1..141
                        note = 3UTR-019 + miR-122 binding site
source                  1..141
                        mol_type = other RNA
                        organism = synthetic construct
SEQUENCE: 518
tgataatagg ctggagcctc ggtggccatg cttcttgccc cttgggcctc ccccagccc       60
ctcctcccct tcctgcaccc gtaccccca aacaccattg tcacactcca gtggtctttg      120
aataaagtct gagtgggcgg c                                                141

SEQ ID NO: 519          moltype = RNA   length = 87
FEATURE                 Location/Qualifiers
misc_feature            1..87
                        note = mmiR-142
source                  1..87
                        mol_type = other RNA
                        organism = synthetic construct
SEQUENCE: 519
gacagtgcag tcacccataa agtagaaagc actactaaca gcactggagg gtgtagtgtt     60
tcctacttta tggatgagtg tactgtg                                         87

SEQ ID NO: 520          moltype = RNA   length = 23
FEATURE                 Location/Qualifiers
misc_feature            1..23
                        note = mmiR-142-3p
source                  1..23
                        mol_type = other RNA
                        organism = synthetic construct
SEQUENCE: 520
tgtagtgttt cctactttat gga                                             23

SEQ ID NO: 521          moltype = RNA   length = 23
FEATURE                 Location/Qualifiers
misc_feature            1..23
                        note = mmiR-142-3p binding site
source                  1..23
                        mol_type = other RNA
                        organism = synthetic construct
SEQUENCE: 521
tccataaagt aggaaacact aca                                             23

SEQ ID NO: 522          moltype = RNA   length = 21
FEATURE                 Location/Qualifiers
misc_feature            1..21
                        note = mmiR-142-5p
source                  1..21
                        mol_type = other RNA
                        organism = synthetic construct
SEQUENCE: 522
cataaagtag aaagcactac t                                               21

SEQ ID NO: 523          moltype = RNA   length = 21
FEATURE                 Location/Qualifiers
misc_feature            1..21
                        note = mmiR-142-5p binding site
source                  1..21
                        mol_type = other RNA
                        organism = synthetic construct
SEQUENCE: 523
agtagtgctt tctactttat g                                               21

SEQ ID NO: 524          moltype = RNA   length = 85
FEATURE                 Location/Qualifiers
misc_feature            1..85
                        note = miR-122
source                  1..85
                        mol_type = other RNA
                        organism = synthetic construct
SEQUENCE: 524
ccttagcaga gctgtggagt gtgacaatgg tgtttgtgtc taaactatca aacgccatta     60
```

```
tcacactaaa tagctactgc taggc                                         85

SEQ ID NO: 525         moltype = RNA   length = 22
FEATURE                Location/Qualifiers
misc_feature           1..22
                       note = miR-122-3p
source                 1..22
                       mol_type = other RNA
                       organism = synthetic construct
SEQUENCE: 525
aacgccatta tcactaaa ta                                              22

SEQ ID NO: 526         moltype = RNA   length = 22
FEATURE                Location/Qualifiers
misc_feature           1..22
                       note = miR-122-3p binding site
source                 1..22
                       mol_type = other RNA
                       organism = synthetic construct
SEQUENCE: 526
tatttagtgt gataatggcg tt                                            22

SEQ ID NO: 527         moltype = RNA   length = 22
FEATURE                Location/Qualifiers
misc_feature           1..22
                       note = miR-122-5p
source                 1..22
                       mol_type = other RNA
                       organism = synthetic construct
SEQUENCE: 527
tggagtgtga caatggtgtt tg                                            22

SEQ ID NO: 528         moltype = RNA   length = 22
FEATURE                Location/Qualifiers
misc_feature           1..22
                       note = miR-122-5p binding site
source                 1..22
                       mol_type = other RNA
                       organism = synthetic construct
SEQUENCE: 528
caaacaccat tgtcacactc ca                                            22

SEQ ID NO: 529         moltype =    length =
SEQUENCE: 529
000

SEQ ID NO: 530         moltype =    length =
SEQUENCE: 530
000

SEQ ID NO: 531         moltype = RNA   length = 262
FEATURE                Location/Qualifiers
misc_feature           1..262
                       note = Tubulin-like
source                 1..262
                       mol_type = other RNA
                       organism = synthetic construct
SEQUENCE: 531
gtacaccggc atcgactaat cagggccagg ctcgaggctt tgtctcccta ccgcgcgccg   60
attctcccgc ctcccagccc cggcgcacgc gcgccccgcc cagcctgctt tccctccgcg  120
ccctcccctc tcctttctcc ctctcagaac cttcctgccg tcgcgtttgc acctcgctgc  180
tccagcctct cgcattccaa ccttccagcc tgcgacctgc ggagacttag ccccatacat  240
accttgaggc gagcttttaa cc                                           262

SEQ ID NO: 532         moltype = RNA   length = 57
FEATURE                Location/Qualifiers
misc_feature           1..57
                       note = GC Scramble #1-UTR
source                 1..57
                       mol_type = other RNA
                       organism = synthetic construct
SEQUENCE: 532
gggaaataag agagaaaaga agagtaagaa gaaatataag aggggcgccc ggccacc      57

SEQ ID NO: 533         moltype = RNA   length = 57
FEATURE                Location/Qualifiers
misc_feature           1..57
                       note = GC Scramble #2-UTR
source                 1..57
```

```
                       mol_type = other RNA
                       organism = synthetic construct
SEQUENCE: 533
gggaaataag agagaaaaga agagtaagaa gaaatataag agcccgcccg cgccacc        57

SEQ ID NO: 534         moltype = RNA  length = 57
FEATURE                Location/Qualifiers
misc_feature           1..57
                       note = GC Scramble #3-UTR
source                 1..57
                       mol_type = other RNA
                       organism = synthetic construct
SEQUENCE: 534
gggaaataag agagaaaaga agagtaagaa gaaatataag agcgccccgc ggccacc        57

SEQ ID NO: 535         moltype = RNA  length = 67
FEATURE                Location/Qualifiers
misc_feature           1..67
                       note = GC1-UTR
source                 1..67
                       mol_type = other RNA
                       organism = synthetic construct
SEQUENCE: 535
gggaaataag agagaaaaga agagtaagaa gaaatataag agcgccccgc ggcgccccgc     60
ggccacc                                                               67
```

MODIFIED MESSENGER RNA COMPRISING FUNCTIONAL RNA ELEMENTS

CROSS-REFERENCE TO RELATED APPLICATIONS

This application is a continuation of U.S. patent application Ser. No. 16/614,245, filed on Nov. 15, 2019, which issued as U.S. Pat. No. 11,485,972 on Nov. 1, 2022, which is a 35 U. S.C. § 371 national stage filing of International Application No. PCT/US2018/033519, filed May 18, 2018, which claims the benefit of U.S. Provisional Application No. 62/508,318 filed on May 18, 2017; U.S. Provisional Application No. 62/519,800 filed on Jun. 14, 2017; and U.S. Provisional Application No. 62/667,824 filed on May 7, 2018. The entire contents of the above-referenced applications are incorporated herein by this reference.

REFERENCE TO SEQUENCE LISTING

The instant application contains a Sequence Listing which has been submitted in XML format via USPTO Patent Center and is hereby incorporated by reference in its entirety. Said XML copy, created on May 9, 2023, is named MRNA_108_C01US_SeqList_ST26.xml and is 699,876 bytes in size.

BACKGROUND

Messenger RNA (mRNA) designed to encode and transiently express a pharmacologically active protein or peptide product is the quintessence of a novel class of mRNA-based therapeutics. Administration of a synthetic and/or in vitro-generated mRNA that structurally resembles natural mRNA can result in the controlled production of therapeutic proteins or peptides via the endogenous and constitutively-active translation machinery (e.g. ribosomes) that exists within the patient's own cells. In recent years, the development and use of mRNA as a therapeutic agent has demonstrated potential for treatment of numerous diseases and for the development of novel approaches in regenerative medicine and vaccination (Sahin et al., (2014) Nat Rev Drug Discov 13(10):759-780).

It is recognized that the control and regulation of mRNA translation is an important development component in order for this class of drugs to establish the desired therapeutic effect. Within the field of mRNA therapeutics, there exists a need to develop mRNA with improved therapeutic effect.

SUMMARY OF THE INVENTION

The present disclosure provides messenger RNAs (mRNAs), including modified mRNAs (mmRNAs) having chemical and/or structural modifications, including RNA elements and/or modified nucleotides, which provide a desired translational regulatory activity to the mRNA. In one aspect, the mRNAs of the disclosure comprise modifications that reduce leaky scanning of 5' UTRs by the cellular translation machinery. Leaky scanning can result in the bypass of the desired initiation codon that begins the open reading frame encoding a polypeptide of interest or a translation product. This bypass can further result in the initiation of polypeptide synthesis from an alternate or alternative initiation codon, and thereby promote the translation of partial, aberrant, or otherwise undesirable open reading frames within the mRNA. The negative impact caused by the failure to initiate translation of the therapeutic protein or peptide at the desired initiator codon, as a consequence of leaky scanning or other mechanisms, poses a challenge in the development of mRNA therapeutics.

Accordingly, the present disclosure provides mRNAs, including mmRNAs having novel chemical and/or structural modifications, which provide a desired translational regulatory activity, including promoting translation of only one open reading frame encoding a desired polypeptide or translation product. In some aspects, the desired translational regulatory activity reduces, inhibits or eliminates the failure to initiate translation of the therapeutic protein or peptide at the desired initiator codon, as a consequence of leaky scanning or other mechanisms, Thus, the present disclosure provides mRNA having chemical and/or structural modifications (e.g., mmRNAs) which are useful to modulate (e.g., control) translation of an mmRNA to produce a desired translation product.

Accordingly, in one aspect the disclosure provides, mRNAs comprising a 5' untranslated region (UTR), an initiation codon, a full open reading frame encoding a polypeptide, a 3' UTR, and at least one modification, wherein the at least one modification provides a translational regulatory activity. In one embodiment, the translational regulatory activity comprises increasing residence time of a 43S pre-initiation complex (PIC) or ribosome at, or proximal to, the initiation codon. In another embodiment, the translational regulatory activity comprises increasing initiation of polypeptide synthesis at or from the initiation codon. In another embodiment, the translational regulatory activity comprises increasing an amount of polypeptide translated from the full open reading frame. In another embodiment, the translational regulatory activity comprises increasing fidelity of initiation codon decoding by the PIC or ribosome. In another embodiment, the translational regulatory activity comprises inhibiting or reducing leaky scanning by the PIC or ribosome. In another embodiment, the translational regulatory activity comprises decreasing a rate of decoding the initiation codon by the PIC or ribosome. In another embodiment, the translational regulatory activity comprises inhibiting or reducing initiation of polypeptide synthesis at any codon within the mmRNA other than the initiation codon. In another embodiment, the translational regulatory activity comprises inhibiting or reducing the amount of polypeptide translated from any open reading frame within the mmRNA other than the full open reading frame. In another embodiment, the translational regulatory activity comprises inhibiting or reducing the production of aberrant translation products. In another embodiment, the translational regulatory activity comprises any combination of the foregoing activities.

In another aspect, the disclosure provides an mRNA comprising at least one modification (e.g., mmRNA), wherein the at least one modification is a structural modification. In one embodiment, the structural modification is a RNA element. In another embodiment, the structural modification is a GC-rich RNA element. In another embodiment, the structural modification is a viral RNA element. In another embodiment, the structural modification is a protein-binding RNA element. In another embodiment, the structural modification is a translation initiation element. In another embodiment, the structural modification is a translation enhancer element. In another embodiment, the structural modification is a translation fidelity enhancing element. In another embodiment, the structural modification is an mRNA nuclear export element. In another embodiment, the structural modification is a codon optimized open reading frame. In another embodiment, the structural modification is a modification of base composition.

In another aspect, the disclosure provides an mRNA comprising at least one modification (e.g., mmRNA), wherein the at least one modification is a chemical modification. In one embodiment, the chemical modification is one or more chemically modified nucleotides. In another embodiment, the chemical modification is one or more deoxyribonucleotides. In another embodiment, the chemical modification is one or more chemical modifications to the mRNA backbone.

In some aspects, the modification in the mRNA is in a 5' UTR, an initiation codon, a full open reading frame, a 3' UTR, or any combination thereof. Thus, in one embodiment, the 5' UTR of an mRNA comprises at least one modification as described herein. In another embodiment, the initiation codon of an mRNA comprises at least one modification as described herein. In another embodiment, the full open reading frame encoding a polypeptide of an mRNA comprises at least one modification as described herein. In another embodiment, the 3' UTR of an mRNA comprises at least one modification as described herein. In another embodiment, a modification comprises any one of the sequences set forth in Table 1. In another embodiment, a 5' UTR comprises any one of the sequences set forth in Table 1. In yet another embodiment, a 5' UTR comprises the sequence V1-UTR as set forth in Table 1.

In another aspect, the disclosure provides an mRNA comprising at least one modification, wherein the at least one modification is a GC-rich element comprising a sequence of linked nucleotides, or derivatives or analogs thereof, located upstream of a Kozak consensus sequence in the 5' UTR. In one embodiment, the GC-rich element is located about 30, about 25, about 20, about 15, about 10, about 5, about 4, about 3, about 2, or about 1 nucleotide(s) upstream of a Kozak consensus sequence in the 5' UTR. In another embodiment, the GC-rich element is located about 15-30, about 15-20, about 15-25, about 10-15, or about 5-10 nucleotides upstream of a Kozak consensus sequence in the 5' UTR. In another embodiment, the GC-rich element is located upstream of and immediately adjacent to a Kozak consensus sequence in the 5' UTR. In another embodiment, the GC-rich element comprises a sequence of about 30, about 20-30, about 20, about 10-20, about 15, about 10-15, about 15, 14, 13, 12, 11, 10, 9, 8, 7, 6, 5, 4, or 3 nucleotides, or derivatives or analogs thereof, linked in any order, wherein the sequence composition is about 70% cytosine, about 60%-70% cytosine, about 60% cytosine, about 50%-60% cytosine, about 50% cytosine, about 40%-50% cytosine, about 40% cytosine, about 30%-40% cytosine, about 30% cytosine. In one embodiment, the GC-rich element comprises a sequence of 3, 4, 5, 6, 7, 8, 9, 10, 11, 12, 13, 14, 15, 16, 17, 18, 19, or 20 nucleotides, or derivatives or analogs thereof, linked in any order, wherein the sequence composition is >50% cytosine. In another embodiment, the GC-rich element comprises a sequence of about 3-30 nucleotides, or derivatives or analogues thereof, wherein the sequence comprises a repeating GC-motif, wherein the repeating GC-motif is [CCG]$_n$, wherein n=1 to 10, 1 to 5, 3, 2, or 1. In another embodiment, the GC-motif is [GCC]$_n$. In another embodiment, the GC-rich element comprises any one of the sequences set forth in Table 1. In a preferred embodiment, the GC-rich element comprises the sequence V1 as set forth in Table 1.

In another aspect, the disclosure provides an mRNA comprising at least one modification, wherein the at least one modification is a GC-rich element comprising a stable RNA secondary structure located upstream of a Kozak consensus sequence in the 5' UTR. In one embodiment, the GC-rich RNA element comprising a stable RNA secondary structure is located about 30, about 25, about 20, about 15, about 10, about 5, about 4, about 3, about 3, or about 1 nucleotide(s) upstream of a Kozak consensus sequence in the 5' UTR. In another embodiment, the GC-rich RNA element comprising a stable RNA secondary structure is located about 15-30, about 15-20, about 15-25, about 10-15, or about 5-10 nucleotides upstream of a Kozak consensus sequence in the 5' UTR. In another embodiment, the GC-rich RNA element comprising a stable RNA secondary structure is located upstream of and immediately adjacent to a Kozak consensus sequence in the 5' UTR.

In another aspect, the disclosure provides an mRNA comprising at least one modification, wherein the at least one modification is a GC-rich RNA element comprising a stable RNA secondary structure located downstream of the initiation codon. In one embodiment, the GC-rich RNA element comprising a stable RNA secondary structure is located about 30, about 25, about 20, about 15, about 10, about 5, about 4, about 3, about 2, or about 1 nucleotide(s) downstream of the initiation codon. In another embodiment, the GC-rich RNA element comprising a stable RNA secondary structure is located about 15-30, about 15-20, about 15-25, about 10-15, or about 5-10 nucleotides downstream of the initiation codon. In another embodiment, the GC-rich RNA element comprising a stable RNA secondary structure is located 20, 19, 18, 17, 16, 15, 14, 13, 12, 11, or 10 nucleotides downstream of the initiation codon.

In another aspect, the disclosure provides an mRNA comprising at least one modification, wherein the at least one modification is a GC-rich RNA element comprising a stable RNA secondary structure located upstream of the initiation codon. In one embodiment, the GC-rich RNA element comprising a stable RNA secondary structure is located about 40, about 35, about 30, about 25, about 20, about 15, about 10, about 5, about 4, about 3, about 2, about 1 nucleotide upstream of the initiation codon. In another embodiment, the GC-rich RNA element comprising a stable RNA secondary structure is located about 15-40, about 15-30, about 15-20, about 15-25, about 10-15, or about 5-10 nucleotides upstream of the initiation codon.

In another aspect, the disclosure provides an mRNA comprising at least one modification, wherein the at least one modification is a GC-rich RNA element comprising a stable RNA secondary structure, wherein the stable RNA secondary structure comprises the initiation codon and one or more additional nucleotides upstream, downstream, or upstream and downstream of the initiation codon. In another embodiment, the GC-rich RNA element comprising a stable RNA secondary structure comprises any one of the sequences set forth in Table 1. In another embodiment, the stable RNA secondary structure comprises a hairpin or a stem-loop. In another embodiment, the stable RNA secondary structure has a deltaG of about −30 kcal/mol, about −20 to −30 kcal/mol, about −20 kcal/mol, about −10 to −20 kcal/mol, about −10 kcal/mol, about −5 to ~10 kcal/mol.

In another aspect, the disclosure provides an mRNA comprising at least one modification, wherein the at least one modification is one or more modified nucleotides, wherein the sequence comprising the initiation codon comprises one or more modified nucleotides that increases binding affinity with the initiator Met-tRNA$_i^{Met}$. In one embodiment, the one or more modified nucleotides comprises 2-thiouridine, 2'-O-methyl-2-thiouridine, 2-selenouridine, 2'-O-methyl ribose, a modified nucleotide in which the ribose moiety is modified with an extra bridge connecting the 2' oxygen and 4' carbon, inosine, 2-methylguanosine, 6-methyl-adenosine, a deoxyribonucleotide.

In another aspect, the disclosure provides an mRNA, including mmRNAs, wherein the mRNA comprises a first polynucleotide, wherein the first polynucleotide is chemically synthesized, and wherein the first polynucleotide comprises a 5' UTR, an initiation codon, and at least one modification, and a second polynucleotide, wherein the second polynucleotide is synthesized by in vitro transcription, and, wherein the second polynucleotide comprises a full open reading frame encoding a polypeptide, and a 3' UTR. In one embodiment, the first polynucleotide and the second polynucleotide are chemically cross-linked. In another embodiment, the first polynucleotide and the second polynucleotide are enzymatically ligated. In another embodiment, the first polynucleotide and the second polynucleotide are operably linked.

In another aspect, the disclosure provides mRNA comprising a 5' UTR, an initiation codon, a full open reading frame encoding a polypeptide, and a 3' UTR, wherein the sequence of the 5' UTR comprises any of the sequences set forth in Table 1.

Another aspect, the disclosure provides a method of isolating a modification having translational regulatory activity, the method comprising synthesizing a 1st control mRNA comprising a polynucleotide sequence comprising an open reading frame encoding eGFP and a $1^{st}$ AUG codon upstream of, in-frame, and operably linked to, the open reading frame encoding eGFP, and, a coding sequence for a 3×FLAG epitope tag upstream of, in-frame, and operably linked to the $1^{st}$ AUG codon, a $2^{nd}$ AUG codon upstream of, in-frame, and operably linked to, the coding sequence for the 3×FLAG epitope tag, a coding sequence for a V5 epitope tag upstream of, in-frame, and operably linked to the $2^{nd}$ AUG codon, a 3rd AUG codon upstream of, in-frame, and operably linked to, the coding sequence for the V5 epitope tag, and a 5' UTR and a 3' UTR. The method further comprising synthesizing a $2^{nd}$ test mmRNA comprising a polynucleotide sequence comprising an open reading frame encoding eGFP, a $1^{st}$ AUG codon upstream of, in-frame, and operably linked to, the open reading frame encoding eGFP, a coding sequence for a 3×FLAG epitope tag upstream of, in-frame, and operably linked to the $1^{st}$ AUG codon, a $2^{nd}$ AUG codon upstream of, in-frame, and operably linked to, the coding sequence for the 3×FLAG epitope tag, a coding sequence for a V5 epitope tag upstream of, in-frame, and operably linked to the $2^{nd}$ AUG codon, a $3^{rd}$ AUG codon upstream of, in-frame, and operably linked to, the coding sequence for the V5 epitope tag, a 5' UTR, a 3' UTR, and a candidate modification. The method further comprising introducing the $1^{st}$ control mmRNA and $2^{nd}$ test mmRNA to conditions suitable for translation of the polynucleotide sequence encoding the reporter polypeptide. The method further comprising measuring the effect of the candidate modification on the initiation of translation of the polynucleotide sequence encoding the reporter polypeptide from each of the three AUG codons.

In some aspects, the disclosure provides messenger RNA (mRNA) comprising
(i) a 5' untranslated region (UTR) comprising at least one RNA element that provides a translational regulatory activity;
(ii) a full open reading frame comprising an initiation codon and encoding a polypeptide; and
(iii) a 3' UTR, wherein the at least one RNA element is a GC-rich RNA element comprising guanine (G) and cytosine (C) nucleobases and, optionally, adenine (A) and uracil (U) nucleobases, or derivatives or analogs thereof, wherein the GC-rich RNA element is at least 50% or greater cytosine (C) nucleobases and is at least 6 nucleotides in length, wherein the GC-rich RNA element is located about 20-30 nucleotides, about 10-20 nucleotides, or about 6-10 nucleotides upstream of the initiation codon in the 5' UTR, and wherein the translational regulatory activity is selected from the group consisting of:
(a) inhibits or reduces leaky scanning of the mRNA by the PIC or ribosome;
(b) increases an amount of a polypeptide translated from the full open reading frame;
(c) increases initiation of polypeptide synthesis at or from the initiation codon;
(d) inhibits or reduces initiation of polypeptide synthesis at any codon within the mRNA other than the initiation codon;
(e) inhibits or reduces an amount of polypeptide translated from any open reading frame within the mRNA other than the full open reading frame;
(f) inhibits or reduces translation of truncated or aberrant translation products from the mRNA; and
(g) a combination of any of (a)-(f).

In some embodiments, the GC-rich RNA element is 6 nucleotides upstream of the initiation codon in the 5' UTR. In some embodiments, the GC-rich RNA element is 7 nucleotides upstream of the initiation codon in the 5' UTR. In some embodiments, the GC-rich RNA element is 8 nucleotides upstream of the initiation codon in the 5' UTR. In some embodiments, the GC-rich RNA element is 9 nucleotides upstream of the initiation codon in the 5' UTR. In some embodiments, the GC-rich RNA element is 10 nucleotides upstream of the initiation codon in the 5' UTR. In some embodiments, the GC-rich RNA element is 11 nucleotides upstream of the initiation codon in the 5' UTR. In some embodiments, the GC-rich RNA element is 12 nucleotides upstream of the initiation codon in the 5' UTR. In some embodiments, the GC-rich RNA element is 13 nucleotides upstream of the initiation codon in the 5' UTR. In some embodiments, the GC-rich RNA element is 14 nucleotides upstream of the initiation codon in the 5' UTR. In some embodiments, the GC-rich RNA element is 15 nucleotides upstream of the initiation codon in the 5' UTR. In some embodiments, the GC-rich RNA element is 16 nucleotides upstream of the initiation codon in the 5' UTR. In some embodiments, the GC-rich RNA element is 17 nucleotides upstream of the initiation codon in the 5' UTR. In some embodiments, the GC-rich RNA element is 18 nucleotides upstream of the initiation codon in the 5' UTR. In some embodiments, the GC-rich RNA element is 19 nucleotides upstream of the initiation codon in the 5' UTR. In some embodiments, the GC-rich RNA element is 20 nucleotides upstream of the initiation codon in the 5' UTR. In some embodiments, the GC-rich RNA element is 21 nucleotides upstream of the initiation codon in the 5' UTR. In some embodiments, the GC-rich RNA element is 22 nucleotides upstream of the initiation codon in the 5' UTR. In some embodiments, the GC-rich RNA element is 23 nucleotides upstream of the initiation codon in the 5' UTR. In some embodiments, the GC-rich RNA element is 24 nucleotides upstream of the initiation codon in the 5' UTR. In some embodiments, the GC-rich RNA element is 25 nucleotides upstream of the initiation codon in the 5' UTR. In some embodiments, the GC-rich RNA element is 26 nucleotides upstream of the initiation codon in the 5' UTR. In some embodiments, the GC-rich RNA element is 27 nucleotides upstream of the initiation codon in the 5' UTR. In some embodiments, the GC-rich RNA element is 28 nucleotides upstream of the initiation codon in the 5' UTR in the 5' UTR. In some embodiments, the GC-rich RNA element is 29 nucleotides upstream of the initiation codon. In some embodiments, the GC-rich RNA element is 30 nucleotides upstream of the initiation codon in the 5' UTR.

In some embodiments, the disclosure provides mRNA comprising a 5' UTR comprising at least one RNA element that provides a translational regulatory activity, wherein the at least one RNA element is a GC-rich RNA element comprising 50% cytosine (C) nucleobases. In some embodiments, the GC-rich RNA element is >50% cytosine (C) nucleobases. In some embodiments, the GC-rich RNA element is >60% cytosine (C) nucleobases. In some embodiments, the GC-rich RNA element is >70% cytosine (C) nucleobases. In some embodiments, the GC-rich RNA element is about 50%-55% cytosine, about 55%-60% cytosine, about 60%-65% cytosine, about 65%-70% cytosine, about 70%-75% cytosine, about 75%-80% cytosine. In some embodiments, the GC-rich RNA element is about 50%-55% cytosine. In some embodiments, the GC-rich RNA element is about 55%-60% cytosine. In some embodiments, the GC-rich RNA element is about 60%-65% cytosine. In some embodiments, the GC-rich RNA element is about 65%-70% cytosine. In some embodiments, the GC-rich RNA element is about 70%-75% cytosine. In some embodiments, the GC-rich RNA element is about 75%-80% cytosine. In some embodiments, the GC-rich RNA element is >80% cytosine (C) nucleobases. In some embodiments, the GC-rich RNA element is 90% cytosine (C) nucleobases. In some embodiments, the GC-rich RNA element is 100% cytosine (C) nucleobases.

In some embodiments, the GC-rich RNA element comprises a nucleotide sequence of about 6-10 nucleotides in length, about 10-15 nucleotides in length, about 15-20 nucleotides in length, about 20-25 nucleotides in length, about 25-30 nucleotides in length. In some embodiments, the GC-rich RNA element is 6, 7, 8, 9, 10, 11, 12, 13, 14, 15, 16, 17, 18, 19, 20, 21, 22, 23, 24, 25, 26, 27, 28, 29 or 30 nucleotides in length. In some embodiments, the GC-rich RNA element is 6 nucleotides in length. In some embodiments, the GC-rich RNA element is 7 nucleotides in length. In some embodiments, the GC-rich RNA element is 8 nucleotides in length. In some embodiments, the GC-rich RNA element is 9 nucleotides in length. In some embodiments, the GC-rich RNA element is 10 nucleotides in length. In some embodiments, the GC-rich RNA element is 11 nucleotides in length. In some embodiments, the GC-rich RNA element is 12 nucleotides in length. In some embodiments, the GC-rich RNA element is 13 nucleotides in length. In some embodiments, the GC-rich RNA element is 14 nucleotides in length. In some embodiments, the GC-rich RNA element is 15 nucleotides in length. In some embodiments, the GC-rich RNA element is 16 nucleotides in length. In some embodiments, the GC-rich RNA element is 17 nucleotides in length. In some embodiments, the GC-rich RNA element is 18 nucleotides in length. In some embodiments, the GC-rich RNA element is 19 nucleotides in length. In some embodiments, the GC-rich RNA element is 20 nucleotides in length. In some embodiments, the GC-rich RNA element is 21 nucleotides in length. In some embodiments, the GC-rich RNA element is 22 nucleotides in length. In some embodiments, the GC-rich RNA element is 23 nucleotides in length. In some embodiments, the GC-rich RNA element is 24 nucleotides in length. In some embodiments, the GC-rich RNA element is 25 nucleotides in length. In some embodiments, the GC-rich RNA element is 26 nucleotides in length. In some embodiments, the GC-rich RNA element is 27 nucleotides in length. In some embodiments, the GC-rich RNA element is 28 nucleotides in length. In some embodiments, the GC-rich RNA element is 29 nucleotides in length. In some embodiments, the GC-rich RNA element is 30 nucleotides in length.

In some embodiments, the GC-rich RNA element does not comprise adenine (A) or uracil (U) or both A and U (or T). In some embodiments, the GC-rich RNA element does not comprise adenine (A). In some embodiments, the GC-rich RNA element does not comprise uracil (U).

In some embodiments, the disclosure provides mRNA comprising a 5' UTR comprising at least one RNA element that provides a translational regulatory activity, wherein the at least one RNA element is a GC-rich RNA element comprising a nucleotide sequence 6 nucleotides in length, or derivatives or analogs thereof, linked in any order, wherein the sequence is >50% cytosine. In some embodiments, the GC-rich RNA element comprises a nucleotide sequence 6 nucleotides in length, wherein the sequence is >50% cytosine, >60% cytosine or >70% cytosine nucleobases.

In some embodiments, the disclosure provides mRNA comprising a 5' UTR comprising at least one RNA element that provides a translational regulatory activity, wherein the at least one RNA element is a GC-rich RNA element comprising a nucleotide sequence 7 nucleotides in length, or derivatives or analogs thereof, linked in any order, wherein the sequence is >50% cytosine. In some embodiments, the GC-rich RNA element comprises a nucleotide sequence 7 nucleotides in length, wherein the sequence is >50% cytosine, >60% cytosine or >70% cytosine nucleobases.

In some embodiments, the disclosure provides mRNA comprising a 5' UTR comprising at least one RNA element that provides a translational regulatory activity, wherein the at least one RNA element is a GC-rich RNA element comprising a nucleotide sequence 8 nucleotides in length, or derivatives or analogs thereof, linked in any order, wherein the sequence is >50% cytosine. In some embodiments, the GC-rich RNA element comprises a nucleotide sequence 8 nucleotides in length, wherein the sequence is >50% cytosine, >60% cytosine or >70% cytosine nucleobases.

In some embodiments, the disclosure provides mRNA comprising a 5' UTR comprising at least one RNA element that provides a translational regulatory activity, wherein the at least one RNA element is a GC-rich RNA element comprising a nucleotide sequence 9 nucleotides in length, or derivatives or analogs thereof, linked in any order, wherein the sequence is >50% cytosine. In some embodiments, the GC-rich RNA element comprises a nucleotide sequence 9 nucleotides in length, wherein the sequence is >50% cytosine, >60% cytosine or >70% cytosine nucleobases.

In some embodiments, the disclosure provides mRNA comprising a 5' UTR comprising at least one RNA element that provides a translational regulatory activity, wherein the at least one RNA element is a GC-rich RNA element comprising a nucleotide sequence 10 nucleotides in length, or derivatives or analogs thereof, linked in any order, wherein the sequence is >50% cytosine. In some embodiments, the GC-rich RNA element comprises a nucleotide sequence 10 nucleotides in length, wherein the sequence is >50% cytosine, >60% cytosine or >70% cytosine nucleobases.

In some embodiments, the GC-rich RNA element comprises a nucleotide sequence 11 nucleotides in length, or derivatives or analogs thereof, linked in any order, wherein the sequence is >50% cytosine. In some embodiments, the GC-rich RNA element comprises a nucleotide sequence 12 nucleotides in length, or derivatives or analogs thereof, linked in any order, wherein the sequence is >50% cytosine. In some embodiments, the GC-rich RNA element comprises a nucleotide sequence 13 nucleotides in length, or derivatives or analogs thereof, linked in any order, wherein the sequence is >50% cytosine. In some embodiments, the GC-rich RNA element comprises a nucleotide sequence 14 nucleotides in length, or derivatives or analogs thereof, linked in any order, wherein the sequence is >50% cytosine. In some embodiments, the GC-rich RNA element comprises a nucleotide sequence 15 nucleotides in length, or derivatives or analogs thereof, linked in any order, wherein the sequence is >50% cytosine. In some embodiments, the GC-rich RNA element comprises a nucleotide sequence 16 nucleotides in length, or derivatives or analogs thereof, linked in any order, wherein the sequence is >50% cytosine. In some embodiments, the GC-rich RNA element comprises a nucleotide sequence 17 nucleotides in length, or derivatives or analogs thereof, linked in any order, wherein the sequence is >50% cytosine. In some embodiments, the GC-rich RNA element comprises a nucleotide sequence 18 nucleotides in length, or derivatives or analogs thereof, linked in any order, wherein the sequence is >50% cytosine. In some embodiments, the GC-rich RNA element comprises a nucleotide sequence 19 nucleotides in length, or derivatives or analogs thereof, linked in any order, wherein the sequence is >50% cytosine. In some embodiments, the GC-rich RNA element comprises a nucleotide sequence 20 nucleotides in length, or derivatives or analogs thereof, linked in any order, wherein the sequence is >50% cytosine.

In some embodiments, the disclosure provides mRNA comprising a 5' UTR comprising at least one RNA element that provides a translational regulatory activity, wherein the at least one RNA element is a GC-rich RNA element comprising a nucleotide sequence 20 nucleotides in length, wherein the sequence is >50% cytosine, >60% cytosine or >70% cytosine nucleobases. In some embodiments, the GC-rich RNA element comprises a nucleotide sequence 21 nucleotides in length, or derivatives or analogs thereof, linked in any order, wherein the sequence is >50% cytosine. In some embodiments, the GC-rich RNA element comprises a nucleotide sequence 22 nucleotides in length, or derivatives or analogs thereof, linked in any order, wherein the sequence is >50% cytosine. In some embodiments, the GC-rich RNA element comprises a nucleotide sequence 23 nucleotides in length, or derivatives or analogs thereof, linked in any order, wherein the sequence is >50% cytosine. In some embodiments, the GC-rich RNA element comprises a nucleotide sequence 24 nucleotides in length, or derivatives or analogs thereof, linked in any order, wherein the sequence is >50% cytosine. In some embodiments, the GC-rich RNA element comprises a nucleotide sequence 25 nucleotides in length, or derivatives or analogs thereof, linked in any order, wherein the sequence is >50% cytosine. In some embodiments, the GC-rich RNA element comprises a nucleotide sequence 26 nucleotides in length, or derivatives or analogs thereof, linked in any order, wherein the sequence is >50% cytosine. In some embodiments, the GC-rich RNA element comprises a nucleotide sequence 27 nucleotides in length, or derivatives or analogs thereof, linked in any order, wherein the sequence is >50% cytosine. In some embodiments, the GC-rich RNA element comprises a nucleotide sequence 28 nucleotides in length, or derivatives or analogs thereof, linked in any order, wherein the sequence is >50% cytosine. In some embodiments, the GC-rich RNA element comprises a nucleotide sequence 29 nucleotides in length, or derivatives or analogs thereof, linked in any order, wherein the sequence is >50% cytosine. In some embodiments, the GC-rich RNA element comprises a nucleotide sequence 30 nucleotides in length, or derivatives or analogs thereof, linked in any order, wherein the sequence is >50% cytosine.

In some embodiments, the disclosure provides mRNA comprising a 5' UTR comprising at least one RNA element that provides a translational regulatory activity, wherein the at least one RNA element is a GC-rich RNA element comprising a nucleotide sequence of about 6-30 guanine (G) and cytosine (C) nucleotides, or derivatives or analogues thereof, wherein the sequence is >50% cytosine, >60% cytosine or >70% cytosine nucleobases, and wherein the GC-rich RNA element comprises a repeating sequence motif. In some embodiments, the repeating sequence motif is $[CCG]_n$, wherein n=2 to 10, 2 to 5, 4, 3 or 2. In some embodiments, the repeating sequence motif is $[CCG]_n$, wherein n=2 to 10. In some embodiments, the repeating sequence motif is $[CCG]_n$, where n=2 to 5. In some embodiments, the repeating sequence motif is $[CCG]_n$, where n=4. In some embodiments, the repeating sequence motif is $[CCG]_n$, where n=3. In some embodiments, the repeating sequence motif is $[CCG]_n$, where n=2. In some embodiments, the repeating sequence motif is $[GCC]_n$, where n=2 to 10, 2 to 5, 4, 3 or 2. In some embodiments, the repeating sequence motif is $[GCC]_n$, where n=2 to 10. In some embodiments, the repeating sequence motif is $[GCC]_n$, where n=2 to 5. In some embodiments, the repeating sequence motif is $[GCC]_n$, where n=4. In some embodiments, the repeating sequence motif is $[GCC]_n$, where n=3. In some embodiments, the repeating sequence motif is $[GCC]_n$, where n=2. In some embodiments, the GC-rich RNA element comprises a nucleotide sequence selected from the group consisting of SEQ ID NO: 9, SEQ ID NO: 10, SEQ ID NO: 11, SEQ ID NO: 7 and SEQ ID NO: 8.

In some embodiments, the disclosure provides mRNA comprising a 5' UTR comprising at least one RNA element that provides a translational regulatory activity, wherein the at least one RNA element is a GC-rich RNA element comprising the nucleotide sequence set forth in SEQ ID NO: 2. In some embodiments, the GC-rich RNA element comprises the nucleotide sequence set forth in SEQ ID NO: 3. In some embodiments, the GC-rich RNA element comprises the nucleotide sequence set forth in SEQ ID NO: 4. In some embodiments, the GC-rich RNA element comprises the nucleotide sequence set forth in SEQ ID NO: 5.

In some aspects, the disclosure provides an mRNA comprising a 5' UTR, wherein the 5' UTR comprises the nucleotide sequence 5'-GGGAAAUAAGAGAGAA AAGAAGAGUAAGAAGAAAUAUAAGAGCCACC-3' set forth in SEQ ID NO: 33, wherein the 5' UTR comprises a GC-rich RNA element of the disclosure located about 20-30 nucleotides, about 10-20 nucleotides, or about 6-10 nucleotides upstream of the 3' end of the 5' UTR sequence set forth in SEQ ID NO: 33. In some embodiments, the GC-rich RNA element is located about 6 nucleotides upstream of the 3' end of the 5' UTR sequence set forth in SEQ ID NO: 33.

In some embodiments, the disclosure provides an mRNA comprising:
(i) a 5' untranslated region (UTR) comprising a GC-rich RNA element that provides a translational regulatory activity;

(ii) a full open reading frame comprising an initiation codon and encoding a polypeptide; and (iii) a 3' UTR, wherein the 5' UTR comprises the nucleotide sequence 5'-GGGAAAUAAGAGAGAAAAGAAGAGUAAGAAGAAAUAUAAGAGCCACC-3' set forth in SEQ ID NO: 33, wherein the GC-rich RNA element comprises the nucleotide sequence set forth in SEQ ID NO: 2, and wherein the 5' UTR comprises the GC-rich RNA element located about 20-30, about 10-20 nucleotides, or about 6-10 nucleotides upstream of the 3' end of the 5' UTR sequence set forth in SEQ ID NO: 33. In some embodiments, the GC-rich RNA element comprising the nucleotide sequence set forth in SEQ ID NO: 2 is located about 6 nucleotides upstream of the 3' end of the 5' UTR sequence set forth in SEQ ID NO: 33

In some aspects, the disclosure provides an mRNA comprising:

(i) a 5' untranslated region (UTR) comprising a GC-rich RNA element that provides a translational regulatory activity;

(ii) a full open reading frame comprising an initiation codon and encoding a polypeptide; and (iii) a 3' UTR, wherein the 5' UTR comprises the nucleotide sequence 5'-GGGAAAUAAGAGAGAAAAGAAGAGUAAGAAGAAAUAUAAGAGCCACC-3' set forth in SEQ ID NO: 33, wherein the GC-rich RNA element comprises the nucleotide sequence set forth in SEQ ID NO: 3, and wherein the GC-rich RNA element is located about 20-30 nucleotides, about 10-20 nucleotides, or about 6-10 nucleotides upstream of the 3' end of the 5' UTR sequence set forth in SEQ ID NO: 33. In some embodiments, the GC-rich RNA element comprising the nucleotide sequence set forth in SEQ ID NO: 3 is located about 6 nucleotides upstream of the 3' end of the 5' UTR sequence set forth in SEQ ID NO: 33.

In some embodiments, the disclosure provides an mRNA comprising:

(i) a 5' untranslated region (UTR) comprising a GC-rich RNA element that provides a translational regulatory activity;

(ii) a full open reading frame comprising an initiation codon and encoding a polypeptide; and (iii) a 3' UTR, wherein the 5' UTR comprises the nucleotide sequence 5'-GGGAAAUAAGAGAGAAAAGAAGAGUAAGAAGAAAUAUAAGAGCCACC-3' set forth in SEQ ID NO: 33, wherein the GC-rich RNA element comprises the nucleotide sequence set forth in SEQ ID NO: 4, and wherein the GC-rich RNA element is located about 20-30 nucleotides, about 10-20 nucleotides, or about 6-10 nucleotides upstream of the 3' end of the 5' UTR sequence set forth in SEQ ID NO: 33. In some embodiments, the GC-rich RNA element comprising the nucleotide sequence set forth in SEQ ID NO: 4 is located about 6 nucleotides upstream of the 3' end of the 5' UTR sequence set forth in SEQ ID NO: 33.

In some embodiments, the disclosure provides an mRNA comprising (i) a 5' untranslated region (UTR) comprising the nucleotide sequence set forth in SEQ ID NO: 34;

(ii) a full open reading frame comprising an initiation codon and encoding a polypeptide; and (iii) a 3' UTR.

In some embodiments, the disclosure provides an mRNA comprising (i) a 5' untranslated region (UTR) comprising the nucleotide sequence set forth in SEQ ID NO: 54;

(ii) a full open reading frame comprising an initiation codon and encoding a polypeptide; and (iii) a 3' UTR.

In some embodiments, the disclosure provides an mRNA comprising (i) a 5' untranslated region (UTR) comprising the nucleotide sequence set forth in SEQ ID NO: 73;

(ii) a full open reading frame comprising an initiation codon and encoding a polypeptide; and (iii) a 3' UTR.

In some aspects, the disclosure provides messenger RNA (mRNA) comprising a second RNA element that provides a translational regulatory activity, wherein the second RNA element comprises a stable RNA secondary structure, and wherein the translational regulatory activity is selected from the group consisting of:

(a) inhibits or reduces leaky scanning of the mRNA by the PIC or ribosome;

(b) increases an amount of a polypeptide translated from the full open reading frame;

(c) increases initiation of polypeptide synthesis at or from the initiation codon;

(d) inhibits or reduces initiation of polypeptide synthesis at any codon within the mRNA other than the initiation codon;

(e) inhibits or reduces an amount of polypeptide translated from any open reading frame within the mRNA other than the full open reading frame;

(f) inhibits or reduces translation of truncated or aberrant translation products from the mRNA; and (g) a combination of any of (a)-(f).

In some embodiments, the stable RNA secondary structure located downstream of the initiation codon in the full open reading frame. In some embodiments, the stable RNA secondary structure is located about 30, about 25, about 20, about 15, about 10, or about 5 nucleotides downstream of the initiation codon. In some embodiments, the stable RNA secondary structure is located about 20, about 15, about 10 or about 5 nucleotides downstream of the initiation codon. In some embodiments, the stable RNA secondary structure is located about 5, about 4, about 3, about 2, about 1 nucleotide downstream of the initiation codon. In some embodiments, the stable RNA secondary structure is located about 15-30, about 15-20, about 15-25, about 10-15, or about 5-10 nucleotides downstream of the initiation codon. In some embodiments, the stable RNA secondary structure is located about 25-30, about 20-25, about 15-20, about 10-15, about 5-10, or about 1-5 nucleotide(s) downstream of the initiation codon in the full open reading frame. In some embodiments, the stable RNA secondary structure is located 20, 19, 18, 17, 16, 15, 14, 13, 12, 11, 10, 9, 8, 7, 6, 5, 4, 3, 2, 1 nucleotide(s) downstream of the initiation codon in the full open reading frame. In some embodiments, the stable RNA secondary structure is located 20, 19, 18, 17, 16, 15, 14, 13, 12, 11, or 10 nucleotides downstream of the initiation codon. In some embodiments, the stable RNA secondary structure is located 15 nucleotides downstream of the initiation codon. In some embodiments, the stable RNA secondary structure is located 14 nucleotides downstream of the initiation codon. In some embodiments, the stable RNA secondary structure is located 13 nucleotides downstream of the initiation codon. In some embodiments, the stable RNA secondary structure is located 12 nucleotides downstream of the initiation codon.

In some embodiments, stable RNA secondary structure located upstream of the initiation codon in the 5' UTR. In some embodiments, the stable RNA secondary structure is located about 25-30, about 20-25, about 15-20, about 10-15, about 5-10, or about 1-5 nucleotide(s) upstream of the initiation codon in the 5' UTR. In some embodiments, the stable RNA secondary structure is located 20, 19, 18, 17, 16, 15, 14, 13, 12, 11, 10, 9, 8, 7, 6, 5, 4, 3, 2, 1 nucleotide(s) upstream of the initiation codon in the 5' UTR. In some embodiments, the stable RNA secondary structure is located about 40, about 35, about 30, about 25, about 20, about 15, about 10, or about 5 nucleotides upstream of the initiation codon. In some embodiments, the stable RNA secondary structure is located about 20, about 15, about 10 or about 5 nucleotides upstream of the initiation codon. In some embodiments, the stable RNA secondary structure is located about 5, about 4, about 3, about 2, about 1 nucleotide upstream of the initiation codon. In some embodiments, the stable RNA secondary structure is located about 15-40, about 15-30, about 15-20, about 15-25, about 10-15, or about 5-10 nucleotides upstream of the initiation codon.

In some embodiments, the stable RNA secondary structure comprises a nucleotide sequence selected from the group consisting of SEQ ID NO: 28, SEQ ID NO: 29, SEQ ID NO: 30, SEQ ID NO: 31, and SEQ ID NO: 32. In some embodiments, the stable RNA secondary structure comprises a nucleotide sequence set forth in SEQ ID NO: 28. In some embodiments, the stable RNA secondary structure comprises a nucleotide sequence set forth in SEQ ID NO: 29. In some embodiments, the stable RNA secondary structure comprises a nucleotide sequence set forth in SEQ ID NO: 30. In some embodiments, the stable RNA secondary structure comprises a nucleotide sequence set forth in SEQ ID NO: 31. In some embodiments, the stable RNA secondary structure comprises a nucleotide sequence set forth in SEQ ID NO: 32.

In some embodiments, the stable RNA secondary structure is a hairpin or a stem-loop.

In some embodiments, the stable RNA secondary structure has a deltaG of about −30 kcal/mol, about −20 to −30 kcal/mol, about −20 kcal/mol, about −10 to −20 kcal/mol, about −10 kcal/mol, about −5 to ~10 kcal/mol.

In some embodiments, the disclosure provides mRNA comprising a 5' UTR comprising at least one RNA element that provides a translational regulatory activity, wherein the initiation codon comprises at least one modified nucleotide, and wherein the at least one modified nucleotide increases binding affinity with the initiator Met-tRNA$_i^{Met}$. In some embodiments, the at least one modified nucleotide is selected from the group consisting of 2-thiouridine, 2'-O-methyl-2-thiouridine, 2-selenouridine, 2'-O-methyl ribose, a modified nucleotide in which the ribose moiety is modified with an extra bridge connecting the 2' oxygen and 4' carbon, inosine, 2-methylguanosine, 6-methyl-adenosine, a deoxyribonucleotide.

In some embodiments, the disclosure provides an mRNA comprising:
 (i) a first polynucleotide, wherein the first polynucleotide is chemically synthesized, wherein the first polynucleotide comprises a 5' UTR; and
 (ii) a second polynucleotide, wherein the second polynucleotide is synthesized by in vitro transcription, and wherein the second polynucleotide comprises a full open reading frame encoding a polypeptide, and a 3' UTR. In some embodiments, (i) and (ii) are chemically cross-linked or enzymatically ligated. In some embodiments, the first polynucleotide and the second polynucleotide are operably linked.

In any one of the aforementioned embodiments, the RNA element provides a translational regulatory activity which increases or enhances potency of the mRNA relative to an mRNA without the RNA element.

In any one of the aforementioned embodiments, the mRNA comprises a poly A tail (e.g., a poly A tail of about 100 nucleotides). In any one of the aforementioned embodiments, the mRNA comprises a 5' Cap 1 structure.

In any one of the aforementioned embodiments, the mRNA comprises at least one chemical modification. In some embodiments, the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methyluridine, 5-methoxyuridine, and 2'-O-methyl uridine. In some embodiments, the chemical modification is selected from the group consisting of pseudouridine or a pseudouridine analog. In some embodiments, the chemical modification is N1-methylpseudouridine. In some embodiments, the mRNA is fully modified with N1-methylpseudouridine.

In some aspects, the disclosure provides a composition comprising any one of the aforementioned mRNAs and a pharmaceutically acceptable carrier.

In some embodiments, the disclosure provides a lipid nanoparticle comprising any one of the aforementioned mRNAs.

In some embodiments, the disclosure provides a pharmaceutical composition comprising a lipid nanoparticle comprising any one of the aforementioned mRNAs, and a pharmaceutically acceptable carrier.

In some embodiments, the disclosure provides a method of inhibiting or reducing leaky scanning of an mRNA by a PIC or ribosome, the method comprising: contacting a cell with any one of the aforementioned mRNAs, any one of the aforementioned compositions, any one of the aforementioned lipid nanoparticles, or any one of the aforementioned pharmaceutical compositions.

In some aspects, the disclosure provides a method of increasing an amount of a polypeptide translated from a full open reading frame comprising an mRNA, the method comprising:
 contacting a cell with any one of the aforementioned mRNAs, any one of the aforementioned compositions, any one of the aforementioned lipid nanoparticles, or any one of the aforementioned pharmaceutical compositions.

In some aspects, the disclosure provides a method of increasing potency of a polypeptide translated from an mRNA, the method comprising: contacting a cell with any one of the aforementioned mRNAs, any one of the aforementioned compositions, any one of the aforementioned lipid nanoparticles, or any one of the aforementioned pharmaceutical compositions.

In some aspects, the disclosure provides a method of increasing initiation of polypeptide synthesis at or from an initiation codon comprising an mRNA, the method comprising: contacting a cell with any one of the aforementioned mRNAs, any one of the aforementioned compositions, any one of the aforementioned lipid nanoparticles, or any one of the aforementioned pharmaceutical compositions.

In some aspects, the disclosure provides a method of inhibiting or reducing initiation of polypeptide synthesis at any codon within an mRNA other than an initiation codon, the method comprising: contacting a cell with any one of the aforementioned mRNAs, any one of the aforementioned compositions, any one of the aforementioned lipid nanoparticles, or any one of the aforementioned pharmaceutical compositions.

In some aspects, the disclosure provides a method of inhibiting or reducing an amount of polypeptide translated from any open reading frame within an mRNA other than a full open reading frame, the method comprising: contacting a cell with any one of the aforementioned mRNAs, any one of the aforementioned compositions, any one of the aforementioned lipid nanoparticles, or any one of the aforementioned pharmaceutical compositions.

In some aspects, the disclosure provides a method of inhibiting or reducing translation of truncated or aberrant translation products from an mRNA, the method comprising: contacting a cell with any one of the aforementioned mRNAs, any one of the aforementioned compositions, any one of the aforementioned lipid nanoparticles, or any one of the aforementioned pharmaceutical compositions.

In some aspects, the disclosure provides a method of treating a disease, the method comprising: administering any one of the aforementioned mRNAs, any one of the aforementioned compositions, any one of the aforementioned lipid nanoparticles, or any one of the aforementioned pharmaceutical compositions, wherein treatment results in the translation of the mRNA, wherein the translation results in the formation of a polypeptide that alleviates the disease or that does not cause or contribute to the disease.

In some aspects, the disclosure provides a kit comprising a container comprising any one of the aforementioned mRNAs, any one of the aforementioned compositions, any one of the aforementioned lipid nanoparticles, or any one of the aforementioned pharmaceutical composition and a package insert comprising instructions for use.

In some embodiments, the disclosure provides a method of identifying an RNA element that provides a translational regulatory activity, the method comprising: (i) synthesizing a $1^{st}$ control mRNA comprising: (a) a polynucleotide sequence comprising an open reading frame encoding a reporter polypeptide, an $1^{st}$ AUG codon upstream of, in-frame, and operably linked to the open reading frame encoding the reporter polypeptide; a coding sequence for a first epitope tag upstream of, in-frame, and operably linked to the $1^{st}$ AUG codon; a $2^{nd}$ AUG codon upstream of, in-frame, and operably linked to the coding sequence for the first epitope tag; a coding sequence for a second epitope tag upstream of, in-frame, and operably linked to the $2^{nd}$ AUG codon; a $3^{rd}$ AUG codon upstream of, in-frame, and operably linked to the coding sequence for the second epitope tag, a 5' UTR and a 3' UTR; and, (ii) synthesizing a $2^{nd}$ test mRNA comprising: (b) a polynucleotide sequence comprising an open reading frame encoding a reporter polypeptide, an $1^{st}$ AUG codon upstream of, in-frame, and operably linked to the open reading frame encoding the reporter polypeptide; a coding sequence for a first epitope tag upstream of, in-frame, and operably linked to the $1^{st}$ AUG codon; a $2^{nd}$ AUG codon upstream of, in-frame, and operably linked to the coding sequence for the first epitope tag; a coding sequence for a second epitope tag upstream of, in-frame, and operably linked to the $2^{nd}$ AUG codon; a $3^{rd}$ AUG codon upstream of, in-frame, and operably linked to the coding sequence for the second epitope tag, a 5' UTR and a 3' UTR, wherein the 5' UTR comprises a test RNA element; and (iii) introducing the $1^{st}$ control mRNA and $2^{nd}$ test mRNA to conditions suitable for translation of the polynucleotide sequence encoding the reporter polypeptide; measuring the effect of the RNA element on the initiation of translation of the polynucleotide sequence encoding the reporter polypeptide from each of the three AUG codons.

In some embodiments, the reporter polypeptide is eGFP. In some embodiments, the epitope tag is selected from the group consisting of: a FLAG tag, a 3×FLAG tag, a Myc tag, a V5 tag, a hemagglutinin A (HA) tag, a histidine tag (e.g. a 6×His tag), an HSV tag, a VSV-G tag, an NE tag, an AviTag, a Calmodulin tag, an E tag, an S tag, an SBP tag, a Softag 1, a Softag 3, a Strep tag, a Ty tag, or an Xpress tag.

BRIEF DESCRIPTION OF DRAWINGS

FIG. 1A depicts a schematic representation of reporter mRNA.

FIG. 1B is a depiction of representative 5' UTR sequences. Sequences in order are set forth in SEQ ID NOs: 536-539 respectively.

FIG. 2A depicts an SDS-PAGE/Western Blot of lysates derived from HeLa cells or murine embryonic fibroblasts (MEFs) that were transfected with reporter mRNAs containing 5' UTRs varying in length and/or base composition. Full-length and truncated translation products were detected using an eGFP-specific antibody.

FIG. 2B depicts an SDS-PAGE/Western Blot of lysates derived from mouse livers from mice that were administered reporter mRNAs containing 5' UTRs varying in length and/or base composition. Full-length and truncated translation products were detected using an eGFP-specific antibody.

FIGS. 2C and 2D depict graphs representing the results of quantitative analysis of formation of truncated protein from experiments described in (A) and (B), respectively.

FIG. 3A provides a schematic representation of reporter mRNA containing a 5' UTR consists of 1×, 2×, 3×, or 4× copies of the standard 5' UTR depicted in FIG. 1B.

FIG. 3B depicts an SDS-PAGE/Western Blot of lysates derived from HeLa cells that were administered reporter mRNA contain 5' UTRs consisting of 1×, 2×, 3×, or 4× copies of the standard 5' UTR as depicted in FIG. 3A.

FIG. 3C provides a graph representing the results of a quantitative analysis of formation of truncated protein from experiments shown in FIG. 3B.

FIG. 3D provides a graph representing the results of at quantitative analysis of formation of total full-length protein from experiments shown in FIG. 3B.

FIG. 4A provides a graph representing the results of small ribosome subunit footprinting analysis, wherein sequencing reads were mapped to a human transcriptome and the number of reads overlapping with each AUG in each mRNA was counted. The number of reads overlapping with each AUG was then normalized to the first AUG.

FIG. 4B provides a graph representing the results of small ribosomal footprinting analysis, wherein the frequency of leaky scanning for each mRNA in primary human hepatocytes was estimated by dividing the mean small subunit read density in the first 500 nt of the coding sequence by the mean small subunit read density in the 5' UTR. This metric was plotted against length of 5' UTR. Each point represents an individual mRNA with at least 100 mapped reads. Black line represents a moving average.

FIG. 8A is a table depicting the sequence of 5' UTRs tested in the reporter construct depicted in FIG. 8B. 5' UTR sequences in order are set forth in SEQ ID NOs: 540-545 respectively.

FIG. 8B is a diagram depicting the reporter construct and system used to test the effect of various 5' UTRs comprising GC-rich RNA elements, as shown in FIG. 8A.

MODIFIED POLYNUCLEOTIDES COMPRISING FUNCTIONAL RNA ELEMENTS

Figure 5A:
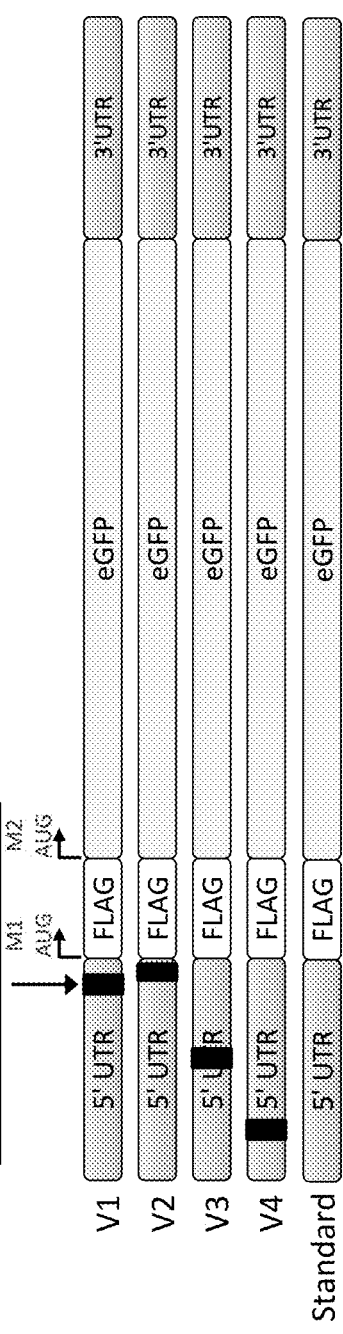
FIG. 5A provides a schematic representation of reporter mRNA containing GC-rich elements in the 5' UTR.

The present disclosure provides synthetic polynucleotides (e.g., mRNAs) comprising a modification (e.g., an RNA element), wherein the modification provides a desired translational regulatory activity. In some embodiments, the disclosure provides a polynucleotide comprising a 5' untranslated region (UTR), an initiation codon, a full open reading frame encoding a polypeptide, a 3' UTR, and at least one modification, wherein the at least one modification provides a desired translational regulatory activity, for example, a modification that promotes and/or enhances the translational fidelity of mRNA translation. In some embodiments, the desired translational regulatory activity is a cis-acting regulatory activity. In some embodiments, the desired translational regulatory activity is an increase in the residence time of the 43S pre-initiation complex (PIC) or ribosome at, or proximal to, the initiation codon. In some embodiments, the desired translational regulatory activity is an increase in the initiation of polypeptide synthesis at or from the initiation codon. In some embodiments, the desired translational regulatory activity is an increase in the amount of polypeptide translated from the full open reading frame. In some embodiments, the desired translational regulatory activity is an increase in the fidelity of initiation codon decoding by the PIC or ribosome. In some embodiments, the desired translational regulatory activity is inhibition or reduction of leaky scanning by the PIC or ribosome. In some embodiments, the desired translational regulatory activity is a decrease in the rate of decoding the initiation codon by the PIC or ribosome. In some embodiments, the desired translational regulatory activity is inhibition or reduction in the initiation of polypeptide synthesis at any codon within the mRNA other than the initiation codon. In some embodiments, the desired translational regulatory activity is inhibition or reduction of the amount of polypeptide translated from any open reading frame within the mRNA other than the full open reading frame. In some embodiments, the desired translational regulatory activity is inhibition or reduction in the production of aberrant translation products. In some embodiments, the desired translational regulatory activity is a combination of one or more of the foregoing translational regulatory activities.

Accordingly, the present disclosure provides a polynucleotide, e.g., an mRNA, comprising an RNA element that comprises a sequence and/or an RNA secondary structure(s) that provides a desired translational regulatory activity as described herein. In some aspects, the mRNA comprises an RNA element that comprises a sequence and/or an RNA secondary structure(s) that promotes and/or enhances the translational fidelity of mRNA translation. In some aspects, the mRNA comprises an RNA element that comprises a sequence and/or an RNA secondary structure(s) that provides a desired translational regulatory activity, such as inhibiting and/or reducing leaky scanning. In some aspects, the disclosure provides an mRNA that comprises an RNA element that comprises a sequence and/or an RNA secondary structure(s) that inhibits and/or reduces leaky scanning thereby promoting the translational fidelity of the mRNA.

RNA Elements

In some embodiments, the disclosure provides mRNAs comprising RNA elements that provide one or more translational regulatory activities. In some embodiments, the disclosure provides mRNAs comprising RNA elements that provide one or more translational regulatory activities which improve potency of an mRNA having the RNA element (e.g., a G C-rich RNA element located in the 5' UTR), relative to an mRNA without the RNA element. An RNA element is a portion, fragment or segment of an RNA molecule that has biological significance (e.g., provides a biological function or activity such as a translational regulatory activity). In some embodiments, an RNA element comprises a GC-rich RNA element. In some embodiments, an RNA element comprises a stable RNA secondary structure. In some embodiments, the RNA element provides one or more translational regulatory activities.

GC-Rich RNA Elements

In some embodiments, the disclosure provides mRNAs with 5' UTRs comprising an RNA element that is a GC-rich RNA element that provides a translational regulatory activity. In some embodiments, the disclosure provides mRNAs with 5' UTRs comprising an RNA element that is a GC-rich RNA element that provides a translational regulatory activity which improves potency of the mRNA having the RNA element relative to an mRNA without the element. In some embodiments, the translational regulatory activity is selected from the group consisting of:

(a) inhibits or reduces leaky scanning of the mRNA by the PIC or ribosome;
(b) increases an amount of a polypeptide translated from the full open reading frame;
(c) increases initiation of polypeptide synthesis at or from the initiation codon;
(d) inhibits or reduces initiation of polypeptide synthesis at any codon within the mRNA other than the initiation codon;
(e) inhibits or reduces an amount of polypeptide translated from any open reading frame within the mRNA other than the full open reading frame;
(f) inhibits or reduces translation of truncated or aberrant translation products from the mRNA; and
(g) a combination of any of (a)-(g).

In some embodiments, the GC-rich RNA element inhibits or reduces leaky scanning of the mRNA by the PIC or ribosome. In some embodiments, the GC-rich RNA element inhibits or reduces leaky scanning of the mRNA by the PIC or ribosome and improves (e.g., increases or enhances) potency of the mRNA. In some embodiments, the GC-rich RNA element increases an amount of a polypeptide translated from the full open reading frame. In some embodiments, the GC-rich RNA element increases an amount of a polypeptide translated from the full open reading frame and improves (e.g., increases or enhances) potency of the mRNA. In some embodiments, the GC-rich RNA element increases potency of a polypeptide translated from the mRNA. In some embodiments, the GC-rich RNA element increases potency of a polypeptide translated from the mRNA and improves (e.g., increases or enhances) potency of the mRNA. In some embodiments, the GC-rich RNA element increases initiation of polypeptide synthesis at or from the initiation codon. In some embodiments, the GC-rich RNA element increases initiation of polypeptide synthesis at or from the initiation codon and improves (e.g., increases or enhances) potency of the mRNA. In some embodiments, the GC-rich RNA element inhibits or reduces initiation of polypeptide synthesis at any codon within the mRNA other than the initiation codon. In some embodiments, the GC-rich RNA element inhibits or reduces initiation of polypeptide synthesis at any codon within the mRNA other than the initiation codon and improves (e.g., increases or enhances) potency of the mRNA. In some embodiments, the GC-rich RNA element inhibits or reduces an amount of polypeptide translated from any open reading frame within the mRNA other than the full open reading frame. In some embodiments, the GC-rich RNA element inhibits or reduces an amount of polypeptide translated from any open reading frame within the mRNA other than the full open reading frame and improves (e.g., increases or enhances) potency of the mRNA. In some embodiments, the GC-rich RNA element inhibits or reduces translation of truncated or aberrant translation products from the mRNA. In some embodiments, the GC-rich RNA element inhibits or reduces translation of truncated or aberrant translation products from the mRNA and improves (e.g., increases or enhances) potency of the mRNA.

In some embodiments, the GC-rich RNA element comprises guanine (G) and cytosine (C) nucleobases, or derivatives or analogues thereof and, optionally, adenine (A) and uracil (U) nucleobases, or derivatives or analogues thereof. In some embodiments, the GC-rich RNA element does not comprise adenine (A) nucleobases. In some embodiments, the GC-rich RNA element does not comprise uracil (U) nucleobases. In some embodiments, the GC-rich RNA element does not comprise adenine (A) or uracil (U) nucleobases.

In some embodiments, the GC-rich RNA element is at least 50% or greater cytosine (C) nucleobases. In some embodiments, The GC-rich RNA element is about 50%-55% cytosine, about 55%-60% cytosine, about 60%-65% cytosine, about 65%-70% cytosine, about 70%-75% cytosine or about 75%-80% cytosine. In some embodiments, the GC-rich RNA element is >50% cytosine, >60% cytosine or >70% cytosine nucleobases. In some embodiments, the GC-rich RNA element is >50% cytosine. In some embodiments, the GC-rich RNA element is >60% cytosine. In some embodiments, the GC-rich RNA element is >70% cytosine.

In some embodiments, the GC-rich RNA element is at least 6 nucleotides in length. In some embodiments, the GC-rich RNA element comprises a nucleotide sequence of about 6-10 nucleotides in length, about 10-15 nucleotides in length, about 15-20 nucleotides in length, about 20-25 nucleotides in length or about 25-30 nucleotides in length. In some embodiments, the GC-rich RNA element is 6, 7, 8, 9, 10, 11, 12, 13, 14, 15, 16, 17, 18, 19, 20, 21, 22, 23, 24, 25, 26, 27, 28, 29 or 30 nucleotides in length.

In some embodiments, the GC-rich RNA The mRNA of any one of claims 1-5, wherein the GC-rich RNA element comprises a nucleotide sequence 6 nucleotides in length and comprises >50% cytosine, >60% cytosine or >70% cytosine nucleobases. In some embodiments, the GC-rich RNA element comprises a nucleotide sequence 7 nucleotides in length and comprises >50% cytosine, >60% cytosine or >70% cytosine nucleobases. In some embodiments, the GC-rich RNA element comprises a nucleotide sequence 8 nucleotides in length and comprises >50% cytosine, >60% cytosine or >70% cytosine nucleobases. In some embodiments, the GC-rich RNA element comprises a nucleotide sequence 9 nucleotides in length and >50% cytosine, >60% cytosine or >70% cytosine nucleobases. In some embodiments, the GC-rich RNA element comprises a nucleotide sequence 10 nucleotides in length and comprises >50% cytosine, >60% cytosine or >70% cytosine nucleobases. In some embodiments, the GC-rich RNA element comprises a nucleotide sequence 20 nucleotides in length, wherein the sequence is >50% cytosine, >60% cytosine or >70% cytosine nucleobases. In some embodiments, the GC-rich RNA element comprises a nucleotide sequence of about 6-30 guanine (G) and cytosine (C) nucleotides, or derivatives or analogues thereof, wherein the sequence is >50% cytosine, >60% cytosine or >70% cytosine nucleobases, and wherein the sequence comprises a repeating sequence motif.

In any of the foregoing or related aspects, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is 70-80% cytosine, 60-70% cytosine, 50%-60% cytosine, 40-50% cytosine, 30-40% cytosine bases. In any of the foregoing or related aspects, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is about 80% cytosine, about 70% cytosine, about 60% cytosine, about 50% cytosine, about 40% cytosine, or about 30% cytosine.

In any of the foregoing or related aspects, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is 70-80% cytosine, 60-70% cytosine, 50%-60% cytosine, 40-50% cytosine, or 30-40% cytosine. In any of the foregoing or related aspects, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is about 80% cytosine, about 70% cytosine, about 60% cytosine, about 50% cytosine, about 40% cytosine, or about 30% cytosine.

In some embodiments, the disclosure provides an mRNA comprising a GC-rich RNA element, wherein the GC-rich RNA element is located about 20-30 nucleotides, about 10-20 nucleotides, or about 6-10 nucleotides upstream of an initiation codon and within a 5' UTR. In some embodiments, the GC-rich RNA element is located 6 nucleotides upstream of an initiation codon and within a 5' UTR. In some embodiments, the GC-rich RNA element is located about 20-30 nucleotides, about 10-20 nucleotides, or about 6-10 nucleotides upstream of the 3' end of the 5' UTR. In some embodiments, the GC-rich RNA element upstream of a Kozak sequence in a 5' UTR. In some embodiments, the GC-rich RNA element is upstream of a Kozak consensus sequence in a 5' UTR. In some embodiments, the GC-rich RNA element is upstream of a Kozak-like sequence in a 5' UTR.

In some embodiments, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA, and wherein the GC-rich RNA element comprises a sequence of 3, 4, 5, 6, 7, 8, 9, 10, 11, 12, 13, 14, 15, 16, 17, 18, 19, or 20 nucleotides, or derivatives or analogs thereof, linked in any order, wherein the sequence composition is >50% cytosine. In some embodiments, the sequence composition is >55% cytosine, >60% cytosine, >65% cytosine, >70% cytosine, >75% cytosine, >80% cytosine, >85% cytosine, or >90% cytosine.

In other aspects, the disclosure provides an mRNA comprising a GC-rich RNA element, wherein the GC-rich RNA element comprises a repeating sequence motif. In some embodiments the repeating sequence motif is $[CCG]_n$, wherein n=2 to 10, 2 to 5, 4, 3 or 2. In some embodiments, the repeating sequence motif is $[GCC]_n$, where n=2 to 10, 2 to 5, 4, 3 or 2. In some embodiments, a GC-rich RNA element comprising a repeating sequence motif comprises the nucleotide sequence set forth in SEQ ID NO: 12. In some embodiments, a GC-rich RNA element comprising a repeating sequence motif comprises the nucleotide sequence set forth in SEQ ID NO: 13. In some embodiments, a GC-rich RNA element comprising a repeating sequence motif comprises the nucleotide sequence set forth in SEQ ID NO: 14. In some embodiments, a GC-rich RNA element comprising a repeating sequence motif comprises the nucleotide sequence set forth in SEQ ID NO: 15. In some embodiments, a GC-rich RNA element comprising a repeating sequence motif comprises the nucleotide sequence set forth in SEQ ID NO: 16. In some embodiments, a GC-rich RNA element comprising a repeating sequence motif comprises the nucleotide sequence set forth in SEQ ID NO: 17. In some embodiments, a GC-rich RNA element comprising a repeating sequence motif comprises the nucleotide sequence set forth in SEQ ID NO: 18. In some embodiments, a GC-rich RNA element comprising a repeating sequence motif comprises the nucleotide sequence set forth in SEQ ID NO: 19. In some embodiments, a GC-rich RNA element comprising a repeating sequence motif comprises the nucleotide sequence set forth in SEQ ID NO: 20. In some embodiments, a GC-rich RNA element comprising a repeating sequence motif comprises the nucleotide sequence set forth in SEQ ID NO: 21. In some embodiments, a GC-rich RNA element comprising a repeating sequence motif comprises the nucleotide sequence set forth in SEQ ID NO: 22. In some embodiments, a GC-rich RNA element comprising a repeating sequence motif comprises the nucleotide sequence set forth in SEQ ID NO: 23. In some embodiments, a GC-rich RNA element comprising a repeating sequence motif comprises the nucleotide sequence set forth in SEQ ID NO: 24. In some embodiments, a GC-rich RNA element comprising a repeating sequence motif comprises the nucleotide sequence set forth in SEQ ID NO: 25. In some embodiments, a GC-rich RNA element comprising a repeating sequence motif comprises the nucleotide sequence set forth in SEQ ID NO: 26. In some embodiments, a GC-rich RNA element comprising a repeating sequence motif comprises the nucleotide sequence set forth in SEQ ID NO: 27.

In other aspects, the disclosure provides an mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA, and wherein the GC-rich RNA element comprises a sequence of about 3-30, 5-25, 10-20, 15-20 or about 20, about 15, about 12, about 10, about 6 or about 3 nucleotides, or derivatives or analogues thereof, wherein the sequence comprises a repeating GC-motif, wherein the repeating GC-motif is $[CCG]_n$, wherein n=1 to 10, n=2 to 8, n=3 to 6, or n=4 to 5. In some embodiments, the sequence comprises a repeating GC-motif $[CCG]_n$, wherein n=1, 2, 3, 4 or 5. In some embodiments, the sequence comprises a repeating GC-motif $[CCG]_n$, wherein n=1, 2, or 3. In some embodiments, the sequence comprises a repeating GC-motif [CCG]$_n$, wherein n=1. In some embodiments, the sequence comprises a repeating GC-motif [CCG]$_n$, wherein n=2. In some embodiments, the sequence comprises a repeating GC-motif [CCG]$_n$, wherein n=3. In some embodiments, the sequence comprises a repeating GC-motif [CCG]$_n$, wherein n=4. In some embodiments, the sequence comprises a repeating GC-motif [CCG]$_n$, wherein n=5.

In another aspect, the disclosure provides mRNAs comprising a GC-rich RNA element, wherein the GC-rich RNA element is located in the 5' UTR upstream of the 3' end of the 5' UTR, and wherein the GC-rich RNA element comprises any one of the GC-rich RNA elements comprising a nucleotide sequence set forth in SEQ ID NO: 2 to SEQ ID NO: 27. In one embodiment, the disclosure provides mRNAs comprising a GC-rich RNA element, wherein the GC-rich RNA element is located in the 5' UTR upstream of the 3' end of the 5' UTR, wherein the GC-rich RNA element comprises any one of the GC-rich RNA elements comprising a nucleotide sequence set forth in SEQ ID NO: 2 to SEQ ID NO: 27, and wherein the GC-rich RNA element is located about 20-30 nucleotides, about 10-20 nucleotides, or about 6-10 nucleotides upstream of the 3' end of the 5' UTR.

In one embodiment, the disclosure provides a mRNA comprising a GC-rich RNA element, wherein the GC-rich RNA element is located in the 5' UTR upstream of the 3' end of the 5' UTR, wherein the GC-rich RNA element comprises any one of the GC-rich RNA elements comprising a nucleotide sequence set forth in SEQ ID NO: 2 to SEQ ID NO: 27, and wherein the GC-rich RNA element is located about 20-30 nucleotides upstream of the 3' end of the 5' UTR. In one embodiment, the disclosure provides a mRNA comprising a GC-rich RNA element, wherein the GC-rich RNA element is located in the 5' UTR upstream of the 3' end of the 5' UTR, wherein the GC-rich RNA element comprises any one of the GC-rich RNA elements comprising a nucleotide sequence set forth in SEQ ID NO: 2 to SEQ ID NO: 27, and wherein the GC-rich RNA element is located about 10-20 nucleotides upstream of the 3' end of the 5' UTR. In one embodiment, the disclosure provides a mRNA comprising a GC-rich RNA element, wherein the GC-rich RNA element is located in the 5' UTR upstream of the 3' end of the 5' UTR, wherein the GC-rich RNA element comprises any one of the GC-rich RNA elements comprising a nucleotide sequence set forth in SEQ ID NO: 2 to SEQ ID NO: 27, and wherein the GC-rich RNA element is located about 6-10 nucleotides upstream of the 3' end of the 5' UTR. In one embodiment, the disclosure provides a mRNA comprising a GC-rich RNA element, wherein the GC-rich RNA element is located in the 5' UTR upstream of the 3' end of the 5' UTR, wherein the GC-rich RNA element comprises any one of the GC-rich RNA elements comprising a nucleotide sequence set forth in SEQ ID NO: 2 to SEQ ID NO: 27, and wherein the GC-rich RNA element is located about 6 nucleotides upstream of the 3' end of the 5' UTR.

In one embodiment, the disclosure provides a mRNA comprising a GC-rich RNA element comprising the nucleotide sequence set forth in SEQ ID NO: 2, and wherein the GC-rich RNA element is located about 6 nucleotides upstream of the 3' end of the 5' UTR. In one embodiment, the disclosure provides a mRNA comprising a GC-rich RNA element comprising any one of the GC-rich RNA elements set forth in SEQ ID NO: 3 to SEQ ID NO: 27, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 4, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 5, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 6, and wherein the GC-rich RNA element is located about 6 nucleotides upstream of the 3' end of the 5' UTR. In one embodiment, the disclosure provides a mRNA comprising a GC-rich RNA element, wherein the GC-rich RNA element is located in the 5' UTR upstream of the 3' end of the 5' UTR, wherein the GC-rich RNA element comprises the nucleotide sequence set forth in SEQ ID NO: 7, and wherein the GC-rich RNA element is located about 6 nucleotides upstream of the 3' end of the 5' UTR. In one embodiment, the disclosure provides a mRNA comprising a GC-rich RNA element, wherein the GC-rich RNA comprises the nucleotide sequence set forth in SEQ ID NO: 8, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 9, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 10, and wherein the GC-rich RNA element is located about 6 nucleotides upstream of the 3' end of the 5' UTR.

In one embodiment, the disclosure provides a mRNA comprising a GC-rich RNA element comprising the nucleotide sequence set forth in SEQ ID NO: 11, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 12, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 13, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 14, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 15, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 16, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 17, and wherein the GC-rich RNA element is located about 6 nucleotides upstream of the 3' end of the 5' UTR. In one embodiment, the disclosure provides an mRNA comprising a GC-rich RNA element comprising the nucleotide sequence set forth in SEQ ID NO: 18, and wherein the GC-rich RNA element is located about 6 nucleotides upstream of the 3' end of the 5' UTR. In one embodiment, the disclosure provides an mRNA comprising a GC-rich RNA element comprising the nucleotide sequence set forth in SEQ ID NO: 19, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 20, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 21, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 22, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 23, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 24, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 25, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 26, and wherein the GC-rich RNA element is located about 6 nucleotides upstream of the 3' end of the 5' UTR. In one embodiment, the disclosure provides a mRNA comprising a GC-rich RNA element comprising the nucleotide sequence set forth in SEQ ID NO: 27, and wherein the GC-rich RNA element is located about 6 nucleotides upstream of the 3' end of the 5' UTR.

In another aspect, the disclosure provides an mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element comprises any one of the sequences set forth in SEQ ID NO: 2 to SEQ ID NO: 27.

In one embodiment, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located about 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA.

In another aspect, the disclosure provides an mRNA comprising a GC-rich RNA element comprises a nucleotide sequence selected from the group consisting of SEQ ID NO: 9, SEQ ID NO: 10, SEQ ID NO: 11, SEQ ID NO: 7 and SEQ ID NO: 8. In some embodiments, the mRNA provided by the disclosure comprises a GC-rich RNA element comprising the nucleotide sequence set forth in SEQ ID NO: 2. In some embodiments, the mRNA provided by the disclosure comprises a GC-rich RNA element comprising the nucleotide sequence set forth in SEQ ID NO: 3. In some embodiments, the disclosure provides an mRNA comprising a GC-rich RNA element comprising the nucleotide sequence set forth in SEQ ID NO: 4 or SEQ ID NO: 5.

In other aspects, the disclosure provides a modified mRNA comprising at least one modification, wherein at least one modification is a GC-rich RNA element comprising the nucleotide sequence V1 [CCCCGGCGCC] (SEQ ID NO: 2) as set forth in Table 1, or derivatives or analogs thereof, preceding a Kozak consensus sequence in the 5' UTR of the mRNA. In some embodiments, the GC-rich element comprises the nucleotide sequence V1 [CCCCGGCGCC] (SEQ ID NO: 2) as set forth in Table 1 located immediately adjacent to and upstream of the Kozak consensus sequence in the 5' UTR of the mRNA. In some embodiments, the GC-rich element comprises the nucleotide sequence V1 [CCCCGGCGCC] (SEQ ID NO: 2) as set forth in Table 1 located 1, 2, 3, 4, 5, 6, 7, 8, 9 or 10 bases upstream of the Kozak consensus sequence in the 5' UTR of the mRNA. In other embodiments, the GC-rich element comprises the nucleotide sequence V1 [CCCCGGCGCC] (SEQ ID NO: 2) as set forth in Table 1 located 1-3, 3-5, 5-7, 7-9, 9-12, or 12-15 bases upstream of the Kozak consensus sequence in the 5' UTR of the mRNA.

In other aspects, the disclosure provides a modified mRNA comprising at least one modification, wherein at least one modification is a GC-rich RNA element comprising the nucleotide sequence V2 [CCCCGGC] (SEQ ID NO: 3) as set forth in Table 1, or derivatives or analogs thereof, preceding a Kozak consensus sequence in the 5' UTR of the mRNA. In some embodiments, the GC-rich element comprises the nucleotide sequence V2 [CCCCGGC] (SEQ ID NO: 3) as set forth in Table 1 located immediately adjacent to and upstream of the Kozak consensus sequence in the 5' UTR of the mRNA. In some embodiments, the GC-rich element comprises the nucleotide sequence V2 [CCCCGGC] (SEQ ID NO: 3) as set forth in Table 1 located 1, 2, 3, 4, 5, 6, 7, 8, 9 or 10 bases upstream of the Kozak consensus sequence in the 5' UTR of the mRNA. In other embodiments, the GC-rich element comprises the nucleotide sequence V2 [CCCCGGC] (SEQ ID NO: 3) as set forth in Table 1 located 1-3, 3-5, 5-7, 7-9, 9-12, or 12-15 bases upstream of the Kozak consensus sequence in the 5' UTR of the mRNA.

In other aspects, the disclosure provides a modified mRNA comprising at least one modification, wherein at least one modification is a GC-rich RNA element comprising the sequence EK2 [GCCGCC] (SEQ ID NO: 10) as set forth in Table 1, or derivatives or analogs thereof, preceding a Kozak consensus sequence in the 5' UTR of the mRNA. In some embodiments, the GC-rich element comprises the sequence EK2 [GCCGCC] (SEQ ID NO: 10) as set forth in Table 1 located immediately adjacent to and upstream of the Kozak consensus sequence in the 5' UTR of the mRNA. In some embodiments, the GC-rich element comprises the sequence EK2 [GCCGCC] (SEQ ID NO: 10) as set forth in Table 1 located 1, 2, 3, 4, 5, 6, 7, 8, 9 or 10 bases upstream of the Kozak consensus sequence in the 5' UTR of the mRNA. In other embodiments, the GC-rich element comprises the sequence EK2 [GCCGCC] (SEQ ID NO: 10) as set forth in Table 1 located 1-3, 3-5, 5-7, 7-9, 9-12, or 12-15 bases upstream of the Kozak consensus sequence in the 5' UTR of the mRNA.

In yet other aspects, the disclosure provides a modified mRNA comprising at least one modification, wherein at least one modification is a GC-rich RNA element comprising the sequence V1 [CCCCGGCGCC] (SEQ ID NO: 2) as set forth in Table 1, or derivatives or analogs thereof, preceding a Kozak consensus sequence in the 5' UTR of the mRNA, wherein the 5' UTR comprises the following sequence shown in Table 1:

(SEQ ID NO: 33)
GGGAAATAAGAGAGAAAAGAAGAGTAAGAAGAAATATAAGAGCCACC.

In some embodiments, the GC-rich element comprises the sequence V1 (SEQ ID NO: 2) as set forth in Table 1 located immediately adjacent to and upstream of the Kozak consensus sequence in the 5' UTR sequence shown in Table 1. In some embodiments, the GC-rich element comprises the sequence V1 (SEQ ID NO: 2) as set forth in Table 1 located 1, 2, 3, 4, 5, 6, 7, 8, 9 or 10 bases upstream of the Kozak consensus sequence in the 5' UTR of the mRNA, wherein the 5' UTR comprises the following sequence shown in Table 1:

(SEQ ID NO: 33)
GGGAAATAAGAGAGAAAAGAAGAGTAAGAAGAAATATAAGAGCCACC.

In other embodiments, the GC-rich element comprises the sequence V1 (SEQ ID NO: 2) as set forth in Table 1 located 1-3, 3-5, 5-7, 7-9, 9-12, or 12-15 bases upstream of the Kozak consensus sequence in the 5' UTR of the mRNA, wherein the 5' UTR comprises the following sequence shown in Table 1:

(SEQ ID NO: 33)
GGGAAATAAGAGAGAAAAGAAGAGTAAGAAGAAATATAAGAGCCACC.

In some embodiments, the 5' UTR comprises the following sequence set forth in Table 1:

(SEQ ID NO: 33)
GGGAAATAAGAGAGAAAAGAAGAGTAAGAAGAAATATAAGACCCCGGCGC

CGCCACC.

In some embodiments, the disclosure provides an mRNA comprising a 5' UTR, wherein the 5' UTR comprises the nucleotide sequence 5'-GGGAAAUAAGAGAGAA AAGAAGAGUAAGAAGAAAUAUAAGAGCCACC-3' set forth in SEQ ID NO: 33, wherein the 5' UTR comprises a GC-rich RNA element located about 20-30, about 10-20 nucleotides, or about 6-10 nucleotides upstream of the 3' end of the 5' UTR sequence set forth in SEQ ID NO: 33. In some embodiments, the disclosure provides an mRNA comprising: (i) a 5' untranslated region (UTR) comprising a GC-rich RNA element that provides a translational regulatory activity described herein; (ii) a full open reading frame comprising an initiation codon and encoding a polypeptide; and (iii) a 3' UTR, wherein the 5' UTR comprises the nucleotide sequence 5'-GGGAAAUAAGAGAGA AAAGAAGAGUAAGAAGAAAUAUAAGAGCCACC-3' set forth in SEQ ID NO: 33, wherein the GC-rich RNA element comprises the nucleotide sequence set forth in SEQ ID NO: 2, and wherein the 5' UTR comprises the GC-rich RNA element located about 20-30, about 10-20 nucleotides, or about 6-10 nucleotides upstream of the 3' end of the 5' UTR sequence set forth in SEQ ID NO: 33. In some embodiments, the disclosure provides an mRNA comprising: (i) a 5' untranslated region (UTR) comprising a GC-rich RNA element that provides a translational regulatory activity described herein; (ii) a full open reading frame comprising an initiation codon and encoding a polypeptide; and (iii) a 3' UTR, wherein the 5' UTR comprises the nucleotide sequence 5'-GGGAAAUAAGAGAGAAAAG AAGAGUAAGAAGAAAUAUAAGAGCCACC-3' set forth in SEQ ID NO: 33, wherein the GC-rich RNA element comprises the nucleotide sequence set forth in SEQ ID NO: 3, and wherein the GC-rich RNA element is located about 20-30 nucleotides, about 10-20 nucleotides, or about 6-10 nucleotides upstream of the 3' end of the 5' UTR sequence set forth in SEQ ID NO: 33. In some embodiments, the disclosure provides an mRNA comprising: (i) a 5' untranslated region (UTR) comprising a GC-rich RNA element that provides a translational regulatory activity described herein; (ii) a full open reading frame comprising an initiation codon and encoding a polypeptide; and (iii) a 3' UTR, wherein the 5' UTR comprises the nucleotide sequence 5'-GG GAAAUAAGAGAGAAAAGAAGAGUAAGAAGAAAU AUAAGAGCCACC-3' set forth in SEQ ID NO: 33, wherein the GC-rich RNA element comprises the nucleotide sequence set forth in SEQ ID NO: 4, and wherein the GC-rich RNA element is located about 20-30 nucleotides, about 10-20 nucleotides, or about 6-10 nucleotides upstream of the 3' end of the 5' UTR sequence set forth in SEQ ID NO: 33.

In some embodiments, the disclosure provides an mRNA comprising (i) a 5' untranslated region (UTR) comprising the nucleotide sequence set forth in SEQ ID NO: 34; (ii) a full open reading frame comprising an initiation codon and encoding a polypeptide; and (iii) a 3' UTR.

In some embodiments, the disclosure provides an mRNA comprising (i) a 5' untranslated region (UTR) comprising the nucleotide sequence set forth in SEQ ID NO: 54; (ii) a full open reading frame comprising an initiation codon and encoding a polypeptide; and (iii) a 3' UTR.

An mRNA comprising (i) a 5' untranslated region (UTR) comprising the nucleotide sequence set forth in SEQ ID NO: 73 (CG1-UTR) (ii) a full open reading frame comprising an initiation codon and encoding a polypeptide; and (iii) a 3' UTR.

Stable RNA Secondary Structures

In some embodiments, the disclosure provides mRNAs comprising RNA elements that provide one or more translational regulatory activities arising from the formation of a secondary structure. Without being bound by theory, it is thought that an RNA element that provides a function (e.g, a translational regulatory activity) by the formation of a secondary structure (e.g. a stable RNA secondary structure) is distinguished from an RNA element that provide a translational regulatory activity provided by the RNA element's primary structure or sequence (e.g., a GC-rich RNA element). Typical examples of stable RNA secondary structures include duplexes, hairpins, and stem-loops.

Accordingly, in some embodiments, the disclosure provides mRNAs comprising an RNA element that comprises a stable RNA secondary structure that provides a translational regulatory activity. In some embodiments, the translational regulatory activity is selected from the group consisting of:
  (a) inhibits or reduces leaky scanning of the mRNA by the PIC or ribosome;
  (b) increases an amount of a polypeptide translated from the full open reading frame;
  (c) increases initiation of polypeptide synthesis at or from the initiation codon;

(d) inhibits or reduces initiation of polypeptide synthesis at any codon within the mRNA other than the initiation codon;

(e) inhibits or reduces an amount of polypeptide translated from any open reading frame within the mRNA other than the full open reading frame;

(f) inhibits or reduces translation of truncated or aberrant translation products from the mRNA; and (g) a combination of any of (a)-(f).

In some embodiments, the stable RNA secondary structure inhibits or reduces leaky scanning of the mRNA by the PIC or ribosome. In some embodiments, the stable RNA secondary structure inhibits or reduces leaky scanning of the mRNA by the PIC or ribosome and improves (e.g., increases or enhances) potency of the mRNA. In some embodiments, the Stable RNA secondary structure increases an amount of a polypeptide translated from the full open reading frame. In some embodiments, the stable RNA secondary structure increases an amount of a polypeptide translated from the full open reading frame and improves (e.g., increases or enhances) potency of the mRNA. In some embodiments, the stable RNA secondary structure increases potency of a polypeptide translated from the mRNA. In some embodiments, the stable RNA secondary structure increases potency of a polypeptide translated from the mRNA and improves (e.g., increases or enhances) potency of the mRNA. In some embodiments, the stable RNA secondary structure increases initiation of polypeptide synthesis at or from the initiation codon. In some embodiments, the stable RNA secondary structure increases initiation of polypeptide synthesis at or from the initiation codon and improves (e.g., increases or enhances) potency of the mRNA. In some embodiments, the stable RNA secondary structure inhibits or reduces initiation of polypeptide synthesis at any codon within the mRNA other than the initiation codon. In some embodiments, the stable RNA secondary structure inhibits or reduces initiation of polypeptide synthesis at any codon within the mRNA other than the initiation codon and improves (e.g., increases or enhances) potency of the mRNA. In some embodiments, the stable RNA secondary structure inhibits or reduces an amount of polypeptide translated from any open reading frame within the mRNA other than the full open reading frame. In some embodiments, the stable RNA secondary structure inhibits or reduces an amount of polypeptide translated from any open reading frame within the mRNA other than the full open reading frame and improves (e.g., increases or enhances) potency of the mRNA. In some embodiments, the stable RNA secondary structure inhibits or reduces translation of truncated or aberrant translation products from the mRNA. In some embodiments, the stable RNA secondary structure inhibits or reduces translation of truncated or aberrant translation products from the mRNA and improves (e.g., increases or enhances) potency of the mRNA. In some embodiments, the stable RNA secondary structure is located downstream of the initiation codon in the full open reading frame. In some embodiments, the stable RNA secondary structure is located about 25-30, about 20-25, about 15-20, about 10-15, about 5-10, or about 1-5 nucleotide(s) downstream of the initiation codon in the full open reading frame. In some embodiments, the stable RNA secondary structure is located 20, 19, 18, 17, 16, 15, 14, 13, 12, 11, 10, 9, 8, 7, 6, 5, 4, 3, 2, 1 nucleotide(s) downstream of the initiation codon in the full open reading frame. In some embodiments, the stable RNA secondary structure is located upstream of the initiation codon in the 5' UTR.

In some embodiments, the stable RNA secondary structure is located about 25-30, about 20-25, about 15-20, about 10-15, about 5-10, or about 1-5 nucleotide(s) upstream of the initiation codon in the 5' UTR. In some embodiments, the stable RNA secondary structure is located 20, 19, 18, 17, 16, 15, 14, 13, 12, 11, 10, 9, 8, 7, 6, 5, 4, 3, 2, 1 nucleotide(s) upstream of the initiation codon in the 5' UTR.

In some embodiments, the stable RNA secondary structure comprises a nucleotide sequence selected from the group consisting of SEQ ID NO: 28, SEQ ID NO: 29, SEQ ID NO: 30, SEQ ID NO: 31, and SEQ ID NO: 32.

In another aspect, the disclosure provides a modified mRNA comprising at least one modification, wherein at least one modification is a GC-rich RNA element comprising a stable RNA secondary structure comprising a sequence of nucleotides, or derivatives or analogs thereof, linked in an order which forms a hairpin or a stem-loop. In one embodiment, the stable RNA secondary structure is upstream or downstream of the initiation codon. In another embodiment, the stable RNA secondary structure is located about 30, about 25, about 20, about 15, about 10, or about 5 nucleotides upstream or downstream of the initiation codon. In another embodiment, the stable RNA secondary structure is located about 20, about 15, about 10 or about 5 nucleotides upstream or downstream of the initiation codon. In another embodiment, the stable RNA secondary structure is located about 5, about 4, about 3, about 2, about 1 nucleotides upstream or downstream of the initiation codon. In another embodiment, the stable RNA secondary structure is located about 15-30, about 15-20, about 15-25, about 10-15, or about 5-10 nucleotides upstream or downstream of the initiation codon. In another embodiment, the stable RNA secondary structure is located 12-15 nucleotides upstream and downstream of the initiation codon. In another embodiment, the stable RNA secondary structure comprises the initiation codon. In another embodiment, the stable RNA secondary structure has a deltaG of about −30 kcal/mol, about −20 to −30 kcal/mol, about −20 kcal/mol, about −10 to −20 kcal/mol, about −10 kcal/mol, about −5 to ~10 kcal/mol.

In another embodiment, the modification is operably linked to an open reading frame encoding a polypeptide and wherein the modification and the open reading frame are heterologous.

In another embodiment, the sequence of the GC-rich RNA element is comprised exclusively of guanine (G) and cytosine (C) nucleobases.

In some aspects, the disclosure provides an mRNA having one or more structural modifications that inhibits leaky scanning and/or promotes the translational fidelity of mRNA translation, wherein at least one of the structural modifications is a GC-rich RNA element. In some aspects, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA. In one embodiment, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA. In some embodiments, the RNA element comprises natural and/or modified nucleotides. In some embodiments, the RNA element comprises of a sequence of linked nucleotides, or derivatives or analogs thereof, that provides a desired translational regulatory activity as described herein. In some embodiments, the RNA element comprises a sequence of linked nucleotides, or derivatives or analogs thereof, that forms or folds into a stable RNA secondary structure, wherein the RNA secondary structure provides a desired translational regulatory activity as described herein. RNA elements can be identified and/or characterized based on the primary sequence of the element (e.g., GC-rich RNA element), by RNA secondary structure formed by the element (e.g. stem-loop), by the location of the element within the RNA molecule (e.g., located within the 5' UTR of an mRNA), by the biological function and/or activity of the element (e.g., "translational enhancer element"), and any combination thereof.

Exemplary 5' UTRs, and modifications including GC-rich elements, and stable RNA secondary structures (e.g. hairpins) provided by the disclosure are set forth in Table 1. These 5' UTRs, and modifications including GC-rich elements, and stable RNA secondary structures, and any combination thereof, are useful in the mRNAs of the disclosure.

TABLE 1

| 5' UTRs | Sequence |
| --- | --- |
| Standard | GGGAAATAAGAGAGAAAAGAAGAGTAAGAAGAAATATA AGAGCCACC (SEQ ID NO: 33) |
| V1-UTR | GGGAAATAAGAGAGAAAAGAAGAGTAAGAAGAAATATA AGACCCCGGCGCCGCCACC (SEQ ID NO: 34) |
| V2-UTR | GGGAAATAAGAGAGAAAAGAAGAGTAAGAAGAAATATA AGACCCCGGCGCCACC (SEQ ID NO: 54) |
| CG1-UTR | GGGAAATAAGAGAGAAAAGAAGAGTAAGAAGAAATATA AGAGCGCCCCGCGGCGCCCCGCGGCCACC (SEQ ID NO: 73) |
| CG2-UTR | GGGAAATAAGAGAGAAAAGAAGAGTAAGAAGAAATATA AGACCCGCCCGCCCCGCCCCGCCGCCACC (SEQ ID NO: 92) |
| KT1-UTR | GGGCCCGCCGCCAAC (SEQ ID NO: 472) |
| KT2-UTR | GGGCCCGCCGCCACC (SEQ ID NO: 473) |
| KT3-UTR | GGGCCCGCCGCCGAC (SEQ ID NO: 474) |
| KT4-UTR | GGGCCCGCCGCCGCC (SEQ ID NO: 475) |
| GC-Rich RNA Elements | Sequence |
| K0 (Traditional Kozak consensus) | [GCCA/GCC] |
| EK1 | [CCCGCC](SEQ ID NO: 9) |
| EK2 | [GCCGCC](SEQ ID NO: 10) |
| EK3 | [CCGCCG](SEQ ID NO: 11) |
| V1 | [CCCCGGCGCC] (SEQ ID NO: 2) |
| V2 | [CCCCGGC] (SEQ ID NO: 3) |
| CG1 | [GCGCCCCGCGGCGCCCCGCG] (SEQ ID NO: 4) |
| CG2 | [CCCGCCCGCCCCGCCCCGCC] (SEQ ID NO: 5) |
| (CCG)$_n$, n = 1-10 | [CCG]$_n$ |
| (GCC)$_n$, n = 1-10 | [GCC]$_n$ |
| Stable RNA Secondary Structures | Sequence |
| SL1 | CCGCGGCGCCCCGCGG (--9.90 kcal/mol) (SEQ ID NO: 28) |
| SL2 | GCGCGCAUAUAGCGCGC (-10.90 kcal/mol) (SEQ ID NO: 29) |
| SL3 | CATGGTGGCGGCCCGCCGCCACCATG (-22.10 kcal/mol) (SEQ ID NO: 30) |

TABLE 1-continued

| | | |
|---|---|---|
| SL4 | CATGGTGGCCCGCCGCCACCATG | (−14.90 kcal/mol) (SEQ ID NO: 31) |
| SL5 | CATGGTGCCCGCCGCCACCATG | (−8.00 kcal/mol) (SEQ ID NO: 32) |

Methods to Identify and Characterize the Function of RNA Elements

In one aspect, the disclosure provides methods to identify and/or characterize RNA elements that provide a desired translational regulatory activity of the disclosure, including those that modulate (e.g., reduce) leaking scanning to polynucleotides (e.g., mRNA).

Ribosome Profiling

In one aspect, RNA elements that provide a desired translational regulatory activity, including modulation of leaking scanning, to polynucleotides e.g., mRNA, are identified and/or characterized by ribosome profiling.

Ribosome profiling is a technique that allows the determination of the number and position of ribosomes bound to mRNAs (see e.g., Ingolia et al., (2009) Science 324(5924): 218-23, incorporated herein by reference). The technique is based on protection by the ribosome of a region or segment of mRNA from ribonuclease digestion, which region or segment is subsequently assayed. In this approach, a cell lysate is treated with ribonucleases, leading to generation of 80S ribosomes with fragments of mRNA to which they are bound. The 80S ribosomes are then purified by techniques known in the art (e.g., density gradient centrifugation), and mRNA fragments that are protected by the ribosomes are isolated. Protection results in the generation of a 30-bp fragment of RNA termed a 'footprint'. The number and sequence of RNA footprints can be analyzed by methods known in the art (e.g., Ribo-seq, RNA-seq). The footprint is roughly centered on the A-site of the ribosome. During translation, a ribosome may dwell at a particular position or location along an mRNA (e.g., at an initiation codon). Footprints generated at these dwell positions are more abundant than footprints generated at positions along the mRNA where the ribosome is more processive. Studies have shown that more footprints are generated at positions where the ribosome exhibits decreased processivity (dwell positions) and fewer footprints where the ribosome exhibits increased processivity (Gardin et al., (2014) eLife 3:e03735). High-throughput sequencing of these footprints provides information on the mRNA locations (sequence of footprints) of ribosomes and generates a quantitative measure of ribosome density (number of footprints comprising a particular sequence) along an mRNA. Accordingly, ribosome profiling data provides information that can be used to identify and/or characterize RNA elements that provide a desired translational regulatory activity of the disclosure, including those that reduce leaky scanning, to polynucleotides as described herein e.g., mRNA.

Ribosome profiling can also be used to determine the extent of ribosome density (aka "ribosome loading") on an mRNA. It is known that dissociated ribosomal subunits initiate translation at the initiation codon within the 5'-terminal region of mRNA. Upon initiation, the translating ribosome moves along the mRNA chain toward the 3'-end of mRNA, thus vacating the initiation site for loading the next ribosome on the mRNA. In this way a group of ribosomes moving one after another and translating the same mRNA chain is formed. Such a group is referred to as a "polyribosome" or "polysome" (Warner et al., (1963) Proc Natl Acad Sci USA 49:122-129). The number of different mRNA fragments protected by ribosomes per mRNA, per region of an mRNA (e.g., a 5' UTR), or per location in an mRNA (e.g., an initiation codon) indicates an extent of ribosome density. In general, an increase in the number of ribosomes bound to an mRNA (i.e. ribosome density) is associated with increased levels of protein synthesis.

Accordingly, in some embodiments, an increase in ribosome density of a polynucleotide (e.g., an mRNA) comprising one or more of the modifications or RNA elements of the disclosure, relative to a polynucleotide (e.g., an mRNA) that does not comprise the one or more modifications or RNA elements, is determined by ribosome profiling. In some embodiments, an increase in ribosome density of a polynucleotide (e.g., an mRNA) comprising a GC-rich element of the disclosure, relative to a polynucleotide (e.g., an mRNA) that does not comprise the GC-rich element, is determined by ribosome density.

Ribosome profiling is also used to determine the time, extent, rate and/or fidelity of ribosome decoding of a particular codon of an mRNA (and by extension the expected number of corresponding RNA-seq reads in a library of isolated footprints), which in turn is determined by the amount of time a ribosome spends at a particular codon (dwell time). The latter is referred to as a "codon elongation rate" or a "codon decoding rate". Relative dwell time of ribosomes between two locations in an mRNA, instead of the actual or absolute dwell time at a single location, can also be determined by the comparing the number of sequencing reads of protected mRNA fragments at each location (e.g., a codon) (O'Connor et al., (2016) Nature Commun 7:12915). For example, initiation of polypeptide synthesis at or from an initiation codon can be determined from an observed increase in dwell time of ribosomes at the initiation codon relative to dwell time of ribosomes at a downstream alternate or alternative initiation codon in an mRNA. Accordingly, initiation of polypeptide synthesis at or from an initiation codon in a polynucleotide (e.g., an mRNA) comprising one or more modifications or RNA elements of the disclosure, relative to a polynucleotide (e.g., an mRNA) that does not comprise the one or more modifications or RNA elements, can be determined from an observed increase in the dwell time of ribosomes at the initiation codon relative to the dwell time of ribosomes at a downstream alternate or alternative initiation codon in each polynucleotide (e.g., mRNA).

In some embodiments, an increase in residence time or the time of occupancy (dwell time) of a ribosome at a discrete position or location (e.g., an initiation codon) along a polynucleotide (e.g., an mRNA) comprising one or more of the modifications or RNA elements of the disclosure, relative to a polynucleotide (e.g., an mRNA) that does not comprise the one or more modifications or RNA elements, is determined by ribosome profiling. In some aspects, an increase in residence time or the time of occupancy of a ribosome at an initiation codon in a polynucleotide (e.g., mRNA) comprising a GC-rich element of the disclosure relative to a polynucleotide (e.g., mRNA) that does not comprise the GC-rich element, is determined by ribosome profiling.

In other aspects, an increase in the initiation of polypeptide synthesis at or from the initiation codon in polynucleotide (e.g., an mRNA) comprising one or more of the modifications or RNA elements of the disclosure, relative to a polynucleotide (e.g., an mRNA) that does not comprise the one or more modifications or RNA elements, is determined by ribosome profiling. In some embodiments, an increase in the initiation of polypeptide synthesis at or from the initiation codon in a polynucleotide (e.g., mRNA) comprising a GC-rich element of the disclosure relative to a polynucleotide (e.g., mRNA) that does not comprise the GC-rich element, is determined by ribosome profiling.

In some embodiments, an increase in fidelity of initiation codon decoding by the ribosome of a polynucleotide (e.g., an mRNA) comprising one or more of the modifications or RNA elements of the disclosure, relative to a polynucleotide (e.g., mRNA) that does not comprise the one or more modifications or RNA elements, is determined by ribosome profiling. In some embodiments, an increase in fidelity of initiation codon decoding by the ribosome of a polynucleotide (e.g., mRNA) comprising a GC-rich element of the disclosure relative to a polynucleotide (e.g., mRNA) that does not comprise the GC-rich element, is determined by ribosome profiling.

In some embodiments, an increase in fidelity of initiation codon decoding by the ribosome of a polynucleotide (e.g., an mRNA) comprising one or more of the modifications or RNA elements of the disclosure, relative to a polynucleotide (e.g., an mRNA) that does not comprise the one or more modifications or RNA elements, is determined by ribosome profiling. In some embodiments, an increase in fidelity of initiation codon decoding by the ribosome in a polynucleotide (e.g., mRNA) comprising a GC-rich element of the disclosure relative to a polynucleotide (e.g., mRNA) that does not comprise the GC-rich element, is determined by ribosome profiling.

In some embodiments, a decrease in a rate of decoding an initiation codon by the ribosome of a polynucleotide (e.g., an mRNA) comprising one or more of the modifications or RNA elements of the disclosure, relative to a polynucleotide (e.g., an mRNA) that does not comprise the one or more modifications or RNA elements, is determined by ribosome profiling. In some embodiments, a decrease in a rate of decoding an initiation codon by the ribosome of a polynucleotide (e.g., mRNA) comprising a GC-rich element of the disclosure relative to a polynucleotide (e.g., mRNA) that does not comprise the GC-rich element, is determined by ribosome profiling.

Small Ribosomal Subunit Mapping

In some aspects, RNA elements that provide a desired translational regulatory activity, including modulation of leaking scanning, to polynucleotides e.g., mRNA, are identified and/or characterized by small ribosomal subunit mapping.

Small ribosomal subunit (SSU) mapping is a technique similar to ribosome profiling that allows the determination of the number and position of small 40S ribosomal subunits or pre-initiation complexes (PICs) comprising small 40S ribosomal subunits bound to mRNAs. Similar to the technique of ribosome profiling described herein, small ribosomal subunit mapping involves analysis of a region or segment of mRNA protected by the 40S subunit from ribonuclease digestion, resulting in a 'footprint', the number and sequence of which can be analyzed by methods known in the art (e.g., RNA-seq). As described herein, the current model of mRNA translation initiation postulates that the pre-initiation complex (alternatively "43 S pre-initiation complex"; abbreviated as "PIC") translocates from the site of recruitment on the mRNA (typically the 5' cap) to the initiation codon by scanning nucleotides in a 5' to 3' direction until the first AUG codon that resides within a specific translation-promotive nucleotide context (the Kozak sequence) is encountered (Kozak (1989) J Cell Biol 108: 229-241). "Leaky scanning" by the PIC, whereby the PIC bypasses the initiation codon of an mRNA and instead continues scanning downstream until an alternate or alternative initiation codon is recognized, can occur and result in a decrease in translation efficiency and/or the production of an undesired, aberrant translation product. Thus, analysis of the number of SSUs positioned, or mapped, over AUGs downstream of the first AUG in an mRNA allows for the determination of the extent or frequency at which leaky scanning occurs. SSU mapping provides information that can be used to identify or determine a characteristic (e.g., a translational regulatory activity) of a modification or RNA element of the disclosure, that affects the activity of a small 40S ribosomal subunit (SSU or a PIC comprising the SSU.

Accordingly, an inhibition or reduction of leaky scanning by an SSU or a PIC comprising an SSU of a polynucleotide (e.g., an mRNA) comprising one or more of the modifications or RNA elements of the disclosure, relative to a polynucleotide (e.g., an mRNA) that does not comprise the one or more modifications or RNA elements, is determined by small ribosomal subunit mapping. In some aspects, an inhibition or reduction of leaky scanning by an SSU or a PIC comprising an SSU of a polynucleotide (e.g., an mRNA) comprising a GC-rich element of the disclosure, relative to a polynucleotide (e.g., an mRNA) that does not comprise the GC-rich element, is determined by small ribosomal subunit mapping.

In some embodiments, an increase in residence time or the time of occupancy (dwell time) of an SSU or a PIC comprising an SSU at a discrete position or location (e.g., an initiation codon) along a polynucleotide (e.g. an mRNA) comprising one or more of the modifications or RNA elements of the disclosure, relative to a polynucleotide (e.g., an mRNA) that does not comprise the one or more modifications or RNA elements, is determined by ribosome profiling. In some embodiments, an increase in residence time or the time of occupancy of an SSU or a PIC comprising an SSU at an initiation codon in a polynucleotide (e.g., an mRNA) comprising a GC-rich element of the disclosure, relative to a polynucleotide (e.g., an mRNA) that does not comprise the GC-rich element, is determined by ribosome profiling.

In some embodiments, an increase in the initiation of polypeptide synthesis at or from the initiation codon in polynucleotide (e.g., an mRNA) comprising one or more of the modifications or RNA elements of the disclosure, relative to a polynucleotide (e.g., an mRNA) that does not comprise the one or more modifications or RNA elements, is determined by ribosome profiling. In some embodiments, an increase in the initiation of polypeptide synthesis at or from the initiation codon in a polynucleotide (e.g., an mRNA) comprising a GC-rich element of the disclosure, relative to a polynucleotide (e.g., an mRNA) that does not comprise the GC-rich element, is determined by ribosome profiling.

In some embodiments, an increase in fidelity of initiation codon decoding by an SSU or a PIC comprising an SSU of a polynucleotide (e.g., an mRNA) comprising one or more of the modifications or RNA elements of the disclosure, relative to a polynucleotide that does not comprise the one or more modifications or RNA elements, is determined by ribosome profiling. In some embodiments, an increase in fidelity of initiation codon decoding by an SSU or a PIC comprising an SSU of a polynucleotide (e.g., an mRNA) comprising a GC-rich element of the disclosure, relative to a polynucleotide (e.g., an mRNA) that does not comprise the GC-rich element, is determined by ribosome profiling.

In some embodiments, an increase in fidelity of initiation codon decoding by an SSU or a PIC comprising an SSU of a polynucleotide (e.g., an mRNA) comprising one or more of the modifications or RNA elements of the disclosure, relative to a polynucleotide that does not comprise the one or more modifications or RNA elements, is determined by ribosome profiling. In some embodiments, an increase in fidelity of initiation codon decoding by an SSU or a PIC comprising an SSU of a polynucleotide (e.g., an mRNA) comprising a GC-rich element of the disclosure, relative to a polynucleotide (e.g., an mRNA) that does not comprise the GC-rich element, is determined by ribosome profiling.

In some embodiments, a decrease in a rate of decoding an initiation codon comprising a polynucleotide (e.g., an mRNA) comprising any one or more of the modifications or RNA elements of the disclosure, relative to a polynucleotide (e.g., an mRNA) that does not comprise the one or more modifications or RNA elements, is determined by ribosome profiling. In some embodiments, a decrease in a rate of decoding an initiation codon decoding by the ribosome of a polynucleotide (e.g., an mRNA) comprising a GC-rich element of the disclosure, relative to a polynucleotide (e.g., an mRNA) that does not comprise the GC-rich element, is determined by ribosome profiling.

RiboFrame-Seq

In some aspects, RNA elements that provide a desired translational regulatory activity, including modulation of leaking scanning, to polynucleotides e.g., mRNA, are identified and/or characterized by RiboFrame-seq.

RiboFrame-seq is an assay that allows for the high-throughput measurement of leaky scanning for many different 5'-UTR sequences. A population of mRNAs is generated with a library of different 5' UTR sequences, each of which contains a 5' cap and a coding sequence that encodes a polypeptide comprising two to three different epitope tags, each in a different frame and preceded by an AUG. The mRNA population is transfected into cells and allowed to be translated. Cells are then lysed and immunoprecipitations performed against each of the encoded epitope tags. Each of these immunoprecipitations is designed to isolate a nascent polypeptide chain encoding the particular epitope, as well as the active ribosome performing its synthesis, and the mRNA that encodes it. The complement of 5'-UTRs present in each immunoprecipitate is then analyzed by methods known in the art (e.g., RNA-seq). The 5'-UTRs comprising sequences (e.g. RNA elements) that correlate with reduced, inhibited or low leaky scanning are characterized by being abundant in the immunoprecipitate corresponding to the first epitope tag relative to the other immunoprecipitates.

Accordingly, in some embodiments, a modification or RNA element having a translational regulatory activity of the disclosure is identified or characterized by RiboFrame-seq. In some aspects, a modification or RNA element having reduced, inhibited or low leaky scanning when located in a 5' UTR of an mRNA are identified or characterized by being abundant in the immunoprecipitate corresponding to the first epitope tag relative to the other immunoprecipitates as determined by RiboFrame-seq.

Western Blot (Immunodetection)

In some aspects, the disclosure provides a method of identifying, isolating, and/or characterizing a modification (e.g., an RNA element) that provides a translational regulatory activity by synthesizing a 1st control mRNA comprising a polynucleotide sequence comprising an open reading frame encoding a reporter polypeptide (e.g., eGFP) and a 1st AUG codon upstream of, in-frame, and operably linked to, the open reading frame encoding the reporter polypeptide. The 1st control mRNA also comprises a coding sequence for a first epitope tag (e.g. 3×FLAG) upstream of, in-frame, and operably linked to the 1st AUG codon, a 2nd AUG codon upstream of, in-frame, and operably linked to, the coding sequence for the first epitope tag. Optionally, the 1st control mRNA further comprises a coding sequence for a second epitope tag (e.g. V5) upstream of, in-frame, and operably linked to the 2nd AUG codon, and a 3rd AUG codon upstream of, in-frame, and operably linked to, the coding sequence for the second epitope tag. The 1st control mRNA also comprises a 5' UTR and a 3' UTR. The method further comprises synthesizing a 2nd test mRNA comprising a polynucleotide sequence comprising the 1st control mRNA and further comprising a modification (e.g. an RNA element). The method further comprises introducing the 1st control mRNA and 2nd test mRNA to conditions suitable for translation of the polynucleotide sequence encoding the reporter polypeptide. The method further comprises measuring the effect of the candidate modification on the amount of reporter polypeptide from each of the three AUG codons. Following transfection of this mRNA into cells, the cell lysate is analyzed by Western blot using antibodies that specifically bind to and detect the reporter polypeptide. This analysis generates two or three bands: a higher band that corresponds to protein generated from the first AUG and lower bands derived from protein generated from the second AUG and, optionally, third AUG.

Leaky scanning is calculated as abundance of the lower bands divided by the sum of the abundance of both bands, as determined by methods known in the art (e.g. densitometry). A test mRNA comprising one or more modifications or RNA elements of the disclosure, that correlate with reduced, inhibited or low leaky scanning is characterized by an increase in amount of polypeptide comprising the second epitope tag compared to the amount of polypeptide that does not comprise an epitope tag, optionally, the amount of polypeptide comprising the first epitope tag, translated from the test mRNA, relative to the control mRNA that does not comprise the one or more modifications or RNA elements. Accordingly, in some embodiments, a modification or RNA element having a translational regulatory activity of the disclosure, is identified by Western blot.

In some embodiments, an inhibition or reduction in leaky scanning of a polynucleotide (e.g., an mRNA) comprising one or more of the modifications or RNA elements of the disclosure, relative to a polynucleotide (e.g., an mRNA) that does not comprise the one or more modifications or RNA elements, is determined by Western blot. In some embodiments, an inhibition or reduction in leaky scanning of a polynucleotide (e.g., an mRNA) comprising a GC-rich element of the disclosure, relative to a polynucleotide (e.g., an mRNA) that does not comprise the GC-rich element, is determined by Western blot.

In some embodiments, an increase in the initiation of polypeptide synthesis at or from the initiation codon comprising a polynucleotide (e.g., an mRNA) comprising any one or more of the modifications or RNA elements of the disclosure, relative to a polynucleotide that does not comprise the one or more modifications or RNA elements, is determined by Western blot. In some embodiments, an increase in the initiation of polypeptide synthesis at or from the initiation codon comprising a polynucleotide (e.g., an mRNA) comprising a GC-rich element of the disclosure, relative to a polynucleotide (e.g., an mRNA) that does not comprise the GC-rich element, is determined by Western blot.

In some embodiments, an increase in an amount of polypeptide translated from the full open reading frame comprising a polynucleotide (e.g., an mRNA) comprising any one or more of the modifications or RNA elements of the disclosure, relative to a polynucleotide (e.g., an mRNA) that does not comprise the one or more modifications or RNA elements, is determined by Western blot. In some embodiments, an increase in an amount of polypeptide translated from the full open reading frame comprising a polynucleotide (e.g., an mRNA) comprising a GC-rich element of the disclosure, relative to a polynucleotide (e.g., an mRNA) that does not comprise the GC-rich element, is determined by Western blot.

In some embodiments, an inhibition or reduction in an amount of polypeptide translated from any open reading frame other than a full open reading frame comprising a polynucleotide (e.g., an mRNA) comprising one or more of the modifications or RNA elements of the disclosure, relative to a polynucleotide (e.g., an mRNA) that does not comprise the one or more modifications or RNA elements, is determined by Western blot. In some embodiments, an inhibition or reduction in an amount of polypeptide translated from any open reading frame other than a full open reading frame comprising a polynucleotide (e.g., an mRNA) comprising a GC-rich element of the disclosure, relative to a polynucleotide (e.g., an mRNA) that does not comprise the GC-rich element, is determined by Western blot.

In some embodiments, an inhibition or reduction in the production of aberrant translation products translated from a polynucleotide (e.g., an mRNA) comprising any one or more of the modifications or RNA elements of the disclosure, relative to a polynucleotide (e.g., an mRNA) that does not comprise the one or more modifications or RNA elements, is determined by Western blot. In some embodiments, an inhibition or reduction in the production of aberrant translation products translated from a polynucleotide (e.g., an mRNA) comprising a GC-rich element of the disclosure, relative to a polynucleotide (e.g., an mRNA) that does not comprise the GC-rich element, is determined by Western blot.

In some embodiments, leaky scanning by a 43S pre-initiation complex (PIC) or ribosome of a polynucleotide (e.g., an mRNA) comprising one or more of the modifications or RNA elements (e.g., GC-rich element) of the disclosure is decreased by about 80%-100%, about 60%-80%, about 40%-60%, about 20%-40%, about 10%-20%, about 5%-10%, about 1%-5% relative to a polynucleotide (e.g., an mRNA) that does not comprise the one or more modifications or RNA elements, as determined by SSU mapping and/or ribosome profiling methods, as described herein.

In some embodiments, leaky scanning by a 43S pre-initiation complex (PIC) or ribosome of a polynucleotide (e.g., an mRNA) comprising any one or more of the modifications or RNA elements of the disclosure is decreased by about 80%-100%, about 60%-80%, about 40%-60%, about 20%-40%, about 10%-20%, about 5%-10%, about 1%-5% and an amount of a polypeptide translated from a full reading frame is increased by about 80%-100%, about 60%-80%, about 40%-60%, about 20%-40%, about 10%-20%, about 5%-10%, about 1%-5% relative to a polynucleotide (e.g., an mRNA) that does not comprise the one or more modification or RNA elements, as determined by SSU mapping and Western blot, respectively, as described herein.

In some embodiments, leaky scanning by the 43S pre-initiation complex (PIC) or ribosome of a polynucleotide (e.g., an mRNA) comprising any one or more of the modifications or RNA elements (e.g., GC-rich element) of the disclosure is decreased by about 80%-100%, about 60%-80%, about 40%-60%, about 20%-40%, about 10%-20%, about 5%-10%, about 1%-5%, an amount of a polypeptide translated from a full open reading frame is increased by about 80%-100%, about 60%-80%, about 40%-60%, about 20%-40%, about 10%-20%, about 5%-10%, about 1%-5%, and potency of the polypeptide is increased by about 80%-100%, about 60%-80%, about 40%-60%, about 20%-40%, about 10%-20%, about 5%-10%, about 1%-5%, relative to a polynucleotide (e.g., an mRNA) that does not comprise the one or more modification or RNA elements, as determined by SSU mapping and Western blot.

Another RNA element known to regulate translation of mRNA is the five-prime cap (5' cap), which is a specially altered nucleotide the 5' end of natural mRNA co-transcriptionally. This process, known as mRNA capping, is highly regulated and is vital in the creation of stable and mature messenger RNA able to undergo translation. In eukaryotes, the structure of the 5' cap consists of a guanine nucleotide connected to 5' end of an mRNA via an unusual 5' to 5' triphosphate linkage. This guanosine is methylated on the 7 position directly after capping in vivo by a methyltransferase, and as such, is sometimes referred to as a 7-methylguanylate cap, and abbreviated m7G. A 5' cap structure or cap species is a compound including two nucleoside moieties joined by a linker and may be selected from a naturally occurring cap, a non-naturally occurring cap or cap analog, or an anti-reverse cap analog (ARCA). A cap species may include one or more modified nucleosides and/or linker moieties. For example, a natural mRNA cap may include a guanine nucleotide and a guanine (G) nucleotide methylated at the 7 position joined by a triphosphate linkage at their 5' positions, e.g., m7G(5')ppp(5')G, commonly written as m7GpppG. A cap species may also be an anti-reverse cap analog. A non-limiting list of possible cap species includes m7GpppG, m7Gpppm7G, m73'dGpppG, m27,O3'GpppG, m27,O3'GppppG, m27,O2'GppppG, m7Gpppm7G, m73'dGpppG, m27,O3'GpppG, m27,O3'GppppG, and m27,O2'GppppG. Accordingly, in some embodiments, the mRNAs disclosed herein comprise a 5' cap, or derivative, analog, or modification thereof.

An early event in translation initiation involves the formation of the 43S pre-initiation complex (PIC) composed of the small 40S ribosomal subunit, the initiator transfer RNA (Met-tRNAiMet), and several various eIFs. Following recruitment to the mRNA, the PIC biochemically interrogates or "scans" the sequence of the mRNA molecule in search of an initiation codon. In some embodiments of the mRNAs disclosed herein, the mRNAs comprise at least one initiation codon. In some embodiments, the initiation codon is an AUG codon. In some embodiments, the initiation codon comprises one or more modified nucleotides.

Similar to polypeptides, polynucleotides, particularly RNA, can fold into a variety of complex three dimensional structures. The ability of a nucleic acid to form a complex, functional three dimensional structure is exemplified by a transfer RNA molecule (tRNA), which is a single chain of ~70-90 nucleotides in length that folds into an L-shaped 3D structure allowing it to fit into the P and A sites of a ribosome and function as the physical link between the polypeptide coding sequence of mRNA and the amino acid sequence of the polypeptide. Since base pairing between complementary sequences of nucleobases determines the overall secondary (and ultimately tertiary) structure of nucleic acid molecules, sequences predicted to or known to be able to adopt a particular structure (e.g. a stem-loop) are vital considerations in the design and utility of some types of functional elements or motifs (e.g. RNA elements). Nucleic acid secondary structure is generally divided into duplexes (contiguous base pairs) and various kinds of loops (unpaired nucleotides flanked or surrounded by duplexes). As is known in the art, stable RNA secondary structures, or combinations of them, can be further classified and usefully described as, but not limited to, simple loops, tetraloops, pseudoknots, hairpins, helicies, and stem-loops. Secondary structure can also be usefully depicted as a list of nucleobases which are paired in a nucleic acid molecule.

The function(s) of a nucleic acid secondary structure are emergent from the thermodynamic properties of the secondary structure. For example, the thermodynamic stability of an RNA hairpin/stemloop structure is characterized by its free energy change (deltaG). For a spontaneous process, i.e. the formation of a stable RNA hairpin/stemloop, deltaG is negative. The lower the deltaG value, the more energy is required to reverse the process, i.e. the more energy is required to denature or melt ('unfold') the RNA hairpin/stemloop. The stability of an RNA hairpin/stemloop will contribute to its biological function: e.g. in the context of translation, a more stable RNA structure with a relatively low deltaG can act a physical barrier for the ribosome (Kozak, 1986; Babendure et al., 2006), leading to inhibition of protein synthesis. In contrast, a weaker or moderately stable RNA structure can be beneficial as translational enhancer, as the translational machinery will recognize it as signal for a temporary pause, but ultimately the structure will open up and allow translation to proceed (Kozal, 1986; Kozak, 1990; Babendure et al., 2006). To assign an absolute number to the deltaG value that defines a stable versus a weak/moderately stable RNA hairpin/stemloop is difficult and is very much driven by its context (sequence and structural context, biological context). In the context of the above mentioned examples by Kozak, 1986, Kozak, 1990 and Babendure et al., 2006, stable hairpins/stemloops are characterized by approximate deltaG values lower than −30 kcal/mol, while weak/moderately stable hairpins are characterized by approximate deltaG values between −10 and −30 kcal/mol.

Accordingly, in some embodiments, an mRNA comprises at least one modification, wherein the at least one modification is a structural modification. In some embodiments, the structural modification is an RNA element. In some embodiments, the structural modification is a GC-rich RNA element. In some embodiments, the structural modification is a viral RNA element. In some embodiments, the structural modification is a protein-binding RNA element. In some embodiments, the structural modification is a translation initiation element. In some embodiments, the structural modification is a translation enhancer element. In some embodiments, the structural modification is a translation fidelity enhancing element. In some embodiments, the structural modification is an mRNA nuclear export element. In some embodiments, the structural modification is a stable RNA secondary structure.

The mRNAs of the present disclosure, or regions thereof, may be codon optimized. Codon optimization methods are known in the art and may be useful for a variety of purposes: matching codon frequencies in host organisms to ensure proper folding, bias GC content to increase mRNA stability or reduce secondary structures, minimize tandem repeat codons or base runs that may impair gene construction or expression, customize transcriptional and translational control regions, insert or remove proteins trafficking sequences, remove/add post translation modification sites in encoded proteins (e.g., glycosylation sites), add, remove or shuffle protein domains, insert or delete restriction sites, modify ribosome binding sites and mRNA degradation sites, adjust translation rates to allow the various domains of the protein to fold properly, or to reduce or eliminate problem secondary structures within the polynucleotide. Codon optimization tools, algorithms and services are known in the art; non-limiting examples include services from GeneArt (Life Technologies), DNA2.0 (Menlo Park, CA) and/or proprietary methods. In one embodiment, the mRNA sequence is optimized using optimization algorithms, e.g., to optimize expression in mammalian cells or enhance mRNA stability. Accordingly in some embodiments, an mmRNA comprises a structural modification, wherein the structural modification is a codon optimized open reading frame. In some embodiments, the structural modification is a modification of base composition.

mRNA Construct Components

An mRNA may be a naturally or non-naturally occurring mRNA. An mRNA may include one or more modified nucleobases, nucleosides, or nucleotides, as described below, in which case it may be referred to as a "modified mRNA" or "mmRNA." As described herein "nucleoside" is defined as a compound containing a sugar molecule (e.g., a pentose or ribose) or derivative thereof in combination with an organic base (e.g., a purine or pyrimidine) or a derivative thereof (also referred to herein as "nucleobase"). As described herein, "nucleotide" is defined as a nucleoside including a phosphate group.

An mRNA may include a 5' untranslated region (5'-UTR), a 3' untranslated region (3'-UTR), and/or a coding region (e.g., an open reading frame). An exemplary 5' UTR for use in the constructs is shown in SEQ ID NO: 33. An mRNA may include any suitable number of base pairs, including tens (e.g., 10, 20, 30, 40, 50, 60, 70, 80, 90 or 100), hundreds (e.g., 200, 300, 400, 500, 600, 700, 800, or 900) or thousands (e.g., 1000, 2000, 3000, 4000, 5000, 6000, 7000, 8000, 9000, 10,000) of base pairs. Any number (e.g., all, some, or none) of nucleobases, nucleosides, or nucleotides may be an analog of a canonical species, substituted, modified, or otherwise non-naturally occurring. In certain embodiments, all of a particular nucleobase type may be modified.

In some embodiments, an mRNA as described herein may include a 5' cap structure, a chain terminating nucleotide, optionally a Kozak sequence (also known as a Kozak consensus sequence), a stem loop, a polyA sequence, and/or a polyadenylation signal.

A 5' cap structure or cap species is a compound including two nucleoside moieties joined by a linker and may be selected from a naturally occurring cap, a non-naturally occurring cap or cap analog, or an anti-reverse cap analog (ARCA). A cap species may include one or more modified nucleosides and/or linker moieties. For example, a natural mRNA cap may include a guanine nucleotide and a guanine (G) nucleotide methylated at the 7 position joined by a triphosphate linkage at their 5' positions, e.g., $m^7G(5')ppp(5')G$, commonly written as $m^7GpppG$. A cap species may also be an anti-reverse cap analog. A non-limiting list of possible cap species includes $m^7GpppG$, $m^7Gpppm7G$, m⁷3'dGpppG, m₂⁷,O3'GpppG, m₂⁷,O3'GppppG, m₂⁷,O2'GppppG, m⁷Gpppm⁷G, m⁷3'dGpppG, m₂⁷,O3'GpppG, m₂⁷,O3'GppppG, and m₂⁷,O2'GppppG.

An mRNA may instead or additionally include a chain terminating nucleoside. For example, a chain terminating nucleoside may include those nucleosides deoxygenated at the 2' and/or 3' positions of their sugar group. Such species may include 3'-deoxyadenosine (cordycepin), 3'-deoxyuridine, 3'-deoxycytosine, 3'-deoxyguanosine, 3'-deoxythymine, and 2',3'-dideoxynucleosides, such as 2',3'-dideoxyadenosine, 2',3'-dideoxyuridine, 2',3'-dideoxycytosine, 2',3'-dideoxyguanosine, and 2',3'-dideoxythymine. In some embodiments, incorporation of a chain terminating nucleotide into an mRNA, for example at the 3'-terminus, may result in stabilization of the mRNA, as described, for example, in International Patent Publication No. WO 2013/103659.

An mRNA may instead or additionally include a stem loop, such as a histone stem loop. A stem loop may include 2, 3, 4, 5, 6, 7, 8, or more nucleotide base pairs. For example, a stem loop may include 4, 5, 6, 7, or 8 nucleotide base pairs. A stem loop may be located in any region of an mRNA. For example, a stem loop may be located in, before, or after an untranslated region (a 5' untranslated region or a 3' untranslated region), a coding region, or a polyA sequence or tail. In some embodiments, a stem loop may affect one or more function(s) of an mRNA, such as initiation of translation, translation efficiency, and/or transcriptional termination.

An mRNA may instead or additionally include a polyA sequence and/or polyadenylation signal. A polyA sequence may be comprised entirely or mostly of adenine nucleotides or analogs or derivatives thereof. A polyA sequence may be a tail located adjacent to a 3' untranslated region of an mRNA. In some embodiments, a polyA sequence may affect the nuclear export, translation, and/or stability of an mRNA.

An mRNA may instead or additionally include a microRNA binding site.

In some embodiments, an mRNA is a bicistronic mRNA comprising a first coding region and a second coding region with an intervening sequence comprising an internal ribosome entry site (IRES) sequence that allows for internal translation initiation between the first and second coding regions, or with an intervening sequence encoding a self-cleaving peptide, such as a 2A peptide. IRES sequences and 2A peptides are typically used to enhance expression of multiple proteins from the same vector. A variety of IRES sequences are known and available in the art and may be used, including, e.g., the encephalomyocarditis virus IRES.

5' UTR and Translation Initiation

In certain embodiments, the polynucleotide (e.g., mRNA) encoding a polypeptide of the present disclosure comprises a 5' UTR and/or a translation initiation sequence. Natural 5' UTRs comprise sequences involved in translation initiation. For example, Kozak sequences comprise natural 5' UTRs and are commonly known to be involved in the process by which the ribosome initiates translation of many genes. 5' UTRs also have been known to form secondary structures which are involved in elongation factor binding.

By engineering the features typically found in abundantly expressed genes of specific target organs, one can enhance the stability and protein production of the polynucleotides of the disclosure. For example, introduction of 5' UTR of mRNA known to be upregulated in cancers, such as c-myc, could be used to enhance expression of a nucleic acid molecule, such as a polynucleotide, in cancer cells. Untranslated regions useful in the design and manufacture of polynucleotides include, but are not limited to, those disclosed in International Patent Publication No. WO 2014/164253 (see also US20160022840).

Shown in Table 2 is a listing of exemplary 5' UTRs. Variants of 5' UTRs can be utilized wherein one or more nucleotides are added or removed to the termini, including A, U, C or G.

TABLE 2

Exemplary 5'-UTRs

| 5' UTR Identifier | Name/ Description | Sequence | SEQ ID NO. |
|---|---|---|---|
| 5UTR-001 | Upstream UTR | GGGAAAUAAGAGAGAAAAGAA GAGUAAGAAGAAAUAUAAGAG CCACC | 476 |
| 5UTR-002 | Upstream UTR | GGGAGAUCAGAGAGAAAAGAA GAGUAAGAAGAAAUAUAAGAG CCACC | 477 |
| 5UTR-003 | Upstream UTR | GGAAUAAAAGUCUCAACACAA CAUAUACAAAACAAACGAAUC UCAAGCAAUCAAGCAUUCUAC UUCUAUUGCAGCAAUUUAAAU CAUUUCUUUUAAAGCAAAAGC AAUUUUCUGAAAAUUUUCACC AUUUACGAACGAUAGCAAC | 478 |
| 5UTR-004 | Upstream UTR | GGGAGACAAGCUUGGCAUUCC GGUACUGUUGGUAAAGCCACC | 479 |
| 5UTR-005 | Upstream UTR | GGGAGAUCAGAGAGAAAAGAA GAGUAAGAAGAAAUAUAAGAG CCACC | 480 |
| 5UTR-006 | Upstream UTR | GGAAUAAAAGUCUCAACACAA CAUAUACAAAACAAACGAAUC UCAAGCAAUCAAGCAUUCUAC UUCUAUUGCAGCAAUUUAAAU CAUUUCUUUUAAAGCAAAAGC AAUUUUCUGAAAAUUUUCACC AUUUACGAACGAUAGCAAC | 481 |
| 5UTR-007 | Upstream UTR | GGGAGACAAGCUUGGCAUUCC GGUACUGUUGGUAAAGCCACC | 482 |
| 5UTR-008 | Upstream UTR | GGGAAUUAACAGAGAAAAGAA GAGUAAGAAGAAAUAUAAGAG CCACC | 483 |
| 5UTR-009 | Upstream UTR | GGGAAAUUAGACAGAAAAGAA GAGUAAGAAGAAAUAUAAGAG CCACC | 484 |
| 5UTR-010 | Upstream UTR | GGGAAAUAAGAGAGUAAAGAA CAGUAAGAAGAAAUAUAAGAG CCACC | 485 |
| 5UTR-011 | Upstream UTR | GGGAAAAAGAGAGAAAAGAA GACUAAGAAGAAAUAUAAGAG CCACC | 486 |
| 5UTR-012 | Upstream UTR | GGGAAAUAAGAGAGAAAAGAA GAGUAAGAAGAUAUAUAAGAG CCACC | 487 |
| 5UTR-013 | Upstream UTR | GGGAAAUAAGAGACAAAACAA GAGUAAGAAGAAAUAUAAGAG CCACC | 488 |
| 5UTR-014 | Upstream UTR | GGGAAAUUAGAGAGUAAAGAA CAGUAAGUAGAAUUAAAAGAG CCACC | 489 |
| 5UTR-015 | Upstream UTR | GGGAAAUAAGAGAGAAUAGAA GAGUAAGAAGAAAUAUAAGAG CCACC | 490 |

TABLE 2-continued

Exemplary 5'-UTRs

| 5' UTR Identifier | Name/ Description | Sequence | SEQ ID NO. |
|---|---|---|---|
| 5UTR-016 | Upstream UTR | GGGAAAUAAGAGAGAAAAGAA GAGUAAGAAGAAAAUUAAGAG CCACC | 491 |
| 5UTR-017 | Upstream UTR | GGGAAAUAAGAGAGAAAAGAA GAGUAAGAAGAAAUUUAAGAG CCACC | 492 |
| 5UTR-018 | Upstream UTR | GGGAAAUAAGAGAGAAAAGAA GAGUAAGAAGAAAUAUAAGAG CCACC | 493 |
| 5UTR-019 | Upstream UTR | UCAAGCUUUUGGACCCUCGUA CAGAAGCUAAUACGACUCACU AUAGGGAAAUAAGAGAGAAAA GAAGAGUAAGAAGAAAUAUAA GAGCCACC | 494 |
| 5UTR-020 | Upstream UTR | GGACAGAUCGCCUGGAGACGC CAUCCACGCUGUUUUGACCUC CAUAGAAGACACCGGGACCGA UCCAGCCUCCGCGCCCGGGAA CGGUGCAUUGGAACGCGGAUU CCCCGUGCCAAGAGUGACUCA CCGUCCUUGACACG | 495 |
| 5UTR-021 | Upstream UTR | GGCGCUGCCUACGGAGGUGGC AGCCAUCUCCUUCUCGGCAUC | 496 |

Other non-UTR sequences can also be used as regions or subregions within the polynucleotides. For example, introns or portions of introns sequences can be incorporated into regions of the polynucleotides. Incorporation of intronic sequences can increase protein production as well as polynucleotide levels.

Combinations of features can be included in flanking regions and can be contained within other features. For example, the ORF can be flanked by a 5' UTR which can contain a strong Kozak translational initiation signal and/or a 3' UTR which can include an oligo(dT) sequence for templated addition of a poly-A tail. A 5' UTR can comprise a first polynucleotide fragment and a second polynucleotide fragment from the same and/or different genes such as the 5' UTRs described in U.S. Patent Application Publication No. 2010-0293625.

These UTRs or portions thereof can be placed in the same orientation as in the transcript from which they were selected or can be altered in orientation or location. Hence a 5' or 3' UTR can be inverted, shortened, lengthened, made with one or more other 5' UTRs or 3' UTRs.

In some embodiments, the UTR sequences can be changed in some way in relation to a reference sequence. For example, a 3' or 5' UTR can be altered relative to a wild type or native UTR by the change in orientation or location as taught above or can be altered by the inclusion of additional nucleotides, deletion of nucleotides, swapping or transposition of nucleotides. Any of these changes producing an "altered" UTR (whether 3' or 5') comprise a variant UTR.

In some embodiments, a double, triple or quadruple UTR such as a 5' or 3' UTR can be used. As used herein, a "double" UTR is one in which two copies of the same UTR are encoded either in series or substantially in series. For example, a double beta-globin 3' UTR can be used as described in U.S. Patent Application Publication No. 2010-0129877.

In some embodiments, flanking regions can be heterologous. In some embodiments, the 5' untranslated region can be derived from a different species than the 3' untranslated region. The untranslated region can also include translation enhancer elements (TEE). As a non-limiting example, the TEE can include those described in U.S. Patent Application Publication No. 2009-0226470.

In some embodiments, the mRNAs provided by the disclosure comprise a 5' UTR comprising a T7 leader sequence at the 5' end of the 5' UTR. In some embodiments, the mRNA of the disclosure comprises a 5' UTR comprising a T7 leader sequence comprising the sequence GGGAGA at the 5' end of the 5' UTR. In some embodiments, the mRNA of the disclosure comprises a 5' UTR comprising a T7 leader sequence comprising the sequence GGGAAA at the 5' end of the 5' UTR. In some embodiments, the mRNA comprises a 5' UTR which does not comprise a T7 leader sequence at the 5' end of the 5' UTR.

In another aspect, the disclosure provides an mRNA comprising a 5' UTR, wherein the nucleotide sequence of the 5' UTR comprises any one of the nucleotide sequences set forth in SEQ ID NO: 1 to SEQ ID NO: 497. In another embodiment, the disclosure provides an mRNA comprising a 5' UTR, wherein the nucleotide sequence of the 5' UTR comprises the nucleotide sequence set forth in SEQ ID NO: 33. In another embodiment, the disclosure provides an mRNA comprising a 5' UTR, wherein the nucleotide sequence of the 5' UTR comprises the nucleotide sequence set forth in SEQ ID NO: 34. In another embodiment, the disclosure provides an mRNA comprising a 5' UTR, wherein the nucleotide sequence of the 5' UTR comprises the nucleotide sequence set forth in SEQ ID NO: 52. In another embodiment, the disclosure provides an mRNA comprising a 5' UTR, wherein the nucleotide sequence of the 5' UTR comprises the nucleotide sequence set forth in SEQ ID NO: 53. In another embodiment, the disclosure provides an mRNA comprising a 5' UTR, wherein the nucleotide sequence of the 5' UTR comprises the nucleotide sequence set forth in SEQ ID NO: 54. In another embodiment, the disclosure provides an mRNA comprising a 5' UTR, wherein the nucleotide sequence of the 5' UTR comprises the nucleotide sequence set forth in SEQ ID NO: 73.

3' UTR and the AU Rich Elements

In certain embodiments, the polynucleotide (e.g., mRNA) encoding a polypeptide further comprises a 3' UTR. 3'-UTR is the section of mRNA that immediately follows the translation termination codon and often contains regulatory regions that post-transcriptionally influence gene expression. Regulatory regions within the 3'-UTR can influence polyadenylation, translation efficiency, localization, and stability of the mRNA. In one embodiment, the 3'-UTR useful for the disclosure comprises a binding site for regulatory proteins or microRNAs. In some embodiments, the 3'-UTR has a silencer region, which binds to repressor proteins and inhibits the expression of the mRNA. In other embodiments, the 3'-UTR comprises an AU-rich element. Proteins bind AREs to affect the stability or decay rate of transcripts in a localized manner or affect translation initiation. In other embodiments, the 3'-UTR comprises the sequence AAUAAA that directs addition of several hundred adenine residues called the poly(A) tail to the end of the mRNA transcript.

Table 3 shows a listing of 3'-untranslated regions useful for the mRNAs encoding a polypeptide. Variants of 3' UTRs can be utilized wherein one or more nucleotides are added or removed to the termini, including A, U, C or G.

TABLE 3

Exemplary 3'-Untranslated Regions

| 3' UTR Identifier | Name/Description | Sequence | SEQ ID NO. |
|---|---|---|---|
| 3UTR-001 | Creatine Kinase | GCGCCUGCCCACCUGCCACCGACUGCUGGAACCCAGCCAGUGGGAGGGCCUGGCCCACCAGAGUCCUGCUCCCUCACUCCUCGCCCCGCCCCUGUCCCAGAGUCCCACCUGGGGGCUCUCUCCACCCUUCUCAGAGUUCCAGUUUCAACCAGAGUUCCAACCAAUGGGCUCCAUCCUCUGGAUUCUGGCCAAUGAAAUAUCUCCCUGGCAGGGUCCUCUUCUUUUCCCAGAGCUCCACCCCAACCAGGAGCUCUAGUUAAUGGAGAGCUCCCAGCACACUCGAGCUUGUGCUUUGUCUCCACGCAAAGCGAUAAAUAAAAGCAUUGGUGGCCUUUGUCUUUGAAUAAAGCCUGAGUAGGAAGUCUAGA | 497 |
| 3UTR-002 | Myoglobin | GCCCCUGCCGCUCCCACCCCCACCCAUCUGGGCCCCGGGUUCAAGAGAGAGCGGGGUCUGAUCUCGUGUAGCCAUAUAGAGUUUGCUUCUGAGUGUCUGCUUUGUUUAGUAGAGGUGGGCAGGAGGAGCUGAGGGGCUGGGGCUGGGGUGUUGAAGUUGGCUUUGCAUGCCCAGCGAUGCGCCUCCCUGUGGGAUGUCAUCACCCUGGGAACCGGGAGUGCCCUUGGCUCACUGUGUUCUGCAUGGUUUGGAUCUGAAUUAAUUGUCCUUUCUUCUAAAAUCCCAACCGAACUUCUUCCAACCUCCAAACUGGCUGUAACCCCAAAUCCAAGCCAUUAACUACACCUGACAGUAGCAAUUGUCUGAUUAAUCACUGGCCCCUUGAAGACAGCAGAAUGUCCCUUUGCAAUGAGGAGGAGAUCUGGGCUGGGCGGGCCAGCUGGGGAAGCAUUUGACUAUCUGGAACUUGUGUGUGCCUCCUCAGGUAUGGCAGUGACUCACCUGGUUUUAAUAAAACAACCUGCAACAUCUCAUGGUCUUUGAAUAAAGCCUGAGUAGGAAGUCUAGA | 498 |
| 3UTR-003 | α-actin | ACACACUCCACCUCCAGCACGCGACUUCUCAGGACGACGAAUCUUCUCAAUGGGGGGGCGGCUGAGCUCCAGCCACCCCGCAGUCACUUUCUUUGUAACAACUUCCGUUGCUGCCAUCGUAAACUGACACAGUGUUUAUAACGUGUACAUACAUUAACUUAUUACCUCAUUUUGUUAUUUUUCGAAACAAAGCCCUGUGGAAGAAAUGGAAAACUUGAAGAAGCAUUUAAAGUCAUUCUGUUAAGCUGCGUAAAUGGUCUUUGAAUAAAGCCUGAGUAGGAAGUCUAGA | 499 |
| 3UTR-004 | Albumin | CAUCACAUUUAAAAGCAUCUCAGCCUACCAUGAGAAUAAGAGAAAGAAAAUGAAGAUCAAAAGCUUAUUCAUCUGUUUUCUUUUUCGUUGGUGUAAAGCCAACACCCUGUCUAAAAAACAUAAAUUUCUUUAAUCAUUUUGCCUCUUUUCUCUGUGCUUCAAUUAAUAAAAAAUGGAAAGAAUCUAAUAGAGUGGUACAGCACUGUUAUUUUUCAAAGAUGUGUUGCUAUCCUGAAAAUUCUGUAGGUUCUGUGGAAGUUCCAGUGUUCUCUCUUAUUCCACUUCGGUAGAGGAUUUCUAGUUUCUUGUGGGCUAAUUAAAUCAUUAUACUCUUCUAAUGGUCUUUGAAUAAAGCCUGAGUAGGAAGUCUAGA | 500 |
| 3UTR-005 | α-globin | GCUGCCUUCUGCGGGGCUUGCCUUCUGGCCAUGCCCUUCUUCUCUCCCUUGCACCUGUACCUCUUGGUCUUUGAAUAAAGCCUGAGUAGGAAGGCGGCCGCUCGAGCAUGCAUCUAGA | 501 |
| 3UTR-006 | G-CSF | GCCAAGCCCUCCCCAUCCCAUGUAUUUAUCUCUAUUUAAUAUUUAUGUCUAUUUAAGCCUCAUAUUUAAAGACAGGGAAGAGCAGAACGGAGCCCCAGGCCUCUGUGUCCUUCCCUGCAUUUCUGAGUUUCAUUCUCCUGCCUGUAGCAGUGAGAAAAAGCUCCUGUCCUCCCAUCCCCUGGACUGGGAGGUAGAUAGGUAAAUACCAAGUAUUUAUUACUAUGACUGCUCCCCAGCCCUGGCUCUGCAAUGGGCACUGGGAUGAGCCGCUGUGAGCCCCUGGUCCUGAGGGUCCCCACCUGGGACCCUUGAGAGUAUCAGGUCUCCCACGUGGGAGACAAGAAAUCCCUGUUUAAUAUUUAAACAGCAGUGUUCCCCAUCUGGGUCCUUGCACCCCUCACUCUGGCCUCAGCCGACUGCACAGCGGCCCCUGCAUCCCCUUGGCUGUGAGGCCCCUGGACAAGCAGAGGUGGCCAGAGCUGGGAGGCAUGGCCCUGGGGUCCCACGAAUUUGCUGGGGAAUCUCGUUUUUCUCUUAAGACUUUUGGGACAUGGUUUGACUCCCGAACAUCACCGACGCGUCUCCUGUUUUUCUGGGUGGCCUCGGGACACCUGCCCUGCCCCCACGAGGGUCAGGACUGUGACUCUUUUUAGGGCCAGGCAGGUGCCUGGACAUUUGCCUUGCUGGACGGGGACUGGGGAUGUGGGAGGGAGCAGACAGGAGGAAUCAUGUCAGGCCUGUGUGUGAAAGGAAGCUCCACUGUCACCUCUCACCUCUUCACCCCCACUCACCAGUGUCCCCUCCACUGUCACAUUGUAACUGAACUUCAGGAUAAUAAAGUGUUUGCCUCCAUGGUCUUUGAAUAAAGCCUGAGUAGGAAGGCGGCCGCUCGAGCAUGCAUCUAGA | 502 |
| 3UTR-007 | Col1a2; collagen, type I, alpha 2 | ACUCAAUCUAAAUUAAAAAAGAAAGAAAUUUGAAAAAACUUUCUCUUUGCCAUUUCUUCUUCUUCUUUUUAACUGAAAGCUGAAUCCUUCCAUUUCUUCUGCACAUCUACUUGCUUAAAUUGUGGGAAAGAGAAAAGAAGGAUUGAUCAGAGCAUUGUGCAAUACAGUUUCAUUAACUCCUUCCCCCGCUCCCCCAAAAAUUUGAAUUUUUUUUUCAACACUCUUACACCUGUUAUGGAAAAUGUCAACCUUUGUAAGAAAACCAAAAUAAAAAUUGAAAAAUAAAAACCAUAAACAUUUGCACCACUUGUGGCUUUUGAAUAUCUUCCACAGAGGGAAGUUUAAAACCCAAACUUCCAAAGGUUUAAACUACCUCAAAACACUUUCCCAUGAGUGUGAUCCACAUUGUUAGGUGCUGACCUAGACAGAGAUGAACUGAGGUCCUUGUUUUGUUUUGUCAUAAUACAAAGGUGCUAAUUAAUAGUAUUUCAGAUACUUGAAGAAUGUUGAUGGUGCUAGAGAAUUGAGAAAAUACUCCUGUAUUGAGUUGUAUCGUGUGGUGUAUUUUUAAAAAUUUGAUUUAGCAUUCAUAUUUUCCAUCUUAUUCCCAAUUAAAAGUAUGCAGAUUAUUUGCCCAAAUCUUCUUCAGAUUCAGCAUUUGUUCUUUGCCAGUCUCAUUUUCAUCUUCUUCCAUGGUUCCACAGAAGCUUUGUUUCUUGGGCAAGCAGAAAAAUUAAAUUGUACCUAUUUUGUAUAUGUGAGAUGUUUAAAUAAAUUGUGAAAAAAUGAAAUAAGCAUGUUUGGUUUUCCAAAAGAACAUAU | 503 |

TABLE 3-continued

Exemplary 3'-Untranslated Regions

| 3' UTR Identifier | Name/Description | Sequence | SEQ ID NO. |
|---|---|---|---|
| 3UTR-008 | Col6a2; collagen, type VI, alpha 2 | CGCCGCCGCCCGGGCCCCGCAGUCGA GGGUCGUGAGCCCACCCCGUCCAUGG UGCUAAGCGGGCCCGGGUCCCACACG GCCAGCACCGCUGCUCACUCGGACGA CGCCCUGGGCCUGCACCUCUCCAGCU CCUCCCACGGGGUCCCCGUAGCCCCG GCCCCCGCCCAGCCCCAGGUCUCCCC AGGCCCUCCGCAGGCUGCCCGGCCUC CCUCCCCCUGCAGCCAUCCCAAGGCU CCUGACCUACCUGGCCCCUGAGCUCU GGAGCAAGCCCUGACCCAAUAAAGGC UUUGAACCCAU | 504 |
| 3UTR-009 | RPN1; ribophorin I | GGGGCUAGAGCCCUCUCCGCACAGCG UGGAGACGGGGCAAGGAGGGGGGUUA UUAGGAUGGUGGUUUUGUUUUGCUU UGUUUAAAGCCGUGGGAAAAUGGCAC AACUUUACCUCUGUGGGAGAUGCAAC ACUGAGAGCCAAGGGGUGGGAGUUGG GAUAAUUUUUAUAUAAAAGAAGUUUU UCCACUUUGAAUUGCUAAAAGUGGCA UUUUUCCUAUGUGCAGUCACUCCUCU CAUUUCUAAAAUAGGGACGUGGCCAG GCACGGUGGCUCAUGCCUGUAAUCCC AGCACUUUGGGAGGCCGAGGCAGGCG GCUCACGAGGUCAGGAGAUCGAGACU AUCCUGGCUAACACGGUAAAACCCUG UCUCUACUAAAAGUACAAAAAAUUAG CUGGGCGUGGUGGUGGGCACCUGUAG UCCCAGCUACUCGGGAGGCUGAGGCA GGAGAAAGGCAUGAAUCCAAGAGGCA GAGCUUGCAGUGAGCUGAGAUCGCGC CAUUGCACUCCAGCCUGGGCAACAGU GUUAAGACUCUGUCUCAAAUAUAAAU AAAUAAAUAAAUAAAUAAAUAA AUAAAAAUAAAGCGAGAUGUUGCCCU CAAA | 505 |
| 3UTR-010 | LRP1; low density lipoprotein receptor-related protein 1 | GGCCCUGCCCCGUCGGACUGCCCCCA GAAAGCCUCCUGCCCCCUGCCAGUGA AGUCCUUCAGUGAGCCCCUCCCCAGC CAGCCCUUCCCUGGCCCCGCCGGAUG UAUAAAUGUAAAAUGAAGGAAUUAC AUUUUAUAUGUGAGCGAGCAAGCCGG CAAGCGAGCACAGUAUUAUUUCUCCA UCCCCUCCCUGCCUGCUCCUUGGCAC CCCCAUGCUGCCUUCAGGGAGACAGG CAGGGAGGGCUUGGGGCUGCACCUCC UACCCUCCCACCAGAACGCACCCCAC UGGGAGAGCUGGUGGUGCAGCCUUCC CCUCCCUGUAUAAGCACUUUGCCAA GGCUCUCCCCUCUCGCCCCAUCCCUG CUUGCCCGCCCACAGCUUCCUGAG GGCUAAUUCUGGGAAGGGAGAGUUCU UUGCUGCCCCUGUCUGGAAGACUGG CUCUGGGUGAGGUAGGCGGGAAGGA UGGAGUGUUUAGUUCUUGGGGGAGG CCACCCCAAACCCCAGCCCCAACUCC AGGGGCACCUAUGAGAUGGCCAUGCU CAACCCCCCUCCCAGACAGGCCCUCC CUGUCUCCAGGGCCCCCACCGAGGUU CCCAGGGCUGGAGACUUCCUCUGGUA AACAUUCCUCACCGCCUCCCCUCCCU GGGGACGCCAAGGAGGUGGGCCACAC CCAGGAAGGGAAAGCGGGCAGCCCCG UUUGGGGACGUGAACGUUUUAAUAA UUUUUGCUGAAUUCCUUUACAACUAA AUAACACAGAUAUUGUUAUAAAUAAA AUUGU | 506 |
| 3UTR-011 | Nnt1; cardiotrophin-like cytokine factor 1 | AUAUUAAGGAUCAAGCUGUUAGCUAA UAAUGCCACCUCCUGCAGUUUUGGGAA CAGGCAAAUAAAGUAUCAGUAUACAU GGUGAUGUACAUCUGUAGCAAAGCUC UUGGAGAAAAUGAAGACUGAAGAAAG CAAAGCAAAAACUGUAUAGAGAGAUU UUUCAAAAGCAGUAUCCCUCAAUUU UAAAAAAGGAUUGAAAAUUCUAAAUG UCUUUCUGUGCAUAUUUUUGUGUUA GGAAUCAAAAGUAUUUUAUAAAAGGA GAAAGAACAGCCUCAUUUUAGAUGUA GUCCUGUUGGAUUUUUUAUGCCUCCU CAGUAACCAGAAAUGUUUUAAAAAAC UAAGUGUUAGGAUUUCAAGACAACA UUAUACAUGGCUCUGAAAUAUCUGAC ACAAUGUAAACAUUGCAGGCACCUGC AUUUUAUGUUUUUUUUUUCAACAAAU GUGACUAAUUGUUUGCAAUUUCAA CCGCAGUUUGAAUUAAUCAUAUCAAA UCAGUUUUAAUUUUUUAAAUUGUACU UCAGAGUCUAUAUUUCAAGGGCACAU UUUCUCACUACUAUUUUAAUACAUUA AAGGACUAAAUAAUCUUUCAGAGAUG CUGGAAACAAAUCAUUUGCUUUAUAU GUUUCAUUAGAAUACCAAUGAAACAU ACAACUUGAAAAUUAGUAAUAGUAUU UUUGAAGAUCCCAUUUCUAAUUGGAG AUCUCUUUAAUUUCGAUCAACUUAUA AUGUGUAGUACAUAUAUUAAGUGCACU UGAGUGGAAUUCAACAUUUGACUAAU AAAAUGAGUUCAUCAUGUUGGCAAGU GAUGUGGCAAUUAUCUCUGGUGACAA AAGAGUAAAAUCAAAUAUUUCUGCCU GUUACAAAUAUCAAGGAAGACCUGCU ACUAUGAAAUAGAUGACAUUAAUCUG UCUUCACUGUUUAUAAUACGGAUGGA UUUUUUUCAAAUCAGUGUGUGUUUU GAGGUCUUAUGUAAUGAUGACAUUU GAGAGAAAUGGUGGCUUUUUUUAGCU ACCUCUUUGUCAUUUAAGCACCAGU AAAGAUCAUGUCUUUUUAUAGAAGUG UAGAUUUCUUUGUGACUUUGCUAUC GUGCCUAAAGCUCUAAAUAUAGGUGA AUGUGUGAUGAAUACUCAGAUUAUUU GUCUCUCUAUAUAAUUAGUUUGGUAC UAAGUUUCUCAAAAAAUUAUUAACAC AUGAAGACAAUCUCUAAACCAGAAA AAGAAGUAGUACAAAUUUUGUUACUG UAAUGCUCGCGUUUAGUGAGUUUAAA ACACACAGUACUUUUGUUUUUAUAA UCAGUUUCUAUUUUGCUGUGCCUGAG AUUAAGAUCUGUGUAUGUGUGUGUGU GUGUGUGCGUUUGUGUGUUAAAGC AGAAAAGACUUUUUAAAAGUUUUAA GUGAAAAUGCAAUUUGUUAAUUGAU CUUGAUCACUAGUAAACUCAGGGCU GAAUUAUACCAUGUAUAUUCUAUUAG AAGAAAGUAAACACCAUCUUUAUUCC UGCCCUUUUCUUCUCUCAAGUAGU UGUAGUUAUAUCUAGAAAGAAGCAAU UUUGAUUUCUUGAAAAGGUAGUUCCU GCACUCAGUUUAAACUAAAAAUAAUC AUACUUGGAUUUAUUUAUUUUUGUC AUAGUAAAAUUUUAAUUUAUAUAUA UUUUUAUUUAGUAUUAUCUAUUUCUU UGCUAUUUGCCAAUCCUUUGUCAUCA AUUGUGUUAAAUGAAAAAAUUCA UGCCUGUUCAUUUAUUUAUACUUUA UGGUUAGGAUAUUUAAGGAUUUU GUAUAUAUAAUUUCUUAAAUUAAUAU UCCAAAAGGUUAGUGGACUAGAUUUU UAAAUUAUGGCAAAAAUCUAAAAACA | 507 |

TABLE 3-continued

Exemplary 3'-Untranslated Regions

| 3' UTR Identifier | Name/Description | Sequence | SEQ ID NO. |
|---|---|---|---|
| | | ACAAAAAUGAUUUUUAUACAUUCUAU UUCAUUAUUCCUCUUUUUCCAAUAAG UCAUACAAUUGGUAGAUAUGACUAUU UUUAUUUUUGUAUUAUUCACUAUAUC UUUAUGAUAUUUAAGUAUAAAUAAUU AAAAAAAUUUAAUUGUACCUUUAUAGUC UGUCACCAAAAAAAAAAAAUUAUCUG UAGGUAGUGAAAUGCUAAUGUUGAUU UGUCUUUAAGGGCUUGUUAACUAUCC UUUAUUUUCUCAUUUGUCUUAAAUUA GGAGUUUGUGUUUAAAUUACUCAUCU AAGCAAAAAUGUAUAUAAAUCCCAU UACUGGGUAUAUACCCAAAGGAUUAU AAAUCAUGCUGCUAUAAAGACACAUG CACACGAUGUUUAUUGCAGCACUAU UCACAAUAGCAAAGACUUGGAACCAA CCCAAAUGUCCAUCAAUGAUAGACUU GAUUAAGAAAAUGUGCACAUAUACAC CAUGGAAAUACUAUGCAGCCAUAAAAA AGGAUGAGUUCAUGUCCUUUGUAGGG ACAUGGAUAAAGCUGGAAACCAUCAU UCUGAGCAAACUAUUGCAAGGACAGA AAACCAAACACUGCAUGUUCUCACUC AUAGGUGGGAAUUGAACAAUGAGAAC ACUUGGACACAAGGUGGGGAACACCA CACACCAGGGCCUGUCAUGGGGUGGG GGGAGUGGGGAGGGGAUAGCAUUAGGA GAUAUACCUAAUGUAAAUGAUGAGUU AAUGGGUGCAGCACACCAACAUGGCA CAUGUAUACAUAUGUAGCAAACCUGC ACGUUGUGCACAUGUACCCUAGAACU UAAAGUAUAAUUAAAAAAAAAAAGAA AACAGAAGCUAUUUAUAAAGAAGUUA UUUGCUGAAAUAAAUGUGAUCUUUCC CAUUAAAAAAAAUAAAGAAAUUUGGG GUAAAAAAACACAAUAUAUUGUAUUC UUGAAAAAUUCUAAGAGAGUGGAUGU GAAGUGUUCUCACCACAAAAGUGAUA ACUAAUUGAGGUAAUGCACAUAUUAA UUAGAAGAUUUUGUCAUUCCUACAAU GUAUAUAUACUUUAAAAAAUAUGUUAUA CACAAUAAAUACAUACAUUAAAAAAAU AAGUAAAUGUA | |
| 3UTR-012 | Col6a1; collagen, type VI, alpha 1 | CCCACCCUGCACGCCGGCACCAAACC CUGUCCUCCCACCCCUCCCCACUCAU CACUAAACAGAGUAAAAUGUGAUGCG AAUUUUCCCGACCAACCUGAUUCGCU AGAUUUUUUAAGGAAAAGCUUGGA AAGCCAGGACACAACGCUGCUGCCUG CUUUGUGCAGGGUCCUCCGGGGCUCA GCCCUGAGUUGGCAUCACCUGCGCAG GGCCCUCUGGGGCUCAGCCCUGAGCU AGUGUCACCUGCACAGGGCCCUCUGA GGCUCAGCCCUGAGCUGGCGUCACCU GUGCAGGGCCCUCUGGGGCUCAGCCC UGAGCUGGCCUCACCUGGGGUUCCCA CCCCGGGCUCUCCUGCCCUGCCCUCC UGCCCGCCCUCCCUCCUGCCUGCGCA GCUCCUUCCCUAGGCACCUCUGUGCU GCAUCCCACCAGCCUGAGCAAGACGC CCUCUCGGGGCCUGUGCCGCACUAGC CUCCCUCUCCUCUGUCCCCAUAGCUG GUUUUCCCACCAAUCCUCACCUAAC AGUUACUUUACAAUUACAAAGC AAGCUCUUCUCCUCAGCUUGGGGCAG CCAUUGGCCUCUGUCUCGUUUUGGGA AACCAAGGUCAGGAGGCCGUUGCAGA CAUAAAUCUGGCGACUGGGAAAAUGU CCCCCUGCUGCCUCGGGGCUUGGUGUCC CCCGGACCGGUUUCCCCCUGGGGCAGUUUUCCA GGGGCGGGGUGCCGCCCCCGGACCUGGGGCCCAGUGCUUGUCCCUGGGGCCGUGGGUUGGGUGCCUGCCU CCUUCCCUCCCAGCCUGACCGCCCUCCAGCUUCAGCC GAUUCCGGCCUCCUCCAGCUUGGCUGGCUCACCAAUCGCCUGGUGCCGAGGAGGUAGCAGCUGCUCACUUGCCUCAGCCCCUCCUUUGGGCCUGCACACAUUGGGGACCGGUCAAGCCACCAAGCCGAGCGUCUGGGUAACCCCUGGGGAGCAAGCCGCUGCUGGGGGCUGGCAGUGAGCCCUGGCUGCAGGCGUGCGACCGGUGCAGGGCUGUGAGCGAGCGCGUCCUGCCCCUGACCCCGGAGGCCUGGGCACUGCCCUGGAUCGCCCACCCCGGCCCUGCCCGCCCUGGAGGCCGCUGCUGACCAGCACUGACCCGACCUCAGAGAGUACUCGCAGGGGCGCUGGCUGCACUCAAGACCCUCGAGA | 508 |
| 3UTR-013 | Calr; calreticulin | UUAACGGUGCUAACCCCGUCUGCUCC UCCCUCCCGCAGAGACUGGGGCCUGG ACUGGACAUGAGAGCCCCUUGGUGCC ACAGAGGGCUGUGUCUUACUAGAAAC AACGCAAACCUCUCCCUUCCUCAGAAU AGUGAUGUGUUCGACGUUUUAUCAAA GGCCCCCUUUCUAUGUUCAUGUUAGU UUUGCUCCUUCUGUGUUUUUUCUGA ACCAUAUCCAUGUUGCUGACUUUUCC AAAUAAAGGUUUUCACUCCUCUC | 509 |
| 3UTR-014 | Col1a1; collagen, type I, alpha 1 | CUCCCUCCAUCCCAACCUGGCUCCCU CCCACCCAACCAACUUUCCCCCCAAC CCGGAAACAGACAAGCAACCCAAACU GAACCCCUCAAAAGCCAAAAAAUGG GAGACAAUUUCACAUGGACUUUGGAA AAUAUUUUUUCCUUUGCAUUCAUCU CUCAAACUUAGUUUUUAUCUUUGACC AACGAACAUGACCAAAAACCAAAG UGCAUUCAACCUUACCAAAAAAAAAA AAAAAAAAGAUAAUAUAAAUAACUU UUUAAAAAGGAAGCUUGGUCCACUU GCUUGAAGACCCAUGCGGGGUAAGU CCCUUUCUGCCCGUUGGGCUUAUGAA ACCCCAAUGCUGCCCUUUCUGCUCCUU UUCUCCACACCCCCUUGGGGCCUCC CCUCCACUCCUUCCCAAAUCUGUCUC CCCAGAAGACACAGGAAACAAUGUAU UGUCUGCCCAGCAAUCAAAGGCAAUG CUCAAACACCCAAGUGGCCCCCACCC UCAGCCCGCUCCUGCCCGCCCAGCAC CCCCAGGCCUGGGGGGACCUGGGGUU CUCAGACUGCCAAAGAAGCCUUGCCA UCUGGCGCUCCCAUGCUCUUGCAAC AUCUCCCUUCGUUUUUGAGGGGGGUC AUGCCGGGGAGCCACCAGCCCCUCA CUGGGUUCGGAGGAGAGUCAGGAAGG GCCACGACAAAGCAGAAACAUCGGAU UUGGGGAACGCGUGUCAAUCCCUUGU GCCGCAGGGCUGGCGGGAGAGACUG UUCUGUUCCUUGUGUAACUGUGUUGC UGAAAGACUACCUCGUUCUUGUCUUG AUGUGUCACCGGGGCAACUGCCUGGG GGCGGGUGGGAGGGGUGGAAGC GGCGGGGAUGGGCGGGGUGGAAGC GGCUCCCAUUUUAUACCAAAGGUGC UACAUCUAUGUGAUGGGUGGGGUGGG GAGGGAAUCACUGGUGCUAUAGAAAU UGAGAUGCCCCCCAGGCCAGCAAAU GUUCCUUUUUGUUCAAAGUCUAUUU | 510 |

TABLE 3-continued

Exemplary 3'-Untranslated Regions

| 3' UTR Identifier | Name/ Description | Sequence | SEQ ID NO. |
|---|---|---|---|
| | | UAUUCCUUGAUAUUUUCUUUUUUUU UUUUUUUUUUUGUGGAUGGGGACUUG UGAAUUUUUCUAAAGGUGCUAUUUAA CAUGGGAGGAGAGCGUGUGCGGCUCC AGCCCAGCCCGCUGCUCACUUUCCAC CCUCUCUCCACCUGCCUCUGGCUUCU CAGGCCUCUGCUCUCCGACCUCUCUC CUCUGAAACCCUCCUCCACAGCUGCA GCCCAUCCUCCCGGCUCCCUCCUAGU CUGUCCUGCGUCCUCUGUCCCCGGGU UUCAGAGACAACUUCCCAAAGCACAA AGCAGUUUUUCCCCCUAGGGGUGGGA GGAAGCAAAAGACUCUGUACCUAUUU UGUAUGUGUAUAAUAAUUUGAGAUGU UUUUAAUUAUUUUGAUUGCUGGAAUA AAGCAUGUGGAAAUGACCCAAACAUA AUCCGCAGUGGCUCCCUAAUUUCCUU CUUUGGAGUUGGGGGAGGGGUAGACA UGGGGAAGGGGCUUUGGGGUGAUGGG CUUGCCUUCCAUUCCUGCCCUUUCCC UCCCCACUAUUCUCUUCUAGAUCCCU CCAUAACCCCACUCCCCUUUCUCUCA CCCUUCUUAUACCGCAAACCUUUCUA CUUCCUCUUUCAUUUUCUAUUCUUGC AAUUUCCUUGCACCUUUUCCAAAUCC UCUUCUCCCCUGCAAUACCAUACAGG CAAUCCACGUGCACAACACACACACA CACUCUUCACAUCUGGGGUUGUCCAA ACCUCAUACCCACUCCCCUUCAAGCC CAUCCACUCUCCACCCCUGGAUGCC CUGCACUUGGUGGCGUGGGAUGCUC AUGGAUACUGGGAGGGUGAGGGGAGU GGAACCCGUGAGGAGGACCUGGGGGC CUCUCCCUUGAACUGACAUGAAGGGUC AUCUGGCCUCUGCUCCCUUCUCACCC ACGCUGACCUCCUGCCGAAGGAGCAA CGCAACAGGAGAGGGGUCUGCUGAGC CUGGCGAGGGUCUGGGAGGGACCAGG AGGAAGGCGUGCUCCCUGCUCGCUGU CCUGGCCCUGGGGGAGUGAGGGAGAC AGACACCUGGGAGAGCUGUGGGGAAG GCACUCGCACCGUGCUCUUUGGGAAGG AAGGAGACCUGGCCCUGCUCACCACG GACUGGGUGCCUCGACCUCCUGAAUC CCCAGAACACAACCCCCCUGGGCUGG GGUGGUCUGGGGAACCAUCGUGCCCC CGCCUCCCGCCUACUCCUUUUUAAGC UU | |
| 3UTR-015 | Plod1; pro-collagen-lysine, 2-oxoglu-tarate 5-dioxy-genase 1 | UUGGCCAGGCCUGACCCUCUUGGACC UUUCUUCUUUGCCGACAACCACUGCC CAGCAGCCUCUGGGACCUCGGGGUCC CAGGGAACCCAGUCCAGCCUCCUGGC UGUUGACUUCCCAUUGCUCUUGGAGC CACCAAUCAAAGAGAUUCAAAGAGAU UCCUGCAGGCCAGAGGCGGAACACAC CUUUAUGGCUGGGGCUCUCCGUGGUG UUCUGGACCCAGCCCCUGGAGACACC AUUCACUUUUACUGCUUUGUAGUGAC UCGUGCUCUCCAACCUGUCUUCCUGA AAAACCAAGCCCCCUUCCCCCACCU CUUCCAUGGGGUGAGACUUGAGCAGA ACAGGGGCUUCCCCAAGUUGCCCAGA AAGACUGUCUGGGUGAGAAGCCAUGG CCAGAGCUGCUCCCAGGCACAGGUGU UGCACCAGGGACUUCUGCUUCAAGUU UUGGGGUAAAGACACCUGGAUCAGAC UCCAAGGGCUGCCCUGAGUCUGGGAC UUCUGCCUCCAUGGCUGGUCAUGAGA GCAAACCGUAGUCCCCUGGAGACAGC GACUCCAGAGAACUCUUGGGAGACA GAAGAGGCAUCUGUGCACAGCUCGAU CUUCUACUUGCCUGUGGGGAGGGGAG UGACAGGUCCACACACCACUGGGU | 511 |
| 3UTR-016 | Nucb1; nucleobin-din 1 | CACCCUGUCCUGGAUGCCUCUGAAGA GAGGGACAGACCGUCAGAAACUGGAG AGUUUCUAUUAAAGGUCAUUUAAACC A UCCUCCGGGACCCCAGCCCUCAGGAU UCCUGAUGCUCCAAGGCGACUGAUGG GCGCUGGAUGAAGUGGCACAGUCAGC UUCCCUGGGGGCUGGUGUCAUGUUGG GCUCCUGGGGCGGGGCACGGCCUGG CAUUUCACGCAUUGCUGCCACCCCAG GUCCACCUGUCUCCACUUUCACAGCC UCCAAGUCUGUGGCUCUUCCCUUCUG UCCUCCGAGGGGCUUGCCUUCUCUCG UGUCCAGUGAGGUGCUCAGUGAUCGG CUUAACUUAGAGAAGCCCGCCCCCUC CCCUUCUCCGUCUGUCCCAAGAGGGU CUGCUCUGAGCCUGCGUUCCUAGGUG GCUCGGCCUCAGCUGCCUGGGUUGUG GCCGCCCUAGCAUCCUGUAUGCCCAC AGCUACUGGAAUCCCCGCUGCUGCUC CGGGCCAAGCUUCUGGUUGAUUAAUG AGGGCAUGGGGUGGUCCCUCAAGACC UUCCCCUACCUUUUGUGGAACCAGUG AUGCCUCAAAGACAGUGUCCCCUCCA CAGCUGGGUGCCAGGGGCAGGGGAUC CUCAGUAUAGCCGGUGAACCCUGAUA CCAGGAGCCUGGGCCUCCCUGAACCC CUGGCUUCCAGCCAUCUCAUCGCCAG CCUCCUCCUGGACCUCUUGGCCCCCA GCCCCUUCCCCACACAGCCCCAGAAG GGUCCCAGAGCUGACCCCACUCCAGG ACCUAGGCCCAGCCCCUCAGCCUCAU CUGGAGCCCCUGAAGACCAGUCCCAC CCACCUUUCUGGCCUCAUCUGACACU GCUCCGCAUCCUGCUGUGUGUCCUGU UCCAUGUUCCGGUUCCAUCCAAAUAC ACUUUCUGGAACAAA | 512 |
| 3UTR-017 | α-globin | GCUGGAGCCUCGGUGGCCAUGCUUCU UGCCCCUUGGGCCUCCCCCCAGCCCC UCCUCCCCUUCCUGCACCCGUACCCC CGUGGUCUUUGAAUAAAGUCUGAGUG GGCGGC | 513 |
| 3UTR-018 | Downstream UTR | UAAUAGGCUGGAGCCUCGGUGGCCAU GCUUCUUGCCCCUUGGGCCUCCCCCC AGCCCCUCCUCCCCUUCCUGCACCCG UACCCCCGUGGUCUUUGAAUAAAGUC UGAGUGGGCGGC | 514 |
| 3UTR-019 | Downstream UTR | UGAUAAUAGGCUGGAGCCUCGGUGGC CAUGCUUCUUGCCCCUUGGGCCUCCC CCCAGCCCCUCCUCCCCUUCCUGCAC CCGUACCCCCUGGUCUUUGAAUAAAG UCUGAGUGGGCGGC | 515 |

In certain embodiments, the 3' UTR sequence useful for the disclosure comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of SEQ ID NOs: 497-515 and any combination thereof. In a particular embodiment, the 3' UTR sequence further comprises a miRNA binding site, e.g., miR-122 binding site. In other embodiments, a 3'UTR sequence useful for the disclosure comprises 3' UTR-018 (SEQ ID NO: 514).

In certain embodiments, the 3' UTR sequence comprises one or more miRNA binding sites, e.g., miR-122 binding sites, or any other heterologous nucleotide sequences therein, without disrupting the function of the 3' UTR. Some examples of 3' UTR sequences comprising a miRNA binding site are listed in Table 4.

TABLE 4

Exemplary 3' UTR with miRNA Binding Sites

| 3' UTR Identifier/ miRNA BS | Name/ Descrip- tion | Sequence | SEQ ID NO. |
|---|---|---|---|
| 3UTR-018 + miR-122- 5p binding site | Down- stream UTR | UAAUAGGCUGGAGCCUCGGUGGC CAUGCUUCUUGCCCCUUGGGCCUC CCCCCAGCCCCUCCUCCCCUUCCU GCACCCGUACCCCCCAAACACCAU UGUCACACUCCAGUGGUCUUUGA AUAAAGUCUGAGUGGGCGGC | 516 |
| 3UTR-018 + miR-122- 3p binding site | Down- stream UTR | UAAUAGGCUGGAGCCUCGGUGGC CAUGCUUCUUGCCCCUUGGGCCUC CCCCCAGCCCCUCCUCCCCUUCCU GCACCCGUACCCCCUAUUUAGUGU GAUAAUGGCGUUGUGGUCUUUGA AUAAAGUCUGAGUGGGCGGC | 517 |
| 3UTR-019 + miR-122 binding site | Down- stream UTR | UGAUAAUAGGCUGGAGCCUCGGU GGCCAUGCUUCUUGCCCCUUGGGC CUCCCCCCAGCCCCUCCUCCCCUU CCUGCACCCGUACCCCCCAAACAC CAUUGUCACACUCCAGUGGUCUU UGAAUAAAGUCUGAGUGGGCGGC | 518 |

*miRNA binding site is boxed or underlined.

In certain embodiments, the 3' UTR sequence useful for the disclosure comprises a nucleotide sequence at least about 60%, at least about 70%, at least about 80%, at least about 90%, at least about 95%, at least about 96%, at least about 97%, at least about 98%, at least about 99%, or about 100% identical to the sequence set forth as SEQ ID NO: 514 or 515.

Regions Having a 5' Cap

The polynucleotide comprising an mRNA encoding a polypeptide of the present disclosure can further comprise a 5' cap. The 5' cap useful for polypeptide encoding mRNA can bind the mRNA Cap Binding Protein (CBP), thereby increasing mRNA stability. The cap can further assist the removal of 5' proximal introns removal during mRNA splicing. In some embodiments, the polynucleotide comprising an mRNA encoding a polypeptide of the present disclosure comprises a non-hydrolyzable cap structure preventing decapping and thus increasing mRNA half-life. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, MA) can be used with α-thio-guanosine nucleotides according to the manufacturer's instructions to create a phosphorothioate linkage in the 5'-ppp-5' cap. Additional modified guanosine nucleotides can be used such as α-methyl-phosphonate and seleno-phosphate nucleotides.

In certain embodiments, the 5' cap comprises 2'-O-methylation of the ribose sugars of 5'-terminal and/or 5'-anteterminal nucleotides on the 2'-hydroxyl group of the sugar ring. In other embodiments, the caps for the polypeptide-encoding mRNA include cap analogs, which herein are also referred to as synthetic cap analogs, chemical caps, chemical cap analogs, or structural or functional cap analogs, differ from natural (i.e. endogenous, wild-type or physiological) 5'-caps in their chemical structure, while retaining cap function. Cap analogs can be chemically (i.e. non-enzymatically) or enzymatically synthesized and/or linked to the polynucleotides of the disclosure.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine ($m^7$G-3'mppp-G; which can equivalently be designated 3' O-Me-m7G(5)ppp(5')G). The 3'-O atom of the other, unmodified, guanine becomes linked to the 5'-terminal nucleotide of the capped polynucleotide. The N7- and 3'-O-methylated guanine provides the terminal moiety of the capped polynucleotide.

Another exemplary cap is mCAP, which is similar to ARCA but has a 2'-O-methyl group on guanosine (i.e., N7,2'-O-dimethyl-guanosine-51-triphosphate-5'-guanosine, $m^7$Gm-ppp-G).

In some embodiments, the cap is a dinucleotide cap analog. As a non-limiting example, the dinucleotide cap analog can be modified at different phosphate positions with a boranophosphate group or a phoshoroselenoate group such as the dinucleotide cap analogs described in U.S. Pat. No. 8,519,110.

In another embodiment, the cap is a cap analog is a N7-(4-chlorophenoxyethyl) substituted dinucleotide form of a cap analog known in the art and/or described herein. Non-limiting examples of a N7-(4-chlorophenoxyethyl) substituted dinucleotide form of a cap analog include a N7-(4-chlorophenoxyethyl)-G(5')ppp(5')G and a N7-(4-chlorophenoxyethyl)-$m^{3'-O}$G(5')ppp(5')G cap analog. See, e.g., the various cap analogs and the methods of synthesizing cap analogs described in Kore et al. (2013) Bioorganic & Medicinal Chemistry 21:4570-4574. In another embodiment, a cap analog of the present disclosure is a 4-chloro/bromophenoxyethyl analog.

While cap analogs allow for the concomitant capping of a polynucleotide or a region thereof, in an in vitro transcription reaction, up to 20% of transcripts can remain uncapped. This, as well as the structural differences of a cap analog from an endogenous 5'-cap structures of nucleic acids produced by the endogenous, cellular transcription machinery, can lead to reduced translational competency and reduced cellular stability.

An mRNA of the present disclosure can also be capped post-manufacture (whether IVT or chemical synthesis), using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects.

Non-limiting examples of more authentic 5' cap structures of the present disclosure are those which, among other things, have enhanced binding of cap binding proteins, increased half-life, reduced susceptibility to 5' endonucleases and/or reduced 5' decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7mG(5')ppp(5')N,pN2p (cap 0), 7mG(5')ppp(5')NlmpNp (cap 1), and 7mG(5')-ppp(5')NlmpN2mp (cap 2).

According to the present disclosure, 5' terminal caps can include endogenous caps or cap analogs. According to the present disclosure, a 5' terminal cap can comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

Poly-A Tails

In some embodiments, a polynucleotide comprising an mRNA encoding a polypeptide of the present disclosure further comprises a poly A tail. In further embodiments, terminal groups on the poly-A tail can be incorporated for stabilization. In other embodiments, a poly-A tail comprises des-3' hydroxyl tails. The useful poly-A tails can also include structural moieties or 2'-Omethyl modifications as taught by Li et al. (2005) Current Biology 15:1501-1507.

In one embodiment, the length of a poly-A tail, when present, is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides).

In some embodiments, the polynucleotide or region thereof includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In some embodiments, the poly-A tail is designed relative to the length of the overall polynucleotide or the length of a particular region of the polynucleotide. This design can be based on the length of a coding region, the length of a particular feature or region or based on the length of the ultimate product expressed from the polynucleotides.

In this context, the poly-A tail can be 10, 20, 30, 40, 50, 60, 70, 80, 90, or 100% greater in length than the polynucleotide or feature thereof. The poly-A tail can also be designed as a fraction of the polynucleotides to which it belongs. In this context, the poly-A tail can be 10, 20, 30, 40, 50, 60, 70, 80, or 90% or more of the total length of the construct, a construct region or the total length of the construct minus the poly-A tail. Further, engineered binding sites and conjugation of polynucleotides for Poly-A binding protein can enhance expression.

Additionally, multiple distinct polynucleotides can be linked together via the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In some embodiments, the polynucleotides of the present disclosure are designed to include a polyA-G Quartet region. The G-quartet is a cyclic hydrogen bonded array of four guanine nucleotides that can be formed by G-rich sequences in both DNA and RNA. In this embodiment, the G-quartet is incorporated at the end of the poly-A tail. The resultant polynucleotide is assayed for stability, protein production and other parameters including half-life at various time points. It has been discovered that the polyA-G quartet results in protein production from an mRNA equivalent to at least 75% of that seen using a poly-A tail of 120 nucleotides alone.

Start Codon Region

In some embodiments, an mRNA of the present disclosure further comprises regions that are analogous to or function like a start codon region.

In some embodiments, the translation of a polynucleotide initiates on a codon which is not the start codon AUG. Translation of the polynucleotide can initiate on an alternative start codon such as, but not limited to, ACG, AGG, AAG, CTG/CUG, GTG/GUG, ATA/AUA, ATT/AUU, TTG/UUG. See Touriol et al. (2003) Biology of the Cell 95:169-178 and Matsuda and Mauro (2010) PLoS ONE 5:11. As a non-limiting example, the translation of a polynucleotide begins on the alternative start codon ACG. As another non-limiting example, polynucleotide translation begins on the alternative start codon CTG or CUG. As yet another non-limiting example, the translation of a polynucleotide begins on the alternative start codon GTG or GUG.

Nucleotides flanking a codon that initiates translation such as, but not limited to, a start codon or an alternative start codon, are known to affect the translation efficiency, the length and/or the structure of the polynucleotide. See, e.g., Matsuda and Mauro (2010) PLoS ONE 5:11. Masking any of the nucleotides flanking a codon that initiates translation can be used to alter the position of translation initiation, translation efficiency, length and/or structure of a polynucleotide.

In some embodiments, a masking agent is used near the start codon or alternative start codon in order to mask or hide the codon to reduce the probability of translation initiation at the masked start codon or alternative start codon. Non-limiting examples of masking agents include antisense locked nucleic acids (LNA) polynucleotides and exon-junction complexes (EJCs). See, e.g., Matsuda and Mauro (2010) PLoS ONE 5:11, describing masking agents LNA polynucleotides and EJCs.

In another embodiment, a masking agent is used to mask a start codon of a polynucleotide in order to increase the likelihood that translation will initiate on an alternative start codon. In some embodiments, a masking agent is used to mask a first start codon or alternative start codon in order to increase the chance that translation will initiate on a start codon or alternative start codon downstream to the masked start codon or alternative start codon.

In some embodiments, a start codon or alternative start codon is located within a perfect complement for a miR binding site. The perfect complement of a miR binding site can help control the translation, length and/or structure of the polynucleotide similar to a masking agent. As a non-limiting example, the start codon or alternative start codon is located in the middle of a perfect complement for a miR-122 binding site. The start codon or alternative start codon can be located after the first nucleotide, second nucleotide, third nucleotide, fourth nucleotide, fifth nucleotide, sixth nucleotide, seventh nucleotide, eighth nucleotide, ninth nucleotide, tenth nucleotide, eleventh nucleotide, twelfth nucleotide, thirteenth nucleotide, fourteenth nucleotide, fifteenth nucleotide, sixteenth nucleotide, seventeenth nucleotide, eighteenth nucleotide, nineteenth nucleotide, twentieth nucleotide or twenty-first nucleotide.

In another embodiment, the start codon of a polynucleotide is removed from the polynucleotide sequence in order to have the translation of the polynucleotide begin on a codon which is not the start codon. Translation of the polynucleotide can begin on the codon following the removed start codon or on a downstream start codon or an alternative start codon. In a non-limiting example, the start codon ATG or AUG is removed as the first 3 nucleotides of the polynucleotide sequence in order to have translation initiate on a downstream start codon or alternative start codon. The polynucleotide sequence where the start codon was removed can further comprise at least one masking agent for the downstream start codon and/or alternative start codons in order to control or attempt to control the initiation of translation, the length of the polynucleotide and/or the structure of the polynucleotide.

Stop Codon Region

In some embodiments, mRNA of the present disclosure can further comprise at least one stop codon or at least two stop codons before the 3' untranslated region (UTR). The stop codon can be selected from UGA, UAA, and UAG. In some embodiments, the polynucleotides of the present disclosure include the stop codon UGA and one additional stop codon. In a further embodiment the addition stop codon can be UAA. In another embodiment, the polynucleotides of the present disclosure include three stop codons, four stop codons, or more.

Modified mRNAs

In some embodiments, an mRNA of the disclosure comprises one or more modified nucleobases, nucleosides, or nucleotides (termed "modified mRNAs" or "mmRNAs"). In some embodiments, modified mRNAs may have useful properties, including enhanced stability, intracellular retention, enhanced translation, and/or the lack of a substantial induction of the innate immune response of a cell into which the mRNA is introduced, as compared to a reference unmodified mRNA. Therefore, use of modified mRNAs may enhance the efficiency of protein production, intracellular retention of nucleic acids, as well as possess reduced immunogenicity.

Accordingly, in some embodiments, an mRNA described herein comprises a modification, wherein the modification is the incorporation of one or more chemically modified nucleotides. In some embodiments, one or more chemically modified nucleotides is incorporated into the initiation codon of the mmRNA and functions to increases binding affinity between the initiation codon and the anticodon of the initiator Met-tRNAiMet. In some embodiments, the one or more chemically modified nucleotides is 2-thiouridine. In some embodiments, the one or more chemically modified nucleotides is 2'-O-methyl-2-thiouridine. In some embodiments, the one or more chemically modified nucleotides is 2-selenouridine. In some embodiments, the one or more chemically modified nucleotides is 2'-O-methyl ribose. In some embodiments, the one or more chemically modified nucleotides is selected from a locked nucleic acid, inosine, 2-methylguanosine, or 6-methyl-adenosine. In some embodiments, deoxyribonucleotides are incorporated into mmRNA.

An mmRNA of the disclosure may include any suitable number of base pairs, including tens (e.g., 10, 20, 30, 40, 50, 60, 70, 80, 90 or 100), hundreds (e.g., 200, 300, 400, 500, 600, 700, 800, or 900) or thousands (e.g., 1000, 2000, 3000, 4000, 5000, 6000, 7000, 8000, 9000, 10,000) of base pairs. Any number (e.g., all, some, or none) of nucleobases, nucleosides, or nucleotides may be an analog of a canonical species, substituted, modified, or otherwise non-naturally occurring. In certain embodiments, all of a particular nucleobase type may be modified.

In some embodiments, an mRNA may instead or additionally include a chain terminating nucleoside. For example, a chain terminating nucleoside may include those nucleosides deoxygenated at the 2' and/or 3' positions of their sugar group. Such species may include 3'-deoxyadenosine (cordycepin), 3'-deoxyuridine, 3'-deoxycytosine, 3'-deoxyguanosine, 3'-deoxythymine, and 2',3'-dideoxynucleosides, such as 2',3'-dideoxyadenosine, 2',3'-dideoxyuridine, 2',3'-dideoxycytosine, 2',3'-dideoxyguanosine, and 2',3'-dideoxythymine. In some embodiments, incorporation of a chain terminating nucleotide into an mRNA, for example at the 3'-terminus, may result in stabilization of the mRNA, as described, for example, in International Patent Publication No. WO 2013/103659.

An mRNA may instead or additionally include a stem loop, such as a histone stem loop. A stem loop may include 2, 3, 4, 5, 6, 7, 8, or more nucleotide base pairs. For example, a stem loop may include 4, 5, 6, 7, or 8 nucleotide base pairs. A stem loop may be located in any region of an mRNA. For example, a stem loop may be located in, before, or after an untranslated region (a 5' untranslated region or a 3' untranslated region), a coding region, or a polyA sequence or tail. In some embodiments, a stem loop may affect one or more function(s) of an mRNA, such as initiation of translation, translation efficiency, and/or transcriptional termination.

Numerous approaches for the chemical modification of mRNA to improve translation efficiency and reduce immunogenicity are known, including modifications at the 5' cap, 5' and 3'-UTRs, the open reading frame, and the poly(A) tail (Sahin et al., (2014) Nat Rev Drug Discovery 13:759-780). For example, pseudouridine (ψ) modified mRNA was shown to increased expression of encoded erythropoietin (Kariko et al., (2012) Mol Ther 20:948-953). A combination of 2-thiouridine (s2U) and 5-methylcytidine (5meC) in modified mRNAs was shown to extended the expression of encoded protein (Kormann et al., (2011) Nat Biotechnol 29:154-157). A recent study demonstrated the induction of vascular regeneration using modified (5meC and w) mRNA encoding human vascular endothelial growth factor (Zangi et al., (2013) Nat Biotechnol 31:898-907). These studies demonstrate the utility of incorporating chemically modified nucleotides to achieve mRNA structural and functional optimization In some embodiments, an mRNA includes one or more (e.g., 1, 2, 3 or 4) different modified nucleobases, nucleosides, or nucleotides. In some embodiments, an mRNA includes one or more (e.g., 1, 2, 3, 4, 5, 6, 7, 8, 9, 10, 20, 30, 40, 50, 60, 70, 80, 90, 100, or more) different modified nucleobases, nucleosides, or nucleotides. In some embodiments, the modified mRNA may have reduced degradation in a cell into which the mRNA is introduced, relative to a corresponding unmodified mRNA.

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine (ho$^5$U), 5-aminoallyl-uridine, 5-halo-uridine (e.g., 5-iodo-uridineor 5-bromo-uridine), 3-methyl-uridine (m$^3$U), 5-methoxy-uridine (mo$^5$U), uridine 5-oxyacetic acid (cmo$^5$U), uridine 5-oxyacetic acid methyl ester (mcmo$^5$U), 5-carboxymethyl-uridine (cm$^5$U), 1-carboxymethyl-pseudouridine, 5-carboxyhydroxymethyl-uridine (chm$^5$U), 5-carboxyhydroxymethyl-uridine methyl ester (mchm$^5$U), 5-methoxycarbonylmethyl-uridine (mcm$^5$U), 5-methoxycarbonylmethyl-2-thio-uridine (mcm$^5$s$^2$U), 5-aminomethyl-2-thio-uridine (nm$^5$s$^2$U), 5-methylaminomethyl-uridine (mnm$^5$U), 5-methylaminomethyl-2-thio-uridine (mnm$^5$s$^2$U), 5-methylaminomethyl-2-seleno-uridine (mnm$^5$se$^2$U), 5-carbamoylmethyl-uridine (ncm$^5$U), 5-carboxymethylaminomethyl-uridine (cmnm$^5$U), 5-carboxymethylaminomethyl-2-thio-uridine (cmnm$^5$s$^2$U), 5-propynyl-uridine, 1-propynyl-pseudouridine, 5-taurinomethyl-uridine (τm$^5$U), 1-taurinomethyl-pseudouridine, 5-taurinomethyl-2-thio-uridine(τm$^5$s$^2$U), 1-taurinomethyl-4-thio-pseudouridine, 5-methyl-uridine (m$^5$U, i.e., having the nucleobase deoxythymine), 1-methyl-pseudouridine (m$^1$ψ), 5-methyl-2-thio-uridine (m$^5$ s$^2$U), 1-methyl-4-thio-pseudouridine (m$^1$s$^4$ψ), 4-thio-1-methyl-pseudouridine, 3-methyl-pseudouridine (m$^3$ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m$^5$D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine (acp$^3$U), 1-methyl-3-(3-amino-3-carboxypropyl)pseudouridine (acp$^3$ψ), 5-(isopentenylaminomethyl)uridine (inm$^5$U), 5-(isopentenylaminomethyl)-2-thio-uridine (inm$^5$s$^2$U), α-thio-uridine, 2'-O-methyl-uridine (Um), 5,2'-O-dimethyl-uridine (m$^5$Um), 2'-O-methyl-pseudouridine (ψm), 2-thio-2'-O-methyl-uridine (s$^2$Um), 5-methoxycarbonylmethyl-2'-O-methyl-uridine (mcm$^5$Um), 5-carbamoylmethyl-2'-O-methyl-uridine (ncm$^5$Um), 5-carboxymethylaminomethyl-2'-O-methyl-uridine (cmnm$^5$Um), 3,2'-O-dimethyl-uridine (m$^3$Um), and 5-(isopentenylaminomethyl)-2'-O-methyl-uridine (inm$^5$Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine (m$^3$C), N4-acetyl-cytidine (ac$^4$C), 5-formyl-cytidine (f$^5$C), N4-methyl-cytidine (m$^4$C), 5-methyl-cytidine (m$^5$C), 5-halo-cytidine (e.g., 5-iodo-cytidine), 5-hydroxymethyl-cytidine (hm$^5$C), 1-methyl-pseudoisocytidine, pyrrolo-cytidine, pyrrolo-pseudoisocytidine, 2-thio-cytidine (s$^2$C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k$_2$C), α-thio-cytidine, 2'-O-methyl-cytidine (Cm), 5,2'-O-dimethyl-cytidine (m$^5$Cm), N4-acetyl-2'-O-methyl-cytidine (ac$^4$Cm), N4,2'-O-dimethyl-cytidine (m$^4$Cm), 5-formyl-2'-O-methyl-cytidine (f$^5$Cm), N4,N4,2'-O-trimethyl-cytidine (m$^{42}$Cm), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include α-thio-adenosine, 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2, 6-diaminopurine, 7-deaza-8-aza-2,6-diaminopurine, 1-methyl-adenosine (m$^1$A), 2-methyl-adenine (m$^2$A), N6-methyl-adenosine (m$^6$A), 2-methylthio-N6-methyl-adenosine (ms$^2$m$^6$A), N6-isopentenyl-adenosine (i$^6$A), 2-methylthio-N6-isopentenyl-adenosine (ms$^2$i$^6$A), N6-(cis-hydroxyisopentenyl)adenosine (io$^6$A), 2-methylthio-N6-(cis-hydroxyisopentenyl)adenosine (ms$^2$io$^6$A), N6-glycinylcarbamoyl-adenosine (g$^6$A), N6-threonylcarbamoyl-adenosine (t$^6$A), N6-(m$^6$t$^6$A), methyl-N6-threonylcarbamoyl-adenosine2-methylthio-N6-threonylcarbamoyl-adenosine (ms$^2$g$^6$A), N6,N6-dimethyl-adenosine (m$^6{}_2$A), N6-hydroxynorvalylcarbamoyl-adenosine (hn$^6$A), 2-methylthio-N6-hydroxynorvalylcarbamoyl-adenosine (ms$^2$hn$^6$A), N6-acetyl-adenosine (ac$^6$A), 7-methyl-adenine, 2-methylthio-adenine, 2-methoxy-adenine, α-thio-adenosine, 2'-O-methyl-adenosine (Am), N6,2'-O-dimethyl-adenosine (m$^6$Am), N6,N6,2'-O-trimethyl-adenosine (m$^6{}_2$Am), 1,2'-O-dimethyl-adenosine (m$^1$Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include α-thio-guanosine, inosine (I), 1-methyl-inosine (m$^1$I), wyosine (imG), methylwyosine (mimG), 4-demethyl-wyosine (imG-14), isowyosine (imG2), wybutosine (yW), peroxywybutosine (o$_{2y}$W), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine (preQ$_0$), 7-aminomethyl-7-deaza-guanosine (preQ$_1$), archaeosine (G$^+$), 7-deaza-8-aza-guanosine, 6-thio-guanosine, 6-thio-7-deaza-guanosine, 6-thio-7-deaza-8-aza-guanosine, 7-methyl-guanosine (m$^7$G), 6-thio-7-methyl-guanosine, 7-methyl-inosine, 6-methoxy-guanosine, 1-methyl-guanosine (m$^1$G), N2-methyl-guanosine (m$^2$G), N2,N2-dimethyl-guanosine (m$^2{}_2$G), N2,7-dimethyl-guanosine (m$^{2,7}$G), N2, N2,7-dimethyl-guanosine (m$^{2,2,7}$G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m$^2$Gm), N2,N2-dimethyl-2'-O-methyl-guanosine (m$^{22}$Gm), 1-methyl-2'-O-methyl-guanosine (m$^1$Gm), N2,7-dimethyl-2'-O-methyl-guanosine (m$^{2,7}$Gm), 2'-O-methyl-inosine (Im), 1,2'-O-dimethyl-inosine (m$^1$Im), 2'-O-ribosylguanosine (phosphate) (Gr(p)), 1-thio-guanosine, O6-methyl-guanosine, 2'-F-ara-guanosine, and 2'-F-guanosine.

In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is pseudouridine (ψ), N1-methylpseudouridine (m$^1$ψ), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is a modified cytosine. Exemplary nucleobases and nucleosides having a modified cytosine include N4-acetyl-cytidine ($ac^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, 2-thio-cytidine ($s^2C$), 2-thio-5-methyl-cytidine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is a modified adenine. Exemplary nucleobases and nucleosides having a modified adenine include 7-deaza-adenine, 1-methyl-adenosine ($m^1A$), 2-methyl-adenine ($m^2A$), N6-methyl-adenosine ($m^6A$). In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is a modified guanine. Exemplary nucleobases and nucleosides having a modified guanine include inosine (I), 1-methyl-inosine ($m^1I$), wyosine (imG), methylwyosine (mimG), 7-deaza-guanosine, 7-cyano-7-deaza-guanosine ($preQ_0$), 7-aminomethyl-7-deaza-guanosine ($preQ_1$), 7-methyl-guanosine ($m^7G$), 1-methyl-guanosine ($m^1G$), 8-oxo-guanosine, 7-methyl-8-oxo-guanosine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is 1-methyl-pseudouridine ($m^1\psi$), 5-methoxy-uridine ($mo^5U$), 5-methyl-cytidine ($m^5C$), pseudouridine ($\psi$), α-thio-guanosine, or α-thio-adenosine. In some embodiments, an mRNA of the disclosure includes a combination of one or more of the aforementioned modified nucleobases (e.g., a combination of 2, 3 or 4 of the aforementioned modified nucleobases.)

In some embodiments, the mRNA comprises pseudouridine ($\psi$). In some embodiments, the mRNA comprises pseudouridine ($\psi$) and 5-methyl-cytidine ($m^5C$). In some embodiments, the mRNA comprises 1-methyl-pseudouridine ($m^1\psi$). In some embodiments, the mRNA comprises 1-methyl-pseudouridine ($m^1\psi$) and 5-methyl-cytidine ($m^5C$). In some embodiments, the mRNA comprises 2-thiouridine ($s^2U$). In some embodiments, the mRNA comprises 2-thiouridine and 5-methyl-cytidine ($m^5C$). In some embodiments, the mRNA comprises 5-methoxy-uridine ($mo^5U$). In some embodiments, the mRNA comprises 5-methoxy-uridine ($mo^5U$) and 5-methyl-cytidine ($m^5C$). In some embodiments, the mRNA comprises 2'-O-methyl uridine. In some embodiments, the mRNA comprises 2'-O-methyl uridine and 5-methyl-cytidine ($m^5C$). In some embodiments, the mRNA comprises N6-methyl-adenosine ($m^6A$). In some embodiments, the mRNA comprises N6-methyl-adenosine ($m^6A$) and 5-methyl-cytidine ($m^5C$).

In certain embodiments, an mRNA of the disclosure is uniformly modified (i.e., fully modified, modified throughout the entire sequence) for a particular modification. For example, an mRNA can be uniformly modified with 5-methyl-cytidine ($m^5C$), meaning that all cytosine residues in the mRNA sequence are replaced with 5-methyl-cytidine ($m^5C$). Similarly, mRNAs of the disclosure can be uniformly modified for any type of nucleoside residue present in the sequence by replacement with a modified residue such as those set forth above.

In some embodiments, an mRNA of the disclosure may be modified in a coding region (e.g., an open reading frame encoding a polypeptide). In other embodiments, an mRNA may be modified in regions besides a coding region. For example, in some embodiments, a 5'-UTR and/or a 3'-UTR are provided, wherein either or both may independently contain one or more different nucleoside modifications. In such embodiments, nucleoside modifications may also be present in the coding region.

Examples of nucleoside modifications and combinations thereof that may be present in mmRNAs of the present disclosure include, but are not limited to, those described in PCT Patent Application Publications: WO2012045075, WO2014081507, WO2014093924, WO2014164253, and WO2014159813.

The mmRNAs of the disclosure can include a combination of modifications to the sugar, the nucleobase, and/or the internucleoside linkage. These combinations can include any one or more modifications described herein.

Examples of modified nucleosides and modified nucleoside combinations are provided below in Table 5 and Table 6. These combinations of modified nucleotides can be used to form the mmRNAs of the disclosure. In certain embodiments, the modified nucleosides may be partially or completely substituted for the natural nucleotides of the mRNAs of the disclosure. As a non-limiting example, the natural nucleotide uridine may be substituted with a modified nucleoside described herein. In another non-limiting example, the natural nucleoside uridine may be partially substituted (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9% of the natural uridines) with at least one of the modified nucleoside disclosed herein.

TABLE 5

Combinations of Nucleoside Modifications

| Modified Nucleotide | Modified Nucleotide Combination |
|---|---|
| α-thio-cytidine | α-thio-cytidine/5-iodo-uridine |
| | α-thio-cytidine/N1-methyl-pseudouridine |
| | α-thio-cytidine/a-thio-uridine |
| | a-thio-cytidine/5-methyl-uridine |
| | α-thio-cytidine/pseudo-uridine |
| | about 50% of the cytosines are α-thio-cytidine |
| pseudoisocytidine | pseudoisocytidine/5-iodo-uridine |
| | pseudoisocytidine/N1-methyl-pseudouridine |
| | pseudoisocytidine/α-thio-uridine |
| | pseudoisocytidine/5-methyl-uridine |
| | pseudoisocytidine/pseudouridine |
| | about 25% of cytosines are pseudoisocytidine |
| | pseudoisocytidine/about 50% of uridines are N1-methyl-pseudouridine and about 50% of uridines are pseudouridine |
| | pseudoisocytidine/about 25% of uridines are N1-methyl-pseudouridine and about 25% of uridines are pseudouridine |
| pyrrolo-cytidine | pyrrolo-cytidine/5-iodo-uridine |
| | pyrrolo-cytidine/N1-methyl-pseudouridine |
| | pyrrolo-cytidine/α-thio-uridine |

TABLE 5-continued

Combinations of Nucleoside Modifications

| Modified Nucleotide | Modified Nucleotide Combination |
|---|---|
|  | pyrrolo-cytidine/5-methyl-uridine |
|  | pyrrolo-cytidine/pseudouridine |
|  | about 50% of the cytosines are pyrrolo-cytidine |
| 5-methyl-cytidine | 5-methyl-cytidine/5-iodo-uridine |
|  | 5-methyl-cytidine/N1-methyl-pseudouridine |
|  | 5-methyl-cytidine/α-thio-uridine |
|  | 5-methyl-cytidine/5-methyl-uridine |
|  | 5-methyl-cytidine/pseudouridine |
|  | about 25% of cytosines are 5-methyl-cytidine |
|  | about 50% of cytosines are 5-methyl-cytidine |
|  | 5-methyl-cytidine/5-methoxy-uridine |
|  | 5-methyl-cytidine/5-bromo-uridine |
|  | 5-methyl-cytidine/2-thio-uridine |
|  | 5-methyl-cytidine/about 50% of uridines are 2-thio-uridine |
|  | about 50% of uridines are 5-methyl-cytidine/ about 50% of uridines are 2-thio-uridine |
| N4-acetyl-cytidine | N4-acetyl-cytidine/5-iodo-uridine |
|  | N4-acetyl-cytidine/N1-methyl-pseudouridine |
|  | N4-acetyl-cytidine/α-thio-uridine |
|  | N4-acetyl-cytidine/5-methyl-uridine |
|  | N4-acetyl-cytidine/pseudouridine |
|  | about 50% of cytosines are N4-acetyl-cytidine |
|  | about 25% of cytosines are N4-acetyl-cytidine |
|  | N4-acetyl-cytidine/5-methoxy-uridine |
|  | N4-acetyl-cytidine/5-bromo-uridine |
|  | N4-acetyl-cytidine/2-thio-uridine |
|  | about 50% of cytosines are N4-acetyl-cytidine/ about 50% of uridines are 2-thio-uridine |

TABLE 6

Modified Nucleosides and Combinations Thereof 1-(2,2,2-Trifluoroethyl)pseudo-UTP
1-Ethyl-pseudo-UTP
1-Methyl-pseudo-U-alpha-thio-TP
1-methyl-pseudouridine TP, ATP, GTP, CTP
1-methyl-pseudo-UTP/5-methyl-CTP/ATP/GTP
1-methyl-pseudo-UTP/CTP/ATP/GTP
1-Propyl-pseudo-UTP
25% 5-Aminoallyl-CTP + 75 % CTP/25% 5-Methoxy-UTP + 75% UTP
25% 5-Aminoallyl-CTP + 75% CTP/75% 5-Methoxy-UTP + 25% UTP
25% 5-Bromo-CTP + 75% CTP/25% 5-Methoxy-UTP + 75% UTP
25% 5-Bromo-CTP + 75% CTP/75% 5-Methoxy-UTP + 25% UTP
25% 5-Bromo-CTP + 75% CTP/1-Methyl-pseudo-UTP
25% 5-Carboxy-CTP + 75% CTP/25% 5-Methoxy-UTP + 75% UTP
25% 5-Carboxy-CTP + 75% CTP/75% 5-Methoxy-UTP + 25% UTP
25% 5-Ethyl-CTP + 75% CTP/25% 5-Methoxy-UTP + 75% UTP
25% 5-Ethyl-CTP + 75% CTP/75% 5-Methoxy-UTP + 25% UTP
25% 5-Ethynyl-CTP + 75% CTP/25% 5-Methoxy-UTP + 75% UTP
25% 5-Ethynyl-CTP + 75% CTP/75% 5-Methoxy-UTP + 25% UTP
25% 5-Fluoro-CTP + 75% CTP/25% 5-Methoxy-UTP + 75% UTP
25% 5-Fluoro-CTP + 75% CTP/75% 5-Methoxy-UTP + 25% UTP
25% 5-Formyl-CTP + 75% CTP/25% 5-Methoxy-UTP + 75% UTP
25% 5-Formyl-CTP + 75% CTP/75% 5-Methoxy-UTP + 25% UTP
25% 5-Hydroxymethyl-CTP + 75% CTP/25% 5-Methoxy-UTP + 75% UTP
25% 5-Hydroxymethyl-CTP + 75% CTP/75% 5-Methoxy-UTP + 25% UTP
25% 5-Iodo-CTP + 75% CTP/25% 5-Methoxy-UTP + 75% UTP
25% 5-Iodo-CTP + 75% CTP/75% 5-Methoxy-UTP + 25% UTP
25% 5-Methoxy-CTP + 75% CTP/25% 5-Methoxy-UTP + 75% UTP
25% 5-Methoxy-CTP + 75% CTP/75% 5-Methoxy-UTP + 25% UTP
25% 5-Methyl-CTP + 75% CTP/25% 5-Methoxy-UTP + 75% 1-Methyl-pseudo-UTP
25% 5-Methyl-CTP + 75% CTP/25% 5-Methoxy-UTP + 75% UTP
25% 5-Methyl-CTP + 75% CTP/50% 5-Methoxy-UTP + 50% 1-Methyl-pseudo-UTP
25% 5-Methyl-CTP + 75% CTP/50% 5-Methoxy-UTP + 50% UTP
25% 5-Methyl-CTP + 75% CTP/5-Methoxy-UTP
25% 5-Methyl-CTP + 75% CTP/75% 5-Methoxy-UTP + 25% 1-Methyl-pseudo-UTP TABLE 6-continued Modified Nucleosides and Combinations Thereof 25% 5-Methyl-CTP + 75% CTP/75% 5-Methoxy-UTP + 25% UTP
25% 5-Phenyl-CTP + 75% CTP/25% 5-Methoxy-UTP + 75% UTP
25% 5-Phenyl-CTP + 75% CTP/75% 5-Methoxy-UTP + 25% UTP
25% 5-Trifluoromethyl-CTP + 75% CTP/25% 5-Methoxy-UTP + 75% UTP
25% 5-Trifluoromethyl-CTP + 75% CTP/75% 5-Methoxy-UTP + 25% UTP
25% 5-Trifluoromethyl-CTP + 75% CTP/1-Methyl-pseudo-UTP
25% N4-c-CTP + 75% CTP/25% 5-Methoxy-UTP + 75% UTP
25% N4-Ac-CTP + 75% CTP/75% 5-Methoxy-UTP + 25% UTP
25% N4-Bz-CTP + 75% CTP/25% 5-Methoxy-UTP + 75% UTP
25% N4-Bz-CTP + 75% CTP/75% 5-Methoxy-UTP + 25% UTP
25% N4-Methyl-CTP + 75% CTP/25% 5-Methoxy-UTP + 75% UTP
25% N4-Methyl-CTP + 75% CTP/75% 5-Methoxy-UTP + 25% UTP
25% Pseudo-iso-CTP + 75% CTP/25% 5-Methoxy-UTP + 75% UTP
25% Pseudo-iso-CTP + 75% CTP/75% 5-Methoxy-UTP + 25% UTP
25% 5-Bromo-CTP/75% CTP/Pseudo-UTP
25% 5-methoxy-UTP/25% 5-methyl-CTP/ATP/GTP
25% 5-methoxy-UTP/5-methyl-CTP/ATP/GTP
25% 5-methoxy-UTP/75% 5-methyl-CTP/ATP/GTP
25% 5-methoxy-UTP/CTP/ATP/GTP
25% 5-metoxy-UTP/50% 5-methyl-CTP/ATP/GTP
2-Amino-ATP
2-Thio-CTP
2-thio-pseudouridine TP, ATP, GTP, CTP
2-Thio-pseudo-UTP
2-Thio-UTP
3-Methyl-CTP
3-Methyl-pseudo-UTP
4-Thio-UTP
50% 5-Bromo-CTP + 50% CTP/1-Methyl-pseudo-UTP
50% 5-Hydroxymethyl-CTP + 50% CTP/1-Methyl-pseudo-UTP
50% 5-methoxy-UTP/5-methyl-CTP/ATP/GTP
50% 5-Methyl-CTP + 50% CTP/25% 5-Methoxy-UTP + 75% 1-Methyl-pseudo-UTP
50% 5-Methyl-CTP + 50% CTP/25% 5-Methoxy-UTP + 75% UTP
50% 5-Methyl-CTP + 50% CTP/50% 5-Methoxy-UTP + 50% 1-Methyl-pseudo-UTP
50% 5-Methyl-CTP + 50% CTP/50% 5-Methoxy-UTP + 50% UTP
50% 5-Methyl-CTP + 50% CTP/5-Methoxy-UTP
50% 5-Methyl-CTP + 50% CTP/75% 5-Methoxy-UTP + 25% 1-Methyl-pseudo-UTP
50% 5-Methyl-CTP + 50% CTP/75% 5-Methoxy-UTP + 25% UTP
50% 5-Trifluoromethyl-CTP + 50% CTP/1-Methyl-pseudo-UTP
50% 5-Bromo-CTP/50% CTP/Pseudo-UTP
50% 5-methoxy-UTP/25% 5-methyl-CTP/ATP/GTP
50% 5-methoxy-UTP/50% 5-methyl-CTP/ATP/GTP
50% 5-methoxy-UTP/75% 5-methyl-CTP/ATP/GTP
50% 5-methoxy-UTP/CTP/ATP/GTP
5-Aminoallyl-CTP
5-Aminoallyl-CTP/5-Methoxy-UTP
5-Aminoallyl-UTP
5-Bromo-CTP
5-Bromo-CTP/5-Methoxy-UTP
5-Bromo-CTP/1-Methyl-pseudo-UTP
5-Bromo-CTP/Pseudo-UTP
5-bromocytidine TP, ATP, GTP, UTP
5-Bromo-UTP
5-Carboxy-CTP/5-Methoxy-UTP
5-Ethyl-CTP/5-Methoxy-UTP
5-Ethynyl-CTP/5-Methoxy-UTP
5-Fluoro-CTP/5-Methoxy-UTP
5-Formyl-CTP/5-Methoxy-UTP
5-Hydroxy-methyl-CTP/5-Methoxy-UTP
5-Hydroxymethyl-CTP
5-Hydroxymethyl-CTP/1-Methyl-pseudo-UTP
5-Hydroxymethyl-CTP/5-Methoxy-UTP
5-hydroxymethyl-cytidine TP, ATP, GTP, UTP
5-Iodo-CTP/5-Methoxy-UTP
5-Me-CTP/5-Methoxy-UTP
5-Methoxy carbonyl methyl-UTP
5-Methoxy-CTP/5-Methoxy-UTP
5-methoxy-uridine TP, ATP, GTP, UTP
5-methoxy-UTP
5-Methoxy-UTP
5-Methoxy-UTP/N6-Isopentenyl-ATP
5-methoxy-UTP/25% 5-methyl-CTP/ATP/GTP
5-methoxy-UTP/5-methyl-CTP/ATP/GTP

TABLE 6-continued

Modified Nucleosides and Combinations Thereof 5-methoxy-UTP/75% 5-methyl-CTP/ATP/GTP
5-methoxy-UTP/CTP/ATP/GTP
5-Methyl-2-thio-UTP
5-Methylaminomethyl-UTP
5-Methyl-CTP/5-Methoxy-UTP
5-Methyl-CTP/5-Methoxy-UTP(cap 0)
5-Methyl-CTP/5-Methoxy-UTP(No cap)
5-Methyl-CTP/25% 5-Methoxy-UTP + 75% 1-Methyl-pseudo-UTP
5-Methyl-CTP/25% 5-Methoxy-UTP + 75% UTP
5-Methyl-CTP/50% 5-Methoxy-UTP + 50% 1-Methyl-pseudo-UTP
5-Methyl-CTP/50% 5-Methoxy-UTP + 50% UTP
5-Methyl-CTP/5-Methoxy-UTP/N6—Me-ATP
5-Methyl-CTP/75% 5-Methoxy-UTP + 25% 1-Methyl-pseudo-UTP
5-Methyl-CTP/75% 5-Methoxy-UTP + 25% UTP
5-Phenyl-CTP/5-Methoxy-UTP
5-Trifluoro-methyl-CTP/5-Methoxy-UTP
5-Trifluoromethyl-CTP
5-Trifluoromethyl-CTP/5-Methoxy-UTP
5-Trifluoromethyl-CTP/1-Methyl-pseudo-UTP
5-Trifluoromethyl-CTP/Pseudo-UTP
5-Trifluoromethyl-UTP
5-trifluromethylcytidine TP, ATP, GTP, UTP
75% 5-Aminoallyl-CTP + 25% CTP/25% 5-Methoxy-UTP + 75% UTP
75% 5-Aminoallyl-CTP + 25% CTP/75% 5-Methoxy-UTP + 25% UTP
75% 5-Bromo-CTP + 25% CTP/25% 5-Methoxy-UTP + 75% UTP
75% 5-Bromo-CTP + 25% CTP/75% 5-Methoxy-UTP + 25% UTP
75% 5-Carboxy-CTP + 25% CTP/25% 5-Methoxy-UTP + 75% UTP
75% 5-Carboxy-CTP + 25% CTP/75% 5-Methoxy-UTP + 25% UTP
75% 5-Ethyl-CTP + 25% CTP/25% 5-Methoxy-UTP + 75% UTP
75% 5-Ethyl-CTP + 25% CTP/75% 5-Methoxy-UTP + 25% UTP
75% 5-Ethynyl-CTP + 25% CTP/25% 5-Methoxy-UTP + 75% UTP
75% 5-Ethynyl-CTP + 25% CTP/75% 5-Methoxy-UTP + 25% UTP
75% 5-Fluoro-CTP + 25% CTP/25% 5-Methoxy-UTP + 75% UTP
75% 5-Fluoro-CTP + 25% CTP/75% 5-Methoxy-UTP + 25% UTP
75% 5-Formyl-CTP + 25% CTP/25% 5-Methoxy-UTP + 75% UTP
75% 5-Formyl-CTP + 25% CTP/75% 5-Methoxy-UTP + 25% UTP
75% 5-Hydroxymethyl-CTP + 25% CTP/25% 5-Methoxy-UTP + 75% UTP
75% 5-Hydroxymethyl-CTP + 25% CTP/75% 5-Methoxy-UTP + 25% UTP
75% 5-Iodo-CTP + 25% CTP/25% 5-Methoxy-UTP + 75% UTP
75% 5-Iodo-CTP + 25% CTP/75% 5-Methoxy-UTP + 25% UTP
75% 5-Methoxy-CTP + 25% CTP/25% 5-Methoxy-UTP + 75% UTP
75% 5-Methoxy-CTP + 25% CTP/75% 5-Methoxy-UTP + 25% UTP
75% 5-methoxy-UTP/5-methyl-CTP/ATP/GTP
75% 5-Methyl-CTP + 25% CTP/25% 5-Methoxy-UTP + 75% 1-Methyl-pseudo-UTP
75% 5-Methyl-CTP + 25% CTP/25% 5-Methoxy-UTP + 75% UTP
75% 5-Methyl-CTP + 25% CTP/50% 5-Methoxy-UTP + 50% 1-Methyl-pseudo-UTP
75% 5-Methyl-CTP + 25% CTP/50% 5-Methoxy-UTP + 50% UTP
75% 5-Methyl-CTP + 25% CTP/5-Methoxy-UTP
75% 5-Methyl-CTP + 25% CTP/75% 5-Methoxy-UTP + 25% 1-Methyl-pseudo-UTP
75% 5-Methyl-CTP + 25% CTP/75% 5-Methoxy-UTP + 25% UTP
75% 5-Phenyl-CTP + 25% CTP/25% 5-Methoxy-UTP + 75% UTP
75% 5-Phenyl-CTP + 25% CTP/75% 5-Methoxy-UTP + 25% UTP
75% 5-Trifluoromethyl-CTP + 25% CTP/25% 5-Methoxy-UTP + 75% UTP
75% 5-Trifluoromethyl-CTP + 25% CTP/75% 5-Methoxy-UTP + 25% UTP
75% 5-Trifluoromethyl-CTP + 25% CTP/1-Methyl-pseudo-UTP
75% N4-c-CTP + 25% CTP/25% 5-Methoxy-UTP + 75% UTP
75% N4-Ac-CTP + 25% CTP/75% 5-Methoxy-UTP + 25% UTP
75% N4-Bz-CTP + 25% CTP/25% 5-Methoxy-UTP + 75% UTP
75% N4-Bz-CTP + 25% CTP/75% 5-Methoxy-UTP + 25% UTP
75% N4-Methyl-CTP + 25% CTP/25% 5-Methoxy-UTP + 75% UTP
75% N4-Methyl-CTP + 25% CTP/75% 5-Methoxy-UTP + 25% UTP
75% Pseudo-iso-CTP + 25% CTP/25% 5-Methoxy-UTP + 75% UTP
75% Pseudo-iso-CTP + 25% CTP/75% 5-Methoxy-UTP + 25% UTP
75% 5-Bromo-CTP/25% CTP/1-Methyl-pseudo-UTP
75% 5-Bromo-CTP/25% CTP/Pseudo-UTP
75% 5-methoxy-UTP/25% CTP/5-methyl-CTP/ATP/GTP
75% 5-methoxy-UTP/50% 5-methyl-CTP/ATP/GTP
75% 5-methoxy-UTP/75% 5-methyl-CTP/ATP/GTP
75% 5-methoxy-UTP/CTP/ATP/GTP
8-Aza-ATP
Alpha-thio-CTP

TABLE 6-continued

Modified Nucleosides and Combinations Thereof

CTP/25% 5-Methoxy-UTP + 75% 1-Methyl-pseudo-UTP
CTP/25% 5-Methoxy-UTP + 75% UTP
CTP/50% 5-Methoxy-UTP + 50% 1-Methyl-pseudo-UTP
CTP/50% 5-Methoxy-UTP + 50% UTP
CTP/5-Methoxy-UTP
CTP/5-Methoxy-UTP (cap 0)
CTP/5-Methoxy-UTP(No cap)
CTP/75% 5-Methoxy-UTP + 25% 1-Methyl-pseudo-UTP
CTP/75% 5-Methoxy-UTP + 25% UTP
CTP/UTP(No cap)
N1—Me-GTP
N4-c-CTP
N4Ac-CTP/1-Methyl-pseudo-UTP
N4Ac-CTP/5-Methoxy-UTP
N4-acetyl-cytidine TP, ATP, GTP, UTP
N4-Bz-CTP/5-Methoxy-UTP
N4-methyl CTP
N4-Methyl-CTP/5-Methoxy-UTP
Pseudo-iso-CTP/5-Methoxy-UTP
PseudoU-alpha-thio-TP
pseudouridine TP, ATP, GTP, CTP
pseudo-UTP/5-methyl-CTP/ATP/GTP
UTP-5-oxyacetic acid Me ester
Xanthosine According to the disclosure, polynucleotides of the disclosure may be synthesized to comprise the combinations or single modifications of Table 5 or Table 6.

Where a single modification is listed, the listed nucleoside or nucleotide represents 100 percent of that A, U, G or C nucleotide or nucleoside having been modified. Where percentages are listed, these represent the percentage of that particular A, U, G or C nucleobase triphosphate of the total amount of A, U, G, or C triphosphate present. For example, the combination: 25% 5-Aminoallyl-CTP+75% CTP/25% 5-Methoxy-UTP+75% UTP refers to a polynucleotide where 25% of the cytosine triphosphates are 5-Aminoallyl-CTP while 75% of the cytosines are CTP; whereas 25% of the uracils are 5-methoxy UTP while 75% of the uracils are UTP. Where no modified UTP is listed then the naturally occurring ATP, UTP, GTP and/or CTP is used at 100% of the sites of those nucleotides found in the polynucleotide. In this example all of the GTP and ATP nucleotides are left unmodified.

The mRNAs of the present disclosure, or regions thereof, may be codon optimized. Codon optimization methods are known in the art and may be useful for a variety of purposes: matching codon frequencies in host organisms to ensure proper folding, bias GC content to increase mRNA stability or reduce secondary structures, minimize tandem repeat codons or base runs that may impair gene construction or expression, customize transcriptional and translational control regions, insert or remove proteins trafficking sequences, remove/add post translation modification sites in encoded proteins (e.g., glycosylation sites), add, remove or shuffle protein domains, insert or delete restriction sites, modify ribosome binding sites and mRNA degradation sites, adjust translation rates to allow the various domains of the protein to fold properly, or to reduce or eliminate problem secondary structures within the polynucleotide. Codon optimization tools, algorithms and services are known in the art; non-limiting examples include services from GeneArt (Life Technologies), DNA2.0 (Menlo Park, CA) and/or proprietary methods. In one embodiment, the mRNA sequence is optimized using optimization algorithms, e.g., to optimize expression in mammalian cells or enhance mRNA stability.

In certain embodiments, the present disclosure includes polynucleotides having at least 80%, at least 85%, at least 90%, at least 95%, at least 98%, or at least 99% sequence identity to any of the polynucleotide sequences described herein.

mRNAs of the present disclosure may be produced by means available in the art, including but not limited to in vitro transcription (IVT) and synthetic methods. Enzymatic (IVT), solid-phase, liquid-phase, combined synthetic methods, small region synthesis, and ligation methods may be utilized. In one embodiment, mRNAs are made using IVT enzymatic synthesis methods. Methods of making polynucleotides by IVT are known in the art and are described in International Application PCT/US2013/30062, the contents of which are incorporated herein by reference in their entirety. Accordingly, the present disclosure also includes polynucleotides, e.g., DNA, constructs and vectors that may be used to in vitro transcribe an mRNA described herein.

Non-natural modified nucleobases may be introduced into polynucleotides, e.g., mRNA, during synthesis or post-synthesis. In certain embodiments, modifications may be on internucleoside linkages, purine or pyrimidine bases, or sugar. In particular embodiments, the modification may be introduced at the terminal of a polynucleotide chain or anywhere else in the polynucleotide chain; with chemical synthesis or with a polymerase enzyme. Examples of modified nucleic acids and their synthesis are disclosed in PCT application No. PCT/US2012/058519. Synthesis of modified polynucleotides is also described in Verma and Eckstein, Annual Review of Biochemistry, vol. 76, 99-134 (1998).

Either enzymatic or chemical ligation methods may be used to conjugate polynucleotides or their regions with different functional moieties, such as targeting or delivery agents, fluorescent labels, liquids, nanoparticles, etc. Conjugates of polynucleotides and modified polynucleotides are reviewed in Goodchild, Bioconjugate Chemistry, vol. 1(3), 165-187 (1990).

MicroRNA (miRNA) Binding Sites

Polynucleotides of the disclosure can include regulatory elements, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. In some embodiments, polynucleotides including such regulatory elements are referred to as including "sensor sequences." Non-limiting examples of sensor sequences are described in U.S. Publication 2014/0200261, the contents of which are incorporated herein by reference in their entirety.

In some embodiments, a polynucleotide (e.g., a ribonucleic acid (RNA), e.g., a messenger RNA (mRNA)) of the disclosure comprises an open reading frame (ORF) encoding a polypeptide of interest and further comprises one or more miRNA binding site(s). Inclusion or incorporation of miRNA binding site(s) provides for regulation of polynucleotides of the disclosure, and in turn, of the polypeptides encoded therefrom, based on tissue-specific and/or cell-type specific expression of naturally-occurring miRNAs.

A miRNA, e.g., a natural-occurring miRNA, is a 19-25 nucleotide long noncoding RNA that binds to a polynucleotide and down-regulates gene expression either by reducing stability or by inhibiting translation of the polynucleotide. A miRNA sequence comprises a "seed" region, i.e., a sequence in the region of positions 2-8 of the mature miRNA. A miRNA seed can comprise positions 2-8 or 2-7 of the mature miRNA. In some embodiments, a miRNA seed can comprise 7 nucleotides (e.g., nucleotides 2-8 of the mature miRNA), wherein the seed-complementary site in the corresponding miRNA binding site is flanked by an adenosine (A) opposed to miRNA position 1. In some embodiments, a miRNA seed can comprise 6 nucleotides (e.g., nucleotides 2-7 of the mature miRNA), wherein the seed-complementary site in the corresponding miRNA binding site is flanked by an adenosine (A) opposed to miRNA position 1. See, for example, Grimson A, Farh K K, Johnston W K, Garrett-Engele P, Lim L P, Bartel D P; Mol Cell. 2007 Jul. 6; 27(1):91-105. miRNA profiling of the target cells or tissues can be conducted to determine the presence or absence of miRNA in the cells or tissues. In some embodiments, a polynucleotide (e.g., a ribonucleic acid (RNA), e.g., a messenger RNA (mRNA)) of the disclosure comprises one or more microRNA binding sites, microRNA target sequences, microRNA complementary sequences, or microRNA seed complementary sequences. Such sequences can correspond to, e.g., have complementarity to, any known microRNA such as those taught in US Publication US2005/0261218 and US Publication US2005/0059005, the contents of each of which are incorporated herein by reference in their entirety.

As used herein, the term "microRNA (miRNA or miR) binding site" refers to a sequence within a polynucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polynucleotide of the disclosure comprising an ORF encoding a polypeptide of interest and further comprises one or more miRNA binding site(s). In exemplary embodiments, a 5'UTR and/or 3'UTR of the polynucleotide (e.g., a ribonucleic acid (RNA), e.g., a messenger RNA (mRNA)) comprises the one or more miRNA binding site(s).

A miRNA binding site having sufficient complementarity to a miRNA refers to a degree of complementarity sufficient to facilitate miRNA-mediated regulation of a polynucleotide, e.g., miRNA-mediated translational repression or degradation of the polynucleotide. In exemplary aspects of the disclosure, a miRNA binding site having sufficient complementarity to the miRNA refers to a degree of complementarity sufficient to facilitate miRNA-mediated degradation of the polynucleotide, e.g., miRNA-guided RNA-induced silencing complex (RISC)-mediated cleavage of mRNA. The miRNA binding site can have complementarity to, for example, a 19-25 nucleotide miRNA sequence, to a 19-23 nucleotide miRNA sequence, or to a 22 nucleotide miRNA sequence. A miRNA binding site can be complementary to only a portion of a miRNA, e.g., to a portion less than 1, 2, 3, or 4 nucleotides of the full length of a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with a miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with an miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In other embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polynucleotide comprising the miRNA binding site. In other embodiments, the miRNA binding site has imperfect complementarity so that a RISC complex comprising the miRNA induces instability in the polynucleotide comprising the miRNA binding site. In another embodiment, the miRNA binding site has imperfect complementarity so that a RISC complex comprising the miRNA represses transcription of the polynucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polynucleotide of the disclosure, the polynucleotide can be targeted for degradation or reduced translation, provided the miRNA in question is available. This can reduce off-target effects upon delivery of the polynucleotide. For example, if a polynucleotide of the disclosure is not intended to be delivered to a tissue or cell but ends up is said tissue or cell, then a miRNA abundant in the tissue or cell can inhibit the expression of the gene of interest if one or multiple binding sites of the miRNA are engineered into the 5'UTR and/or 3'UTR of the polynucleotide.

Conversely, miRNA binding sites can be removed from polynucleotide sequences in which they naturally occur in order to increase protein expression in specific tissues. For example, a binding site for a specific miRNA can be removed from a polynucleotide to improve protein expression in tissues or cells containing the miRNA.

In one embodiment, a polynucleotide of the disclosure can include at least one miRNA-binding site in the 5'UTR and/or 3'UTR in order to regulate cytotoxic or cytoprotective mRNA therapeutics to specific cells such as, but not limited to, normal and/or cancerous cells. In another embodiment, a polynucleotide of the disclosure can include two, three, four, five, six, seven, eight, nine, ten, or more miRNA-binding sites in the 5'-UTR and/or 3'-UTR in order to regulate cytotoxic or cytoprotective mRNA therapeutics to specific cells such as, but not limited to, normal and/or cancerous cells.

Regulation of expression in multiple tissues can be accomplished through introduction or removal of one or more miRNA binding sites, e.g., one or more distinct miRNA binding sites. The decision whether to remove or insert a miRNA binding site can be made based on miRNA expression patterns and/or their profilings in tissues and/or cells in development and/or disease. Identification of miRNAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

miRNAs and miRNA binding sites can correspond to any known sequence, including non-limiting examples described in U.S. Publication Nos. 2014/0200261, 2005/0261218, and 2005/0059005, each of which are incorporated herein by reference in their entirety. Exemplary representative microRNAs and microRNA binding sites are shown in Table 7.

TABLE 7

Representative microRNAs and microRNA binding sites

| SEQ ID NO. | Description | Sequence |
|---|---|---|
| 519 | miR-142 | GACAGUGCAGUCACCCAUAAAGUAGAAAGCAC UACUAACAGCACUGGAGGGUGUAGUGUUUCC UACUUUAUGGAUGAGUGUACUGUG |
| 520 | miR-142-3p | UGUAGUGUUUCCUACUUUAUGGA |
| 521 | miR-142-3p binding site | UCCAUAAAGUAGGAAACACUACA |
| 522 | miR-142-5p | CAUAAAGUAGAAAGCACUACU |
| 523 | miR-142-5p binding site | AGUAGUGCUUUCUACUUUAUG |
| 524 | miR-122 | CCUUAGCAGAGCUGUGGAGUGUGACAAUGGU GUUUGUGUCUAAACUAUCAAACGCCAUUAUCA CACUAAAUAGCUACUGCUAGGC |
| 525 | miR-122-3p | AACGCCAUUAUCACACUAAAUA |
| 526 | miR-122-3p binding site | UAUUUAGUGUGAUAAUGGCGUU |
| 527 | miR-122-5p | UGGAGUGUGACAAUGGUGUUUG |
| 528 | miR-122-5p binding site | CAAACACCAUUGUCACACUCCA |

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, miRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific miRNAs are involved in immunogenicity, autoimmunity, the immune response to infection, inflammation, as well as unwanted immune response after gene therapy and tissue/organ transplantation. Immune cell specific miRNAs also regulate many aspects of development, proliferation, differentiation and apoptosis of hematopoietic cells (immune cells). For example, miR-142 and miR-146 are exclusively expressed in immune cells, particularly abundant in myeloid dendritic cells. It has been demonstrated that the immune response to a polynucleotide can be shut-off by adding miR-142 binding sites to the 3'-UTR of the polynucleotide, enabling more stable gene transfer in tissues and cells. miR-142 efficiently degrades exogenous polynucleotides in antigen presenting cells and suppresses cytotoxic elimination of transduced cells (e.g., Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing a miR-142 binding site into the 5'UTR and/or 3'UTR of a polynucleotide of the disclosure can selectively repress gene expression in antigen presenting cells through miR-142 mediated degradation, limiting antigen presentation in antigen presenting cells (e.g., dendritic cells) and thereby preventing antigen-mediated immune response after the delivery of the polynucleotide. The polynucleotide is then stably expressed in target tissues or cells without triggering cytotoxic elimination.

In one embodiment, binding sites for miRNAs that are known to be expressed in immune cells, in particular, antigen presenting cells, can be engineered into a polynucleotide of the disclosure to suppress the expression of the polynucleotide in antigen presenting cells through miRNA mediated RNA degradation, subduing the antigen-mediated immune response. Expression of the polynucleotide is maintained in non-immune cells where the immune cell specific miRNAs are not expressed. For example, in some embodiments, to prevent an immunogenic reaction against a liver specific protein, any miR-122 binding site can be removed and a miR-142 (and/or mirR-146) binding site can be engineered into the 5'UTR and/or 3'UTR of a polynucleotide of the disclosure.

To further drive the selective degradation and suppression in APCs and macrophage, a polynucleotide of the disclosure can include a further negative regulatory element in the 5'UTR and/or 3'UTR, either alone or in combination with miR-142 and/or miR-146 binding sites. As a non-limiting example, the further negative regulatory element is a Constitutive Decay Element (CDE).

In one embodiment, the binding sites of embryonic stem cell specific miRNAs can be included in or removed from the 3'UTR of a polynucleotide of the disclosure to modulate the development and/or differentiation of embryonic stem cells, to inhibit the senescence of stem cells in a degenerative condition (e.g. degenerative diseases), or to stimulate the senescence and apoptosis of stem cells in a disease condition (e.g. cancer stem cells).

Many miRNA expression studies are conducted to profile the differential expression of miRNAs in various cancer cells/tissues and other diseases. Some miRNAs are abnormally over-expressed in certain cancer cells and others are under-expressed.

As a non-limiting example, miRNA binding sites for miRNAs that are over-expressed in certain cancer and/or tumor cells can be removed from the 3'UTR of a polynucleotide of the disclosure, restoring the expression suppressed by the over-expressed miRNAs in cancer cells, thus ameliorating the corresponsive biological function, for instance, transcription stimulation and/or repression, cell cycle arrest, apoptosis and cell death. Normal cells and tissues, wherein miRNAs expression is not up-regulated, will remain unaffected.

miRNA can also regulate complex biological processes such as angiogenesis (e.g., miR-132) (Anand and Cheresh Curr Opin Hematol 2011 18:171-176). In the polynucleotides of the disclosure, miRNA binding sites that are involved in such processes can be removed or introduced, in order to tailor the expression of the polynucleotides to biologically relevant cell types or relevant biological processes. In this context, the polynucleotides of the disclosure are defined as auxotrophic polynucleotides.

In some embodiments, the therapeutic window and/or differential expression (e.g., tissue-specific expression) of a polypeptide of the disclosure may be altered by incorporation of a miRNA binding site into an mRNA encoding the polypeptide. In one example, an mRNA may include one or more miRNA binding sites that are bound by miRNAs that have higher expression in one tissue type as compared to another. In another example, an mRNA may include one or more miRNA binding sites that are bound by miRNAs that have lower expression in a cancer cell as compared to a non-cancerous cell of the same tissue of origin. When present in a cancer cell that expresses low levels of such an miRNA, the polypeptide encoded by the mRNA typically will show increased expression.

Liver cancer cells (e.g., hepatocellular carcinoma cells) typically express low levels of miR-122 as compared to normal liver cells. Therefore, an mRNA encoding a polypeptide that includes at least one miR-122 binding site (e.g., in the 3'-UTR of the mRNA) will typically express comparatively low levels of the polypeptide in normal liver cells and comparatively high levels of the polypeptide in liver cancer cells.

In some embodiments, a miRNA binding site is inserted in the polynucleotide of the disclosure in any position of the polynucleotide (e.g., the 5'UTR and/or 3'UTR). In some embodiments, the 5'UTR comprises a miRNA binding site. In some embodiments, the 3'UTR comprises a miRNA binding site. In some embodiments, the 5'UTR and the 3'UTR comprise a miRNA binding site. The insertion site in the polynucleotide can be anywhere in the polynucleotide as long as the insertion of the miRNA binding site in the polynucleotide does not interfere with the translation of a functional polypeptide in the absence of the corresponding miRNA; and in the presence of the miRNA, the insertion of the miRNA binding site in the polynucleotide and the binding of the miRNA binding site to the corresponding miRNA are capable of degrading the polynucleotide or preventing the translation of the polynucleotide.

miRNA gene regulation can be influenced by the sequence surrounding the miRNA such as, but not limited to, the species of the surrounding sequence, the type of sequence (e.g., heterologous, homologous, exogenous, endogenous, or artificial), regulatory elements in the surrounding sequence and/or structural elements in the surrounding sequence. The miRNA can be influenced by the 5'UTR and/or 3'UTR. As a non-limiting example, a non-human 3'UTR can increase the regulatory effect of the miRNA sequence on the expression of a polypeptide of interest compared to a human 3'UTR of the same sequence type.

In one embodiment, other regulatory elements and/or structural elements of the 5'UTR can influence miRNA mediated gene regulation. One example of a regulatory element and/or structural element is a structured IRES (Internal Ribosome Entry Site) in the 5'UTR, which is necessary for the binding of translational elongation factors to initiate protein translation. EIF4A2 binding to this secondarily structured element in the 5'-UTR is necessary for miRNA mediated gene expression (Meijer H A et al., Science, 2013, 340, 82-85, incorporated herein by reference in its entirety). The polynucleotides of the disclosure can further include this structured 5'UTR in order to enhance microRNA mediated gene regulation.

At least one miRNA binding site can be engineered into the 3'UTR of a polynucleotide of the disclosure. In this context, at least two, at least three, at least four, at least five, at least six, at least seven, at least eight, at least nine, at least ten, or more miRNA binding sites can be engineered into a 3'UTR of a polynucleotide of the disclosure. For example, 1 to 10, 1 to 9, 1 to 8, 1 to 7, 1 to 6, 1 to 5, 1 to 4, 1 to 3, 2, or 1 miRNA binding sites can be engineered into the 3'UTR of a polynucleotide of the disclosure. In one embodiment, miRNA binding sites incorporated into a polynucleotide of the disclosure can be the same or can be different miRNA sites. A combination of different miRNA binding sites incorporated into a polynucleotide of the disclosure can include combinations in which more than one copy of any of the different miRNA sites are incorporated. In another embodiment, miRNA binding sites incorporated into a polynucleotide of the disclosure can target the same or different tissues in the body. As a non-limiting example, through the introduction of tissue-, cell-type-, or disease-specific miRNA binding sites in the 3'-UTR of a polynucleotide of the disclosure, the degree of expression in specific cell types (e.g., hepatocytes, myeloid cells, endothelial cells, cancer cells, etc.) can be reduced.

In one embodiment, a miRNA binding site can be engineered near the 5' terminus of the 3'UTR, about halfway between the 5' terminus and 3' terminus of the 3'UTR and/or near the 3' terminus of the 3'UTR in a polynucleotide of the disclosure. As a non-limiting example, a miRNA binding site can be engineered near the 5' terminus of the 3'UTR and about halfway between the 5' terminus and 3' terminus of the 3'UTR. As another non-limiting example, a miRNA binding site can be engineered near the 3' terminus of the 3'UTR and about halfway between the 5' terminus and 3' terminus of the 3'UTR. As yet another non-limiting example, a miRNA binding site can be engineered near the 5' terminus of the 3'UTR and near the 3' terminus of the 3'UTR.

In another embodiment, a 3'UTR can comprise 1, 2, 3, 4, 5, 6, 7, 8, 9, or 10 miRNA binding sites. The miRNA binding sites can be complementary to a miRNA, miRNA seed sequence, and/or miRNA sequences flanking the seed sequence.

In one embodiment, a polynucleotide of the disclosure can be engineered to include more than one miRNA site expressed in different tissues or different cell types of a subject. As a non-limiting example, a polynucleotide of the disclosure can be engineered to include miR-192 and miR-122 to regulate expression of the polynucleotide in the liver and kidneys of a subject. In another embodiment, a polynucleotide of the disclosure can be engineered to include more than one miRNA site for the same tissue.

In some embodiments, the therapeutic window and or differential expression associated with the polypeptide encoded by a polynucleotide of the disclosure can be altered with a miRNA binding site. For example, a polynucleotide encoding a polypeptide that provides a death signal can be designed to be more highly expressed in cancer cells by virtue of the miRNA signature of those cells. Where a cancer cell expresses a lower level of a particular miRNA, the polynucleotide encoding the binding site for that miRNA (or miRNAs) would be more highly expressed. Hence, the polypeptide that provides a death signal triggers or induces cell death in the cancer cell. Neighboring noncancer cells, harboring a higher expression of the same miRNA would be less affected by the encoded death signal as the polynucleotide would be expressed at a lower level due to the effects of the miRNA binding to the binding site or "sensor" encoded in the 3'UTR. Conversely, cell survival or cytoprotective signals can be delivered to tissues containing cancer and non-cancerous cells where a miRNA has a higher expression in the cancer cells—the result being a lower survival signal to the cancer cell and a larger survival signal to the normal cell. Multiple polynucleotides can be designed and administered having different signals based on the use of miRNA binding sites as described herein.

In some embodiments, the expression of a polynucleotide of the disclosure can be controlled by incorporating at least one sensor sequence in the polynucleotide and formulating the polynucleotide for administration. As a non-limiting example, a polynucleotide of the disclosure can be targeted to a tissue or cell by incorporating a miRNA binding site and formulating the polynucleotide in a lipid nanoparticle comprising a cationic lipid, including any of the lipids described herein.

A polynucleotide of the disclosure can be engineered for more targeted expression in specific tissues, cell types, or biological conditions based on the expression patterns of miRNAs in the different tissues, cell types, or biological conditions. Through introduction of tissue-specific miRNA binding sites, a polynucleotide of the disclosure can be designed for optimal protein expression in a tissue or cell, or in the context of a biological condition.

In some embodiments, a polynucleotide of the disclosure can be designed to incorporate miRNA binding sites that either have 100% identity to known miRNA seed sequences or have less than 100% identity to miRNA seed sequences. In some embodiments, a polynucleotide of the disclosure can be designed to incorporate miRNA binding sites that have at least: 60%, 65%, 70%, 75%, 80%, 85%, 90%, 95%, 96%, 97%, 98%, or 99% identity to known miRNA seed sequences. The miRNA seed sequence can be partially mutated to decrease miRNA binding affinity and as such result in reduced downmodulation of the polynucleotide. In essence, the degree of match or mis-match between the miRNA binding site and the miRNA seed can act as a rheostat to more finely tune the ability of the miRNA to modulate protein expression. In addition, mutation in the non-seed region of a miRNA binding site can also impact the ability of a miRNA to modulate protein expression.

In one embodiment, a miRNA sequence can be incorporated into the loop of a stem loop.

In another embodiment, a miRNA seed sequence can be incorporated in the loop of a stem loop and a miRNA binding site can be incorporated into the 5' or 3' stem of the stem loop.

In one embodiment, a translation enhancer element (TEE) can be incorporated on the 5'end of the stem of a stem loop and a miRNA seed can be incorporated into the stem of the stem loop. In another embodiment, a TEE can be incorporated on the 5' end of the stem of a stem loop, a miRNA seed can be incorporated into the stem of the stem loop and a miRNA binding site can be incorporated into the 3' end of the stem or the sequence after the stem loop. The miRNA seed and the miRNA binding site can be for the same and/or different miRNA sequences.

In one embodiment, the incorporation of a miRNA sequence and/or a TEE sequence changes the shape of the stem loop region which can increase and/or decrease translation. (see e.g, Kedde et al., "A Pumilio-induced RNA structure switch in p27-3'UTR controls miR-221 and miR-22 accessibility." Nature Cell Biology. 2010, incorporated herein by reference in its entirety).

In one embodiment, the 5'-UTR of a polynucleotide of the disclosure can comprise at least one miRNA sequence. The miRNA sequence can be, but is not limited to, a 19 or 22 nucleotide sequence and/or a miRNA sequence without the seed.

In one embodiment the miRNA sequence in the 5'UTR can be used to stabilize a polynucleotide of the disclosure described herein.

In another embodiment, a miRNA sequence in the 5'UTR of a polynucleotide of the disclosure can be used to decrease the accessibility of the site of translation initiation such as, but not limited to a start codon. See, e.g., Matsuda et al., PLoS One. 2010 11(5):e15057; incorporated herein by reference in its entirety, which used antisense locked nucleic acid (LNA) oligonucleotides and exon-junction complexes (EJCs) around a start codon (−4 to +37 where the A of the AUG codons is +1) in order to decrease the accessibility to the first start codon (AUG). Matsuda showed that altering the sequence around the start codon with an LNA or EJC affected the efficiency, length and structural stability of a polynucleotide. A polynucleotide of the disclosure can comprise a miRNA sequence, instead of the LNA or EJC sequence described by Matsuda et al, near the site of translation initiation in order to decrease the accessibility to the site of translation initiation. The site of translation initiation can be prior to, after or within the miRNA sequence. As a non-limiting example, the site of translation initiation can be located within a miRNA sequence such as a seed sequence or binding site. As another non-limiting example, the site of translation initiation can be located within a miR-122 sequence such as the seed sequence or the mir-122 binding site.

In some embodiments, a polynucleotide of the disclosure can include at least one miRNA in order to dampen the antigen presentation by antigen presenting cells. The miRNA can be the complete miRNA sequence, the miRNA seed sequence, the miRNA sequence without the seed, or a combination thereof. As a non-limiting example, a miRNA incorporated into a polynucleotide of the disclosure can be specific to the hematopoietic system. As another non-limiting example, a miRNA incorporated into a polynucleotide of the disclosure to dampen antigen presentation is miR-142-3p.

In some embodiments, a polynucleotide of the disclosure can include at least one miRNA in order to dampen expression of the encoded polypeptide in a tissue or cell of interest. As a non-limiting example, a polynucleotide of the disclosure can include at least one miR-122 binding site in order to dampen expression of an encoded polypeptide of interest in the liver. As another non-limiting example a polynucleotide of the disclosure can include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In some embodiments, a polynucleotide of the disclosure can comprise at least one miRNA binding site in the 3'UTR in order to selectively degrade mRNA therapeutics in the immune cells to subdue unwanted immunogenic reactions caused by therapeutic delivery. As a non-limiting example, the miRNA binding site can make a polynucleotide of the disclosure more unstable in antigen presenting cells. Non-limiting examples of these miRNAs include mir-142-5p, mir-142-3p, mir-146a-5p, and mir-146-3p.

In one embodiment, a polynucleotide of the disclosure comprises at least one miRNA sequence in a region of the polynucleotide that can interact with a RNA binding protein.

In some embodiments, the polynucleotide of the disclosure (e.g., a RNA, e.g., a mRNA) comprising (i) a sequence-optimized nucleotide sequence (e.g., an ORF) and (ii) a miRNA binding site (e.g., a miRNA binding site that binds to miR-142).

In some embodiments, the polynucleotide of the disclosure comprises a uracil-modified sequence encoding a polypeptide disclosed herein and a miRNA binding site disclosed herein, e.g., a miRNA binding site that binds to miR-142 or miR-122. In some embodiments, the uracil-modified sequence encoding a polypeptide comprises at least one chemically modified nucleobase, e.g., 5-methoxyuracil. In some embodiments, at least 95% of a type of nucleobase (e.g., uracil) in a uracil-modified sequence encoding a polypeptide of the disclosure are modified nucleobases. In some embodiments, at least 95% of uricil in a uracil-modified sequence encoding a polypeptide is 5-methoxyuridine. In some embodiments, the polynucleotide comprising a nucleotide sequence encoding a polypeptide disclosed herein and a miRNA binding site is formulated with a delivery agent, e.g., a compound having the Formula (I), e.g., any of Compounds 1-147.

Preparation of High Purity RNA

In order to enhance the purity of synthetically produced RNA, modified in vitro transcription (IVT) processes which produce RNA preparations having vastly different properties from RNA produced using a traditional IVT process may be used. The RNA preparations produced according to these methods have properties that enable the production of qualitatively and quantitatively superior compositions. Even when coupled with extensive purification processes, RNA produced using traditional IVT methods is qualitatively and quantitatively distinct from the RNA preparations produced by the modified IVT processes. For instance, the purified RNA preparations are less immunogenic in comparison to RNA preparations made using traditional IVT. Additionally, increased protein expression levels with higher purity are produced from the purified RNA preparations.

Traditional IVT reactions are performed by incubating a DNA template with an RNA polymerase and equimolar quantities of nucleotide triphosphates, including GTP, ATP, CTP, and UTP in a transcription buffer. An RNA transcript having a 5' terminal guanosine triphosphate is produced from this reaction. These reactions also result in the production of a number of impurities such as double stranded and single stranded RNAs which are immunostimulatory and may have an additive impact. The purity methods described herein prevent formation of reverse complements and thus prevent the innate immune recognition of both species. In some embodiments the modified IVT methods result in the production of RNA having significantly reduced T cell activity than an RNA preparation made using prior art methods with equimolar NTPs. The prior art attempts to remove these undesirable components using a series of subsequent purification steps. Such purification methods are undesirable because they involve additional time and resources and also result in the incorporation of residual organic solvents in the final product, which is undesirable for a pharmaceutical product. It is labor and capital intensive to scale up processes like reverse phase chromatography (RP): utilizing for instance explosion proof facilities, HPLC columns and purification systems rated for high pressure, high temperature, flammable solvents etc. The scale and throughput for large scale manufacture are limited by these factors. Subsequent purification is also required to remove alkylammonium ion pair utilized in RP process. In contrast the methods described herein even enhance currently utilized methods (eg RP). Lower impurity load leads to higher purification recovery of full length RNA devoid of cytokine inducing contaminants eg. higher quality of materials at the outset.

The modified IVT methods involve the manipulation of one or more of the reaction parameters in the IVT reaction to produce a RNA preparation of highly functional RNA without one or more of the undesirable contaminants produced using the prior art processes. One parameter in the IVT reaction that may be manipulated is the relative amount of a nucleotide or nucleotide analog in comparison to one or more other nucleotides or nucleotide analogs in the reaction mixture (e.g., disparate nucleotide amounts or concentration). For instance, the IVT reaction may include an excess of a nucleotides, e.g., nucleotide monophosphate, nucleotide diphosphate or nucleotide triphosphate and/or an excess of nucleotide analogs and/or nucleoside analogs. The methods produce a high yield product which is significantly more pure than products produced by traditional IVT methods.

Nucleotide analogs are compounds that have the general structure of a nucleotide or are structurally similar to a nucleotide or portion thereof. In particular, nucleotide analogs are nucleotides which contain, for example, an analogue of the nucleic acid portion, sugar portion and/or phosphate groups of the nucleotide. Nucleotides include, for instance, nucleotide monophosphates, nucleotide diphosphates, and nucleotide triphosphates. A nucleotide analog, as used herein is structurally similar to a nucleotide or portion thereof but does not have the typical nucleotide structure (nucleobase-ribose-phosphate). Nucleoside analogs are compounds that have the general structure of a nucleoside or are structurally similar to a nucleoside or portion thereof. In particular, nucleoside analogs are nucleosides which contain, for example, an analogue of the nucleic acid and/or sugar portion of the nucleoside.

The nucleotide analogs useful in the methods are structurally similar to nucleotides or portions thereof but, for example, are not polymerizable by T7. Nucleotide/nucleoside analogs as used herein (including C, T, A, U, G, dC, dT, dA, dU, or dG analogs) include for instance, antiviral nucleotide analogs, phosphate analogs (soluble or immobilized, hydrolyzable or non-hydrolyzable), dinucleotide, trinucleotide, tetranucleotide, e.g., a cap analog, or a precursor/substrate for enzymatic capping (vaccinia, or ligase), a nucleotide labelled with a functional group to facilitate ligation/conjugation of cap or 5' moiety (IRES), a nucleotide labelled with a 5' PO4 to facilitate ligation of cap or 5' moiety, or a nucleotide labelled with a functional group/protecting group that can be chemically or enzymatically cleavable. Antiviral nucleotide/nucleoside analogs include but are not limited to Ganciclovir, Entecavir, Telbivudine, Vidarabine and Cidofovir.

The IVT reaction typically includes the following: an RNA polymerase, e.g., a T7 RNA polymerase at a final concentration of, e.g., 1000-12000 U/mL, e.g., 7000 U/mL; the DNA template at a final concentration of, e.g., 10-70 nM, e.g., 40 nM; nucleotides (NTPs) at a final concentration of e.g., 0.5-10 mM, e.g., 7.5 mM each; magnesium at a final concentration of, e.g., 12-60 mM, e.g., magnesium acetate at 40 mM; a buffer such as, e.g., HEPES or Tris at a pH of, e.g., 7-8.5, e.g. 40 mM Tris HCl, pH 8. In some embodiments 5 mM dithiothreitol (DTT) and/or 1 mM spermidine may be included. In some embodiments, an RNase inhibitor is included in the IVT reaction to ensure no RNase induced degradation during the transcription reaction. For example, murine RNase inhibitor can be utilized at a final concentration of 1000 U/mL. In some embodiments a pyrophosphatase is included in the IVT reaction to cleave the inorganic pyrophosphate generated following each nucleotide incorporation into two units of inorganic phosphate. This ensures that magnesium remains in solution and does not precipitate as magnesium pyrophosphate. For example, an E. coli inorganic pyrophosphatase can be utilized at a final concentration of 1 U/mL.

Similar to traditional methods, the modified method may also be produced by forming a reaction mixture comprising a DNA template, and one or more NTPs such as ATP, CTP, UTP, GTP (or corresponding analog of aforementioned components) and a buffer. The reaction is then incubated under conditions such that the RNA is transcribed. However, the modified methods utilize the presence of an excess amount of one or more nucleotides and/or nucleotide analogs that can have significant impact on the end product. These methods involve a modification in the amount (e.g., molar amount or quantity) of nucleotides and/or nucleotide analogs in the reaction mixture. In some aspects, one or more nucleotides and/or one or more nucleotide analogs may be added in excess to the reaction mixture. An excess of nucleotides and/or nucleotide analogs is any amount greater than the amount of one or more of the other nucleotides such as NTPs in the reaction mixture. For instance, an excess of a nucleotide and/or nucleotide analog may be a greater amount than the amount of each or at least one of the other individual NTPs in the reaction mixture or may refer to an amount greater than equimolar amounts of the other NTPs.

In the embodiment when the nucleotide and/or nucleotide analog that is included in the reaction mixture is an NTP, the NTP may be present in a higher concentration than all three of the other NTPs included in the reaction mixture. The other three NTPs may be in an equimolar concentration to one another. Alternatively one or more of the three other NTPs may be in a different concentration than one or more of the other NTPs.

Thus, in some embodiments the IVT reaction may include an equimolar amount of nucleotide triphosphate relative to at least one of the other nucleotide triphosphates.

In some embodiments the RNA is produced by a process or is preparable by a process comprising
(a) forming a reaction mixture comprising a DNA template and NTPs including adenosine triphosphate (ATP), cytidine triphosphate (CTP), uridine triphosphate (UTP), guanosine triphosphate (GTP) and optionally guanosine diphosphate (GDP), and (eg. buffer containing T7 co-factor eg. magnesium).
(b) incubating the reaction mixture under conditions such that the RNA is transcribed,
wherein the concentration of at least one of GTP, CTP, ATP, and UTP is at least 2× greater than the concentration of any one or more of ATP, CTP or UTP or the reaction further comprises a nucleotide analog and wherein the concentration of the nucleotide analog is at least 2× greater than the concentration of any one or more of ATP, CTP or UTP.

In some embodiments the ratio of concentration of GTP to the concentration of any one ATP, CTP or UTP is at least 2:1, at least 3:1, at least 4:1, at least 5:1 or at least 6:1. The ratio of concentration of GTP to concentration of ATP, CTP and UTP is, in some embodiments 2:1, 4:1 and 4:1, respectively. In other embodiments the ratio of concentration of GTP to concentration of ATP, CTP and UTP is 3:1, 6:1 and 6:1, respectively. The reaction mixture may comprise GTP and GDP and wherein the ratio of concentration of GTP plus GDP to the concentration of any one of ATP, CTP or UTP is at least 2:1, at least 3:1, at least 4:1, at least 5:1 or at least 6:1 In some embodiments the ratio of concentration of GTP plus GDP to concentration of ATP, CTP and UTP is 3:1, 6:1 and 6:1, respectively.

In some embodiments the method involves incubating the reaction mixture under conditions such that the RNA is transcribed, wherein the effective concentration of phosphate in the reaction is at least 150 mM phosphate, at least 160 mM, at least 170 mM, at least 180 mM, at least 190 mM, at least 200 mM, at least 210 mM or at least 220 mM. The effective concentration of phosphate in the reaction may be 180 mM. The effective concentration of phosphate in the reaction in some embodiments is 195 mM. In other embodiments the effective concentration of phosphate in the reaction is 225 mM.

In other embodiments the RNA is produced by a process or is preparable by a process comprising wherein a buffer magnesium-containing buffer is used when forming the reaction mixture comprising a DNA template and ATP, CTP, UTP, GTP. In some embodiments the magnesium-containing buffer comprises Mg2+ and wherein the molar ratio of concentration of ATP plus CTP plus UTP pus GTP to concentration of Mg2+ is at least 1.0, at least 1.25, at least 1.5, at least 1.75, at least 1.85, at least 3 or higher. The molar ratio of concentration of ATP plus CTP plus UTP pus GTP to concentration of Mg2+ may be 1.5. The molar ratio of concentration of ATP plus CTP plus UTP pus GTP to concentration of Mg2+ in some embodiments is 1.88. The molar ratio of concentration of ATP plus CTP plus UTP pus GTP to concentration of Mg2+ in some embodiments is 3.

In some embodiments the composition is produced by a process which does not comprise an dsRNase (e.g., RNaseIII) treatment step. In other embodiments the composition is produced by a process which does not comprise a reverse phase (RP) chromatography purification step. In yet other embodiments the composition is produced by a process which does not comprise a high-performance liquid chromatography (HPLC) purification step.

In some embodiments the ratio of concentration of GTP to the concentration of any one ATP, CTP or UTP is at least 2:1, at least 3:1, at least 4:1, at least 5:1 or at least 6:1 to produce the RNA.

The purity of the products may be assessed using known analytical methods and assays. For instance, the amount of reverse complement transcription product or cytokine-inducing RNA contaminant may be determined by high-performance liquid chromatography (such as reverse-phase chromatography, size-exclusion chromatography), Bioanalyzer chip-based electrophoresis system, ELISA, flow cytometry, acrylamide gel, a reconstitution or surrogate type assay. The assays may be performed with or without nuclease treatment (P1, RNase III, RNase H etc.) of the RNA preparation. Electrophoretic/chromatographic/mass spec analysis of nuclease digestion products may also be performed.

In some embodiments the purified RNA preparations comprise contaminant transcripts that have a length less than a full length transcript, such as for instance at least 100, 200, 300, 400, 500, 600, 700, 800, or 900 nucleotides less than the full length. Contaminant transcripts can include reverse or forward transcription products (transcripts) that have a length less than a full length transcript, such as for instance at least 100, 200, 300, 400, 500, 600, 700, 800, or 900 nucleotides less than the full length. Exemplary forward transcripts include, for instance, abortive transcripts. In certain embodiments the composition comprises a tri-phosphate poly-U reverse complement of less than 30 nucleotides. In some embodiments the composition comprises a tri-phosphate poly-U reverse complement of any length hybridized to a full length transcript. In other embodiments the composition comprises a single stranded tri-phosphate forward transcript. In other embodiments the composition comprises a single stranded RNA having a terminal tri-phosphate-G. In other embodiments the composition comprises single or double stranded RNA of less than 12 nucleotides or base pairs (including forward or reverse complement transcripts). In any of these embodiments the composition may include less than 50%, 45%, 40%, 35%, 30%, 25%, 20%, 15%, 10%, 9%, 8%, 7%, 6%, 5%, 4%, 3%, 2%, 1%, or 0.5% of any one of or combination of these less than full length transcripts.

Delivery Agents a. Lipid Compound

The present disclosure provides pharmaceutical compositions with advantageous properties. The lipid compositions described herein may be advantageously used in lipid nanoparticle compositions for the delivery of therapeutic and/or prophylactic agents, e.g., mRNAs, to mammalian cells or organs. For example, the lipids described herein have little or no immunogenicity. For example, the lipid compounds disclosed herein have a lower immunogenicity as compared to a reference lipid (e.g., MC3, KC2, or DLinDMA). For example, a formulation comprising a lipid disclosed herein and a therapeutic or prophylactic agent, e.g., mRNA, has an increased therapeutic index as compared to a corresponding formulation which comprises a reference lipid (e.g., MC3, KC2, or DLinDMA) and the same therapeutic or prophylactic agent.

In certain embodiments, the present application provides pharmaceutical compositions comprising:
(a) a polynucleotide comprising a nucleotide sequence encoding a polypeptide; and
(b) a delivery agent.

Lipid Nanoparticle Formulations

In some embodiments, nucleic acids of the invention (e.g. mRNA) are formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the invention can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entirety.

Nucleic acids of the present disclosure (e.g. mRNA) are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises a molar ratio of 20-60% ionizable cationic lipid. For example, the lipid nanoparticle may comprise a molar ratio of 20-50%, 20-40%, 20-30%, 30-60%, 30-50%, 30-40%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol. For example, the lipid nanoparticle may comprise a molar ratio of 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% sterol. In some embodiments, the lipid nanoparticle comprises a molar ratio of 25%, 30%, 35%, 40%, 45%, 50%, or 55% sterol.

In some embodiments, the lipid nanoparticle comprises a molar ratio of 0.5-15% PEG-modified lipid. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid, 5-25% non-cationic lipid, 25-55% sterol, and 0.5-15% PEG-modified lipid.

Ionizable Lipids

In some aspects, the ionizable lipids of the present disclosure may be one or more of compounds of Formula (I):

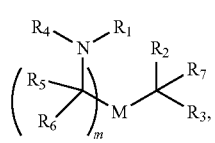

(I)

or their N-oxides, or salts or isomers thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of hydrogen, a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —N(R)S(O)$_2$R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, each $R_6$ is independently selected from the group consisting of $C_{1-3}$ alkyl, $C_{2-3}$ alkenyl, and H;

M and M' are independently selected from —C(O)O—, —OC(O)—, —OC(O)-M"-C(O)O—, —C(O)N(R')—, and H;

—N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group, in which M" is a bond, $C_{1-13}$ alkyl or $C_{2-13}$ alkenyl;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-15}$ alkyl and $C_{3-15}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and wherein when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In certain embodiments, a subset of compounds of Formula (I) includes those of Formula (IA):

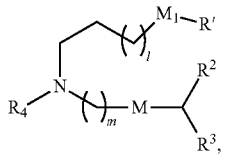

(IA)

or its N-oxide, or a salt or isomer thereof, wherein 1 is selected from 1, 2, 3, 4, and 5; m is selected from 5, 6, 7, 8, and 9; $M_1$ is a bond or M'; $R_4$ is hydrogen, unsubstituted $C_{1-3}$ alkyl, or —$(CH_2)_nQ$, in which Q is
OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, m is 5, 7, or 9. For example, Q is OH, —NHC(S)N(R)$_2$, or —NHC(O)N(R)$_2$. For example, Q is —N(R)C(O)R, or —N(R)S(O)$_2$R.

In certain embodiments, a subset of compounds of Formula (I) includes those of Formula (IB):

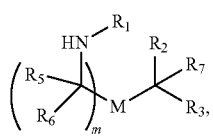

(IB)

or its N-oxide, or a salt or isomer thereof in which all variables are as defined herein. For example, m is selected from 5, 6, 7, 8, and 9; $R_4$ is hydrogen, unsubstituted $C_{1-3}$ alkyl, or —$(CH_2)_nQ$, in which Q is
OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, m is 5, 7, or 9. For example, Q is
OH, —NHC(S)N(R)$_2$, or —NHC(O)N(R)$_2$. For example, Q is —N(R)C(O)R, or —N(R)S(O)$_2$R.

In certain embodiments, a subset of compounds of Formula (I) includes those of Formula (II):

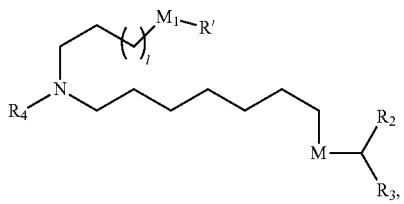

(II)

or its N-oxide, or a salt or isomer thereof, wherein 1 is selected from 1, 2, 3, 4, and 5; $M_1$ is a bond or M'; $R_4$ is hydrogen, unsubstituted $C_{1-3}$ alkyl, or —$(CH_2)_nQ$, in which n is 2, 3, or 4, and Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected
from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In one embodiment, the compounds of Formula (I) are of Formula (IIa),

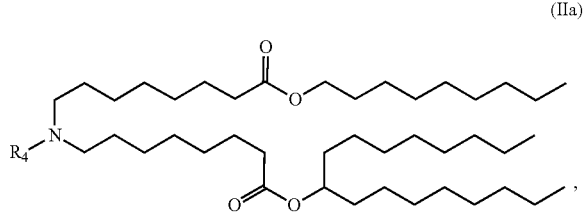

(IIa)

or their N-oxides, or salts or isomers thereof, wherein $R_4$ is as described herein.

In another embodiment, the compounds of Formula (I) are of Formula (IIb),

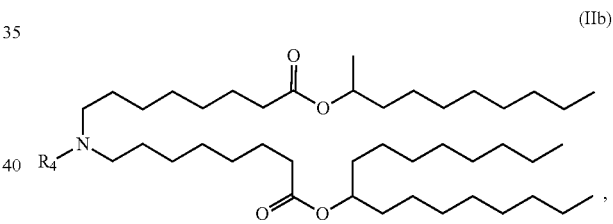

(IIb)

or their N-oxides, or salts or isomers thereof, wherein $R_4$ is as described herein.

In another embodiment, the compounds of Formula (I) are of Formula (IIc) or (IIe):

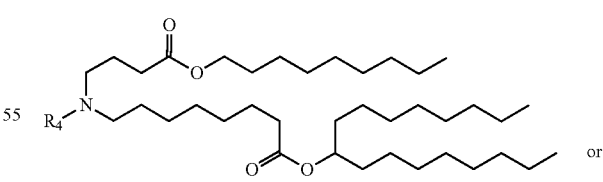

(IIc)

or

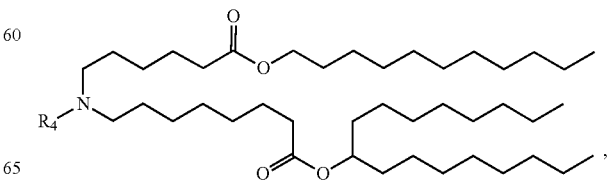

(IIe)

or their N-oxides, or salts or isomers thereof, wherein $R_4$ is as described herein.

In another embodiment, the compounds of Formula (I) are of Formula (IIf):

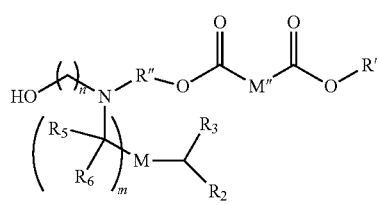

or their N-oxides, or salts or isomers thereof, wherein M is —C(O)O— or —OC(O)—, M" is $C_{1-6}$ alkyl or $C_{2-6}$ alkenyl, $R_2$ and $R_3$ are independently selected from the group consisting of $C_{5-14}$ alkyl and $C_{5-14}$ alkenyl, and n is selected from 2, 3, and 4.

In a further embodiment, the compounds of Formula (I) are of Formula (IId),

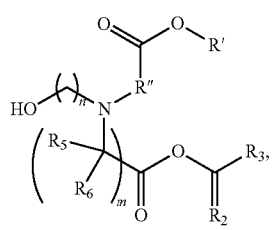

or their N-oxides, or salts or isomers thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In a further embodiment, the compounds of Formula (I) are of Formula (IIg),

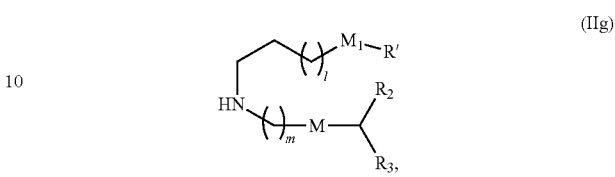

or their N-oxides, or salts or isomers thereof, wherein l is selected from 1, 2, 3, 4, and 5; m is selected from 5, 6, 7, 8, and 9; $M_1$ is a bond or M'; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, M" is $C_{1-6}$ alkyl (e.g., $C_{1-4}$ alkyl) or $C_{2-6}$ alkenyl (e.g. $C_{2-4}$ alkenyl). For example, $R_2$ and $R_3$ are independently selected from the group consisting of $C_{5-14}$ alkyl and $C_{5-14}$ alkenyl.

In some embodiments, the ionizable lipids are one or more of the compounds described in U.S. Application Nos. 62/220,091, 62/252,316, 62/253,433, 62/266,460, 62/333,557, 62/382,740, 62/393,940, 62/471,937, 62/471,949, 62/475,140, and 62/475,166, and PCT Application No. PCT/US2016/052352.

In some embodiments, the ionizable lipids are selected from Compounds 1-280 described in U.S. Application No. 62/475,166.

In some embodiments, the ionizable lipid is

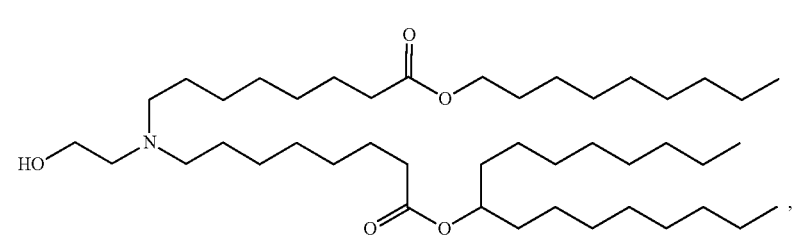

(Compound II)

or a salt thereof.

In some embodiments, the ionizable lipid is

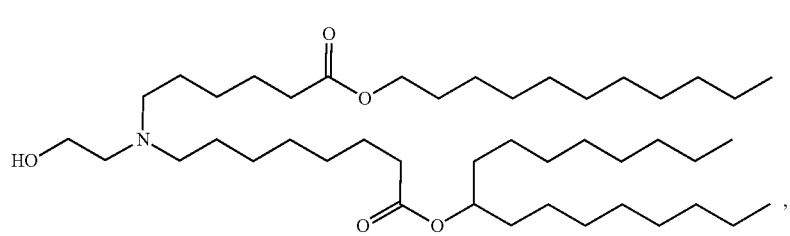

(Compound III)

or a salt thereof.

In some embodiments, the ionizable lipid is

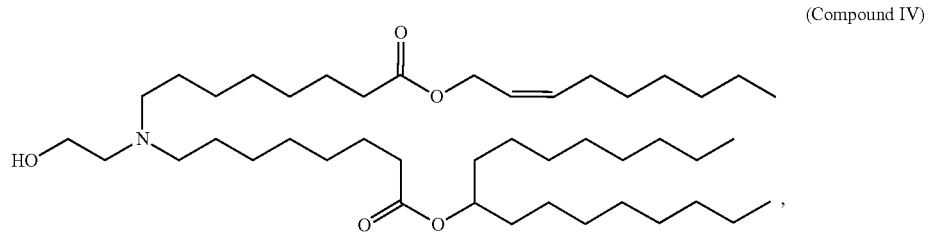 [SMILES: CCCCCC/C=C\COC(=O)CCCCCCCN(CCO)CCCCCCCC(=O)OC(CCCCCCCC)CCCCCCCC]

(Compound IV)

or a salt thereof.

In some embodiments, the ionizable lipid is

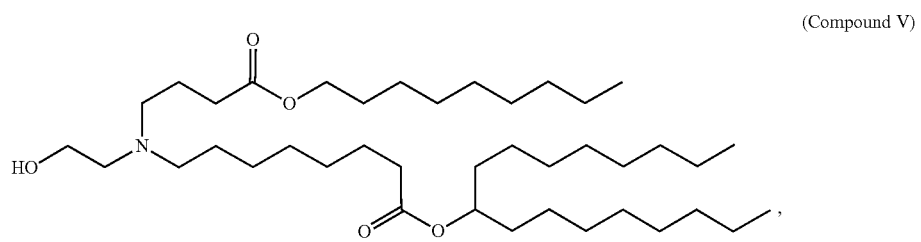 [SMILES: CCCCCCCCCOC(=O)CCCN(CCO)CCCCCCCC(=O)OC(CCCCCCCC)CCCCCCCC]

(Compound V)

or a salt thereof.

The central amine moiety of a lipid according to Formula (I), (IA), (IB), (II), (IIa), (IIb), (IIc), (IId), (IIe), (IIf), or (IIg) may be protonated at a physiological pH. Thus, a lipid may have a positive or partial positive charge at physiological pH. Such lipids may be referred to as cationic or ionizable (amino)lipids. Lipids may also be zwitterionic, i.e., neutral molecules having both a positive and a negative charge.

In some aspects, the ionizable lipids of the present disclosure may be one or more of compounds of formula (III),

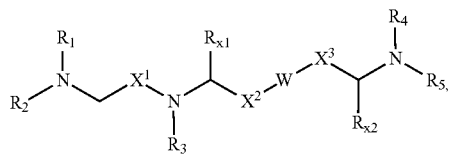

(III)

or salts or isomers thereof, wherein

W is

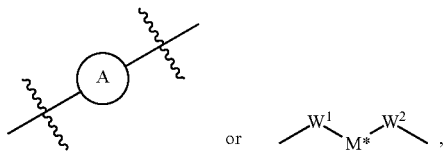 or ring A is

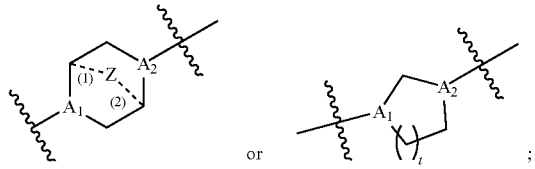

t is 1 or 2;
$A_1$ and $A_2$ are each independently selected from CH or N;
Z is $CH_2$ or absent wherein when Z is $CH_2$, the dashed lines (1) and (2) each represent a single bond; and when Z is absent, the dashed lines (1) and (2) are both absent;
$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";
$R_{X1}$ and $R_{X2}$ are each independently H or $C_{1-3}$ alkyl;
each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, —C(O)S—, —SC(O)—, an aryl group, and a heteroaryl group;
M* is $C_1$-$C_6$ alkyl,
$W^1$ and $W^2$ are each independently selected from the group consisting of —O— and —N($R_6$)—;
each $R_6$ is independently selected from the group consisting of H and $C_{1-5}$ alkyl;
$X^1$, $X^2$, and $X^3$ are independently selected from the group consisting of a bond, —$CH_2$—, —$(CH_2)_2$—, —CHR—, —CHY—, —C(O)—, —C(O)O—, —OC(O)—, —$(CH_2)_n$-C(O)—, —C(O)—$(CH_2)_n$—, —$(CH_2)_n$—C(O)O—, —OC(O)—$(CH_2)_n$—, —$(CH_2)_n$—OC(O)—, —C(O)O—$(CH_2)_n$—, —CH(OH)—, —C(S)—, and —CH(SH)—;
each Y is independently a $C_{3-6}$ carbocycle;
each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H;

each R" is independently selected from the group consisting of $C_{3-12}$ alkyl, $C_{3-12}$ alkenyl and —R*MR'; and n is an integer from 1-6;

when ring A is

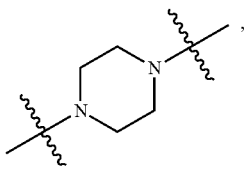 [SMILES: *N1CCN(*)CC1]

then
i) at least one of $X^1$, $X^2$, and $X^3$ is not —$CH_2$—; and/or
ii) at least one of $R_1$, $R_2$, $R_3$, $R_4$, and $R_5$ is —R"MR'.

In some embodiments, the compound is of any of formulae (IIIa1)-(IIIa8):

(IIIa1)
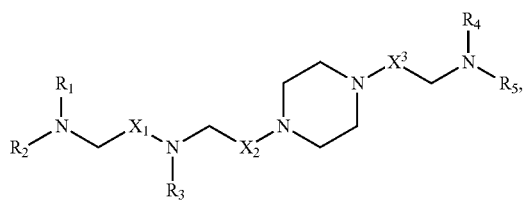

(IIIa2)
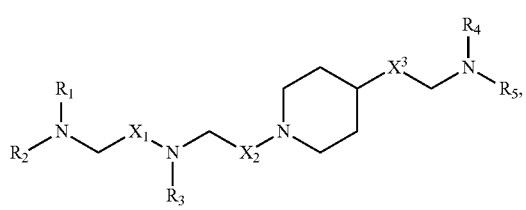

(IIIa3)
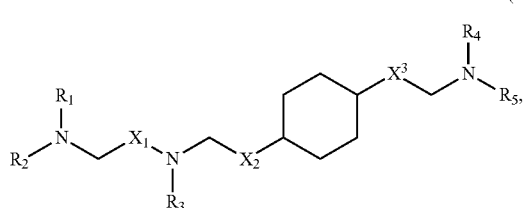

(IIIa4)
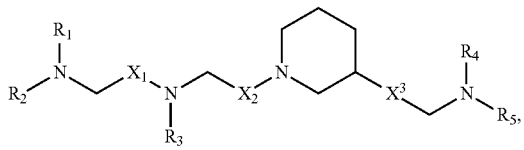

(IIIa5')
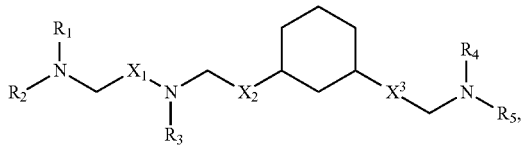

(IIIa6)
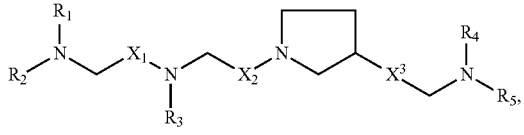

(IIIa7)
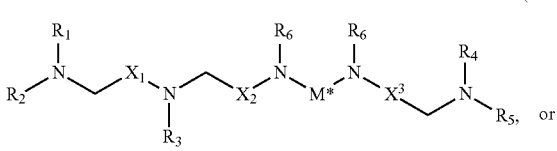

(IIIa8)
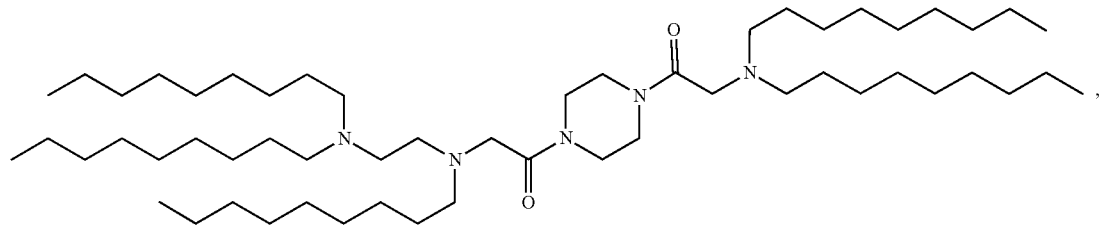

In some embodiments, the ionizable lipids are one or more of the compounds described in U.S. Application Nos. 62/271,146, 62/338,474, 62/413,345, and 62/519,826, and PCT Application No. PCT/US2016/068300.

In some embodiments, the ionizable lipids are selected from Compounds 1-156 described in U.S. Application No. 62/519,826.

In some embodiments, the ionizable lipids are selected from Compounds 1-16, 42-66, 68-76, and 78-156 described in U.S. Application No. 62/519,826.

In some embodiments, the ionizable lipid is (Compound VI)

or a salt thereof.

The central amine moiety of a lipid according to Formula (III), (IIIa1), (IIIa2), (IIIa3), (IIIa4), (IIIa5), (IIIa6), (IIIa7), or (IIIa8) may be protonated at a physiological pH. Thus, a lipid may have a positive or partial positive charge at physiological pH. Such lipids may be referred to as cationic or ionizable (amino)lipids. Lipids may also be zwitterionic, i.e., neutral molecules having both a positive and a negative charge.

Phospholipids

The lipid composition of the lipid nanoparticle composition disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

In some embodiments, a phospholipid of the invention comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In certain embodiments, a phospholipid useful or potentially useful in the present invention is an analog or variant of DSPC. In certain embodiments, a phospholipid useful or potentially useful in the present invention is a compound of Formula (IV):

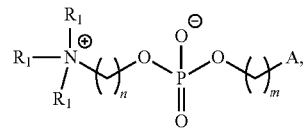

(IV)

or a salt thereof, wherein:

each $R^1$ is independently optionally substituted alkyl; or optionally two $R^1$ are joined together with the intervening atoms to form optionally substituted monocyclic carbocyclyl or optionally substituted monocyclic heterocyclyl; or optionally three Ware joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2, 3, 4, 5, 6, 7, 8, 9, or 10;

A is of the formula:

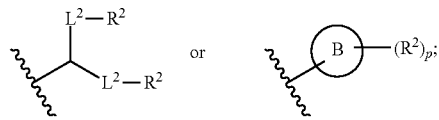

each instance of $L^2$ is independently a bond or optionally substituted $C_{1-6}$ alkylene, wherein one methylene unit of the optionally substituted $C_{1-6}$ alkylene is optionally replaced with O, N($R^N$), S, C(O), C(O)N($R^N$), $NR^NC(O)$, C(O)O, OC(O), OC(O)O, OC(O)N($R^N$), $NR^NC(O)O$, or $NR^NC(O)N(R^N)$;

each instance of $R_2$ is independently optionally substituted $C_{1-30}$ alkyl, optionally substituted $C_{1-30}$ alkenyl, or optionally substituted $C_{1-30}$ alkynyl; optionally wherein one or more methylene units of $R_2$ are independently replaced with optionally substituted carbocyclylene, optionally substituted heterocyclylene, optionally substituted arylene, optionally substituted heteroarylene, N($R^N$), O, S, C(O), C(O)N($R^N$), $NR^NC(O)$, $NR^NC(O)N(R^N)$, C(O)O, OC(O), —OC(O)O, OC(O)N($R^N$), $NR^NC(O)O$, C(O)S, SC(O), C(=$NR^N$), C(=$NR^N$)N($R^N$), $NR^NC(=NR^N)$, $NR^NC(=NR^N)N(R^N)$, C(S), C(S)N($R^N$), $NR^NC(S)$, $NR^NC(S)N(R^N)$, S(O), OS(O), S(O)O, —OS(O)O, $OS(O)_2$, $S(O)_2O$, $OS(O)_2O$, N($R^N$)S(O), S(O)N($R^N$), $N(R^N)S(O)N(R^N)$, OS(O)N($R^N$), $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or —N($R^N$)$S(O)_2O$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

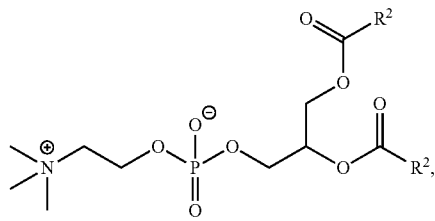

wherein each instance of $R^2$ is independently unsubstituted alkyl, unsubstituted alkenyl, or unsubstituted alkynyl.

In some embodiments, the phospholipids may be one or more of the phospholipids described in U.S. Application No. 62/520,530.

(i) Phospholipid Head Modifications

In certain embodiments, a phospholipid useful or potentially useful in the present invention comprises a modified phospholipid head (e.g., a modified choline group). In certain embodiments, a phospholipid with a modified head is DSPC, or analog thereof, with a modified quaternary amine. For example, in embodiments of Formula (IV), at least one of $R^1$ is not methyl. In certain embodiments, at least one of $R^1$ is not hydrogen or methyl. In certain embodiments, the compound of Formula (IV) is of one of the following formulae:

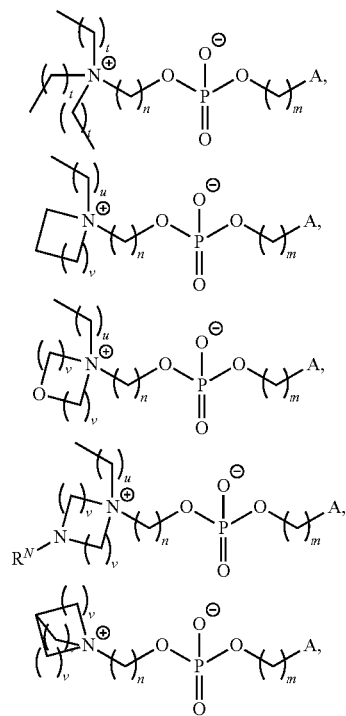

or a salt thereof, wherein:

each t is independently 1, 2, 3, 4, 5, 6, 7, 8, 9, or 10;

each u is independently 0, 1, 2, 3, 4, 5, 6, 7, 8, 9, or 10; and each v is independently 1, 2, or 3.

In certain embodiments, a compound of Formula (IV) is of Formula (IV-a):

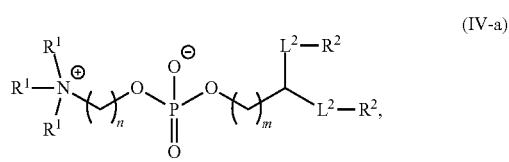

(IV-a)

or a salt thereof.

In certain embodiments, a phospholipid useful or potentially useful in the present invention comprises a cyclic moiety in place of the glyceride moiety. In certain embodiments, a phospholipid useful in the present invention is DSPC, or analog thereof, with a cyclic moiety in place of the glyceride moiety. In certain embodiments, the compound of Formula (IV) is of Formula (IV-b):

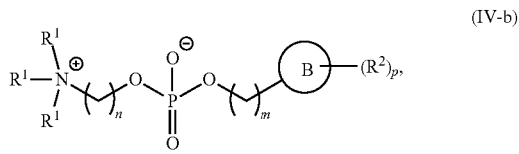

(IV-b)

or a salt thereof.

(ii) Phospholipid Tail Modifications

In certain embodiments, a phospholipid useful or potentially useful in the present invention comprises a modified tail. In certain embodiments, a phospholipid useful or potentially useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (IV) is of Formula (IV-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), C(O)N($R^N$), —$NR^N$C(O), $NR^N$C(O)N($R^N$), C(O)O, OC(O), OC(O)O, OC(O)N($R^N$), $NR^N$C(O)O, C(O)S, SC(O), C(=$NR^N$), C(=$NR^N$)N($R^N$), $NR^N$C(=$NR^N$), $NR^N$C(=$NR^N$)N($R^N$), C(S), C(S)N($R^N$), $NR^N$C(S), —$NR^N$C(S)N($R^N$), S(O), OS(O), S(O)O, OS(O)O, OS(O)$_2$, S(O)$_2$O, OS(O)$_2$O, N($R^N$)S(O), —S(O)N($R^N$), N($R^N$)S(O)N($R^N$), OS(O)N($R^N$), N($R^N$)S(O)O, S(O)$_2$, N($R^N$)S(O)$_2$, S(O)$_2$N($R^N$), —N($R^N$)S(O)$_2$N($R^N$), OS(O)$_2$N($R^N$), or N($R^N$)S(O)$_2$O.

In certain embodiments, the compound of Formula (IV) is of Formula (IV-c):

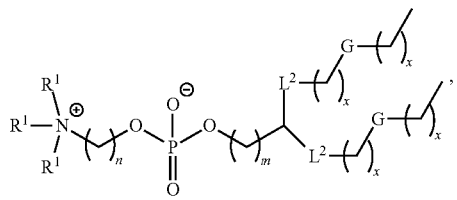

(IV-c)

or a salt thereof, wherein:

each x is independently an integer between 0-30, inclusive; and each instance is G is independently selected from the group consisting of optionally substituted carbocyclylene, optionally substituted heterocyclylene, optionally substituted arylene, optionally substituted heteroarylene, N(R$^N$), O, S, C(O), C(O)N(R$^N$), NR$^N$C(O), NR$^N$C(O)N(R$^N$), C(O)O, OC(O), OC(O)O, OC(O)N(R$^N$), NR$^N$C(O)O, C(O)S, SC(O), C(=NR$^N$), C(=NR$^N$)N(R$^N$), NR$^N$C(=NR$^N$), NR$^N$C(=NR$^N$)N(R$^N$), C(S), C(S)N(R$^N$), NR$^N$C(S), NR$^N$C(S)N(R$^N$), S(O), OS(O), S(O)O, OS(O)O, OS(O)$_2$, S(O)$_2$O, OS(O)$_2$O, N(R$^N$)S(O), S(O)N(R$^N$), N(R$^N$)S(O)N(R$^N$), —OS(O)N(R$^N$), N(R$^N$)S(O)O, S(O)$_2$, N(R$^N$)S(O)$_2$, S(O)$_2$N(R$^N$), N(R$^N$)S(O)$_2$N(R$^N$), OS(O)$_2$N(R$^N$), or N(R$^N$)S(O)$_2$O. Each possibility represents a separate embodiment of the present invention.

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful or potentially useful in the present invention is a compound of Formula (IV), wherein n is 1, 3, 4, 5, 6, 7, 8, 9, or 10. For example, in certain embodiments, a compound of Formula (IV) is of one of the following formulae:

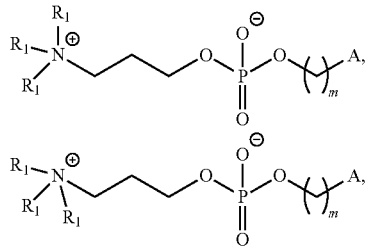

or a salt thereof.

Alternative Lipids

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful.

In certain embodiments, an alternative lipid is used in place of a phospholipid of the present disclosure.

In certain embodiments, an alternative lipid of the invention is oleic acid.

In certain embodiments, the alternative lipid is one of the following:

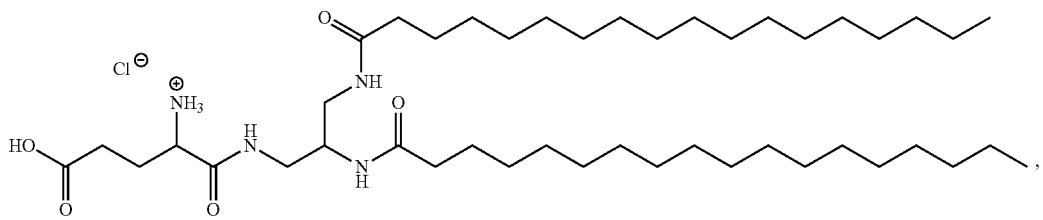

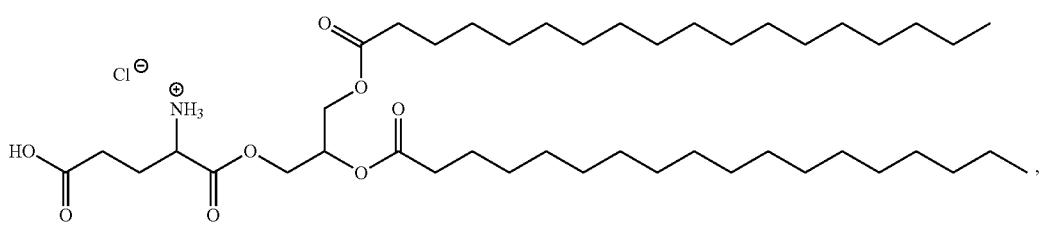

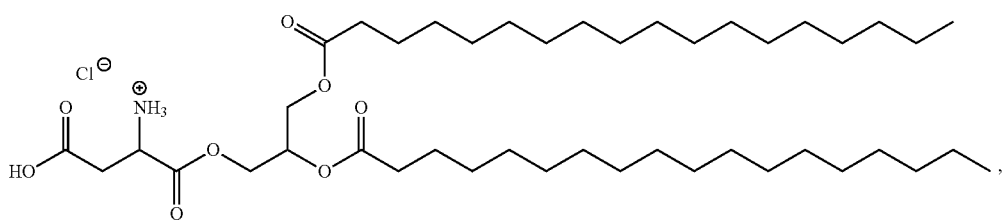

-continued

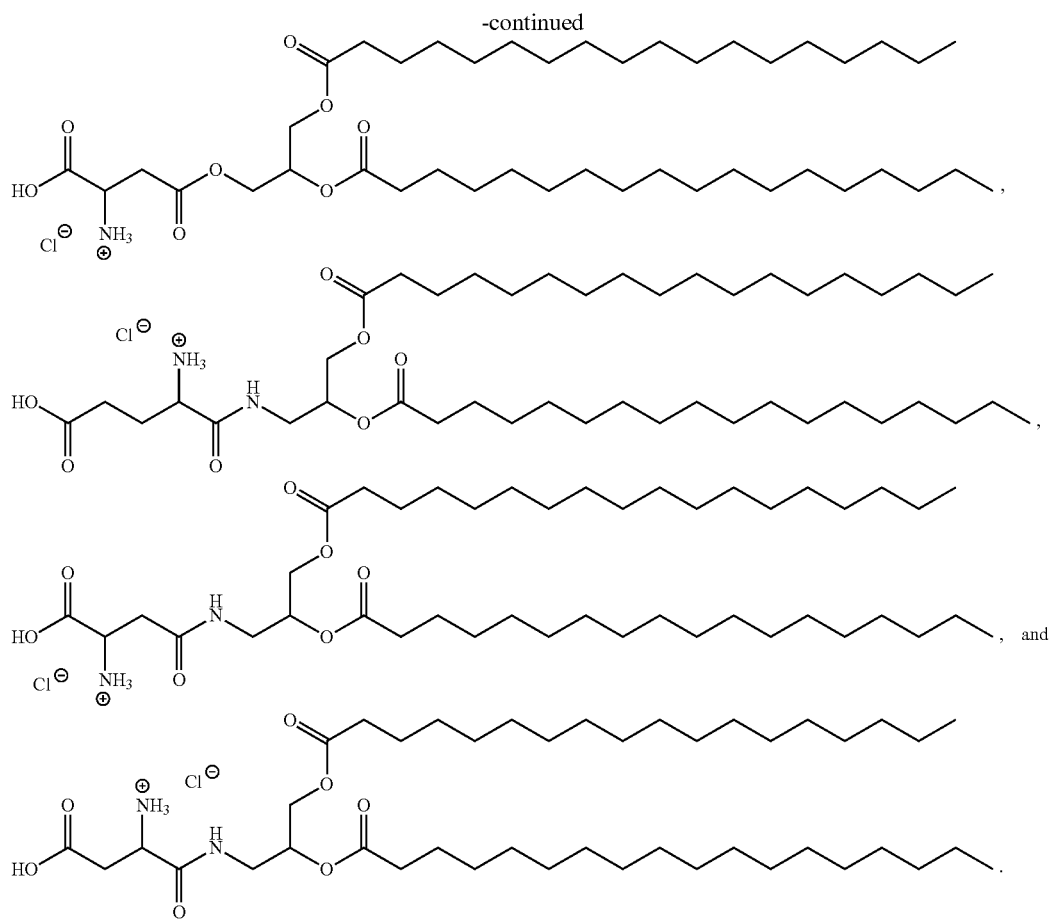

, and

.

Structural Lipids

The lipid composition of a pharmaceutical composition disclosed herein can comprise one or more structural lipids. As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol.

In some embodiments, the structural lipids may be one or more of the structural lipids described in U.S. Application No. 62/520,530.

Polyethylene Glycol (PEG)-Lipids

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example an mPEG-NH$_2$, has a size of about 1000, 2000, 5000, 10,000, 15,000 or 20,000 daltons. In one embodiment, the PEG-lipid is PEG$_{2k}$-DMG.

In one embodiment, the lipid nanoparticles described herein can comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

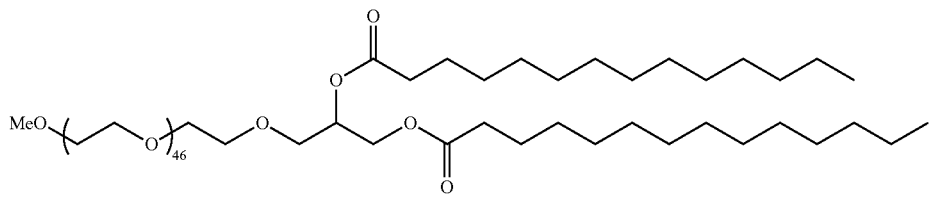

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In certain embodiments, a PEG lipid useful in the present invention is a compound of Formula (V). Provided herein are compounds of Formula (V):

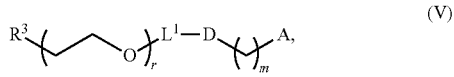

(V)

or salts thereof, wherein:

$R_3$ is —$OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_1$-10 alkylene is independently replaced with optionally substituted carbocyclylene, optionally substituted heterocyclylene, optionally substituted arylene, optionally substituted heteroarylene, O, N($R^N$), S, C(O), C(O)N($R^N$), $NR^N$C(O), C(O)O, OC(O), OC(O)O, OC(O)N($R^N$), $NR^N$C(O)O, or $NR^N$C(O)N($R^N$);

D is a moiety obtained by click chemistry or a moiety cleavable under physiological conditions;

m is 0, 1, 2, 3, 4, 5, 6, 7, 8, 9, or 10;

A is of the formula:

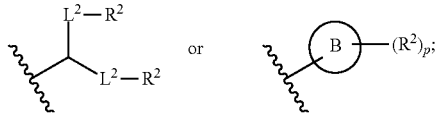

each instance of $L^2$ is independently a bond or optionally substituted $C_{1-6}$ alkylene, wherein one methylene unit of the optionally substituted $C_{1-6}$ alkylene is optionally replaced with O, N($R^N$), S, C(O), C(O)N($R^N$), $NR^N$C(O), C(O)O, OC(O), OC(O)O, OC(O)N($R^N$), $NR^N$C(O)O, or $NR^N$C(O)N($R^N$);

each instance of $R_2$ is independently optionally substituted $C_{1-30}$ alkyl, optionally substituted $C_{1-30}$ alkenyl, or optionally substituted $C_{1-30}$ alkynyl; optionally wherein one or more methylene units of $R_2$ are independently replaced with optionally substituted carbocyclylene, optionally substituted heterocyclylene, optionally substituted arylene, optionally substituted heteroarylene, N($R^N$), O, S, C(O), C(O)N($R^N$), $NR^N$C(O), $NR^N$C(O)N($R^N$), C(O)O, OC(O), —OC(O)O, OC(O)N($R^N$), $NR^N$C(O)O, C(O)S, SC(O), C(=$NR^N$), C(=$NR^N$)N($R^N$), $NR^N$C(=$NR^N$), $NR^N$C(=$NR^N$)N($R^N$), C(S), C(S)N($R^N$), $NR^N$C(S), $NR^N$C(S)N($R^N$), S(O), OS(O), S(O)O, —OS(O)O, OS(O)$_2$, S(O)$_2$O, OS(O)$_2$O, N($R^N$)S(O), S(O)N($R^N$), N($R^N$)S(O)N($R^N$), OS(O)N($R^N$), N($R^N$)S(O)O, S(O)$_2$, N($R^N$)S(O)$_2$, S(O)$_2$N($R^N$), N($R^N$)S(O)$_2$N($R^N$), OS(O)$_2$N($R^N$), or —N($R^N$)S(O)$_2$O;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (V) is a PEG-OH lipid (i.e., $R_3$ is —$OR^O$, and $R^O$ is hydrogen). In certain embodiments, the compound of Formula (V) is of Formula (V-OH):

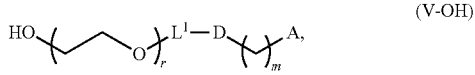
(V-OH)

or a salt thereof.

In certain embodiments, a PEG lipid useful in the present invention is a PEGylated fatty acid. In certain embodiments, a PEG lipid useful in the present invention is a compound of Formula (VI). Provided herein are compounds of Formula (VI):

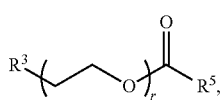
(VI)

or a salts thereof, wherein:

$R_3$ is —$OR^O$;

$R^O$ is hydrogen, optionally substituted alkyl or an oxygen protecting group;

r is an integer between 1 and 100, inclusive;

$R_5$ is optionally substituted $C_{10-40}$ alkyl, optionally substituted $C_{10-40}$ alkenyl, or optionally substituted $C_{10-40}$ alkynyl; and optionally one or more methylene groups of $R_5$ are replaced with optionally substituted carbocyclylene, optionally substituted heterocyclylene, optionally substituted arylene, optionally substituted heteroarylene, $N(R^N)$, O, S, C(O), C(O)N($R^N$), —$NR^NC(O)$, $NR^NC(O)N(R^N)$, C(O)O, OC(O), OC(O)O, OC(O)N($R^N$), $NR^NC(O)O$, C(O)S, SC(O), C(=$NR^N$), C(=$NR^N$)N($R^N$), $NR^NC$(=$NR^N$), $NR^NC$(=$NR^N$)N($R^N$), C(S), C(S)N($R^N$), $NR^NC(S)$, —$NR^NC(s)N(R^N)$, S(O), OS(O), S(O)O, OS(O)O, $OS(O)_2$, $S(O)_2O$, $OS(O)_2O$, N($R^N$)S(O), —S(O)N($R^N$), N($R^N$)S(O)N($R^N$), OS(O)N($R^N$), N($R^N$)S(O)O, $S(O)_2$, N($R^N$)$S(O)_2$, $S(O)_2N(R^N)$, —N($R^N$)$S(O)_2$N($R^N$), $OS(O)_2N(R^N)$, or N($R^N$)$S(O)_2O$; and each instance of $R^N$ is independently hydrogen, optionally substituted alkyl, or a nitrogen protecting group.

In certain embodiments, the compound of Formula (VI) is of Formula (VI-OH):

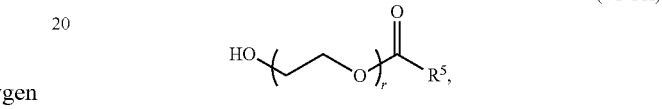
(VI-OH)

or a salt thereof. In some embodiments, r is 45.

In yet other embodiments the compound of Formula (VI) is:

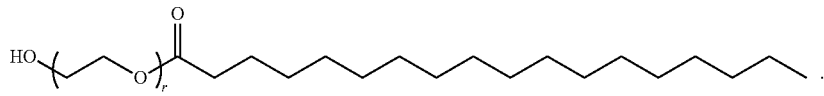

or a salt thereof.

In one embodiment, the compound of Formula (VI) is

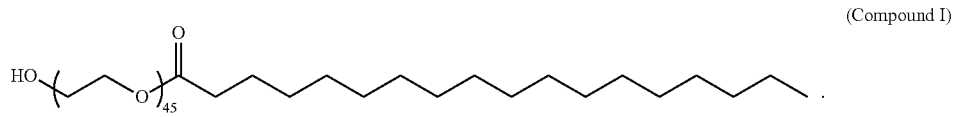
(Compound I)

In some aspects, the lipid composition of the pharmaceutical compositions disclosed herein does not comprise a PEG-lipid.

In some embodiments, the PEG-lipids may be one or more of the PEG lipids described in U.S. Application No. 62/520,530.

In some embodiments, a PEG lipid of the invention comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG, PEG-c-DOMG (also referred to as PEG-DOMG), PEG-DSG and/or PEG-DPG.

In some embodiments, a LNP of the invention comprises an ionizable cationic lipid of any of Formula I, II or III, a phospholipid comprising DSPC, a structural lipid, and a PEG lipid comprising PEG-DMG.

In some embodiments, a LNP of the invention comprises an ionizable cationic lipid of any of Formula I, II or III, a phospholipid comprising DSPC, a structural lipid, and a PEG lipid comprising a compound having Formula VI.

In some embodiments, a LNP of the invention comprises an ionizable cationic lipid of Formula I, II or III, a phospholipid comprising a compound having Formula IV, a structural lipid, and the PEG lipid comprising a compound having Formula V or VI.

In some embodiments, a LNP of the invention comprises an ionizable cationic lipid of Formula I, II or III, a phospholipid comprising a compound having Formula IV, a structural lipid, and the PEG lipid comprising a compound having Formula V or VI.

In some embodiments, a LNP of the invention comprises an ionizable cationic lipid of Formula I, II or III, a phospholipid having Formula IV, a structural lipid, and a PEG lipid comprising a compound having Formula VI.

In some embodiments, a LNP of the invention comprises an ionizable cationic lipid of

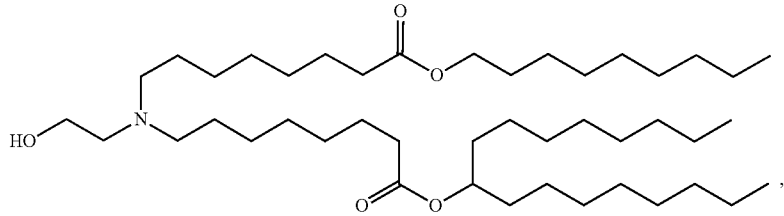 [SMILES: CCCCCCCCCOC(=O)CCCCCCCN(CCO)CCCCCCCC(=O)OC(CCCCCCCC)CCCCCCCC]

and a PEG lipid comprising Formula VI.

In some embodiments, a LNP of the invention comprises an ionizable cationic lipid of

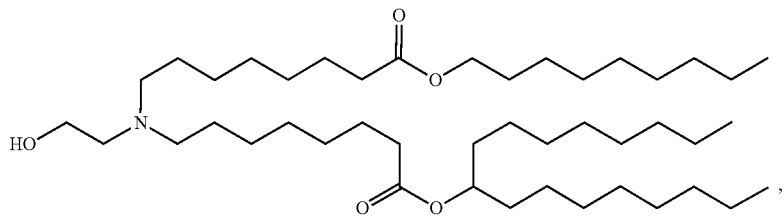 [SMILES: CCCCCCCCCOC(=O)CCCCCCCN(CCO)CCCCCCCC(=O)OC(CCCCCCCC)CCCCCCCC]

and an alternative lipid comprising oleic acid.

In some embodiments, a LNP of the invention comprises an ionizable cationic lipid of

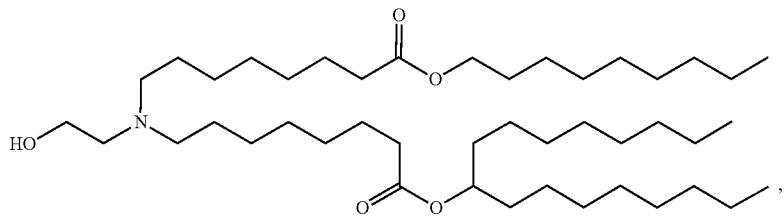 [SMILES: CCCCCCCCCOC(=O)CCCCCCCN(CCO)CCCCCCCC(=O)OC(CCCCCCCC)CCCCCCCC]

an alternative lipid comprising oleic acid, a structural lipid comprising cholesterol, and a PEG lipid comprising a compound having Formula VI.

In some embodiments, a LNP of the invention comprises an ionizable cationic lipid of

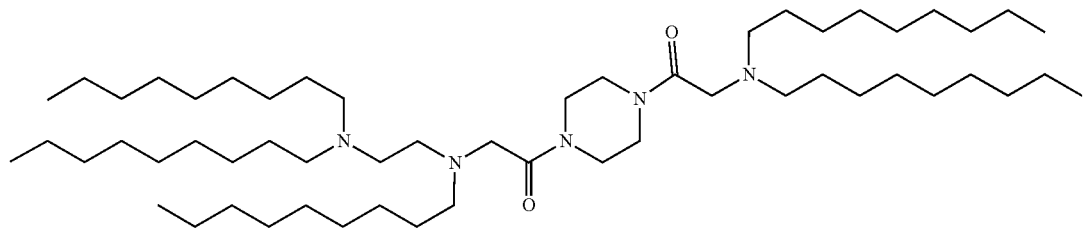 [SMILES: CCCCCCCCCN(CCCCCCCCC)CCN(CCCCCCCCC)CC(=O)N1CCN(C(=O)CN(CCCCCCCCC)CCCCCCCCC)CC1]

a phospholipid comprising DOPE, a structural lipid comprising cholesterol, and a PEG lipid comprising a compound having Formula VI.

In some embodiments, a LNP of the invention comprises an ionizable cationic lipid of a phospholipid comprising DOPE, a structural lipid comprising cholesterol, and a PEG lipid comprising a compound having Formula VII.

In some embodiments, a LNP of the invention comprises an N:P ratio of from about 2:1 to about 30:1.

In some embodiments, a LNP of the invention comprises an N:P ratio of about 6:1.

In some embodiments, a LNP of the invention comprises an N:P ratio of about 3:1.

In some embodiments, a LNP of the invention comprises a wt/wt ratio of the ionizable cationic lipid component to the RNA of from about 10:1 to about 100:1.

In some embodiments, a LNP of the invention comprises a wt/wt ratio of the ionizable cationic lipid component to the RNA of about 20:1.

In some embodiments, a LNP of the invention comprises a wt/wt ratio of the ionizable cationic lipid component to the RNA of about 10:1.

In some embodiments, a LNP of the invention has a mean diameter from about 50 nm to about 150 nm.

In some embodiments, a LNP of the invention has a mean diameter from about 70 nm to about 120 nm.

As used herein, the term "alkyl", "alkyl group", or "alkylene" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The notation "$C_{1-14}$ alkyl" means an optionally substituted linear or branched, saturated hydrocarbon including 1 14 carbon atoms. Unless otherwise specified, an alkyl group described herein refers to both unsubstituted and substituted alkyl groups.

As used herein, the term "alkenyl", "alkenyl group", or "alkenylene" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "C2-14 alkenyl" means an optionally substituted linear or branched hydrocarbon including 2 14 carbon atoms and at least one carbon-carbon double bond. An alkenyl group may include one, two, three, four, or more carbon-carbon double bonds. For example, C18 alkenyl may include one or more double bonds. A C18 alkenyl group including two double bonds may be a linoleyl group. Unless otherwise specified, an alkenyl group described herein refers to both unsubstituted and substituted alkenyl groups.

As used herein, the term "alkynyl", "alkynyl group", or "alkynylene" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one carbon-carbon triple bond, which is optionally substituted. The notation "C2-14 alkynyl" means an optionally substituted linear or branched hydrocarbon including 2 14 carbon atoms and at least one carbon-carbon triple bond. An alkynyl group may include one, two, three, four, or more carbon-carbon triple bonds. For example, C18 alkynyl may include one or more carbon-carbon triple bonds. Unless otherwise specified, an alkynyl group described herein refers to both unsubstituted and substituted alkynyl groups.

As used herein, the term "carbocycle" or "carbocyclic group" means an optionally substituted mono- or multi-cyclic system including one or more rings of carbon atoms. Rings may be three, four, five, six, seven, eight, nine, ten, eleven, twelve, thirteen, fourteen, fifteen, sixteen, seventeen, eighteen, nineteen, or twenty membered rings. The notation "C3-6 carbocycle" means a carbocycle including a single ring having 3-6 carbon atoms. Carbocycles may include one or more carbon-carbon double or triple bonds and may be non-aromatic or aromatic (e.g., cycloalkyl or aryl groups). Examples of carbocycles include cyclopropyl, cyclopentyl, cyclohexyl, phenyl, naphthyl, and 1,2 dihydronaphthyl groups. The term "cycloalkyl" as used herein means a non-aromatic carbocycle and may or may not include any double or triple bond. Unless otherwise specified, carbocycles described herein refers to both unsubstituted and substituted carbocycle groups, i.e., optionally substituted carbocycles.

As used herein, the term "heterocycle" or "heterocyclic group" means an optionally substituted mono- or multi-cyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, twelve, thirteen, or fourteen membered rings. Heterocycles may include one or more double or triple bonds and may be non-aromatic or aromatic (e.g., heterocycloalkyl or heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. The term "heterocycloalkyl" as used herein means a non-aromatic heterocycle and may or may not include any double or triple bond. Unless otherwise specified, heterocycles described herein refers to both unsubstituted and substituted heterocycle groups, i.e., optionally substituted heterocycles.

As used herein, the term "heteroalkyl", "heteroalkenyl", or "heteroalkynyl", refers respectively to an alkyl, alkenyl, alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. Unless otherwise specified, heteroalkyls, heteroalkenyls, or heteroalkynyls described herein refers to both unsubstituted and substituted heteroalkyls, heteroalkenyls, or heteroalkynyls, i.e., optionally substituted heteroalkyls, heteroalkenyls, or heteroalkynyls.

As used herein, a "biodegradable group" is a group that may facilitate faster metabolism of a lipid in a mammalian entity. A biodegradable group may be selected from the group consisting of, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)2-, an aryl group, and a heteroaryl group. As used herein, an "aryl group" is an optionally substituted carbocyclic group including one or more aromatic rings. Examples of aryl groups include phenyl and naphthyl groups. As used herein, a "heteroaryl group" is an optionally substituted heterocyclic group including one or more aromatic rings. Examples of heteroaryl groups include pyrrolyl, furyl, thiophenyl, imidazolyl, oxazolyl, and thiazolyl. Both aryl and heteroaryl groups may be optionally substituted. For example, M and M' can be selected from the non-limiting group consisting of optionally substituted phenyl, oxazole, and thiazole. In the formulas herein, M and M' can be independently selected from the list of biodegradable groups above. Unless otherwise specified, aryl or heteroaryl groups described herein refers to both unsubstituted and substituted groups, i.e., optionally substituted aryl or heteroaryl groups.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., C(O)OH), an alcohol (e.g., a hydroxyl, OH), an ester (e.g., C(O)OR OC(O)R), an aldehyde (e.g., C(O)H), a carbonyl (e.g., C(O)R, alternatively represented by C=O), an acyl halide (e.g., C(O)X, in which X is a halide selected from bromide, fluoride, chloride, and iodide), a carbonate (e.g., OC(O)OR), an alkoxy (e.g., OR), an acetal (e.g., C(OR)2R"", in which each OR are alkoxy groups that can be the same or different and R" " is an alkyl or alkenyl group), a phosphate (e.g., P(O)43-), a thiol (e.g., SH), a sulfoxide (e.g., S(O)R), a sulfinic acid (e.g., S(O)OH), a sulfonic acid (e.g., S(O)2OH), a thial (e.g., C(S)H), a sulfate (e.g., S(O)42-), a sulfonyl (e.g., S(O)2), an amide (e.g., C(O)NR2, or N(R)C(O)R), an azido (e.g., N3), a nitro (e.g., NO2), a cyano (e.g., CN), an isocyano (e.g., NC), an acyloxy (e.g., OC(O)R), an amino (e.g., $NR_2$, NRH, or NH2), a carbamoyl (e.g., OC(O)NR2, OC(O)NRH, or OC(O)NH2), a sulfonamide (e.g., S(O)2NR2, S(O)2NRH, S(O)2NH2, N(R)S(O)2R, N(H)S(O)2R, N(R)S(O)2H, or N(H)S(O)2H), an alkyl group, an alkenyl group, and a cyclyl (e.g., carbocyclyl or heterocyclyl) group. In any of the preceding, R is an alkyl or alkenyl group, as defined herein. In some embodiments, the substituent groups themselves may be further substituted with, for example, one, two, three, four, five, or six substituents as defined herein. For example, a C1 6 alkyl group may be further substituted with one, two, three, four, five, or six substituents as described herein.

Compounds of the disclosure that contain nitrogens can be converted to N-oxides by treatment with an oxidizing agent (e.g., 3-chloroperoxybenzoic acid (mCPBA) and/or hydrogen peroxides) to afford other compounds of the disclosure. Thus, all shown and claimed nitrogen-containing compounds are considered, when allowed by valency and structure, to include both the compound as shown and its N-oxide derivative (which can be designated as N☐O or N+—O—). Furthermore, in other instances, the nitrogens in the compounds of the disclosure can be converted to N-hydroxy or N-alkoxy compounds. For example, N-hydroxy compounds can be prepared by oxidation of the parent amine by an oxidizing agent such as m CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted C1-C 6 alkyl, C1-C6 alkenyl, C1-C6 alkynyl, 3-14-membered carbocycle or 3-14-membered heterocycle) derivatives.

Other Lipid Composition Components

The lipid composition of a pharmaceutical composition disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof).

A polymer can be included in and/or used to encapsulate or partially encapsulate a pharmaceutical composition disclosed herein (e.g., a pharmaceutical composition in lipid nanoparticle form). A polymer can be biodegradable and/or biocompatible. A polymer can be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The ratio between the lipid composition and the polynucleotide range can be from about 10:1 to about 60:1 (wt/wt).

In some embodiments, the ratio between the lipid composition and the polynucleotide can be about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide encoding a therapeutic agent is about 20:1 or about 15:1.

In some embodiments, the pharmaceutical composition disclosed herein can contain more than one polypeptides. For example, a pharmaceutical composition disclosed herein can contain two or more polynucleotides (e.g., RNA, e.g., mRNA).

In one embodiment, the lipid nanoparticles described herein can comprise polynucleotides (e.g., mRNA) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

Nanoparticle Compositions

In some embodiments, the pharmaceutical compositions disclosed herein are formulated as lipid nanoparticles (LNP). Accordingly, the present disclosure also provides nanoparticle compositions comprising (i) a lipid composition comprising a delivery agent such as compound as described herein, and (ii) a polynucleotide encoding a polypeptide. In such nanoparticle composition, the lipid composition disclosed herein can encapsulate the polynucleotide encoding a polypeptide.

Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

In one embodiment, a lipid nanoparticle comprises an ionizable lipid, a structural lipid, a phospholipid, and mRNA. In some embodiments, the LNP comprises an ionizable lipid, a PEG-modified lipid, a sterol and a structural lipid. In some embodiments, the LNP has a molar ratio of about 20-60% ionizable lipid:about 5-25% structural lipid:about 25-55% sterol; and about 0.5-15% PEG-modified lipid.

In some embodiments, the LNP has a polydispersity value of less than 0.4. In some embodiments, the LNP has a net neutral charge at a neutral pH. In some embodiments, the LNP has a mean diameter of 50-150 nm. In some embodiments, the LNP has a mean diameter of 80-100 nm.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid". In certain embodiments, an ionizable lipid molecule may comprise an amine group, and can be referred to as an ionizable amino lipid. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups.

Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure.

In addition to these, an ionizable lipid may also be a lipid including a cyclic amine group.

In one embodiment, the ionizable lipid may be selected from, but not limited to, a ionizable lipid described in International Publication Nos. WO2013086354 and WO2013116126; the contents of each of which are herein incorporated by reference in their entirety.

In yet another embodiment, the ionizable lipid may be selected from, but not limited to, formula CLI-CLXXXXII of U.S. Pat. No. 7,404,969; each of which is herein incorporated by reference in their entirety.

In one embodiment, the lipid may be a cleavable lipid such as those described in International Publication No. WO2012170889, herein incorporated by reference in its entirety. In one embodiment, the lipid may be synthesized by methods known in the art and/or as described in International Publication Nos. WO2013086354; the contents of each of which are herein incorporated by reference in their entirety.

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

The size of the nanoparticles can help counter biological reactions such as, but not limited to, inflammation, or can increase the biological effect of the polynucleotide.

As used herein, "size" or "mean size" in the context of nanoparticle compositions refers to the mean diameter of a nanoparticle composition.

In one embodiment, the polynucleotide encoding a polypeptide is formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

The term "encapsulation efficiency" of a polynucleotide describes the amount of the polynucleotide that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the polynucleotide in a solution containing the nanoparticle composition before and after breaking up the nanoparticle composition with one or more organic solvents or detergents.

Fluorescence can be used to measure the amount of free polynucleotide in a solution. For the nanoparticle compositions described herein, the encapsulation efficiency of a polynucleotide can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

The amount of a polynucleotide present in a pharmaceutical composition disclosed herein can depend on multiple factors such as the size of the polynucleotide, desired target and/or application, or other properties of the nanoparticle composition as well as on the properties of the polynucleotide.

For example, the amount of an mRNA useful in a nanoparticle composition can depend on the size (expressed as length, or molecular mass), sequence, and other characteristics of the mRNA. The relative amounts of a polynucleotide in a nanoparticle composition can also vary.

The relative amounts of the lipid composition and the polynucleotide present in a lipid nanoparticle composition of the present disclosure can be optimized according to considerations of efficacy and tolerability. For compositions including an mRNA as a polynucleotide, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1. In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a polynucleotide. Such method comprises using any of the pharmaceutical compositions disclosed herein and producing lipid nanoparticles in accordance with methods of production of lipid nanoparticles known in the art. See, e.g., Wang et al. (2015) "Delivery of oligonucleotides with lipid nanoparticles" Adv. Drug Deliv. Rev. 87:68-80; Silva et al. (2015) "Delivery Systems for Biopharmaceuticals. Part I: Nanoparticles and Microparticles" Curr. Pharm. Technol. 16: 940-954; Naseri et al. (2015) "Solid Lipid Nanoparticles and Nanostructured Lipid Carriers: Structure, Preparation and Application" Adv. Pharm. Bull. 5:305-13; Silva et al. (2015) "Lipid nanoparticles for the delivery of biopharmaceuticals" Curr. Pharm. Biotechnol. 16:291-302, and references cited therein.

Other Delivery Agents a. Liposomes, Lipoplexes, and Lipid Nanoparticles

In some embodiments, the compositions or formulations of the present disclosure comprise a delivery agent, e.g., a liposome, a lioplexes, a lipid nanoparticle, or any combination thereof. The polynucleotides described herein (e.g., a polynucleotide comprising a nucleotide sequence encoding a polypeptide) can be formulated using one or more liposomes, lipoplexes, or lipid nanoparticles. Liposomes, lipoplexes, or lipid nanoparticles can be used to improve the efficacy of the polynucleotides directed protein production as these formulations can increase cell transfection by the polynucleotide; and/or increase the translation of encoded protein. The liposomes, lipoplexes, or lipid nanoparticles can also be used to increase the stability of the polynucleotides.

Liposomes are artificially-prepared vesicles that can primarily be composed of a lipid bilayer and can be used as a delivery vehicle for the administration of pharmaceutical formulations. Liposomes can be of different sizes. A multilamellar vesicle (MLV) can be hundreds of nanometers in diameter, and can contain a series of concentric bilayers separated by narrow aqueous compartments. A small unicellular vesicle (SUV) can be smaller than 50 nm in diameter, and a large unilamellar vesicle (LUV) can be between 50 and 500 nm in diameter. Liposome design can include, but is not limited to, opsonins or ligands to improve the attachment of liposomes to unhealthy tissue or to activate events such as, but not limited to, endocytosis. Liposomes can contain a low or a high pH value in order to improve the delivery of the pharmaceutical formulations.

The formation of liposomes can depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

As a non-limiting example, liposomes such as synthetic membrane vesicles can be prepared by the methods, apparatus and devices described in U.S. Pub. Nos. US20130177638, US20130177637, US20130177636, US20130177635, US20130177634, US20130177633, US20130183375, US20130183373, and US20130183372. In some embodiments, the polynucleotides described herein can be encapsulated by the liposome and/or it can be contained in an aqueous core that can then be encapsulated by the liposome as described in, e.g., Intl. Pub. Nos. WO2012031046, WO2012031043, WO2012030901, WO2012006378, and WO2013086526; and U.S. Pub. Nos. US20130189351, US20130195969 and US20130202684. Each of the references in herein incorporated by reference in its entirety.

In some embodiments, the polynucleotides described herein can be formulated in a cationic oil-in-water emulsion where the emulsion particle comprises an oil core and a cationic lipid that can interact with the polynucleotide anchoring the molecule to the emulsion particle. In some embodiments, the polynucleotides described herein can be formulated in a water-in-oil emulsion comprising a continuous hydrophobic phase in which the hydrophilic phase is dispersed. Exemplary emulsions can be made by the methods described in Intl. Pub. Nos. WO2012006380 and WO201087791, each of which is herein incorporated by reference in its entirety.

In some embodiments, the polynucleotides described herein can be formulated in a lipid-polycation complex. The formation of the lipid-polycation complex can be accomplished by methods as described in, e.g., U.S. Pub. No. US20120178702. As a non-limiting example, the polycation can include a cationic peptide or a polypeptide such as, but not limited to, polylysine, polyornithine and/or polyarginine and the cationic peptides described in Intl. Pub. No. WO2012013326 or U.S. Pub. No. US20130142818. Each of the references is herein incorporated by reference in its entirety.

In some embodiments, the polynucleotides described herein can be formulated in a lipid nanoparticle (LNP) such as those described in Intl. Pub. Nos. WO2013123523, WO2012170930, WO2011127255 and WO2008103276; and U.S. Pub. No. US20130171646, each of which is herein incorporated by reference in its entirety.

Lipid nanoparticle formulations typically comprise one or more lipids. In some embodiments, the lipid is an ionizable lipid (e.g., an ionizable amino lipid), sometimes referred to in the art as an "ionizable cationic lipid". In some embodiments, lipid nanoparticle formulations further comprise other components, including a phospholipid, a structural lipid, and a molecule capable of reducing particle aggregation, for example a PEG or PEG-modified lipid.

Exemplary ionizable lipids include, but not limited to, any one of Compounds 1-342 disclosed herein, DLin-MC3-DMA (MC3), DLin-DMA, DLenDMA, DLin-D-DMA, DLin-K-DMA, DLin-M-C2-DMA, DLin-K-DMA, DLin-KC2-DMA, DLin-KC3-DMA, DLin-KC4-DMA, DLin-C2K-DMA, DLin-MP-DMA, DODMA, 98N12-5, C12-200, DLin-C-DAP, DLin-DAC, DLinDAP, DLinAP, DLin-EG-DMA, DLin-2-DMAP, KL10, KL22, KL25, Octyl-CLinDMA, Octyl-CLinDMA (2R), Octyl-CLinDMA (2S), and any combination thereof. Other exemplary ionizable lipids include, (13Z,16Z)—N,N-dimethyl-3-nonyldocosa-13,16-dien-1-amine (L608), (20Z,23Z)—N,N-dimethylnonacosa-20,23-dien-10-amine, (17Z,20Z)—N,N-dimemyl-hexacosa-17,20-dien-9-amine, (16Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, N,N-dimethyl-1-[(1S,2R)-2-octylcyclopropyl] eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine, and (11E,20Z,23Z)—N,N-dimethylnonacosa-11,20,2-trien-10-amine, and any combination thereof.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin. In some embodiments, the phospholipids are DLPC, DMPC, DOPC, DPPC, DSPC, DUPC, 18:0 Diether PC, DLnPC, DAPC, DHAPC, DOPE, 4ME 16:0 PE, DSPE, DLPE, DLnPE, DAPE, DHAPE, DOPG, and any combination thereof. In some embodiments, the phospholipids are MPPC, MSPC, PMPC, PSPC, SMPC, SPPC, DHAPE, DOPG, and any combination thereof. In some embodiments, the amount of phospholipids (e.g., DSPC) in the lipid composition ranges from about 1 mol % to about 20 mol %.

The structural lipids include sterols and lipids containing sterol moieties. In some embodiments, the structural lipids include cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the amount of the structural lipids (e.g., cholesterol) in the lipid composition ranges from about 20 mol % to about 60 mol %.

The PEG-modified lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG DMPE, PEG-DPPC, or a PEG-DSPE lipid. In some embodiments, the PEG-lipid are 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In some embodiments, the PEG moiety has a size of about 1000, 2000, 5000, 10,000, 15,000 or 20,000 daltons. In some embodiments, the amount of PEG-lipid in the lipid composition ranges from about 0 mol % to about 5 mol %.

In some embodiments, the LNP formulations described herein can additionally comprise a permeability enhancer molecule. Non-limiting permeability enhancer molecules are described in U.S. Pub. No. US20050222064, herein incorporated by reference in its entirety.

The LNP formulations can further contain a phosphate conjugate. The phosphate conjugate can increase in vivo circulation times and/or increase the targeted delivery of the nanoparticle. Phosphate conjugates can be made by the methods described in, e.g., Intl. Pub. No. WO2013033438 or U.S. Pub. No. US20130196948. The LNP formulation can also contain a polymer conjugate (e.g., a water soluble conjugate) as described in, e.g., U.S. Pub. Nos. US20130059360, US20130196948, and US20130072709. Each of the references is herein incorporated by reference in its entirety.

The LNP formulations can comprise a conjugate to enhance the delivery of nanoparticles of the present invention in a subject. Further, the conjugate can inhibit phagocytic clearance of the nanoparticles in a subject. In some embodiments, the conjugate can be a "self" peptide designed from the human membrane protein CD47 (e.g., the "self" particles described by Rodriguez et al, Science 2013 339, 971-975, herein incorporated by reference in its entirety). As shown by Rodriguez et al. the self peptides delayed macrophage-mediated clearance of nanoparticles which enhanced delivery of the nanoparticles.

The LNP formulations can comprise a carbohydrate carrier. As a non-limiting example, the carbohydrate carrier can include, but is not limited to, an anhydride-modified phytoglycogen or glycogen-type material, phytoglycogen octenyl succinate, phytoglycogen beta-dextrin, anhydride-modified phytoglycogen beta-dextrin (e.g., Intl. Pub. No. WO2012109121, herein incorporated by reference in its entirety).

The LNP formulations can be coated with a surfactant or polymer to improve the delivery of the particle. In some embodiments, the LNP can be coated with a hydrophilic coating such as, but not limited to, PEG coatings and/or coatings that have a neutral surface charge as described in U.S. Pub. No. US20130183244, herein incorporated by reference in its entirety.

The LNP formulations can be engineered to alter the surface properties of particles so that the lipid nanoparticles can penetrate the mucosal barrier as described in U.S. Pat. No. 8,241,670 or Intl. Pub. No. WO2013110028, each of which is herein incorporated by reference in its entirety.

The LNP engineered to penetrate mucus can comprise a polymeric material (i.e., a polymeric core) and/or a polymer-vitamin conjugate and/or a tri-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates.

LNP engineered to penetrate mucus can also include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase.

In some embodiments, the mucus penetrating LNP can be a hypotonic formulation comprising a mucosal penetration enhancing coating. The formulation can be hypotonic for the epithelium to which it is being delivered. Non-limiting examples of hypotonic formulations can be found in, e.g., Intl. Pub. No. WO2013110028, herein incorporated by reference in its entirety.

In some embodiments, the polynucleotide described herein is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, MA), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In some embodiments, the polynucleotides described herein are formulated as a solid lipid nanoparticle (SLN), which can be spherical with an average diameter between 10 to 1000 nm. SLN possess a solid lipid core matrix that can solubilize lipophilic molecules and can be stabilized with surfactants and/or emulsifiers. Exemplary SLN can be those as described in Intl. Pub. No. WO2013105101, herein incorporated by reference in its entirety.

In some embodiments, the polynucleotides described herein can be formulated for controlled release and/or targeted delivery. As used herein, "controlled release" refers to a pharmaceutical composition or compound release profile that conforms to a particular pattern of release to effect a therapeutic outcome. In one embodiment, the polynucleotides can be encapsulated into a delivery agent described herein and/or known in the art for controlled release and/or targeted delivery. As used herein, the term "encapsulate" means to enclose, surround or encase. As it relates to the formulation of the compounds of the invention, encapsulation can be substantial, complete or partial. The term "substantially encapsulated" means that at least greater than 50, 60, 70, 80, 85, 90, 95, 96, 97, 98, 99, or greater than 99% of the pharmaceutical composition or compound of the invention can be enclosed, surrounded or encased within the delivery agent. "Partially encapsulation" means that less than 10, 10, 20, 30, 40 50 or less of the pharmaceutical composition or compound of the invention can be enclosed, surrounded or encased within the delivery agent.

Advantageously, encapsulation can be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, or greater than 99% of the pharmaceutical composition or compound of the invention are encapsulated in the delivery agent.

In some embodiments, the polynucleotides described herein can be encapsulated in a therapeutic nanoparticle, referred to herein as "therapeutic nanoparticle polynucleotides." Therapeutic nanoparticles can be formulated by methods described in, e.g., Intl. Pub. Nos. WO2010005740, WO2010030763, WO2010005721, WO2010005723, and WO2012054923; and U.S. Pub. Nos. US20110262491, US20100104645, US20100087337, US20100068285, US20110274759, US20100068286, US20120288541, US20120140790, US20130123351 and US20130230567; and U.S. Pat. Nos. 8,206,747, 8,293,276, 8,318,208 and 8,318,211, each of which is herein incorporated by reference in its entirety.

In some embodiments, the therapeutic nanoparticle polynucleotide can be formulated for sustained release. As used herein, "sustained release" refers to a pharmaceutical composition or compound that conforms to a release rate over a specific period of time. The period of time can include, but is not limited to, hours, days, weeks, months and years. As a non-limiting example, the sustained release nanoparticle of the polynucleotides described herein can be formulated as disclosed in Intl. Pub. No. WO2010075072 and U.S. Pub. Nos. US20100216804, US20110217377, US20120201859 and US20130150295, each of which is herein incorporated by reference in their entirety.

In some embodiments, the therapeutic nanoparticle polynucleotide can be formulated to be target specific, such as those described in Intl. Pub. Nos. WO2008121949, WO2010005726, WO2010005725, WO2011084521 and WO2011084518; and U.S. Pub. Nos. US20100069426, US20120004293 and US20100104655, each of which is herein incorporated by reference in its entirety.

The LNPs can be prepared using microfluidic mixers or micromixers. Exemplary microfluidic mixers can include, but are not limited to, a slit interdigital micromixer including, but not limited to those manufactured by Microinnova (Allerheiligen bei Wildon, Austria) and/or a staggered herringbone micromixer (SHM) (see Zhigaltsev et al., "Bottom-up design and synthesis of limit size lipid nanoparticle systems with aqueous and triglyceride cores using millisecond microfluidic mixing," Langmuir 28:3633-40 (2012); Belliveau et al., "Microfluidic synthesis of highly potent limit-size lipid nanoparticles for in vivo delivery of siRNA," Molecular Therapy-Nucleic Acids. 1:e37 (2012); Chen et al., "Rapid discovery of potent siRNA-containing lipid nanoparticles enabled by controlled microfluidic formulation," J. Am. Chem. Soc. 134(16):6948-51 (2012); each of which is herein incorporated by reference in its entirety). Exemplary micromixers include Slit Interdigital Microstructured Mixer (SIMM-V2) or a Standard Slit Interdigital Micro Mixer (SSIMM) or Caterpillar (CPMM) or Impinging-jet (IJMM) from the Institut für Mikrotechnik Mainz GmbH, Mainz Germany. In some embodiments, methods of making LNP using SHM further comprise mixing at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Pub. Nos. US20040262223 and US20120276209, each of which is incorporated herein by reference in its entirety.

In some embodiments, the polynucleotides described herein can be formulated in lipid nanoparticles using microfluidic technology (see Whitesides, George M., "The Origins and the Future of Microfluidics," Nature 442: 368-373 (2006); and Abraham et al., "Chaotic Mixer for Microchannels," Science 295: 647-651 (2002); each of which is herein incorporated by reference in its entirety). In some embodiments, the polynucleotides can be formulated in lipid nanoparticles using a micromixer chip such as, but not limited to, those from Harvard Apparatus (Holliston, MA) or Dolomite Microfluidics (Royston, UK). A micromixer chip can be used for rapid mixing of two or more fluid streams with a split and recombine mechanism.

In some embodiments, the polynucleotides described herein can be formulated in lipid nanoparticles having a diameter from about 1 nm to about 100 nm such as, but not limited to, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles can have a diameter from about 10 to 500 nm. In one embodiment, the lipid nanoparticle can have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the polynucleotides can be delivered using smaller LNPs. Such particles can comprise a diameter from below 0.1 μm up to 100 nm such as, but not limited to, less than 0.1 μm, less than 1.0 μm, less than 5 μm, less than 10 μm, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, or less than 975 um.

The nanoparticles and microparticles described herein can be geometrically engineered to modulate macrophage and/or the immune response. The geometrically engineered particles can have varied shapes, sizes and/or surface charges to incorporate the polynucleotides described herein for targeted delivery such as, but not limited to, pulmonary delivery (see, e.g., Intl. Pub. No. WO2013082111, herein incorporated by reference in its entirety). Other physical features the geometrically engineering particles can include, but are not limited to, fenestrations, angled arms, asymmetry and surface roughness, charge that can alter the interactions with cells and tissues.

In some embodiment, the nanoparticles described herein are stealth nanoparticles or target-specific stealth nanoparticles such as, but not limited to, those described in U.S. Pub. No. US20130172406, herein incorporated by reference in its entirety. The stealth or target-specific stealth nanoparticles can comprise a polymeric matrix, which can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates, or combinations thereof.

b. Lipidoids

In some embodiments, the compositions or formulations of the present disclosure comprise a delivery agent, e.g., a lipidoid. The polynucleotides described herein (e.g., a polynucleotide comprising a nucleotide sequence encoding a polypeptide) can be formulated with lipidoids. Complexes, micelles, liposomes or particles can be prepared containing these lipidoids and therefore to achieve an effective delivery of the polynucleotide, as judged by the production of an encoded protein, following the injection of a lipidoid formulation via localized and/or systemic routes of administration. Lipidoid complexes of polynucleotides can be administered by various means including, but not limited to, intravenous, intramuscular, or subcutaneous routes.

The synthesis of lipidoids is described in literature (see Mahon et al., Bioconjug. Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

Formulations with the different lipidoids, including, but not limited to penta[3-(1-laurylaminopropionyl)]-triethylenetetramine hydrochloride (TETA-5LAP; also known as 98N12-5, see Murugaiah et al., Analytical Biochemistry, 401:61 (2010)), C12-200 (including derivatives and variants), and MD1, can be tested for in vivo activity. The lipidoid "98N12-5" is disclosed by Akinc et al., Mol Ther. 2009 17:872-879. The lipidoid "C12-200" is disclosed by Love et al., Proc Natl Acad Sci USA. 2010 107:1864-1869 and Liu and Huang, Molecular Therapy. 2010 669-670. Each of the references is herein incorporated by reference in its entirety.

In one embodiment, the polynucleotides described herein can be formulated in an aminoalcohol lipidoid. Aminoalcohol lipidoids can be prepared by the methods described in U.S. Pat. No. 8,450,298 (herein incorporated by reference in its entirety).

The lipidoid formulations can include particles comprising either 3 or 4 or more components in addition to polynucleotides. Lipidoids and polynucleotide formulations comprising lipidoids are described in Intl. Pub. No. WO 2015051214 (herein incorporated by reference in its entirety.

c. Hyaluronidase

In some embodiments, the polynucleotides described herein (e.g., a polynucleotide comprising a nucleotide sequence encoding a polypeptide) and hyaluronidase for injection (e.g., intramuscular or subcutaneous injection). Hyaluronidase catalyzes the hydrolysis of hyaluronan, which is a constituent of the interstitial barrier. Hyaluronidase lowers the viscosity of hyaluronan, thereby increases tissue permeability (Frost, Expert Opin. Drug Deliv. (2007) 4:427-440). Alternatively, the hyaluronidase can be used to increase the number of cells exposed to the polynucleotides administered intramuscularly, or subcutaneously.

d. Nanoparticle Mimics

In some embodiments, the polynucleotides described herein (e.g., a polynucleotide comprising a nucleotide sequence encoding a polypeptide) is encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example, the polynucleotides described herein can be encapsulated in a non-viron particle that can mimic the delivery function of a virus (see e.g., Intl. Pub. No. WO2012006376 and U.S. Pub. Nos. US20130171241 and US20130195968, each of which is herein incorporated by reference in its entirety).

e. Self-Assembled Nanoparticles, or Self-Assembled Macromolecules

In some embodiments, the compositions or formulations of the present disclosure comprise the polynucleotides described herein (e.g., a polynucleotide comprising a nucleotide sequence encoding a polypeptide) in self-assembled nanoparticles, or amphiphilic macromolecules (AMs) for delivery. AMs comprise biocompatible amphiphilic polymers that have an alkylated sugar backbone covalently linked to poly(ethylene glycol). In aqueous solution, the AMs self-assemble to form micelles. Nucleic acid self-assembled nanoparticles are described in Intl. Appl. No. PCT/US2014/027077, and AMs and methods of forming AMs are described in U.S. Pub. No. US20130217753, each of which is herein incorporated by reference in its entirety.

f. Cations and Anions

In some embodiments, the compositions or formulations of the present disclosure comprise the polynucleotides described herein (e.g., a polynucleotide comprising a nucleotide sequence encoding a polypeptide) and a cation or anion, such as $Zn^{2+}$, $Ca^{2+}$, $Cu^{2+}$, $Mg^{2+}$ and combinations thereof. Exemplary formulations can include polymers and a polynucleotide complexed with a metal cation as described in, e.g., U.S. Pat. Nos. 6,265,389 and 6,555,525, each of which is herein incorporated by reference in its entirety. In some embodiments, cationic nanoparticles can contain a combination of divalent and monovalent cations. The delivery of polynucleotides in cationic nanoparticles or in one or more depot comprising cationic nanoparticles can improve polynucleotide bioavailability by acting as a long-acting depot and/or reducing the rate of degradation by nucleases.

g. Amino Acid Lipids

In some embodiments, the compositions or formulations of the present disclosure comprise the polynucleotides described herein (e.g., a polynucleotide comprising a nucleotide sequence encoding a polypeptide) that is formulation with an amino acid lipid. Amino acid lipids are lipophilic compounds comprising an amino acid residue and one or more lipophilic tails. Non-limiting examples of amino acid lipids and methods of making amino acid lipids are described in U.S. Pat. No. 8,501,824. The amino acid lipid formulations can deliver a polynucleotide in releasable form that comprises an amino acid lipid that binds and releases the polynucleotides. As a non-limiting example, the release of the polynucleotides described herein can be provided by an acid-labile linker as described in, e.g., U.S. Pat. Nos. 7,098,032, 6,897,196, 6,426,086, 7,138,382, 5,563,250, and 5,505,931, each of which is herein incorporated by reference in its entirety.

h. Interpolyelectrolyte Complexes

In some embodiments, the compositions or formulations of the present disclosure comprise the polynucleotides described herein (e.g., a polynucleotide comprising a nucleotide sequence encoding a polypeptide) in an interpolyelectrolyte complex. Interpolyelectrolyte complexes are formed when charge-dynamic polymers are complexed with one or more anionic molecules. Non-limiting examples of charge-dynamic polymers and interpolyelectrolyte complexes and methods of making interpolyelectrolyte complexes are described in U.S. Pat. No. 8,524,368, herein incorporated by reference in its entirety.

i. Crystalline Polymeric Systems

In some embodiments, the compositions or formulations of the present disclosure comprise the polynucleotides described herein (e.g., a polynucleotide comprising a nucleotide sequence encoding a polypeptide) in crystalline polymeric systems. Crystalline polymeric systems are polymers with crystalline moieties and/or terminal units comprising crystalline moieties. Exemplary polymers are described in U.S. Pat. No. 8,524,259 (herein incorporated by reference in its entirety).

j. Polymers, Biodegradable Nanoparticles, and Core-Shell Nanoparticles

In some embodiments, the compositions or formulations of the present disclosure comprise the polynucleotides described herein (e.g., a polynucleotide comprising a nucleotide sequence encoding a polypeptide) and a natural and/or synthetic polymer. The polymers include, but not limited to, polyethenes, polyethylene glycol (PEG), poly(l-lysine)(PLL), PEG grafted to PLL, cationic lipopolymer, biodegradable cationic lipopolymer, polyethyleneimine (PEI), cross-linked branched poly(alkylene imines), a polyamine derivative, a modified poloxamer, elastic biodegradable polymer, biodegradable copolymer, biodegradable polyester copolymer, biodegradable polyester copolymer, multiblock copolymers, poly[α-(4-aminobutyl)-L-glycolic acid) (PAGA), biodegradable cross-linked cationic multi-block copolymers, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyureas, polystyrenes, polyamines, polylysine, poly(ethylene imine), poly(serine ester), poly(L-lactide-co-L-lysine), poly(4-hydroxy-L-proline ester), amine-containing polymers, dextran polymers, dextran polymer derivatives or combinations thereof.

Exemplary polymers include, DYNAMIC POLYCONJUGATE® (Arrowhead Research Corp., Pasadena, CA) formulations from MIRUS® Bio (Madison, WI) and Roche Madison (Madison, WI), PHASERX™ polymer formulations such as, without limitation, SMARTT POLYMER TECHNOLOGY™ (PHASERX®, Seattle, WA), DMRI/DOPE, poloxamer, VAXFECTIN® adjuvant from Vical (San Diego, CA), chitosan, cyclodextrin from Calando Pharmaceuticals (Pasadena, CA), dendrimers and poly(lactic-co-glycolic acid) (PLGA) polymers. RONDEL™ (RNAi/Oligonucleotide Nanoparticle Delivery) polymers (Arrowhead Research Corporation, Pasadena, CA) and pH responsive co-block polymers such as PHASERX® (Seattle, WA).

The polymer formulations allow a sustained or delayed release of the polynucleotide (e.g., following intramuscular or subcutaneous injection). The altered release profile for the polynucleotide can result in, for example, translation of an encoded protein over an extended period of time. The polymer formulation can also be used to increase the stability of the polynucleotide. Sustained release formulations can include, but are not limited to, PLGA microspheres, ethylene vinyl acetate (EVAc), poloxamer, GELSITE® (Nanotherapeutics, Inc. Alachua, FL), HYLENEX® (Halozyme Therapeutics, San Diego CA), surgical sealants such as fibrinogen polymers (Ethicon Inc. Cornelia, GA), TISSELL® (Baxter International, Inc. Deerfield, IL), PEG-based sealants, and COSEAL® (Baxter International, Inc. Deerfield, IL).

As a non-limiting example modified mRNA can be formulated in PLGA microspheres by preparing the PLGA microspheres with tunable release rates (e.g., days and weeks) and encapsulating the modified mRNA in the PLGA microspheres while maintaining the integrity of the modified mRNA during the encapsulation process. EVAc are non-biodegradable, biocompatible polymers that are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Durasesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C.

As a non-limiting example, the polynucleotides described herein can be formulated with the polymeric compound of PEG grafted with PLL as described in U.S. Pat. No. 6,177,274. As another non-limiting example, the polynucleotides described herein can be formulated with a block copolymer such as a PLGA-PEG block copolymer (see e.g., U.S. Pub. No. US20120004293 and U.S. Pat. Nos. 8,236,330 and 8,246,968), or a PLGA-PEG-PLGA block copolymer (see e.g., U.S. Pat. No. 6,004,573). Each of the references is herein incorporated by reference in its entirety.

In some embodiments, the polynucleotides described herein can be formulated with at least one amine-containing polymer such as, but not limited to polylysine, polyethylene imine, poly(amidoamine) dendrimers, poly(amine-co-esters) or combinations thereof. Exemplary polyamine polymers and their use as delivery agents are described in, e.g., U.S. Pat. Nos. 8,460,696, 8,236,280, each of which is herein incorporated by reference in its entirety.

In some embodiments, the polynucleotides described herein can be formulated in a biodegradable cationic lipopolymer, a biodegradable polymer, or a biodegradable copolymer, a biodegradable polyester copolymer, a biodegradable polyester polymer, a linear biodegradable copolymer, PAGA, a biodegradable cross-linked cationic multi-block copolymer or combinations thereof as described in, e.g., U.S. Pat. Nos. 6,696,038, 6,517,869, 6,267,987, 6,217,912, 6,652,886, 8,057,821, and 8,444,992; U.S. Pub. Nos. US20030073619, US20040142474, US20100004315, US2012009145 and US20130195920; and Intl Pub. Nos. WO2006063249 and WO2013086322, each of which is herein incorporated by reference in its entirety.

In some embodiments, the polynucleotides described herein can be formulated in or with at least one cyclodextrin polymer as described in U.S. Pub. No. US20130184453. In some embodiments, the polynucleotides described herein can be formulated in or with at least one crosslinked cation-binding polymers as described in Intl. Pub. Nos. WO2013106072, WO2013106073 and WO2013106086. In some embodiments, the polynucleotides described herein can be formulated in or with at least PEGylated albumin polymer as described in U.S. Pub. No. US20130231287. Each of the references is herein incorporated by reference in its entirety.

In some embodiments, the polynucleotides disclosed herein can be formulated as a nanoparticle using a combination of polymers, lipids, and/or other biodegradable agents, such as, but not limited to, calcium phosphate. Components can be combined in a core-shell, hybrid, and/or layer-by-layer architecture, to allow for fine-tuning of the nanoparticle for delivery (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in their entireties). As a non-limiting example, the nanoparticle can comprise a plurality of polymers such as, but not limited to hydrophilic-hydrophobic polymers (e.g., PEG-PLGA), hydrophobic polymers (e.g., PEG) and/or hydrophilic polymers (Intl. Pub. No. WO20120225129, herein incorporated by reference in its entirety).

The use of core-shell nanoparticles has additionally focused on a high-throughput approach to synthesize cationic cross-linked nanogel cores and various shells (Siegwart et al., Proc Natl Acad Sci USA. 2011 108:12996-13001; herein incorporated by reference in its entirety). The complexation, delivery, and internalization of the polymeric nanoparticles can be precisely controlled by altering the chemical composition in both the core and shell components of the nanoparticle. For example, the core-shell nanoparticles can efficiently deliver siRNA to mouse hepatocytes after they covalently attach cholesterol to the nanoparticle.

In some embodiments, a hollow lipid core comprising a middle PLGA layer and an outer neutral lipid layer containing PEG can be used to delivery of the polynucleotides as described herein. In some embodiments, the lipid nanoparticles can comprise a core of the polynucleotides disclosed herein and a polymer shell, which is used to protect the polynucleotides in the core. The polymer shell can be any of the polymers described herein and are known in the art. The polymer shell can be used to protect the polynucleotides in the core.

Core-shell nanoparticles for use with the polynucleotides described herein are described in U.S. Pat. No. 8,313,777 or Intl. Pub. No. WO2013124867, each of which is herein incorporated by reference in their entirety.

k. Peptides and Proteins

In some embodiments, the compositions or formulations of the present disclosure comprise the polynucleotides described herein (e.g., a polynucleotide comprising a nucleotide sequence encoding a polypeptide) that is formulated with peptides and/or proteins to increase transfection of cells by the polynucleotide, and/or to alter the biodistribution of the polynucleotide (e.g., by targeting specific tissues or cell types), and/or increase the translation of encoded protein (e.g., Intl. Pub. Nos. WO2012110636 and WO2013123298. In some embodiments, the peptides can be those described in U.S. Pub. Nos. US20130129726, US20130137644 and US20130164219. Each of the references is herein incorporated by reference in its entirety.

l. Conjugates

In some embodiments, the compositions or formulations of the present disclosure comprise the polynucleotides described herein (e.g., a polynucleotide comprising a nucleotide sequence encoding a polypeptide) that is covalently linked to a carrier or targeting group, or including two encoding regions that together produce a fusion protein (e.g., bearing a targeting group and therapeutic protein or peptide) as a conjugate. The conjugate can be a peptide that selectively directs the nanoparticle to neurons in a tissue or organism, or assists in crossing the blood-brain barrier.

The conjugates include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand can also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

In some embodiments, the conjugate can function as a carrier for the polynucleotide disclosed herein. The conjugate can comprise a cationic polymer such as, but not limited to, polyamine, polylysine, polyalkylenimine, and polyethylenimine that can be grafted to with poly(ethylene glycol). Exemplary conjugates and their preparations are described in U.S. Pat. No. 6,586,524 and U.S. Pub. No. US20130211249, each of which herein is incorporated by reference in its entirety.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as an endothelial cell or bone cell. Targeting groups can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent fructose, or aptamers. The ligand can be, for example, a lipopolysaccharide, or an activator of p38 MAP kinase.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein. As a non-limiting example, the targeting group can be a glutathione receptor (GR)-binding conjugate for targeted delivery across the blood-central nervous system barrier as described in, e.g., U.S. Pub. No. US2013021661012 (herein incorporated by reference in its entirety).

In some embodiments, the conjugate can be a synergistic biomolecule-polymer conjugate, which comprises a long-acting continuous-release system to provide a greater therapeutic efficacy. The synergistic biomolecule-polymer conjugate can be those described in U.S. Pub. No. US20130195799. In some embodiments, the conjugate can be an aptamer conjugate as described in Intl. Pat. Pub. No. WO2012040524. In some embodiments, the conjugate can be an amine containing polymer conjugate as described in U.S. Pat. No. 8,507,653. Each of the references is herein incorporated by reference in its entirety. In some embodiments, the polynucleotides can be conjugated to SMARTT POLYMER TECHNOLOGY® (PHASERX®, Inc. Seattle, WA).

In some embodiments, the polynucleotides described herein are covalently conjugated to a cell penetrating polypeptide, which can also include a signal sequence or a targeting sequence. The conjugates can be designed to have increased stability, and/or increased cell transfection; and/or altered the biodistribution (e.g., targeted to specific tissues or cell types).

In some embodiments, the polynucleotides described herein can be conjugated to an agent to enhance delivery. In some embodiments, the agent can be a monomer or polymer such as a targeting monomer or a polymer having targeting blocks as described in Intl. Pub. No. WO2011062965. In some embodiments, the agent can be a transport agent covalently coupled to a polynucleotide as described in, e.g., U.S. Pat. Nos. 6,835,393 and 7,374,778. In some embodiments, the agent can be a membrane barrier transport enhancing agent such as those described in U.S. Pat. Nos. 7,737,108 and 8,003,129. Each of the references is herein incorporated by reference in its entirety.

Pharmaceutical Compositions

The present disclosure includes pharmaceutical compositions comprising an mRNA or a nanoparticle (e.g., a lipid nanoparticle) described herein, in combination with one or more pharmaceutically acceptable excipient, carrier or diluent. In particular embodiments, the mRNA is present in a nanoparticle, e.g., a lipid nanoparticle. In particular embodiments, the mRNA or nanoparticle is present in a pharmaceutical composition. In various embodiments, the one or more mRNA present in the pharmaceutical composition is encapsulated in a nanoparticle, e.g., a lipid nanoparticle. In particular embodiments, the molar ratio of the first mRNA to the second mRNA is about 1:50, about 1:25, about 1:10, about 1:5, about 1:4, about 1:3, about 1:2, about 1:1, about 2:1, about 3:1, about 4:1, or about 5:1, about 10:1, about 25:1 or about 50:1. In particular embodiments, the molar ratio of the first mRNA to the second mRNA is greater than 1:1.

In some embodiments, a composition described herein comprises an mRNA encoding a polypeptide. In some embodiments, the polypeptide is a therapeutic polypeptide. In some embodiments, the polypeptide is an enzyme. In some embodiments, the polypeptide is an antibody. In some embodiments, the polypeptide comprises an antigen.

Pharmaceutical compositions may optionally include one or more additional active substances, for example, therapeutically and/or prophylactically active substances. Pharmaceutical compositions of the present disclosure may be sterile and/or pyrogen-free. General considerations in the formulation and/or manufacture of pharmaceutical agents may be found, for example, in *Remington: The Science and Practice of Pharmacy* 21$^{st}$ ed., Lippincott Williams & Wilkins, 2005 (incorporated herein by reference in its entirety). In particular embodiments, a pharmaceutical composition comprises an mRNA and a lipid nanoparticle, or complexes thereof.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may include between 0.1% and 100%, e.g., between 0.5% and 70%, between 1% and 30%, between 5% and 80%, or at least 80% (w/w) active ingredient.

The mRNAs of the disclosure can be formulated using one or more excipients to: (1) increase stability; (2) increase cell transfection; (3) permit the sustained or delayed release (e.g., from a depot formulation of the mRNA); (4) alter the biodistribution (e.g., target the mRNA to specific tissues or cell types); (5) increase the translation of a polypeptide encoded by the mRNA in vivo; and/or (6) alter the release profile of a polypeptide encoded by the mRNA in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present disclosure can include, without limitation, lipidoids, liposomes, lipid nanoparticles (e.g., liposomes and micelles), polymers, lipoplexes, core-shell nanoparticles, peptides, proteins, carbohydrates, cells transfected with mRNAs (e.g., for transplantation into a subject), hyaluronidase, nanoparticle mimics and combinations thereof. Accordingly, the formulations of the disclosure can include one or more excipients, each in an amount that together increases the stability of the mRNA, increases cell transfection by the mRNA, increases the expression of a polypeptide encoded by the mRNA, and/or alters the release profile of a mRNA-encoded polypeptide. Further, the mRNAs of the present disclosure may be formulated using self-assembled nucleic acid nanoparticles.

Various excipients for formulating pharmaceutical compositions and techniques for preparing the composition are known in the art (see Remington: *The Science and Practice of Pharmacy*, 21$^{st}$ Edition, A. R. Gennaro, Lippincott, Williams & Wilkins, Baltimore, MD, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition. Excipients may include, for example: antiadherents, antioxidants, binders, coatings, compression aids, disintegrants, dyes (colors), emollients, emulsifiers, fillers (diluents), film formers or coatings, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

In some embodiments, the formulations described herein may include at least one pharmaceutically acceptable salt. Examples of pharmaceutically acceptable salts that may be included in a formulation of the disclosure include, but are not limited to, acid addition salts, alkali or alkaline earth metal salts, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

In some embodiments, the formulations described herein may contain at least one type of polynucleotide. As a non-limiting example, the formulations may contain 1, 2, 3, 4, 5 or more than 5 mRNAs described herein. In some embodiments, the formulations described herein may contain at least one mRNA encoding a polypeptide and at least one nucleic acid sequence such as, but not limited to, an siRNA, an shRNA, a snoRNA, and an miRNA.

Liquid dosage forms for e.g., parenteral administration include, but are not limited to, pharmaceutically acceptable emulsions, microemulsions, nanoemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and/or suspending agents. In certain embodiments for parenteral administration, compositions are mixed with solubilizing agents such as CREMAPHOR®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables. Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In some embodiments, pharmaceutical compositions including at least one mRNA described herein are administered to mammals (e.g., humans). Although the descriptions of pharmaceutical compositions provided herein are principally directed to pharmaceutical compositions which are suitable for administration to humans, it will be understood by the skilled artisan that such compositions are generally suitable for administration to any other animal, e.g., to a non-human mammal. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys. In particular embodiments, a subject is provided with two or more mRNAs described herein. In particular embodiments, the first and second mRNAs are provided to the subject at the same time or at different times, e.g., sequentially. In particular embodiments, the first and second mRNAs are provided to the subject in the same pharmaceutical composition or formulation, e.g., to facilitate uptake of both mRNAs by the same cells.

The present disclosure also includes kits comprising a container comprising a mRNA encoding a polypeptide that enhances an immune response. In another embodiment, the kit comprises a container comprising a mRNA encoding a polypeptide that enhances an immune response, as well as one or more additional mRNAs encoding one or more antigens or interest. In other embodiments, the kit comprises a first container comprising the mRNA encoding a polypeptide that enhances an immune response and a second container comprising one or more mRNAs encoding one or more antigens of interest. In particular embodiments, the mRNAs for enhancing an immune response and the mRNA(s) encoding an antigen(s) are present in the same or different nanoparticles and/or pharmaceutical compositions. In particular embodiments, the mRNAs are lyophilized, dried, or freeze-dried.

Methods And Use

The disclosure provides methods using the mRNAs, compositions, lipid nanoparticles, or pharmaceutical compositions disclosed herein. In some aspects, the mRNAs described herein are used to increase the amount and/or quality of a polypeptide (e.g., a therapeutic polypeptide) encoded by and translated from the mRNA. In some embodiments, the mRNAs described herein are used to reduce the translation of partial, aberrant, or otherwise undesirable open reading frames within the mRNA. In some embodiments, the mRNA described herein are used to initiate translation of a polypeptide (e.g., a therapeutic polypeptide) at a desired initiator codon.

In some embodiments, the methods described herein are useful for increasing the potency of an mRNA encoding a polypeptide. In one embodiment, the disclosure provides a method of inhibiting or reducing leaky scanning of an mRNA by a PIC or ribosome, the method comprising contacting a cell with an mRNA, a composition, a lipid nanoparticle, or a pharmaceutical composition according to the disclosure.

In some embodiments, the disclosure provides a method of increasing an amount of a polypeptide translated from a full open reading frame comprising an mRNA, the method comprising contacting a cell with an mRNA, a composition, a lipid nanoparticle, or a pharmaceutical composition according to the disclosure.

In some embodiments, the disclosure provides a method of increasing potency of a polypeptide translated from an mRNA, the method comprising contacting a cell with an mRNA, a composition, a lipid nanoparticle, or a pharmaceutical composition according to the disclosure.

In some embodiments, the disclosure provides a method of increasing initiation of polypeptide synthesis at or from an initiation codon comprising an mRNA, the method comprising contacting a cell with an mRNA, a composition, a lipid nanoparticle, or a pharmaceutical composition according to the disclosure.

In some embodiments, the disclosure provides a method of inhibiting or reducing initiation of polypeptide synthesis at any codon within an mRNA other than an initiation codon, the method comprising contacting a cell with an mRNA, a composition, a lipid nanoparticle, or a pharmaceutical composition according to the disclosure.

In some embodiments, the disclosure provides a method of inhibiting or reducing an amount of polypeptide translated from any open reading frame within an mRNA other than a full open reading frame, the method comprising contacting a cell with an mRNA, a composition, a lipid nanoparticle, or a pharmaceutical composition according to the disclosure.

In some embodiments, the disclosure provides method of inhibiting or reducing translation of truncated or aberrant translation products from an mRNA, the method comprising contacting a cell with an mRNA, a composition, a lipid nanoparticle, or a pharmaceutical composition according to the disclosure.

In one embodiment, the method comprises administering to the subject a composition of the disclosure (or lipid nanoparticle thereof, or pharmaceutical composition thereof) comprising at least one mRNA construct encoding a polypeptide (e.g., a therapeutic polypeptide)

Compositions of the disclosure are administered to the subject at an effective amount or effective dose. In general, an effective amount of the composition will allow for efficient production of the encoded polypeptide in the cell. Metrics for efficiency may include polypeptide translation (indicated by polypeptide expression), level of mRNA degradation, and immune response indicators.

Therapeutic Methods

The mRNA provided by the disclosure can be used in a variety of clinical or therapeutic applications. In some embodiments, the disclosure provides method of treating a disease, the method comprising administering an mRNA, a composition, a lipid nanoparticle, or a pharmaceutical composition according to the disclosure.

In some embodiments, a subject having a disease is provided with or administered a nanoparticle (e.g., a lipid nanoparticle) comprising the mRNA(s). In further related embodiments, the subject is provided with or administered a pharmaceutical composition of the disclosure to the subject. In particular embodiments, the pharmaceutical composition comprises an mRNA(s) encoding a polypeptide as described herein, or it comprises a nanoparticle comprising the mRNA(s). In particular embodiments, the mRNA(s) is present in a nanoparticle, e.g., a lipid nanoparticle. In particular embodiments, the mRNA(s) or nanoparticle is present in a pharmaceutical composition.

In certain embodiments, the subject in need thereof has been diagnosed with a disease (e.g., cancer) or is considered to be at risk of developing a disease In some embodiments, the disease is, for example, an infectious disease, a cardiovascular disease, a rare genetic disease, or cancer. In some embodiments, the cancer is liver cancer, colorectal cancer, a melanoma cancer, a pancreatic cancer, a NSCLC, a cervical cancer or a head or neck cancer. In some embodiments, the cancer is a hematopoietic cancer. In some embodiments, the cancer is an acute myeloid leukemia, a chronic myeloid leukemia, a chronic myelomonocytic leukemia, a myelodysplastic syndrome (including refractory anemias and refractory cytopenias) or a myeloproliferative neoplasm or disease (including polycythemia vera, essential thrombocytosis and primary myelofibrosis). In other embodiments, the cancer is a blood-based cancer or a hematopoetic cancer. Selectivity for a particular cancer type can be achieved through the combination of use of an appropriate LNP formulation (e.g., targeting specific cell types) in combination with appropriate regulatory site(s) (e.g., microRNAs) engineered into the mRNA constructs.

In some embodiments, the mRNA(s), nanoparticle, or pharmaceutical composition is administered to the patient parenterally. In particular embodiments, the subject is a mammal, e.g., a human. In various embodiments, the subject is provided with an effective amount of the mRNA(s).

The methods of treating cancer can further include treatment of the subject with additional agents that enhance an anti-tumor response in the subject and/or that are cytotoxic to the tumor (e.g., chemotherapeutic agents). Suitable therapeutic agents for use in combination therapy include small molecule chemotherapeutic agents, including protein tyrosine kinase inhibitors, as well as biological anti-cancer agents, such as anti-cancer antibodies, including but not limited to those discussed further below. Combination therapy can include administering to the subject an immune checkpoint inhibitor to enhance anti-tumor immunity, such as PD-1 inhibitors, PD-L1 inhibitors and CTLA-4 inhibitors. Other modulators of immune checkpoints may target OX-40, OX-40L or ICOS. In one embodiment, an agent that modulates an immune checkpoint is an antibody. In another embodiment, an agent that modulates an immune checkpoint is a protein or small molecule modulator. In another embodiment, the agent (such as an mRNA) encodes an antibody modulator of an immune checkpoint. Non-limiting examples of immune checkpoint inhibitors that can be used in combination therapy include pembrolizumab, alemtuzumab, nivolumab, pidilizumab, ofatumumab, rituximab, MEDI0680 and PDR001, AMP-224, PF-06801591, BGB-A317, REGN2810, SHR-1210, TSR-042, affimer, avelumab (MSB0010718C), atezolizumab (MPDL3280A), durvalumab (MEDI4736), BMS936559, ipilimumab, tremelimumab, AGEN1884, MEDI6469 and MOXR0916.

A pharmaceutical composition including one or more mRNAs of the disclosure may be administered to a subject by any suitable route. In some embodiments, compositions of the disclosure are administered by one or more of a variety of routes, including parenteral (e.g., subcutaneous, intracutaneous, intravenous, intraperitoneal, intramuscular, intraarticular, intraarterial, intrasynovial, intrasternal, intrathecal, intralesional, or intracranial injection, as well as any suitable infusion technique), oral, trans- or intra-dermal, interdermal, rectal, intravaginal, topical (e.g., by powders, ointments, creams, gels, lotions, and/or drops), mucosal, nasal, buccal, enteral, vitreal, intratumoral, sublingual, intranasal; by intratracheal instillation, bronchial instillation, and/or inhalation; as an oral spray and/or powder, nasal spray, and/or aerosol, and/or through a portal vein catheter. In some embodiments, a composition may be administered intravenously, intramuscularly, intradermally, intra-arterially, intratumorally, subcutaneously, or by inhalation. In some embodiments, a composition is administered intramuscularly. However, the present disclosure encompasses the delivery of compositions of the disclosure by any appropriate route taking into consideration likely advances in the sciences of drug delivery. In general, the most appropriate route of administration will depend upon a variety of factors including the nature of the pharmaceutical composition including one or more mRNAs (e.g., its stability in various bodily environments such as the bloodstream and gastrointestinal tract), and the condition of the patient (e.g., whether the patient is able to tolerate particular routes of administration).

In certain embodiments, compositions of the disclosure may be administered at dosage levels sufficient to deliver from about 0.0001 mg/kg to about 10 mg/kg, from about 0.001 mg/kg to about 10 mg/kg, from about 0.005 mg/kg to about 10 mg/kg, from about 0.01 mg/kg to about 10 mg/kg, from about 0.1 mg/kg to about 10 mg/kg, from about 1 mg/kg to about 10 mg/kg, from about 2 mg/kg to about 10 mg/kg, from about 5 mg/kg to about 10 mg/kg, from about 0.0001 mg/kg to about 5 mg/kg, from about 0.001 mg/kg to about 5 mg/kg, from about 0.005 mg/kg to about 5 mg/kg, from about 0.01 mg/kg to about 5 mg/kg, from about 0.1 mg/kg to about 5 mg/kg, from about 1 mg/kg to about 5 mg/kg, from about 2 mg/kg to about 5 mg/kg, from about 0.0001 mg/kg to about 1 mg/kg, from about 0.001 mg/kg to about 1 mg/kg, from about 0.005 mg/kg to about 1 mg/kg, from about 0.01 mg/kg to about 1 mg/kg, or from about 0.1 mg/kg to about 1 mg/kg in a given dose, where a dose of 1 mg/kg provides 1 mg of mRNA or nanoparticle per 1 kg of subject body weight. In particular embodiments, a dose of about 0.005 mg/kg to about 5 mg/kg of mRNA or nanoparticle of the disclosure may be administrated.

A dose may be administered one or more times per day, in the same or a different amount, to obtain a desired level of mRNA expression and/or effect (e.g., a therapeutic effect) . The desired dosage may be delivered, for example, three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In some embodiments, a single dose may be administered, for example, prior to or after a surgical procedure or in the instance of an acute disease, disorder, or condition. The specific therapeutically effective, prophylactically effective, or otherwise appropriate dose level for any particular patient will depend upon a variety of factors including the severity and identify of a disorder being treated, if any; the one or more mRNAs employed; the specific composition employed; the age, body weight, general health, sex, and diet of the patient; the time of administration, route of administration, and rate of excretion of the specific pharmaceutical composition employed; the duration of the treatment; drugs used in combination or coincidental with the specific pharmaceutical composition employed; and like factors well known in the medical arts.

An mRNA or composition (e.g., a pharmaceutical composition) of the disclosure may be administered by any route which results in a therapeutically effective outcome. These include, but are not limited to, intradermal, intramuscular, intranasal, and/or subcutaneous administration. The present disclosure provides methods comprising administering RNA compositions and lipid nanoparticles of the disclosure to a subject in need thereof. The exact amount required will vary from subject to subject, depending on the species, age, and general condition of the subject, the severity of the disease, the particular composition, its mode of administration, its mode of activity, and the like. RNA compositions and lipid nanoparticles of the disclosure are typically formulated in dosage unit form for ease of administration and uniformity of dosage. It will be understood, however, that the total daily usage of RNA (e.g., mRNA) compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The effective amount of an RNA composition or lipid nanoparticle of the disclosure, as provided herein, may be as low as 10 µg, administered for example as a single dose or as two 5 µg doses. In some embodiments, the effective amount is a total dose of 10 µg-300 µg. For example, the effective amount may be a total dose of 10 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 110 µg, 120 µg, 130 µg, 140 µg, 150 µg, 160 µg, 170 µg, 180 µg, 190 µg or 200 µg, 210 µg, 220 µg, 230 µg, 240 µg, 250 µg, 260 µg, 270 µg, 280 µg, 290 µg or 300 µg. In some embodiments, the effective amount is a total dose of 10 µg-300 µg. In some embodiments, the effective amount is a total dose of 30 µg-100 µg or 50 µg-200 µg.

In some embodiments, RNA (e.g., mRNA) compositions and lipid nanoparticles may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No. WO2013078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, RNA (e.g., mRNA) compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, RNA (e.g., mRNA) compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, RNA (e.g., mRNA) compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a RNA (e.g., mRNA) composition may be administered three or four times.

In some embodiments, RNA (e.g., mRNA) compositions or lipid nanoparticles comprising the same may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments, the RNA (e.g., mRNA) composition or lipid nanoparticles comprising the same for use in a method of vaccinating a subject is administered the subject a single dosage of between 10 µg/kg and 400 µg/kg of the nucleic acid vaccine in an effective amount to vaccinate the subject. In some embodiments, the RNA composition or lipid nanoparticles comprising the same for use in a method of vaccinating a subject is administered the subject a single dosage of between 10 µg and 400 µg of the nucleic acid vaccine in an effective amount to vaccinate the subject. In some embodiments, a RNA (e.g., mRNA) composition or lipid nanoparticles comprising the same for use in a method of vaccinating a subject is administered to the subject as a single dosage of 25-1000 µg (e.g., a single dosage of mRNA encoding an antigen). In some embodiments, a RNA composition is administered to the subject as a single dosage of 25, 50, 100, 150, 200, 250, 300, 350, 400, 450, 500, 550, 600, 650, 700, 750, 800, 850, 900, 950 or 1000 µg. For example, a RNA composition may be administered to a subject as a single dose of 25-100, 25-500, 50-100, 50-500, 50-1000, 100-500, 100-1000, 250-500, 250-1000, or 500-1000 µg. In some embodiments, a RNA (e.g., mRNA) composition or lipid nanoparticles comprising the same for use in a method of vaccinating a subject is administered to the subject as two dosages, the combination of which equals 25-1000 µg of the RNA (e.g., mRNA) composition.

An RNA (e.g., mRNA) composition or lipid nanoparticles comprising the same described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

In some embodiments, a pharmaceutical composition of the disclosure may be administered in combination with another agent, for example, another therapeutic agent, a prophylactic agent, and/or a diagnostic agent. By "in combination with," it is not intended to imply that the agents must be administered at the same time and/or formulated for delivery together, although these methods of delivery are within the scope of the present disclosure. For example, one or more compositions including one or more different mRNAs may be administered in combination. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of compositions of the disclosure, or imaging, diagnostic, or prophylactic compositions thereof in combination with agents that improve their bioavailability, reduce and/or modify their metabolism, inhibit their excretion, and/or modify their distribution within the body.

Exemplary therapeutic agents that may be administered in combination with the compositions of the disclosure include, but are not limited to, cytotoxic, chemotherapeutic, and other therapeutic agents. Cytotoxic agents may include, for example, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, rachelmycin, and analogs thereof. Radioactive ions may also be used as therapeutic agents and may include, for example, radioactive iodine, strontium, phosphorous, palladium, cesium, iridium, cobalt, yttrium, samarium, and praseodymium. Other therapeutic agents may include, for example, antimetabolites (e.g., methotrexate, 6-mercaptopurine, 6-thioguanine, cytarabine, and 5-fluorouracil, and decarbazine), alkylating agents (e.g., mechlorethamine, thiotepa, chlorambucil, rachelmycin, melphalan, carmustine, lomustine, cyclophosphamide, busulfan, dibromomannitol, streptozotocin, mitomycin C, and cis-dichlorodiamine platinum (II) (DDP), and cisplatin), anthracyclines (e.g., daunorubicin and doxorubicin), antibiotics (e.g., dactinomycin, bleomycin, mithramycin, and anthramycin), and antimitotic agents (e.g., vincristine, vinblastine, taxol, and maytansinoids).

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer may be administered concurrently with a chemotherapeutic agent), or they may achieve different effects (e.g., control of any adverse effects).

Immune checkpoint inhibitors such as pembrolizumab or nivolumab, which target the interaction between programmed death receptor 1/programmed death ligand 1 (PD-1/PD-L1) and PD-L2, have been recently approved for the treatment of various malignancies and are currently being investigated in clinical trials for various cancers including melanoma, head and neck squamous cell carcinoma (HNSCC).

Accordingly, one aspect of the disclosure relates to combination therapy in which a subject is previously treated with a PD-1 antagonist prior to administration of a lipid nanoparticle or composition of the present disclosure. In another aspect, the subject has been treated with a monoclonal antibody that binds to PD-1 prior to administration of a lipid nanoparticle or composition of the present disclosure. In another aspect, the subject has been administered a lipid nanoparticle or composition of the disclosure prior to treatment with an anti-PD-1 monoclonal antibody therapy. In some aspects, the anti-PD-1 monoclonal antibody therapy comprises nivolumab, pembrolizumab, pidilizumab, or any combination thereof. In some aspects, the anti-PD-1 monoclonal antibody comprises pembrolizumab.

In another aspect, the subject has been treated with a monoclonal antibody that binds to PD-L1 prior to administration of a lipid nanoparticle or composition of the present disclosure. In another aspect, the subject is administered a lipid nanoparticle or composition prior to treatment with an anti-PD-L1 monoclonal antibody therapy. In some aspects, the anti-PD-L1 monoclonal antibody therapy comprises durvalumab, avelumab, MEDI473, BMS-936559, aezolizumab, or any combination thereof.

In some aspects, the subject has been treated with a CTLA-4 antagonist prior to treatment with the compositions of present disclosure. In another aspect, the subject has been previously treated with a monoclonal antibody that binds to CTLA-4 prior to administration of a lipid nanoparticle or composition of the present disclosure. In some aspects, the subject has been administered a lipid nanoparticle or composition prior to treatment with an anti-CTLA-4 monoclonal antibody. In some aspects, the anti-CTLA-4 antibody therapy comprises ipilimumab or tremelimumab.

In any of the foregoing or related aspects, the disclosure provides a lipid nanoparticle, and an optional pharmaceutically acceptable carrier, or a pharmaceutical composition for use in treating or delaying progression of cancer in an individual, wherein the treatment comprises administration of the composition in combination with a second composition, wherein the second composition comprises a checkpoint inhibitor polypeptide and an optional pharmaceutically acceptable carrier.

In any of the foregoing or related aspects, the disclosure provides use of a lipid nanoparticle, and an optional pharmaceutically acceptable carrier, in the manufacture of a medicament for treating or delaying progression of cancer in an individual, wherein the medicament comprises the lipid nanoparticle and an optional pharmaceutically acceptable carrier and wherein the treatment comprises administration of the medicament in combination with a composition comprising a checkpoint inhibitor polypeptide and an optional pharmaceutically acceptable carrier.

In any of the foregoing or related aspects, the disclosure provides a kit comprising a container comprising a lipid nanoparticle, and an optional pharmaceutically acceptable carrier, or a pharmaceutical composition, and a package insert comprising instructions for administration of the lipid nanoparticle or pharmaceutical composition for treating or delaying progression of cancer in an individual. In some aspects, the package insert further comprises instructions for administration of the lipid nanoparticle or pharmaceutical composition in combination with a composition comprising a checkpoint inhibitor polypeptide and an optional pharmaceutically acceptable carrier for treating or delaying progression of cancer in an individual.

In any of the foregoing or related aspects, the disclosure provides a kit comprising a medicament comprising a lipid nanoparticle, and an optional pharmaceutically acceptable carrier, or a pharmaceutical composition, and a package insert comprising instructions for administration of the medicament alone or in combination with a composition comprising a checkpoint inhibitor polypeptide and an optional pharmaceutically acceptable carrier for treating or delaying progression of cancer in an individual. In some aspects, the kit further comprises a package insert comprising instructions for administration of the first medicament prior to, current with, or subsequent to administration of the second medicament for treating or delaying progression of cancer in an individual.

In any of the foregoing or related aspects, the disclosure provides a lipid nanoparticle, a composition, or the use thereof, or a kit comprising a lipid nanoparticle or a composition as described herein, wherein the checkpoint inhibitor polypeptide inhibits PD1, PD-L1, CTLA4, or a combination thereof. In some aspects, the checkpoint inhibitor polypeptide is an antibody. In some aspects, the checkpoint inhibitor polypeptide is an antibody selected from an anti-CTLA4 antibody or antigen-binding fragment thereof that specifically binds CTLA4, an anti-PD1 antibody or antigen-binding fragment thereof that specifically binds PD1, an anti-PD-L1 antibody or antigen-binding fragment thereof that specifically binds PD-L1, and a combination thereof. In some aspects, the checkpoint inhibitor polypeptide is an anti-PD-L1 antibody selected from atezolizumab, avelumab, or durvalumab. In some aspects, the checkpoint inhibitor polypeptide is an anti-CTLA-4 antibody selected from tremelimumab or ipilimumab. In some aspects, the checkpoint inhibitor polypeptide is an anti-PD1 antibody selected from nivolumab or pembrolizumab. In some aspects, the checkpoint inhibitor polypeptide is an anti-PD1 antibody, wherein the anti-PD1 antibody is pembrolizumab.

In related aspects, the disclosure provides a method of reducing or decreasing a size of a tumor or inhibiting a tumor growth in a subject in need thereof comprising administering to the subject any of the foregoing or related lipid nanoparticles of the disclosure, or any of the foregoing or related compositions of the disclosure.

In related aspects, the disclosure provides a method inducing an anti-tumor response in a subject with cancer comprising administering to the subject any of the foregoing or related lipid nanoparticles of the disclosure, or any of the foregoing or related compositions of the disclosure. In some aspects, the anti-tumor response comprises a T-cell response. In some aspects, the T-cell response comprises CD8+ T cells.

In some aspects of the foregoing methods, the method further comprises administering a second composition comprising a checkpoint inhibitor polypeptide, and an optional pharmaceutically acceptable carrier. In some aspects, the checkpoint inhibitor polypeptide inhibits PD1, PD-L1, CTLA4, or a combination thereof. In some aspects, the checkpoint inhibitor polypeptide is an antibody. In some aspects, the checkpoint inhibitor polypeptide is an antibody selected from an anti-CTLA4 antibody or antigen-binding fragment thereof that specifically binds CTLA4, an anti-PD1 antibody or antigen-binding fragment thereof that specifically binds PD1, an anti-PD-L1 antibody or antigen-binding fragment thereof that specifically binds PD-L1, and a combination thereof. In some aspects, the checkpoint inhibitor polypeptide is an anti-PD-L1 antibody selected from atezolizumab, avelumab, or durvalumab. In some aspects, the checkpoint inhibitor polypeptide is an anti-CTLA-4 antibody selected from tremelimumab or ipilimumab. In some aspects, the checkpoint inhibitor polypeptide is an anti-PD1 antibody selected from nivolumab or pembrolizumab. In some aspects, the checkpoint inhibitor polypeptide is an anti-PD1 antibody, wherein the anti-PD1 antibody is pembrolizumab.

In some aspects of any of the foregoing or related methods, the composition comprising the checkpoint inhibitor polypeptide is administered by intravenous injection. In some aspects, the composition comprising the checkpoint inhibitor polypeptide is administered once every 2 to 3 weeks. In some aspects, the composition comprising the checkpoint inhibitor polypeptide is administered once every 2 weeks or once every 3 weeks. In some aspects, the composition comprising the checkpoint inhibitor polypeptide is administered prior to, concurrent with, or subsequent to administration of the lipid nanoparticle or pharmaceutical composition thereof.

In any of the foregoing or related aspects, the disclosure provides pharmaceutical composition comprising the lipid nanoparticle, and a pharmaceutically acceptable carrier. In some aspects, the pharmaceutical composition is formulated for intramuscular delivery.

DETAILED DESCRIPTION

Definitions

As used herein, the terms "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Base Composition: As used herein, the term "base composition" refers to the proportion of the total bases of a nucleic acid consisting of guanine+cytosine or thymine (or uracil)+adenine nucleotides.

Base Pair: As used herein, the term "base pair" refers to two nucleobases on opposite complementary nucleic acid strands that interact via the formation of specific hydrogen bonds. As used herein, the term "Watson-Crick base pairing", used interchangeably with "complementary base pairing", refers to a set of base pairing rules, wherein a purine always binds with a pyrimidine such that the nucleobase adenine (A) forms a complementary base pair with thymine (T) and guanine (G) forms a complementary base pair with cytosine (C) in DNA molecules. In RNA molecules, thymine is replaced by uracil (U), which, similar to thymine (T), forms a complementary base pair with adenine (A). The complementary base pairs are bound together by hydrogen bonds and the number of hydrogen bonds differs between base pairs. As in known in the art, guanine (G)-cytosine (C) base pairs are bound by three (3) hydrogen bonds and adenine (A)-thymine (T) or uracil (U) base pairs are bound by two (2) hydrogen bonds. Base pairing interactions that do not follow these rules can occur in natural, non-natural, and synthetic nucleic acids and are referred to herein as "non-Watson-Crick base pairing" or alternatively "non-complementary base pairing".

Codon: As used herein, the term "codon" refers to a sequence of three nucleotides that together form a unit of genetic code in a DNA or RNA molecule. A codon is operationally defined by the initial nucleotide from which translation starts and sets the frame for a run of successive nucleotide triplets, which is known as an "open reading frame" (ORF). For example, the string GGGAAACCC, if read from the first position, contains the codons GGG, AAA, and CCC; if read from the second position, it contains the codons GGA and AAC; and if read from the third position, GAA and ACC. Thus, every nucleic sequence read in its 5'→3' direction comprises three reading frames, each producing a possibly distinct amino acid sequence (in the given example, Gly-Lys-Pro, Gly-Asn, or Glu-Thr, respectively). DNA is double-stranded defining six possible reading frames, three in the forward orientation on one strand and three reverse on the opposite strand. Open reading frames encoding polypeptides are typically defined by a start codon, usually the first AUG codon in the sequence.

Conjugated: As used herein, the term "conjugated," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. In some embodiments, two or more moieties may be conjugated by direct covalent chemical bonding. In other embodiments, two or more moieties may be conjugated by ionic bonding or hydrogen bonding.

Contacting: As used herein, the term "contacting" means establishing a physical connection between two or more entities. For example, contacting a cell with an mRNA or a lipid nanoparticle composition means that the cell and mRNA or lipid nanoparticle are made to share a physical connection. Methods of contacting cells with external entities both in vivo, in vitro, and ex vivo are well known in the biological arts. In exemplary embodiments of the disclosure, the step of contacting a mammalian cell with a composition (e.g., an isolated mRNA, nanoparticle, or pharmaceutical composition of the disclosure) is performed in vivo. For example, contacting a lipid nanoparticle composition and a cell (for example, a mammalian cell) which may be disposed within an organism (e.g., a mammal) may be performed by any suitable administration route (e.g., parenteral administration to the organism, including intravenous, intramuscular, intradermal, and subcutaneous administration). For a cell present in vitro, a composition (e.g., a lipid nanoparticle or an isolated mRNA) and a cell may be contacted, for example, by adding the composition to the culture medium of the cell and may involve or result in transfection. Moreover, more than one cell may be contacted by a nanoparticle composition.

Denaturation: As used herein, the term "denaturation" refers to the process by which the hydrogen bonding between base paired nucleotides in a nucleic acid is disrupted, resulting in the loss of secondary and/or tertiary nucleic acid structure (e.g. the separation of previously annealed strands). Denaturation can occur by the application of an external substance, energy, or biochemical process to a nucleic acid. For example, local denaturation of nucleic acid structure by enzymatic activity occurs when biologically important transactions such as DNA replication, transcription, translation, or DNA repair need to occur. Folded structures (e.g. secondary and tertiary nucleic acid structures) of an mRNA can constitute a barrier to the scanning function of the PIC or the elongation function of the ribosome, resulting in a lower translation rate. During translation initiation, helicase activity provided by eIFs (e.g. eIF4A) can denature or unwind duplexed, double-stranded RNA structure to facilitate PIC scanning.

Epitope Tag: As used herein, the term "epitope tag" refers to an artificial epitope, also known as an antigenic determinant, which is fused to a polypeptide sequence by placing the sequence encoding the epitope in-frame with the coding sequence or open reading frame of a polypeptide. An epitope-tagged polypeptides is considered a fusion protein. Epitope tags are relatively short peptide sequences ranging from about 10-30 amino acids in length. Epitope tags are usually fused to either the N- or C-terminus in order to minimize tertiary structure disruptions that may alter protein function. Epitope tags are reactive to high-affinity antibodies that can be reliably produced in many different species. Exemplary epitope tags include the V5-tag, Myc-tag, HA-tag and 3×FLAG-tag. These tags are useful for detection or purification of fusion proteins by Western blotting, immunofluorescence, or immunoprecipitation techniques.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Identity: As used herein, the term "identity" refers to the overall relatedness between polymeric molecules, e.g., between polynucleotide molecules (e.g., DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in *Computational Molecular Biology*, Lesk, A. M., ed., Oxford University Press, New York, 1988; *Biocomputing: Informatics and Genome Projects*, Smith, D. W., ed., Academic Press, New York, 1993; *Sequence Analysis in Molecular Biology*, von Heinje, G., Academic Press, 1987; *Computer Analysis of Sequence Data*, Part I, Griffin, A. M., and Griffin, H. G., eds., Humana Press, New Jersey, 1994; and *Sequence Analysis Primer*, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., *SIAM J Applied Math.*, 48:1073 (1988); incorporated herein by reference. Techniques for determining identity are codified in publicly available computer programs. Exemplary computer software to determine homology between two sequences include, but are not limited to, GCG program package, Devereux et al., *Nucleic Acids Research,* 12(1): 387,1984, BLASTP, BLASTN, and FASTA, Altschul, S. F. et al., *J. Molec. Biol.,* 215, 403, 1990.

Fragment: A "fragment," as used herein, refers to a portion. For example, fragments of proteins may include polypeptides obtained by digesting full-length protein isolated from cultured cells or obtained through recombinant DNA techniques.

Fusion Protein: The term "fusion protein" means a polypeptide sequence that is comprised of two or more polypeptide sequences linked by a peptide bond(s). "Fusion proteins" that do not occur in nature can be generated using recombinant DNA techniques.

GC-rich: As used herein, the term "GC-rich" refers to the nucleobase composition of a polynucleotide (e.g., mRNA), or any portion thereof (e.g., an RNA element), comprising guanine (G) and/or cytosine (C) nucleobases, or derivatives or analogs thereof, wherein the GC-content is greater than 50%. The term "GC-rich" refers to all, or to a portion, of a polynucleotide, including, but not limited to, a gene, a non-coding region, a 5' UTR, a 3' UTR, an open reading frame, an RNA element, a sequence motif, or any discrete sequence, fragment, or segment thereof which comprises greater than 50% GC-content. In some embodiments of the disclosure, GC-rich polynucleotides, or any portions thereof, are exclusively comprised of guanine (G) and/or cytosine (C) nucleobases.

GC-content: As used herein, the term "GC-content" refers to the percentage of nucleobases in a polynucleotide (e.g., mRNA), or a portion thereof (e.g., an RNA element), that are either guanine (G) and cytosine (C) nucleobases, or derivatives or analogs thereof, (from a total number of possible nucleobases, including adenine (A) and thymine (T) or uracil (U), and derivatives or analogs thereof, in DNA and in RNA). The term "GC-content" refers to all, or to a portion, of a polynucleotide, including, but not limited to, a gene, a non-coding region, a 5' or 3' UTR, an open reading frame, an RNA element, a sequence motif, or any discrete sequence, fragment, or segment thereof.

Genetic code: As used herein, the term "genetic code" refers to the set of rules by which genetic information encoded within genetic material (DNA or RNA sequences) is translated by the ribosome into polypeptides. The code defines how sequences of nucleotide triplets, referred to as "codons", specify which amino acid will be added next during protein synthesis. A three-nucleotide codon in a nucleic acid sequence specifies a single amino acid. The vast majority of genes are encoded with a single scheme of rules referred to as the canonical or standard genetic code, or simply the genetic code, though variant codes (such as in human mitochondria) exist.

Heterologous: As used herein, "heterologous" indicates that a sequence (e.g., an amino acid sequence or the polynucleotide that encodes an amino acid sequence) is not normally present in a given natural polypeptide or polynucleotide. For example, an amino acid sequence that corresponds to a domain or motif of one protein may be heterologous to a second protein.

Hybridization: As used herein, the term "hybridization" refers to the process of a first single-stranded nucleic acid, or a portion, fragment, or region thereof, annealing to a second single-stranded nucleic acid, or a portion, fragment, or region thereof, either from the same or separate nucleic acid molecules, mediated by Watson-Crick base pairing to form a secondary and/or tertiary structure. Complementary strands of linked nucleobases able to undergo hybridization can be from either the same or separate nucleic acids. Due to the thermodynamically favorable hydrogen bonding interaction between complementary base pairs, hybridization is a fundamental property of complementary nucleic acid sequences. Such hybridization of nucleic acids, or a portion or fragment thereof, may occur with "near" or "substantial" complementarity, as well as with exact complementarity.

Initiation Codon: As used herein, the term "initiation codon", used interchangeably with the term "start codon", refers to the first codon of an open reading frame that is translated by the ribosome and is comprised of a triplet of linked adenine-uracil-guanine nucleobases. The initiation codon is depicted by the first letter codes of adenine (A), uracil (U), and guanine (G) and is often written simply as "AUG". Although natural mRNAs may use codons other than AUG as the initiation codon, which are referred to herein as "alternative initiation codons", the initiation codons of polynucleotides described herein use the AUG codon. During the process of translation initiation, the sequence comprising the initiation codon is recognized via complementary base-pairing to the anticodon of an initiator tRNA (Met-tRNA$_i^{Met}$) bound by the ribosome. Open reading frames may contain more than one AUG initiation codon, which are referred to herein as "alternate initiation codons".

The initiation codon plays a critical role in translation initiation. The initiation codon is the first codon of an open reading frame that is translated by the ribosome. Typically, the initiation codon comprises the nucleotide triplet AUG, however, in some instances translation initiation can occur at other codons comprised of distinct nucleotides. The initiation of translation in eukaryotes is a multistep biochemical process that involves numerous protein-protein, protein-RNA, and RNA-RNA interactions between messenger RNA molecules (mRNAs), the 40S ribosomal subunit, other components of the translation machinery (e.g., eukaryotic initiation factors; eIFs). The current model of mRNA translation initiation postulates that the pre-initiation complex (alternatively "43 S pre-initiation complex"; abbreviated as "PIC") translocates from the site of recruitment on the mRNA (typically the 5' cap) to the initiation codon by scanning nucleotides in a 5' to 3' direction until the first AUG codon that resides within a specific translation-promotive nucleotide context (the Kozak sequence) is encountered (Kozak (1989) J Cell Biol 108: 229-241). Scanning by the PIC ends upon complementary base-pairing between nucleotides comprising the anticodon of the initiator Met-tRNA$_i^{Met}$ transfer RNA and nucleotides comprising the initiation codon of the mRNA. Productive base-pairing between the AUG codon and the Met-tRNA$_i^{Met}$ anticodon elicits a series of structural and biochemical events that culminate in the joining of the large 60S ribosomal subunit to the PIC to form an active ribosome that is competent for translation elongation.

Insertion: As used herein, an "insertion" or an "addition" refers to a change in an amino acid or nucleotide sequence resulting in the addition of one or more amino acid residues or nucleotides, respectively, to a molecule as compared to a reference sequence, for example, the sequence found in a naturally-occurring molecule.

Insertion Site: As used herein, an "insertion site" is a position or region of a scaffold polypeptide that is amenable to insertion of an amino acid sequence of a heterologous polypeptide. It is to be understood that an insertion site also may refer to the position or region of the polynucleotide that encodes the polypeptide (e.g., a codon of a polynucleotide that codes for a given amino acid in the scaffold polypeptide). In some embodiments, insertion of an amino acid sequence of a heterologous polypeptide into a scaffold polypeptide has little to no effect on the stability (e.g., conformational stability), expression level, or overall secondary structure of the scaffold polypeptide.

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Kozak Sequence: The term "Kozak sequence" (also referred to as "Kozak consensus sequence") refers to a translation initiation enhancer element to enhance expression of a gene or open reading frame, and which in eukaryotes, is located in the 5' UTR. The Kozak consensus sequence was originally defined as the sequence GCCRCC, where R=a purine, following an analysis of the effects of single mutations surrounding the initiation codon (AUG) on translation of the preproinsulin gene (Kozak (1986) Cell 44:283-292). Polynucleotides disclosed herein comprise a Kozak consensus sequence, or a derivative or modification thereof. (Examples of translational enhancer compositions and methods of use thereof, see U.S. Pat. No. 5,807,707 to Andrews et al., incorporated herein by reference in its entirety; U.S. Pat. No. 5,723,332 to Chernajovsky, incorporated herein by reference in its entirety; U.S. Pat. No. 5,891,665 to Wilson, incorporated herein by reference in its entirety.)

Leaky scanning: As used herein, the term "leaky scanning" refers to a biological phenomenon whereby the PIC bypasses the initiation codon of an mRNA and instead continues scanning downstream until an alternate or alternative initiation codon is recognized. Depending on the frequency of occurrence, the bypass of the initiation codon by the PIC can result in a decrease in translation efficiency. Furthermore, translation from this downstream AUG codon can occur, which will result in the production of an undesired, aberrant translation product that may not be capable of eliciting the desired therapeutic response. In some cases, the aberrant translation product may in fact cause a deleterious response (Kracht et al., (2017) Nat Med 23(4):501-507).

mRNA: As used herein, an "mRNA" refers to a messenger ribonucleic acid. An mRNA may be naturally or non-naturally occurring or synthetic. For example, an mRNA may include modified and/or non-naturally occurring components such as one or more nucleobases, nucleosides, nucleotides, or linkers. An mRNA may include a cap structure, a 5' transcript leader, a 5' untranslated region, an initiator codon, an open reading frame, a stop codon, a chain terminating nucleoside, a stem-loop, a hairpin, a polyA sequence, a polyadenylation signal, and/or one or more cis-regulatory elements. An mRNA may have a nucleotide sequence encoding a polypeptide. Translation of an mRNA, for example, in vivo translation of an mRNA inside a mammalian cell, may produce a polypeptide. Traditionally, the basic components of a natural mRNA molecule include at least a coding region, a 5'-untranslated region (5'-UTR), a 3'UTR, a 5' cap and a polyA sequence.

Modified: As used herein "modified" or "modification" refers to a changed state or a change in composition or structure of a polynucleotide (e.g., mRNA). Polynucleotides may be modified in various ways including chemically, structurally, and/or functionally. For example, polynucleotides may be structurally modified by the incorporation of one or more RNA elements, wherein the RNA element comprises a sequence and/or an RNA secondary structure(s) that provides one or more functions (e.g., translational regulatory activity). Accordingly, polynucleotides of the disclosure may be comprised of one or more modifications (e.g., may include one or more chemical, structural, or functional modifications, including any combination thereof).

Nucleobase: As used herein, the term "nucleobase" (alternatively "nucleotide base" or "nitrogenous base") refers to a purine or pyrimidine heterocyclic compound found in nucleic acids, including any derivatives or analogs of the naturally occurring purines and pyrimidines that confer improved properties (e.g., binding affinity, nuclease resistance, chemical stability) to a nucleic acid or a portion or segment thereof. Adenine, cytosine, guanine, thymine, and uracil are the nucleobases predominately found in natural nucleic acids. Other natural, non-natural, and/or synthetic nucleobases, as known in the art and/or described herein, can be incorporated into nucleic acids.

Nucleoside/Nucleotide: As used herein, the term "nucleoside" refers to a compound containing a sugar molecule (e.g., a ribose in RNA or a deoxyribose in DNA), or derivative or analog thereof, covalently linked to a nucleobase (e.g., a purine or pyrimidine), or a derivative or analog thereof (also referred to herein as "nucleobase"), but lacking an internucleoside linking group (e.g., a phosphate group). As used herein, the term "nucleotide" refers to a nucleoside covalently bonded to an internucleoside linking group (e.g., a phosphate group), or any derivative, analog, or modification thereof that confers improved chemical and/or functional properties (e.g., binding affinity, nuclease resistance, chemical stability) to a nucleic acid or a portion or segment thereof.

Nucleic acid: As used herein, the term "nucleic acid" is used in its broadest sense and encompasses any compound and/or substance that includes a polymer of nucleotides, or derivatives or analogs thereof. These polymers are often referred to as "polynucleotides". Accordingly, as used herein the terms "nucleic acid" and "polynucleotide" are equivalent and are used interchangeably. Exemplary nucleic acids or polynucleotides of the disclosure include, but are not limited to, ribonucleic acids (RNAs), deoxyribonucleic acids (DNAs), DNA-RNA hybrids, RNAi-inducing agents, RNAi agents, siRNAs, shRNAs, mRNAs, modified mRNAs, miRNAs, antisense RNAs, ribozymes, catalytic DNA, RNAs that induce triple helix formation, threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

Nucleic Acid Structure: As used herein, the term "nucleic acid structure" (used interchangeably with "polynucleotide structure") refers to the arrangement or organization of atoms, chemical constituents, elements, motifs, and/or sequence of linked nucleotides, or derivatives or analogs thereof, that comprise a nucleic acid (e.g., an mRNA). The term also refers to the two-dimensional or three-dimensional state of a nucleic acid. Accordingly, the term "RNA structure" refers to the arrangement or organization of atoms, chemical constituents, elements, motifs, and/or sequence of linked nucleotides, or derivatives or analogs thereof, comprising an RNA molecule (e.g., an mRNA) and/or refers to a two-dimensional and/or three dimensional state of an RNA molecule. Nucleic acid structure can be further demarcated into four organizational categories referred to herein as "molecular structure", "primary structure", "secondary structure", and "tertiary structure" based on increasing organizational complexity.

Open Reading Frame: As used herein, the term "open reading frame", abbreviated as "ORF", refers to a segment or region of an mRNA molecule that encodes a polypeptide. The ORF comprises a continuous stretch of non-overlapping, in-frame codons, beginning with the initiation codon and ending with a stop codon, and is translated by the ribosome.

Pre-Initiation Complex: As used herein, the term "pre-initiation complex" (alternatively "43 S pre-initiation complex"; abbreviated as "PIC") refers to a ribonucleoprotein complex comprising a 40S ribosomal subunit, eukaryotic initiation factors (eIF1, eIF1A, eIF3, eIF5), and the eIF2-GTP-Met-tRNA$_i^{Met}$ ternary complex, that is intrinsically capable of attachment to the 5' cap of an mRNA molecule and, after attachment, of performing ribosome scanning of the 5' UTR.

Polypeptide: As used herein, the term "polypeptide" or "polypeptide of interest" refers to a polymer of amino acid residues typically joined by peptide bonds that can be produced naturally (e.g., isolated or purified) or synthetically.

Potency: As used herein, the term "potency" refers to an amount, level or concentration of a substance (e.g., an mRNA) that is required to produce a given response or effect. The potency of a substance may be defined by its $EC_{50}$ value if the substance produces an agonistic response or effect or its $IC_{50}$ value if the substance produces an antagonistic response or effect. As used herein, the term "$EC_{50}$" refers to the concentration of a substance (e.g., an mRNA) which induces a response or effect, either in an in vitro or an in vivo assay, which is 50% of the maximal response or effect, i.e., halfway between the maximal response or effect and the baseline. As used herein, the term "$IC_{50}$" refers to the concentration of a substance (e.g., an mRNA) which inhibits a response or effect, either in an in vitro or an in vivo assay, which is 50% of the maximal response or effect, i.e., halfway between the maximal response or effect and the baseline.

Increase in Potency: As used herein, the term "increase in potency" (e.g., of a substance, for example, an mRNA) refers to a potency which is improved (increased, or enhanced) relative to the potency of a similar or comparable substance for which the potency has not been improved. Increased potency is typically observed as a decrease in the amount, level or concentration of a substance (e.g., an mRNA) required to produce a given response or effect. In some embodiments, an increase in potency can be observed as an improved (increased or enhanced) response or effect, resulting from a given amount, level or concentration of a substance (e.g., an mRNA).

In some embodiments, an increase in potency of an mRNA results from an RNA element (e.g., a G C-rich RNA element located in the 5' UTR of the mRNA) that provides a desired translational regulatory activity. In some embodiments, an increase in potency results from an RNA element (e.g., a G C-rich RNA element located in the 5' UTR of the mRNA) which increases an amount of polypeptide translated from an mRNA. In some embodiments, an increase in the potency of an mRNA results from an RNA element (e.g., a G C-rich RNA element located in the 5' UTR of the mRNA) which increases the number of polypeptide molecules translated per mRNA molecule. In some embodiments, an increase in the potency of an mRNA results from an RNA element (e.g., a G C-rich RNA element located in the 5' UTR of the mRNA) which increases the number of polypeptide molecules translated per mRNA molecule per unit time. In some embodiments, an increase in potency of an mRNA results from an RNA element (e.g., a G C-rich RNA element located in the 5' UTR of the mRNA) which increases an amount of functional polypeptide translated from an mRNA relative to the total amount of polypeptide translated from an mRNA. In some embodiments, an increase in potency of an mRNA results from an RNA element (e.g., a G C-rich RNA element located in the 5' UTR of the mRNA) due to an increase in mRNA translation fidelity by (i) an inhibition or reduction in leaky scanning (ii) an increase in codon decoding fidelity, or (iii) minimizing or inhibiting stop codon read through, or any combination of (i), (ii) and (iii). In some embodiments, an increase in potency of an mRNA results from an RNA element (e.g., a G C-rich RNA element located in the 5' UTR of the mRNA) due to an increase in an amount of functional polypeptide at a particular site or location (e.g., by targeting the polypeptide to a specific site or location in a cell or in the extracellular environment). In some embodiments, an increase in potency of an mRNA results from an RNA element (e.g., a G C-rich RNA element located in the 5' UTR of the mRNA) which increases an amount of polypeptide translated from an mRNA by increasing the half-life of the mRNA.

In some embodiments, the disclosure provides an mRNA comprising a 5' UTR comprising an RNA element that increases the potency of the mRNA. In some embodiments, the RNA element is any one of the GC-rich RNA elements described herein. In some embodiments, the RNA element is any one of the stable RNA secondary structures described herein. In some embodiments, the disclosure provides an mRNA comprising a modification that increases potency of the mRNA. In some embodiments, potency of the mRNA is increased 1-fold, 1.5-fold, 2-fold, 2.5-fold, 3-fold, 3.5-fold, 4-fold, 4.5-fold, 5-fold, 10-fold relative to an mRNA without the modification (e.g., without the RNA element). In some embodiments, the potency of the mRNA molecule is increased by 5%, 10%, 20%, 30%, 40%, 50%, 60%, 70%, 80%, 90%. In some embodiments, the potency of the mRNA molecule is increased by about 5%-10%, by about 10%-20%, by about 20%-40%, by about 40%-60%, by about 60%-80%, by about 90% relative to an mRNA without the modification (e.g., without the RNA element).

RNA element: As used herein, the term "RNA element" refers to a portion, fragment, or segment of an RNA molecule that provides a biological function and/or has biological activity (e.g., translational regulatory activity). Modification of a polynucleotide by the incorporation of one or more RNA elements, such as those described herein, provides one or more desirable functional properties to the modified polynucleotide. RNA elements, as described herein, can be naturally-occurring, non-naturally occurring, synthetic, engineered, or any combination thereof. For example, naturally-occurring RNA elements that provide a regulatory activity include elements found throughout the transcriptomes of viruses, prokaryotic and eukaryotic organisms (e.g., humans). RNA elements in particular eukaryotic mRNAs and translated viral RNAs have been shown to be involved in mediating many functions in cells. Exemplary natural RNA elements include, but are not limited to, translation initiation elements (e.g., internal ribosome entry site (IRES), see Kieft et al., (2001) RNA 7(2):194-206), translation enhancer elements (e.g., the APP mRNA translation enhancer element, see Rogers et al., (1999) J Biol Chem 274(10):6421-6431), mRNA stability elements (e.g., AU-rich elements (AREs), see Garneau et al., (2007) Nat Rev Mol Cell Biol 8(2):113-126), translational repression element (see e.g., Blumer et al., (2002) Mech Dev 110(1-2):97-112), protein-binding RNA elements (e.g., iron-responsive element, see Selezneva et al., (2013) J Mol Biol 425(18):3301-3310), cytoplasmic polyadenylation elements (Villalba et al., (2011) Curr Opin Genet Dev 21(4):452-457), and catalytic RNA elements (e.g., ribozymes, see Scott et al., (2009) Biochim Biophys Acta 1789(9-10):634-641).

Residence time: As used herein, the term "residence time" refers to the time of occupancy of a pre-initiation complex (PIC) or a ribosome at a discrete position or location along an mRNA molecule.

Stable RNA Secondary Structure: As used herein, the term "stable RNA secondary structure" refers to a structure, fold, or conformation adopted by an RNA molecule, or local segment or portion thereof, that is persistently maintained under physiological conditions and characterized by a low free energy state. Typical examples of stable RNA secondary structures include duplexes, hairpins, and stem-loops. Stable RNA secondary structures are known in the art to exhibit various biological activities.

Subject: As used herein, the term "subject" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants. In some embodiments, a subject may be a patient.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of a disease, disorder, and/or condition.

Transcription start site: As used herein, the term "transcription start site" refers to a specific nucleotide in the sense strand of a DNA molecule where transcription by an RNA polymerase initiates and that corresponds to the first nucleotide in the transcript. The transcription start site is typically located downstream of a promoter, which is a region of DNA that initiations transcription. For example, the T7 RNA polymerase initiates transcription at the underlined G in the promoter sequence 5' TAATACGACTCACTATAG 3'. The polymerase then transcribes using the opposite DNA strand as a template. In some embodiments, the transcription start site for a T7 RNA polymerase is referred to as a "T7 start site". The first base in the transcript will be a G. The DNA contacts made by T7 RNA polymerase have been mapped during binding and during the subsequent initiation of transcription. The RNA polymerase alone protects 19 bases in a region from −21 to −3. Synthesis of the trinucleotide r(GGG) expands the length of the sequence protected by the RNA polymerase and stabilizes the complex. The formation of a hexanucleotide mRNA, r(GGGAGA) further extends the protected region, stabilizes the complex, and results in increased transcriptional efficiency (Ikeda and Richardson (1986) Proc Natl Acad Sci 83:3614-3618). The sequence GGGAGA is referred to as a "T7 leader sequence". Accordingly, in some embodiments, the mRNAs provided by the disclosure comprise a 5' UTR comprising a T7 leader sequence at the 5' end of the 5' UTR. In some embodiments, the mRNA of the disclosure comprises a 5' UTR comprising a T7 leader sequence comprising the sequence GGGAGA at the 5' end of the 5' UTR. In some embodiments, the mRNA of the disclosure comprises a 5' UTR comprising a T7 leader sequence comprising the sequence GGGAAA at the 5' end of the 5' UTR. In some embodiments, the mRNA comprises a 5' UTR which does not comprise a T7 leader sequence.

Targeting moiety: As used herein, a "targeting moiety" is a compound or agent that may target a nanoparticle to a particular cell, tissue, and/or organ type.

Therapeutic Agent: The term "therapeutic agent" refers to any agent that, when administered to a subject, has a therapeutic, diagnostic, and/or prophylactic effect and/or elicits a desired biological and/or pharmacological effect.

Translational Regulatory Activity: As used herein, the term "translational regulatory activity" (used interchangeably with "translational regulatory function") refers to a biological function, mechanism, or process that modulates (e.g., regulates, influences, controls, varies) the activity of the translational apparatus, including the activity of the PIC and/or ribosome. In some aspects, the desired translation regulatory activity promotes and/or enhances the translational fidelity of mRNA translation. In some aspects, the desired translational regulatory activity reduces and/or inhibits leaky scanning.

Translation of a polynucleotide comprising an open reading frame encoding a polypeptide can be controlled and regulated by a variety of mechanisms that are provided by various cis-acting nucleic acid structures. For example, naturally-occurring, cis-acting RNA elements that form hairpins or other higher-order (e.g., pseudoknot) intramolecular mRNA secondary structures can provide a translational regulatory activity to a polynucleotide, wherein the RNA element influences or modulates the initiation of polynucleotide translation, particularly when the RNA element is positioned in the 5' UTR close to the 5'-cap structure (Pelletier and Sonenberg (1985) Cell 40(3):515-526; Kozak (1986) Proc Natl Acad Sci 83:2850-2854). Cis-acting RNA elements can also affect translation elongation, being involved in numerous frameshifting events (Namy et al., (2004) Mol Cell 13(2):157-168). Internal ribosome entry sequences (IRES) represent another type of cis-acting RNA element that are typically located in 5' UTRs, but have also been reported to be found within the coding region of naturally-occurring mRNAs (Holcik et al. (2000) Trends Genet 16(10):469-473). In cellular mRNAs, IRES often coexist with the 5'-cap structure and provide mRNAs with the functional capacity to be translated under conditions in which cap-dependent translation is compromised (Gebauer et al., (2012) Cold Spring Harb Perspect Biol 4(7):a012245). Another type of naturally-occurring cis-acting RNA element comprises upstream open reading frames (uORFs). Naturally-occurring uORFs occur singularly or multiply within the 5' UTRs of numerous mRNAs and influence the translation of the downstream major ORF, usually negatively (with the notable exception of GCN4 mRNA in yeast and ATF4 mRNA in mammals, where uORFs serve to promote the translation of the downstream major ORF under conditions of increased eIF2 phosphorylation (Hinnebusch (2005) Annu Rev Microbiol 59:407-450)). Additional exemplary translational regulatory activities provided by components, structures, elements, motifs, and/or specific sequences comprising polynucleotides (e.g., mRNA) include, but are not limited to, mRNA stabilization or destabilization (Baker & Parker (2004) Curr Opin Cell Biol 16(3):293-299), translational activation (Villalba et al., (2011) Curr Opin Genet Dev 21(4):452-457), and translational repression (Blumer et al., (2002) Mech Dev 110(1-2):97-112). Studies have shown that naturally-occurring, cis-acting RNA elements can confer their respective functions when used to modify, by incorporation into, heterologous polynucleotides (Goldberg-Cohen et al., (2002) J Biol Chem 277(16):13635-13640).

Transfect: As used herein, the terms "transfect", "transfection" or "transfecting" refer to the act or method of introducing a molecule, usually a nucleic acid, into a cell.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

Uridine Content: The terms "uridine content" or "uracil content" are interchangeable and refer to the amount of uracil or uridine present in a certain nucleic acid sequence. Uridine content or uracil content can be expressed as an absolute value (total number of uridine or uracil in the sequence) or relative (uridine or uracil percentage respect to the total number of nucleobases in the nucleic acid sequence).

Uridine Modified Sequence: The terms "uridine-modified sequence" refers to a sequence optimized nucleic acid (e.g., a synthetic mRNA sequence) with a different overall or local uridine content (higher or lower uridine content) or with different uridine patterns (e.g., gradient distribution or clustering) with respect to the uridine content and/or uridine patterns of a candidate nucleic acid sequence. In the content of the present disclosure, the terms "uridine-modified sequence" and "uracil-modified sequence" are considered equivalent and interchangeable.

A "high uridine codon" is defined as a codon comprising two or three uridines, a "low uridine codon" is defined as a codon comprising one uridine, and a "no uridine codon" is a codon without any uridines. In some embodiments, a uridine-modified sequence comprises substitutions of high uridine codons with low uridine codons, substitutions of high uridine codons with no uridine codons, substitutions of low uridine codons with high uridine codons, substitutions of low uridine codons with no uridine codons, substitution of no uridine codons with low uridine codons, substitutions of no uridine codons with high uridine codons, and combinations thereof. In some embodiments, a high uridine codon can be replaced with another high uridine codon. In some embodiments, a low uridine codon can be replaced with another low uridine codon. In some embodiments, a no uridine codon can be replaced with another no uridine codon. A uridine-modified sequence can be uridine enriched or uridine rarefied.

Uridine Enriched: As used herein, the terms "uridine enriched" and grammatical variants refer to the increase in uridine content (expressed in absolute value or as a percentage value) in a sequence optimized nucleic acid (e.g., a synthetic mRNA sequence) with respect to the uridine content of the corresponding candidate nucleic acid sequence. Uridine enrichment can be implemented by substituting codons in the candidate nucleic acid sequence with synonymous codons containing less uridine nucleobases. Uridine enrichment can be global (i.e., relative to the entire length of a candidate nucleic acid sequence) or local (i.e., relative to a subsequence or region of a candidate nucleic acid sequence).

Uridine Rarefied: As used herein, the terms "uridine rarefied" and grammatical variants refer to a decrease in uridine content (expressed in absolute value or as a percentage value) in an sequence optimized nucleic acid (e.g., a synthetic mRNA sequence) with respect to the uridine content of the corresponding candidate nucleic acid sequence. Uridine rarefication can be implemented by substituting codons in the candidate nucleic acid sequence with synonymous codons containing less uridine nucleobases. Uridine rarefication can be global (i.e., relative to the entire length of a candidate nucleic acid sequence) or local (i.e., relative to a subsequence or region of a candidate nucleic acid sequence).

OTHER EMBODIMENTS

E1. A modified messenger RNA (mmRNA), wherein the mmRNA comprises: a 5'untranslated region (UTR), an initiation codon, a full open reading frame encoding a polypeptide, a 3' UTR, and at least one modification, wherein the modification provides a translational regulatory activity selected from:
  (a) increasing residence time of a 43S pre-initiation complex (PIC) or ribosome at, or proximal to, the initiation codon;
  (b) increasing initiation of polypeptide synthesis at or from the initiation codon;
  (c) increasing an amount of polypeptide translated from the full open reading frame;
  (d) increasing fidelity of initiation codon decoding by the PIC or ribosome;
  (e) inhibiting or reducing leaky scanning by the PIC or ribosome;
  (f) decreasing a rate of decoding the initiation codon by the PIC or ribosome;
  (g) inhibiting or reducing initiation of polypeptide synthesis at any codon within the mmRNA other than the initiation codon;
  (h) inhibiting or reducing the amount of polypeptide translated from any open reading frame within the mmRNA other than the full open reading frame;
  (i) inhibiting or reducing the production of aberrant translation products; and
a combination of any of (a)-(i).

E2. The mmRNA of embodiment 1, wherein the at least one modification is a structural modification selected from: a RNA element, a GC-rich RNA element, a viral RNA element, a protein-binding RNA element, a translation initiation element, a translation enhancer element, a translation fidelity enhancing element, an mRNA nuclear export element, a codon optimized open reading frame, or a modification of base composition.

E3. The mmRNA of embodiment 1, wherein the at least one modification is a chemical modification selected from: one or more chemically modified nucleotides, one or more deoxyribonucleotides, or one or more chemical modifications to the mmRNA backbone.

E4. The mmRNA of any of embodiments 1-3, wherein the 5' UTR comprises the at least one modification.

E5. The mmRNA of any of embodiments 1-4, wherein the initiation codon comprises the at least one modification.

E6. The mmRNA of any of embodiments 1-5, wherein the full open reading frame encoding a polypeptide comprises the at least one modification.

E7. The mmRNA of any of embodiments 1-6, wherein the 3' UTR comprises the at least one modification.

E8. The mmRNA of any of embodiments 1-7, wherein the at least one modification is a GC-rich RNA element comprising a sequence of linked nucleotides, or derivatives or analogs thereof, located upstream of a Kozak consensus sequence in the 5' UTR.

E9. The mmRNA of embodiment 8, wherein the GC-rich RNA element is located about 30, about 25, about 20, about 15, about 10, or about 5 nucleotides upstream of a Kozak consensus sequence in the 5' UTR.

E10. The mmRNA of embodiment 8, wherein the GC-rich RNA element is located about 20, about 15, about 10 or about 5 nucleotides upstream of a Kozak consensus sequence in the 5' UTR.

E11. The mmRNA of embodiment 8, wherein the GC-rich RNA element is located about 5, about 4, about 3, about 2, or about 1 nucleotide upstream of a Kozak consensus sequence in the 5' UTR.

E12. The mmRNA of embodiment 8, wherein the GC-rich RNA element is located about 15-30, about 15-20, about 15-25, about 10-15, or about 5-10 nucleotides upstream of a Kozak consensus sequence in the 5' UTR.

E13. The mmRNA of embodiment 8, wherein the GC-rich RNA element is upstream of and immediately adjacent to a Kozak consensus sequence in the 5' UTR.

E14. The mmRNA of any one of embodiments 8-13, wherein the GC-rich RNA element comprises a sequence of about 30, about 20-30, about 20, about 10-20, about 15, about 10-15, about 15, 14, 13, 12, 11, 10, 9, 8, 7, 6, 5, 4, or 3 nucleotides, or derivatives or analogs thereof, linked in any order, wherein the sequence is about 70% cytosine, about 60%-70% cytosine, about 60% cytosine, about 50%-60% cytosine, about 50% cytosine, about 40%-50% cytosine, about 40% cytosine, about 30%-40% cytosine, about 30% cytosine.

E15. The mmRNA of any one of embodiments 8-13, wherein the GC-rich RNA element comprises a sequence of 3 nucleotides, or derivatives or analogs thereof, linked in any order, wherein the sequence is >50% cytosine.

E16. The mmRNA of any one of embodiments 8-13, wherein the GC-rich RNA element comprises a sequence of 4 nucleotides, or derivatives or analogs thereof, linked in any order, wherein the sequence is >50% cytosine.

E17. The mmRNA of any one of embodiments 8-13, wherein the GC-rich RNA element comprises a sequence of 5 nucleotides, or derivatives or analogs thereof, linked in any order, wherein the sequence is >50% cytosine.

E18. The mmRNA of any one of embodiments 8-13, wherein the GC-rich RNA element comprises a sequence of 6 nucleotides, or derivatives or analogs thereof, linked in any order, wherein the sequence is >50% cytosine.

E19. The mmRNA of any one of embodiments 8-13, wherein the GC-rich RNA element comprises a sequence of 7 nucleotides, or derivatives or analogs thereof, linked in any order, wherein the sequence is >50% cytosine.

E20. The mmRNA of any one of embodiments 8-13, wherein the GC-rich RNA element comprises a sequence of 8 nucleotides, or derivatives or analogs thereof, linked in any order, wherein the sequence is >50% cytosine.

E21. The mmRNA of any one of embodiments 8-13, wherein the GC-rich RNA element comprises a sequence of 9 nucleotides, or derivatives or analogs thereof, linked in any order, wherein the sequence is >50% cytosine.

E22. The mmRNA of any one of embodiments 8-13, wherein the GC-rich RNA element comprises a sequence of 10 nucleotides, or derivatives or analogs thereof, linked in any order, wherein the sequence is >50% cytosine.

E23. The mmRNA of any one of embodiments 8-13, wherein the GC-rich RNA element comprises a sequence of 11 nucleotides, or derivatives or analogs thereof, linked in any order, wherein the sequence is >50% cytosine.

E24. The mmRNA of any one of embodiments 8-13, wherein the GC-rich RNA element comprises a sequence of 12 nucleotides, or derivatives or analogs thereof, linked in any order, wherein the sequence is >50% cytosine.

E25. The mmRNA of any one of embodiments 8-13, wherein the GC-rich RNA element comprises a sequence of 13 nucleotides, or derivatives or analogs thereof, linked in any order, wherein the sequence is >50% cytosine.

E26. The mmRNA of any one of embodiments 8-13, wherein the GC-rich RNA element comprises a sequence of 14 nucleotides, or derivatives or analogs thereof, linked in any order, wherein the sequence is >50% cytosine.

E27. The mmRNA of any one of embodiments 8-13, wherein the GC-rich RNA element comprises a sequence of 15 nucleotides, or derivatives or analogs thereof, linked in any order, wherein the sequence is >50% cytosine.

E28. The mmRNA of any one of embodiments 8-13, wherein the GC-rich RNA element comprises a sequence of 16 nucleotides, or derivatives or analogs thereof, linked in any order, wherein the sequence is >50% cytosine.

E29. The mmRNA of any one of embodiments 8-13, wherein the GC-rich RNA element comprises a sequence of 17 nucleotides, or derivatives or analogs thereof, linked in any order, wherein the sequence is >50% cytosine.

E30. The mmRNA of any one of embodiments 8-13, wherein the GC-rich RNA element comprises a sequence of 18 nucleotides, or derivatives or analogs thereof, linked in any order, wherein the sequence is >50% cytosine.

E31. The mmRNA of any one of embodiments 8-13, wherein the GC-rich RNA element comprises a sequence of 19 nucleotides, or derivatives or analogs thereof, linked in any order, wherein the sequence is >50% cytosine.

E32. The mmRNA of any one of embodiments 8-13, wherein the GC-rich RNA element comprises a sequence of 20 nucleotides, or derivatives or analogs thereof, linked in any order, wherein the sequence is >50% cytosine.

E33. The mmRNA of any one of embodiments 8-13, wherein the GC-rich RNA element comprises a sequence of about 3-30 guanine and cytosine nucleotides, or derivatives or analogues thereof, wherein the sequence comprises a repeating GC-motif.

E34. The mmRNA of embodiment 33, wherein the repeating GC-motif is $[CCG]_n$, wherein n=1 to 10.

E35. The mmRNA of embodiment 33, wherein the repeating GC-motif is $[CCG]_n$, where n=1 to 5.

E36. The mmRNA of embodiment 33, wherein the repeating GC-motif is $[CCG]_n$, where n=3.

E37. The mmRNA of embodiment 33, wherein the repeating GC-motif is $[CCG]_n$, where n=2.

E38. The mmRNA of embodiment 33, wherein the repeating GC-motif is $[CCG]_n$, where n=1.

E39. The mmRNA of embodiment 33, wherein the repeating GC-motif is $[GCC]_n$, where n=1 to 10.

E40. The mmRNA of embodiment 33, wherein the repeating GC-motif is $[GCC]_n$, where n=1 to 5.

E41. The mmRNA of embodiment 33, wherein the repeating GC-motif is $[GCC]_n$, where n=3.

E42. The mmRNA of embodiment 33, wherein the repeating GC-motif is $[GCC]_n$, where n=2.

E43. The mmRNA of embodiment 33, wherein the repeating GC-motif is $[GCC]_n$, where n=1.

E44. The mmRNA of any one of embodiments 8-13, wherein the sequence of the GC-rich RNA element comprises the sequence of EK1 [CCCGCC] (SEQ ID NO: 9) as set forth in Table 1.

E45. The mmRNA of any one of embodiments 8-13, wherein the sequence of the GC-rich RNA element comprises the sequence of EK2 [GCCGCC] (SEQ ID NO: 10) as set forth in Table 1.

E46. The mmRNA of any one of embodiments 8-13, wherein the sequence of the GC-rich RNA element comprises the sequence of EK3 [CCGCCG] (SEQ ID NO: 11) as set forth in Table 1.

E47. The mmRNA of any one of embodiments 8-13, wherein the sequence of the GC-rich RNA element comprises the sequence of V1 [CCCCGGCGCC] (SEQ ID NO: 2) as set forth in Table 1.

E48. The mmRNA of any one of embodiments 8-13, wherein the sequence of the GC-rich RNA element comprises the sequence of V2 [CCCCGGC] (SEQ ID NO: 3) as set forth in Table 1.

E49. The mmRNA of any one of embodiments 8-13, wherein the sequence of the GC-rich RNA element comprises the sequence of CG1 [GCGCCCCGCGGCGCCCCGCG] (SEQ ID NO: 4) as set forth in Table 1.

E50. The mmRNA of any one of embodiments 8-13, wherein the sequence of the GC-rich RNA element comprises the sequence of CG2 [CCCGCCCGCCCCGCCCCGCC] (SEQ ID NO: 5) as set forth in Table 1.

E51. The mmRNA of any one of embodiments 1-7, wherein the at least one modification is a GC-rich RNA element comprising a stable RNA secondary structure located upstream of a Kozak consensus sequence in the 5' UTR.

E52. The mmRNA of embodiment 51, wherein the GC-rich RNA element comprising a stable RNA secondary structure is located about 30, about 25, about 20, about 15, about 10, or about 5 nucleotides upstream of a Kozak consensus sequence in the 5' UTR.

E53. The mmRNA of embodiment 51, wherein the GC-rich RNA element comprising a stable RNA secondary structure is located about 20, about 15, about 10 or about 5 nucleotides upstream of a Kozak consensus sequence in the 5' UTR.

E54. The mmRNA of embodiment 51, wherein the GC-rich RNA element comprising a stable RNA secondary structure is located about 5, about 4, about 3, about 2, or about 1 nucleotide upstream of a Kozak consensus sequence in the 5' UTR.

E55. The mmRNA of embodiment 51, wherein the GC-rich RNA element comprising a stable RNA secondary structure is located about 15-30, about 15-20, about 15-25, about 10-15, or about 5-10 nucleotides upstream of a Kozak consensus sequence in the 5' UTR.

E56. The mmRNA of embodiment 51, wherein the GC-rich RNA element comprising a stable RNA secondary structure is located upstream of and immediately adjacent to a Kozak consensus sequence in the 5' UTR.

E57. The mmRNA of any one of embodiments 1-7, wherein the at least one modification is a GC-rich RNA element comprising a stable RNA secondary structure located downstream of the initiation codon.

E58. The mmRNA of embodiment 57, wherein the GC-rich RNA element comprising a stable RNA secondary structure is located about 30, about 25, about 20, about 15, about 10, or about 5 nucleotides downstream of the initiation codon.

E59. The mmRNA of embodiment 57, wherein the GC-rich RNA element comprising a stable RNA secondary structure is located about 20, about 15, about 10 or about 5 nucleotides downstream of the initiation codon.

E60. The mmRNA of embodiment 57, wherein the GC-rich RNA element comprising a stable RNA secondary structure is located about 5, about 4, about 3, about 2, about 1 nucleotide downstream of the initiation codon.

E61. The mmRNA of embodiment 57, wherein the GC-rich RNA element comprising a stable RNA secondary structure is located about 15-30, about 15-20, about 15-25, about 10-15, or about 5-10 nucleotides downstream of the initiation codon.

E62. The mmRNA of embodiment 57, wherein the GC-rich RNA element comprising a stable RNA secondary structure is located 20, 19, 18, 17, 16, 15, 14, 13, 12, 11, or 10 nucleotides downstream of the initiation codon.

E63. The mmRNA of embodiment 57, wherein the GC-rich RNA element comprising a stable RNA secondary structure is located 15 nucleotides downstream of the initiation codon.

E64. The mmRNA of embodiment 57, wherein the GC-rich RNA element comprising a stable RNA secondary structure is located 14 nucleotides downstream of the initiation codon.

E64. The mmRNA of embodiment 57, wherein the GC-rich RNA element comprising a stable RNA secondary structure is located 13 nucleotides downstream of the initiation codon.

E66. The mmRNA of embodiment 57, wherein the GC-rich RNA element comprising a stable RNA secondary structure is located 12 nucleotides downstream of the initiation codon.

E67. The mmRNA of any one of embodiments 1-7, wherein the at least one modification is a GC-rich RNA element comprising a stable RNA secondary structure located upstream of the initiation codon in the 5' UTR.

E68. The mmRNA of embodiments 67, wherein the GC-rich RNA element comprising a stable RNA secondary structure is located about 40, about 35, about 30, about 25, about 20, about 15, about 10, or about 5 nucleotides upstream of the initiation codon.

E69. The mmRNA of embodiment 67, wherein the GC-rich RNA element comprising a stable RNA secondary structure is located about 20, about 15, about 10 or about 5 nucleotides upstream of the initiation codon.

E70. The mmRNA of embodiment 67, wherein the GC-rich RNA element comprising a stable RNA secondary structure is located about 5, about 4, about 3, about 2, about 1 nucleotide upstream of the initiation codon.

E71. The mmRNA of embodiment 67, wherein the GC-rich RNA element comprising a stable RNA secondary structure is located about 15-40, about 15-30, about 15-20, about 15-25, about 10-15, or about 5-10 nucleotides upstream of the initiation codon.

E72. The mmRNA of any one of embodiments 1-7, wherein the at least one modification is a GC-rich RNA element comprising a stable RNA secondary structure, wherein the stable RNA secondary structure comprises the initiation codon and one or more additional nucleotides upstream, downstream, or upstream and downstream of the initiation codon.

E73. The mmRNA of any one of embodiments 51-72, wherein the sequence of the GC-rich RNA element comprising a stable RNA secondary structure comprises the sequence of SL1 [CCGCGGCGCCCCGCGG] (SEQ ID NO: 28) as set forth in Table 1.

E74. The mmRNA of any one of embodiments 51-72, wherein the sequence of the GC-rich RNA element comprising a stable RNA secondary structure comprises the sequence of SL2 [GCGCGCAUAUAGCGCGC] (SEQ ID NO: 29) as set forth in Table 1.

E75. The mmRNA of any one of embodiments 51-72, wherein the sequence of the GC-rich RNA element comprising a stable RNA secondary structure comprises the sequence of SL3 [CATGGTGGCGGCCCGCCGCCAC-CATG] (SEQ ID NO: 30) as set forth in Table 1.

E76. The mmRNA of any one of embodiments 51-72, wherein the sequence of the GC-rich RNA element comprising a stable RNA secondary structure comprises the sequence of SL4 [CATGGTGGCCCGCCGCCACCATG] (SEQ ID NO: 31) as set forth in Table 1.

E77. The mmRNA of any one of embodiments 51-72, wherein the sequence of the GC-rich RNA element comprising a stable RNA secondary structure comprises the sequence of SL5 [CATGGTGCCCGCCGCCACCATG] (SEQ ID NO: 32) as set forth in Table 1.

E78. The mmRNA of any one of the preceding embodiments, wherein the stable RNA secondary structure is a hairpin or a stem-loop.

E79. The mmRNA of any of the preceding embodiments, wherein the stable RNA secondary structure has a deltaG of about −30 kcal/mol, about −20 to −30 kcal/mol, about −20 kcal/mol, about −10 to −20 kcal/mol, about −10 kcal/mol, about −5 to ~10 kcal/mol.

E80. The mmRNA of any one of embodiments 1-7, wherein the at least one modification is one or more chemically modified nucleotides, wherein the sequence comprising the initiation codon comprises one or more modified nucleotides that increases binding affinity with the initiator Met-tRNA$_i^{Met}$.

E81. The mmRNA of embodiment 80, wherein the one or more chemically modified nucleotides comprises 2-thiouridine.

E82. The mmRNA of embodiment 80, wherein the one or more chemically modified nucleotides comprises 2'-O-methyl-2-thiouridine.

E83. The mmRNA of embodiment 80, wherein the one or more chemically modified nucleotides comprises 2-selenouridine.

E84. The mmRNA of embodiment 80, wherein the one or more chemically modified nucleotides comprises 2'-O-methyl ribose.

E85. The mmRNA of embodiment 80, wherein the one or more chemically modified nucleotides comprises a modified nucleotide in which the ribose moiety is modified with an extra bridge connecting the 2' oxygen and 4' carbon.

E86. The mmRNA of embodiment 80, wherein the one or more chemically modified nucleotides comprises inosine.

E87. The mmRNA of embodiment 80, wherein the one or more chemically modified nucleotides comprises 2-methylguanosine.

E88. The mmRNA of embodiment 80, wherein the one or more chemically modified nucleotides comprises 6-methyladenosine.

E89. The mmRNA of embodiment 80, wherein the one or more chemically modified nucleotides comprises a deoxyribonucleotide.

E90. The mmRNA of any of the preceding embodiments, wherein the mmRNA comprises:
  (i) a first polynucleotide, wherein the first polynucleotide is chemically synthesized, and wherein the first polynucleotide comprises a 5' UTR, an initiation codon, and at least one modification, and;
  (ii) a second polynucleotide, wherein the second polynucleotide is synthesized by in vitro translation, and, wherein the second polynucleotide comprises a full open reading frame encoding a polypeptide, and a 3' UTR.

E91. The mmRNA of embodiment 90, wherein the first polynucleotide and the second polynucleotide are chemically cross-linked.

E92. The mmRNA of embodiment 90, wherein the first polynucleotide and the second polynucleotide are enzymatically ligated.

E93. The mmRNA of embodiment 90-92, wherein the first polynucleotide and the second polynucleotide are operably linked.

E94. A modified mRNA comprising a 5' UTR, an initiation codon, a full open reading frame encoding a polypeptide, and a 3' UTR, wherein the 5' UTR comprises the sequence of the V1-UTR [GGGAAATAAGAGAGAAAAGAAGAGT AAGAAGAAATATAAGACCCCGGCGCCGCCACC] (SEQ ID NO: 34) as set forth in Table 1.

E95. A modified mRNA comprising a 5' UTR, an initiation codon, a full open reading frame encoding a polypeptide, and a 3' UTR, wherein the 5' UTR comprises the sequence of the V2-UTR [GGGAAATAAGAGAGAAAAGAAGAGT AAGAAGAAATATAAGACCCCGGCGCCACC] (SEQ ID NO: 54) as set forth in Table 1.

E96. A modified mRNA comprising a 5' UTR, an initiation codon, a full open reading frame encoding a polypeptide, and a 3' UTR, wherein the 5' UTR comprises the sequence of the CG1-UTR [GGGAAATAAGAGAGAAA AGAAGAGTAAGAAGAAATATAAGAGCGCCCCGCGG CGCCCCGCGGCCACC] (SEQ ID NO: 73) as set forth in Table 1.

E97. A modified mRNA comprising a 5' UTR, an initiation codon, a full open reading frame encoding a polypeptide, and a 3' UTR, wherein the 5' UTR comprises the sequence of the CG2-UTR [GGGAAATAAGAGAGA AAAGAAGAGTAAGAAGAAATATAA- GACCCGCCCGCCCCGCCCCGCCGCCACC] (SEQ ID NO: 92) as set forth in Table 1.

E98. A modified mRNA comprising a 5' UTR, an initiation codon, a full open reading frame encoding a polypeptide, and a 3' UTR, wherein the 5' UTR comprises the sequence of the KT1-UTR [GGGCCCGCCGCCAAC] (SEQ ID NO: 472) as set forth in Table 1.

E99. A modified mRNA comprising a 5' UTR, an initiation codon, a full open reading frame encoding a polypeptide, and a 3' UTR, wherein the 5' UTR comprises the sequence of the KT2-UTR [GGGCCCGCCGCCACC] (SEQ ID NO: 473) as set forth in Table 1.

E100. A modified mRNA comprising a 5' UTR, an initiation codon, a full open reading frame encoding a polypeptide, and a 3' UTR, wherein the 5' UTR comprises the sequence of the KT3-UTR [GGGCCCGCCGCCGAC] (SEQ ID NO: 474) as set forth in Table 1.

E101. A modified mRNA comprising a 5' UTR, an initiation codon, a full open reading frame encoding a polypeptide, and a 3' UTR, wherein the 5' UTR comprises the sequence of the KT4-UTR [GGGCCCGCCGCCGCC] (SEQ ID NO: 475) as set forth in Table 1.

E102. A method of isolating/identifying a modification having translational regulatory activity, the method comprising:
  (i) synthesizing a $1^{st}$ control mRNA comprising
    (a) a polynucleotide sequence comprising an open reading frame encoding eGFP, and; an $1^{st}$ AUG codon upstream of, in-frame, and operably linked to, the open reading frame encoding eGFP, and; a coding sequence for a 3×FLAG epitope tag upstream of, in-frame, and operably linked to the $1^{st}$ AUG codon, and; a $2^{nd}$ AUG codon upstream of, in-frame, and operably linked to, the coding sequence for the 3×FLAG epitope tag, and; a coding sequence for a V5 epitope tag upstream of, in-frame, and operably linked to the $2^{nd}$ AUG codon, and; a $3^{rd}$ AUG codon upstream of, in-frame, and operably linked to, the coding sequence for the V5 epitope tag, and; a 5' UTR and a 3' UTR; and (ii) synthesizing a 2$^{nd}$ test mmRNA comprising
  (b) a polynucleotide sequence comprising an open reading frame encoding eGFP, and; an 1$^{st}$ AUG codon upstream of, in-frame, and operably linked to, the open reading frame encoding eGFP, and; a coding sequence for a 3×FLAG epitope tag upstream of, in-frame, and operably linked to the 1$^{st}$ AUG codon, and; a 2$^{nd}$ AUG codon upstream of, in-frame, and operably linked to, the coding sequence for the 3×FLAG epitope tag, and; a coding sequence for a V5 epitope tag upstream of, in-frame, and operably linked to the 2$^{nd}$ AUG codon, and; a 3$^{rd}$ AUG codon upstream of, in-frame, and operably linked to, the coding sequence for the V5 epitope tag, and; a 5' UTR, a 3' UTR, and a candidate modification.

(iii) introducing the 1$^{st}$ control mRNA and 2$^{nd}$ test mmRNA to conditions suitable for translation of the polynucleotide sequence encoding the reporter polypeptide;

(iv) measuring the effect of the candidate modification on the initiation of translation of the polynucleotide sequence encoding the reporter polypeptide from each of the three AUG codons.

EXAMPLES

Materials & Methods

Synthesis of mRNA. mRNAs were synthesized in vitro from linearized DNA templates which include the 5' UTR, 3'UTR and polyA tail, followed by addition of a 5' CAP. All 5' UTRs depicted in the Figures are shown as DNA sequences for purposes of in vitro transcription. 5' UTR sequences tested in the Examples are summarized in Table 8 and are depicted as RNA.

TABLE 8

| 5' UTR | Sequence | GC-Rich RNA Element |
|---|---|---|
| Standard | GGGAAAUAAGAGAGAAAAGAAGAGUAAGAAGAAAUAUA AGAGCCACC (SEQ ID NO: 33) | none |
| 6nt | GGGAAA (SEQ ID NO: 529) | none |
| 6nt (TISU) | GGCAAG (SEQ ID NO: 530) | none |
| Tubulin-like | GUACACCGGCAUCGACUAAUCAGGGCCAGGCUCGAGGC UUUGUCUCCCUACCGCGCGCCGAUUCUCCCGCCUCCCA GCCCCGGCGCACGCGCGCCCCGCCCAGCCUGCUUUCCC UCCGCGCCCUCCCCUCUCCUUUCUCCCUCUCAGAACCU UCCUGCCGUCGCGUUUGCACCUCGCUGCUCCAGCCUCU CGCAUUCCAACCUUCCAGCCUGCGACCUGCGGAGACUU AGCCCCAUACAUACCUUGAGGCGAGCUUUUAACC (SEQ ID NO: 531) | none |
| V1-UTR | GGGAAAUAAGAGAGAAAAGAAGAGUAAGAAGAAAUAUA AGACCCCGGCGCCGCCACC (SEQ ID NO: 35) | (V1) CCCCGGCGCC |
| V2-UTR | GGGAAAUAAGAGAGAAAAGAAGAGUAAGAAGAAAUAUA AGACCCCGGCGCCACC (SEQ ID NO: 54) | (V2) CCCCGGC |
| V3-UTR | GGGAAAUAAGAGAGAAAAGAAGACCCCGGCGCCGUAAG AAGAAAUAUAAGAGCCACC (SEQ ID NO: 52) | (V1) CCCCGGCGCC |
| V4-UTR | GGGCCCCGGCGCCAAAUAAGAGAGAAAAGAAGAGUAAG AAGAAAUAUAAGAGCCAC (SEQ ID NO: 53) | (V1) CCCCGGCGCC |
| GC Scramble #1-UTR | GGGAAAUAAGAGAGAAAAGAAGAGUAAGAAGAAAUAUA AGAGGGGCGCCCGGCCACC (SEQ ID NO: 532) | (GC Scramble #1) GGGGCGCCCG |
| GC Scramble #2-UTR | GGGAAAUAAGAGAGAAAAGAAGAGUAAGAAGAAAUAUA AGAGCCCGCCCGCGCCACC (SEQ ID NO: 533) | (GC Scramble #2) GCCCGCCCGC |
| GC Scramble #3-UTR | GGGAAAUAAGAGAGAAAAGAAGAGUAAGAAGAAAUAUA AGAGCGCCCCGCGGCCACC (SEQ ID NO: 534) | (GC Scramble #3-UTR) GCGCCCCGCG |
| GC1-UTR | GGGAAAUAAGAGAGAAAAGAAGAGUAAGAAGAAAUAUA AGAGCGCCCCGCGGCGCCCCGCGGCCACC (SEQ ID NO: 535) | (GC1) GCGCCCCGCGG CGCCCCGCG |

Cell culture and transfection. HeLa (ATCC), primary human hepatocytes (BioReclamation IVT), AML12 (ATCC #CRL-2254) and MEF cells (Oriental Bioservice Inc., Minamiyayamashiro Laboratory) were cultured under standard conditions. Cells were transfected with reporter mRNA using Lipofectamine 2000 or MC3 following standard protocols.

Luciferase assay in mice. Animal studies were performed in accordance with the National Institutes of Health Guide for Care and Use of Laboratory Animals and approved by the Institutional Animal Care and Use Committee of Moderna Therapeutics. Female BALB/c mice, 8 weeks old, weighing 18-23 g and female Sprague Dawley rats, 8 weeks old, weighing 275-300 g (Charles River Laboratories, Wilmington, MA), were pre-warmed using a heating lamp before injected in the lateral tail vein using a 1-mL syringe with a 27G ½" needle (Becton Dickson, San Diego, MA) with MC3-encapsulated 0.05 mg/kg mRNA encoding Luc. Luciferin, the substrate of luciferase, was injected intraperitoneally into mice or rat at a dose of ~150 mg/kg body weight. 20 minutes after Luciferin injection, animals were euthanized. Whole body imaging imaging was carried out on the IVIS spectrum by using Living Image Software (Perkin Elmer, Waltham, MA).

Analysis of leaky scanning using an eGFP reporter construct. Cells were harvested and lysed using 5×RIPA Buffer (Boston BIOproducts; Cat: BP-115-5X) in the presence of protease and phosphatase inhibitors (ThermoScientific; Halt Protease & Phosphatase Inhibitor Cat: 78446). Protein concentration was assessed by BioRad DC Protein Assay (Cat: 5000113) following the manufacturer's instructions. Total protein lysates were analyzed by SDS-PAGE/Western blot analysis using primary antibodies against eGFP (Abcam; ab290 rabbit, ab6673 goat), V5-tag (Abcam; ab27671 mouse) and FLAG-tag (Abcam; ab18230 mouse) in combination with secondary antibodies (LICOR; Green, goat, anti-mouse 926-32210; Red, goat, anti-rabbit 926-68071; Red, donkey, anti-mouse 926-68072). An antibody against vinculin (Abcam; ab18058 mouse) was used as loading control. A LI-COR Odyssey CLx system was used for imaging of Western blots and densitometric analysis of translation products. The amounts of eGFP synthesized starting at the first (M1), second (M2) or third AUG (M3) codon, respectively, were quantitated. The percent of truncated protein was determined as (M2+M3)/(M1+M2+M3), setting (M1+M2+M3) to 100%. Total eGFP expression was determined as (M1+M2+M3)/(vinculin).

40S footprinting. Cells were lysed, then immediately crosslinked with formaldehyde at a final concentration of 1.5%. Following buffer exchange, the lysate was treated with a cocktail of RNases T1, A, and I. The digested lysate was centrifuged through a sucrose gradient and the small subunit peak selected for reverse crosslinking and RNA extraction. rRNA was depleted using the NEBNext rRNA Depletion kit, and the resulting RNA was converted into a cDNA library using the NEBNext Small RNA Library Prep Set. Following deep sequencing, reads were mapped to the human transcriptome HeLa cells of human hepatocytes as indicated.

Example 1: The Length and Base Composition of 5' UTRs Comprising Reporter mRNAs Affects Leaky Scanning and the Fidelity of Translation Initiation DNA plasmid constructs were generated and used to produce reporter mRNAs, via in vitro transcription, as described in the Materials & Methods. The reporter mRNAs contain a 5' UTR with a Kozak consensus sequence preceding, or upstream of, a sequence encoding a V5 epitope tag and a 3×FLAG epitope tag fused in-frame with a sequence encoding eGFP, followed by a 3' UTR. The sequences encoding the V5 epitope tag and the 3×FLAG epitope tag are each preceded by an in-frame AUG codon upstream of the eGFP AUG codon, as is shown in FIG. 1A. The reporter mRNAs are designed such that translation initiation from the $1^{st}$ AUG codon downstream of the 5' UTR would produce an eGFP polypeptide fused to a V5 epitope tag and to a 3×FLAG epitope tag at the N-terminus. Translation initiation from the $2^{nd}$ AUG codon downstream of the 5' UTR would produce an eGFP polypeptide fused only to a 3×FLAG epitope tag at the N-terminus. Translation initiation at the $3^{rd}$ AUG codon downstream of the 5' UTR would produce only an eGFP polypeptide containing no epitope tags. This design provides the ability to assess the effect of various 5' UTRs (FIG. 1B) on translation initiation at each AUG codon as a function of the production of polypeptides of discrete lengths (each detectable using an anti-GFP antibody) and with differential reactivity to anti-V5 and/or anti-FLAG antibodies, depending on the presence or absence of the corresponding epitope tag. The production of a full-length translation product (reactive to a V5-specific antibody) and products from leaky scanning arising from translation initiation at the 2nd and 3rd AUG (not reactive to a V5-specific antibody, but reactive to FLAG- and eGFP-specific antibodies, respectively) is monitored by standard SDS-PAGE/Western blot techniques, as described in the Materials & Methods.

In cell-based experiments, a full-length translation product (V5-Flag-eGFP (M1)) and truncated translation products (Flag-eGFP (M2); eGFP(M3)) were detected by Western blotting (FIG. 2A) after electrophoretic separation of proteins from HeLa cells or murine embryonic fibroblasts (MEFs) that were independently transfected with reporter mRNAs containing 5' UTRs varying in length and/or base composition, as described in the Materials & Methods (Table 8). Strikingly, a relatively long 5' UTR derived from the mammalian tubulin gene (labeled "262nt tub-like"; FIGS. 2A and 2B) drastically reduced the formation of the truncated translation products FLAG-eGFP (M2) and eGFP (M3), demonstrating that the length of the 5' UTR of the reporter mRNAs affects translation initiation and leaky scanning in these cell types. In addition, the amount of truncated protein products translated from reporter mRNAs containing two short 5' UTRs (labeled "6nt" and "6nt (TISU)"; FIG. 2A) varying only in base composition was evaluated. Cells transfected with reporter mRNA containing the 6nt (TISU) 5' UTR produced less truncated translation products relative to cells transfected with reporter mRNA containing the 6nt 5' UTR, demonstrating that the base composition of the 5' UTRs also affects translation initiation and leaky scanning. The amount of truncated products translated from the reporter mRNAs was quantified by densitometry and is shown as a percentage of the total amount of all translation products detectable by Western blot (FIGS. 2C and 2D). Similar results were obtained from in vivo experiments using cells derived from liver after intravenous administration of 0.5 mg/kg of reporter mRNAs as shown in FIGS. 2B and 2D.

Example 2: Increasing the Length of Reporter mRNA 5' UTRs Decreases Both Leaky Scanning and Translation Efficiency To better reveal the contribution of 5' UTR length on leaky scanning, reporter mRNAs were generated containing 5' UTRs of increasing length (Table 8) upstream of a sequence encoding a 3×FLAG epitope tag fused in-frame with a sequence encoding eGFP, followed by a 3' UTR. The sequence encoding the 3×FLAG epitope tag is preceded by an in-frame AUG codon and is upstream of the eGFP AUG codon, as shown in FIG. 3A. The reporter mRNAs are designed such that translation initiation from the $1^{st}$ AUG codon downstream of the 5' UTR would produce an eGFP polypeptide fused to a 3×FLAG epitope tag at the N-terminus. Translation initiation from the $2^{nd}$ AUG codon downstream of the 5' UTR would produce only an eGFP polypeptide containing no epitope tags. This design provides the ability to assess the effect of 5' UTR length on translation initiation at each AUG codon as a function of the production of polypeptides of discrete lengths (each detectable using an anti-GFP antibody) and with differential reactivity to an anti-FLAG antibody, depending on the presence or absence of the epitope tag. The production of a full-length translation product (reactive to both FLAG- and eGFP-specific antibody) and products from leaky scanning arising from translation initiation at the $2^{nd}$ AUG (only reactive to eGFP-specific antibodies) is monitored by standard SDS-PAGE/Western blot techniques, as described in the Materials & Methods.

In cell-based experiments, a full-length translation product (FLAG-eGFP (M1)) and a truncated translation product (eGFP (M2)) were detected by Western blotting after electrophoretic separation of proteins from HeLa cells that were independently transfected with reporter mRNAs containing 5' UTRs varying in length, as shown (FIG. 3B). As was suggested by the results of experiments described in Example 1, reporter mRNAs containing 5' UTRs of increasing length correlated with less translation of the truncated translation product eGFP (M2) (FIG. 3C), again demonstrating that the length of the 5' UTR of the reporter mRNAs can affect translation initiation and leaky scanning. In addition, the amount of total translation product translated from reporter mRNAs decreased with increasing length of the 5' UTR (FIG. 3D), as measured by the densitometric analysis of all anti-eGFP reactive bands from the Western blot in FIG. 3B.

Figure 12A:
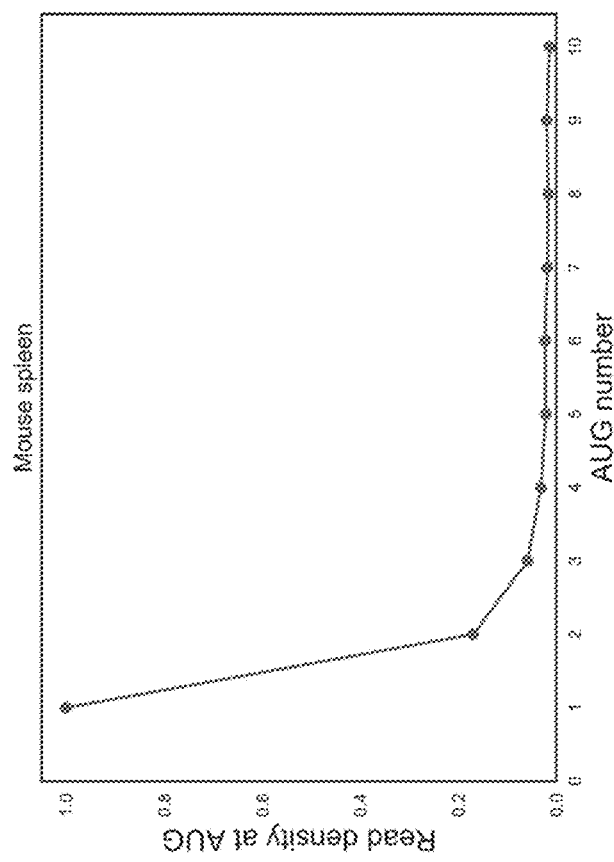
FIG. 12A provides a graph representing the results of small ribosome subunit footprinting analysis using HeLa cells, wherein sequencing reads were mapped to a human transcriptome and the number of reads overlapping with each AUG in each mRNA was counted. The number of reads overlapping with each AUG was then normalized to the first AUG.
Figure 12B:
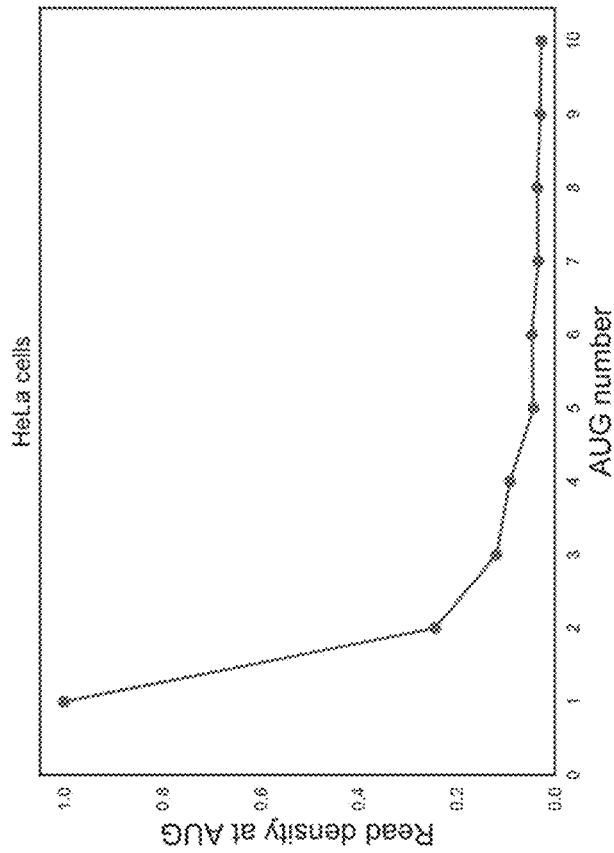
FIG. 12B provides a graph representing the results of small ribosome subunit footprinting analysis using mouse spleen cells, wherein sequencing reads were mapped to a mouse transcriptome and the number of reads overlapping with each AUG in each mRNA was counted. The number of reads overlapping with each AUG was then normalized to the first AUG.

These findings are also supported by analysis of small ribosomal subunit footprinting on cellular mRNAs. FIG. 4A illustrates the relative density of small subunits, where deep sequencing reads were mapped to the transcriptome of HeLa cells and the number of reads overlapping with each AUG in each mRNA was counted. The number of reads overlapping with each AUG was then normalized to the $1^{st}$ AUG, showing a significant density of small ribosomal subunits at the $2^{nd}$, $3^{rd}$ etc. AUG codon. In a separate experiment performed in the absence of crosslinking, a similar pattern is observed in both HeLa cells (FIG. 12A) and mouse spleens (FIG. 12B), where the density of small ribosomal subunits at the $1^{st}$ AUG decreases with each subsequent AUG in the mRNA.

The frequency of leaky scanning dependent on 5' UTR length (FIG. 4B) for each mRNA in primary human hepatocytes was estimated by dividing the mean small subunit read density in the first 500 nt of the coding sequence by the mean small subunit read density in the 5'UTR. In FIG. 4B, leaky scanning was plotted against the length of 5'UTR; each point represents an individual mRNA with at least 100 mapped reads. The black line represents a moving average.

Example 3: GC-Rich RNA Elements Located Proximal to the Kozak Consensus Sequence of Reporter mRNAs Decrease Leaky Scanning and Increase the Fidelity of Translation Initiation The Kozak consensus sequence [GCCACC] located immediately upstream of the $1^{st}$ AUG codon from the 5' end is not enough to guarantee a high fidelity of translation initiation for the reporter mRNAs described in the preceding Examples, as shown by a significant level of leaky scanning observed by two independent assay systems.

To better reveal the contribution of 5' UTR base composition on leaky scanning, reporter mRNAs were generated with 5' UTRs containing GC-rich RNA elements (Table 8). The approximate location of these GC-rich RNA elements is depicted in FIG. 5A. These 5' UTRs are followed by a sequence encoding a 3×FLAG epitope tag fused in-frame with a sequence encoding eGFP, followed by a 3' UTR. The sequence encoding the 3×FLAG epitope tag is preceded by an in-frame AUG codon and is upstream of the eGFP AUG codon, as shown in FIG. 5A. As in the previous Examples, these reporter mRNAs are designed such that translation initiation from the $1^{st}$ AUG codon downstream of the 5' UTR would produce an eGFP polypeptide fused to a 3×FLAG epitope tag at the N-terminus. Translation initiation from the $2^{nd}$ AUG codon downstream of the 5' UTR would produce only an eGFP polypeptide containing no epitope tags. This design provides the ability to assess the effect of the presence and position of GC-rich RNA elements on translation initiation at each AUG codon as a function of the production of polypeptides of discrete lengths (each detectable using an anti-GFP antibody) and with differential reactivity to an anti-FLAG antibody, depending on the presence or absence of the epitope tag. The production of a full-length translation product (reactive to both FLAG- and eGFP-specific antibody) and products from leaky scanning arising from translation initiation at the $2^{nd}$ AUG (only reactive to eGFP-specific antibodies) is monitored by standard SDS-PAGE/Western blot techniques, as described in the Materials & Methods.

Figure 5B:
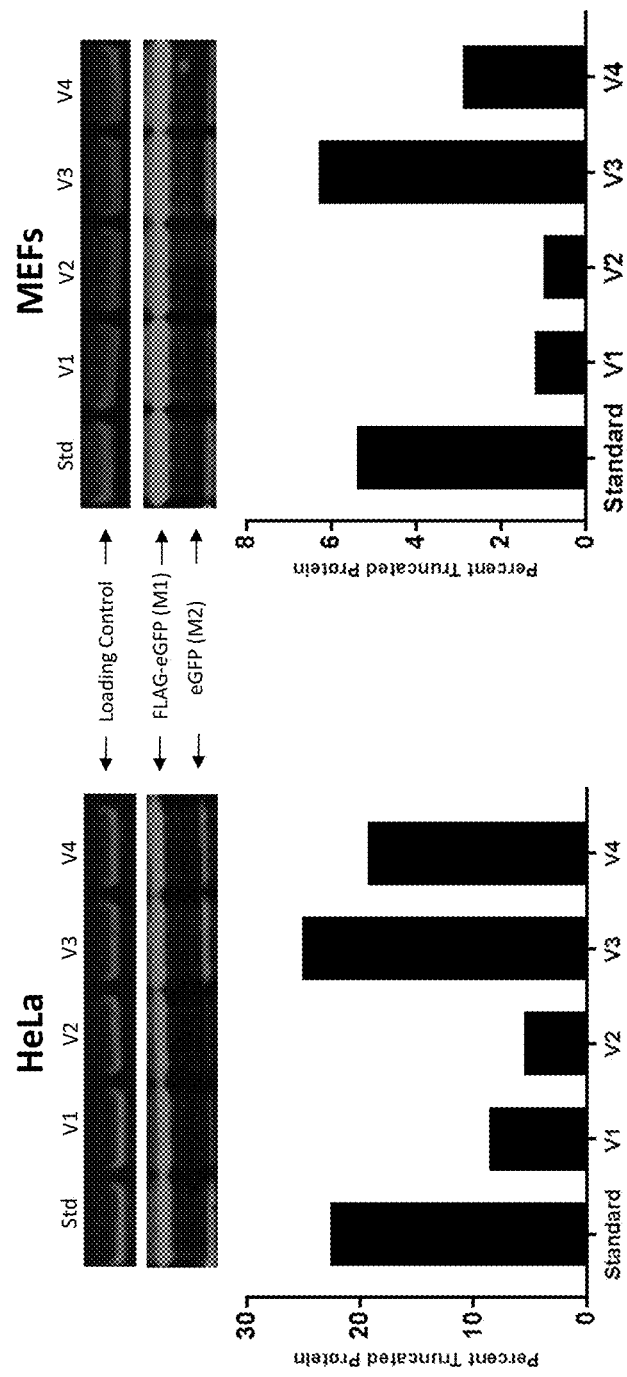
FIG. 5B provides a picture and graph representing the results of experiments, wherein HeLa cells or murine embryonic fibroblasts (MEFs) were transfected with reporter mRNAs containing 5' UTRs with GC-rich RNA elements as indicated in FIG. 5A. Full-length and truncated translation products were visualized by SDS-PAGE/Western blot analysis using an eGFP-specific antibody. Quantitative analysis of formation of truncated protein is shown below Western blots.
Figure 6A:
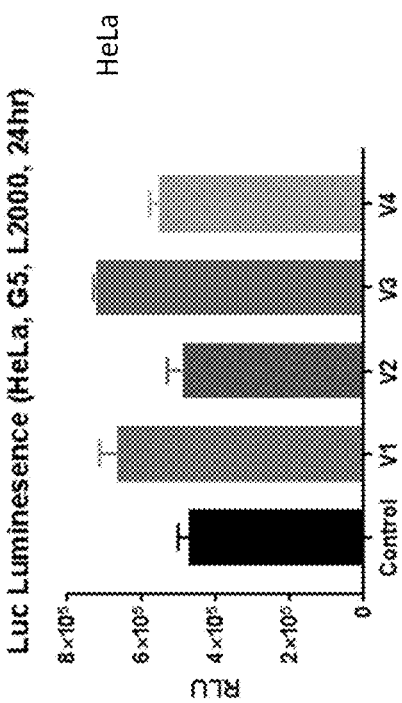
FIGS. 6A and 6B provides graphs representing the results of experiments, wherein HeLa cells or human hepatocytes, as indicated, were transfected with reporter mRNAs for human Erythropoietin (Epo) containing 5' UTRs with GC-rich RNA elements depicted in FIG. 5A and the amount of Epo was quantified.
Figure 6B:
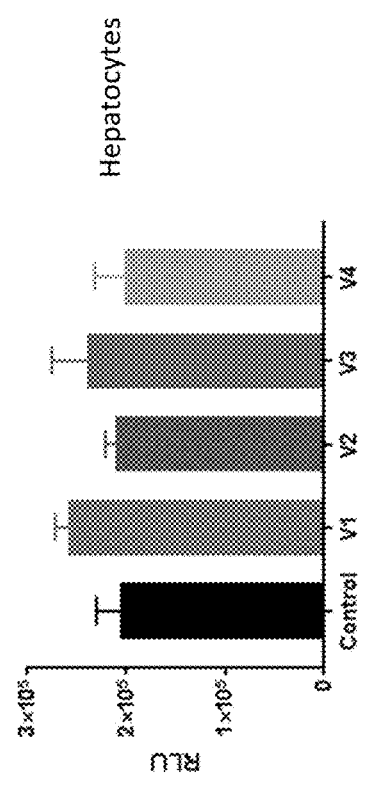
Figure 6C:
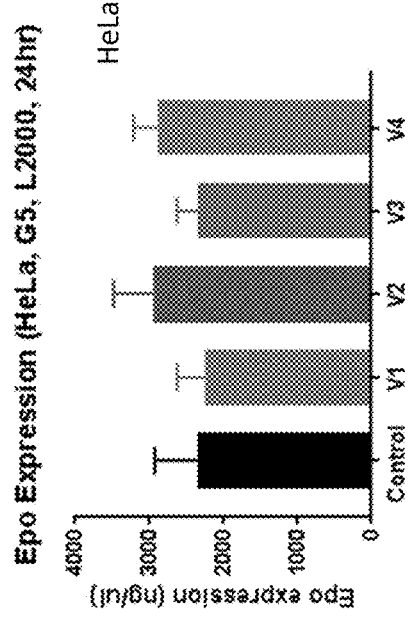
FIGS. 6C and 6D provides a graphs representing the results of experiments, wherein HeLa cells or human hepatocytes, as indicated, were transfected with reporter mRNAs for luciferase (Luc) containing 5' UTRs with GC-rich RNA elements depicted in FIG. 5A and the amount of Luc was quantified.
Figure 6D:
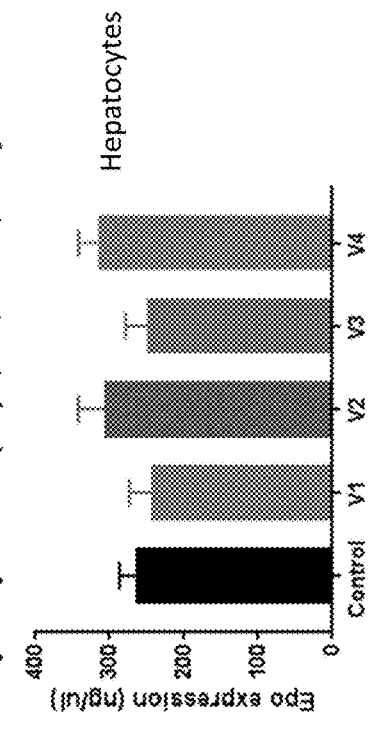

In cell-based experiments, a full-length translation product (Flag-eGFP (M1)) and a truncated translation product (eGFP(M2)) were detected by Western blotting after electrophoretic separation of proteins from HeLa cells or MEFs that were independently transfected with reporter mRNAs containing 5' UTRs encoding GC-rich RNA elements located proximal to or distal from the Kozak consensus sequence preceding the $1^{st}$ AUG codon from the 5' end, as shown (FIG. 5A). The insertion of a 10 nt RNA element composed of C and G residues [CCCCGGCGCC; V1] (SEQ ID NO: 2) upstream of the Kozak consensus sequence significantly reduced leaky scanning (FIG. 5B), without affecting the overall translational efficiency as illustrated for two different reporter constructs, human Erythropoietin (Epo, FIGS. 6A and B) and luciferase (Luc, FIGS. 6C and D). A related 7 nt RNA element inserted upstream of the Kozak consensus sequence also composed of C and G residues [CCCCGGC; V2] (SEQ ID NO: 3) also decreased the amount of the truncated translation product eGFP (M2) in both HeLa cells and MEFs. As was suggested by the results of experiments described in Example 1, modifying the base composition of 5' UTRs by insertion of GC-rich RNA elements correlated with less translation of the truncated translation product eGFP (M2) (FIG. 5B), again demonstrating that the base composition of the 5' UTR of the reporter mRNAs can affect translation initiation and leaky scanning in these cell types. Furthermore, the position of the V1 GC-rich RNA element was also shown to have an effect on leaky scanning. As shown in FIGS. 5A and 5B, leaky scanning is reduced when these GC-rich RNA elements are proximal to the Kozak consensus sequence or initiation codon (M1). The V3-UTR (V3) and V4-UTRs (V4), which comprise the V1 GC-rich RNA element but located farther upstream from the initiation codon AUG (M1) (Table 8), are not as effective at decreasing leaky scanning, as shown in FIG. 5B.

Figure 7B:
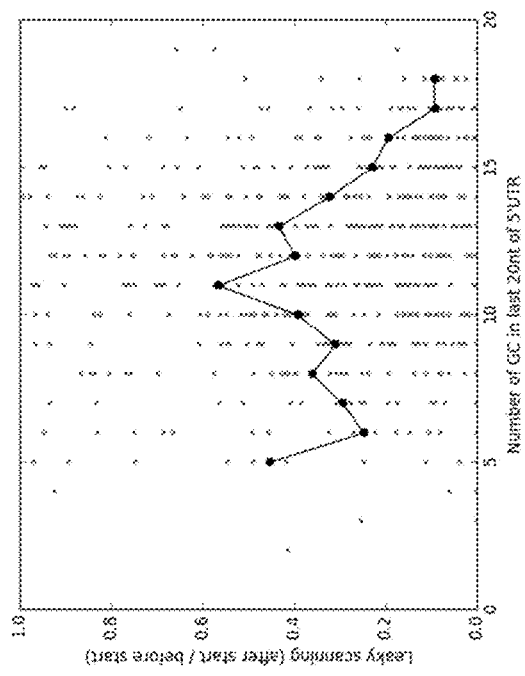
FIG. 7B provides a graph representing the results of small ribosome subunit footprinting analysis, wherein the frequency of leaky scanning for each mRNA in primary human hepatocytes was quantified and plotted against number of G and C bases in the final 20 nt of the 5' UTR. Each point represents an individual mRNA with at least 100 mapped reads. Black line represents a moving average.
Figure 7A:
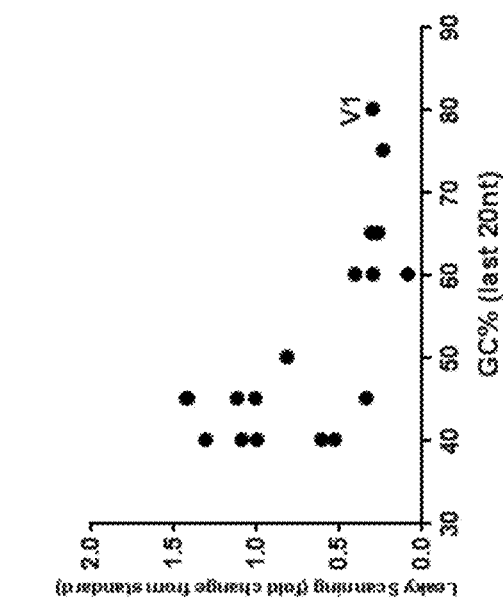
FIG. 7A provides a graph depicting leaky scanning efficiency of 254 different 5' UTRs from natural and synthetic sources, varying in base composition and length, that were tested in HeLa cells with the eGFP reporter depicted in FIG. 3, as measured by quantitative analysis of immunoblots.

Example 4: GC Content of the 20 nts Preceding the Kozak Consensus Sequence in Reporter mRNAs Correlates with Leaky Scanning To assess the impact of GC content on leaky scanning, 254 different 5' UTRs from natural and synthetic sources, varying base composition and length, were tested with the eGFP reporter described in Example 3, where translation initiation from the 1$^{st}$ AUG codon downstream of the 5' UTR would produce an eGFP polypeptide fused to a 3×FLAG epitope tag at the N-terminus. Translation initiation from the 2$^{nd}$ AUG codon downstream of the 5' UTR would produce only an eGFP polypeptide containing no epitope tags. The top 24 sequences that performed well in terms of overall translation efficiency were analyzed further for leaky scanning. FIG. 7A shows leaky scanning observed for each of the 5' UTR constructs, all shorter than 100 nucleotides in length, normalized to leaky scanning observed for the standard 5' UTR (FIG. 1, Table 8). Clearly, increased GC content in the final nucleotides of the 5' UTR, i.e. those nucleotides preceding the initiation codon, decreases leaky scanning. As shown above, the insertion of a 10 nt RNA element composed of C and G residues [CCCCGGCGCC; V1] (SEQ ID NO: 2) into the standard 5' UTR resulted in a significant decrease of leaky scanning.

A similar correlation is found globally across human mRNAs. In FIG. 7B, the frequency of leaky scanning for each mRNA in primary hepatocytes was estimated by dividing the mean small subunit read density in the first 500 nt of the coding sequence by the mean small subunit read density in the 5' UTR and plotted against the number of G and C bases in the final 20 nt of the 5' UTR; each point represents an individual mRNA with at least 100 mapped reads. The black line represents a moving average.

Example 5: mRNAs with 5' UTRs Comprising GC-Rich RNA Elements with Greater than 40% Cytosine Located Upstream of the Kozak Consensus Sequence Decrease Leaky Scanning To further characterize the ability of GC-rich RNA elements to decrease leaky scanning, 5' UTRs with GC-rich RNA elements comprising greater than 40% cytosine nucleobases were tested with the eGFP reporter described in Example 1. The 5' UTRs (tested are shown in the table in FIG. 8A. A schematic of the reporter construct with the relative location of the GC-rich RNA elements is shown in FIG. 8B.

Figure 9A:
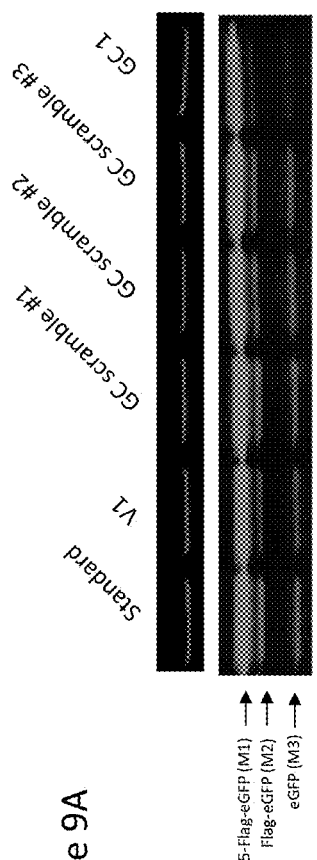
FIG. 9A depicts an SDS-PAGE/Western Blot of lysates derived from hepatocytes that were administered reporter mRNA contain 5' UTRs as indicated 5' UTR as depicted in FIG. 8A.
Figure 9B:
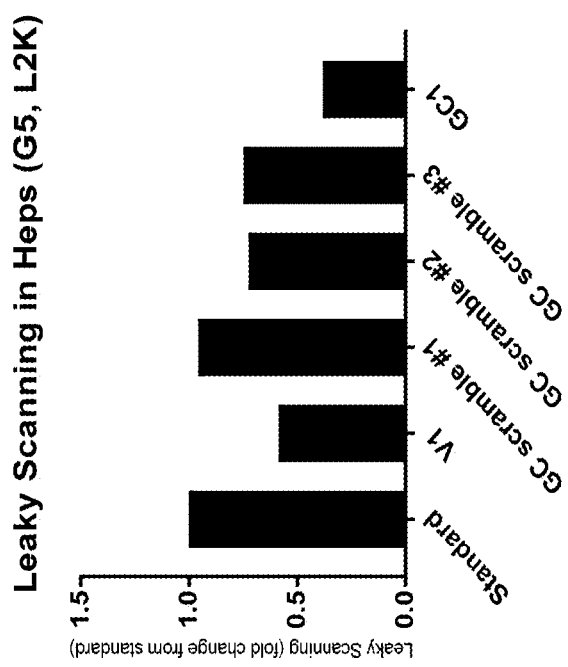
FIG. 9B provides a graph representing the results of a quantitative analysis of formation of truncated protein from experiments shown in FIG. 9A.

Similar to the results shown in FIG. 5B, the presence of the GC-rich RNA element V1, as well as GC scramble #2, GC scramble #3 and GC1, which comprise 60%-70% cytosine nucleobases, decreased leaky scanning of the reporter mRNA, as shown as a reduction in the amount of FLAG-eGFP (M2) and eGFP (M3) polypeptide (FIGS. 9A and 9B), determined by standard SDS-PAGE/Western blot techniques, as described in the Materials & Methods. The 5' UTR containing the GC-rich RNA element GC scramble #1, which comprises 40% cytosine nucleobases, did not appreciably decrease leaky scanning compared to the standard 5' UTR, which does not comprise a GC-rich RNA element. Taken together, these data demonstrate that the cytosine content of the GC-rich RNA element impacts the ability of the 5' UTR to decrease leaky scanning.

Example 6: mRNAs with 5' UTR Comprising GC-Rich RNA Elements Increase Potency of Translated Polypeptides To determine the effect of GC-rich RNA elements on the potency of polypeptides translated from an mRNA, reporter mRNAs encoding luciferase or eGFP were generated containing 5' UTRs comprising the GC-rich RNA elements V1 or V2, as described in Table 8, and evaluated both in vivo and in vitro.

Figure 10:
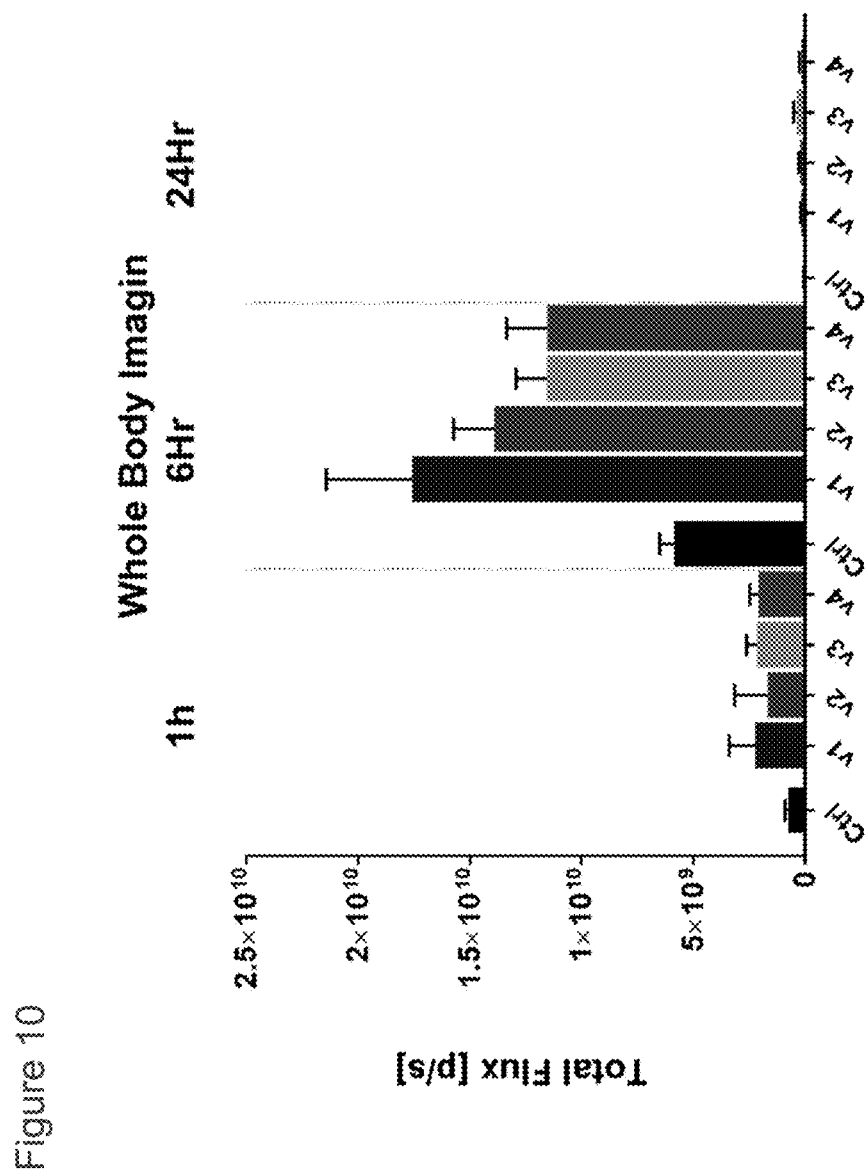
FIG. 10 provides a graph depicting the results of whole body imaging analysis of mice administered mRNAs comprising various 5' UTRs, as indicated, and encoding luciferase. Luminescence signal is given in total flux (p/s).

To evaluate the potency of polypeptides translated from mRNA comprising 5' UTRs with GC-rich RNA elements in vivo, BALB/c mice were injected intravenously with 0.05 mg/kg mRNA encoding luciferase downstream of an 5'UTR comprising a GC-rich RNA element (V1 or V2) formulated in an lipid nanoparticle. At various time points post-injection, as indicated, whole body imaging using IVIS was performed to quantify the luciferase signal (total flux). At 6 hours, mRNA encoding luciferase and comprising the V1-UTR or V2-UTR produced higher luminescence than with the comparator control mRNA that does not comprise a GC-rich RNA element (FIG. 10) or with mRNA comprising V3-UTR or V4-UTR. The V3-UTR (V3) and V4-UTRs (V4) (Table 8) comprise the V1 GC-rich RNA element but located farther upstream from the initiation codon AUG of the luciferase gene. Notably, the V1-UTR produced the highest luciferase signal. These data suggest that GC-rich RNA elements tested increase the potency of the polypeptide translated from the mRNA.

Figure 11A:
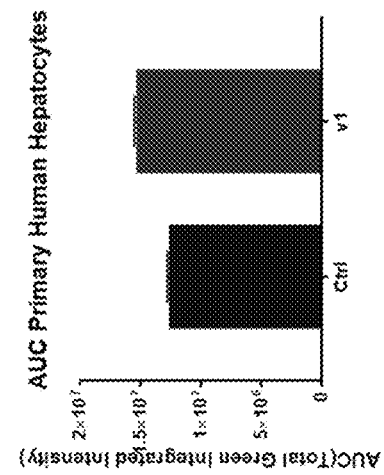
FIGS. 11A, 11B, and 11C provides graphs depicting the results of fluorescence imaging analysis of cells administered mRNAs comprising V1-UTR and encoding eGFP in various cell types as indicated.
Figure 11B:
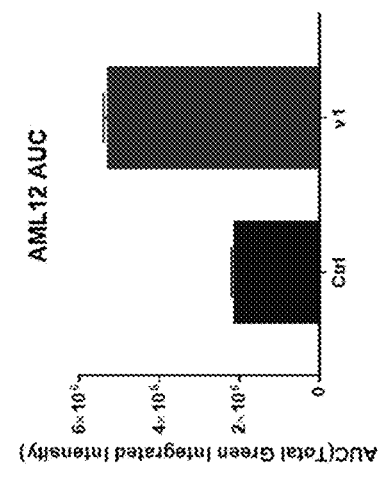
Figure 11C:
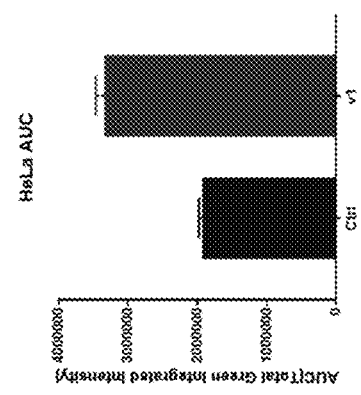

To evaluate the potency of polypeptides translated from mRNA comprising 5' UTRs with GC-rich RNA elements in vitro, HeLa cells (FIG. 11A), AML12 (mouse hepatocyte cell line) cells (FIG. 11B), and primary human hepatocytes (FIG. 11C) were transfected with mRNA encoding deg-eGFP (eGFP fused to a PEST domain on the C-terminal end to mediate rapid degradation of the protein) and comprising an 5' UTR with the V1 GC-rich RNA element (v1) or with a control mRNA encoding eGFP and comprising a 5' UTR that does not contain a GC-rich RNA element (Ctrl). An image of the fluorescent cells was taken every hour for 48 hours using a live-cell analysis system (IncuCyte). The total fluorescent intensity of the cells (AUC) for each cell type transfected with each mRNA is shown in FIGS. 11A, 11B, and 11C. Total fluorescence is higher in all cell types transfected with the mRNA comprising V1 compared to control mRNA, suggesting the V1 GC-rich RNA element increased the potency of the eGFP polypeptide in vitro.

EQUIVALENTS AND SCOPE

Those skilled in the art will recognize, or be able to ascertain using no more than routine experimentation, many equivalents to the specific embodiments in accordance with the disclosure described herein. The scope of the present disclosure is not intended to be limited to the Description below, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

TABLE 9

SEQUENCE LISTING

| SEQ ID NO | Description | Sequence |
|---|---|---|
| 1 | Kozak Consensus Sequence | GCCRCC, where R = A or G |
| 2 | V1 | CCCCGGCGCC |
| 3 | V2 | CCCCGGC |
| 4 | CG1 | GCGCCCCGCGGCGCCCCGCG |
| 5 | CG2 | CCCGCCCGCCCCGCCCCGCC |
| 6 | GC Scramble #1 | GGGGCGCCCG |
| 7 | GC Scramble #2 | GCCCGCCCGC |
| 8 | GC Scramble #3 | GCGCCCCGCG |
| 9 | EK1 | CCCGCC |
| 10 | EK2 | GCCGCC |
| 11 | EK3 | CCGCCG |
| 12 | (CCG)3 | CCGCCGCCG |
| 13 | (CCG)4 | CCGCCGCCGCCG |
| 14 | (CCG)5 | CCGCCGCCGCCGCCG |
| 15 | (CCG)6 | CCGCCGCCGCCGCCGCCG |
| 16 | (CCG)7 | CCGCCGCCGCCGCCGCCGCCG |
| 17 | (CCG)8 | CCGCCGCCGCCGCCGCCGCCGCCG |
| 18 | (CCG)9 | CCGCCGCCGCCGCCGCCGCCGCCGCCG |
| 19 | (CCG)10 | CCGCCGCCGCCGCCGCCGCCGCCGCCGCCG |
| 20 | (GCC)3 | GCCGCCGCC |
| 21 | (GCC)4 | GCCGCCGCCGCC |
| 22 | (GCC)5 | GCCGCCGCCGCCGCC |
| 23 | (GCC)6 | GCCGCCGCCGCCGCCGCC |
| 24 | (GCC)7 | GCCGCCGCCGCCGCCGCCGCC |
| 25 | (GCC)8 | GCCGCCGCCGCCGCCGCCGCCGCC |
| 26 | (GCC)9 | GCCGCCGCCGCCGCCGCCGCCGCCGCC |
| 27 | (GCC)10 | GCCGCCGCCGCCGCCGCCGCCGCCGCCGCC |
| 28 | SL1 | CCGCGGCGCCCCGCGG |
| 29 | SL2 | GCGCGCAUAUAGCGCGC |
| 30 | SL3 | CAUGGUGGCGGCCCGCCGCCACCAUG |
| 31 | SL4 | CAUGGUGGCCCGCCGCCACCAUG |

TABLE 9-continued

SEQUENCE LISTING

| SEQ ID NO | Description | Sequence |
|---|---|---|
| 32 | SL5 | CAUGGUGCCCGCCGCCACCAUG |
| 33 | Standard UTR | GGGAAAUAAGAGAGAAAAGAAGAGUAAGAAGAAAUAUAAGAG CCACC |
| 34 | V1-UTR | GGGAAAUAAGAGAGAAAAGAAGAGUAAGAAGAAAUAUAAGAC CCCGGCGCCGCCACC |
| 35 | V1-1-UTR | GGGAAAUAAGAGAGAAAAGAAGAGUAAGAAGAAAUAUAAGCCC CGGCGCCAGCCACC |
| 36 | V1-2-UTR | GGGAAAUAAGAGAGAAAAGAAGAGUAAGAAGAAAUAUAACCCC GGCGCCGAGCCACC |
| 37 | V1-3-UTR | GGGAAAUAAGAGAGAAAAGAAGAGUAAGAAGAAAUAUACCCCG GCGCCAGAGCCACC |
| 38 | V1-4-UTR | GGGAAAUAAGAGAGAAAAGAAGAGUAAGAAGAAAUAUCCCCGG CGCCAAGAGCCACC |
| 39 | V1-5-UTR | GGGAAAUAAGAGAGAAAAGAAGAGUAAGAAGAAAUACCCCGGC GCCUAAGAGCCACC |
| 40 | V1-6-UTR | GGGAAAUAAGAGAGAAAAGAAGAGUAAGAAGAAAUCCCCGGCG CCAUAAGAGCCACC |
| 41 | V1-7-UTR | GGGAAAUAAGAGAGAAAAGAAGAGUAAGAAGAAACCCCGGCGC CUAUAAGAGCCACC |
| 42 | V1-8-UTR | GGGAAAUAAGAGAGAAAAGAAGAGUAAGAAGAACCCCGGCGCC AUAUAAGAGCCACC |
| 43 | V1-9-UTR | GGGAAAUAAGAGAGAAAAGAAGAGUAAGAAGACCCCGGCGCCA AUAUAAGAGCCACC |
| 44 | V1-10-UTR | GGGAAAUAAGAGAGAAAAGAAGAGUAAGAAGCCCCGGCGCCAA AUAUAAGAGCCACC |
| 45 | V1-11-UTR | GGGAAAUAAGAGAGAAAAGAAGAGUAAGAACCCCGGCGCCGAA AUAUAAGAGCCACC |
| 46 | V1-12-UTR | GGGAAAUAAGAGAGAAAAGAAGAGUAAGACCCCGGCGCCAGAA AUAUAAGAGCCACC |
| 47 | V1-13-UTR | GGGAAAUAAGAGAGAAAAGAAGAGUAAGCCCCGGCGCCAAGAA AUAUAAGAGCCACC |
| 48 | V1-14-UTR | GGGAAAUAAGAGAGAAAAGAAGAGUAACCCCGGCGCCGAAGAA AUAUAAGAGCCACC |
| 49 | V1-15-UTR | GGGAAAUAAGAGAGAAAAGAAGAGUACCCCGGCGCCAGAAGAA AUAUAAGAGCCACC |
| 50 | V1-16-UTR | GGGAAAUAAGAGAGAAAAGAAGAGUCCCCGGCGCCAAGAAGAA AUAUAAGAGCCACC |
| 51 | V1-17-UTR | GGGAAAUAAGAGAGAAAAGAAGAGCCCCGGCGCCUAAGAAGAA AUAUAAGAGCCACC |
| 52 | V3-UTR | GGGAAAUAAGAGAGAAAAGAAGACCCCGGCGCCGUAAGAAGAA AUAUAAGAGCCACC |
| 53 | V4-UTR | GGGCCCCGGCGCCAAAUAAGAGAGAAAAGAAGAGUAAGAAGAA AUAUAAGAGCCACC |
| 54 | V2-UTR | GGGAAAUAAGAGAGAAAAGAAGAGUAAGAAGAAAUAUAAGAC CCCGGCGCCACC |
| 55 | V2-1-UTR | GGGAAAUAAGAGAGAAAAGAAGAGUAAGAAGAAAUAUAAGCCC CGGCAGCCACC |
| 56 | V2-2-UTR | GGGAAAUAAGAGAGAAAAGAAGAGUAAGAAGAAAUAUAACCCC GGCGAGCCACC |

TABLE 9-continued

SEQUENCE LISTING

| SEQ ID NO | Description | Sequence |
|---|---|---|
| 57 | V2-3-UTR | GGGAAAUAAGAGAGAAAAGAAGAGUAAGAAGAAAUAUACCCCG GCAGAGCCACC |
| 58 | V2-4-UTR | GGGAAAUAAGAGAGAAAAGAAGAGUAAGAAGAAAUAUCCCCGG CAAGAGCCACC |
| 59 | V2-5-UTR | GGGAAAUAAGAGAGAAAAGAAGAGUAAGAAGAAAUACCCCGGC UAAGAGCCACC |
| 60 | V2-6-UTR | GGGAAAUAAGAGAGAAAAGAAGAGUAAGAAGAAAUCCCCGGCA UAAGAGCCACC |
| 61 | V2-7-UTR | GGGAAAUAAGAGAGAAAAGAAGAGUAAGAAGAAACCCCGGCUA UAAGAGCCACC |
| 62 | V2-8-UTR | GGGAAAUAAGAGAGAAAAGAAGAGUAAGAAGAACCCCGGCAUA UAAGAGCCACC |
| 63 | V2-9-UTR | GGGAAAUAAGAGAGAAAAGAAGAGUAAGAAGACCCCGGCAAUA UAAGAGCCACC |
| 64 | V2-10-UTR | GGGAAAUAAGAGAGAAAAGAAGAGUAAGAAGCCCCGGCAAAUA UAAGAGCCACC |
| 65 | V2-11-UTR | GGGAAAUAAGAGAGAAAAGAAGAGUAAGAACCCCGGCGAAAUA UAAGAGCCACC |
| 66 | V2-12-UTR | GGGAAAUAAGAGAGAAAAGAAGAGUAAGACCCCGGCAGAAAUA UAAGAGCCACC |
| 67 | V2-13-UTR | GGGAAAUAAGAGAGAAAAGAAGAGUAAGCCCCGGCAAGAAAUA UAAGAGCCACC |
| 68 | V2-14-UTR | GGGAAAUAAGAGAGAAAAGAAGAGUAACCCCGGCGAAGAAAUA UAAGAGCCACC |
| 69 | V2-15-UTR | GGGAAAUAAGAGAGAAAAGAAGAGUACCCCGGCAGAAGAAAUA UAAGAGCCACC |
| 70 | V2-16-UTR | GGGAAAUAAGAGAGAAAAGAAGAGUCCCCGGCAAGAAGAAAUA UAAGAGCCACC |
| 71 | V2-17-UTR | GGGAAAUAAGAGAGAAAAGAAGAGCCCCGGCUAAGAAGAAAUA UAAGAGCCACC |
| 72 | V2-18-UTR | GGGAAAUAAGAGAGAAAAGAAGACCCCGGCGUAAGAAGAAAUA UAAGAGCCACC |
| 73 | CG1-UTR | GGGAAAUAAGAGAGAAAAGAAGAGUAAGAAGAAAUAUAAGAG CGCCCCGCGGCGCCCCGCGGCCACC |
| 74 | CG1-1-UTR | GGGAAAUAAGAGAGAAAAGAAGAGUAAGAAGAAAUAUAAGGC GCCCCGCGGCGCCCCGCGAGCCACC |
| 75 | CG1-2-UTR | GGGAAAUAAGAGAGAAAAGAAGAGUAAGAAGAAAUAUAAGCG CCCCGCGGCGCCCCGCGGAGCCACC |
| 76 | CG1-3-UTR | GGGAAAUAAGAGAGAAAAGAAGAGUAAGAAGAAAUAUAGCGC CCCGCGGCGCCCCGCGAGAGCCACC |
| 77 | CG1-4-UTR | GGGAAAUAAGAGAGAAAAGAAGAGUAAGAAGAAAUAUGCGCCC CGCGGCGCCCCGCGAAGAGCCACC |
| 78 | CG1-5-UTR | GGGAAAUAAGAGAGAAAAGAAGAGUAAGAAGAAAUAGCGCCCC GCGGCGCCCCGCGUAAGAGCCACC |
| 79 | CG1-6-UTR | GGGAAAUAAGAGAGAAAAGAAGAGUAAGAAGAAAUGCGCCCCG CGGCGCCCCGCGAUAAGAGCCACC |
| 80 | CG1-7-UTR | GGGAAAUAAGAGAGAAAAGAAGAGUAAGAAGAAAGCGCCCCGC GGCGCCCCGCGUAUAAGAGCCACC |
| 81 | CG1-8-UTR | GGGAAAUAAGAGAGAAAAGAAGAGUAAGAAGAAGCGCCCCGCG GCGCCCCGCGAUAUAAGAGCCACC |

TABLE 9-continued

| SEQ ID NO | Description | Sequence |
|---|---|---|
| 82 | CG1-9-UTR | GGGAAAUAAGAGAGAAAAGAAGAGUAAGAAGAGCGCCCCGCGG CGCCCCGCGAAUAUAAGAGCCACC |
| 83 | CG1-10-UTR | GGGAAAUAAGAGAGAAAAGAAGAGUAAGAAGGCGCCCCGCGGC GCCCCGCGAAAUAUAAGAGCCACC |
| 84 | CG1-11-UTR | GGGAAAUAAGAGAGAAAAGAAGAGUAAGAAGCGCCCCGCGGCG CCCCGCGGAAAUAUAAGAGCCACC |
| 85 | CG1-12-UTR | GGGAAAUAAGAGAGAAAAGAAGAGUAAGAGCGCCCCGCGGCGC CCCGCGAGAAAUAUAAGAGCCACC |
| 86 | CG1-13-UTR | GGGAAAUAAGAGAGAAAAGAAGAGUAAGGCGCCCCGCGGCGCC CCGCGAAGAAAUAUAAGAGCCACC |
| 87 | CG1-14-UTR | GGGAAAUAAGAGAGAAAAGAAGAGUAAGCGCCCCGCGGCGCCC CGCGGAAGAAAUAUAAGAGCCACC |
| 88 | CG1-15-UTR | GGGAAAUAAGAGAGAAAAGAAGAGUAAGCGCCCCGCGGCGCCCC GCGAGAAGAAAUAUAAGAGCCACC |
| 89 | CG1-16-UTR | GGGAAAUAAGAGAGAAAAGAAGAGUGCGCCCCGCGGCGCCCCG CGAAGAAGAAAUAUAAGAGCCACC |
| 90 | CG1-17-UTR | GGGAAAUAAGAGAGAAAAGAAGAGGCGCCCCGCGGCGCCCCGC GUAAGAAGAAAUAUAAGAGCCACC |
| 91 | CG1-18-UTR | GGGAAAUAAGAGAGAAAAGAAGAGCGCCCCGCGGCGCCCCGCG GUAAGAAGAAAUAUAAGAGCCACC |
| 92 | CG2-UTR | GGGAAAUAAGAGAGAAAAGAAGAGUAAGAAGAAAUAUAAGAC CCGCCCGCCCCGCCCCGCCGCCACC |
| 93 | CG2-1-UTR | GGGAAAUAAGAGAGAAAAGAAGAGUAAGAAGAAAUAUAAGCCC GCCCGCCCCGCCCCGCCAGCCACC |
| 94 | CG2-2-UTR | GGGAAAUAAGAGAGAAAAGAAGAGUAAGAAGAAAUAUAACCCG CCCGCCCCGCCCCGCCGAGCCACC |
| 95 | CG2-3-UTR | GGGAAAUAAGAGAGAAAAGAAGAGUAAGAAGAAAUAUACCCGC CCGCCCCGCCCCGCCAGAGCCACC |
| 96 | CG2-4-UTR | GGGAAAUAAGAGAGAAAAGAAGAGUAAGAAGAAAUAUCCCGCC CGCCCCGCCCCGCCAAGAGCCACC |
| 97 | CG2-5-UTR | GGGAAAUAAGAGAGAAAAGAAGAGUAAGAAGAAAUACCCGCCC GCCCCGCCCCGCCUAAGAGCCACC |
| 98 | CG2-6-UTR | GGGAAAUAAGAGAGAAAAGAAGAGUAAGAAGAAAUCCCGCCCG CCCCGCCCCGCCAUAAGAGCCACC |
| 99 | CG2-7-UTR | GGGAAAUAAGAGAGAAAAGAAGAGUAAGAAGAAACCCGCCCGC CCCGCCCCGCCUAUAAGAGCCACC |
| 100 | CG2-8-UTR | GGGAAAUAAGAGAGAAAAGAAGAGUAAGAAGAACCCGCCCGCC CCGCCCCGCCAUAUAAGAGCCACC |
| 101 | CG2-9-UTR | GGGAAAUAAGAGAGAAAAGAAGAGUAAGAAGACCCGCCCGCCC CGCCCCGCCAAUAUAAGAGCCACC |
| 102 | CG2-10-UTR | GGGAAAUAAGAGAGAAAAGAAGAGUAAGAAGCCCGCCCGCCCC GCCCCGCCAAAUAUAAGAGCCACC |
| 103 | CG2-11-UTR | GGGAAAUAAGAGAGAAAAGAAGAGUAAGAACCCGCCCGCCCCG CCCCGCCGAAAUAUAAGAGCCACC |
| 104 | CG2-12-UTR | GGGAAAUAAGAGAGAAAAGAAGAGUAAGACCCGCCCGCCCCGC CCCGCCAGAAAUAUAAGAGCCACC |
| 105 | CG2-13-UTR | GGGAAAUAAGAGAGAAAAGAAGAGUAAGCCCGCCCGCCCCGCC CCGCCAAGAAAUAUAAGAGCCACC |
| 106 | CG2-14-UTR | GGGAAAUAAGAGAGAAAAGAAGAGUAACCCGCCCGCCCCGCCCC GCCGAAGAAAUAUAAGAGCCACC |

TABLE 9-continued

SEQUENCE LISTING

| SEQ ID NO | Description | Sequence |
|---|---|---|
| 107 | CG2-15-UTR | GGGAAAUAAGAGAGAAAAGAAGAGUACCCGCCCGCCCCGCCCCGCCAGAAGAAAUAUAAGAGCCACC |
| 108 | CG2-16-UTR | GGGAAAUAAGAGAGAAAAGAAGAGUCCCGCCCGCCCCGCCCCGCCAAGAAGAAAUAUAAGAGCCACC |
| 109 | CG2-17-UTR | GGGAAAUAAGAGAGAAAAGAAGAGCCCGCCCGCCCCGCCCCGCCUAAGAAGAAAUAUAAGAGCCACC |
| 110 | CG2-18-UTR | GGGAAAUAAGAGAGAAAAGAAGACCCGCCCGCCCCGCCCCGCCGUAAGAAGAAAUAUAAGAGCCACC |
| 111 | EK1-UTR | GGGAAAUAAGAGAGAAAAGAAGAGUAAGAAGAAAUAUAAGACCCGCCGCCACC |
| 112 | EK1-1-UTR | GGGAAAUAAGAGAGAAAAGAAGAGUAAGAAGAAAUAUAAGCCCGCCAGCCACC |
| 113 | EK1-2-UTR | GGGAAAUAAGAGAGAAAAGAAGAGUAAGAAGAAAUAUAACCCGCCGAGCCACC |
| 114 | EK1-3-UTR | GGGAAAUAAGAGAGAAAAGAAGAGUAAGAAGAAAUAUACCCGCCAGAGCCACC |
| 115 | EK1-4-UTR | GGGAAAUAAGAGAGAAAAGAAGAGUAAGAAGAAAUAUCCCGCCAAGAGCCACC |
| 116 | EK1-5-UTR | GGGAAAUAAGAGAGAAAAGAAGAGUAAGAAGAAAUACCCGCCUAAGAGCCACC |
| 117 | EK1-6-UTR | GGGAAAUAAGAGAGAAAAGAAGAGUAAGAAGAAAUCCCGCCAUAAGAGCCACC |
| 118 | EK1-7-UTR | GGGAAAUAAGAGAGAAAAGAAGAGUAAGAAGAAACCCGCCUAUAAGAGCCACC |
| 119 | EK1-8-UTR | GGGAAAUAAGAGAGAAAAGAAGAGUAAGAAGAACCCGCCAUAUAAGAGCCACC |
| 120 | EK1-9-UTR | GGGAAAUAAGAGAGAAAAGAAGAGUAAGAAGACCCGCCAAUAUAAGAGCCACC |
| 121 | EK1-10-UTR | GGGAAAUAAGAGAGAAAAGAAGAGUAAGAAGCCCGCCAAAUAUAAGAGCCACC |
| 122 | EK1-11-UTR | GGGAAAUAAGAGAGAAAAGAAGAGUAAGAACCCGCCGAAAUAUAAGAGCCACC |
| 123 | EK1-12-UTR | GGGAAAUAAGAGAGAAAAGAAGAGUAAGACCCGCCAGAAAUAUAAGAGCCACC |
| 124 | EK1-13-UTR | GGGAAAUAAGAGAGAAAAGAAGAGUAAGCCCGCCAAGAAAUAUAAGAGCCACC |
| 125 | EK1-14-UTR | GGGAAAUAAGAGAGAAAAGAAGAGUAACCCGCCGAAGAAAUAUAAGAGCCACC |
| 126 | EK1-15-UTR | GGGAAAUAAGAGAGAAAAGAAGAGUACCCGCCAGAAGAAAUAUAAGAGCCACC |
| 127 | EK1-16-UTR | GGGAAAUAAGAGAGAAAAGAAGAGUCCCGCCAAGAAGAAAUAUAAGAGCCACC |
| 128 | EK1-17-UTR | GGGAAAUAAGAGAGAAAAGAAGAGCCCGCCUAAGAAGAAAUAUAAGAGCCACC |
| 129 | EK1-18-UTR | GGGAAAUAAGAGAGAAAAGAAGACCCGCCGUAAGAAGAAAUAUAAGAGCCACC |
| 130 | EK2-UTR | GGGAAAUAAGAGAGAAAAGAAGAGUAAGAAGAAAUAUAAGAGCCGCCGCCACC |
| 131 | EK2-1-UTR | GGGAAAUAAGAGAGAAAAGAAGAGUAAGAAGAAAUAUAAGGCCGCCAGCCACC |

TABLE 9-continued

SEQUENCE LISTING

| SEQ ID NO | Description | Sequence |
|---|---|---|
| 132 | EK2-2-UTR | GGGAAAUAAGAGAGAAAAGAAGAGUAAGAAGAAAUAUAAGCCGCCGAGCCACC |
| 133 | EK2-3-UTR | GGGAAAUAAGAGAGAAAAGAAGAGUAAGAAGAAAUAUAGCCGCCAGAGCCACC |
| 134 | EK2-4-UTR | GGGAAAUAAGAGAGAAAAGAAGAGUAAGAAGAAAUAUGCCGCCAAGAGCCACC |
| 135 | EK2-5-UTR | GGGAAAUAAGAGAGAAAAGAAGAGUAAGAAGAAAUAGCCGCCUAAGAGCCACC |
| 136 | EK2-6-UTR | GGGAAAUAAGAGAGAAAAGAAGAGUAAGAAGAAAUGCCGCCAUAAGAGCCACC |
| 137 | EK2-7-UTR | GGGAAAUAAGAGAGAAAAGAAGAGUAAGAAGAAAGCCGCCUAUAAGAGCCACC |
| 138 | EK2-8-UTR | GGGAAAUAAGAGAGAAAAGAAGAGUAAGAAGAAGCCGCCAUAUAAGAGCCACC |
| 139 | EK2-9-UTR | GGGAAAUAAGAGAGAAAAGAAGAGUAAGAAGAGCCGCCAAUAUAAGAGCCACC |
| 140 | EK2-10-UTR | GGGAAAUAAGAGAGAAAAGAAGAGUAAGAAGGCCGCCAAAUAUAAGAGCCACC |
| 141 | EK2-11-UTR | GGGAAAUAAGAGAGAAAAGAAGAGUAAGAAGCCGCCGAAAUAUAAGAGCCACC |
| 142 | EK2-12-UTR | GGGAAAUAAGAGAGAAAAGAAGAGUAAGAGCCGCCAGAAAUAUAAGAGCCACC |
| 143 | EK2-13-UTR | GGGAAAUAAGAGAGAAAAGAAGAGUAAGGCCGCCAAGAAAUAUAAGAGCCACC |
| 144 | EK2-14-UTR | GGGAAAUAAGAGAGAAAAGAAGAGUAAGCCGCCGAAGAAAUAUAAGAGCCACC |
| 145 | EK2-15-UTR | GGGAAAUAAGAGAGAAAAGAAGAGUAGCCGCCAGAAGAAAUAUAAGAGCCACC |
| 146 | EK2-16-UTR | GGGAAAUAAGAGAGAAAAGAAGAGUGCCGCCAAGAAGAAAUAUAAGAGCCACC |
| 147 | EK2-17-UTR | GGGAAAUAAGAGAGAAAAGAAGAGGCCGCCUAAGAAGAAAUAUAAGAGCCACC |
| 148 | EK2-18-UTR | GGGAAAUAAGAGAGAAAAGAAGAGCCGCCGUAAGAAGAAAUAUAAGAGCCACC |
| 149 | EK3-UTR | GGGAAAUAAGAGAGAAAAGAAGAGUAAGAAGAAAUAUAAGACCGCCGGCCACC |
| 150 | EK3-1-UTR | GGGAAAUAAGAGAGAAAAGAAGAGUAAGAAGAAAUAUAAGCCGCCGAGCCACC |
| 151 | EK3-2-UTR | GGGAAAUAAGAGAGAAAAGAAGAGUAAGAAGAAAUAUAACCGCCGGAGCCACC |
| 152 | EK3-3-UTR | GGGAAAUAAGAGAGAAAAGAAGAGUAAGAAGAAAUAUACCGCCGAGAGCCACC |
| 153 | EK3-4-UTR | GGGAAAUAAGAGAGAAAAGAAGAGUAAGAAGAAAUAUCCGCCGAAGAGCCACC |
| 154 | EK3-5-UTR | GGGAAAUAAGAGAGAAAAGAAGAGUAAGAAGAAAUACCGCCGUAAGAGCCACC |
| 155 | EK3-6-UTR | GGGAAAUAAGAGAGAAAAGAAGAGUAAGAAGAAAUCCGCCGAUAAGAGCCACC |
| 156 | EK3-7-UTR | GGGAAAUAAGAGAGAAAAGAAGAGUAAGAAGAAACCGCCGUAUAAGAGCCACC |

TABLE 9-continued

| SEQ ID NO | Description | Sequence |
|---|---|---|
| 157 | EK3-8-UTR | GGGAAAUAAGAGAGAAAAGAAGAGUAAGAAGAACCGCCGAUAU AAGAGCCACC |
| 158 | EK3-9-UTR | GGGAAAUAAGAGAGAAAAGAAGAGUAAGAAGACCGCCGAAUAU AAGAGCCACC |
| 159 | EK3-10-UTR | GGGAAAUAAGAGAGAAAAGAAGAGUAAGAAGCCGCCGAAAUAU AAGAGCCACC |
| 160 | EK3-11-UTR | GGGAAAUAAGAGAGAAAAGAAGAGUAAGAACCGCCGGAAAUAU AAGAGCCACC |
| 161 | EK3-12-UTR | GGGAAAUAAGAGAGAAAAGAAGAGUAAGACCGCCGAGAAAUAU AAGAGCCACC |
| 162 | EK3-13-UTR | GGGAAAUAAGAGAGAAAAGAAGAGUAAGCCGCCGAAGAAAUAU AAGAGCCACC |
| 163 | EK3-14-UTR | GGGAAAUAAGAGAGAAAAGAAGAGUAACCGCCGGAAGAAAUAU AAGAGCCACC |
| 164 | EK3-15-UTR | GGGAAAUAAGAGAGAAAAGAAGAGUACCGCCGAGAAGAAAUAU AAGAGCCACC |
| 165 | EK3-16-UTR | GGGAAAUAAGAGAGAAAAGAAGAGUCCGCCGAAGAAGAAAUAU AAGAGCCACC |
| 166 | EK3-17-UTR | GGGAAAUAAGAGAGAAAAGAAGAGCCGCCGUAAGAAGAAAUAU AAGAGCCACC |
| 167 | EK3-18-UTR | GGGAAAUAAGAGAGAAAAGAAGACCGCCGGUAAGAAGAAAUAU AAGAGCCACC |
| 168 | (CCG)3-UTR | GGGAAAUAAGAGAGAAAAGAAGAGUAAGAAGAAAUAUAAGAC CGCCGCCGGCCACC |
| 169 | (CCG)3-1-UTR | GGGAAAUAAGAGAGAAAAGAAGAGUAAGAAGAAAUAUAAGCC GCCGCCGAGCCACC |
| 170 | (CCG)3-2-UTR | GGGAAAUAAGAGAGAAAAGAAGAGUAAGAAGAAAUAUAACCGC CGCCGGAGCCACC |
| 171 | (CCG)3-3-UTR | GGGAAAUAAGAGAGAAAAGAAGAGUAAGAAGAAAUAUACCGCC GCCGAGAGCCACC |
| 172 | (CCG)3-4-UTR | GGGAAAUAAGAGAGAAAAGAAGAGUAAGAAGAAAUAUCCGCCG CCGAAGAGCCACC |
| 173 | (CCG)3-5-UTR | GGGAAAUAAGAGAGAAAAGAAGAGUAAGAAGAAAUACCGCCGC CGUAAGAGCCACC |
| 174 | (CCG)3-6-UTR | GGGAAAUAAGAGAGAAAAGAAGAGUAAGAAGAAAUCCGCCGCC GAUAAGAGCCACC |
| 175 | (CCG)3-7-UTR | GGGAAAUAAGAGAGAAAAGAAGAGUAAGAAGAAACCGCCGCCG UAUAAGAGCCACC |
| 176 | (CCG)3-8-UTR | GGGAAAUAAGAGAGAAAAGAAGAGUAAGAAGAACCGCCGCCGA UAUAAGAGCCACC |
| 177 | (CCG)3-9-UTR | GGGAAAUAAGAGAGAAAAGAAGAGUAAGAAGACCGCCGCCGAA UAUAAGAGCCACC |
| 178 | (CCG)3-10-UTR | GGGAAAUAAGAGAGAAAAGAAGAGUAAGAAGCCGCCGCCGAAA UAUAAGAGCCACC |
| 179 | (CCG)3-11-UTR | GGGAAAUAAGAGAGAAAAGAAGAGUAAGAACCGCCGCCGGAAA UAUAAGAGCCACC |
| 180 | (CCG)3-12-UTR | GGGAAAUAAGAGAGAAAAGAAGAGUAAGACCGCCGCCGAGAAA UAUAAGAGCCACC |
| 181 | (CCG)3-13-UTR | GGGAAAUAAGAGAGAAAAGAAGAGUAAGCCGCCGCCGAAGAAA UAUAAGAGCCACC |

TABLE 9-continued

SEQUENCE LISTING

| SEQ ID NO | Description | Sequence |
|---|---|---|
| 182 | (CCG)3-14-UTR | GGGAAAUAAGAGAGAAAAGAAGAGUAACCGCCGCCGGAAGAAAUAUAAGAGCCACC |
| 183 | (CCG)3-15-UTR | GGGAAAUAAGAGAGAAAAGAAGAGUACCGCCGCCGAGAAGAAAUAUAAGAGCCACC |
| 184 | (CCG)3-16-UTR | GGGAAAUAAGAGAGAAAAGAAGAGUCCGCCGCCGAAGAAGAAAUAUAAGAGCCACC |
| 185 | (CCG)3-17-UTR | GGGAAAUAAGAGAGAAAAGAAGAGCCGCCGCCGUAAGAAGAAAUAUAAGAGCCACC |
| 186 | (CCG)3-18-UTR | GGGAAAUAAGAGAGAAAAGAAGACCGCCGCCGGUAAGAAGAAAUAUAAGAGCCACC |
| 187 | (CCG)4-UTR | GGGAAAUAAGAGAGAAAAGAAGAGUAAGAAGAAAUAUAAGACCGCCGCCGCCGGCCACC |
| 188 | (CCG)4-1-UTR | GGGAAAUAAGAGAGAAAAGAAGAGUAAGAAGAAAUAUAAGCCGCCGCCGCCGAGCCACC |
| 189 | (CCG)4-2-UTR | GGGAAAUAAGAGAGAAAAGAAGAGUAAGAAGAAAUAUAACCGCCGCCGCCGGAGCCACC |
| 190 | (CCG)4-3-UTR | GGGAAAUAAGAGAGAAAAGAAGAGUAAGAAGAAAUAUACCGCCGCCGCCGAGAGCCACC |
| 191 | (CCG)4-4-UTR | GGGAAAUAAGAGAGAAAAGAAGAGUAAGAAGAAAUAUCCGCCGCCGCCGAAGAGCCACC |
| 192 | (CCG)4-5-UTR | GGGAAAUAAGAGAGAAAAGAAGAGUAAGAAGAAAUACCGCCGCCGCCGUAAGAGCCACC |
| 193 | (CCG)4-6-UTR | GGGAAAUAAGAGAGAAAAGAAGAGUAAGAAGAAAUCCGCCGCCGCCGAUAAGAGCCACC |
| 194 | (CCG)4-7-UTR | GGGAAAUAAGAGAGAAAAGAAGAGUAAGAAGAAACCGCCGCCGCCGUAUAAGAGCCACC |
| 195 | (CCG)4-8-UTR | GGGAAAUAAGAGAGAAAAGAAGAGUAAGAAGAACCGCCGCCGCCGAUAUAAGAGCCACC |
| 196 | (CCG)4-9-UTR | GGGAAAUAAGAGAGAAAAGAAGAGUAAGAAGACCGCCGCCGCCGAAUAUAAGAGCCACC |
| 197 | (CCG)4-10-UTR | GGGAAAUAAGAGAGAAAAGAAGAGUAAGAAGCCGCCGCCGCCGAAAUAUAAGAGCCACC |
| 198 | (CCG)4-11-UTR | GGGAAAUAAGAGAGAAAAGAAGAGUAAGAACCGCCGCCGCCGGAAAUAUAAGAGCCACC |
| 199 | (CCG)4-12-UTR | GGGAAAUAAGAGAGAAAAGAAGAGUAAGACCGCCGCCGCCGAGAAAUAUAAGAGCCACC |
| 200 | (CCG)4-13-UTR | GGGAAAUAAGAGAGAAAAGAAGAGUAAGCCGCCGCCGCCGAAGAAAUAUAAGAGCCACC |
| 201 | (CCG)4-14-UTR | GGGAAAUAAGAGAGAAAAGAAGAGUAACCGCCGCCGCCGGAAGAAAUAUAAGAGCCACC |
| 202 | (CCG)4-15-UTR | GGGAAAUAAGAGAGAAAAGAAGAGUACCGCCGCCGCCGAGAAGAAAUAUAAGAGCCACC |
| 203 | (CCG)4-16-UTR | GGGAAAUAAGAGAGAAAAGAAGAGUCCGCCGCCGCCGAAGAAGAAAUAUAAGAGCCACC |
| 204 | (CCG)4-17-UTR | GGGAAAUAAGAGAGAAAAGAAGAGCCGCCGCCGCCGUAAGAAGAAAUAUAAGAGCCACC |
| 205 | (CCG)4-18-UTR | GGGAAAUAAGAGAGAAAAGAAGACCGCCGCCGCCGGUAAGAAGAAAUAUAAGAGCCACC |
| 206 | (CCG)5-UTR | GGGAAAUAAGAGAGAAAAGAAGAGUAAGAAGAAAUAUAAGACCGCCGCCGCCGCCGGCCACC |

TABLE 9-continued

SEQUENCE LISTING

| SEQ ID NO | Description | Sequence |
|---|---|---|
| 207 | (CCG)5-1-UTR | GGGAAAUAAGAGAGAAAAGAAGAGUAAGAAGAAAUAUAAGCCGCCGCCGCCGCCGAGCCACC |
| 208 | (CCG)5-2-UTR | GGGAAAUAAGAGAGAAAAGAAGAGUAAGAAGAAAUAUAACCGCCGCCGCCGCCGGAGCCACC |
| 209 | (CCG)5-3-UTR | GGGAAAUAAGAGAGAAAAGAAGAGUAAGAAGAAAUAUACCGCCGCCGCCGCCGAGAGCCACC |
| 210 | (CCG)5-4-UTR | GGGAAAUAAGAGAGAAAAGAAGAGUAAGAAGAAAUAUCCGCCGCCGCCGCCGAAGAGCCACC |
| 211 | (CCG)5-5-UTR | GGGAAAUAAGAGAGAAAAGAAGAGUAAGAAGAAAUACCGCCGCCGCCGCCGUAAGAGCCACC |
| 212 | (CCG)5-6-UTR | GGGAAAUAAGAGAGAAAAGAAGAGUAAGAAGAAAUCCGCCGCCGCCGCCGAUAAGAGCCACC |
| 213 | (CCG)5-7-UTR | GGGAAAUAAGAGAGAAAAGAAGAGUAAGAAGAAACCGCCGCCGCCGCCGUAUAAGAGCCACC |
| 214 | (CCG)5-8-UTR | GGGAAAUAAGAGAGAAAAGAAGAGUAAGAAGAACCGCCGCCGCCGCCGAUAUAAGAGCCACC |
| 215 | (CCG)5-9-UTR | GGGAAAUAAGAGAGAAAAGAAGAGUAAGAAGACCGCCGCCGCCGCCGAAUAUAAGAGCCACC |
| 216 | (CCG)5-10-UTR | GGGAAAUAAGAGAGAAAAGAAGAGUAAGAAGCCGCCGCCGCCGCCGAAAUAUAAGAGCCACC |
| 217 | (CCG)5-11-UTR | GGGAAAUAAGAGAGAAAAGAAGAGUAAGAACCGCCGCCGCCGCCGCGGAAAUAUAAGAGCCACC |
| 218 | (CCG)5-12-UTR | GGGAAAUAAGAGAGAAAAGAAGAGUAAGACCGCCGCCGCCGCCGGAGAAAUAUAAGAGCCACC |
| 219 | (CCG)5-13-UTR | GGGAAAUAAGAGAGAAAAGAAGAGUAAGCCGCCGCCGCCGCCGAAGAAAUAUAAGAGCCACC |
| 220 | (CCG)5-14-UTR | GGGAAAUAAGAGAGAAAAGAAGAGUAACCGCCGCCGCCGCCGGAAGAAAUAUAAGAGCCACC |
| 221 | (CCG)5-15-UTR | GGGAAAUAAGAGAGAAAAGAAGAGUACCGCCGCCGCCGCCGAGAAGAAAUAUAAGAGCCACC |
| 222 | (CCG)5-16-UTR | GGGAAAUAAGAGAGAAAAGAAGAGUCCGCCGCCGCCGCCGAAGAAGAAAUAUAAGAGCCACC |
| 223 | (CCG)5-17-UTR | GGGAAAUAAGAGAGAAAAGAAGAGCCGCCGCCGCCGCCGUAAGAAGAAAUAUAAGAGCCACC |
| 224 | (CCG)5-18-UTR | GGGAAAUAAGAGAGAAAAGAAGACCGCCGCCGCCGCCGGUAAGAAGAAAUAUAAGAGCCACC |
| 225 | (CCG)6-UTR | GGGAAAUAAGAGAGAAAAGAAGAGUAAGAAGAAAUAUAAGACCGCCGCCGCCGCCGGCCACC |
| 226 | (CCG)6-1-UTR | GGGAAAUAAGAGAGAAAAGAAGAGUAAGAAGAAAUAUAAGCCGCCGCCGCCGCCGAGCCACC |
| 227 | (CCG)6-2-UTR | GGGAAAUAAGAGAGAAAAGAAGAGUAAGAAGAAAUAUAACCGCCGCCGCCGCCGGAGCCACC |
| 228 | (CCG)6-3-UTR | GGGAAAUAAGAGAGAAAAGAAGAGUAAGAAGAAAUAUACCGCCGCCGCCGCCGAGAGCCACC |
| 229 | (CCG)6-4-UTR | GGGAAAUAAGAGAGAAAAGAAGAGUAAGAAGAAAUAUCCGCCGCCGCCGCCGAAGAGCCACC |
| 230 | (CCG)6-5-UTR | GGGAAAUAAGAGAGAAAAGAAGAGUAAGAAGAAAUACCGCCGCCGCCGCCGUAAGAGCCACC |
| 231 | (CCG)6-6-UTR | GGGAAAUAAGAGAGAAAAGAAGAGUAAGAAGAAAUCCGCCGCCGCCGCCGAUAAGAGCCACC |

TABLE 9-continued

SEQUENCE LISTING

| SEQ ID NO | Description | Sequence |
|---|---|---|
| 232 | (CCG)6-7-UTR | GGGAAAUAAGAGAGAAAAGAAGAGUAAGAAGAAACCGCCGCCG CCGCCGCCGUAUAAGAGCCACC |
| 233 | (CCG)6-8-UTR | GGGAAAUAAGAGAGAAAAGAAGAGUAAGAAGAACCGCCGCCGC CGCCGCCGAUAUAAGAGCCACC |
| 234 | (CCG)6-9-UTR | GGGAAAUAAGAGAGAAAAGAAGAGUAAGAAGACCGCCGCCGCC GCCGCCGAAUAUAAGAGCCACC |
| 235 | (CCG)6-10-UTR | GGGAAAUAAGAGAGAAAAGAAGAGUAAGAAGCCGCCGCCGCCG CCGCCGAAAUAUAAGAGCCACC |
| 236 | (CCG)6-11-UTR | GGGAAAUAAGAGAGAAAAGAAGAGUAAGAACCGCCGCCGCCGC CGCCGGAAAUAUAAGAGCCACC |
| 237 | (CCG)6-12-UTR | GGGAAAUAAGAGAGAAAAGAAGAGUAAGACCGCCGCCGCCGCC GCCGAGAAAUAUAAGAGCCACC |
| 238 | (CCG)6-13-UTR | GGGAAAUAAGAGAGAAAAGAAGAGUAAGCCGCCGCCGCCGCCG CCGAAGAAAUAUAAGAGCCACC |
| 239 | (CCG)6-14-UTR | GGGAAAUAAGAGAGAAAAGAAGAGUAACCGCCGCCGCCGCCGC CGGAAGAAAUAUAAGAGCCACC |
| 240 | (CCG)6-15-UTR | GGGAAAUAAGAGAGAAAAGAAGAGUACCGCCGCCGCCGCCGCC GAGAAGAAAUAUAAGAGCCACC |
| 241 | (CCG)6-16-UTR | GGGAAAUAAGAGAGAAAAGAAGAGUCCGCCGCCGCCGCCGCCG AAGAAGAAAUAUAAGAGCCACC |
| 242 | (CCG)6-17-UTR | GGGAAAUAAGAGAGAAAAGAAGAGCCGCCGCCGCCGCCGCCGU AAGAAGAAAUAUAAGAGCCACC |
| 243 | (CCG)6-18-UTR | GGGAAAUAAGAGAGAAAAGAAGACCGCCGCCGCCGCCGCCGGU AAGAAGAAAUAUAAGAGCCACC |
| 244 | (CCG)7-UTR | GGGAAAUAAGAGAGAAAAGAAGAGUAAGAAGAAAUAUAAGAC CGCCGCCGCCGCCGCCGGCCACC |
| 245 | (CCG)7-1-UTR | GGGAAAUAAGAGAGAAAAGAAGAGUAAGAAGAAAUAUAAGCC GCCGCCGCCGCCGCCGAGCCACC |
| 246 | (CCG)7-2-UTR | GGGAAAUAAGAGAGAAAAGAAGAGUAAGAAGAAAUAUAACCGC CGCCGCCGCCGCCGGAGCCACC |
| 247 | (CCG)7-3-UTR | GGGAAAUAAGAGAGAAAAGAAGAGUAAGAAGAAAUAUACCGCC GCCGCCGCCGCCGAGAGCCACC |
| 248 | (CCG)7-4-UTR | GGGAAAUAAGAGAGAAAAGAAGAGUAAGAAGAAAUAUCCGCCG CCGCCGCCGCCGAAGAGCCACC |
| 249 | (CCG)7-5-UTR | GGGAAAUAAGAGAGAAAAGAAGAGUAAGAAGAAAUACCGCCGC CGCCGCCGCCGUAAGAGCCACC |
| 250 | (CCG)7-6-UTR | GGGAAAUAAGAGAGAAAAGAAGAGUAAGAAGAAAUCCGCCGCC GCCGCCGCCGAUAAGAGCCACC |
| 251 | (CCG)7-7-UTR | GGGAAAUAAGAGAGAAAAGAAGAGUAAGAAGAAACCGCCGCCG CCGCCGCCGUAUAAGAGCCACC |
| 252 | (CCG)7-8-UTR | GGGAAAUAAGAGAGAAAAGAAGAGUAAGAAGAACCGCCGCCGC CGCCGCCGAUAUAAGAGCCACC |
| 253 | (CCG)7-9-UTR | GGGAAAUAAGAGAGAAAAGAAGAGUAAGAAGACCGCCGCCGCC GCCGCCGAAUAUAAGAGCCACC |
| 254 | (CCG)7-10-UTR | GGGAAAUAAGAGAGAAAAGAAGAGUAAGAAGCCGCCGCCGCCG CCGCCGAAAUAUAAGAGCCACC |
| 255 | (CCG)7-11-UTR | GGGAAAUAAGAGAGAAAAGAAGAGUAAGAACCGCCGCCGCCGC CGCCGGAAAUAUAAGAGCCACC |
| 256 | (CCG)7-12-UTR | GGGAAAUAAGAGAGAAAAGAAGAGUAAGACCGCCGCCGCCGCC GCCGAGAAAUAUAAGAGCCACC |

TABLE 9-continued

| SEQ ID NO | Description | Sequence |
|---|---|---|
| 257 | (CCG)7-13-UTR | GGGAAAUAAGAGAGAAAAGAAGAGUAAGCCGCCGCCGCCGCCG CCGCCGAAGAAAUAUAAGAGCCACC |
| 258 | (CCG)7-14-UTR | GGGAAAUAAGAGAGAAAAGAAGAGUAACCGCCGCCGCCGCCGC CGCCGGAAGAAAUAUAAGAGCCACC |
| 259 | (CCG)7-15-UTR | GGGAAAUAAGAGAGAAAAGAAGAGUACCGCCGCCGCCGCCGCC GCCGAGAAGAAAUAUAAGAGCCACC |
| 260 | (CCG)7-16-UTR | GGGAAAUAAGAGAGAAAAGAAGAGUCCGCCGCCGCCGCCGCCG CCGAAGAAGAAAUAUAAGAGCCACC |
| 261 | (CCG)7-17-UTR | GGGAAAUAAGAGAGAAAAGAAGAGCCGCCGCCGCCGCCGCCGC CGUAAGAAGAAAUAUAAGAGCCACC |
| 262 | (CCG)7-18-UTR | GGGAAAUAAGAGAGAAAAGAAGACCGCCGCCGCCGCCGCCGCC GGUAAGAAGAAAUAUAAGAGCCACC |
| 263 | (CCG)8-UTR | GGGAAAUAAGAGAGAAAAGAAGAGUAAGAAGAAAUAUAAGAC CGCCGCCGCCGCCGCCGCCGGCCACC |
| 264 | (CCG)8-1-UTR | GGGAAAUAAGAGAGAAAAGAAGAGUAAGAAGAAAUAUAAGCC GCCGCCGCCGCCGCCGCCGAGCCACC |
| 265 | (CCG)8-2-UTR | GGGAAAUAAGAGAGAAAAGAAGAGUAAGAAGAAAUAUAACCGC CGCCGCCGCCGCCGCCGGAGCCACC |
| 266 | (CCG)8-3-UTR | GGGAAAUAAGAGAGAAAAGAAGAGUAAGAAGAAAUAUACCGCC GCCGCCGCCGCCGCCGAGAGCCACC |
| 267 | (CCG)8-4-UTR | GGGAAAUAAGAGAGAAAAGAAGAGUAAGAAGAAAUAUCCGCCG CCGCCGCCGCCGCCGAAGAGCCACC |
| 268 | (CCG)8-5-UTR | GGGAAAUAAGAGAGAAAAGAAGAGUAAGAAGAAAUACCGCCGC CGCCGCCGCCGCCGUAAGAGCCACC |
| 269 | (CCG)8-6-UTR | GGGAAAUAAGAGAGAAAAGAAGAGUAAGAAGAAAUCCGCCGCC GCCGCCGCCGCCGAUAAGAGCCACC |
| 270 | (CCG)8-7-UTR | GGGAAAUAAGAGAGAAAAGAAGAGUAAGAAGAAACCGCCGCCG CCGCCGCCGCCGUAUAAGAGCCACC |
| 271 | (CCG)8-8-UTR | GGGAAAUAAGAGAGAAAAGAAGAGUAAGAAGAACCGCCGCCGC CGCCGCCGCCGAUAUAAGAGCCACC |
| 272 | (CCG)8-9-UTR | GGGAAAUAAGAGAGAAAAGAAGAGUAAGAAGACCGCCGCCGCC GCCGCCGCCGAAUAUAAGAGCCACC |
| 273 | (CCG)8-10-UTR | GGGAAAUAAGAGAGAAAAGAAGAGUAAGAAGCCGCCGCCGCCG CCGCCGCCGAAAUAUAAGAGCCACC |
| 274 | (CCG)8-11-UTR | GGGAAAUAAGAGAGAAAAGAAGAGUAAGAACCGCCGCCGCCGC CGCCGCCGGAAAUAUAAGAGCCACC |
| 275 | (CCG)8-12-UTR | GGGAAAUAAGAGAGAAAAGAAGAGUAAGACCGCCGCCGCCGCC GCCGCCGAGAAAUAUAAGAGCCACC |
| 276 | (CCG)8-13-UTR | GGGAAAUAAGAGAGAAAAGAAGAGUAAGCCGCCGCCGCCGCCG CCGCCGAAGAAAUAUAAGAGCCACC |
| 277 | (CCG)8-14-UTR | GGGAAAUAAGAGAGAAAAGAAGAGUAACCGCCGCCGCCGCCGC CGCCGGAAGAAAUAUAAGAGCCACC |
| 278 | (CCG)8-15-UTR | GGGAAAUAAGAGAGAAAAGAAGAGUACCGCCGCCGCCGCCGCC GCCGCGAGAAGAAAUAUAAGAGCCACC |
| 279 | (CCG)8-16-UTR | GGGAAAUAAGAGAGAAAAGAAGAGUCCGCCGCCGCCGCCGCCG CCGCCGAAGAAGAAAUAUAAGAGCCACC |
| 280 | (CCG)8-17-UTR | GGGAAAUAAGAGAGAAAAGAAGAGCCGCCGCCGCCGCCGCCGC CGCCGUAAGAAGAAAUAUAAGAGCCACC |
| 281 | (CCG)8-18-UTR | GGGAAAUAAGAGAGAAAAGAAGACCGCCGCCGCCGCCGCCGCC GCCGGUAAGAAGAAAUAUAAGAGCCACC |

TABLE 9-continued

SEQUENCE LISTING

| SEQ ID NO | Description | Sequence |
|---|---|---|
| 282 | (CCG)9-UTR | GGGAAAUAAGAGAGAAAAGAAGAGUAAGAAGAAAUAUAAGAC CGCCGCCGCCGCCGCCGCCGCCGCCGGCCACC |
| 283 | (CCG)9-1-UTR | GGGAAAUAAGAGAGAAAAGAAGAGUAAGAAGAAAUAUAAGCC GCCGCCGCCGCCGCCGCCGCCGCCGAGCCACC |
| 284 | (CCG)9-2-UTR | GGGAAAUAAGAGAGAAAAGAAGAGUAAGAAGAAAUAUAACCGC CGCCGCCGCCGCCGCCGCCGCCGGAGCCACC |
| 285 | (CCG)9-3-UTR | GGGAAAUAAGAGAGAAAAGAAGAGUAAGAAGAAAUAUACCGCC GCCGCCGCCGCCGCCGCCGCCGAGAGCCACC |
| 286 | (CCG)9-4-UTR | GGGAAAUAAGAGAGAAAAGAAGAGUAAGAAGAAAUAUCCGCCG CCGCCGCCGCCGCCGCCGCCGAAGAGCCACC |
| 287 | (CCG)9-5-UTR | GGGAAAUAAGAGAGAAAAGAAGAGUAAGAAGAAAUACCGCCGC CGCCGCCGCCGCCGCCGCCGUAAGAGCCACC |
| 288 | (CCG)9-6-UTR | GGGAAAUAAGAGAGAAAAGAAGAGUAAGAAGAAAUCCGCCGCC GCCGCCGCCGCCGCCGCCGAUAAGAGCCACC |
| 289 | (CCG)9-7-UTR | GGGAAAUAAGAGAGAAAAGAAGAGUAAGAAGAAACCGCCGCCG CCGCCGCCGCCGCCGCCGUAUAAGAGCCACC |
| 290 | (CCG)9-8-UTR | GGGAAAUAAGAGAGAAAAGAAGAGUAAGAAGAACCGCCGCCGC CGCCGCCGCCGCCGCCGAUAUAAGAGCCACC |
| 291 | (CCG)9-9-UTR | GGGAAAUAAGAGAGAAAAGAAGAGUAAGAAGACCGCCGCCGCC GCCGCCGCCGCCGCCGAAUAUAAGAGCCACC |
| 292 | (CCG)9-10-UTR | GGGAAAUAAGAGAGAAAAGAAGAGUAAGAAGCCGCCGCCGCCG CCGCCGCCGCCGCCGAAAUAUAAGAGCCACC |
| 293 | (CCG)9-11-UTR | GGGAAAUAAGAGAGAAAAGAAGAGUAAGAACCGCCGCCGCCGC CGCCGCCGCCGCCGGAAAUAUAAGAGCCACC |
| 294 | (CCG)9-12-UTR | GGGAAAUAAGAGAGAAAAGAAGAGUAAGACCGCCGCCGCCGCC GCCGCCGCCGCCGAGAAAUAUAAGAGCCACC |
| 295 | (CCG)9-13-UTR | GGGAAAUAAGAGAGAAAAGAAGAGUAAGCCGCCGCCGCCGCCG CCGCCGCCGCCGAAGAAAUAUAAGAGCCACC |
| 296 | (CCG)9-14-UTR | GGGAAAUAAGAGAGAAAAGAAGAGUAACCGCCGCCGCCGCCGC CGCCGCCGCCGGAAGAAAUAUAAGAGCCACC |
| 297 | (CCG)9-15-UTR | GGGAAAUAAGAGAGAAAAGAAGAGUACCGCCGCCGCCGCCGCC GCCGCCGCCGAGAAGAAAUAUAAGAGCCACC |
| 298 | (CCG)9-16-UTR | GGGAAAUAAGAGAGAAAAGAAGAGUCCGCCGCCGCCGCCGCCG CCGCCGCCGAAGAAGAAAUAUAAGAGCCACC |
| 299 | (CCG)9-17-UTR | GGGAAAUAAGAGAGAAAAGAAGAGCCGCCGCCGCCGCCGCCGC CGCCGCCGUAAGAAGAAAUAUAAGAGCCACC |
| 300 | (CCG)9-18-UTR | GGGAAAUAAGAGAGAAAAGAAGACCGCCGCCGCCGCCGCCGCC GCCGCCGGUAAGAAGAAAUAUAAGAGCCACC |
| 301 | (CCG)10-UTR | GGGAAAUAAGAGAGAAAAGAAGAGUAAGAAGAAAUAUAAGAC CGCCGCCGCCGCCGCCGCCGCCGCCGGCCACC |
| 302 | (CCG)10-1-UTR | GGGAAAUAAGAGAGAAAAGAAGAGUAAGAAGAAAUAUAAGCC GCCGCCGCCGCCGCCGCCGCCGCCGAGCCACC |
| 303 | (CCG)10-2-UTR | GGGAAAUAAGAGAGAAAAGAAGAGUAAGAAGAAAUAUAACCGC CGCCGCCGCCGCCGCCGCCGCCGGAGCCACC |
| 304 | (CCG)10-3-UTR | GGGAAAUAAGAGAGAAAAGAAGAGUAAGAAGAAAUAUACCGCC GCCGCCGCCGCCGCCGCCGCCGCCGAGAGCCACC |
| 305 | (CCG)10-4-UTR | GGGAAAUAAGAGAGAAAAGAAGAGUAAGAAGAAAUAUCCGCCG CCGCCGCCGCCGCCGCCGCCGCCGAAGAGCCACC |
| 306 | (CCG)10-5-UTR | GGGAAAUAAGAGAGAAAAGAAGAGUAAGAAGAAAUACCGCCGC CGCCGCCGCCGCCGCCGCCGCCGUAAGAGCCACC |

TABLE 9-continued

SEQUENCE LISTING

| SEQ ID NO | Description | Sequence |
|---|---|---|
| 307 | (CCG)10-6-UTR | GGGAAAUAAGAGAGAAAAGAAGAGUAAGAAGAAAUCCGCCGCC GCCGCCGCCGCCGCCGCCGCCGAUAAGAGCCACC |
| 308 | (CCG)10-7-UTR | GGGAAAUAAGAGAGAAAAGAAGAGUAAGAAGAAACCGCCGCCG CCGCCGCCGCCGCCGCCGCCGUAUAAGAGCCACC |
| 309 | (CCG)10-8-UTR | GGGAAAUAAGAGAGAAAAGAAGAGUAAGAAGAACCGCCGCCGC CGCCGCCGCCGCCGCCGCCGAUAUAAGAGCCACC |
| 310 | (CCG)10-9-UTR | GGGAAAUAAGAGAGAAAAGAAGAGUAAGAAGACCGCCGCCGCC GCCGCCGCCGCCGCCGCCGAAUAUAAGAGCCACC |
| 311 | (CCG)10-10-UTR | GGGAAAUAAGAGAGAAAAGAAGAGUAAGAAGCCGCCGCCGCCG CCGCCGCCGCCGCCGCCGAAAUAUAAGAGCCACC |
| 312 | (CCG)10-11-UTR | GGGAAAUAAGAGAGAAAAGAAGAGUAAGAACCGCCGCCGCCGC CGCCGCCGCCGCCGCCGGAAAUAUAAGAGCCACC |
| 313 | (CCG)10-12-UTR | GGGAAAUAAGAGAGAAAAGAAGAGUAAGACCGCCGCCGCCGCC GCCGCCGCCGCCGCCGAGAAAUAUAAGAGCCACC |
| 314 | (CCG)10-13-UTR | GGGAAAUAAGAGAGAAAAGAAGAGUAAGCCGCCGCCGCCGCCG CCGCCGCCGCCGCCGAAGAAAUAUAAGAGCCACC |
| 315 | (CCG)10-14-UTR | GGGAAAUAAGAGAGAAAAGAAGAGUAACCGCCGCCGCCGCCGC CGCCGCCGCCGCCGGAAGAAAUAUAAGAGCCACC |
| 316 | (CCG)10-15-UTR | GGGAAAUAAGAGAGAAAAGAAGAGUACCGCCGCCGCCGCCGCC GCCGCCGCCGCCGAGAAGAAAUAUAAGAGCCACC |
| 317 | (CCG)10-16-UTR | GGGAAAUAAGAGAGAAAAGAAGAGUCCGCCGCCGCCGCCGCCG CCGCCGCCGCCGAAGAAGAAAUAUAAGAGCCACC |
| 318 | (CCG)10-17-UTR | GGGAAAUAAGAGAGAAAAGAAGAGCCGCCGCCGCCGCCGCCGC CGCCGCCGCCGUAAGAAGAAAUAUAAGAGCCACC |
| 319 | (CCG)10-18-UTR | GGGAAAUAAGAGAGAAAAGAAGACCGCCGCCGCCGCCGCCGCC GCCGCCGCCGGUAAGAAGAAAUAUAAGAGCCACC |
| 320 | (GCC)3-UTR | GGGAAAUAAGAGAGAAAAGAAGAGUAAGAAGAAAUAUAAGAG CCGCCGCCGCCACC |
| 321 | (GCC)3-1-UTR | GGGAAAUAAGAGAGAAAAGAAGAGUAAGAAGAAAUAUAAGGC CGCCGCCAGCCACC |
| 322 | (GCC)3-2-UTR | GGGAAAUAAGAGAGAAAAGAAGAGUAAGAAGAAAUAUAAGCC GCCGCCGAGCCACC |
| 323 | (GCC)3-3-UTR | GGGAAAUAAGAGAGAAAAGAAGAGUAAGAAGAAAUAUAGCCG CCGCCAGAGCCACC |
| 324 | (GCC)3-4-UTR | GGGAAAUAAGAGAGAAAAGAAGAGUAAGAAGAAAUAUGCCGCC GCCAAGAGCCACC |
| 325 | (GCC)3-5-UTR | GGGAAAUAAGAGAGAAAAGAAGAGUAAGAAGAAAUAGCCGCCG CCUAAGAGCCACC |
| 326 | (GCC)3-6-UTR | GGGAAAUAAGAGAGAAAAGAAGAGUAAGAAGAAAUGCCGCCGC CAUAAGAGCCACC |
| 327 | (GCC)3-7-UTR | GGGAAAUAAGAGAGAAAAGAAGAGUAAGAAGAAAGCCGCCGCC UAUAAGAGCCACC |
| 328 | (GCC)3-8-UTR | GGGAAAUAAGAGAGAAAAGAAGAGUAAGAAGAAGCCGCCGCCA UAUAAGAGCCACC |
| 329 | (GCC)3-9-UTR | GGGAAAUAAGAGAGAAAAGAAGAGUAAGAAGAGCCGCCGCCAA UAUAAGAGCCACC |
| 330 | (GCC)3-10-UTR | GGGAAAUAAGAGAGAAAAGAAGAGUAAGAAGGCCGCCGCCAAA UAUAAGAGCCACC |
| 331 | (GCC)3-11-UTR | GGGAAAUAAGAGAGAAAAGAAGAGUAAGAAGCCGCCGCCGAAA UAUAAGAGCCACC |

TABLE 9-continued

SEQUENCE LISTING

| SEQ ID NO | Description | Sequence |
|---|---|---|
| 332 | (GCC)3-12-UTR | GGGAAAUAAGAGAGAAAAGAAGAGUAAGAGCCGCCGCCAGAAA<br>UAUAAGAGCCACC |
| 333 | (GCC)3-13-UTR | GGGAAAUAAGAGAGAAAAGAAGAGUAAGGCCGCCGCCAAGAAA<br>UAUAAGAGCCACC |
| 334 | (GCC)3-14-UTR | GGGAAAUAAGAGAGAAAAGAAGAGUAAGCCGCCGCCGAAGAAA<br>UAUAAGAGCCACC |
| 335 | (GCC)3-15-UTR | GGGAAAUAAGAGAGAAAAGAAGAGUAGCCGCCGCCAGAAGAAA<br>UAUAAGAGCCACC |
| 336 | (GCC)3-16-UTR | GGGAAAUAAGAGAGAAAAGAAGAGUGCCGCCGCCAAGAAGAAA<br>UAUAAGAGCCACC |
| 337 | (GCC)3-17-UTR | GGGAAAUAAGAGAGAAAAGAAGAGGCCGCCGCCUAAGAAGAAA<br>UAUAAGAGCCACC |
| 338 | (GCC)3-18-UTR | GGGAAAUAAGAGAGAAAAGAAGAGCCGCCGCCGUAAGAAGAAA<br>UAUAAGAGCCACC |
| 339 | (GCC)4-UTR | GGGAAAUAAGAGAGAAAAGAAGAGUAAGAAGAAAUAUAAGAG<br>CCGCCGCCGCCACC |
| 340 | (GCC)4-1-UTR | GGGAAAUAAGAGAGAAAAGAAGAGUAAGAAGAAAUAUAAGGC<br>CGCCGCCGCCAGCCACC |
| 341 | (GCC)4-2-UTR | GGGAAAUAAGAGAGAAAAGAAGAGUAAGAAGAAAUAUAAGCC<br>GCCGCCGCCGAGCCACC |
| 342 | (GCC)4-3-UTR | GGGAAAUAAGAGAGAAAAGAAGAGUAAGAAGAAAUAUAGCCG<br>CCGCCGCCAGAGCCACC |
| 343 | (GCC)4-4-UTR | GGGAAAUAAGAGAGAAAAGAAGAGUAAGAAGAAAUAUGCCGCC<br>GCCGCCAAGAGCCACC |
| 344 | (GCC)4-5-UTR | GGGAAAUAAGAGAGAAAAGAAGAGUAAGAAGAAAUAGCCGCCG<br>CCGCCUAAGAGCCACC |
| 345 | (GCC)4-6-UTR | GGGAAAUAAGAGAGAAAAGAAGAGUAAGAAGAAAUGCCGCCGC<br>CGCCAUAAGAGCCACC |
| 346 | (GCC)4-7-UTR | GGGAAAUAAGAGAGAAAAGAAGAGUAAGAAGAAAGCCGCCGCC<br>GCCUAUAAGAGCCACC |
| 347 | (GCC)4-8-UTR | GGGAAAUAAGAGAGAAAAGAAGAGUAAGAAGAAGCCGCCGCCG<br>CCAUAUAAGAGCCACC |
| 348 | (GCC)4-9-UTR | GGGAAAUAAGAGAGAAAAGAAGAGUAAGAAGAGCCGCCGCCGC<br>CAAUAUAAGAGCCACC |
| 349 | (GCC)4-10-UTR | GGGAAAUAAGAGAGAAAAGAAGAGUAAGAAGGCCGCCGCCGCC<br>AAAUAUAAGAGCCACC |
| 350 | (GCC)4-11-UTR | GGGAAAUAAGAGAGAAAAGAAGAGUAAGAAGCCGCCGCCGCCG<br>AAAUAUAAGAGCCACC |
| 351 | (GCC)4-12-UTR | GGGAAAUAAGAGAGAAAAGAAGAGUAAGAGCCGCCGCCGCCAG<br>AAAUAUAAGAGCCACC |
| 352 | (GCC)4-13-UTR | GGGAAAUAAGAGAGAAAAGAAGAGUAAGGCCGCCGCCGCCAAG<br>AAAUAUAAGAGCCACC |
| 353 | (GCC)4-14-UTR | GGGAAAUAAGAGAGAAAAGAAGAGUAAGCCGCCGCCGCCGAAG<br>AAAUAUAAGAGCCACC |
| 354 | (GCC)4-15-UTR | GGGAAAUAAGAGAGAAAAGAAGAGUAGCCGCCGCCGCCAGAAG<br>AAAUAUAAGAGCCACC |
| 355 | (GCC)4-16-UTR | GGGAAAUAAGAGAGAAAAGAAGAGUGCCGCCGCCGCCAAGAAG<br>AAAUAUAAGAGCCACC |
| 356 | (GCC)4-17-UTR | GGGAAAUAAGAGAGAAAAGAAGAGGCCGCCGCCGCCUAAGAAG<br>AAAUAUAAGAGCCACC |

TABLE 9-continued

SEQUENCE LISTING

| SEQ ID NO | Description | Sequence |
|---|---|---|
| 357 | (GCC)4-18-UTR | GGGAAAUAAGAGAGAAAAGAAGAGCCGCCGCCGCCGUAAGAAG AAAUAUAAGAGCCACC |
| 358 | (GCC)5-UTR | GGGAAAUAAGAGAGAAAAGAAGAGUAAGAAGAAAUAUAAGAG CCGCCGCCGCCGCCACC |
| 359 | (GCC)5-1-UTR | GGGAAAUAAGAGAGAAAAGAAGAGUAAGAAGAAAUAUAAGGC CGCCGCCGCCAGCCACC |
| 360 | (GCC)5-2-UTR | GGGAAAUAAGAGAGAAAAGAAGAGUAAGAAGAAAUAUAAGCC GCCGCCGCCGCCGAGCCACC |
| 361 | (GCC)5-3-UTR | GGGAAAUAAGAGAGAAAAGAAGAGUAAGAAGAAAUAUAGCCG CCGCCGCCGCCAGAGCCACC |
| 362 | (GCC)5-4-UTR | GGGAAAUAAGAGAGAAAAGAAGAGUAAGAAGAAAUAUGCCGCC GCCGCCGCCAAGAGCCACC |
| 363 | (GCC)5-5-UTR | GGGAAAUAAGAGAGAAAAGAAGAGUAAGAAGAAAUAGCCGCCG CCGCCGCCUAAGAGCCACC |
| 364 | (GCC)5-6-UTR | GGGAAAUAAGAGAGAAAAGAAGAGUAAGAAGAAAUGCCGCCGC CGCCGCCAUAAGAGCCACC |
| 365 | (GCC)5-7-UTR | GGGAAAUAAGAGAGAAAAGAAGAGUAAGAAGAAAGCCGCCGCC GCCGCCUAUAAGAGCCACC |
| 366 | (GCC)5-8-UTR | GGGAAAUAAGAGAGAAAAGAAGAGUAAGAAGAAGCCGCCGCCG CCGCCAUAUAAGAGCCACC |
| 367 | (GCC)5-9-UTR | GGGAAAUAAGAGAGAAAAGAAGAGUAAGAAGAGCCGCCGCCGC CGCCAAUAUAAGAGCCACC |
| 368 | (GCC)5-10-UTR | GGGAAAUAAGAGAGAAAAGAAGAGUAAGAAGGCCGCCGCCGCC GCCAAAUAUAAGAGCCACC |
| 369 | (GCC)5-11-UTR | GGGAAAUAAGAGAGAAAAGAAGAGUAAGAAGCCGCCGCCGCCG CCGAAAUAUAAGAGCCACC |
| 370 | (GCC)5-12-UTR | GGGAAAUAAGAGAGAAAAGAAGAGUAAGAGCCGCCGCCGCCGC CAGAAAUAUAAGAGCCACC |
| 371 | (GCC)5-13-UTR | GGGAAAUAAGAGAGAAAAGAAGAGUAAGGCCGCCGCCGCCGCC AAGAAAUAUAAGAGCCACC |
| 372 | (GCC)5-14-UTR | GGGAAAUAAGAGAGAAAAGAAGAGUAAGCCGCCGCCGCCGCCG AAGAAAUAUAAGAGCCACC |
| 373 | (GCC)5-15-UTR | GGGAAAUAAGAGAGAAAAGAAGAGUAGCCGCCGCCGCCGCCAG AAGAAAUAUAAGAGCCACC |
| 374 | (GCC)5-16-UTR | GGGAAAUAAGAGAGAAAAGAAGAGUGCCGCCGCCGCCGCCAAG AAGAAAUAUAAGAGCCACC |
| 375 | (GCC)5-17-UTR | GGGAAAUAAGAGAGAAAAGAAGAGGCCGCCGCCGCCGCCUAAG AAGAAAUAUAAGAGCCACC |
| 376 | (GCC)5-18-UTR | GGGAAAUAAGAGAGAAAAGAAGAGCCGCCGCCGCCGCCGUAAG AAGAAAUAUAAGAGCCACC |
| 377 | (GCC)6-UTR | GGGAAAUAAGAGAGAAAAGAAGAGUAAGAAGAAAUAUAAGAG CCGCCGCCGCCGCCGCCACC |
| 378 | (GCC)6-1-UTR | GGGAAAUAAGAGAGAAAAGAAGAGUAAGAAGAAAUAUAAGGC CGCCGCCGCCGCCAGCCACC |
| 379 | (GCC)6-2-UTR | GGGAAAUAAGAGAGAAAAGAAGAGUAAGAAGAAAUAUAAGCC GCCGCCGCCGCCGAGCCACC |
| 380 | (GCC)6-3-UTR | GGGAAAUAAGAGAGAAAAGAAGAGUAAGAAGAAAUAUAGCCG CCGCCGCCGCCAGAGCCACC |
| 381 | (GCC)6-4-UTR | GGGAAAUAAGAGAGAAAAGAAGAGUAAGAAGAAAUAUGCCGCC GCCGCCGCCAAGAGCCACC |

TABLE 9-continued

SEQUENCE LISTING

| SEQ ID NO | Description | Sequence |
|---|---|---|
| 382 | (GCC)6-5-UTR | GGGAAAUAAGAGAGAAAAGAAGAGUAAGAAGAAAUAGCCGCCG CCGCCGCCGCCUAAGAGCCACC |
| 383 | (GCC)6-6-UTR | GGGAAAUAAGAGAGAAAAGAAGAGUAAGAAGAAAUGCCGCCGC CGCCGCCGCCAUAAGAGCCACC |
| 384 | (GCC)6-7-UTR | GGGAAAUAAGAGAGAAAAGAAGAGUAAGAAGAAAGCCGCCGCC GCCGCCGCCUAUAAGAGCCACC |
| 385 | (GCC)6-8-UTR | GGGAAAUAAGAGAGAAAAGAAGAGUAAGAAGAAGCCGCCGCCG CCGCCGCCAUAUAAGAGCCACC |
| 386 | (GCC)6-9-UTR | GGGAAAUAAGAGAGAAAAGAAGAGUAAGAAGAGCCGCCGCCGC CGCCGCCAAUAUAAGAGCCACC |
| 387 | (GCC)6-10-UTR | GGGAAAUAAGAGAGAAAAGAAGAGUAAGAAGGCCGCCGCCGCC GCCGCCAAAUAUAAGAGCCACC |
| 388 | (GCC)6-11-UTR | GGGAAAUAAGAGAGAAAAGAAGAGUAAGAAGCCGCCGCCGCCG CCGCCGAAAUAUAAGAGCCACC |
| 389 | (GCC)6-12-UTR | GGGAAAUAAGAGAGAAAAGAAGAGUAAGAGCCGCCGCCGCCGC CGCCAGAAAUAUAAGAGCCACC |
| 390 | (GCC)6-13-UTR | GGGAAAUAAGAGAGAAAAGAAGAGUAAGGCCGCCGCCGCCGCC GCCAAGAAAUAUAAGAGCCACC |
| 391 | (GCC)6-14-UTR | GGGAAAUAAGAGAGAAAAGAAGAGUAAGCCGCCGCCGCCGCCG CCGAAGAAAUAUAAGAGCCACC |
| 392 | (GCC)6-15-UTR | GGGAAAUAAGAGAGAAAAGAAGAGUAGCCGCCGCCGCCGCCGC CAGAAGAAAUAUAAGAGCCACC |
| 393 | (GCC)6-16-UTR | GGGAAAUAAGAGAGAAAAGAAGAGUGCCGCCGCCGCCGCCGCC AAGAAGAAAUAUAAGAGCCACC |
| 394 | (GCC)6-17-UTR | GGGAAAUAAGAGAGAAAAGAAGAGGCCGCCGCCGCCGCCGCCU AAGAAGAAAUAUAAGAGCCACC |
| 395 | (GCC)6-18-UTR | GGGAAAUAAGAGAGAAAAGAAGAGCCGCCGCCGCCGCCGCCGU AAGAAGAAAUAUAAGAGCCACC |
| 396 | (GCC)7-UTR | GGGAAAUAAGAGAGAAAAGAAGAGUAAGAAGAAAUAUAAGAG CCGCCGCCGCCGCCGCCGCCACC |
| 397 | (GCC)7-1-UTR | GGGAAAUAAGAGAGAAAAGAAGAGUAAGAAGAAAUAUAAGGC CGCCGCCGCCGCCGCCAGCCACC |
| 398 | (GCC)7-2-UTR | GGGAAAUAAGAGAGAAAAGAAGAGUAAGAAGAAAUAUAAGCC GCCGCCGCCGCCGCCGAGCCACC |
| 399 | (GCC)7-3-UTR | GGGAAAUAAGAGAGAAAAGAAGAGUAAGAAGAAAUAUAGCCG CCGCCGCCGCCGCCAGAGCCACC |
| 400 | (GCC)7-4-UTR | GGGAAAUAAGAGAGAAAAGAAGAGUAAGAAGAAAUAUGCCGCC GCCGCCGCCGCCAAGAGCCACC |
| 401 | (GCC)7-5-UTR | GGGAAAUAAGAGAGAAAAGAAGAGUAAGAAGAAAUAGCCGCCG CCGCCGCCGCCGCCUAAGAGCCACC |
| 402 | (GCC)7-6-UTR | GGGAAAUAAGAGAGAAAAGAAGAGUAAGAAGAAAUGCCGCCGC CGCCGCCGCCGCCAUAAGAGCCACC |
| 403 | (GCC)7-7-UTR | GGGAAAUAAGAGAGAAAAGAAGAGUAAGAAGAAAGCCGCCGCC GCCGCCGCCGCCUAUAAGAGCCACC |
| 404 | (GCC)7-8-UTR | GGGAAAUAAGAGAGAAAAGAAGAGUAAGAAGAAGCCGCCGCCG CCGCCGCCGCCAUAUAAGAGCCACC |
| 405 | (GCC)7-9-UTR | GGGAAAUAAGAGAGAAAAGAAGAGUAAGAAGAGCCGCCGCCGC CGCCGCCGCCAAUAUAAGAGCCACC |
| 406 | (GCC)7-10-UTR | GGGAAAUAAGAGAGAAAAGAAGAGUAAGAAGGCCGCCGCCGCC GCCGCCGCCAAAUAUAAGAGCCACC |

TABLE 9-continued

SEQUENCE LISTING

| SEQ ID NO | Description | Sequence |
|---|---|---|
| 407 | (GCC)7-11-UTR | GGGAAAUAAGAGAGAAAAGAAGAGUAAGAAGCCGCCGCCGCCG CCGCCGCCGAAAUAUAAGAGCCACC |
| 408 | (GCC)7-12-UTR | GGGAAAUAAGAGAGAAAAGAAGAGUAAGAGCCGCCGCCGCCGC CGCCGCCAGAAAUAUAAGAGCCACC |
| 409 | (GCC)7-13-UTR | GGGAAAUAAGAGAGAAAAGAAGAGUAAGGCCGCCGCCGCCGCC GCCGCCAAGAAAUAUAAGAGCCACC |
| 410 | (GCC)7-14-UTR | GGGAAAUAAGAGAGAAAAGAAGAGUAAGCCGCCGCCGCCGCCG CCGCCGAAGAAAUAUAAGAGCCACC |
| 411 | (GCC)7-15-UTR | GGGAAAUAAGAGAGAAAAGAAGAGUAGCCGCCGCCGCCGCCGC CGCCAGAAGAAAUAUAAGAGCCACC |
| 412 | (GCC)7-16-UTR | GGGAAAUAAGAGAGAAAAGAAGAGUGCCGCCGCCGCCGCCGCC GCCAAGAAGAAAUAUAAGAGCCACC |
| 413 | (GCC)7-17-UTR | GGGAAAUAAGAGAGAAAAGAAGAGGCCGCCGCCGCCGCCGCCG CCUAAGAAGAAAUAUAAGAGCCACC |
| 414 | (GCC)7-18-UTR | GGGAAAUAAGAGAGAAAAGAAGAGCCGCCGCCGCCGCCGCCGC CGUAAGAAGAAAUAUAAGAGCCACC |
| 415 | (GCC)8-UTR | GGGAAAUAAGAGAGAAAAGAAGAGUAAGAAGAAAUAUAAGAG CCGCCGCCGCCGCCGCCGCCGCCACC |
| 416 | (GCC)8-1-UTR | GGGAAAUAAGAGAGAAAAGAAGAGUAAGAAGAAAUAUAAGGC CGCCGCCGCCGCCGCCGCCAGCCACC |
| 417 | (GCC)8-2-UTR | GGGAAAUAAGAGAGAAAAGAAGAGUAAGAAGAAAUAUAAGCC GCCGCCGCCGCCGCCGCCGAGCCACC |
| 418 | (GCC)8-3-UTR | GGGAAAUAAGAGAGAAAAGAAGAGUAAGAAGAAAUAUAGCCG CCGCCGCCGCCGCCGCCAGAGCCACC |
| 419 | (GCC)8-4-UTR | GGGAAAUAAGAGAGAAAAGAAGAGUAAGAAGAAAUAUGCCGCC GCCGCCGCCGCCGCCAAGAGCCACC |
| 420 | (GCC)8-5-UTR | GGGAAAUAAGAGAGAAAAGAAGAGUAAGAAGAAAUAGCCGCCG CCGCCGCCGCCGCCUAAGAGCCACC |
| 421 | (GCC)8-6-UTR | GGGAAAUAAGAGAGAAAAGAAGAGUAAGAAGAAAUGCCGCCGC CGCCGCCGCCGCCAUAAGAGCCACC |
| 422 | (GCC)8-7-UTR | GGGAAAUAAGAGAGAAAAGAAGAGUAAGAAGAAAGCCGCCGCC GCCGCCGCCGCCUAUAAGAGCCACC |
| 423 | (GCC)8-8-UTR | GGGAAAUAAGAGAGAAAAGAAGAGUAAGAAGAAGCCGCCGCCG CCGCCGCCGCCAUAUAAGAGCCACC |
| 424 | (GCC)8-9-UTR | GGGAAAUAAGAGAGAAAAGAAGAGUAAGAAGAGCCGCCGCCGC CGCCGCCGCCAAUAUAAGAGCCACC |
| 425 | (GCC)8-10-UTR | GGGAAAUAAGAGAGAAAAGAAGAGUAAGAAGGCCGCCGCCGCC GCCGCCGCCAAAUAUAAGAGCCACC |
| 426 | (GCC)8-11-UTR | GGGAAAUAAGAGAGAAAAGAAGAGUAAGAAGCCGCCGCCGCCG CCGCCGCCGAAAUAUAAGAGCCACC |
| 427 | (GCC)8-12-UTR | GGGAAAUAAGAGAGAAAAGAAGAGUAAGAGCCGCCGCCGCCGC CGCCGCCAGAAAUAUAAGAGCCACC |
| 428 | (GCC)8-13-UTR | GGGAAAUAAGAGAGAAAAGAAGAGUAAGGCCGCCGCCGCCGCC GCCGCCAAGAAAUAUAAGAGCCACC |
| 429 | (GCC)8-14-UTR | GGGAAAUAAGAGAGAAAAGAAGAGUAAGCCGCCGCCGCCGCCG CCGCCGAAGAAAUAUAAGAGCCACC |
| 430 | (GCC)8-15-UTR | GGGAAAUAAGAGAGAAAAGAAGAGUAGCCGCCGCCGCCGCCGC CGCCGCCAGAAGAAAUAUAAGAGCCACC |
| 431 | (GCC)8-16-UTR | GGGAAAUAAGAGAGAAAAGAAGAGUGCCGCCGCCGCCGCCGCC GCCGCCAAGAAGAAAUAUAAGAGCCACC |

TABLE 9-continued

SEQUENCE LISTING

| SEQ ID NO | Description | Sequence |
|---|---|---|
| 432 | (GCC)8-17-UTR | GGGAAAUAAGAGAGAAAAGAAGAGGCCGCCGCCGCCGCCGCCG CCGCCUAAGAAGAAAUAUAAGAGCCACC |
| 433 | (GCC)8-18-UTR | GGGAAAUAAGAGAGAAAAGAAGAGCCGCCGCCGCCGCCGCCGC CGCCGUAAGAAGAAAUAUAAGAGCCACC |
| 434 | (GCC)9-UTR | GGGAAAUAAGAGAGAAAAGAAGAGUAAGAAGAAAUAUAAGAG CCGCCGCCGCCGCCGCCGCCGCCGCCACC |
| 435 | (GCC)9-1-UTR | GGGAAAUAAGAGAGAAAAGAAGAGUAAGAAGAAAUAUAAGGC CGCCGCCGCCGCCGCCGCCGCCAGCCACC |
| 436 | (GCC)9-2-UTR | GGGAAAUAAGAGAGAAAAGAAGAGUAAGAAGAAAUAUAAGCC GCCGCCGCCGCCGCCGCCGCCGAGCCACC |
| 437 | (GCC)9-3-UTR | GGGAAAUAAGAGAGAAAAGAAGAGUAAGAAGAAAUAUAGCCG CCGCCGCCGCCGCCGCCGCCAGAGCCACC |
| 438 | (GCC)9-4-UTR | GGGAAAUAAGAGAGAAAAGAAGAGUAAGAAGAAAUAUGCCGCC GCCGCCGCCGCCGCCGCCAAGAGCCACC |
| 439 | (GCC)9-5-UTR | GGGAAAUAAGAGAGAAAAGAAGAGUAAGAAGAAAUAGCCGCCG CCGCCGCCGCCGCCGCCUAAGAGCCACC |
| 440 | (GCC)9-6-UTR | GGGAAAUAAGAGAGAAAAGAAGAGUAAGAAGAAAUGCCGCCGC CGCCGCCGCCGCCGCCAUAAGAGCCACC |
| 441 | (GCC)9-7-UTR | GGGAAAUAAGAGAGAAAAGAAGAGUAAGAAGAAAGCCGCCGCC GCCGCCGCCGCCGCCUAUAAGAGCCACC |
| 442 | (GCC)9-8-UTR | GGGAAAUAAGAGAGAAAAGAAGAGUAAGAAGAAGCCGCCGCCG CCGCCGCCGCCGCCAUAUAAGAGCCACC |
| 443 | (GCC)9-9-UTR | GGGAAAUAAGAGAGAAAAGAAGAGUAAGAAGAGCCGCCGCCGC CGCCGCCGCCGCCAAUAUAAGAGCCACC |
| 444 | (GCC)9-10-UTR | GGGAAAUAAGAGAGAAAAGAAGAGUAAGAAGGCCGCCGCCGCC GCCGCCGCCGCCAAAUAUAAGAGCCACC |
| 445 | (GCC)9-11-UTR | GGGAAAUAAGAGAGAAAAGAAGAGUAAGAAGCCGCCGCCGCCG CCGCCGCCGCCGAAAUAUAAGAGCCACC |
| 446 | (GCC)9-12-UTR | GGGAAAUAAGAGAGAAAAGAAGAGUAAGAGCCGCCGCCGCCGC CGCCGCCGCCAGAAAUAUAAGAGCCACC |
| 447 | (GCC)9-13-UTR | GGGAAAUAAGAGAGAAAAGAAGAGUAAGGCCGCCGCCGCCGCC GCCGCCGCCAAGAAAUAUAAGAGCCACC |
| 448 | (GCC)9-14-UTR | GGGAAAUAAGAGAGAAAAGAAGAGUAAGCCGCCGCCGCCGCCG CCGCCGCCGAAGAAAUAUAAGAGCCACC |
| 449 | (GCC)9-15-UTR | GGGAAAUAAGAGAGAAAAGAAGAGUAGCCGCCGCCGCCGCCGC CGCCGCCAGAAGAAAUAUAAGAGCCACC |
| 450 | (GCC)9-16-UTR | GGGAAAUAAGAGAGAAAAGAAGAGUGCCGCCGCCGCCGCCGCC GCCGCCAAGAAGAAAUAUAAGAGCCACC |
| 451 | (GCC)9-17-UTR | GGGAAAUAAGAGAGAAAAGAAGAGGCCGCCGCCGCCGCCGCCG CCGCCUAAGAAGAAAUAUAAGAGCCACC |
| 452 | (GCC)9-18-UTR | GGGAAAUAAGAGAGAAAAGAAGAGCCGCCGCCGCCGCCGCCGC CGCCGCCGUAAGAAGAAAUAUAAGAGCCACC |
| 453 | (GCC)10-UTR | GGGAAAUAAGAGAGAAAAGAAGAGUAAGAAGAAAUAUAAGAG CCGCCGCCGCCGCCGCCGCCGCCGCCGCCACC |
| 454 | (GCC)10-1-UTR | GGGAAAUAAGAGAGAAAAGAAGAGUAAGAAGAAAUAUAAGGC CGCCGCCGCCGCCGCCGCCGCCGCCAGCCACC |
| 455 | (GCC)10-2-UTR | GGGAAAUAAGAGAGAAAAGAAGAGUAAGAAGAAAUAUAAGCC GCCGCCGCCGCCGCCGCCGCCGCCGAGCCACC |
| 456 | (GCC)10-3-UTR | GGGAAAUAAGAGAGAAAAGAAGAGUAAGAAGAAAUAUAGCCG CCGCCGCCGCCGCCGCCGCCGCCAGAGCCACC |

TABLE 9-continued

SEQUENCE LISTING

| SEQ ID NO | Description | Sequence |
|---|---|---|
| 457 | (GCC)10-4-UTR | GGGAAAUAAGAGAGAAAAGAAGAGUAAGAAGAAAUAUGCCGCC GCCGCCGCCGCCGCCGCCGCCGCCAAGAGCCACC |
| 458 | (GCC)10-5-UTR | GGGAAAUAAGAGAGAAAAGAAGAGUAAGAAGAAAUAGCCGCCG CCGCCGCCGCCGCCGCCGCCGCCUAAGAGCCACC |
| 459 | (GCC)10-6-UTR | GGGAAAUAAGAGAGAAAAGAAGAGUAAGAAGAAAUGCCGCCGC CGCCGCCGCCGCCGCCGCCGCCAUAAGAGCCACC |
| 460 | (GCC)10-7-UTR | GGGAAAUAAGAGAGAAAAGAAGAGUAAGAAGAAAGCCGCCGCC GCCGCCGCCGCCGCCGCCGCCUAUAAGAGCCACC |
| 461 | (GCC)10-8-UTR | GGGAAAUAAGAGAGAAAAGAAGAGUAAGAAGAAGCCGCCGCCG CCGCCGCCGCCGCCGCCGCCAUAUAAGAGCCACC |
| 462 | (GCC)10-9-UTR | GGGAAAUAAGAGAGAAAAGAAGAGUAAGAAGAGCCGCCGCCGC CGCCGCCGCCGCCGCCGCCAAUAUAAGAGCCACC |
| 463 | (GCC)10-10-UTR | GGGAAAUAAGAGAGAAAAGAAGAGUAAGAAGGCCGCCGCCGCC GCCGCCGCCGCCGCCGCCAAAUAUAAGAGCCACC |
| 464 | (GCC)10-11-UTR | GGGAAAUAAGAGAGAAAAGAAGAGUAAGAAGCCGCCGCCGCCG CCGCCGCCGCCGCCGCCGAAAUAUAAGAGCCACC |
| 465 | (GCC)10-12-UTR | GGGAAAUAAGAGAGAAAAGAAGAGUAAGAGCCGCCGCCGCCGC CGCCGCCGCCGCCAGAAAUAUAAGAGCCACC |
| 466 | (GCC)10-13-UTR | GGGAAAUAAGAGAGAAAAGAAGAGUAAGGCCGCCGCCGCCGCC GCCGCCGCCGCCAAGAAAUAUAAGAGCCACC |
| 467 | (GCC)10-14-UTR | GGGAAAUAAGAGAGAAAAGAAGAGUAAGCCGCCGCCGCCGCCG CCGCCGCCGCCGAAGAAAUAUAAGAGCCACC |
| 468 | (GCC)10-15-UTR | GGGAAAUAAGAGAGAAAAGAAGAGUAGCCGCCGCCGCCGCCGC CGCCGCCGCCAGAAGAAAUAUAAGAGCCACC |
| 469 | (GCC)10-16-UTR | GGGAAAUAAGAGAGAAAAGAAGAGUGCCGCCGCCGCCGCCGCC GCCGCCGCCGCCAAGAAGAAAUAUAAGAGCCACC |
| 470 | (GCC)10-17-UTR | GGGAAAUAAGAGAGAAAAGAAGAGGCCGCCGCCGCCGCCGCCG CCGCCGCCGCCUAAGAAGAAAUAUAAGAGCCACC |
| 471 | (GCC)10-18-UTR | GGGAAAUAAGAGAGAAAAGAAGAGCCGCCGCCGCCGCCGCCGC CGCCGCCGCCGUAAGAAGAAAUAUAAGAGCCACC |
| 472 | KT1-UTR | GGGCCCGCCGCCAAC |
| 473 | KT2-UTR | GGGCCCGCCGCCACC |
| 474 | KT3-UTR | GGGCCCGCCGCCGAC |
| 475 | KT4-UTR | GGGCCCGCCGCCGCC |

What is claimed is:

1. A method of expressing a messenger RNA (mRNA) in a cell, comprising contacting the cell with the mRNA, wherein the mRNA comprises
   (i) a 5' untranslated region (UTR) comprising an RNA element as set forth in SEQ ID NO: 2; and
   (ii) an open reading frame comprising an initiation codon and encoding a polypeptide;
   wherein the RNA element has a 3'end located 10-20 nucleotides or 6-10 nucleotides upstream of the initiation codon in the 5'UTR, and
   wherein the mRNA comprises one or more chemically modified nucleotides,
   thereby expressing the mRNA in the cell.

2. The method of claim 1, wherein the RNA element has a 3' end located 6, 7, 8, 9, 10, 11, 12, 13, 14, 15, 16, 17, 18, 19, or 20 nucleotides upstream of the initiation codon.

3. The method of claim 1, wherein the mRNA comprises a 5' cap, a 3' UTR, and a poly A tail.

4. The method of claim 1, wherein the mRNA comprises one or more pseudouridines or pseudouridine analogs.

5. The method of claim 1, wherein the mRNA is fully modified with N1-methylpseudouridine.

6. The method of claim 1, wherein the mRNA is formulated in a lipid nanoparticle.

7. A method of expressing a mRNA in a cell, comprising contacting the cell with the mRNA, wherein the mRNA comprises
   (i) a 5'UTR comprising an RNA element inserted into the nucleotide sequence set forth in SEQ ID NO: 33, and
   (ii) an open reading frame comprising an initiation codon and encoding a polypeptide;
   wherein the RNA element is CCCCGGCGCC (SEQ ID NO: 2),
   wherein the RNA element has a 3'end located 10-20 nucleotides or 6-10 nucleotides upstream of the initiation codon in the 5'UTR, and
   wherein the mRNA comprises one or more chemically modified nucleotides,
   thereby expressing the mRNA in the cell.

8. The method of claim 7, wherein the RNA element has a 3'end located 6, 7, 8, 9, 10, 11, 12, 13, 14, 15, 16, 17, 18, 19, or 20 nucleotides upstream of the initiation codon.

9. The mRNA of claim 7, wherein the mRNA comprises a 5' cap, a 3' UTR, and a poly A tail.

10. The method of claim 7, wherein the mRNA comprises one or more pseudouridines or pseudouridine analogs.

11. The method of claim 7, wherein the mRNA is fully modified with N1-methylpseudouridine.

12. The method of claim 7, wherein the mRNA is formulated in a lipid nanoparticle.

13. A method of expressing a mRNA in a cell, comprising contacting the cell with the mRNA, wherein the mRNA comprises
   (i) a 5'UTR comprising a nucleotide sequence as set forth in SEQ ID NO: 34;
   (ii) an open reading frame comprising an initiation codon and encoding a polypeptide; and
   wherein the mRNA comprises one or more chemically modified nucleotides,
   thereby expressing the mRNA in the cell.

14. The method of claim 13, wherein the mRNA comprises a 5' cap, a 3' UTR, and a poly A tail.

15. The method of claim 13, wherein the mRNA comprises one or more pseudouridines or pseudouridine analogs.

16. The method of claim 13, wherein the mRNA is fully modified with N1-methylpseudouridine.

17. The method of claim 13, wherein the mRNA is formulated in a lipid nanoparticle.

18. The method of claim 2, wherein the RNA element has a 3' end located 7 nucleotides upstream of the initiation codon.

19. The method of claim 8, wherein the RNA element has a 3' end located 7 nucleotides upstream of the initiation codon.

* * * * *